US012497610B2

(12) United States Patent
Bauer et al.

(10) Patent No.: US 12,497,610 B2
(45) Date of Patent: *Dec. 16, 2025

(54) FUNCTIONAL GENOMICS USING CRISPR-CAS SYSTEMS FOR SATURATING MUTAGENESIS OF NON-CODING ELEMENTS, COMPOSITIONS, METHODS, LIBRARIES AND APPLICATIONS THEREOF

(71) Applicants: THE BROAD INSTITUTE, INC., Cambridge, MA (US); MASSACHUSETTS INSTITUTE OF TECHNOLOGY, Cambridge, MA (US); CHILDREN'S MEDICAL CENTER CORPORATION, Boston, MA (US)

(72) Inventors: Daniel E. Bauer, Boston, MA (US); Stuart H. Orkin, Boston, MA (US); Neville Espi Sanjana, Cambridge, MA (US); Ophir Shalem, Cambridge, MA (US); Jason Wright, Cambridge, MA (US); Feng Zhang, Cambridge, MA (US)

(73) Assignees: The Broad Institute, Inc., Cambridge, MA (US); Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,958

(22) Filed: Jun. 30, 2023

(65) Prior Publication Data

US 2024/0102004 A1 Mar. 28, 2024

Related U.S. Application Data

(63) Continuation of application No. 18/317,248, filed on May 15, 2023, which is a continuation of application No. 15/807,007, filed on Nov. 8, 2017, now Pat. No. 11,685,917, which is a continuation-in-part of application No. PCT/US2016/031164, filed on May 6, 2016.

(60) Provisional application No. 62/316,421, filed on Mar. 31, 2016, provisional application No. 62/219,498, filed on Sep. 16, 2015, provisional application No. 62/158,882, filed on May 8, 2015.

(51) Int. Cl.
*C12N 15/10* (2006.01)

(52) U.S. Cl.
CPC ....... *C12N 15/1079* (2013.01); *C12N 15/102* (2013.01); *C12N 15/1075* (2013.01); *C12N 15/1082* (2013.01)

(58) Field of Classification Search
None
See application file for complete search history.

(56) References Cited

U.S. PATENT DOCUMENTS

| | | | | |
|---|---|---|---|---|
| 8,697,359 | B1 | 4/2014 | Zhang | |
| 8,993,233 | B2 | 3/2015 | Zhang et al. | |
| 11,572,543 | B2 * | 2/2023 | Bauer | C12N 15/11 |
| 11,685,917 | B2 * | 6/2023 | Bauer | C12N 15/102 435/6.13 |
| 2014/0186919 | A1 | 7/2014 | Zhang et al. | |
| 2014/0242664 | A1 | 8/2014 | Zhang et al. | |
| 2014/0287938 | A1 | 9/2014 | Zhang et al. | |
| 2014/0357530 | A1 | 12/2014 | Zhang et al. | |
| 2015/0044191 | A1 | 2/2015 | Liu | |
| 2016/0251648 | A1 | 9/2016 | Wang et al. | |

FOREIGN PATENT DOCUMENTS

| | | |
|---|---|---|
| WO | 2014018423 A2 | 1/2014 |
| WO | 2014093622 A2 | 6/2014 |
| WO | 2014093701 | 6/2014 |
| WO | 2014204727 | 12/2014 |
| WO | 2015065964 | 5/2015 |

OTHER PUBLICATIONS

Koonin et al., "Diveristy, classification and evolution of CRISPR-Cas systems" 37 Current Opinion in Microbiology 67-78 (Year: 2017).*
Sorek et al., "CRISPR-Mediated Adaptive Immune Systems in Bacteria and Archaea" 82 The Annual Review of Biochemistry 237-266 (Year: 2013).*
Koike-Yusa et al., "Genome-wide recessive genetic screening in mammalian cells with a lentiviral CRISPR-guide RNA library" 32(3) Nature Biotechnology (Year: 2014).*
Bauer et al., "Generation of Genomic Deletions in Mammalian Cell Lines via CRISPR/Cas9" 83 Journal of Visualized Experiments e52118 1-10 (Year: 2014).*
Basak, et al., "BCL11A deletions result in fetal hemoglobin persistence and neurodevelopmental alterations", JCI, 125 (6), Jun. 2015, pp. 2363-2368.
Bauer, et al., "An Erythroid Enhancer of BCL11A Subject to Genetic Variation Determines Fetal Hemoglobin Level", Science, vol. 342, Issue 6155, Oct. 11, 2013, 253-257.
Bauer, et al., "Reawakening fetal hemoglobin: prospects for new therapies for the p. globin disorders", Blood 120 (15),, Oct. 11, 2012, pp. 2945-2953.

(Continued)

*Primary Examiner* — Nancy J Leith
(74) *Attorney, Agent, or Firm* — F. Brent Nix, Esq.; Johnson, Marcou, Isaacs & Nix, LLC; Christopher D. Southgate, Esq.

(57) ABSTRACT

The application relates to a deep scanning mutagenesis library to interrogate phenotypic changes in a population of cells comprising a plurality of CRISPR-Cas system guide RNAs targeting genomic sequences within at least one continuous genomic region, wherein the guide RNAs target at least 100 genomic sequences upstream of a PAM sequence for every 1000 base pairs within the continuous genomic region and methods for their use.

6 Claims, 102 Drawing Sheets

Specification includes a Sequence Listing.

(56) References Cited

OTHER PUBLICATIONS

Bauer, et al., "Update on fetal hemoglobin gene regulation in hemoglobinopathies", Curr. Opin. Pediatr. 23(1), 2011, pp. 1-8.
Canver, et al., "BCL11A enhancer dissection by Cas9-mediated in situ saturating mutagenesis", Nature, vol. 527, Nov. 12, 2015, pp. 192-197.
Canver, et al., "Characterization of Genomic Deletion Efficiency Mediated by Clusted Regularly Interspaced Palindromic Repeats (CRISPR)/Cas9 Nuclease System in Mammalian Cells", J. Biol. Chem. 289 (31), Aug. 1, 2014, pp. 21312-21324.
Chen, et al., "Genome-Wide CRISPR Screen in a Mouse Model of Tumor Growth and Metastasis", Cell, vol. 160, No. 6, Mar. 12, 2015, 1246-1260.
Cong, et al., "Multiplex Genome Engineering Using CRISPR/Cas Systems", Science, vol. 339, No. 6121, Feb. 14, 2013, 819-823.
Crocker, et al., "Low Affinity Binding Site Clusters Confer Hox Specificity and Regulatory Robustness", Cell, 160, Jan. 15, 2015, pp. 191-203.
Cui, et al., "Impact of Alu repeats on the evolution of human p53 binding sites", Biol. Direct 6(2), 2011, pp. 1-20.
Ding, et al., "Epigenetic Activation of AP1 Promotes Squamous Cell Carcinoma Metastasis", Science Signaling, vol. 6, issue 273, Apr. 30, 2013, ra28, 14 pages.
Dixon, et al., "Topological domains in mammalian genomes identified by analysis of chromatin interactions", Nature 485, 2012, 5 pages.
Hardison, et al., "GWAS to therapy by genome edits?", Science, 342(6155), Oct. 11, 2013, 206-207.
Hindorff, et al., "Potential etiologic and functional implications of genome-wide association loci for human diseases and traits", PNAS, 106(23), Jun. 9, 2009, pp. 9362-9367.
Hsu, et al., "Development and Applications of CRISPR-Cas9 for Genome Engineering", Cell, Leading Edge Review, vol. 157,, Jun. 5, 2014, pp. 1262-1278.
Hsu, et al., "DNA targeting specificity of RNA-guided Cas9 nucleases", Nature Biotechnology, 2013, pp. 827-832.
John, et al., "Bcl11a is required for neuronal morphogenesis and sensory circuit formation in dorsal spinal cord development", Development, 139, 2012, pp. 1831-1841.
Kurita, et al., "Establishment of Immortalized Human Erythroid Progenitor Cell Lines Able to Produce Enucleated Red Blood Cells", PLoS One, vol. 8, issue 3, Mar. 2013, e59890.
Kwasnieski, et al., "High-throughput functional testing of ENCODE segmentation predictions", Genome Research, 24, 2014, pp. 1595-1602.
Lieberman-Aiden, et al., "Comprehensive Mapping of Long-Range Interactions Reveals Folding Principles of the Human Genome", Science, 326, 2009, pp. 289-294.
Liu, et al., "Bcl11a is essential for normal lymphoid development", Nature Immunology, 4(6), Jun. 2003, pp. 525-532.
Maher, "The Human Encyclopaedia", Nature, 489, Sep. 6, 2012, pp. 46-48.
Mali, et al., "RNA-Guided Human Genome Engineering via Cas9", Science, vol. 339, No. 6121, Feb. 15, 2013, 823-826.
Mandal, et al., "Efficient Ablation of Genes in Human Hematopoietic Stem and Effector Cells using CRISPR/Cas9", Cell Stem Cell, vol. 15, Issue 5, Nov. 2014, pp. 643-652.
Melnikov, et al., "Systematic dissection and optimization of inducible enhancers in human cells using a massively parallel reporter assay", Nature Biotechnology, vol. 30, 2012, 271-277.
Mundade, et al., "Role of ChIP-seq in the discovery of transcription factor binding sites, differential gene regulation mechanism, epigenetic marks and beyond", Cell Cycle, 13, Sep. 15, 2014, pp. 2847-2852.
Nord, et al., "Rapid and Pervasive Changes in Genome-wide Enhancer Usage during Mammalian Development", Cell, 155, Dec. 19, 2013, pp. 1521-1531.
Patwardhan, et al., "Massively parallel functional dissection of mammalian enhancers in vivo", Nat. Biotechnol., 30 (3), Mar. 2012, pp. 265-270.
Porcu, et al., "The human Beta globin locus introduced by YAC transfer exhibits a specific and reproducible pattern of developmental regulation in transgenic mice", Blood, 90(11), Dec. 1997, pp. 4602-4609.
Ran, et al., "Double Nicking by RNA-Guided CRISPR Cas9 for Enhanced Genome Editing Specificity", Cell, vol. 154, No. 6, Sep. 12, 2013, 1380-1389.
Roadmap Epigenomics Consortium, et al., "Integrative analysis of 111 reference human epigenomes", Nature, 518, Feb. 19, 2015, pp. 317-330.
Sankaran, et al., "Developmental and species-divergent globin switching are driven by BCL11A", Nature, 460, 2009, pp. 1093-1097.
Sankaran, et al., "Human Fetal Hemoglobin Expression Is Regulated by the Developmental Stage-Specific Repressor BCL11A", Science, 322, 2008, pp. 1839-1842.
Sankaran, et al., "The switch from fetal to adult hemoglobin", Cold Spring Harb. Perspect. Med. 3,, 2013, pp. 1-14.
Schaub, et al., "Linking disease associations with regulatory information in the human genome", Genome Research, 22, 2012, pp. 1748-1759.
Schizophrenia Working Group Of, "Biological insights from 108 schizophrenia-associated genetic loci", Nature, 511, 2014, pp. 421-427.
Sexton, et al., "The Role of Chromosome Domains in Shaping the Functional Genome.", Cell, 160, 2015, pp. 1049-1059.
Shalem, et al., "Genome-Scale CRISPR-Cas9 Knockout Screening in Human Cells", Science, vol. 343, No. 6166, 2014, 84-87.
Visel, et al., "ChiP-seq accurately predicts tissue-specific activity of enhancers", Nature, 457, 2009, pp. 854-858.
Wang, et al., "Genetic Screens in Human Cells Using the CRISPR/Cas9 System", Science, vol. 343, No. 6166, Jan. 3, 2014, 80-84.
Xu, et al., "Correction of Sickle Cell Disease in Adult Mice by Interference with Fetal Hemoglobin Silencing", Science, vol. 334, Issue 6058, Nov. 18, 2011, pp. 993-996.
Yu, et al., "Bcl I I a is essential for lymphoid development and negatively regulates p53", J. Exp. Med., 209(13), 2012, pp. 2467-2483.
Zhou, et al., "High-Throughput Screening of A CRISPR/Cas9 Library for Functional Genomics in Human Cells", Nature, vol. 509, No. 7501, May 2014, 487-491.
International Search Report dated Aug. 31, 2016, which issued during prosecution of International Application No. PCT/US2016/031164.
International Preliminary Report on Patentability and Written Opinion of the International Searching Authority dated Nov. 14, 2017, which issued during prosecution of International Application No. PCT/US2016/031164.
Bauer, et al., "An Erythroid Enhancer of BCL11A Subject to Genetic Variation Determines Fetal Hemoglobin Level" Science, 2013, 342:253-257.
Bassett, et al. "A Genome-Wide CRISPR Library for High-Throughput Genetic Screening in *Drosophila* Cells" Journal of Genetics and Genomics, 2015, 42:301-309.
Canver, et al. "BCL11A enhancer dissection by Cas9-mediated in situ saturating mutagenesis" Nature, 2015, 527:192-197, including Supplementary material.
Doench, et al., "Rational design of highly active sgRNAs for CRISPR-Cas9-mediated gene inactivation" Nature Biotechnology, 2014, 32(12):1262-1267, including Supplementary material.
Ho, et al. "Targeting non-coding RNAs with the CRISPR/Cas9 system in human cell lines" Nucleic Acids Research, 2015, 43(3):e17, doi: 10.1093/narlgku1198.
Konerman, et al., "Genome-scale transcriptional activation by an engineered CRISPR-Cas9 complex" Nature, 2015, 517:583-588, including Supplementary Materials.
Mali, et al. "CAS9 transcriptional activators for target specificity screening and paired nickases for cooperative genome engineering" Nature Biotechnology, 2013, 31(9)833-838, including Supplementary Information.

(56) References Cited

OTHER PUBLICATIONS

Pattanayak, et al. "High-throughput profiling of off-target DNA cleavage reveals RNA-programmed Cas9 nuclease specificity" Nature Biotechnology, 2013, 31(9):839-843, including Supplementary Materials.
Sander, et al. "CRISPR-Cas systems for editing, regulating and targeting genomes" Nature Biotechnology, 2014, 32:347-355.
Sanjana, et al. "Improved vectors and genome-wide libraries for vectors and genome-wide libraries for CRISPR screening", HHS Public Access Author Manuscript, 2014, 11(8):783-784.
Sebastiani, et al. "BCL11Aenhancer haplotypes and fetal hemoglobin in sickle cell anemia" Blood Cells, 2015, 54(3):1079-9796.
Shalem, et al. "Genome-Scale CRISPR-Cas9 Knockout Screening in Human Cells" Science, 2014, 343:84-87.
Shalem, et al. "High-throughput functional genomics using CRISP-Cas9" Nature Reviews Genetics, 2015, 16 (5):1471-0056.
Wang, et al. "Gentic Screens in Human Cells Using the CRISPR-Cas9 System" Science, 2013, 80-84, including Supplementary Material.
Zhou, et al. "High-throughput screening of a CRISPR/Cas9 library for functional genomics in human cells" Nature, 2014, 509:487-491.

* cited by examiner

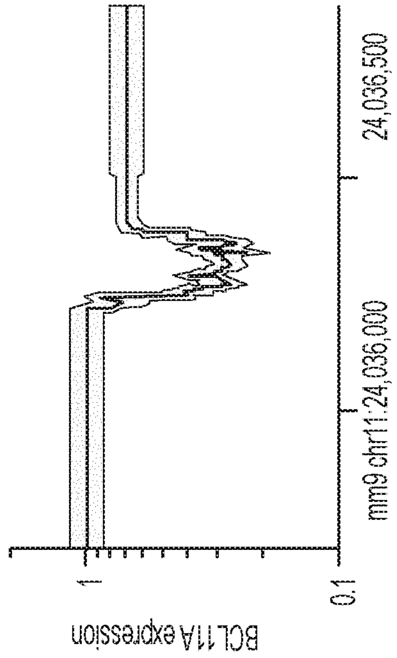
FIG. 14A
| Genotype | Progeny (no.) | Percentage (expected) |
|---|---|---|
| +62 +/+ | 7 | 15.6 (25) |
| +62 +/Δ | 25 | 55.6 (50) |
| +62 Δ/Δ | 13 | 28.9 (25) |
| Total | 45 | 100 (100) |
FIG. 14B
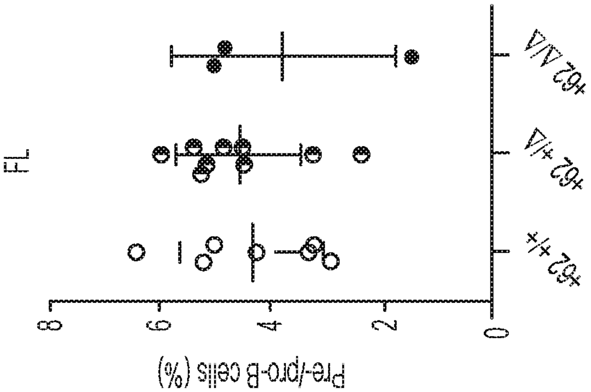
FIG. 14C
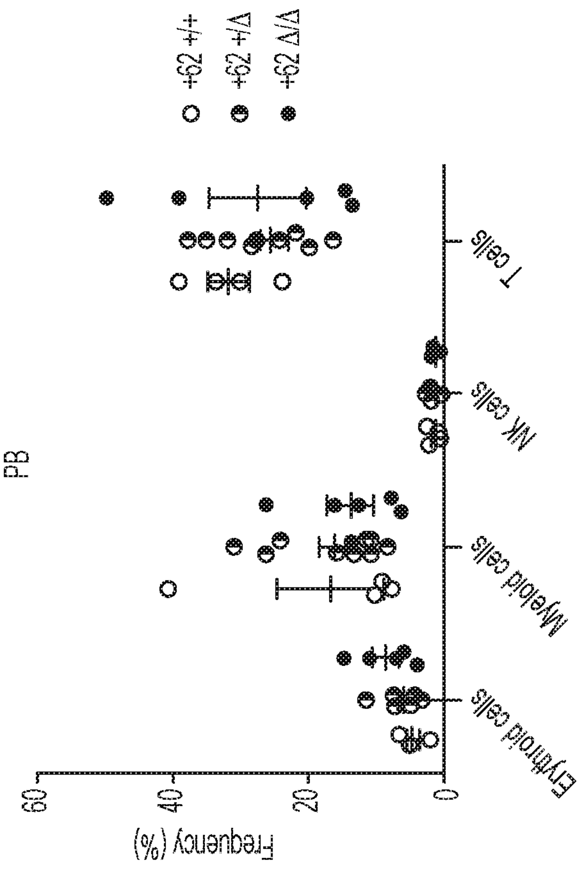
FIG. 14D

| Genotype | Progeny (no.) | Percentage (expected) |
|---|---|---|
| +62 +/+ | 11 | 14.5 (25) |
| +62 +/Δ | 45 | 59.2 (50) |
| +62 Δ/Δ | 20 | 26.3 (25) |
| Total | 76 | 100 (100) |
FIG. 15A
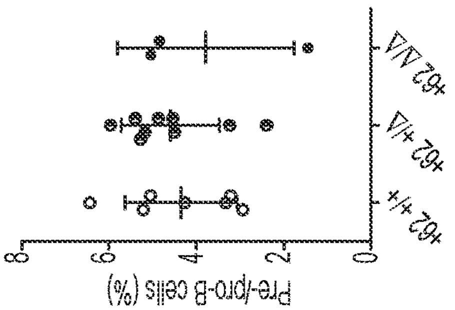
FIG. 15B
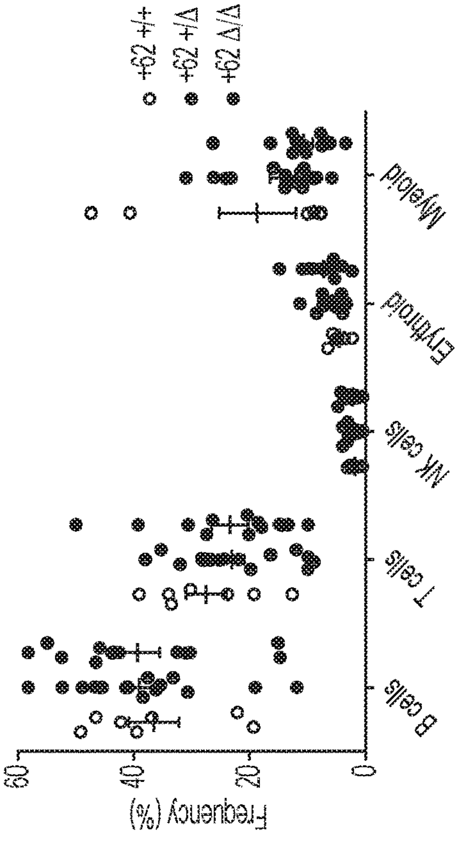
FIG. 15C
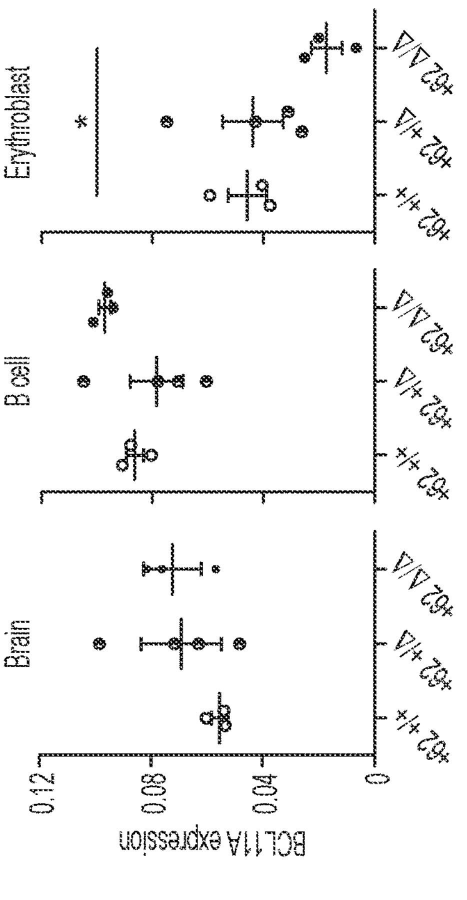
FIG. 15D

| Genotype | Progeny (no.) | Percentage (expected) |
|---|---|---|
| +62 +/+ | 11 | 14.5 (25) |
| +62 +/ | 45 | 59.2 (50) |
| +62 / | 20 | 26.3 (25) |
| Total | 76 | 100 (100) |
*FIG. 30A*
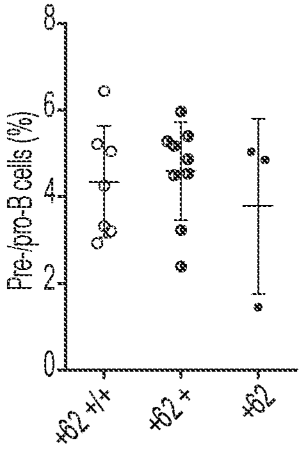
*FIG. 30B*
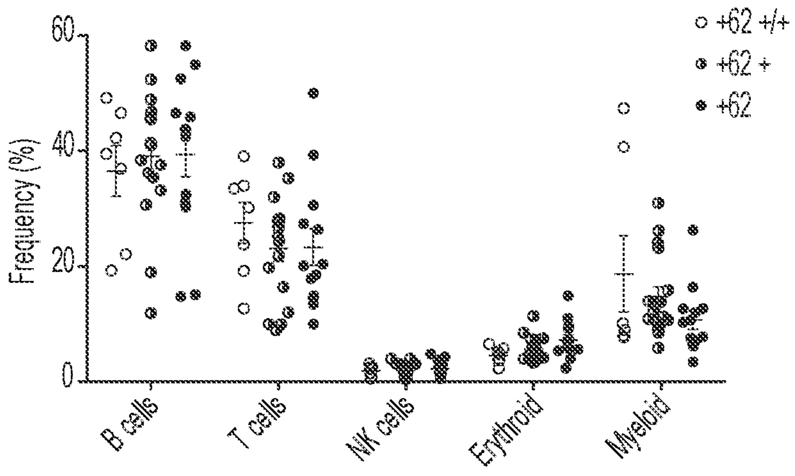
*FIG. 30C*
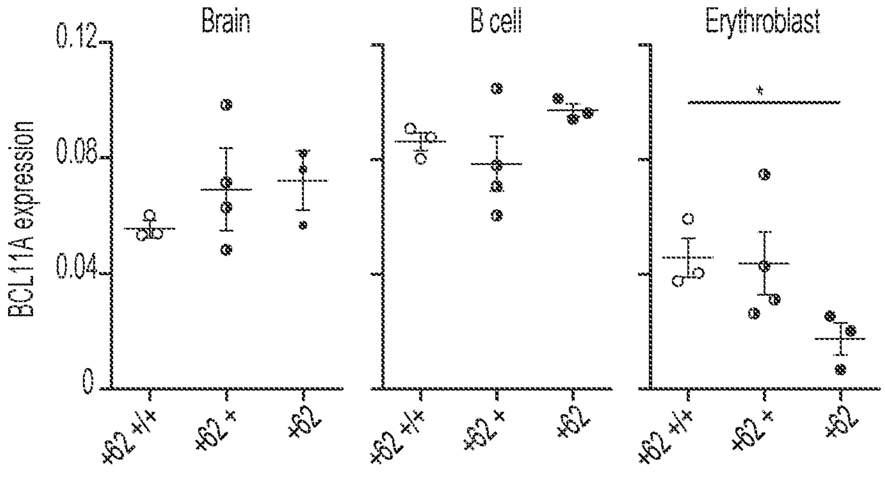
*FIG. 30D*

FUNCTIONAL GENOMICS USING CRISPR-CAS SYSTEMS FOR SATURATING MUTAGENESIS OF NON-CODING ELEMENTS, COMPOSITIONS, METHODS, LIBRARIES AND APPLICATIONS THEREOF

RELATED APPLICATIONS AND INCORPORATION BY REFERENCE

This application is a continuation of U.S. patent application Ser. No. 18/317,248 filed May 15, 2023, which is a continuation application of U.S. patent application Ser. No. 15/807,007, filed Nov. 8, 2017, which is a continuation-in-part of international patent application Serial No. PCT/US2016/031164 filed May 6, 2016, which published as PCT Publication No. WO2016/182893 on Nov. 17, 2016, which claims priority to and benefit of U.S. provisional patent application Ser. No. 62/158,882 filed May 8, 2015, U.S. provisional patent application Ser. No. 62/219,498 filed Sep. 16, 2015 and U.S. provisional patent application Ser. No. 62/316,421 filed Mar. 31, 2016. The contents of each of which are incorporated in their entirety.

Reference is made to U.S. patent application Ser. No. 14/463,253 filed Aug. 19, 2014, which is a continuation of US international application PCT/US2013/074800 filed Dec. 12, 2013, which claims benefit of and priority to U.S. provisional patent application No. 61/736,527 filed Dec. 12, 2012 and 61/802,174 filed Mar. 15, 2013. Reference is also made to U.S. provisional patent application No. 61/960,777 filed on Sep. 25, 2013 and 61/961,980 filed on Oct. 28, 2013. Reference is made to U.S. provisional patent applications 61/758,468; 61/769,046; 61/802,174; 61/806,375; 61/814,263; 61/819,803 and 61/828,130 filed on Jan. 30, 2013; Feb. 25, 2013; Mar. 15, 2013; Mar. 28, 2013; Apr. 20, 2013; May 6, 2013 and May 28, 2013 respectively. Reference is also made to U.S. provisional patent applications 61/836,123, 61/847,537, 61/862,355 and 61/871,301 filed on Jun. 17, 2013; Jul. 17, 2013, Aug. 5, 2013 and Aug. 28, 2013 respectively. Reference is also made to U.S. provisional patent applications 61/736,527 and 61/748,427 on Dec. 12, 2012 and Jan. 2, 2013, respectively. Reference is also made to U.S. provisional patent application 61/791,409 filed on Mar. 15, 2013. Reference is also made to U.S. provisional patent application 61/799,800 filed Mar. 15, 2013. Reference is also made to U.S. provisional patent applications 61/835,931, 61/835,936, 61/836,127, 61/836,101, 61/836,080, and 61/835,973 each filed Jun. 17, 2013.

Reference is also made to the article entitled "BCL11A enhancer dissection by Cas9-mediated in situ saturating mutagenesis" DOI: 10.1038/nature15521, published online Sep. 16, 2015, the article is herein incorporated by reference and is not prior art.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under grant numbers DK093705, HL032262, HL32259, MH100706, MH110049, DK097768, and HG008171 awarded by the National Institutes of Health. The government has certain rights in the invention.

SEQUENCE LISTING

This application contains a sequence listing filed in electronic form as an xml file entitled BROD-3520US-CON2 ST26, created on Oct. 13, 2023, and having a size of 754,124 bytes. The content of the sequence listing is incorporated herein in its entirety.

FIELD OF THE INVENTION

The present invention relates to methods for interrogating phenotypic changes in cell populations and tools therefor.

BACKGROUND OF THE INVENTION

Recent advances in genome sequencing techniques and analysis methods have significantly accelerated the ability to catalog and map genetic factors associated with a diverse range of biological functions and diseases. Functional genomics is a field of molecular biology that may be considered to utilize the vast wealth of data produced by genomic projects (such as genome sequencing projects) to describe gene (and protein) functions and interactions. Contrary to classical genomics, functional genomics focuses on the dynamic aspects such as gene transcription, translation, and protein-protein interactions, as opposed to the static aspects of the genomic information such as DNA sequence or structures, though these static aspects are very important and supplement one's understanding of cellular and molecular mechanisms. Functional genomics attempts to answer questions about the function of DNA at the levels of genes, RNA transcripts, and protein products.

More than 98% of the human genome is noncoding, however, unlike the coding genome there exists no overarching theoretical framework (e.g. protein triplet code) capable of translating noncoding genomic sequence into functional elements (73,2). Evidence from genome-wide association studies (GWAS) suggests many noncoding regions are critical for human health and disease: more than 2600 single-nucleotide polymorphisms (SNPs) have been associated with human disease/traits, the vast majority (>97%) of which occupy noncoding regions (74-75). For example, genome wide association studies in 35,000 schizophrenics identified 98 noncoding variants out of 108 total significant variants (Schizophrenia Working Group of the Psychiatric Genomics Consortium. Nature 511, 421-427 (2014)). The significance of these associations, however, has been difficult to assess, in part because we lack the tools to determine which variants alter functional elements. In recent years, there have been major advances in identifying molecular hallmarks that correlate with putative functional elements in the noncoding genome, such as epigenetic state, chromatin accessibility, transcription factor binding, and evolutionary conservation. Consortium efforts such as the Encyclopedia of DNA Elements (ENCODE) and the Roadmap Epigenomics project have produced a vast amount of genome-scale data that is widely used to predict regulatory function (73,76). However, these predictions largely bypass regions for which there are no hallmarks, and it is difficult to ascertain if these hallmarks play a correlative or truly causal role in function or phenotype (77,78). Experimental efforts to determine causality have employed episomal reporters that utilize preselected DNA fragments with expression serving as a proxy for function (26). These methods assess the DNA fragments in plasmids and are therefore decoupled from the local chromatin context and broader regulatory interactions, both of which are important characteristics of gene regulatory mechanisms. Thus, there is a need for systematic approaches to sift through noncoding variants and determine if and how they affect phenotypes within a native biological context. Genomic libraries are available to interrogate gene function, however, there remains a need for tools for unbiased interrogation of entire regions of genomic loci associated with specific phenotypes.

Citation or identification of any document in this application is not an admission that such document is available as prior art to the present invention.

SUMMARY OF THE INVENTION

CRISPR (Clustered Regularly Interspaced Short Palindromic Repeats) Cas9-mediated gene disruption has been widely used in generating loss-of-function mutations in diverse organisms including mammals (Cong et al., 2013; Mali et al., 2013) (reviewed in (Hsu et al., 2014)). Cas9-based knockout screens have been applied in identifying essential genes and genes involved in drug resistance in various cell lines (Koike-Yusa et al., 2014; Shalem et al., 2014; Wang et al., 2014).

The present inventors have in an unprecedented way adapted the use of the CRISPR/Cas system to interrogate the function of entire continuous genomic regions. Applicants describe here a high-throughput method using pooled CRISPR (Clustered regularly-interspaced short palindromic repeat)-Cas9 libraries to screen noncoding genomic loci to identify functional regions related to phenotype and gene regulation. Previous applications of CRISPR screens within the noncoding genome have focused on select elements, such as miRNAs, enhancers based on predictions derived from chromatin immunoprecipitation (ChIP) of functional hallmarks, or transcription factor binding, but they have not gone beyond these sequences (79-82). Here, Applicants have discovered and characterized regulatory elements of the BCL11A gene that are critical for its expression in erythroid lineage cells. Applicants also comprehensively assayed a total of 715 kb of sequence surrounding three different genes by performing unbiased mutagenesis to uncover functional elements relevant to cancer drug resistance. This approach requires no pre-existing knowledge of the region being screened and enables discovery of both gene-proximal and gene-distal functional elements.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below statements and embodiments, with any other statement and/or embodiments.

In one aspect, the present invention provides for a deep scanning mutagenesis library to interrogate phenotypic changes in a population of cells comprising a plurality of CRISPR-Cas system guide RNAs comprising guide sequences that are capable of targeting a plurality of genomic sequences within at least one continuous genomic region, wherein the guide RNAs target at least 100 genomic sequences comprising non-overlapping cleavage sites upstream of a PAM sequence for every 1000 base pairs within the continuous genomic region. Not being bound by a theory, providing at least 100 guide RNAs, wherein the guide RNAs target at least 100 genomic sequences comprising non-overlapping cleavage sites upstream of a PAM sequence for every 1000 base pairs within a continuous genomic region may result in mutagenesis saturation of the genomic region because cleavage sites for each guide RNA target may differ by about 10 basepairs. Not being bound by a theory, if each guide RNA results in cleavage of 10 basepairs of the 1000 basepairs, then the entire genomic region would be saturated. The library may allow substantial saturating mutagenesis. The library may allow at least 100%, preferably at least about 95%, more preferably at least about 90%, more preferably at least about 80%, more preferably at least about 70%, more preferably at least about 60%, and most preferably at least about 50%, with respect to saturating mutagenesis. The library may comprise guide RNAs wherein the adjacent genomic cleavage distance is between 4 bp and 20 bp. The distance between neighboring guide RNAs for the library may be less than 20 bp. The library may comprise guide RNAs wherein the target cleavage sites may be at least 10 base pairs apart. The library may comprise guide RNAs wherein the genomic cleavage sites may be at least 20 base pairs apart. The guide RNAs may target genomic sequences upstream of every PAM sequence within a continuous genomic region.

The frequency of off target sites for a guide RNA may be less than 500. Not being bound by a theory, off target sites may result in a phenotype associated with another genomic site other than the target site. Any phenotype determined for a sgRNA target site may be confirmed by using sgRNA's targeting the same site in a single experiment. Validation of a target site may also be performed by using a nickase Cas9, as described herein, and two sgRNAs targeting the genomic site of interest.

The PAM sequence may be specific to any Cas protein. Multiple Cas proteins are known that recognize different PAM sequences. Moreover, Cas9 proteins can be engineered to recognize unique PAM sequences. The present inventions allows the use of more than one Cas protein. Not being bound by a theory, the use of more than one Cas protein allows the use of more than one PAM sequence. Not being bound by a theory, there is about one PAM sequence for every 12 base pairs in a eukaryotic cell, thus the use of more than one PAM sequence allows total saturation of a continuous genomic region. The CRISPR-Cas system guide RNAs are selected based upon more than one PAM sequence specific to at least one Cas protein.

Expression of a gene of interest may be altered by said targeting by at least one guide RNA within the plurality of CRISPR-Cas system guide RNAs.

The at least one continuous genomic region may comprise up to the entire genome. The at least one continuous genomic region may comprise a functional element of the genome. The functional element may be within a coding gene, intronic region, promoter, or enhancer. The at least one continuous genomic region comprises at least 50 kb of genomic DNA. The at least one continuous genomic region may comprise a transcription factor binding site. The at least one continuous genomic region may comprise a region of DNase I hypersensitivity. The at least one continuous genomic region may comprise a transcription enhancer or repressor element. The at least one continuous genomic region may comprise a site enriched for an epigenetic signature. The at least one continuous genomic DNA region may comprise an epigenetic insulator. The at least one continuous genomic region may comprise two or more continuous genomic regions that physically interact. The epigenetic signature may be histone acetylation, histone methylation, histone ubiquitination, histone phosphorylation, DNA methylation, or a lack thereof.

The population of cells may be a population of eukaryotic cells or prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

Targeting may result in NHEJ of the continuous genomic region. Targeting may result in editing of the continuous genomic region. The targeting may be about 100 or more sequences. The targeting may be about 1,000 or more sequences. The targeting may be about 100,000 or more sequences.

The targeting may comprise introducing into each cell in the population of cells a vector system of one or more vectors comprising an engineered, non-naturally occurring CRISPR-Cas system comprising:

I. at least one Cas protein, and

II. one or more guide RNAs of the library, wherein components I and II may be on the same or on different vectors of the system, wherein components I and II are integrated into each cell, wherein the guide sequence targets a sequence within the continuous genomic region in each cell in the population of cells, wherein the at least one Cas protein is operably linked to a regulatory element, and wherein when transcribed, the guide RNA comprising the guide sequence directs sequence-specific binding of a CRISPR-Cas system to a target sequence in the continuous genomic region, inducing cleavage of the continuous genomic region by the Cas protein.

The one or more vectors may be plasmid vectors. The regulatory element may be an inducible promoter. The inducible promoter may be a doxycycline inducible promoter.

In another aspect, the present invention provides for a method of screening for genomic sites associated with a change in a phenotype comprising:

introducing the library of any of the preceding claims into a population of cells that are adapted to contain a Cas protein, wherein each cell of the population contains no more than one guide RNA;

sorting the cells into at least two groups based on the phenotype; and determining relative representation of the guide RNAs present in each group, whereby genomic sites associated with the change in phenotype are determined by the representation of guide RNAs present in each group.

The change in phenotype may be a change in expression of a gene of interest. The gene of interest may be upregulated, downregulated, or knocked out. The cells may be sorted into a high expression group and a low expression group.

In another aspect, the present invention provides for a method of screening for genomic sites associated with resistance to a chemical compound comprising:

introducing the library of any of the preceding claims into a population of cells that are adapted to contain a Cas protein, wherein each cell of the population contains no more than one guide RNA;

treating the population of cells with the chemical compound; and determining the representation of guide RNAs after treatment with the chemical compound at a later time point as compared to an early time point, whereby genomic sites associated with resistance to the chemical compound are determined by enrichment of guide RNAs.

The method according to any of the previous statements, may further comprise validation of alteration of the genomic sites targeted by a guide RNA. The validation of alteration of the genomic sites may be by whole genome sequencing. The method according to any of the previous statements, may further comprise determining indels associated with a change in phenotype or resistance to a chemical compound. Determining indels may be by DNA sequencing.

In another aspect, the present invention provides for a method for generating a deep scanning mutagenesis library to interrogate a genomic region of interest, the method comprising generating a plurality of CRISPR-Cas system guide RNAs comprising guide sequences that are capable of targeting a plurality of genomic sequences within said genomic region, wherein the guide RNAs target at least 100 genomic sequences comprising non-overlapping cleavage sites within said genomic region of interest upstream of a PAM sequence.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1*a*.

Schematic of the human BCL11A locus (transcription from right to left) with erythroid chromatin marks and trait-associated haplotype denoted. FIG. 1*b*. Ranked enhancers in primary human adult erythroid precursors by H3K27ac signal intensity, with super-enhancers shaded. FIG. 1*c*-FIG. 1*e*. Deletion of the human composite BCL11A enhancer in HUDEP-2 cells demonstrates its necessity for BCL11A expression normalize to GAPDH, repression of γ-globin mRNA, and repression of HbF. Error bars reflect standard error of the mean (SEM).

FIGS. 2A-211 show the tiled pooled in situ CRISPR-Cas9 BCL11A enhancer screen. FIG. 2*a*, Workflow of CRISPR-Cas9 enhancer screen showing library synthesis, delivery, and analysis. FIGS. 2***g* and 2*h*, sgRNA representation in plasmid pool and cells at conclusion of experiment (left), and in HbF-high and HbF-low pools (right), with dotted lines at x=y and x=8y.

FIGS. 3A-31 show the functional mapping of the BCL11A enhancer. FIG. 3*a*, Mapping sgRNA enrichment scores relative to genomic cleavage positions. Nontargeting sgRNAs pseudo-mapped with 5 bp spacing. FIG. 3*b*, Correlation between dropout and enrichment scores.

FIG. 4*a*-4*c*, Hidden Markov model segmentation of functional enhancer states. HbF enrichment scores shown throughout DHSs +55, +58, +62 by gray lines and circles with blue line representing smoothed enrichment score. DNase I sequencing from primary human erythroblasts. PhyloP (scale from −4.5 to 4.88) and PhastCons (from 0 to 1) estimates of evolutionary conservation among 100 vertebrates.

FIG. 5 shows the primate-specific functional core of the BCL11A enhancer. 200 bps at the functional core of DHSs +55, +58, and +62 defined by HMM states (red-active, green-repressive). HbF enrichment scores shown by gray lines and circles. HbF indel enrichment per nucleotide based on amplicon genomic sequencing of sorted cells exposed to either sgRNA-16 17 (top) or -1621 (bottom). Common SNPs (MAF>1%) shown with HbF-low allele in blue and HbF-high allele in red; no common SNPs present at +58 region. JASP AR motifs ($P<10^{-4}$) depicted in black except for those with allele-specific significance depicted by allelic color. Selected motifs annotated by TF based on known erythroid-specific function or genomic position. Motif LOGOs at key positions with motif scores $P<10^{-3}$ as described in text. Orthologous sequences from representative primates and nonprimates of distributed phylogeny listed. PhyloP (scale from 4.5 to 4.88) and PhastCons (from 0 to 1) estimates of evolutionary conservation among 100 vertebrates. FIG. 5 discloses SEQ ID NOS 620-639, respectively, in order of appearance.

FIG. 6*a*, Mapping sgRNA εy:mCherry enrichment scores to genomic cleavage positions. Nontargeting sgRNAs pseudo-mapped with 5 bp spacing. FIG. 6*b*, BCL11A expression in mouse erythroid clones with deletion or inversion of individual DHSs normalized to controls set as 1. FIG. 6*c*, HMM segmentation of active functional states at +62 ortholog. Enrichment scores shown as gray lines and circles. DNase I sequencing from mouse fetal liver erythroid precursors42. BCL11A expression determined by RT-qPCR displayed as a heat-map in 1 08 hemizygous +62 ortholog deletion clones listed from top to bottom by genomic position of deletion midpoint. PhyloP (scale from −3.3 to 2.1) and PhastCons (from 0 to 1) estimates of evolutionary conservation among 30 vertebrates. FIG. 6*d*, Transgenic human globin expression in E16.5 chimeric β-YAC I +62 deleted fetal livers. FIG. 6*e*-6*f*, BCL11A expression, B cell number, and transgenic human β-like globin expression in β-YAC I +62 deleted mice. *P<0.05 Error bars represent SEM.

FIG. 8*a*, HbF+ fraction in HUDEP-2 cells transduced in arrayed format with 24 sgRNAs from all 5 mapping categories with enrichment scores ranging from the highest to the lowest in the screen. FIG. 8*b*, β-like globin gene expression normalized to reference gene (GAPDH) in primary human erythroid precursors transduced with Cas9 and individual sgRNAs. Erythroid differentiation of primary human erythroid precursors evaluated by CD71 and CD235a surface markers, enucleation frequency (CD235a+ Hoescht 33342−), and morphology by May-Grunwald-Giemsa staining.

FIG. 9*a*, Topology of the Hidden Markov model (HMM) used to infer the three functional enhancer states (Active, Repressive, and Neutral) and based on Gaussian emission of sgRNA enrichment scores. All possible transitions between states are allowed. FIG. 9*b*, Frequency distribution of indels from HUDEP-2 cells exposed to Cas9 and individual sgRNAs, sorted into HbF-high and -low pools, and subjected to deep sequencing of the target site. Indels calculated on a per nucleotide basis throughout an amplicon surrounding the sgRNA-1617 and -1621 cleavage sites (dotted lines). An indel enrichment ratio was calculated by dividing normalized indel frequencies in high-HbF by low-HbF pool.

FIG. 10A discloses SEQ ID NOS 640-659, respectively, in order of appearance. FIG. 10B discloses SEQ ID NOS 660-680, respectively, in order of appearance. FIG. 10C discloses SEQ ID NOS 681-703, respectively, in order of appearance.

FIG. 11*a*, Schematic of the mouse BCL11A locus (transcription from left to right) with erythroid chromatin marks and regions of primary sequence homology to the human DHSs displayed. FIG. 11***j*, Enrichment scores of NGG sgRNAs between six biological replicates. FIG. 11*n*, Distribution of NGG and NAG PAM sgRNAs mapped to genomic cleavage position with vertical lines representing cleavage sites for sgRNAs mapped to plus and minus strands.

FIG. 12*a*, NGG sgRNA representation in plasmid pool and cells at conclusion of experiment (left), and in εy:mCherry-high and εy:mCherry-low pools (right), with dotted lines at x=y and x=8y. FIG. 12*b*, Quantile-quantile plots of sgRNA enrichment scores. FIG. 12*c*, Mapping sgRNA dropout scores of NGG sgRNAs relative to genomic cleavage positions and repetitive elements. Non-targeting sgRNAs pseudo-mapped with 5 bp spacing. FIG. 12*d*, Correlation between dropout and cy enrichment scores.

FIG. 13*a-c*, HMM segmentation of active functional states at +55 and +58 orthologs. Enrichment scores shown as gray lines and circles with blue line representing smoothened enrichment score. DNase I sequencing from mouse fetal liver erythroid precursors42. PhyloP (scale from −3.3 to 2.1) and PhastCons (from 0 to 1) estimates of evolutionary conservation among 30 vertebrates. 13d, Top, BCL11A expression determined by RT-qPCR displayed as a heatmap in 108 hemizygous m+62 ortholog deletion clones ordered by genomic position of deletion midpoint. Each bar demonstrates the genomic position of the deletion breakpoints and the associated color demonstrates the level of BCL11A expression. Bottom, BCL11A expression determined by RT-qPCR in 108 hemizygous m+62 ortholog deletion clones. Per nucleotide mean effect size was calculated as the mean fold change in BCL11A expression from all clones in which that nucleotide was deleted. Gray shading represents one s.d. The BCL11A expression data are shown with same x-axis as in FIG. 13*c* immediately above. e, 200 bps at the functional core of the +62 ortholog defined by HMM state. Enrichment scores shown as gray lines and circles with blue line representing smoothened enrichment score. JASP AR motifs (P<1 o-4) depicted with selected motifs annotated by TF name based on known erythroid-specific function or genomic position. Orthologous human sequences listed. PhyloP (scale from −3.3 to 2.1) and PhastCons (from 0 to 1) estimates of evolutionary conservation among 30 vertebrates. Individual hemizygous clones with indicated breakpoints were evaluated by BCL11A immunoblot (C-control). FIG. 13*e*, 200 bp at the functional 983 core of the m+62 ortholog defined by HMM state. Enrichment scores shown as gray lines and 984 circles with blue line representing smoothed enrichment score. JASPAR motifs (P<10-4) 985 depicted with selected motifs annotated by TF name based on known erythroid-specific function 986 or genomic position. Orthologous human sequences listed. PhyloP (scale from −3.3 to 2.1) and 987 PhastCons (from 0 to 1) estimates of evolutionary conservation among 30 vertebrates. Individual 988 numbered hemizygous deletion clones with indicated breakpoints were evaluated by BCL11A 989 immunoblot (C, control). Clones 9 and 10 encompass the entire m+62 ortholog. FIG. 13E discloses SEQ ID NOS 704 and 704-705, respectively, in order of appearance.

FIGS. 14A-14D shows the requirement of BCL11A erythroid enhancer during murine ontogeny. FIG. 14*a*, BCL11A expression determined by RT-qPCR in 108 hemizygous +62 ortholog deletion clones. Per nucleotide mean effect size was calculated as the mean fold change BCL11A expression of all clones in which that nucleotide was deleted. Gray shading represents one standard deviation. FIG. 14*b*, Progeny of heterozygous BCL11A+62 ortholog deletion intercrosses as compared to expected Mendelian ratio. FIG. 14*c*, BCL11A expression relative to GAPDH in E16.5 brain from various genotypes. Fraction of fetal liver comprised of B cell progenitors at E16.5 from various genotypes. Peripheral blood analysis from 4 week old mice to examine the frequency of various circulating hematopoietic lineages in BCL11a +62 ortholog deletion wild-type, heterozygous, and homozygous mice. 14d, BCL11A expression in β-YAC/+62 deletion mice (each symbol represents the mean expression from technical replicates from an individual mouse). *P<0.05, error bars represent s.e.m.

FIG. 15A-15D shows the requirement of Bcl11a erythroid enhancer during murine ontogeny. a, Progeny of heterozygous Bcl11a m+62 ortholog deletion intercrosses as compared to expected Mendelian ratio. b, Fraction of fetal liver comprised of B cell progenitors at E16.5 from various genotypes. c, Peripheral blood analysis from 4 week old mice to examine the frequency of various circulating hematopoietic lineages in Bcl11a m+62 ortholog deletion wild-type, heterozygous, and homozygous mice. d, BCL11A expression in β-YAC/+62 deletion mice (each symbol represents the mean expression from technical replicates from an individual mouse). *P<0.05, error bars represent s.e.m.

FIG. 17A-1711 shows functional mapping of the BCL11A enhancer. a, Mapping sgRNA HbF enrichment scores relative to genomic cleavage positions. Nontargeting sgRNAs pseudo-mapped with 5 bp spacing. b, Correlation between cellular dropout and HbF enrichment scores. c-e, BCL11A expression normalized to GAPDH, β-like globin expression, and HbF fraction in HUDEP-2 cells with deletion or inversion of individual DHSs. f-h, BCL11A expression normalized to GAPDH, β-like globin expression, and HbF fraction in primary human erythroid precursors transduced with Cas9 and individual sgRNAs. Error bars represent s.e.m.

FIG. 19 shows primate-specific BCL11A enhancer functional core. DHS h+58 functional core defined by maximal HbF enrichment score and Active HMM state. HbF enrichment scores shown by gray lines and circles. HbF indel enrichment per nucleotide based on amplicon genomic sequencing of sorted cells exposed to either sgRNA-1617 or -1621. No common SNPs (MAF>1%) present at this region. JASPAR motifs ($P<10^{-4}$) depicted in black with selected motifs annotated by TF based on known erythroid-specific function or genomic position. Gata1 motif LOGO at sgRNA-1617 cleavage position as described in text. Orthologous sequences listed from representative primates and nonprimates of distributed phylogeny. PhyloP (scale from −4.5 to 4.88) and PhastCons (from 0 to 1) estimates of evolutionary conservation among 100 vertebrates. FIG. 19 discloses SEQ ID NOS 620-639, respectively, in order of appearance.

FIG. 25A discloses SEQ ID NOS 640-659, respectively, in order of appearance. FIG. 25B discloses SEQ ID NOS 660-680, respectively, in order of appearance. FIG. 25C discloses SEQ ID NOS 681-703, respectively, in order of appearance.

FIG. 29 shows evaluation of the m+62 functional core. 200 bp at the functional core of the m+62 ortholog defined by HMM state. Enrichment scores shown as gray lines and circles with blue line representing smoothed enrichment score. JASPAR motifs ($P<10^{-4}$) depicted with selected motifs annotated by TF name based on known erythroid-specific function or genomic position. Orthologous human sequences listed. PhyloP (scale from −3.3 to 2.1) and PhastCons (from 0 to 1) estimates of evolutionary conservation among 30 vertebrates. Individual numbered hemizygous deletion clones with indicated breakpoints were evaluated by BCL11A immunoblot (C, control). Clones 9 and 10 encompass the entire m+62 ortholog. FIG. 29 discloses SEQ ID NOS 704 and 704-705, respectively, in order of appearance.

FIG. 30A-30D shows requirement of Bcl11a erythroid enhancer during murine ontogeny. a, Progeny of heterozygous Bcl11a m+62 ortholog deletion intercrosses as compared to expected Mendelian ratio. b, Fraction of fetal liver comprised of B cell progenitors at E16.5 from various genotypes. c, Peripheral blood analysis from 4 week old mice to examine the frequency of various circulating hematopoietic lineages in Bcl11a m+62 ortholog deletion wild-type, heterozygous, and homozygous mice. d, BCL11A expression in β-YAC/+62 deletion mice (each symbol represents the mean expression from technical replicates from an individual mouse). *$P<0.05$, error bars represent s.e.m.

FIGS. 34B, 34D, 34F and 34H disclose SEQ ID NOS 706-709, respectively.

FIG. 39A discloses SEQ ID NOS 710 and 710-718, respectively, in order of appearance.

FIG. 40 discloses SEQ ID NO: 719.

DETAILED DESCRIPTION OF THE INVENTION

Figure 1A:
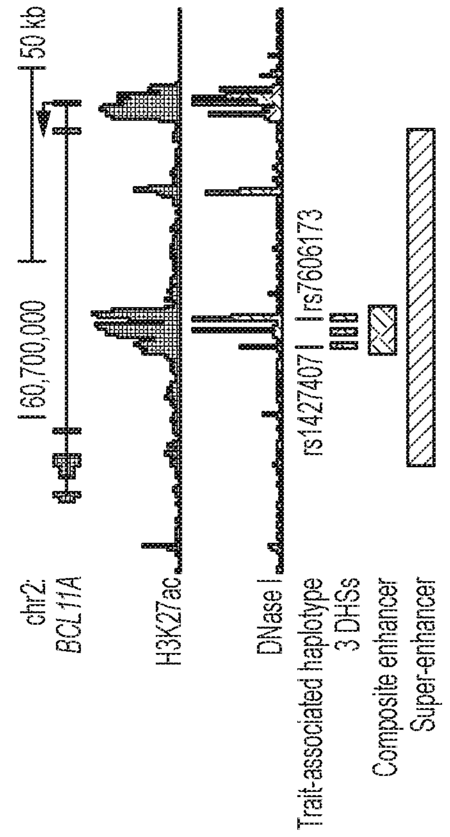
FIGS. 1A-1E show the human erythroid enhancer requirement for BCL11A expression and HbF repression.
Figure 1B:
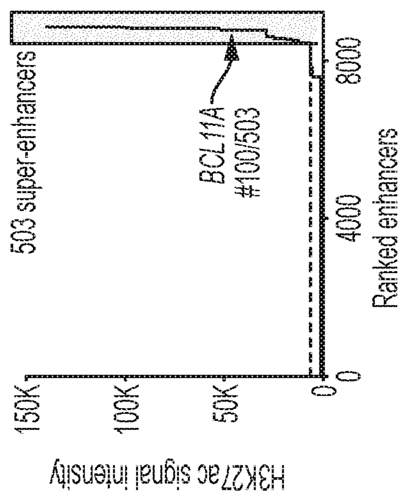

The methods and tools described herein relate to systematically interrogating genomic regions in order to allow the identification of relevant functional units which can be of interest for genome editing.

Accordingly, in one aspect the invention provides methods for interrogating a genomic region said method comprising generating a deep scanning mutagenesis library and interrogating the phenotypic changes within a population of cells modified by introduction of said library.

One aspect of the invention thus comprises a deep scanning mutagenesis library that may comprise a plurality of CRISPR-Cas system guide RNAs that may comprise guide sequences that are capable of targeting genomic sequences within at least one continuous genomic region. More particularly it is envisaged that the guide RNAs of the library should target a representative number of genomic sequences within the genomic region. For instance the guide RNAs should target at least 50, more particularly at least 100, genomic sequences within the envisaged genomic region.

The ability to target a genomic region is determined by the presence of a PAM (protospacer adjacent motif); that is, a short sequence recognized by the CRISPR complex. The precise sequence and length requirements for the PAM will differ depending on the CRISPR enzyme which will be used, but PAMs are typically 2-5 base pair sequences adjacent the protospacer (that is, the target sequence). Examples of PAM sequences known in the art are illustrated in the examples, and the skilled person will be able to identify further PAM sequences for use with a given CRISPR enzyme. In particular embodiments, the PAM sequence can be selected to be specific to at least one Cas protein. In alternative embodiments, the guide sequence RNAs can be selected based upon more than one PAM sequence specific to at least one Cas protein.

In particular embodiments, the library contains at least 100 genomic sequences comprising non-overlapping cleavage sites upstream of a PAM sequence for every 1000 base pairs within the genomic region. In particular embodiments the library comprises guide RNAs targeting genomic sequences upstream of every PAM sequence within the continuous genomic region.

This library comprises guide RNAs that target a genomic region of interest of an organism. In some embodiments of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus.

The methods and tools provided herein are particularly advantageous for interrogating a continuous genomic region. Such a continuous genomic region may comprise up to the entire genome, but particularly advantageous are methods wherein a functional element of the genome is interrogated, which typically encompasses a limited region of the genome, such as a region of 50-100 kb of genomic DNA. Of particular interest is the use of the methods for the interrogation of non-coding genomic regions, such as regions 5' and 3' of the coding region of a gene of interest. Indeed, the methods allow the identification of targets in the 5' and 3' region of a gene which may affect a phenotypic change only under particular circumstances or only for particular cells or tissues in an organism. In particular embodiments, the genomic region of interest comprises a transcription factor binding site, a region of DNase I hypersensitivity, a transcription enhancer or repressor element. In particular embodiments, the genomic region of interest comprises an epigenetic signature for a particular disease or disorder. Additionally or alternatively the genomic region of interest may comprise an epigenetic insulator. In particular embodiments, the guide RNA library is directed to a genomic region which comprises two or more continuous genomic regions that physically interact. In particular embodiments, the genomic region of interest comprises one or more sites susceptible to one or more of histone acetylation, histone methylation, histone ubiquitination, histone phosphorylation, DNA methylation, or a lack thereof.

Examples of genomic regions of interest include regions comprising or 5' or 3' of a gene associated with a signaling biochemical pathway, e.g., a signaling biochemical pathway-associated gene or polynucleotide. Examples of genomic regions include regions comprising or 5' or 3' of a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. The transcribed or translated products may be known or unknown, and may be at a normal or abnormal level. Sites of DNA hypersensitivity and transcription factor binding sites and epigenetic markers of a gene of interest can be determined by accessing publicly available data bases.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B 1 and EP 2 771 468 B 1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to U.S. provisional patent application Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

Zetsche et al., "Cpf1 Is a Single RNA-Guided Endonuclease of a Class 2 CRISPR-Cas System," Cell 163, 1-13 (Oct. 22, 2015).

Shmakov et al., "Discovery and Functional Characterization of Diverse Class 2 CRISPR-Cas Systems," Molecular Cell 60, 1-13 (Available online Oct. 22, 2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epi static gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via nonhomologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to use of the CRISPR-Cas system in plants, mention is made of the University of Arizona web site "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi: 10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6): 1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com).

The CRISPR/Cas system envisaged for use in the context of the invention can make use of any suitable CRISPR enzyme. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell.

The CRISPR/Cas system is used in the present invention to specifically target a multitude of sequences within the continuous genomic region of interest. The targeting typically comprises introducing into each cell of a population of cells a vector system of one or more vectors comprising an engineered, non-naturally occurring CRISPR-Cas system comprising: at least one Cas protein, and one or more guide RNAs of the guide RNA library described herein. In these methods, the Cas protein and the one or more guide RNAs may be on the same or on different vectors of the system and are integrated into each cell, whereby each guide sequence targets a sequence within the continuous genomic region in each cell in the population of cells. The Cas protein is operably linked to a regulatory element to ensure expression in said cell, more particularly a promoter suitable for expression in the cell of the cell population. In particular embodiments, the promoter is an inducible promoter, such as a doxycycline inducible promoter. When transcribed within the cells of the cell population, the guide RNA comprising the guide sequence directs sequence-specific binding of a CRISPR-Cas system to a target sequence in the continuous genomic region. Typically binding of the CRISPR-Cas system induces cleavage of the continuous genomic region by the Cas protein.

Accordingly, the library may be provided as one or more plasmid vectors suitable for introduction into a cell population. The cell population may be a population of eukaryotic cells or prokaryotic cells. In particular embodiments, the population is a population of embryonic stem (ES) cells, neuronal cells, epithelial cells, immune cells, endocrine cells, muscle cells, erythrocytes, lymphocytes, plant cells, or yeast cells.

The application provides methods of screening for genomic sites associated with a change in a phenotype. The change in phenotype can be detectable at one or more levels including at DNA, RNA, protein and/or functional level of the cell. In particular embodiments, the change is detectable as a change in gene expression in the cell. Indeed, where the genomic region of interest is selected as a region which is e.g. 5' or 3' of a gene of interest, the phenotypic change can be determined based on expression of the gene of interest.

The methods of screening for genomic sites associated with a change in phenotype comprise introducing the library of guide RNAs targeting the genomic region of interest as envisaged herein into a population of cells. Typically the cells are adapted to contain a Cas protein. However, in particular embodiments, the Cas protein may also be introduced simultaneously with the guide RNA. The introduction of the library into the cell population in the methods envisage herein is such that each cell of the population contains no more than one guide RNA. Hereafter, the cells are typically sorted based on the observed phenotype and the genomic sites associate with a change in phenotype are identified based on whether or not they give rise to a change in phenotype in the cells. Typically, the methods involve sorting the cells into at least two groups based on the phenotype and determining relative representation of the guide RNAs present in each group, and genomic sites associated with the change in phenotype are determined by the representation of guide RNAs present in each group. In particular embodiments, the different groups will correspond to different expression levels of the gene of interest, such as a high expression group and a low expression group.

The application similarly provides methods of screening for genomic sites associated with resistance to a chemical compound whereby the cells are contacted with the chemical compound and screened based on the phenotypic reaction to said compound. More particularly such methods may comprise introducing the library of CRISPR/Cas system guide RNAs envisaged herein into a population of cells (that are either adapted to contain a Cas protein or whereby the Cas protein is simultaneously introduced), treating the population of cells with the chemical compound; and determining the representation of guide RNAs after treatment with the chemical compound at a later time point as compared to an early time point. In these methods the genomic sites associated with resistance to the chemical compound are determined by enrichment of guide RNAs.

In particular embodiments, the methods may further comprising confirming the alteration of the genomic site in a cell by sequencing the region comprising the genomic site or by whole genome sequencing.

The follow up of the methods provided herein may comprise further validating the genomic site by specifically altering the genomic site and checking whether the phenotypic change is confirmed. Specific alteration of a genomic site can be achieved by different methods such as by CRISPR/Cas system mediated DNA targeting.

The application further relates to screening methods for identifying functional elements in the non-coding genome, more particularly using the libraries described herein, whereby the genomic region of interest is a region of the non-coding genome. Accordingly, the methods envisage targeting Cas9 to intergenic regions surrounding single genes. In particular embodiments the method will comprise generating a library which flanks 100 kb upstream and downstream of target gene with sgRNAs. Optionally Off-target scoring can be used to minimize sequences with many off-targets.

The application further relates to methods for screening for functional elements related to drug resistance using the saturating mutagenesis libraries and methods of the present invention.

Further embodiments described herein relate to therapeutic methods and tools involving genomic disruption of one or more functional regions of a gene, whereby the functional regions are located outside the coding region of the gene. More particularly the functional region is selected from a transcription factor binding site, a region of DNase I hypersensitivity, a transcription enhancer or repressor element. In particular embodiments, the genomic region of interest comprises an epigenetic signature for a particular disease or disorder. Additionally or alternatively the genomic region of interest may comprise an epigenetic insulator. In particular embodiments, the guide RNA library is directed to a genomic region which comprises two or more continuous genomic regions that physically interact. In particular embodiments, the genomic region of interest comprises one or more sites susceptible to one or more of histone acetylation, histone methylation, histone ubiquitination, histone phosphorylation, DNA methylation, or a lack thereof. The methods provided herein allow for targeting of a gene which is dependent on the epigenetic conditions of the DNA, i.e. dependent on the nature of the cell. These embodiments are of particular interest for situation wherein the systemic disruption of gene expression would be detrimental to the organism.

Functional elements may be further defined using chromosome conformation capture (3C) technology, which provides a tool to study the structural organization of a genomic region. 3C technology involves quantitative PCR-analysis of cross-linking frequencies between two given DNA restriction fragments, which gives a measure of their proximity in the nuclear space. Originally developed to analyze the conformation of chromosomes in yeast (Dekker et al., 2002), this technology has been adapted to investigate the relationship between gene expression and chromatin folding at intricate mammalian gene clusters (see, for example, Tolhuis et al., 2002; Palstra et al., 2003; and Drissen et al., 2004). Briefly, 3C technology involves in vivo formaldehyde cross-linking of cells and nuclear digestion of chromatin with a restriction enzyme, followed by ligation of DNA fragments that were cross-linked into one complex. Ligation products are then quantified by PCR. The PCR amplification step requires the knowledge of the sequence information for each of the DNA fragments that are to be amplified. Thus, 3C technology provides a measure of interaction frequencies between selected DNA fragments.

3C technology has been developed to identify interacting elements between selected parts of the genome and both techniques require the design of primers for all restriction fragments analyzed. Recently, new strategies have been developed that allow screening the entire genome in an unbiased manner for DNA segments that physically interact with a DNA fragment of choice. They are based on 3C technology and are collectively referred to as '4C technology'. 4C technology allows the screening of the entire genome in an unbiased manner for DNA segments that physically interact with a DNA fragment of choice. 4C technology depends on the selective ligation of cross-linked DNA fragments to a restriction fragment of choice (the 'bait'). In 4C technology, all the DNA fragments captured by the bait in the population of cells are simultaneously amplified via inverse PCR, using two bait-specific primers that amplify from circularized ligation products.

Essentially two strategies can be pursued to obtain these DNA circles. One strategy relies on the formation of circles during the standard 3C ligation step, i.e. while the DNA is still cross-linked (Zhao et al. (2006) *Nat Genet* 38, 1341-7). Here, circle formation requires both ends of the bait fragment to be ligated to both ends of a captured restriction fragment. If multiple restriction fragments are cross-linked together, circles may still be formed but they can contain more than one captured fragment and will therefore be larger. After de-crosslinking, captured DNA fragments are directly amplified by inverse PCR, using bait-specific primers facing outwards. Restriction enzymes recognizing four or six base pairs can be used in this set up. Four-cutters are preferred in this method though, since they produce smaller restriction fragments (average size 256 bp, versus ~4 kb for six-cutters) and linear PCR amplification of the captured DNA fragments requires that the average product size is small. Essentially, this method therefore comprises the steps of: (a) providing a sample of cross-linked DNA; (b) digesting the cross-linked DNA with a primary restriction enzyme—such as a 4 bp or a 5 bp cutter; (c) ligating the cross-linked nucleotide sequences; (d) reversing the cross linking and (e) amplifying the one or more nucleotide sequences of interest using at least two oligonucleotide primers, wherein each primer hybridizes to the DNA sequences that flank the nucleotide sequences of interest. The amplified sequence(s) can be hybridized to an array in order to assist in determining the frequency of interaction between the DNA sequences.

The second strategy advantageously relies on the formation of DNA circles after the chromatin has been de-cross-linked as is described in U.S. Pat. No. 8,642,295, incorporated herein by reference in its entirety. As described, 4C technology allows an unbiased genome-wide search for DNA fragments that interact with a locus of choice. Briefly, 3C analysis is performed as usual, but omitting the PCR step. The 3C template contains a target sequence or 'bait' (eg. a restriction fragment of choice that encompasses a selected gene) ligated to many different nucleotide sequences of interest (representing this gene's genomic environment). The template is cleaved by another, secondary, restriction enzyme and subsequently religated to form small DNA circles. Advantageously, the one or more nucleotide sequences of interest that are ligated to the target nucleotide sequence are amplified using at least two oligonucleotide primers, wherein at least one primer hybridises to the target sequence. The second primer preferably also hybridizes to the target sequence, such that both primers flank the nucleotide of interest. Alternatively, the second primer hybridizes to an adapter sequence that is ligated to the secondary restriction site, such that the two primers flank the nucleotide of interest. Typically, this yields a pattern of PCR fragments that is highly reproducible between independent amplification reactions and specific for a given tissue. HindIII and DpnII may be used as primary and secondary restriction enzymes. Next, the amplified fragments may be labeled and optionally hybridized to an array, typically against a control sample containing genomic DNA digested with the same combination of restriction enzymes. 3C technology has therefore been modified such that all nucleotide sequences of interest that interact with a target nucleotide sequence are amplified. Practically this means that instead of performing an amplification reaction with primers that are specific for the fragments that one wishes to analyze, an amplification is performed using oligonucleotide primer(s) which hybridize to a DNA sequence that flanks the nucleotide sequences of interest. Advantageously, 4C is not biased towards the design of PCR primers that are included in the PCR amplification step and can therefore be used to search the complete genome for interacting DNA elements.

Another strategy is to perform in situ HiC as described in Rao et al., A 3D Map of the Human Genome at Kilobase Resolution Reveals Principles of Chromatin Looping (Cell 159, 1665-1680, Dec. 18, 2014). Briefly, DNA is digested using a restriction enzyme, DNA-DNA proximity ligation is performed in intact nuclei, and the resulting ligation junctions are quantified with high-throughput sequencing in a genome-wide fashion.

These and Further embodiments described herein are based in part to the discovery of defined functional regions within the BCL11A 12 kb enhancer region that regulate expression of the BCL11A protein.

The functional regions identified for BCL11A are mapped to the previously identified three DNAse1-hypersensitive sites (DHS)+62, +58, and +55. Specifically, the functional regions are found at location 60725424 to 60725688 (+55 functional region); at location 60722238 to 60722466 (+58 functional region); at location 60718042 to 60718186 (+62 functional region) of the human chromosome 2. Genome editing disruption at these regions were functionally verified for expression of the BCL11A mRNA, expression of the BCL11A protein, and ultimately for the enrichment of fetal hemoglobin (HbF) produced. Small single guide RNA (sgRNA) sequences were design to target these functional regions using the CRISPR/Cas9 technology and the disruption results in at least a greater than or equal normalized enrichment of 0.259. In particular, targeting and disrupting the +58 functional region produced super enrichment whereas targeting and disrupting the +55 or +62 functional regions produced moderate enrichments. Therefore, targeting these three +62, +58, and +55 functional regions, alone or in combination, using specifically designed sgRNA and CRISPR technology, can provide therapeutic strategies that interfere with adult hemoglobin and induce fetal hemoglobin synthesis.

Definitions

For convenience, certain terms employed hereinafter are collected here. Unless defined otherwise, all technical and scientific terms used herein have the same meaning as commonly understood by one of ordinary skill in the art to which this invention belongs.

As used herein, the phrase "agent that binds the genomic DNA of the cell on chromosome 2 location 60725424 to 60725688 (+55 functional region), at location 60722238 to 60722466 (+58 functional region), and/or at location 60718042 to 60718186 (+62 functional region)" refers to small molecules, nucleic acids, proteins, peptides or oligonucleotides that can bind to the location within the genomic DNA (e.g., chromosome 2 location 60725424 to 60725688 (+55 functional region), at location 60722238 to 60722466 (+58 functional region), and/or at location 607 1 8042 to 607 1 8 1 86 (+62 functional region)) and represses mRNA or protein expression of BCL11A in a cell by at least 20% compared to the mRNA or protein level of BCL11A in a cell not treated with such an agent. In one embodiment, the agent "interferes with BCL11A interactions with BCL11A binding partners," as that phrase is used herein.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 1 0% lower, at least 20% lower, at least 3 0% lower, at least 40% lower, at least 50% lower, at least 60% lower, at least 70% lower, at least 80% lower, at least 90% lower, at least 1-fold lower, at least 2-fold lower, at least 5-fold lower, at least 1 0 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

As used herein, the term "genetic engineered cell" refers to a cell that comprises at least one genetic modification, as that term is used herein.

As used herein, the term "genetic modification" refers to a disruption at the genomic level resulting in a decrease in BCL11A expression or activity in a cell. Exemplary genetic modifications can include deletions, frame shift mutations, point mutations, exon removal, removal of one or more DNAse1-hypersensitive sites (DHS) (e.g. 1, 2, 3, 4 or more DHS regions), etc.

By "inhibits BCL11A expression" is meant that the amount of expression of BCL11A is at least 5% lower in a cell or cell population treated with a DNA-targeting endonuclease, than a comparable, control cell or cell population, wherein no DNA-targeting endonuclease is present. It is preferred that the percentage of BCL11A expression in a treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added.

By "inhibits BCL11A activity" is meant that the amount of functional activity of BCL11A is at least 5% lower in a cell or cell population treated with the methods described herein, than a comparable, control cell or population, wherein no DNA-targeting endonuclease is present. It is preferred that the percentage of BCL11A activity in a BCL11A -inhibitor treated population is at least 10% lower, at least 20% lower, at least 3 0% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no DNA-targeting endonuclease is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct.

In one embodiment, as used herein, the term "DNA targeting endonuclease" refers to an endonuclease that generates a double-stranded break at a desired position in the genome (e.g., chromosome 2 location 60716189-60728612) without producing undesired off-target double-stranded breaks. The DNA targeting endonuclease can be a naturally occurring endonuclease (e.g., a bacterial meganuclease) or it can be artificially generated (e.g., engineered meganucleases, TALENs, or ZFNs, among others).

In another embodiment, as used herein, the term "DNA targeting endonuclease" refers to an endonuclease that generates a single-stranded break or a "nick" or break on one strand of the DNA phosphate sugar backbone at a desired position in the genome (e.g., chromosome 2 location 60725424 to 60725688 (+55 functional region), at location 60722238 to 60722466 (+58 functional region), and/or at location 60718042 to 60718186 (+62 functional region)) without producing undesired off-target DNA stranded breaks.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the methods and compositions described herein can include such other forms of expression vectors, such as viral vectors (e.g., replication defective retroviruses, lentiviruses, adenoviruses and adeno-associated viruses), which serve equivalent functions.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the DNA-targeting endonuclease can be delivered by way of a vector comprising a regulatory sequence to direct synthesis of the DNAtargeting endonuclease at specific intervals, or over a specific time period. It will be appreciated by those skilled in the art that the design of the expression vector can depend on such factors as the choice of the target cell, the level of expression desired, and the like.

As used herein the term "cleaves" generally refers to the generation of a double-stranded break in the DNA genome at a desired location.

As used herein, the term "effective amount of a composition comprising at least a DNA-targeting endonuclease" refers to an amount of a DNA-targeting endonuclease that yields sufficient endonuclease activity to generate a double-stranded break in the desired location of the genome. In one embodiment, the effective amount of a DNA-targeting endonuclease generates a double-stranded break at the desired genetic locus in at least 20% of the cells in a population contacted with the composition (e.g., at least 30%, at least 40%, at least 50%, at least 60%, at least 70%, at least 80%, at least 90%, at least 95%, at least 99%, or even 100% of the cells in the population comprise a genetic modification produced by the DNAtargeting endonuclease composition).

As used herein the term "increasing the fetal hemoglobin levels" in a cell indicates that fetal hemoglobin is at least 5% higher in populations treated with an agent that disrupts BCL11A mRNA or protein expression (e.g., a DNA-targeting endonuclease) by binding to genomic DNA at chromosome 2 location 60716189-60728612, than in a comparable, control population, wherein no agent is present. It is preferred that the percentage of fetal hemoglobin expression in a population treated with such an agent that binds the genomic DNA at chromosome 2 location 60716189-60728612 is at least 1 0% higher, at least 20% higher, at least 3 0% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the agent that binds genomic DNA at chromosome 2 location 60716189 to 60728612. In one embodiment, any method known in the art can be used to measure an increase in fetal hemoglobin expression, e. g. Western Blot analysis of fetal y-globin protein and quantifying mRNA of fetal y-globin.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or reintroduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of hematopoietic progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not hematopoietic progenitor cells as defined by the terms herein.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of hematopoietic progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein, "prevention" or "preventing," when used in reference to a disease, disorder or symptoms thereof, refers to a reduction in the likelihood that an individual will develop a disease or disorder, e.g., a hemoglobinopathy. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 1 0% on a clinically accepted scale for that disease or disorder) or delayed (e.g., by days, weeks, months or years) symptoms is considered effective prevention.

In connection with contacting a cell with a DNA-targeting endonuclease to decrease BCL11A expression, the phrase "increasing fetal hemoglobin levels in a cell" indicates that fetal hemoglobin in a cell or population of cells is at least 5% higher in the cell or population of cells treated with the DNA-targeting endonuclease, than a comparable, control population, wherein no DNA-targeting endonuclease is present. It is preferred that the fetal hemoglobin expression in a DNA-targeting endonuclease treated cell is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated population. The term "control treated population" is used herein to describe a population of cells that has been treated with identical media, viral induction, nucleic acid sequences, temperature, confluency, flask size, pH, etc., with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a P-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassaemia (HbS/P+), or sickle beta-zero-thalassaemia (HbS/PO). In another preferred embodiment, the hemoglobinopathy is a β-thalassemia. As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the p-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

In one embodiment, the term "effective amount", as used herein, refers to the amount of a cell composition that is safe and sufficient to treat, lesson the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment. As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention.

The term "saturating mutagenesis" refers to cleavage at substantially every base pair (bp) within a target sequence.

The term "cleavage site" refers to any site that can be cleaved by a CRISPR enzyme after binding to a target sequence. In general, wild type *S. pyogenes* Cas9 (SpCas9) is known to make a blunt cut between the 17th and 18th bases in the target sequence (3 bp 5' of the PAM) (Nature Protocols November; 8(11):2281-308).

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Provided herein are nucleic acid molecules that target the three BCL11A enhancer functional regions, these three +62, +58, and +55, compositions comprising the nucleic acid molecules, and methods for increasing fetal hemoglobin levels in a cell by disrupting BCL11A expression at the genomic level. Also provided herein are methods and compositions relating to the treatment of hemoglobinopathies by reinduction of fetal hemoglobin levels. In particular, the nucleic acid molecules target the +62, +58, and/or the +55 enhancer functional regions.

Accordingly, in one embodiment, provided herein is a nucleic acid molecule comprising a nucleic acid sequence that is (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg19 human genome assembly, and wherein the nucleic acid sequence excludes the entire human chromosome 2 and also excludes the entire genomic DNA sequence on the human chromosome 2 from location 60716189 to 60728612.

In one embodiment, provided herein is a nucleic acid molecule consisting essentially of a nucleic acid sequence that is: (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60716189 to 60728612.

In one embodiment, this disclosure provides a vector comprising a nucleic acid sequence which is: (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60716189 to 60728612.

In one embodiment, this disclosure provides a vector consisting essentially a nucleic acid sequence which is: (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 60718186 (+62 functional region); wherein the human chromosome 2 is that according to UCSC Genome Browser hg 19 human genome assembly, and wherein the nucleic acid sequence excludes the entire human chromosome 2 and also excludes the genomic DNA sequence on the human chromosome 2 from location 60716189 to 60728612.

In one embodiment, this disclosure provides a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said cell, or its progeny, relative to said cell prior to said contacting, and wherein the human chromosome 2 is that according to UCSC Genome Browser hg 19 human genome assembly.

In one embodiment, this disclosure provides an isolated genetic engineered human cell having at least one genetic modification on chromosome 2 location 60725424 to 60725688 (+55 functional region), at location 60722238 to 60722466 (+58 functional region), and/or at location 6071 8042 to 60718186 (+62 functional region) according to a method described herein. In one embodiment, the isolated genetic engineered human cell has reduced or decreased mRNA or protein expression of BCL11A compared to a control cell that has no one genetic modification on chromosome 2 location 60716189-60728612.

In one embodiment, this disclosure provides a method for producing an isolated genetic engineered human cell having at least one genetic modification comprising contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, wherein the human chromosome 2 is that according to UCSC Genome Browser hg 19 human genome assembly.

In one embodiment, this disclosure provides a method for producing a progenitor cell having decreased BCL11A mRNA or protein expression, the method comprising contacting an isolated progenitor cell with a nucleic acid molecule described herein or a vector described herein.

In one embodiment, this disclosure provides a method for producing a progenitor cell having decreased BCL11A mRNA or BCL11A protein expression, the method comprising contacting an isolated progenitor cell with an agent that binds the human BCL11A enhancer functional regions located on chromosome 2 at location 60725424 to 60725688 (+55 functional region), at location 60722238 to 60722466 (+58 functional region), and/or at location 60718042 to 60718186 (+62 functional region), where the agent binds to (a) the plus or minus strand of the human chromosome 2 at location 60725424 to 60725688 (+55 functional region); (b) the plus or minus strand of the human chromosome 2 at location 60722238 to 60722466 (+58 functional region); or (c) the plus or minus strand of the human chromosome 2 at location 60718042 to 60718186 (+62 functional region); wherein the human chromosome 2 is that according to UCSC Genome Browser hg 19 human genome assembly, thereby reducing the mRNA or protein expression of BCL11A.

In one embodiment, this disclosure provides a method for increasing fetal hemoglobin levels in a mammal in need thereof, the method comprising the steps of contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 at location 60725424 to 60725688 (+55 functional region), at location 60722238 to 60722466 (+58 functional region), and/or at location 60718042 to 60718186 (+62 functional region), causing at least one genetic modification therein, whereby fetal hemoglobin expression is increased in said mammal, relative to expression prior to said contacting, and wherein the human chromosome 2 is that according to UCSC Genome Browser hg 19 human genome assembly.

In one embodiment, this disclosure provides a method for increasing fetal hemoglobin levels in a mammal in need thereof, the method comprising transplanting an isolated genetic engineered human cell described herein or a composition described herein into the mammal.

Another aspect described herein relates to a use of an isolated genetic engineered human cell having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the purpose of increasing the fetal hemoglobin levels in a mammal.

Another aspect described herein relates to a use of an isolated genetic engineered human cell having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the treatment a hemoglobinopathy in a mammal.

Another aspect described herein relates to a use of an isolated genetic engineered human cell having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the manufacturer of medicament for the treatment a hemoglobinopathy in a mammal whereby the fetal hemoglobin levels in a mammal is increased.

Another aspect described herein is a composition comprising isolated genetic engineered human cells having at least one genetic modification on chromosome 2 location 60725424 to 60725688 (+55 functional region), at location 60722238 to 60722466 (+58 functional region), and/or at location 60718042 to 60718186 (+62 functional region) according to a method described herein. In one embodiment, the composition further comprises a pharmaceutically acceptable carrier.

Another aspect described herein relates to a use of a composition comprising isolated genetic engineered human cells having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the purpose of increasing the fetal hemoglobin levels in a mammal.

Another aspect described herein relates to a use of a composition comprising isolated genetic engineered human cells having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the treatment a hemoglobinopathy in a mammal.

Another aspect described herein relates to a use of a composition comprising isolated genetic engineered human cells having at least one genetic modification on chromosome 2 location 60725424 to 60725688 (+55 functional region), at location 60722238 to 60722466 (+58 functional region), and/or at location 60718042 to 60718186 (+62 functional region) according to a method described herein for the manufacturer of medicament for the treatment a hemoglobinopathy in a mammal whereby the fetal hemoglobin levels in a mammal is increased.

Another aspect described herein is a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), at location 60722238 to 60722466 (+58 functional region), and/or at location 60718042 to 60718186 (+62 functional region) causing at least one genetic modification therein. In one embodiment, the composition further comprises a pharmaceutically acceptable carrier.

Another aspect described herein relates to a use of a composition a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), at location 60722238 to 60722466 (+58 functional region), and/or at location 60718042 to 60718186 (+62 functional region) causing at least one genetic modification therein for the purpose of increasing the fetal hemoglobin levels in a mammal.

Another aspect described herein relates to a use of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), at location 6072223 8 to 60722466 (+58 functional region), and/or at location 60718042 to 60718186 (+62 functional region) causing at least one genetic modification therein for the treatment a hemoglobinopathy in a mammal.

Another aspect described herein relates to a use of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of a human cell on chromosome 2 location 60725424 to 60725688 (+55 functional region), at location 6072223 8 to 60722466 (+58 functional region), and/or at location 60718042 to 60718186 (+62 functional region) causing at least one genetic modification therein for the manufacturer of medicament for the treatment a hemoglobinopathy in a mammal whereby the fetal hemoglobin levels in a mammal is increased.

In one embodiment, provided herein is a use of a nucleic acid molecule comprising a nucleic acid sequence that is: (a) complementary to the plus or minus strand of the human chromosome 2 at location 60725424 to 60725688 (+55 functional region); (b) complementary to the plus or minus strand of the human chromosome 2 at location 60722238 to 60722466 (+58 functional region); or (c) complementary to the plus or minus strand of the human chromosome 2 at location 60718042 to 6071 8186 (+62 functional region), wherein the human chromosome 2 is that according to UCSC Genome Browser hg 19 human genome assembly, and wherein the nucleic acid sequence excludes the entire human chromosome 2 and also excludes the entire genomic DNA sequence on the human chromosome 2 from location 60,716,189 to 60,728,612, for increasing the fetal hemoglobin in a mammal or for the treatment of a hemoglobinopathy in the mammal or for reducing the mRNA or expression of BCL11A, wherein the mRNA or protein expression of BCL11A is reduced.

In one embodiment, provided herein is a use of an effective amount of a composition comprising a nucleic acid molecule described herein or a vector described herein, together with at least a DNA-targeting endonuclease or a vector carrying the coding sequence of a DNA-targeting endonuclease for increasing the fetal hemoglobin in a mammal or for the treatment of a hemoglobinopathy in the mammal or for reducing the mRNA or expression of BCL11A, whereby the DNA-targeting endonuclease cleaves the genomic DNA of a human cell on chromosome 2 location 60725424 to 60725688 (+55 functional region), at location 60722238 to 60722466 (+58 functional region), and/or at location 60718042 to 60718186 (+62 functional region) causing at least one genetic modification therein.

In one embodiment, provided herein is a use of an effective amount of a composition comprising a nucleic acid molecule described herein or a vector described herein, together with at least a DNA-targeting enzyme or a vector carrying the coding sequence of a DNA-targeting enzyme for increasing the fetal hemoglobin in a mammal or for the treatment of a hemoglobinopathy in the mammal or for reducing the mRNA or expression of BCL11A, wherein the DNA-targeting enzyme produces at least one epigenetic modification in the genomic DNA of a human cell on chromosome 2, thereby affecting the mRNA or expression of BCL11A. In one embodiment, the at least one epigenetic modification is at location 60725424 to 60725688 (+55 functional region), at location 60722238 to 60722466 (+58 functional region), and/or at location 60718042 to 60718186 (+62 functional region). In another embodiment, the effect of the one epigenetic modification is reducing the mRNA or protein expression of BCL11A. In one embodiment, the at least one epigenetic modification in the genomic DNA of the cell on chromosome 2 indirectly or directly affects the location 60725424 to 60725688 (+55 functional region), at location 60722238 to 60722466 (+58 functional region), and/or at location 60718042 to 60718186 (+62 functional region) of chromosome 2.

In one embodiment, provided herein is a use of any isolated cells described herein for increasing the fetal hemoglobin in a mammal or for the treatment of a hemoglobinopathy in the mammal.

In one embodiment, provided herein is a use of a composition comprising isolated genetic engineered human cells for increasing the fetal hemoglobin in a mammal or for the treatment of a hemoglobinopathy in the mammal, wherein the cells have at least one genetic modification on chromosome 2 location 60725424 to 60725688 (+55 functional region), at location 60722238 to 60722466 (+58 functional region), and/or at location 60718042 to 60718186 (+62 functional region) (according to UCSC Genome Browser hg 1 9 human genome assembly) made by the process of contacting the cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing at least one genetic modification therein.

In one embodiment, provided herein is a use of a composition comprising isolated genetic engineered human cells for increasing the fetal hemoglobin in a mammal or for the treatment of a hemoglobinopathy in the mammal, wherein the cells have at least one epigenetic modification on chromosome 2. In one embodiment, the at least one epigenetic modification on chromosome 2 is at location 60725424 to 60725688 (+55 functional region), at location 60722238 to 60722466 (+58 functional region), and/or at location 60718042 to 60718186 (+62 functional region) (according to UCSC Genome Browser hg 19 human genome assembly). In another embodiment, at least one epigenetic modification on chromosome 2 is made by the process of contacting the cells with an effective amount of a composition comprising a nucleic acid molecule described herein or a vector described herein, together with at least a DNA-targeting enzyme or a vector carrying the coding sequence of a DNA-targeting enzyme whereby the DNA-targeting enzyme produces at least one epigenetic modification in the genomic DNA of the cell on chromosome 2 which affects the location 60725424 to 60725688 (+55 functional region), at location 60722238 to 60722466 (+58 functional region), and/or at location 60718042 to 60718186 (+62 functional region) (according to UCSC Genome Browser hg 19 human genome assembly) causing therein.

In one embodiment, provided herein is a use of any isolated cells described herein or any one of the compositions described herein for the manufacture of a medicament for increasing the fetal hemoglobin in a mammal in need thereof or for the treatment of a hemoglobinopathy in a mammal.

Another aspect described herein is a method of increasing fetal hemoglobin levels in a cell, the method comprising the steps of: contacting an isolated cell with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in said cell, or its progeny, relative to the cell prior to the contacting.

Another aspect described herein is a method for increasing fetal hemoglobin levels in a mammal in need thereof, the method comprising the steps of: contacting an isolated hematopoietic progenitor cell in said mammal with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in said mammal, relative to expression prior to said contacting.

Another aspect described herein is a method for increasing fetal hemoglobin levels in a mammal in need thereof, the method comprising transplanting an isolated genetic engineered human cell having at least one genetic modification on chromosome 2 location 60725424 to 60725688 (+55 functional region), at location 6072223 8 to 60722466 (+58 functional region), and/or at location 60718042 to 60718186 (+62 functional region) into the mammal.

In one embodiment, this disclosure provides a method for increasing fetal hemoglobin levels in a mammal in need thereof, the method comprising the steps of: providing an isolated population of hematopoietic progenitor cells or hematopoietic stem cells from the mammal in ex vivo, and contacting the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of: isolating a population of hematopoietic progenitor cells or hematopoietic stem cells from the mammal, and contacting in ex vivo the population of hematopoietic progenitor or stem cells with an effective amount of a composition comprising a nucleic acid molecule described herein or a vector described herein, together with at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of: (a) providing isolating a population of hematopoietic progenitor cells or hematopoietic stem cells from the mammal and (b) deleting/adding/substituting the genomic DNA of the cells on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method for increasing fetal hemoglobin levels in a mammal in need thereof, the method comprising the steps of isolating a population of hematopoietic progenitor cells or hematopoietic stem cells from the mammal and ex vivo deleting the genomic DNA of the cells on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting.

In one embodiment, this disclosure provides a method of treatment of a hemoglobinopathy in a mammal comprising the steps of: (a) providing hematopoietic progenitor cells or hematopoietic stem cells or iPSCs; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering of the step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) contacting the cells ex vivo or in vitro with an effective amount of a composition comprising at least a DNA-targeting endonuclease or a vector carrying the coding sequence of a DNA-targeting endonuclease whereby the DNA-targeting endonuclease cleaves the genomic DNA of the cell on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering of the step (b) into the mammal.

In one embodiment, this disclosure provides a method of treatment of a hemoglobinopathy in a mammal comprising the steps of: (a) providing hematopoietic progenitor cells or hematopoietic stem cells or iPSCs; (b) ex vivo deleting the genomic DNA of the cells on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering the cells of step (b) into the mammal.

In one embodiment, this disclosure provides a method of treatment of a hemoglobinopathy in a mammal comprising the steps of: (a) isolating hematopoietic progenitor cells or hematopoietic stem cells from the mammal; (b) ex vivo deleting the genomic DNA of the cells on chromosome 2 location 60725424 to 60725688 (+55 functional region), at location 60722238 to 60722466 (+58 functional region), and/or at location 60718042 to 60718186 (+62 functional region) causing at least one genetic modification therein, whereby fetal hemoglobin expression is increased in the mammal, relative to expression prior to the contacting; and (c) administering of the step (b) into the mammal.

In one embodiment, this disclosure provides a method of treatment of a hemoglobinopathy in a mammal (e.g. a human) comprising introducing a composition described herein comprising isolated genetic engineered cells having at least one genetic modification on chromosome 2 location 60725424 to 60725688 (+55 functional region), at location 60722238 to 60722466 (+58 functional region), and/or at location 60718042 to 60718186 (+62 functional region) whereby fetal hemoglobin expression is increased in the mammal.

In one embodiment, this disclosure provides a method of treatment of a hemoglobinopathy in a mammal (e.g. a human) comprising increasing fetal hemoglobin expression in the mammal by method described herein.

In one embodiment, this disclosure provides a composition comprising isolated genetic engineered human cells described herein.

In one embodiment of this aspect and all other aspects described herein, the nucleic acid sequence is excludes the entire BCL11A enhancer functional regions.

In one embodiment of this aspect and all other aspects described herein, the nucleic acid sequence is excludes the entire SEQ. ID. NOS: 136, 137, and/or 138 identified in Table 8.

In one embodiment of this aspect and all other aspects described herein, the nucleic acid sequence is short and is greater than or equal to 13 base pair (bp). In other embodiments, the nucleic acid sequence is short and is greater than or equal to 15 bp, is greater than or equal to 16 bp, is greater than or equal to 17 bp, is greater than or equal to 18 bp, is greater than or equal to 19 bp, is greater than or equal to 20 bp, is greater than or equal to 21 bp, is greater than or equal to 22 bp, is greater than or equal to 23 bp, is greater than or equal to 24 bp, is greater than or equal to 25 bp, is greater than or equal to 26 bp, is greater than or equal to 27 bp, or is greater than or equal to 28 bp.

In one embodiment of this aspect and all other aspects described herein, the nucleic acid sequence is about 13-30 bp. In other embodiments, the nucleic acid sequence is about 13-20 bp, 13-21 bp, 13-22 bp, 13-23 bp, 13-24 bp, 13-25 bp, 13-26 bp, 13-27 bp, 13-28 bp, 13-29 bp, 14-20 bp, 14-21 bp, 14-22 bp, 14-23 bp, 14-24 bp, 14-25 bp, 14-26 bp, 14-27 bp, 14-28 bp, 14-29 bp, 15-20 bp, 15-21 bp, 15-22 bp, 15-23 bp, 15-24 bp, 15-25 bp, 15-26 bp, 15-27 bp, 15-28 bp, 15-29 bp, 16-20 bp, 16-21 bp, 16-22 bp, 16-23 bp, 16-24 bp, 16-25 bp, 16-26 bp, 16-27 bp, 16-28 bp, 16-29 bp, 17-20 bp, 17-21 bp, 17-22 bp, 17-23 bp, 17-24 bp, 17-25 bp, 17-26 bp, 17-27 bp, 17-28 bp, 17-29 bp, 18-20 bp, 18-21 bp, 18-22 bp, 18-23 bp, 18-24 bp, 18-25 bp, 18-26 bp, 18-27 bp, 18-28 bp, 18-29 bp, 19-21 bp, 19-22 bp, 19-23 bp, 19-24 bp, 19-25 bp, 19-26 bp, 19-27 bp, 19-28 bp, 19-29 bp, 20-22 bp, 20-23 bp, 20-24 bp, 20-25 bp, 20-26 bp, 20-27 bp, 20-28 bp, 20-29 bp, 21-23 bp, 21-24 bp, 21-25 bp, 21-26 bp, 21-27 bp, 21-28 bp, 21-29 bp, 22-24 bp, 22-25 bp, 22-26 bp, 22-27 bp, 22-28 bp, 22-29 bp, 23-25 bp, 23-26 bp, 23-27 bp, 23-28 bp, 23-29 bp, 24-26 bp, 24-27 bp, 24-28 bp, 24-29 bp, 25-27 bp, 25-28 bp, 25-29 bp, 26-28 bp, 26-29 bp, 27-29 bp, 14-30 bp, 15-30 bp, 16-30 bp, 17-30 bp, 18-30 bp, 19-30 bp, 20-30 bp, 21-30 bp, 22-30 bp, 23-30 bp, 24-30 bp, 25-30 bp, 26-30 bp, 27-30 bp, or 28-30 bp.

In one embodiment of this aspect and all other aspects described herein, the nucleic acid sequence is about 20 bp. In other embodiments, the nucleic acid sequence is about 13 bp, is about 14 bp, is about 15 bp, is about 16 bp, is about 17 bp, is about 18 bp, is about 19 bp, is about 20 bp, is about 21 bp, is about 22 bp, is about 23 bp, is about 24 bp, is about 25 bp, is about 26 bp, is about 27 bp, is about 28 bp, is about 29 bp, or is about 30 bp.

In one embodiment of this aspect and all other aspects described herein, the nucleic acid sequence comprises a sequence selected from the group consisting of SEQ ID NOS: 1-94.

In one embodiment of this aspect and all other aspects described herein, the nucleic acid sequence consists essentially of a sequence selected from the group consisting of SEQ ID NOS: 1-94.

In one embodiment of this aspect and all other aspects described herein, the nucleic acid sequence is a sequence selected from the group consisting of SEQ ID NOS: 1-94.

In one embodiment of this aspect and all other aspects described herein, the nucleic acid sequence consists of a sequence selected from the group consisting of SEQ ID NOS: 1-94.

In one embodiment of this aspect and all other aspects described herein, the nucleic acid sequence further comprising a trans-activating CRISPR RNA (tracrRNA) sequence.

In one embodiment of this aspect and all other aspects described herein, the nucleic acid molecule is a single guide RNA (sgRNA).

In one embodiment of this aspect and all other aspects described herein, the nucleic acid molecule comprises a vector.

In one embodiment of this aspect and all other aspects described herein, the vector is a viral vector, such as a lentiviral vector.

In one embodiment of this aspect and all other aspects described herein, the vector is a sgRNA expression vector.

In one embodiment of this aspect and all other aspects described herein, the method further comprising contacting the same isolated progenitor cell with at least a DNA-targeting endonuclease or a vector carrying the coding sequence of a DNA-targeting endonuclease.

In one embodiment of this aspect and all other aspects described herein, the at least a DNAtargeting endonuclease is a Cas (CRISPR-associated) protein.

In one embodiment of this aspect and all other aspects described herein, the Cas protein is Cas9.

In one embodiment of this aspect and all other aspects described herein, the isolated progenitor cell or isolated cell is a hematopoietic progenitor cell or a hematopoietic stem cell.

In one embodiment of this aspect and all other aspects described herein, the hematopoietic progenitor is a cell of the erythroid lineage.

In one embodiment of this aspect and all other aspects described herein, the isolated progenitor cell or isolated cell is an induced pluripotent stem cell.

In one embodiment of this aspect and all other aspects described herein, the isolated progenitor cell or isolated cell is contacted ex vivo or in vitro.

In one embodiment of this aspect and all other aspects described herein, the contacted progenitor cell or contacted cell acquires at least one genetic modification.

In one embodiment of this aspect and all other aspects described herein, the at least one genetic modification is a deletion, insertion or substitution of the nucleic acid sequence.

In one embodiment of this aspect and all other aspects described herein, the least one genetic modification is located between chromosome 2 location 60725424 to 60725688 (+55 functional region), at location 60722238 to 60722466 (+58 functional region), and/or at location 60718042 to 60718186 (+62 functional region).

In one embodiment of this aspect and all other aspects described herein, the contacted progenitor cell or contacted cell acquires at least one epigenetic modification in the BCL11A enhancer functional region.

In one embodiment of this aspect and all other aspects described herein, the at least one epigenetic modification is selected from the group consisting of alteration of DNA methylation, histone tail modification, histone subunit composition and nucleosome positioning.

In one embodiment of this aspect and all other aspects described herein, the at least one epigenetic modification is located between chromosome 2 location 60725424 to 60725688 (+55 functional region), at location 60722238 to 60722466 (+58 functional region), and/or at location 60718042 to 60718186 (+62 functional region).

In one embodiment of this aspect and all other aspects described herein, the isolated cell or isolated population of cells is/are human cell(s).

In one embodiment of this aspect and all other aspects described herein, the isolated cell or isolated population of cells is/are progenitor cell(s).

In one embodiment of this aspect and all other aspects described herein, the human cell is a hematopoietic progenitor cell.

In one embodiment of this aspect and all other aspects described herein, the human cell is an induced pluripotent stem cell.

In one embodiment of this aspect and all other aspects described herein, the induced pluripotent stem cell is hematopoietic progenitor cell.

In one embodiment of this aspect and all other aspects described herein, the hematopoietic progenitor is a cell of the erythroid lineage.

In one embodiment of this aspect and all other aspects described herein, the hematopoietic progenitor cell or isolated is contacted ex vivo or in vitro or in vivo.

In one embodiment of this aspect and all other aspects described herein, the at least one genetic modification is a deletion.

In another embodiment of this aspect and all other aspects described herein, the nucleic acid molecule consists essentially of one or more of the sequences described in Table 7 or SEQ ID NOS: 1-94.

In further embodiment of any treatment method, the method comprises chemotherapy and/or radiation therapy to remove or reduced the endogenous hematopoietic progenitor or stem cells in the mammal.

In one embodiment of any method, the contacted cells having at least one genetic modification can be cryopreserved and stored until the cells are needed for administration into a mammal.

In one embodiment of any described method, the hematopoietic progenitor or stem cells or isolated cells can be substituted with an iPSCs described herein.

In one embodiment of any described method, the hematopoietic progenitor or stem cells or iPSCs or isolated cells are autologous to the mammal, meaning the cells are derived from the same mammal. In another of the embodiments of the described method, the hematopoietic progenitor or stem cells or iPSCs or isolated cells are non-autologous to the mammal, meaning the cells are not derived from the same mammal, but another mammal of the same species. For example, the mammal is a human.

In one embodiment of any treatment method, the method further comprises selecting a mammal in need of increased fetal hemoglobin expression.

In one embodiment of any treatment method, the method further comprises selecting a mammal in need of treatment of a hemoglobinopathy.

In any embodiment of any treatment method described, the hemoglobinopathy is alpha-hemoglobinopathy. In any embodiment of any treatment method described, the hemoglobinopathy is β-thalassemia.

In any embodiment of any treatment method described, the hemoglobinopathy is sickle cell anemia.

The present invention advantageously provides pooled CRISPR-Cas9 guide RNA libraries to perform in situ saturating mutagenesis. Detailed mapping will inform therapeutic genome editing. The present invention also provides for promoter or enhancer "bashing" at the endogenous location, as opposed to ectopic heterologous enhancer assays.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

The inventors have discovered and characterized regulatory elements of the BCL11A gene that are critical for its expression in erythroid lineage cells. Common genetic variants within these sequences are associated with fetal hemoglobin level and beta-globin disorder severity. These sequences comprise distal regulatory elements with an enhancer chromatin signature, possessing accessible chromatin, active histone marks, and occupancy by erythroid transcription factors. These elements interact with the BCL11A promoter and promote gene expression in erythroid cells but not other lineages that express BCL11A such as B lymphocytes. These regulatory elements can be targeted for therapeutic purposes to achieve BCL11A inhibition and fetal hemoglobin reinduction. This can be achieved by mechanisms not limited to genome editing, nucleic acid or protein binding, and epigenetic modification. Advantages of this method include: disruption of a physiologic regulator of fetal hemoglobin level resulting in increased gamma-globin production and reduced beta-globin production; minimal effect on overall globin output or on red blood cell production or function; limitation of impact on cells outside of the erythroid lineage thus reducing potential toxicity.

Enhancers are classically described as distal genetic elements able to positively regulate gene expression in an orientation-independent manner in ectopic heterologous gain-of-function expression experiments (1). These elements coordinate when, where, and how genes are expressed. Enhancer sequences bind transcription factors and chromatin regulators and are correlated with specific chromatin features including reduced DNA methylation, characteristic histone modifications, heightened chromatin accessibility, long-range promoter interactions, and bidirectional transcription. Recent chromatin mapping has demonstrated the abundance of distal regulatory elements bearing an enhancer chromatin signature (2-8).

The biologic importance of enhancers is underscored by gene expression studies showing the predictive power of enhancer profile on lineage-specific programs (9-12). Highly marked and clustered enhancers (e.g. so-called strong enhancers, stretch enhancers, or super-enhancers) are particularly indicative of cellular identity and may help to infer lineage-specific regulatory factors (13-15). Genome-wide association studies reveal enrichment of trait-associated variants in sequences bearing lineage-restricted enhancer signatures (7,13,16-19. Enhancers display signs of evolutionary constraint as well as heightened turnover with evidence of positive selection (20-25).

Despite their importance, enhancers are typically defined by criteria unrelated to in situ functional requirement. Advances in putative enhancer mapping, as well as of large-scale oligonucleotide synthesis, facilitate enhancer reporter assays on a massively parallel scale, allowing a systematic evaluation of the functional significance of enhancer sequences (26-30). Nonetheless, ectopic heterologous enhancer assays cannot address the necessity of an element in its native chromatin environment. The growing appreciation of the nonrandom distribution of distal elements both with respect to the linear genome (for example, into super-enhancer clusters) and within the three-dimensional nuclear environment emphasizes the importance of studying enhancers by perturbing their endogenous condition (15,31).

Insightful observations have been made by mutagenizing enhancers using traditional molecular genetic approaches (32,33). However the low throughput of these classical methods constrains their widespread application. Furthermore the elevated turnover of many enhancer sequences between species may limit the ability to derive conclusions from nonhuman organisms regarding human gene regulation. Advances in genome editing technology make practical the facile modification of the human genome (34,35). High throughput clustered regularly interspaced palindromic repeat (CRISPR)-Cas9 studies have revealed novel genes required for various biologic processes (36-41). Genome editing is likewise suitable for the study of noncoding genetic elements such as enhancers, although these experiments have previously been conducted at low-throughput (42-44).

Materials and Methods

Design and Synthesis of Human and Mouse Lentiviral sgRNA Libraries.

Every 20-mer sequence upstream of an NGG or NAG PAM sequence on the sense or anti-sense strand was identified for both the human and mouse orthologous +55, +58, and +62 DNase hypersensitive site (DHS) as well as BCL11A/BCL11a exon 2. Relative to the human hg 19 reference genome, a reference was used with the following substitutions to approximate a common low-HbF associated haplotype: rs1427407-G, rs1896293-T, rs6706648-T, rs6738440-G, rs7606173-C. Each of the sgRNA oligos were synthesized as previously described (37,41,64) and cloned using a Gibson Assembly master mix (New England Biolabs) into lentiGuide-Puro (Addgene plasmid ID 52963) BsmBI digested, PCR purified, and dephosphorylated. Gibson Assembly products were transformed to electrocompetent E. cloni cells (Lucigen). Sufficient colonies were isolated to ensure 90X library coverage for both human and mouse libraries. Plasmid libraries were deep sequenced (described below) to confirm representation.

To make lentivirus, HEK293T cells were cultured with Dulbecco's Modified Eagle's Medium (DMEM) (Life Technologies) supplemented with 10% fetal bovine serum (FBS) (Omega Scientific) and 2% penicillin-streptomycin (Life Technologies) in 15 cm tissue culture treated petri dishes. HEK293T were transfected at 80% confluence in 12 mL of media with 13.3 μg psPAX2, 6.7 μg VSV-G, and 20 μg of the lentiviral construct plasmid of interest using 1 80 1-1 g of branched polyethylenimine (Sigma). Medium was changed 16-24 hours after transfection. Lentiviral supernatant was collected at 48 and 72 hours posttransfection and subsequently concentrated by ultracentrifugation (24,000 rpm for 2 hours at 4° C. with Beckman Coulter SW 32 Ti rotor).

Tiled Pooled CRISPR-Cas9 Screen for In Situ Functional Mapping the Human BCL11A Erythroid Enhancer.

HUDEP clone 2 (HUDEP-2) was utilized as previously described by from Nakamura and colleagues (49). HUDEP-2 cells were expanded in StemSpan SFEM (Stem Cell Technologies) supplemented with $10^{-6}$ M dexamethasone (Sigma), 100 ng/mL human stem cell factor (SCF) (R&D), 3 IU/mL erythropoietin (Amgen), 1% L-glutamine (Life Technologies), and 2% penicillin/streptomycin (Life Technologies). 1 μg/mL doxycycline (Sigma) was included in the culture to induce expression of the human papilloma virus type 16 E6/E7 genes (49). HUDEP-2 cells were differentiated in Iscove's Modified Dulbecco's Medium (IMDM) supplemented with 330 μg/mL halo-transferrin (Sigma), 10 μg/mL recombinant human insulin (Sigma), 2 IU/mL heparin (Sigma), 5% human solvent detergent pooled plasma AB (Rhode Island Blood Center), 3 IU/mL erythropoietin (Amgen), 100 ng/mL human stem cell factor (SCF) (R&D), 1 μg/mL doxycycline (Sigma), 1% L-glutamine (Life Technologies), and 2% penicillin/streptomycin (Life Technologies).

HUDEP-2 cells with stable Cas9 expression were transduced at low multiplicity with the human sgRNA library lentivirus pool while in expansion medium. Control transductions were performed to ensure transduction rate did not exceed 50%. Cell numbers were maintained throughout the experiment at levels adequate to exceed 1000× representation of the library. 10 μg/mL blasticidin (Sigma) and 1 μg/mL puromycin (Sigma) were added 24 hours after transduction to select for lentiviral library integrants in cells with Cas9. Cells were cultured in expansion media for one week followed by differentiation media for an additional week.

Intracellular staining was performed by fixing cells with 0.05% glutaraldehyde (grade II) (Sigma) for 10 minutes at room temperature. Cells were centrifuged for 5 minutes at 350 g and then resuspended in 0.1% Triton-X100 (Life Technologies) for 5 minutes at room temperature for permeabilization. Triton X-100 was diluted with phosphate buffered saline (PBS) and then centrifuged at 350 g for 15 minutes. Cells were stained with anti-human antibodies for HbF (clone HbF-1 with FITC or APC conjugation; Life Technologies) and B-hemoglobin antibody (clone 37-8 with PerCP-Cy5 or PE conjugation; Santa Cruz) for 20 minutes in the dark. Cells were washed to remove unbound antibody prior to FACS analysis. 0.2 μg HbF and 2 μg of HbA CB-hemoglobin) antibodies were used per 5 million cells. Control cells exposed to a nontargeting sgRNA sample and BCL11A exon 2 were used as negative and positive controls respectively to establish flow cytometry conditions. Populations of cells with the top and bottom 10% of expression of HbF were sorted by FACS.

After sorting the HbF-high and HbF-low pools, library preparation and deep sequencing was performed as previously described (37). Briefly, genomic DNA was extracted using the Qiagen Blood and Tissue kit. Herculase PCR reaction (Agilent) using lentiGuide-Puro specific primers including a handle sequence was performed as follows: Herculase II reaction buffer (1×), forward and reverse primers (0.5 μM each), dimethyl sulfoxide (DMSO) (8%), deoxynucleotide triphosphates (dNTPs) (0.25 mM each), Herculase II Fusion DNA Polymerase (0.5 reactions) using the following cycling conditions: 95° C. for 2 minutes; 20 cycles of 95° C. for 15 seconds, 60° C. for 20 seconds, for 30 seconds; for 5 minutes. Multiple reactions of no more than 200 ng each were used to amplify from 6.6 μg gDNA (=1e6 cell genomes) per pool. Samples were subjected to a second PCR using handle-specific primers to add adaptors and indexes to each sample using the following conditions: Herculase II reaction buffer (1×), forward and reverse primers (0.5 μM each), deoxynucleotide triphosphates (dNTPs) (0.25 mM each), Herculase II Fusion DNA Polymerase (0.5 reactions) with the following cycling conditions: 95° C. for 2 minutes; 25 cycles of 95° C. for 15 seconds, 60° C. for 20 seconds, for 30 seconds; for 5 minutes. PCR products were run on an agarose gel and the band of expected size was gel purified. Illumina MiSeq 150 bp paired end sequencing was performed.

sgRNA sequences present in the plasmid pool as well as in the HbF-high and HbF-low pools were enumerated. Reads were normalized to sequencing depth per library. Dropout score was determined by calculating (1) the ratio of normalized reads in the HbF-high compared to HbF-low pools; (2) log 2 transformation; and (3) median of biological replicates. HbF enrichment score was determined by calculating (1) the ratio of normalized reads in the HbF-high compared to HbF-low pools; (2) log 2 transformation; and (3) median of biological replicates. After exclusion of sgRNAs with dropout scores <2-3 and NAG PAM sgRNAs, a Q-Q plot was made with a line fitted through the first and third quantiles using R software. sgRNA sequences were mapped to the human genome (hg 19) with cleavage positions set to between positions 17 and 18 given PAM positions 21-23. For visual comparisons to targeting sgRNAs, nontargeting sgRNAs were pseudomapped each separated by 5 bp.

Validation in Primary Human CD34+ Hematopoietic Stem and Progenitor Cells (HSPCs)

Primary human CD34+ HSPCs from G-CSF mobilized healthy adult donors were obtained from the Center of Excellence in Molecular Hematology at the Fred Hutchinson Cancer Research Center, Seattle, Washington. CD34+ HSPCs were subject to erythroid differentiation liquid culture as previously described (65). Briefly, HSPCs were thawed on day 0 into erythroid differentiation medium (EDM) consisting of IMDM supplemented with 330 μg/mL holo-human transferrin (Sigma), 10 μg/mL recombinant human insulin (Sigma), 2 IU/mL heparin (Sigma), 5% human solvent detergent pooled plasma AB (Rhode Island Blood Center), 3 IU/mL erythropoietin (Amgen), 1% L-glutamine (Life Technologies), and 2% penicillin/streptomycin (Life Technologies). During days 0-7 of culture, EDM was further supplemented with $10^{-6}$ M hydrocortisone (Sigma), 100 ng/mL human SCF (R&D), and human IL-3 (R&D). During days 7-11 of culture, EDM was supplemented with 100 ng/mL SCF only. During days 11-18 of culture, EDM had no additional supplements.

HSPCs were transduced with LentiCas9-Blast (Addgene plasmid ID52962) 24 hours after thawing in the presence of 10 μM prostaglandin E2 (PGE2) (Cayman Chemical). At 48 hours after thawing, medium was changed and cells were transduced with LentiGuide-Puro or LentiGuide-Crimson cloned with relevant sgRNA sequence in the presence of 10 μM PGE2. At 72 hours after thawing, medium was changed and HSPCs were selected with 10 μg/mL blasticidin (Sigma) and 1 μg/mL puromycin (Sigma) or 10 μg/mL blasticidin followed by sorting for LentiGuide-Crimson+ cells on day 16 of culture. Blasticidin and/or puromycin selection occurred from days 3 to 8 of culture.

Differentiation was assessed on day 18 of culture using anti-human antibodies against the transferrin receptor (CD71) [Clone OKT9 with FITC conjugation; eBioscience] and glycophorin A (CD235a) [Clone HIR2 with PE conjugation; eBioscience]. Enucleation was assessed using 2 μg/mL of the cell-permeable DNA dye Hoechst 33342 (Life Technologies). CD235a+Hoechst 33342-cells were determined to be enucleated erythroid cells. Cells were intracellularly stained for HbF and HbA on day 18 of culture as described above. 50,000-100,000 cells were centrifuged onto microscope slides at 350 rpm for 4 minutes. Slides were stained with Harleco May-May-Grunwald stain (Millipore) for two minutes, Giemsa stain (Sigma) for 12 minutes, and two water washes for 30 seconds each. Slides were air dried and then coverslipped using Fisher Chemical Permount Mounting Medium (Fisher).

PCR primers were designed to amplify the genomic cleavage site for a given sgRNA. Resulting PCR products were subjected to Sanger sequencing. Sequencing traces were used for editing quantification using a previously described publically available tool[66].

Generation of Genomic Deletions in HUDEP-2 Cells.

Tandem sgRNA lentiviruses were transduced into HUDEP-2 with stable Cas9 expression (Table 1). Bulk cultures were incubated for 7-10 days with 10 μg/mL blasticidin (Sigma) and 1 μg/mL puromycin (Sigma) selection to allow for editing. Then bulk cultures were plated clonally at limiting dilution. 96 well plates with greater than 30 clones per plate were excluded to avoid mixed clones. After approximately 14 days of clonal expansion, genomic DNA was extracted using 50 μL QuickExtract DNA Extraction Solution per well (Epicentre). Clones were screened for deletion by conventional PCR with one PCR reaction internal to segment to be deleted ('non-deletion band') and one gap-PCR reaction across the deletion junction ('deletion band') that would only amplify in the presence of deletion (50,67). Biallelic deletion clones were identified as the absence of the non-deletion PCR band and the presence of the deletion PCR band. Inversion clones were identified as previously described by PCR (50,67)(Table 3). Briefly inversion clones had one inverted allele and one deleted allele without the presence of nondeletion alleles. In our experience biallelic inversion clones are very rare events (68). PCR was performed using the Qiagen HotStarTaq 2× master mix and the following cycling conditions: 95° C. for 15 minutes; 35 cycles of 95° C. for 15 seconds, 60° C. for 1 minute, 72° C. for 1 minute; 72° C. for 10 minutes. Alternatively, PCR was also performed using 2× Accuprime Supermix II (Life Technologies) with the following cycling conditions: 94° C. for 2 minutes; 35 cycles of 94° C. for 20 seconds, 60° C. for 20 seconds, 68° C. for 1 min/kb of PCR product; 68° C. for 5 minutes. RNA was extracted from each positive clone using a kit (Qiagen) and quantitative real-time PCR was performed using iQ SYBR Green Supermix (Bio-Rad). Primers used are found in Table 5.

Pooled CRISPR/Cas9 Screen for High Resolution Functional Mapping of Mouse BCHI11A Enhancer.

Murine erythroleukemia (MEL) cells were cultured in DMEM supplemented with 10% FBS (Omega Scientific), 1% L-glutamine (Life Technologies), and 2% penicillin-streptomycin (Life Technologies). εy:mCherry reporter MEL cells with stable Cas9 expression were transduced at low multiplicity with the mouse sgRNA library lentivirus pool. Control transductions were performed to ensure transduction rate did not exceed 50%. Cell numbers were maintained throughout the experiment at levels adequate to exceed 1000× representation of the library. 10 μg/mL blasticidin (Sigma) and 1 μg/mL puromycin (Sigma) were added 24 hours after transduction to select for lentiviral library integrants in cells with Cas9. Subsequently cells were cultured for two weeks. The top and bottom 5% of εγ-mCherry-expressing cells exposed to the library were sorted by FACS. A nontargeting sgRNA sample was used as a negative control and Bcl11a exon 2 as a positive control to establish flow cytometry conditions. After sorting, library preparation and deep sequencing were performed as described for the human library (37).

sgRNA sequences present in the Hbb-εy:mCherry-high and Hbb-εy:mCherry-low pools were enumerated. Dropout and enrichment scores were calculated as described for the human screen. sgRNA sequences were then mapped to the mouse genome (mm9).

Generation of Genomic Deletions in MEL Cells.

Deletions in MEL cells were generated using two sgRNA as previously described (90,76). Briefly, sgRNA sequences were cloned into pX330 (Addgene plasmid ID 42230) using a Golden Gate assembly cloning strategy (Table 1 and 4) MEL cells were electroporated with 5 μg of each pX330-sgRNA plasmid and 0.5 μg pmax-GFP (Lonza) in BTX electroporation buffer using a BTX electroporator (Harvard Apparatus). Approximately 48 hours postelectroporation, the top 1-3% of GFP+ cells were sorted and plated clonally at limiting dilution. Clones were allowed to grow for 7-10 days. Clones were screened for deletion by conventional PCR using the same strategy as with the HUDEP-2 cells (50,67)(Table 2). Inversion clones were identified by PCR as previously described (Table 3).

Generation of genomic deletions in β-YAC mouse embryonic stem cells (mESCs). mESCs were maintained on irradiated mouse embryonic fibroblasts (GlobalStem) and cultured with high glucose DMEM (Life Technologies) supplemented with 20% fetal bovine serum (Omega Scientific), L-glutamine (Life Technologies), penicillin/streptomycin (Life Technologies), non-essential amino acids (Life Technologies), nucleosides, B-mercaptoethanol (Sigma), and leukemia inhibitory factor (Millipore). Cells were passaged using 0.25% trypsin (Life Technologies).

The β-YAC mouse line (A20), previously described as containing a transgene encompassing ~150 kb of the human p-globin locus 55, was used to analyze human globin expression. The mouse line was maintained in a hemizygous state and either used for creation of a β-YAC mESC line or bred with Bell 1a +62 deletion mice. The Bcl11a+62 deletion mice were derived from CRISPR/Cas9 modified CJ9 ES cells. Using Amaxa ES Cell transfection reagent (Lonza), two million CJ9 cells were electroporated with 2 μg of each pX330 plasmid vector containing individual target sequences flanking the +62 site along with 0.5 μg of a GFP plasmid. After 48 hours, the top 5% of GFP expressing cells were sorted, plated on irradiated fibroblasts and maintained. Individual ES cell colonies were then picked and screened for biallelic deletion using the same strategy as HUDEP-2 and MEL cells (50,67). DNA for screening CRISPR/Cas9 modified clones was obtained from gelatin adapted ES cell clones to avoid genomic contamination from the fibroblasts.

Correctly targeted clones with greater than 80% normal karyotype were used to generate mice. Clones were injected into 2.5 day C57B16 blastocysts and implanted into pseudopregnant females. At specified days of development, embryos were taken and analyzed for chimerism and human globin expression by qPCR. Analysis of fetal liver human globin gene expression in the developing chimeric embryos demonstrated a two day delay in globin switching patterns as compared to non-chimeric β-YAC embryos with the earliest timepoint for robust γ-globin repression at embryonic day 16. 5 (E 16.5) (55). Additionally, flow cytometry was used to analyze both fetal liver and spleen from E 18.5 embryos. Single cell suspensions were made by mechanical dissociation and cells were stained with IgM-FITC (Clone 11-41; eBioscience), CD 1 9-PerCP-Cy5.5 (Clone 1D3; eBioscience), CD43-PE (Clone S7; eBioscience), AA4. 1-PECy7 (Clone AA4.1; BD Biosciences), B220-APC (RA3-6B2; Biolegend), and DAPI (Invitrogen).

Adult Mouse Hematopoietic Assays.

Peripheral blood was obtained from the tail vein of 4 week old mice. Blood was collected in heparin coated tubes, red cells lysed with 2% dextran (Sigma), and stained with the following anti-mouse antibodies: CD3e-FITC (Clone 145-2C11; Biolegend), CD 19-PerCP-Cy5.5 (Clone 1D3; eBioscience), CD71-PE (Clone C2; BD Biosciences), NK1.1-PE-Cy5 (Clone PK136; Biolegend), Ter 119-APC (Clone TER-119; Biolegend), Gr-l-eF450 (Clone RB6-8C5; eBioscience), B220-BV605 (RA3-6B2; Biolegend), Mac-1-BV510 (Clone M 1/70; Biolegend), and 7-AAD (BD Biosciences).

Computational Analysis.

Human H3K27ac ChiP-seq was obtained from Xu et al. (12) and mouse H3K27ac ChiP-seq was obtained from Kowalczyk et al (69). Super enhancer analysis was performed using the publically available ROSE algorithm (15).

Figure 10A:
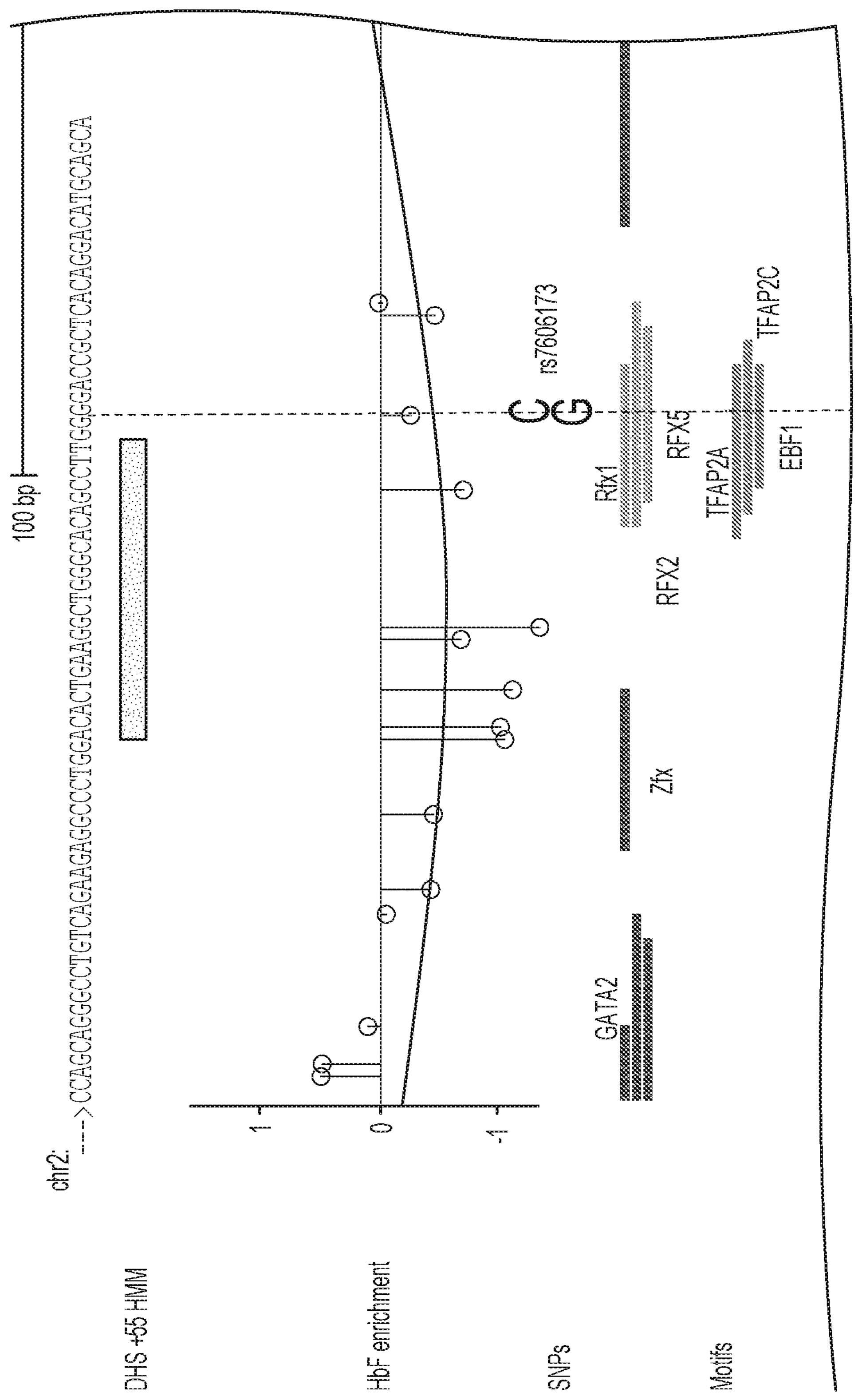
FIGS. 10A-10C shows functional cores of the BCL11A enhancer. a-c, 200 bps at the functional cores of DHSs h+55, h+58, and h+62 defined by HMM states (Active red, Repressive green). HbF enrichment scores shown by gray lines and circles. HbF indel enrichment per nucleotide based on amplicon genomic sequencing of sorted cells exposed to either sgRNA-1617 (top) or -1621 (bottom). Common SNPs (MAF>1%) shown with dotted lines with HbF-low allele in blue and HbF-high allele in red; no common SNPs present at h+58 region. JASPAR motifs ($P<10^{-4}$) depicted in black except for those with allele-specific significance depicted by allelic color. Selected motifs annotated by TF based on known erythroid-specific function or genomic position. Motif LOGOs at key positions with motif scores $P<10^{-3}$ as described in text. Dotted boxes show regions of highest HbF enrichment score at each core with underlying predicted motifs. Orthologous sequences listed from representative primates and nonprimates of distributed phylogeny. PhyloP (scale from −4.5 to 4.88) and PhastCons (from 0 to 1) estimates of evolutionary conservation among 100 vertebrates.
Figure 10A:
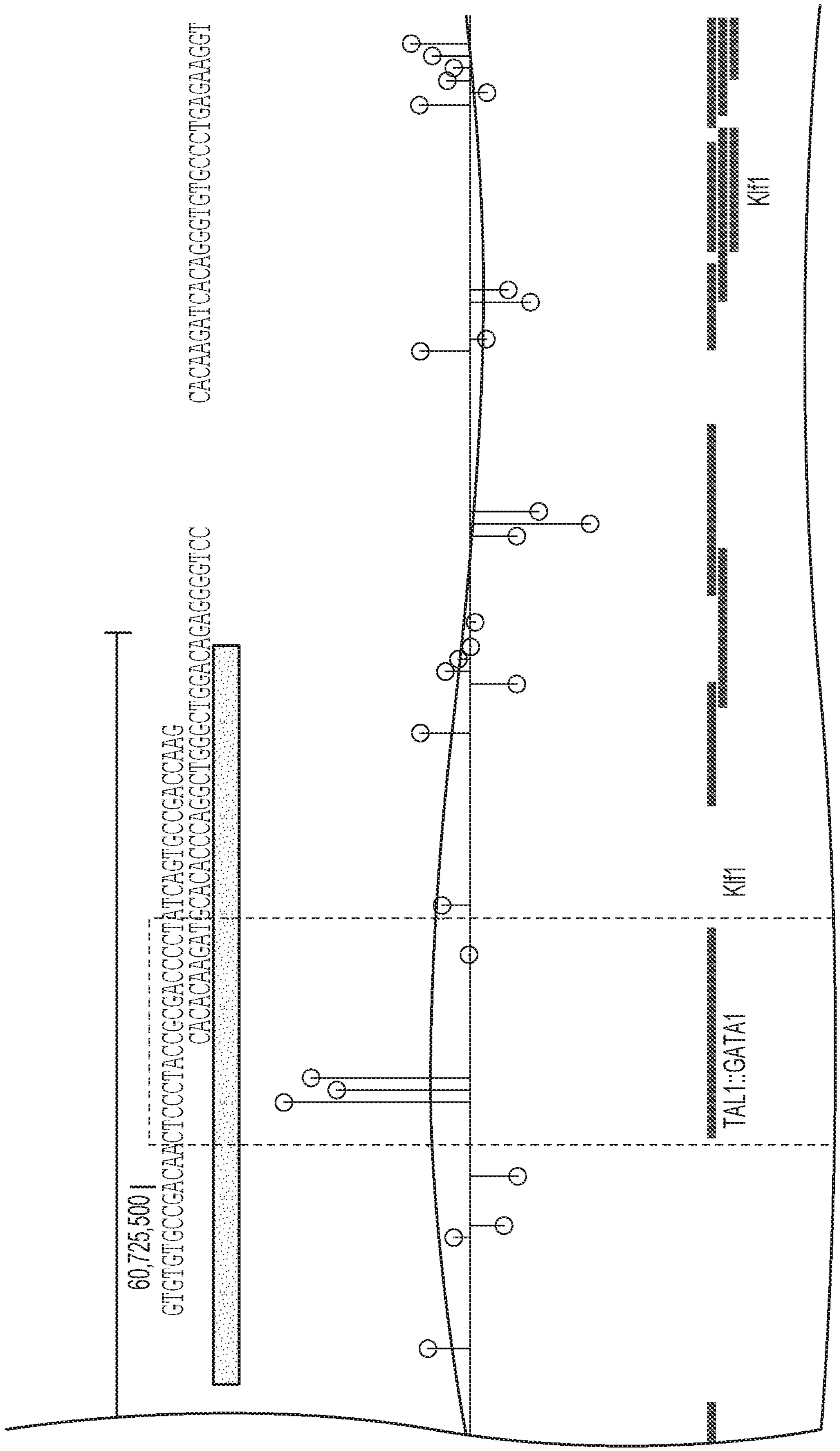
Figure 10A:
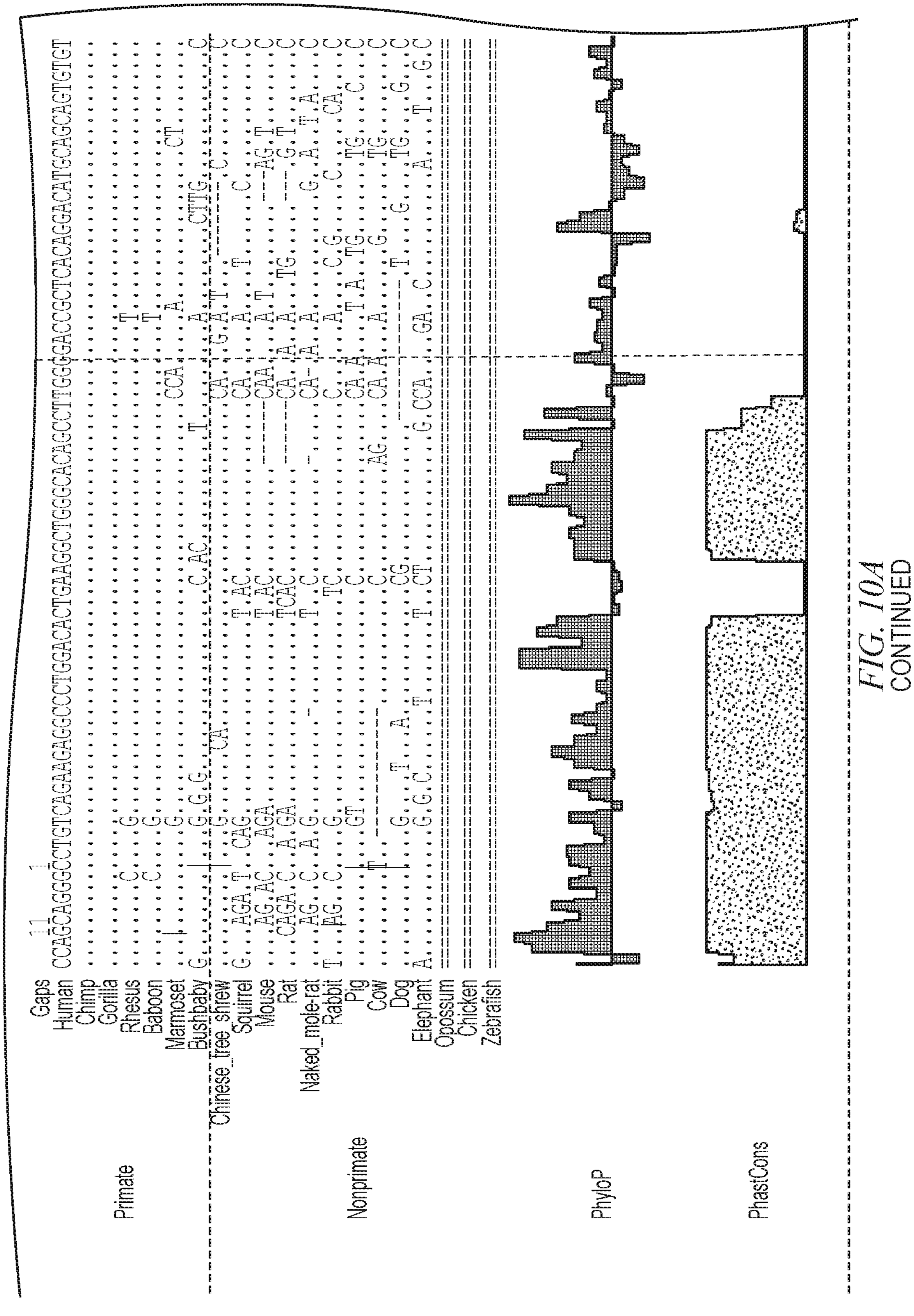
Figure 10A:
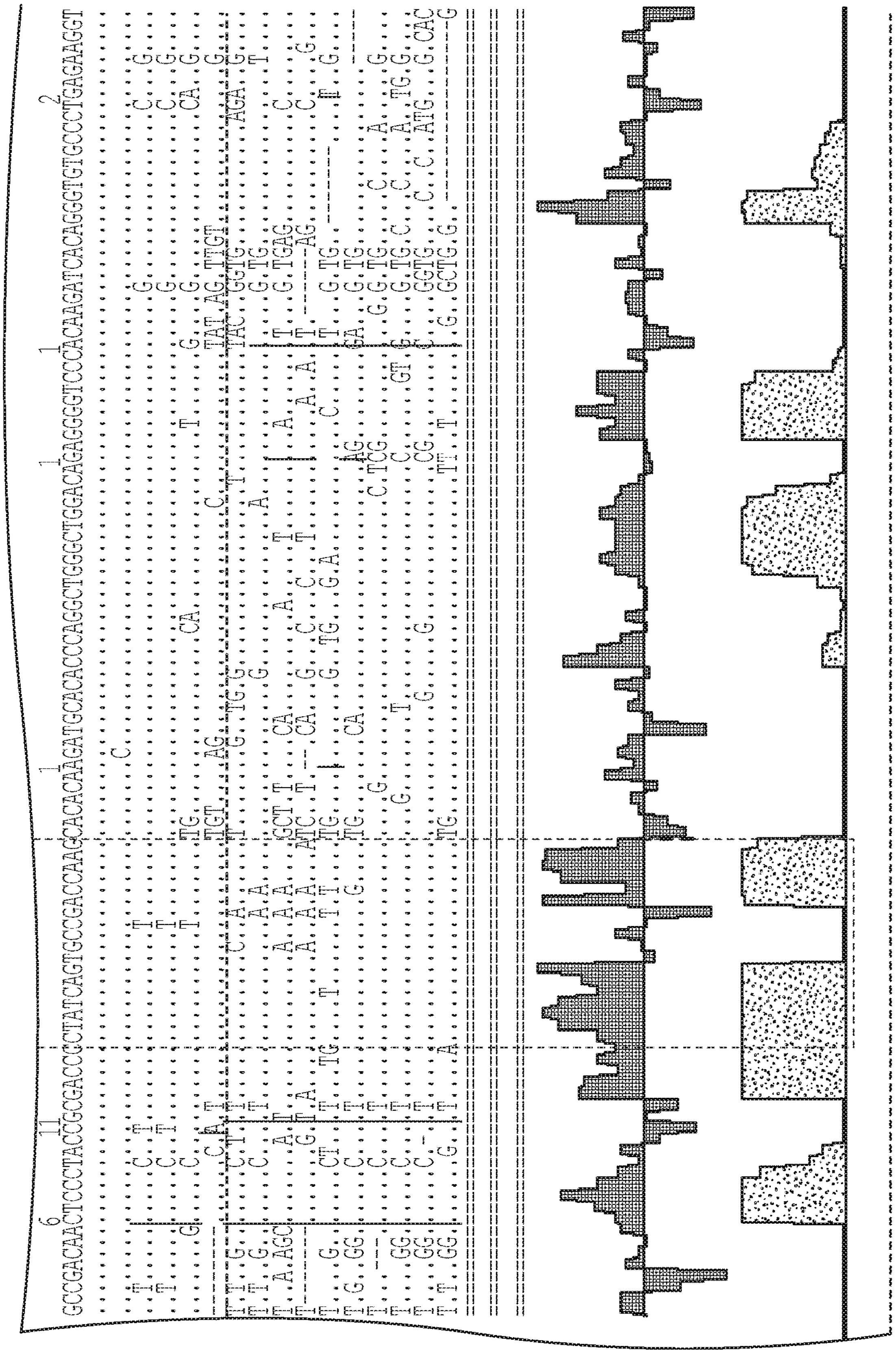

Hidden Markov Model (HMM) segmentation was performed to automatically segment the enrichment score signals into enhancer regions with Active, Repressive and Neutral effect. Applicants designed a HMI with 3 states using the GHMM package obtained from the website of sourceforge. The emission probability for each state was modeled as a Gaussian distribution and all the possible transitions between states were allowed as shown in FIG. 10*a*. Since the signal was not obtained with a constant genomic resolution, Applicants interpolated and smoothed the signal using a Gaussian kernel over 12 bp. To set the initial parameters, Applicants used the 1%, 50% and 99% percentile of the smoothed signal for the prior of the means of the Repressive, Neutral and Active states respectively, while the prior for the standard deviation was set to 0.00 1 for all the three states.

Motif analysis was performed to evaluate the human and mouse enhancer regions for potential binding sites for known transcription factors. Applicants used the FIMO software with a P-value threshold of $<10^{-4}$ (70). For each region Applicants extracted sequences using the hg19 and mm9 assemblies respectively for human and mouse. The motif database was the latest version of the JASPAR database (39).

Deep sequencing paired-end reads of genomic amplicons from genome editing target sites were first filtered for reads with PHRED quality score <30, merged with the FLASH (Fast Length Adjustment of Short reads) software, and subsequently aligned to a reference amplicon using the needle aligner from the EMBOSS suite, obtained from the website of sourceforge, to quantify insertions and deletions. Per nucleotide frequency of deletion of a position, insertion directly adjacent to the position, or no mutation at the position was quantitated using CRISPResso, obtained from the website of github, under lucapinello and CRISPResso.

Cloning lentiCas9-Venus.

Venus template (71) was PCR amplified to add BamHI-HF (5') and EcoRI-HF (3') restriction sites for cloning purposes using the following conditions: KOD buffer (1×), MgS04 (1.5 mM), dNTPs (0.2 mM each), forward primer (0.3 μM; GGCCGGCCG-GATCCGGCGCAACAAACTTCTCTCTGCT-GAAACAAGCCGGAGATGTC GAAGAGAATCCTGGACCGATGGT-GAGCAAGGGCGAGGA (SEQ ID NO: 139)), reverse primer (0.3 μM; GGCCGGCCgaattcTTACTTGTA-CAGCTCGTCCA (SEQ ID NO: 140)), and KOD Hot Start DNA Polymerase (0.02 U/μL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and blunt ended cloned with Zero Blunt PCR cloning kit (Invitrogen). PCR-blunt cloned products and lentiCas9-Blast (Addgene plasmid ID 52962) were separately digested with BamHI-HF and EcoRI-HF in 1× Buffer CutSmart at 37° C. (New England Biolabs). Digest of lentiCas9-Blast was performed to remove the blasticidin cassette. Then digested PCR product was ligated into the lentiCas9 backbone.

Cloning lentiGuide-Crimson.

E2-Crimson template (Clontech) was PCR amplified to add BsiWI (5') and Mlul (3') restriction sites for cloning purposes using the following conditions: KOD buffer (1×), MgS04 (1.5 mM), dNTPs (0.2 mM each), forward primer (0.3 μM; GGCCGGCCCGTACGCGTACGGCCACCATG-GATAGCACTGAGAACGTCATCAAGCCC TT (SEQ ID NO: 141)), reverse primer (0.3 μM; GGCCGGC-CACGCGTCTACTGGAACAGGTGGTGGCGGGCCT (SEQ ID NO: 142)), and KOD Hot Start DNA Polymerase (0.02 U/μL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and cloned with Zero Blunt PCR cloning kit (Invitrogen). Cloned products and lentiGuide-puro were separately digested with BsiWI and Mlul in 1× Buffer 3.1 at 37° C. (New England Biolabs). Digest of lentiGuide-Puro (Addgene plasmid ID52963) was performed to remove the puromycin cassette. Then digested PCR product was ligated into the lentiGuide backbone.

Cloning sgRNAs.

lentiGuide-Puro (Addgene plasmid ID 52963) was digested with BsmBI in IX Buffer 3.1 at 37° C. (New England Biolabs) for linearization. One unit of TSAP thermosensitive Alkaline Phosphatase (Promega) was added for 1 hour at 37° C. to dephosphorylate the linearized lentiGuide and then TSAP was heat inactivated at 74° C. for 15 minutes. Linearized and dephosphorylated lentiGuide was run on an agarose gel and gel purified. sgRNA-specifying oligos were phosphorylated and annealed using the following conditions: sgRNA sequence oligo (10 μM); sgRNA sequence reverse complement oligo (10 μM); T4 ligation buffer (1×) (New England Biolabs); and T4 polynucleotide kinase (5 units) (New England Biolabs) with the following temperature conditions: 37° C. for 30 min; 95° C. for 5 min; and then ramp down to 25° C. at 5° C./min. Annealed oligos were ligated into lentiGuide in a 1:3 ratio (vector:insert) using T4 ligation buffer (1×) and T4 DNA Ligase (750 Units) (New England Biolabs. Plasmids were verified by sequencing using a U6F promoter forward primer CGTAACTTGAAAGTATTTCGATTTCTTGGC (SEQ ID NO: 143).

sgRNA-specifying oligos using sgRNA sequences from the screen library (Extended Data) were obtained and cloned as described into either lentiGuide-Puro or lentiGuide-Crimson. sgRNA constructs were used to produce lentivirus and transduce HUDEP-2 with stable Cas9 expression. Bulk cultures were incubated for 7-10 days with 10 μg/mL blasticidin (Sigma) and 1 μg/mL puromycin (Sigma) selection to allow for editing. Then bulk cultures were plated clonally at limiting dilution without antibiotic selection. Clones were allowed to grow for approximately 14 days and then were genomic DNA was extracted using 50 μL QuickExtract DNA Extraction Solution per well (Epicentre).

lentiTandemGuide Cloning.

lentiGuide-sgRNA 1 was digested with PspXI and Xmai at 37° for four hours (New England Biolabs). Digests were run on an agarose gel and gel purified. lentiGuide-sgRNA2 was linearized using Notl (New England Biolabs). The hU6 promoter and sgRNA chimeric backbone for lentiGuide-sgRNA2 was PCR amplified using the following conditions: KOD buffer (1×), MgS04 (1.5 mM), dNTPs (0.2 mM each), forward primer (0.3 μM; GGCCGGCCgctcgagg-GAGGGCCTATTTCC (SEQ ID NO: 144)), reverse primer (0.3 μM; CCGGCCGGcccgggTTGTGGATGAATACTGCCATTT (SEQ ID NO: 145)), and KOD Hot Start DNA Polymerase (0.02 U/μL) (Millipore). KOD PCR reaction used the following cycling conditions: 95° C. for 2 minutes; 50 cycles of 95° C. for 20 seconds, 60° C. for 20 seconds, and 70° C. for 30 seconds; 60° C. for 5 minutes. PCR products were purified (QIAquick PCR Purification Kit, Qiagen) and blunt ended cloned with Zero Blunt PCR cloning kit (Invitrogen) and transformed and plated. Colonies were screened by digesting minipreps with EcoRI. Mini-preps were then digested with PspXI and Xmai as described above followed by PCR purification. Following PCR purification, sgRNA2 was ligated into digested lentiGuide-sgRNA1. Sequence verified with following primers: GGAGGCTTGGT AGGTTT AAGAA (SEQ ID NO: 146) and CCAATTCCCACTCCTTTCAA (SEQ ID NO: 147).

Generation of HUDEP-2 with Stable Cas9.

LentiCas9-Blast (Addgene plasmid ID 52962) or LentiCas9-Venus were produced as described above and used to transduce HUDEP-2 cells. Transduced cells were selected with 10 μg/mL blasticidin (Sigma) or Venus+ cells were sorted. Functional Cas9 was confirmed using the pXPR-011 (Addgene plasmid ID 59702) GFP reporter assay as previously described (72).

Generation of Hbb-εy:mCherry Reporter MEL Cells.

A reporter MEL line in which mCherry has been knocked into the Hbb-y locus was created (FIG. 10*a*). Briefly, a TALEN-induced DSB was created adjacent to the Hbb-y transcriptional start site. A targeting vector with mCherry and a neomycin cassette were introduced through homology directed repair. Cre-mediated recombination was utilized to remove the neomycin cassette. Long-range PCR spanning each homology arm was utilized to ensure appropriate targeted integration. Cells were tested upon Bcl11 a disruption by RT-qPCR and flow cytometry to confirm expected effects on εy:mCherry derepression. Subsequently CRISPR-Cas9 was used as described above to produce cells with monoallelic composite enhancer deletion to maximize screening sensitivity.

Generation of MEL Cells with Stable Cas9 Expression.

LentiCas9-Blast (Addgene plasmid ID 52962) lentivirus were produced as described above and used to transduce MEL cells. Transduced cells were selected with 10 μg/mL blasticidin (Sigma). Functional Cas9 was confirmed using the pXPR-011 (Addgene plasmid ID 59702) GFP reporter assay as previously described (72).

Results

Human Composite Enhancer

Recently Applicants observed that common genetic variants associated with HbF (a2y2) level and B-hemoglobin disorder clinical severity mark an adult developmental stage- and erythroid-lineage specific intronic enhancer of BCL11A (42), a validated repressor of HbF and therapeutic target for B-hemoglobin disorders (42,45-47). This composite enhancer is composed of three DNase I hypersensitive sites (DHSs), termed +55, +58, and +62 based on distance in kilobases from the transcriptional start site (TSS) (42). The most highly trait-associated haplotype is defined by two SNPs, rs1427407 within +62 and rs7606173 within +55 (FIG. 1*a*). In fact, based on H3K27ac ChiP-seq in primary human adult erythroid precursors, the composite BCL11A enhancer ranks as the #100 most intensely decorated of 503 total human erythroid super-enhancers (FIG. 1*a, b*). Previously Applicants showed that this enhancer possessed ectopic erythroid-restricted, adult-stage specific enhancer activity (42). Moreover, the mouse ortholog of the composite enhancer, defined by primary sequence homology, shared erythroid enhancer chromatin signature, and syntenic position relative to coding sequences, was shown to be required for BCL11A expression and embryonic globin gene repression in a mouse erythroid cell line but dispensable in a mouse B-lymphoid cell line (42). These results recommend disruption of the BCL11A erythroid enhancer as a promising therapeutic strategy for HbF reinduction for the B-hemoglobin disorders (48).

Figure 1C:
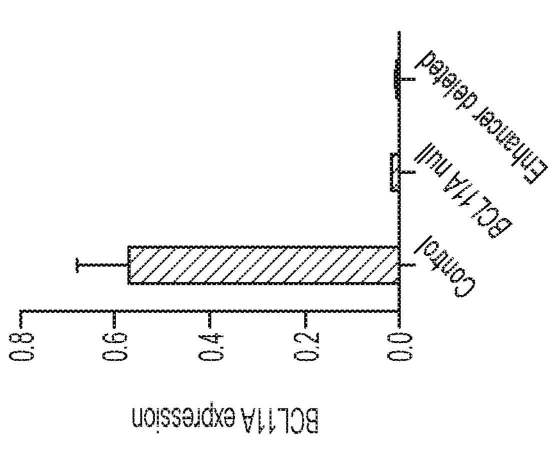
Figure 1D:
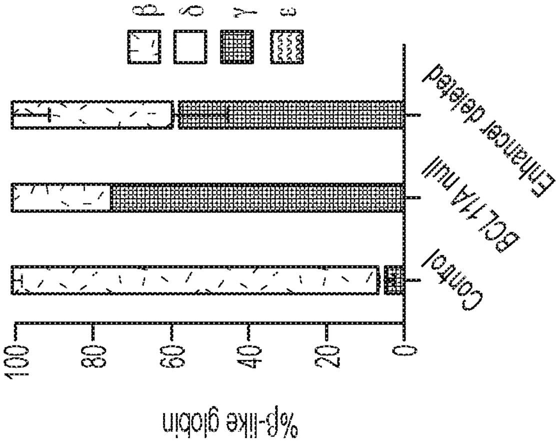
Figure 1E:
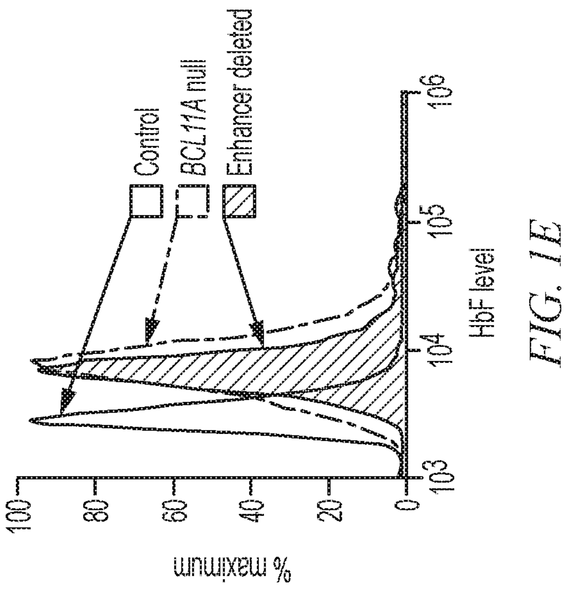

To evaluate the requirement for human BCL11A enhancer sequences, Applicants utilized HUDEP-2 cells, an immortalized human CD34+ hematopoietic stem and progenitor cell (HSPC)-derived erythroid precursor cell line that expresses BCL11A and predominantly β-rather than γ-globin (49). Applicants used the CRISPR-Cas9 nuclease system to generate a clone of HUDEP-2 cells null for BCL11A by targeting coding sequences (FIG. 1*c-d*). These cells demonstrated elevated levels of y-globin mRNA and HbF protein, consistent with the functional requirement of BCL11A for HbF repression (FIG. 1*d*, 1*e*). Deletion of the 12-kb BCL11A composite enhancer with a pair of sgRNAs resulted in near complete loss of BCL11A expression and induction of γ-globin and HbF protein to similar levels as cells with BCL11A knockout (FIG. 1*c*-1*e*), analogous to the requirement of the orthologous mouse composite enhancer for erythroid BCL11A expression (42). Significant HbF induction resulting from deletion of the human BCL11A erythroid composite enhancer encourages targeting these sequences for therapeutic genome editing of the β-hemoglobinopathies (42). Although targeted deletions by paired double strand breaks (DSBs) may be achieved by genome editing, competing genomic outcomes include local insertion/deletion (indel) production at each cleavage site as well as inversion of the intervening segment (34,35,50-52).

Tiled Pooled Enhancer Editing In Situ

Applicants hypothesized that composite enhancers may be composed of a functional hierarchy with essential and dispensable constituent components. A functional hierarchy can enable enhancer disruption by a single DSB at a critical region followed by nonhomologous end joining (NHEJ) repair with indels. Indeed single nucleotide changes themselves may substantively modulate enhancer function. Therefore Applicants reasoned that a tiling set of sgRNAs could uncover critical enhancer regions by disruption of essentially all sequences within an enhancer given the typical indel spectrum of each sgRNA of at least 10 bp (34,35,50,52,53).

Figure 2A:
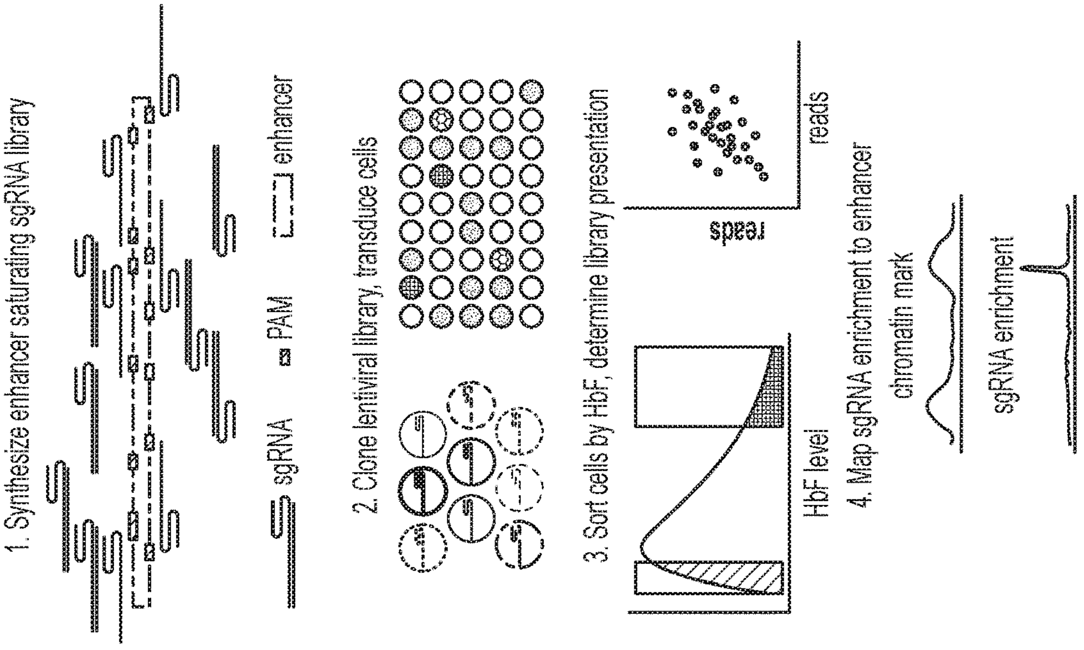
Figure 2B:
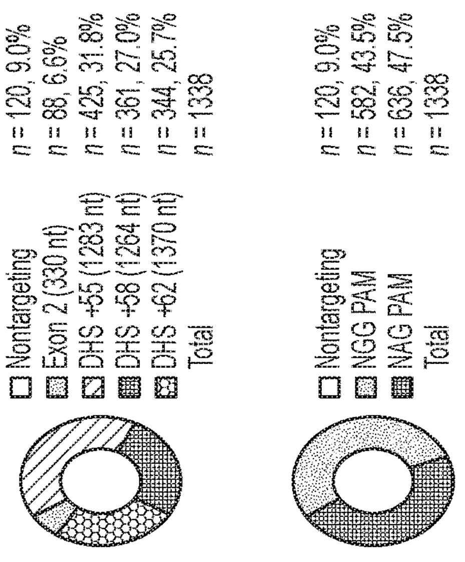
FIG. 2*b*, Library composition by target sequence and PAM restriction.
Figure 2C:
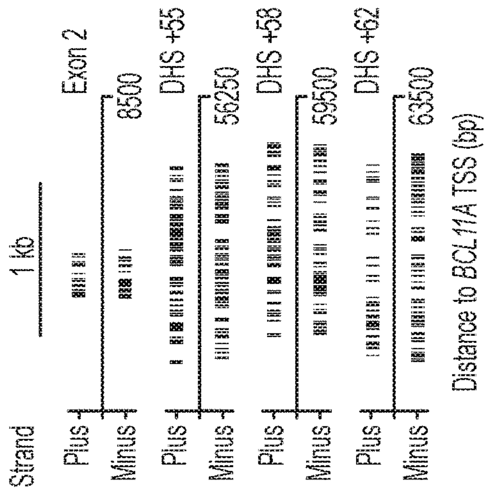
FIG. 2*c*, Distribution of NGG PAM sgRNAs mapped to genomic cleavage position.
Figure 2D:
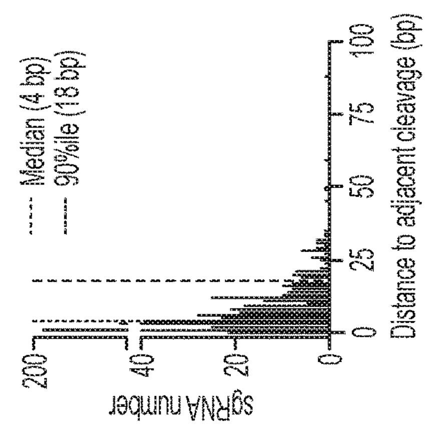
FIG. 2*d*, Distance to adjacent genomic cleavage position for NGG PAM sgRNAs.
Figure 16A:
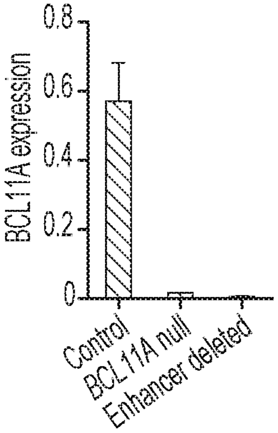
FIG. 16A-16F shows tiled pooled in situ CRISPR-Cas9 BCL11A enhancer screen. a-c, Deletion of the human composite BCL11A enhancer in HUDEP-2 cells demonstrates its necessity for BCL11A expression (normalized to GAPDH), repression of γ-globin mRNA, and repression of HbF. Error bars show s.e.m. d, Workflow of CRISPR-Cas9 enhancer screen showing library synthesis, delivery, and analysis. e, Human NGG PAM sgRNA library distribution. f, Gaps between adjacent genomic cleavages for NGG PAM sgRNAs targeting BCL11A exon-2, h+55, h+58, and h+62.
Figure 16B:
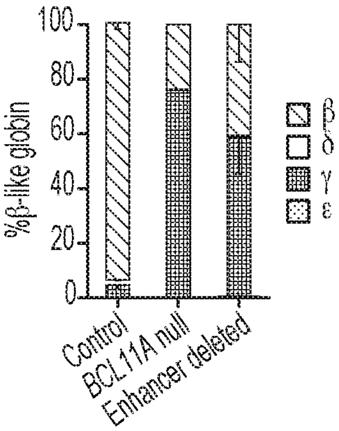
Figure 16C:
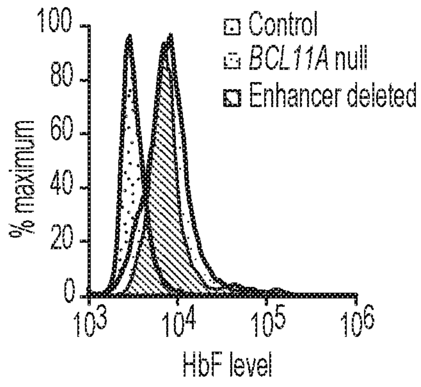
Figure 16D:
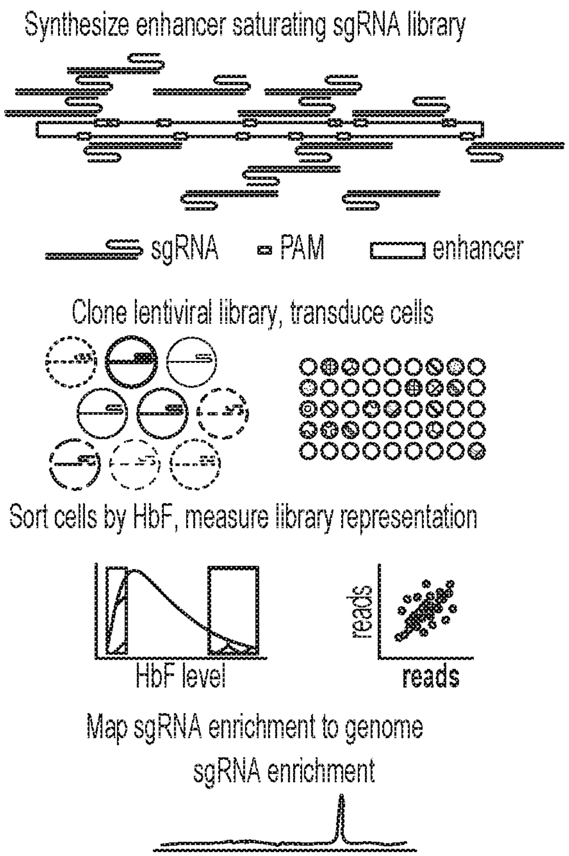
Figure 16E:
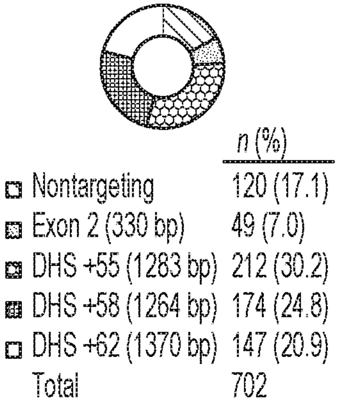
Figure 16F:
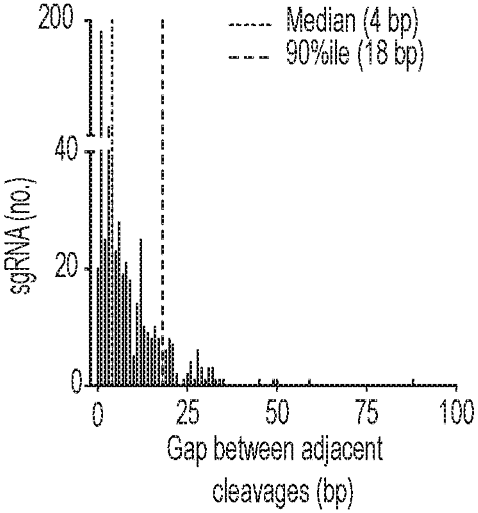
Figure 17A:
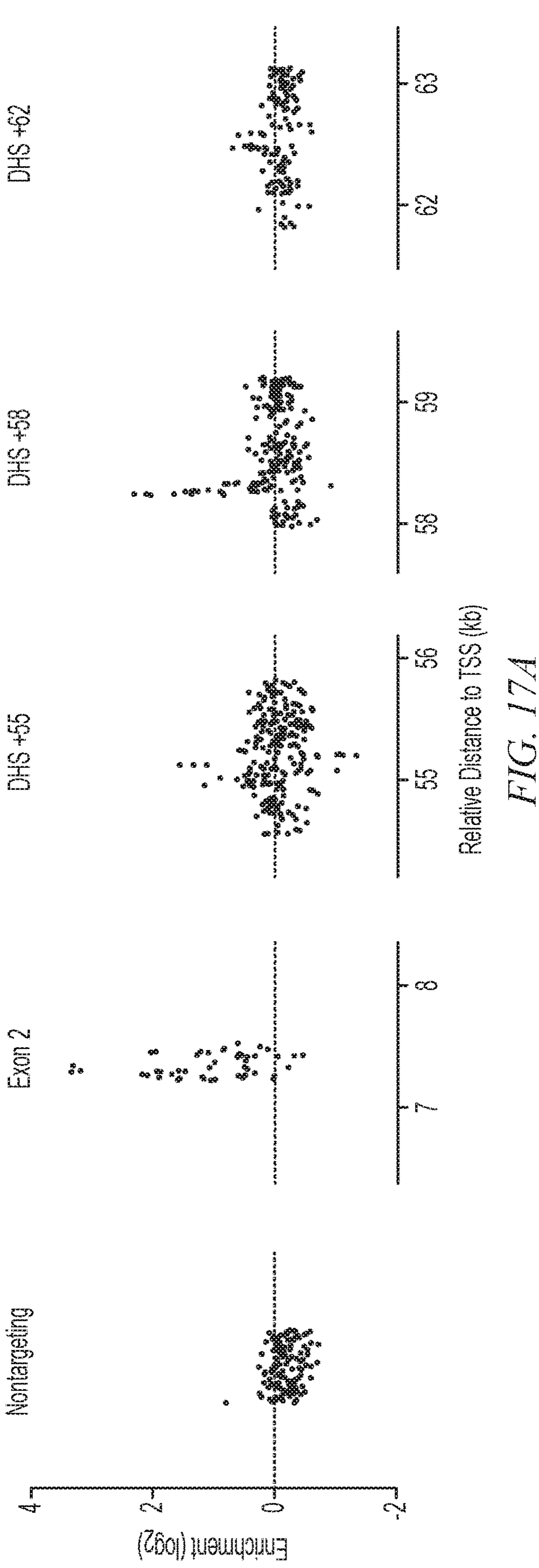
Figure 17B:
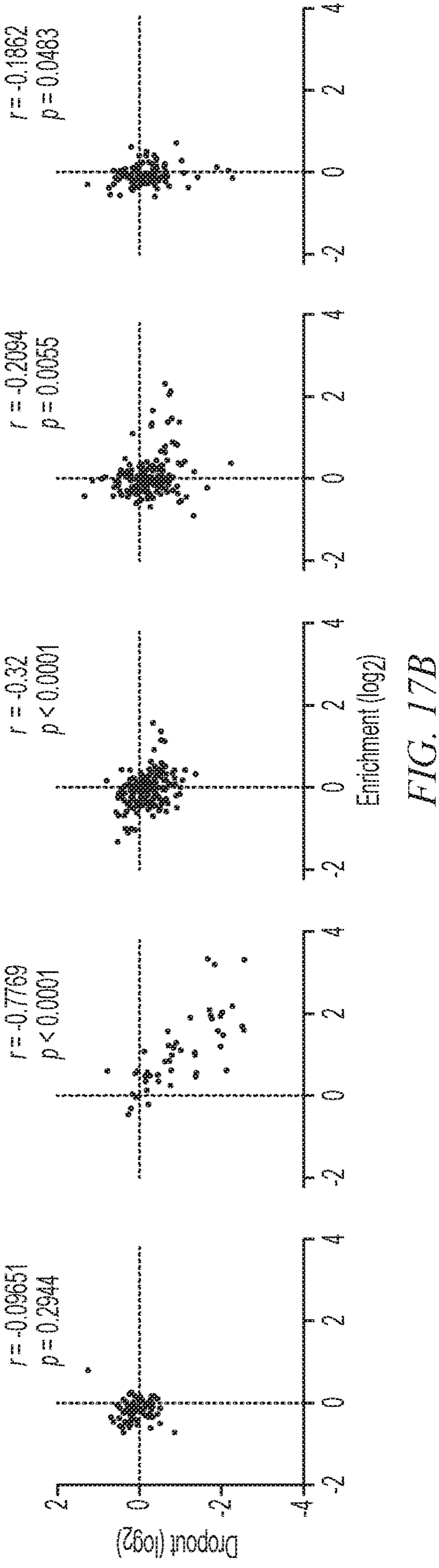
Figures 17C, 17D, 17E, 17F, 17G, 17H:
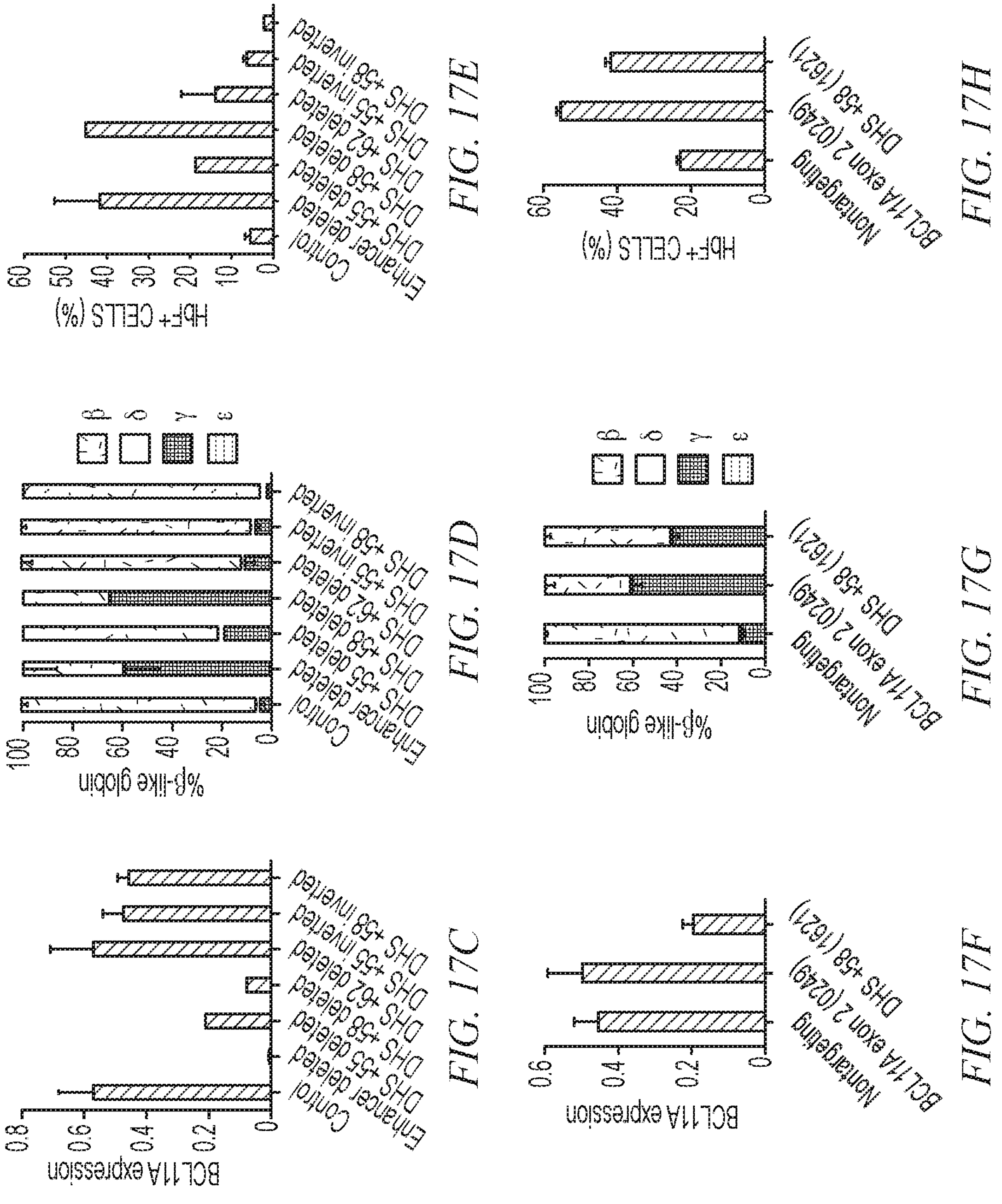
Figure 18A:
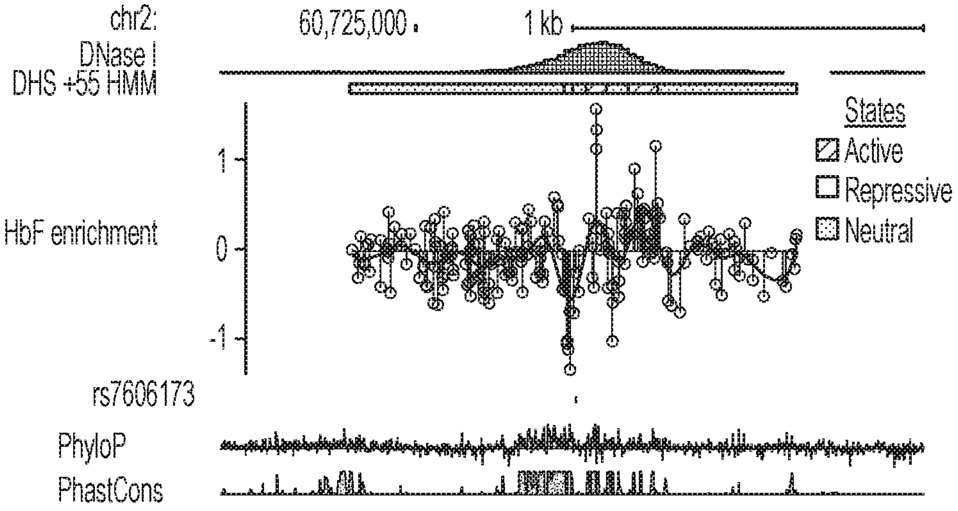
FIG. 18A-18C shows inferred functional enhancer states relative to genomic features. a-c, Hidden Markov model segmentation of functional enhancer states. HbF enrichment scores shown throughout DHSs h+55, h+58, h+62 by gray lines and circles with blue line representing smoothed enrichment score. DNase I sequencing from primary human erythroblasts. PhyloP (scale from −4.5 to 4.88) and PhastCons (from 0 to 1) estimates of evolutionary conservation among 100 vertebrates. Positions of SNPs rs7606173 and rs1427407 denoted which together define the haplotype most highly associated to HbF level (Bauer, D. E. et al. *Science.* 342, 253-257 (2013)).
Figure 18B:
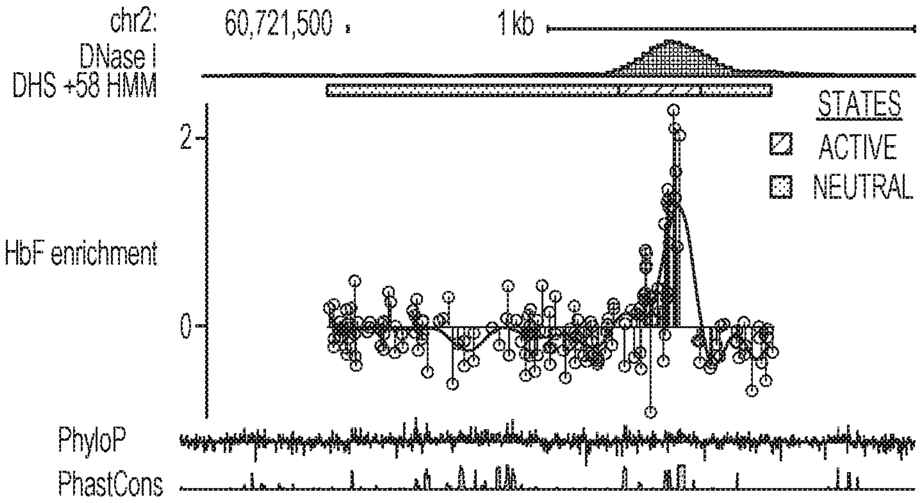
Figure 18C:
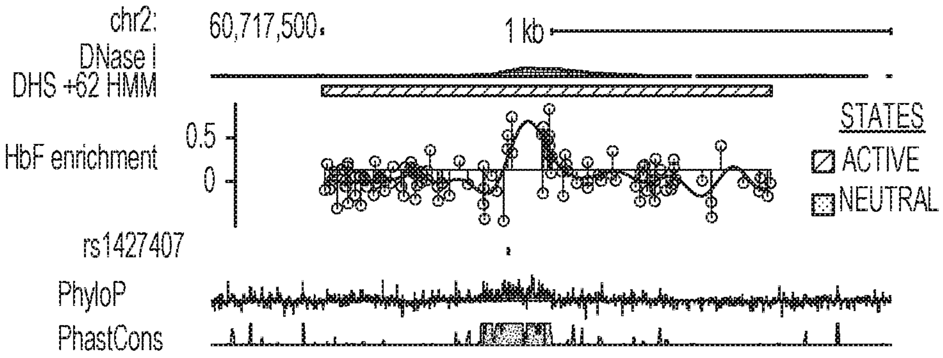
Figure 19:
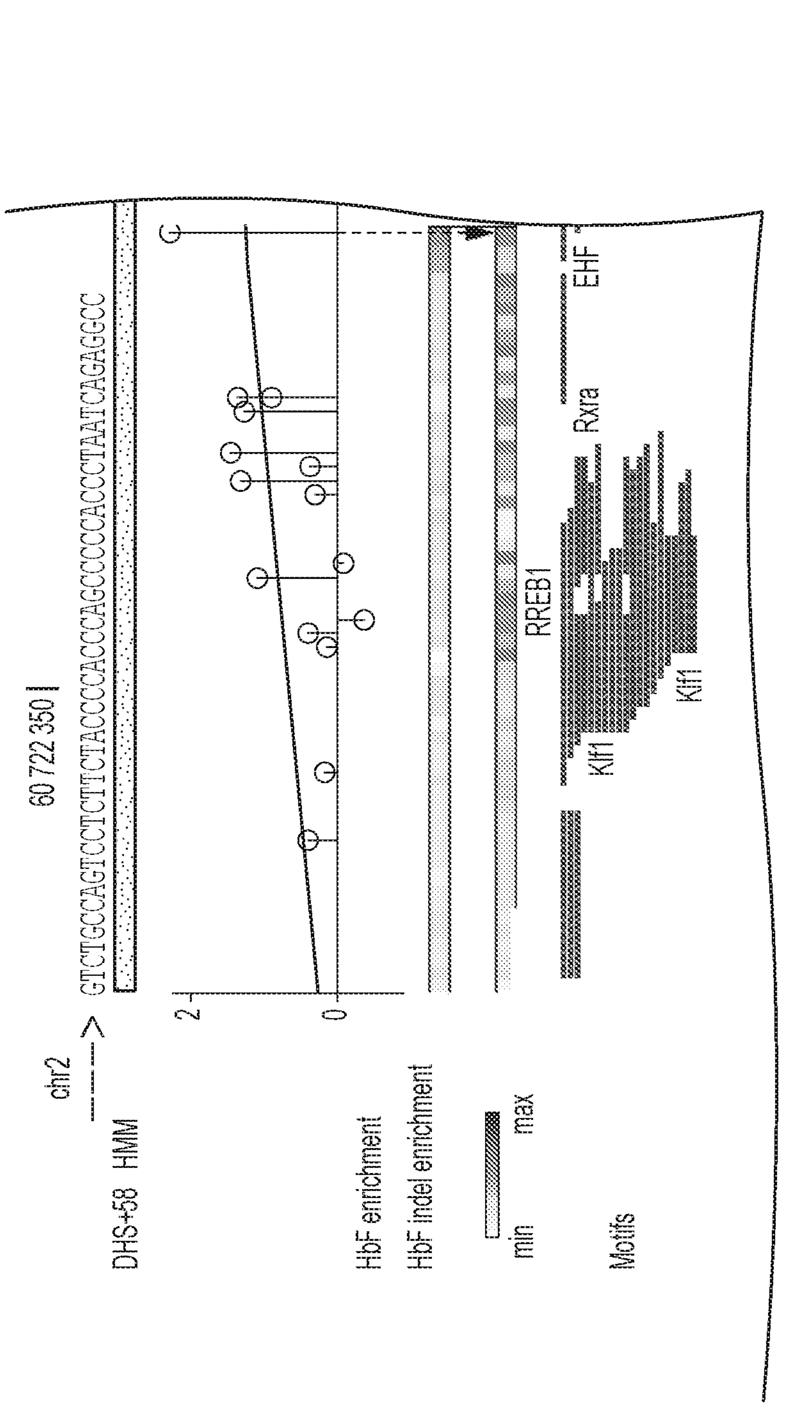
Figure 19:
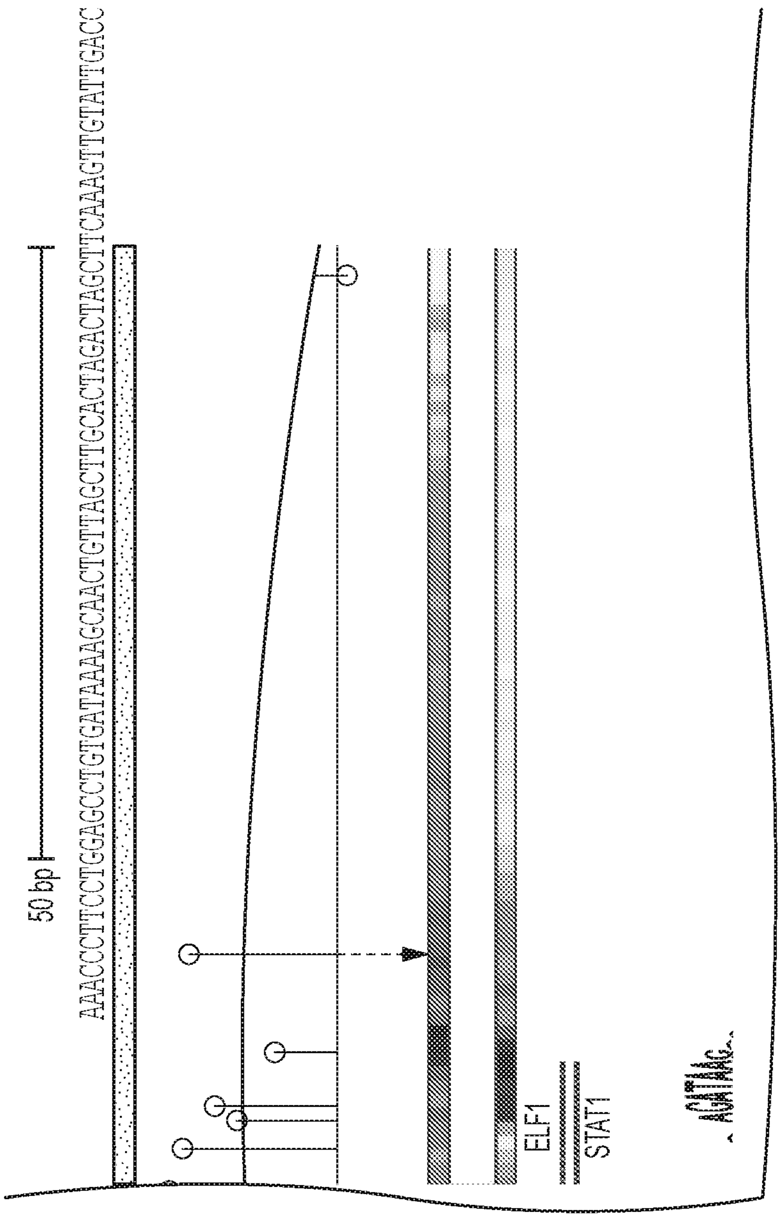
Figure 19:
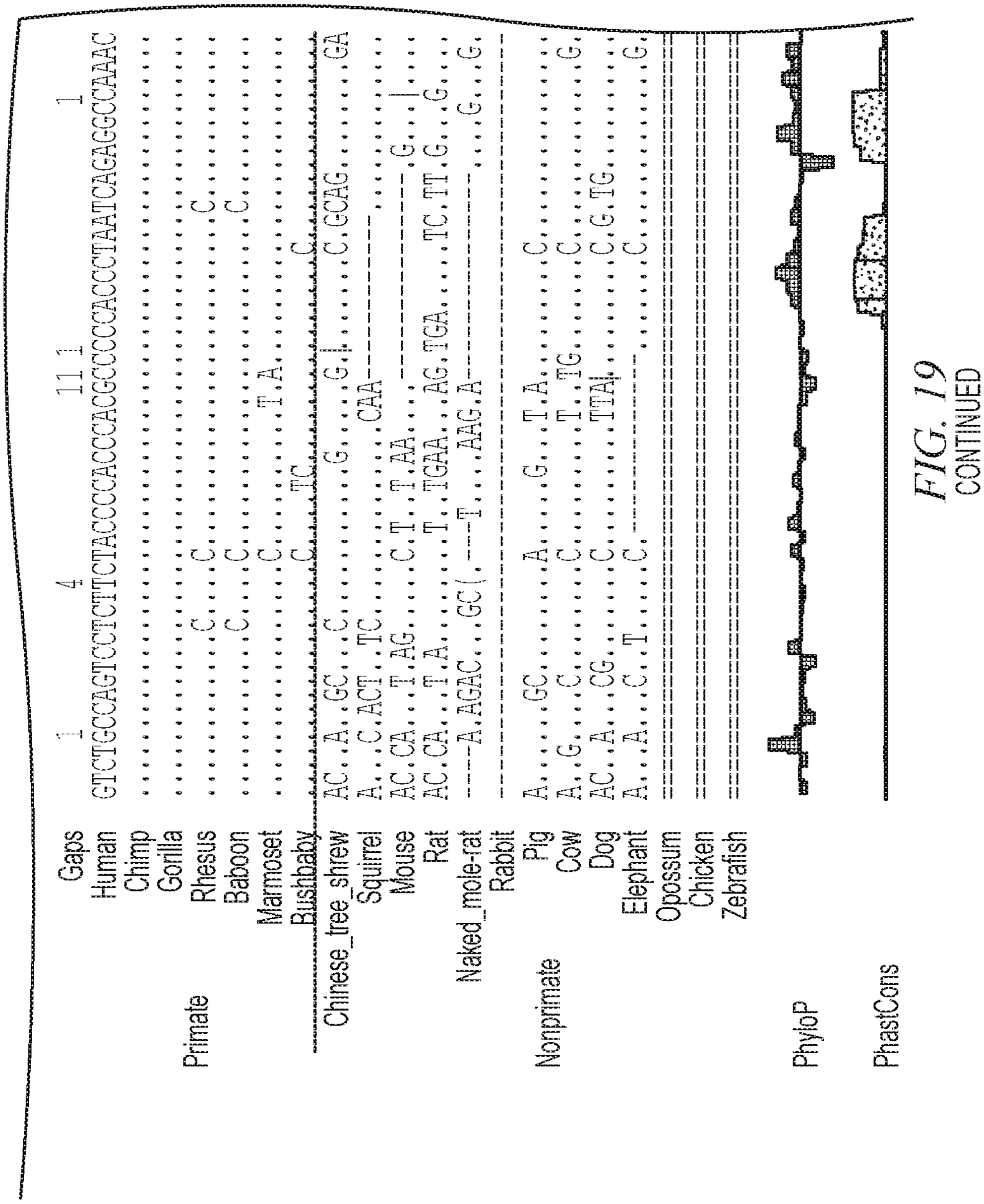
Figure 19:
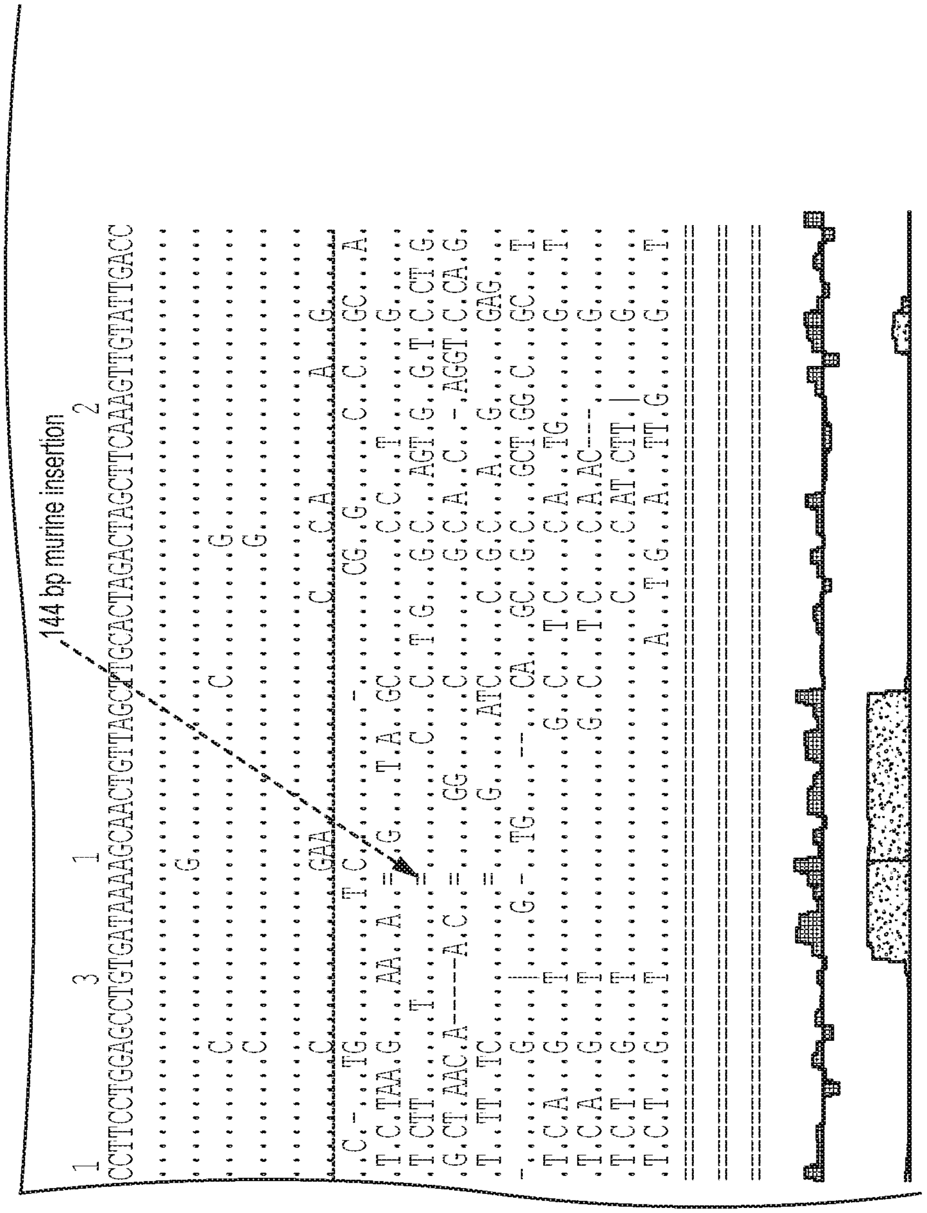
Figure 20A:
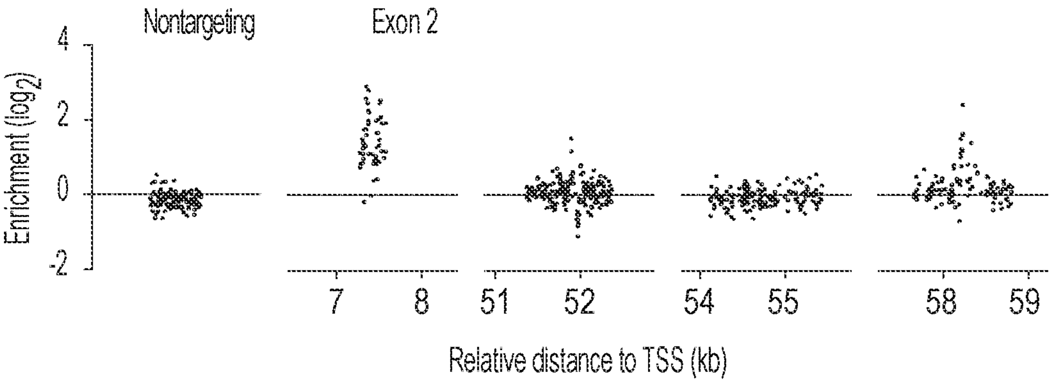
FIG. 20A-20C shows functional sequence requirement at the mouse Bcl11a erythroid enhancer for in vivo hemoglobin switching. a, Mapping sgRNA cy enrichment scores to genomic cleavage positions. Nontargeting sgRNAs pseudo-mapped with 5 bp spacing. b, BCL11A expression in mouse erythroid clones with deletion or inversion of individual DHSs relative to nondeleted controls. c, Transgenic human β-like globin (each symbol represents the mean of at least 3 embryos) expression in β-YAC/+62 deletion mice. *P<0.05, error bars represent s.e.m.
Figure 20B:
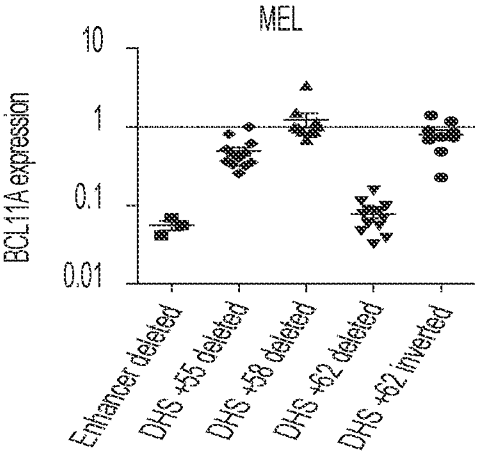
Figure 20C:
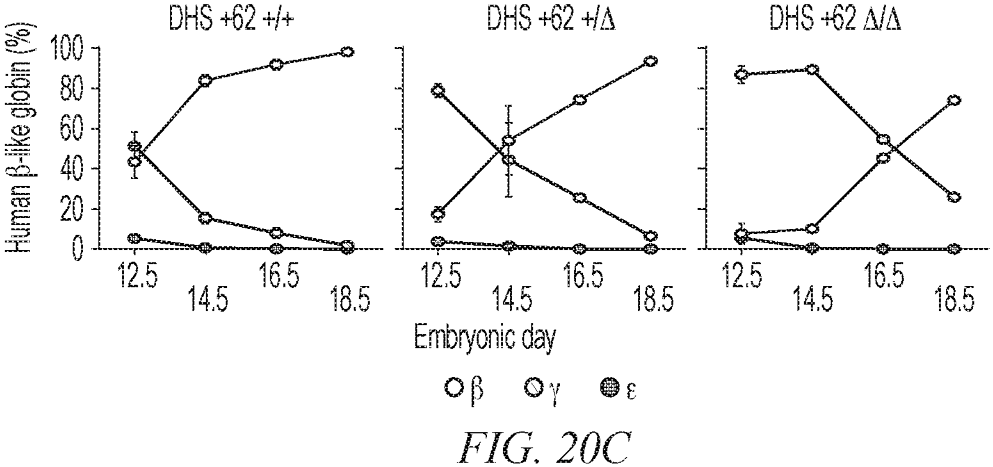
Figure 21B:
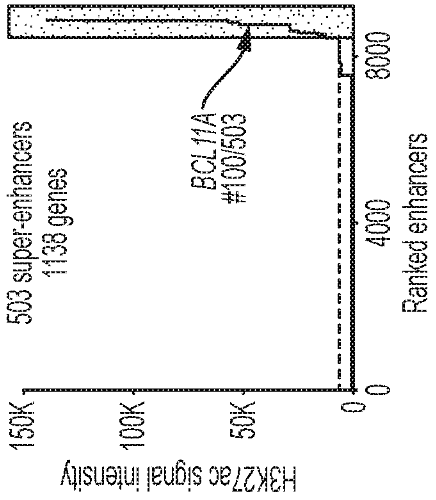
FIG. 21A-21B shows human BCL11A locus. a, Schematic of the human BCL11A locus (hg19, transcription from right to left) with erythroid chromatin marks and trait-associated haplotype denoted, and composite enhancer as previously defined. b, Ranked enhancers in primary human adult erythroid precursors by H3K27ac signal intensity, with super-enhancers shaded, and super-enhancer associated genes indicated.
Figure 21A:
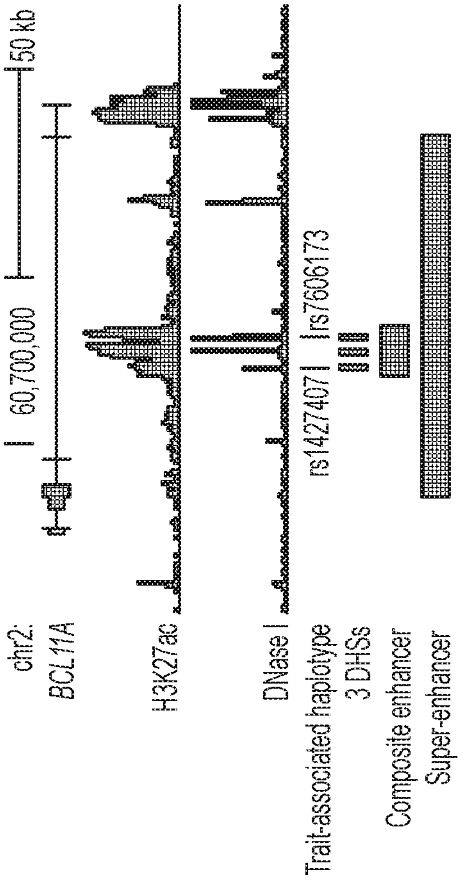
Figure 22A:
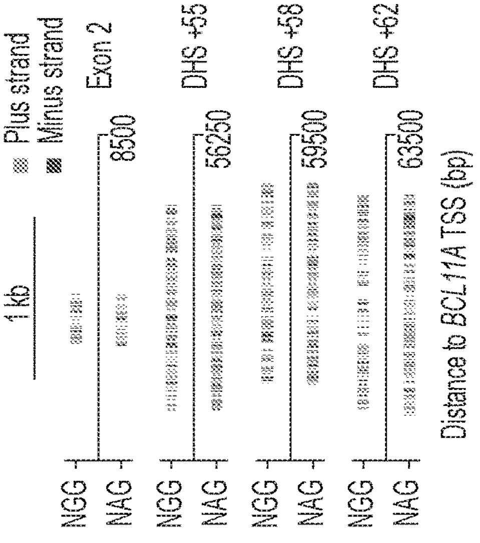
FIG. 22A-22K shows tiled pooled in situ CRISPR-Cas9 BCL11A enhancer screen. a, Distribution of NGG and NAG PAM sgRNAs mapped to genomic cleavage position. The vertical lines represent cleavage sites for sgRNAs mapped to plus and minus strands. b, Gap distance between adjacent genomic cleavage position for NAG PAM sgRNAs. c, Library composition by target sequence and PAM restriction. d. Representation of both NGG and NAG sgRNA (1,338 sgRNAs in total) within the plasmid pool by deep-sequencing. The median was 718 normalized reads and the 10th and 90th percentiles (indicated by the vertical dotted lines) ranged from 337 to 1,205 normalized reads. e, HbF distribution in HUDEP-2 cells transduced with Cas9 and individual sgRNAs, either nontargeting or targeting BCL11A exon 2. f, HbF enrichment scores of NGG sgRNAs in six biological replicates. g, Sort of library-transduced cells into HbF-high and HbF-low pools. h, Control sgRNA enrichment. Boxes demonstrate $25^{th}$, median, and $75^{th}$ percentiles and whiskers minimum and maximum values. ****P<0.0001, ns non-significant. i, NGG sgRNA representation in plasmid pool and cells at conclusion of experiment (left), and in HbF-high and HbF-low pools (right), with dotted lines at x=y and x=8y. j, Quantile-quantile plots of NGG sgRNA enrichment scores. k, Cellular dropout scores of NGG sgRNAs relative to genomic cleavage position and repetitive elements. Nontargeting sgRNAs pseudo-mapped with 5 bp spacing.
Figure 22B:
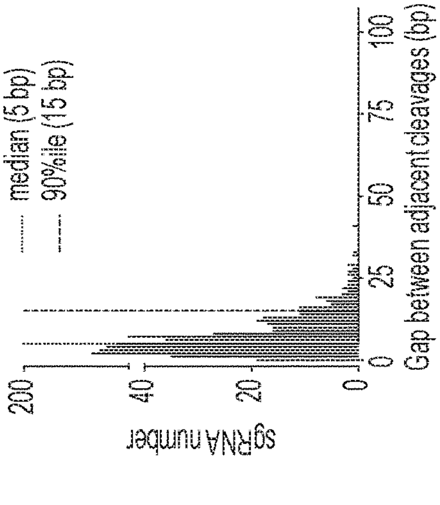
Figure 22C:
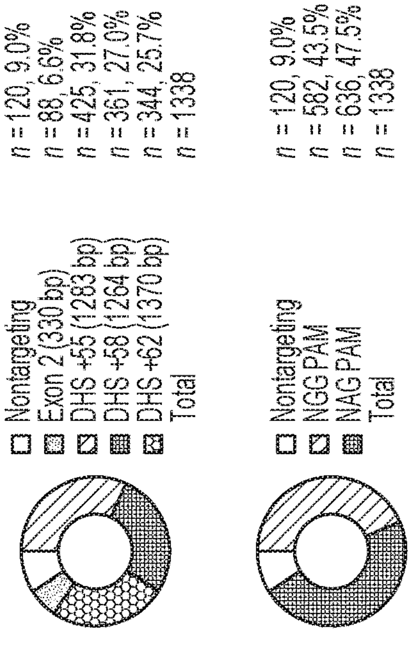
Figure 22D:
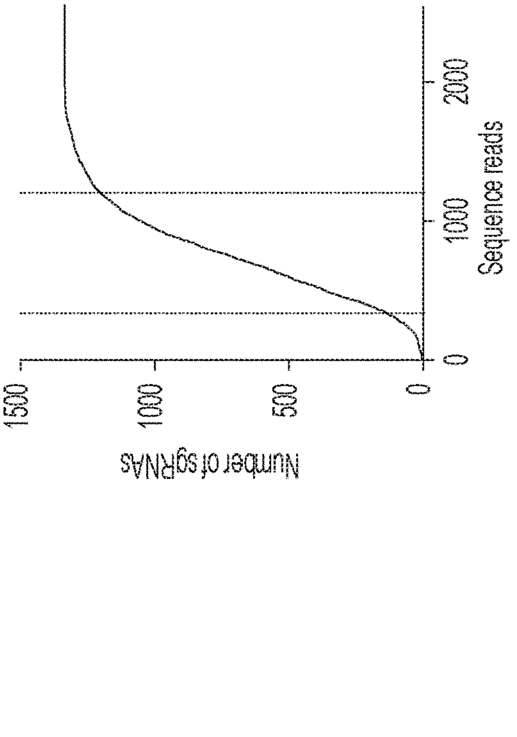
Figure 22E:
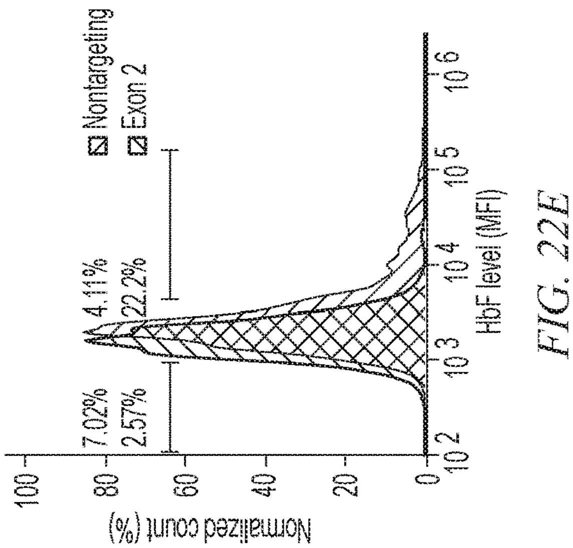
Figure 22G:
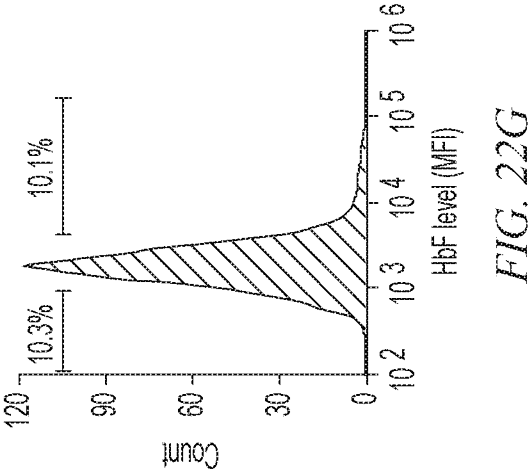
Figure 22H:
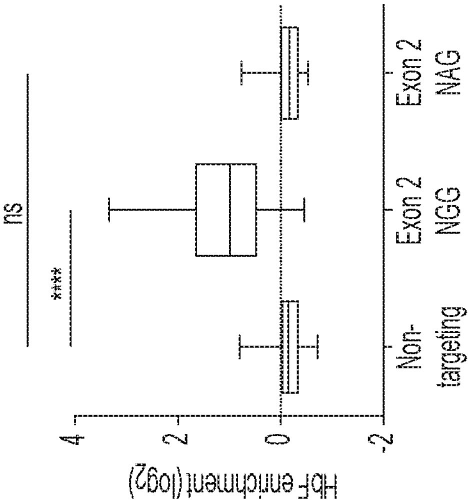
Figure 22F:
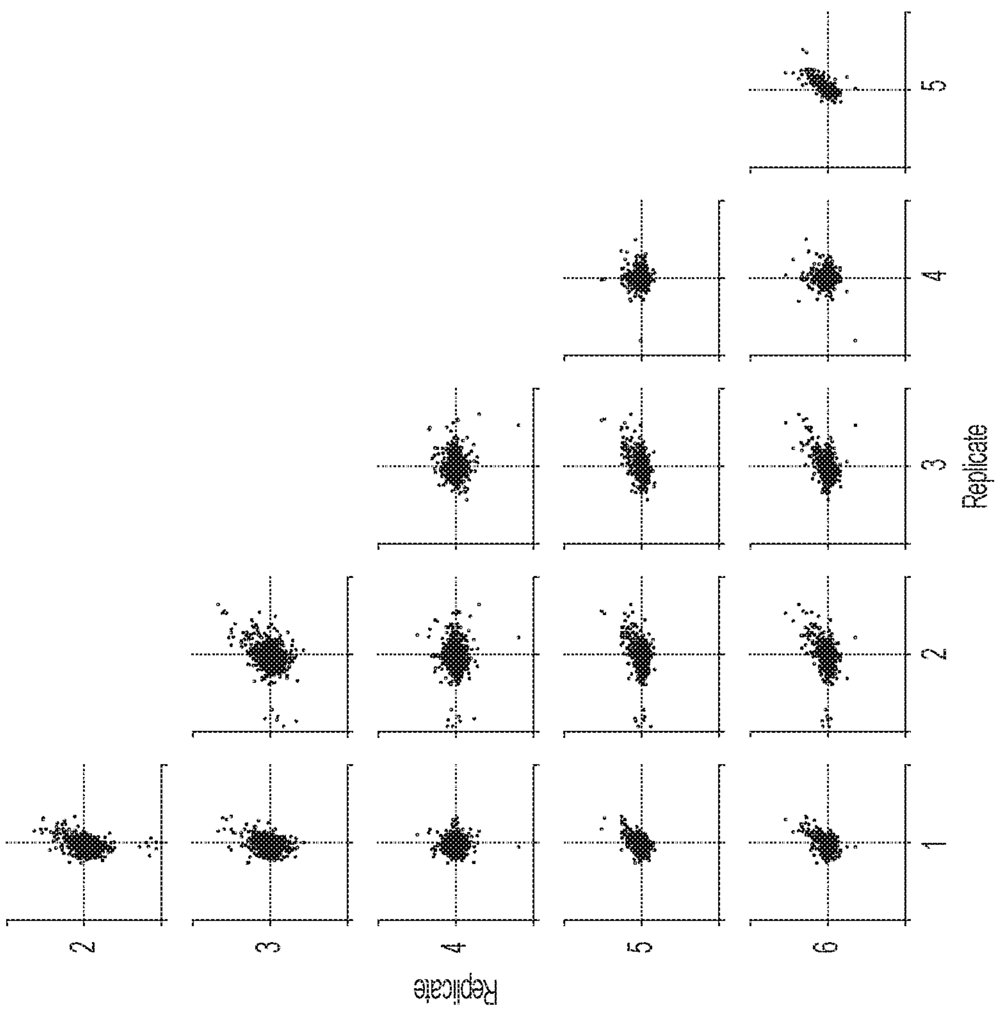
Figure 22I:
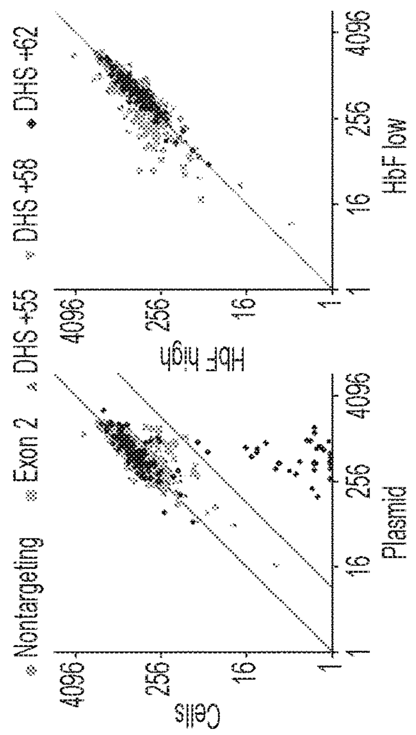
Figure 22J:
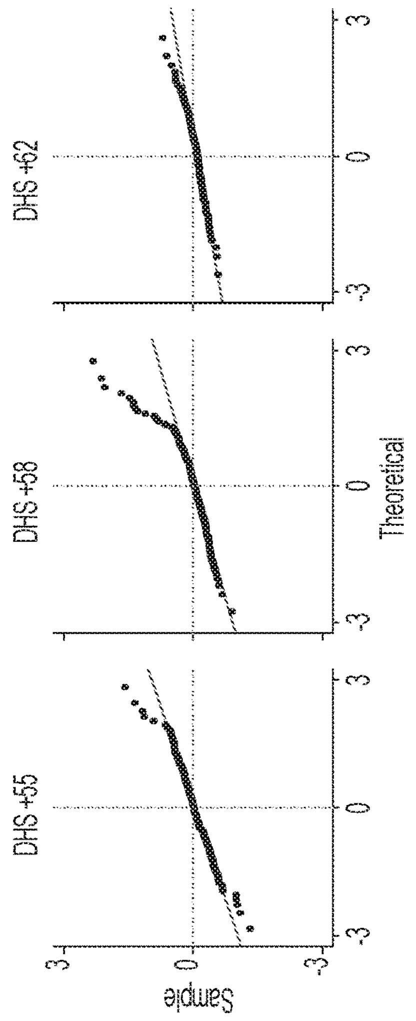
Figure 22K:
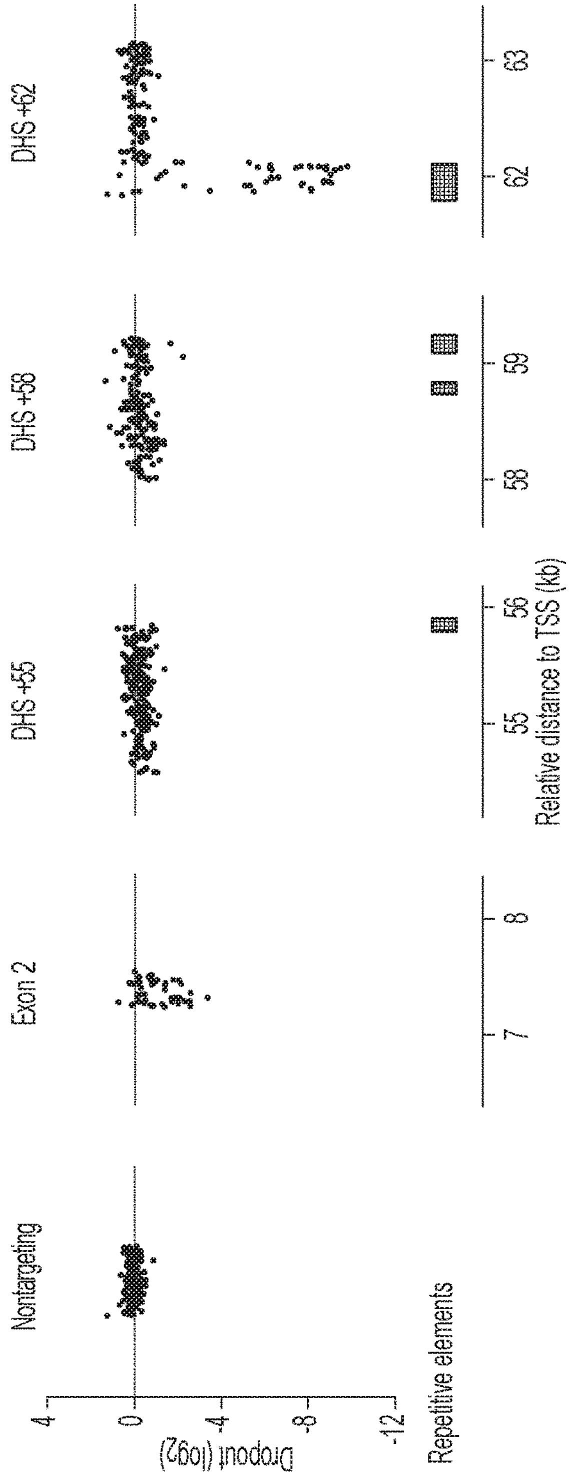

All possible sgRNAs within the human BCL11A composite enhancer DHSs were designed (FIG. 2*a*-*d*) as restricted only by the presence of the SpCas9 NGG protospacer adjacent motif (PAM), which restricts cleavage at an average ⅛ frequency at each genomic position (considering presence on plus and minus strands). The NGG PAM restricted sgRNAs had a median adjacent genomic cleavage distance of 4 bp and 90th percentile of 18 bp (FIG. 2*d*), which indicated that this strategy could approach saturation mutagenesis in situ. NAG may act as an alternate PAM for SpCas9, albeit with lower efficiency. Applicants also designed sgRNAs restricted by the NAG PAM (FIG. 2*b*). Applicants included 120 nontargeting sgRNAs as negative controls as well as 88 sgRNAs tiling exon-2 of BCL11A as positive controls (FIG. 16*e*). The total library included 1,338 sgRNAs.). The library was successfully cloned to a lentiviral vector. The basic experimental schema was to transduce cells with the lentiviral library at low multiplicity such that nearly all selected cells contained a single integrant (FIG. 2*a*). Following expansion, differentiation, sorting by HbF level, genomic DNA isolation, and deep sequencing of integrated sgRNAs, an HbF enrichment score was calculated for each sgRNA by comparing its representation in HbF-high and HbF-low pools (FIG. 7).

Figure 2E:
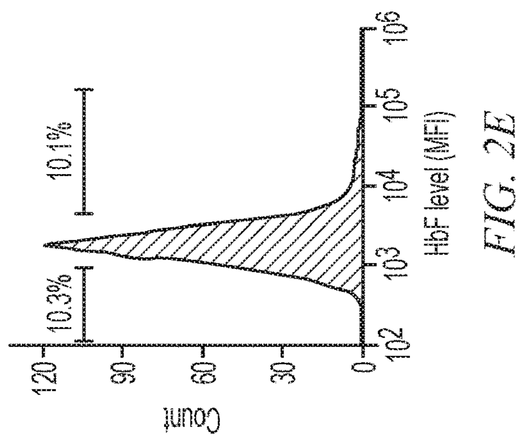
FIG. 2*e*, HbF sort of library transduced cells.
Figure 2F:
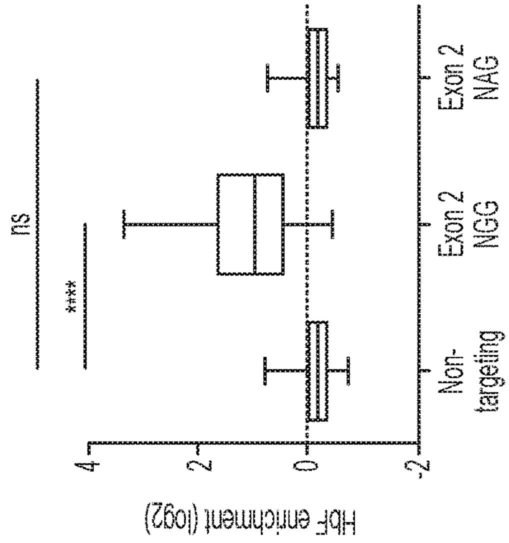
FIG. 2*f*, Control sgRNA enrichment. Boxes demonstrate 25th, median, and 75th percentiles and whiskers minimum and maximum values. **P<0.0001, ns: non-significant.
Figure 2G:
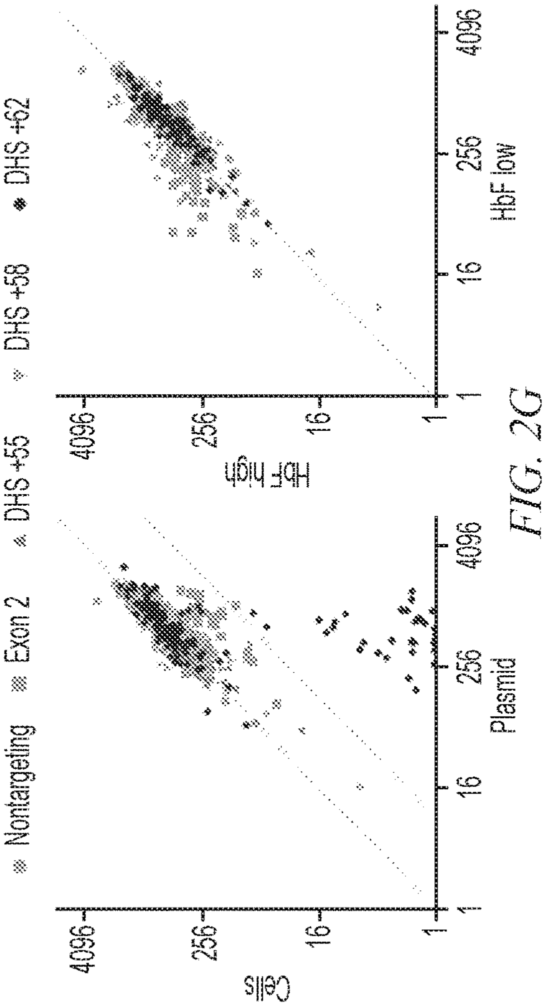

Oligonucleotides were synthesized for the sgRNAs on a microarray and the sgRNAs were cloned as a pool to a lentiviral vector. Deep sequencing of the lentiviral plasmid library demonstrated that 1,337 of 1,338 sgRNAs (99.9%) were successfully cloned. The representation of sgRNAs within the library showed a relatively narrow distribution, with a median of 718 and the 10% and 90% percentile ranging from 337 to 1,205 normalized reads. The basic experimental schema was to transduce cells with the lentiviral library at low multiplicity such that nearly all selected cells contained a single integrant (FIG. 2*a*). Introduction of Cas9 and an individual sgRNA targeting BCL11A exon-2 produced cells with elevated HbF expression, indicating loss of BCL11A function and resultant derepression of BCL11A's target γ-globin. Therefore, Applicants transduced HUDEP-2 cells stably expressing SpCas9 with the pooled library of BCL11A enhancer targeting sgRNAs. Applicants initially expanded the cells for one week, and subsequently transferred them to erythroid differentiation conditions, for a total of two weeks of culture. Then Applicants performed intracellular staining for HbF. Fluorescence activated cell sorting (FACS) was employed to isolate HbF-high and HbF-low pools (consistent with high and low BCL11A activity respectively; FIGS. 2*a* and 2*e*. Applicants enumerated the representation of the library in each pool by deep sequencing. The enrichment of each sgRNA in the HbF-high compared to HbF-low pools was calculated as the loge-ratio of normalized reads. Applicants compared the HbF enrichment of the 120 non-targeting negative control sgRNAs and 88 coding sequence targeted positive controls for both NGG and NAG PAM restricted sgRNAs. Applicants observed equivalent representation of the nontargeting sgRNAs in the high-HbF and low-HbF pools but highly significant enrichment of the NGG sgRNA targeting exon-2 of BCL11A in the HbF-high pool, consistent with a reduction of BCL11A activity (FIGS. 2*f*, 2*g*). One nontargeting sgRNA (#0548) had an enrichment score of 0.803, while the remaining 119/120 nontargeting sgRNAs (99.2%) showed enrichment scores below 0.259. In contrast 40/48 sgRNAs targeting BCL11A exon 2 (83. 3%) showed enrichment scores above 0.259. These results indicate that the large majority of sgRNAs in the library were competent to produce indels. However, exon-2 targeting sgRNAs with NAG PAM restriction did not show significant enrichment so all the NAG restricted sgRNAs were excluded from further analysis (FIG. 2*f*).

The representation of sgRNAs in the initial plasmid pool was compared to the representation of sgRNAs in the cells at the end of in vitro culture. While the majority of the library maintained neutral representation throughout the experiment, Applicants observed a fraction of sgRNAs that were depleted, mainly among the +62 sgRNAs (FIG. 2*g*). Applicants observed that these dropout sgRNAs mapped to repetitive elements within the genome, in particular to a SINE AluSq element that appears in the genome nearly 100,000 times.

Initial design of sgRNAs did not include prediction of off-target cleavage to maximize the resolution of target mutagenesis. Applicants removed from subsequent analysis 35 of 582 (6.0%) NGG PAM sgRNAs with final representation $<2^{-3}$ since these indicated likely BCL11A-independent effects of genomic disruption (FIG. 2*g*).

Figure 2H:
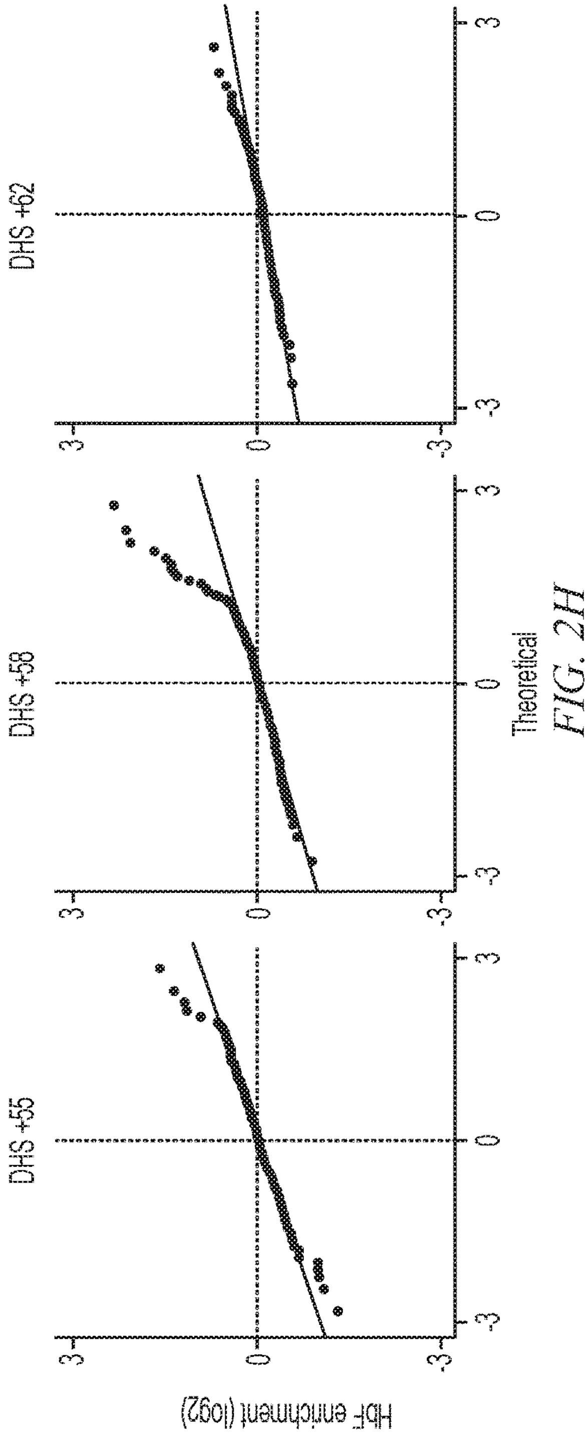
FIG. 2*h*, Quantile-quantile plots of sgRNA enrichment scores.
Figures 3A, 3B:
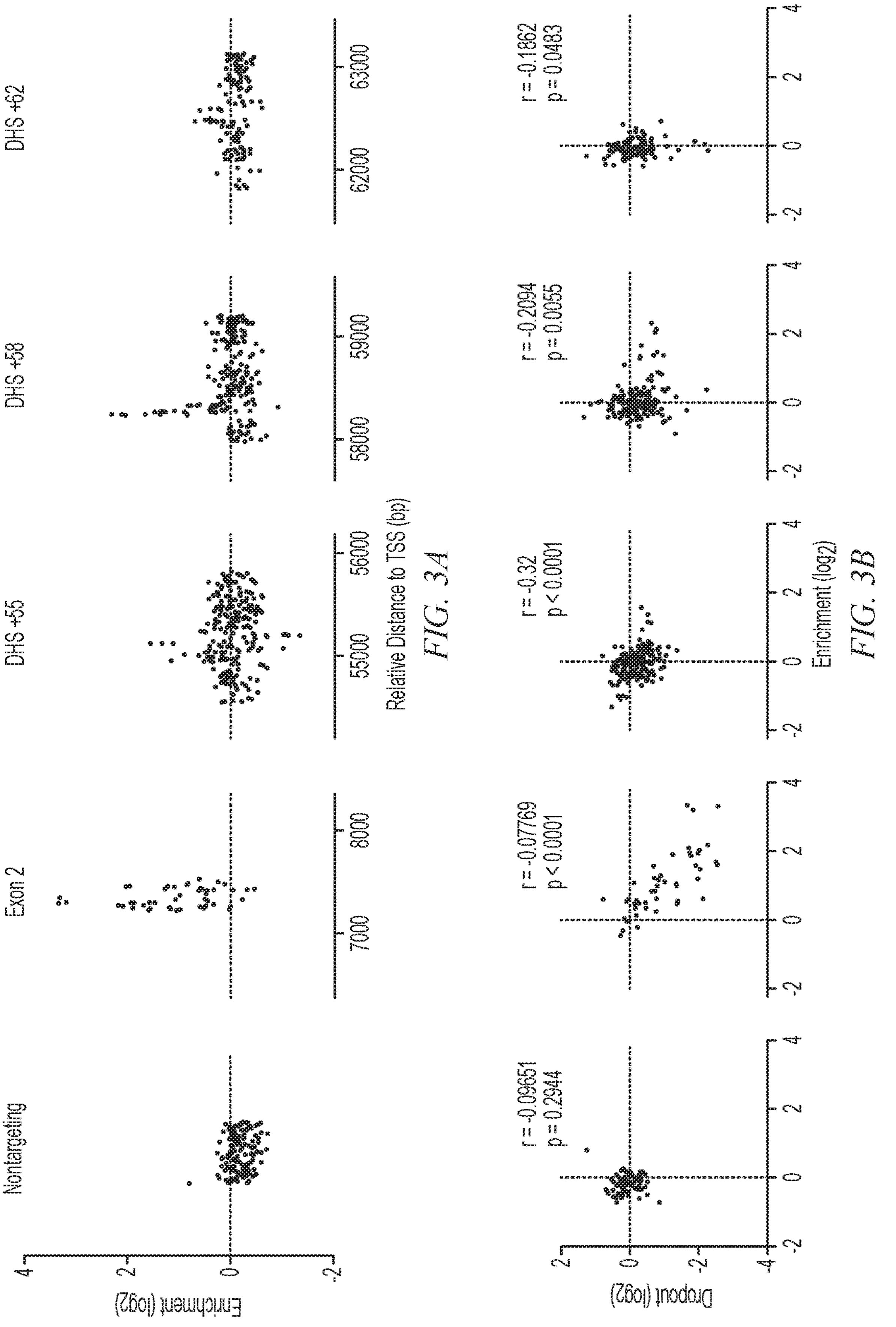

The majority of enhancer targeting sgRNAs showed no significant enrichment or depletion from the HbF-high pool (FIGS. 2*g*, 2*h*). Applicants observed a number of sgRNAs with HbF enrichment at each of the DHSs as well as some with HbF depletion at +55 (FIG. 2*h*). Applicants mapped the enrichment score of each sgRNA to its predicted position of genomic cleavage (FIG. 3*a*). The enriching sgRNAs co localize to discrete genomic positions. For example, Applicants observed a cluster of sgRNAs at +62 with modest enrichment, a cluster at +55 with moderate enrichment (as well as adjacent clusters with depletion), and a cluster at +58 with marked enrichment. Of note, Applicants observed 10 sgRNAs at +58 with cleavage positions within 42 bp each with enrichment scores exceeding 0.99, the median enrichment score of BCL11A exon-2 targeting sgRNAs.

Exon-2 targeted sgRNAs showed a linear correlation between enrichment and dropout from the screen, indicating sgRNAs that result in complete knockout of BCL11A lead to a reduced rate of cellular accumulation inseparable from magnitude of HbF derepression (FIG. 3*b*). For example, Applicants did not observe any exon-2 targeting sgRNAs with potent HbF enrichment that lacked substantial dropout. In contrast, the sgRNAs at +58 associated with marked HbF enrichment showed blunted impact on dropout (FIG. 3*b*). This finding could be consistent with a low residual level of BCL11A adequate to promote cellular accumulation but inadequate to suppress HbF.

Figure 8A:
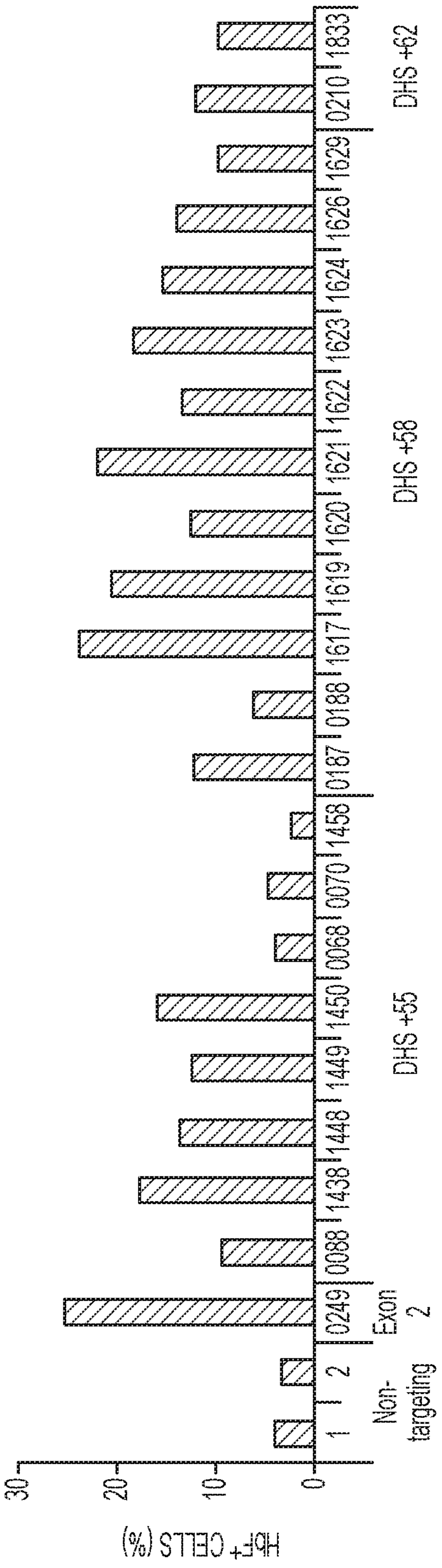
FIGS. 8A-8B shows validation of the enhancer screen.
Figure 9A:
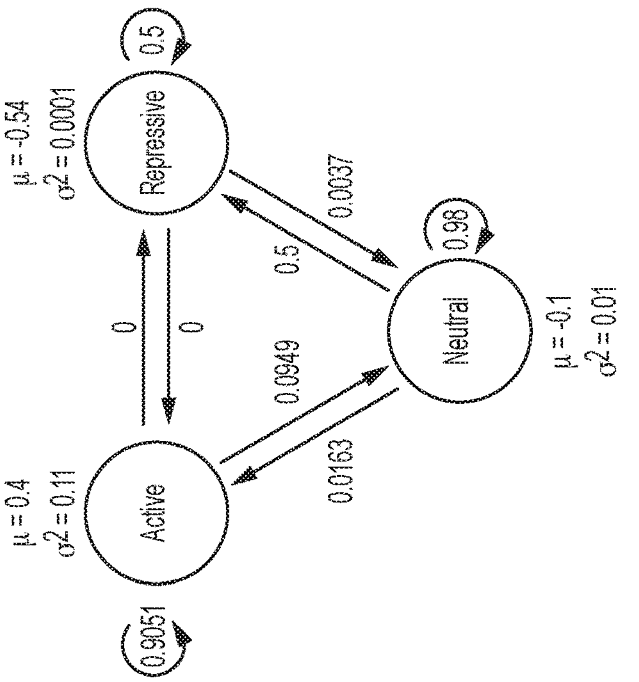
FIGS. 9A-9B shows functional assessment of enhancer sequences.
Figure 23A:
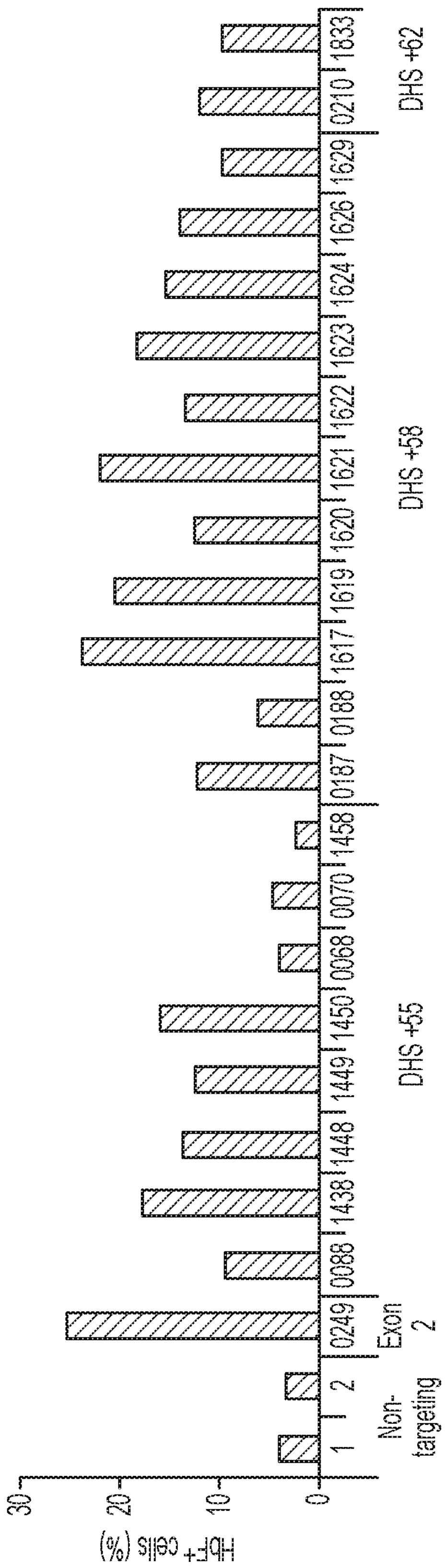
FIG. 23A-23C shows validation of the enhancer screen. a, HbF fraction in HUDEP-2 cells transduced in arrayed format with 24 sgRNAs from all 5 mapping categories with enrichment scores ranging from the highest to the lowest in the screen. b, Correlation between HbF enrichment score from pooled sgRNA screen and HbF fraction by arrayed validation of individual sgRNAs in HUDEP-2 cells. c, Erythroid differentiation of primary human erythroid precursors evaluated by CD71 and CD235a surface markers, enucleation frequency (CD235a$^+$ Hoescht 33342), and morphology by May-Grunwald-Giemsa staining.
Figure 23B:
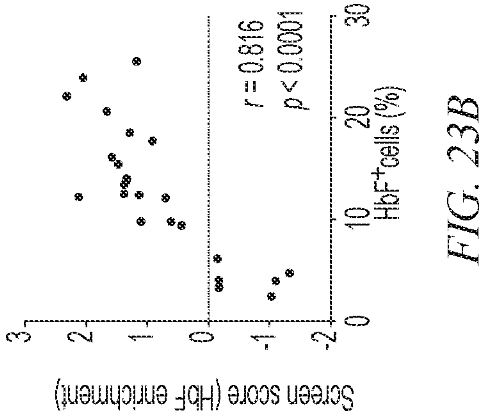
Figure 23C:
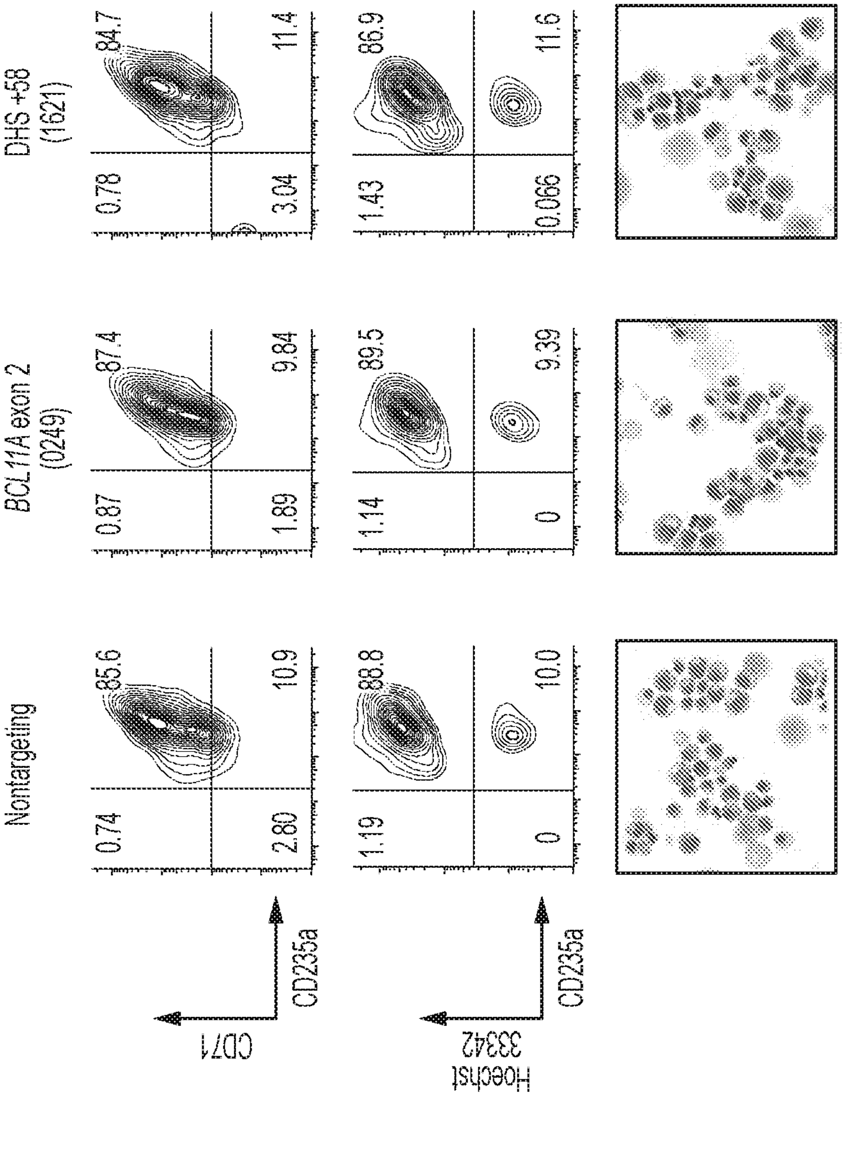
Figure 24B:
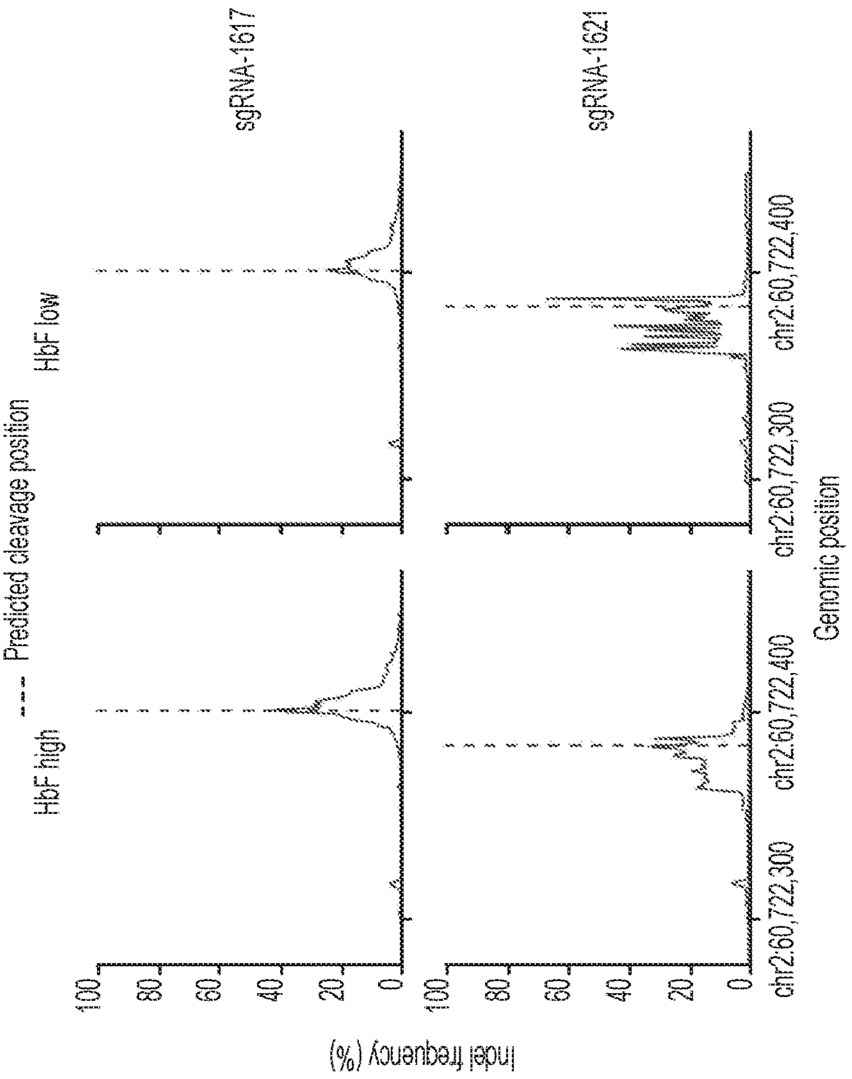
FIG. 24A-24B shows functional assessment of enhancer sequences. a, Topology of the Hidden Markov model (HMM) used to infer the three functional enhancer states (Active, Repressive, and Neutral). The emission probabilities of HbF enrichment scores from each state were modeled as Gaussian distributions (the values of $\mu$ and $\sigma^2$ are shown). The transition probabilities (arrows) are displayed. b, Frequency distribution of indels from HUDEP-2 cells exposed to Cas9 and individual sgRNAs, sorted into HbF-high and -low pools, and subjected to deep sequencing of the target site. Indels calculated on a per nucleotide basis throughout an amplicon surrounding the sgRNA-1617 and -1621 cleavage sites (dotted lines). An indel enrichment ratio was calculated by dividing normalized indel frequencies in the HbF-high pool by those in the HbF-low pool.
Figure 24A:
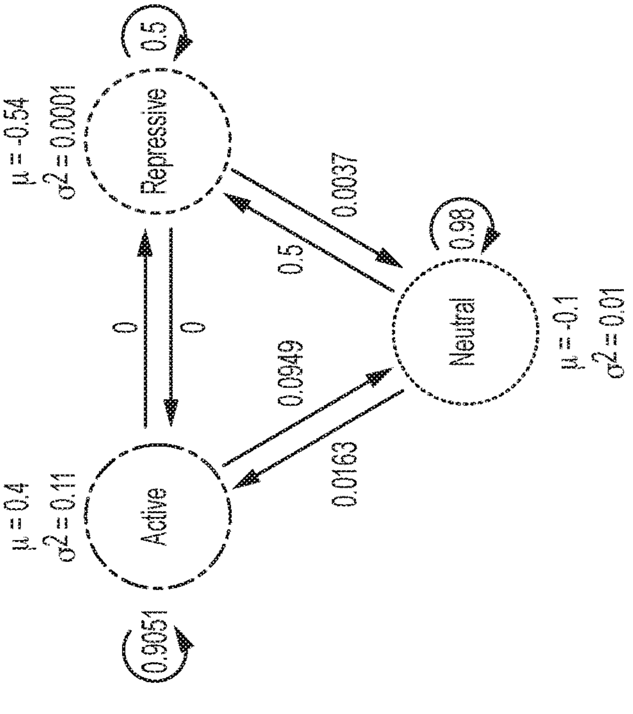
Figure 25A:
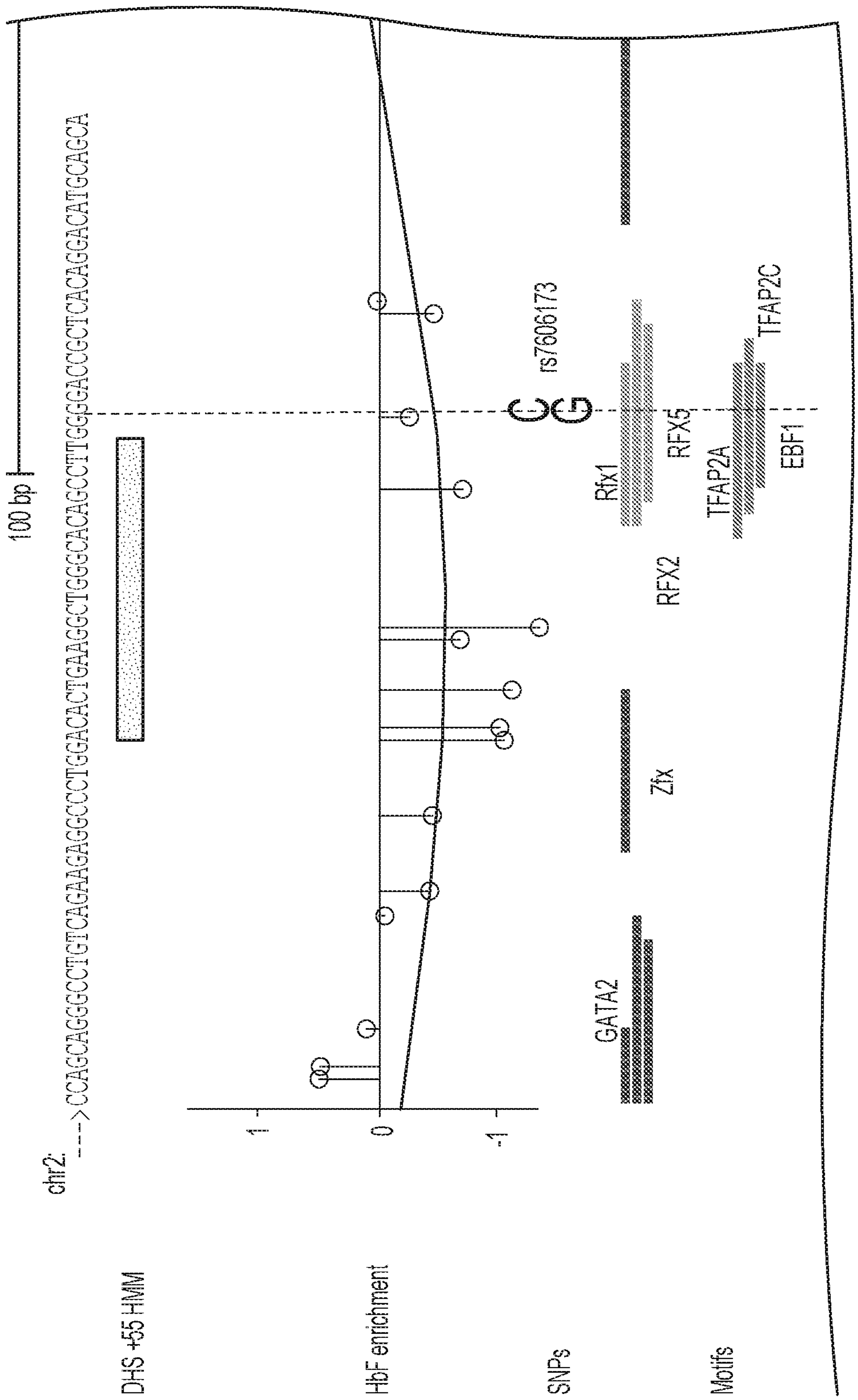
FIG. 25A-25C shows functional cores of the BCL11A enhancer. a-c, 200 bps at the functional cores of DHSs h+55, h+58, and h+62 defined by HMM states (Active red, Repressive green). HbF enrichment scores shown by gray lines and circles. HbF indel enrichment per nucleotide based on amplicon genomic sequencing of sorted cells exposed to either sgRNA-1617 (top) or -1621 (bottom). Common SNPs (MAF>1%) shown with dotted lines with HbF-low allele in blue and HbF-high allele in red; no common SNPs present at h+58 region. JASPAR motifs ($P<10^{-4}$) depicted in black except for those with allele-specific significance depicted by allelic color. Selected motifs annotated by TF based on known erythroid-specific function or genomic position. Motif LOGOs at key positions with motif scores $P<10^{-3}$ as described in text. Dotted boxes show regions of highest HbF enrichment score at each core with underlying predicted motifs. Orthologous sequences listed from representative primates and nonprimates of distributed phylogeny. PhyloP (scale from −4.5 to 4.88) and PhastCons (from 0 to 1) estimates of evolutionary conservation among 100 vertebrates.
Figure 25A:
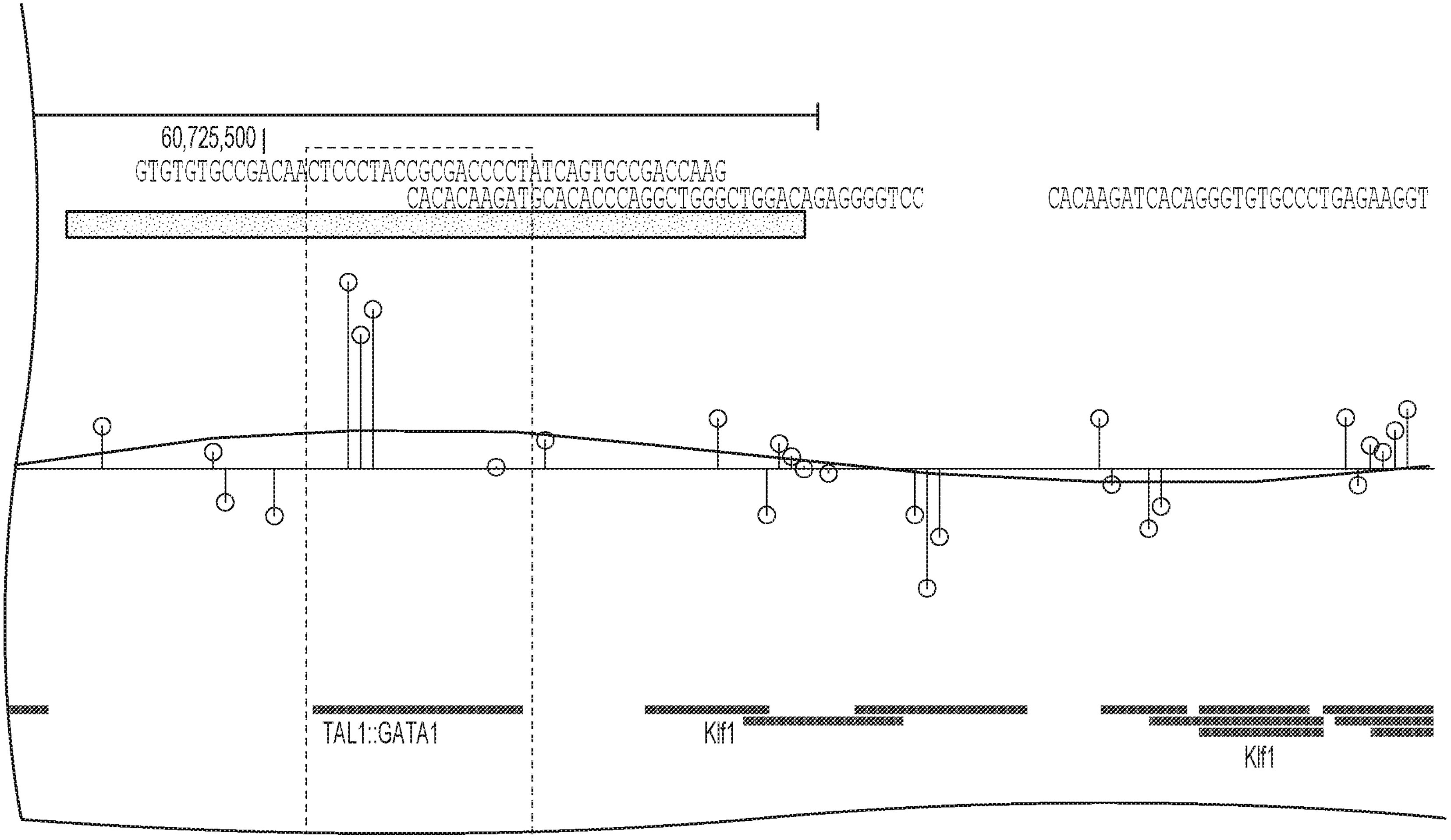
Figure 25A:
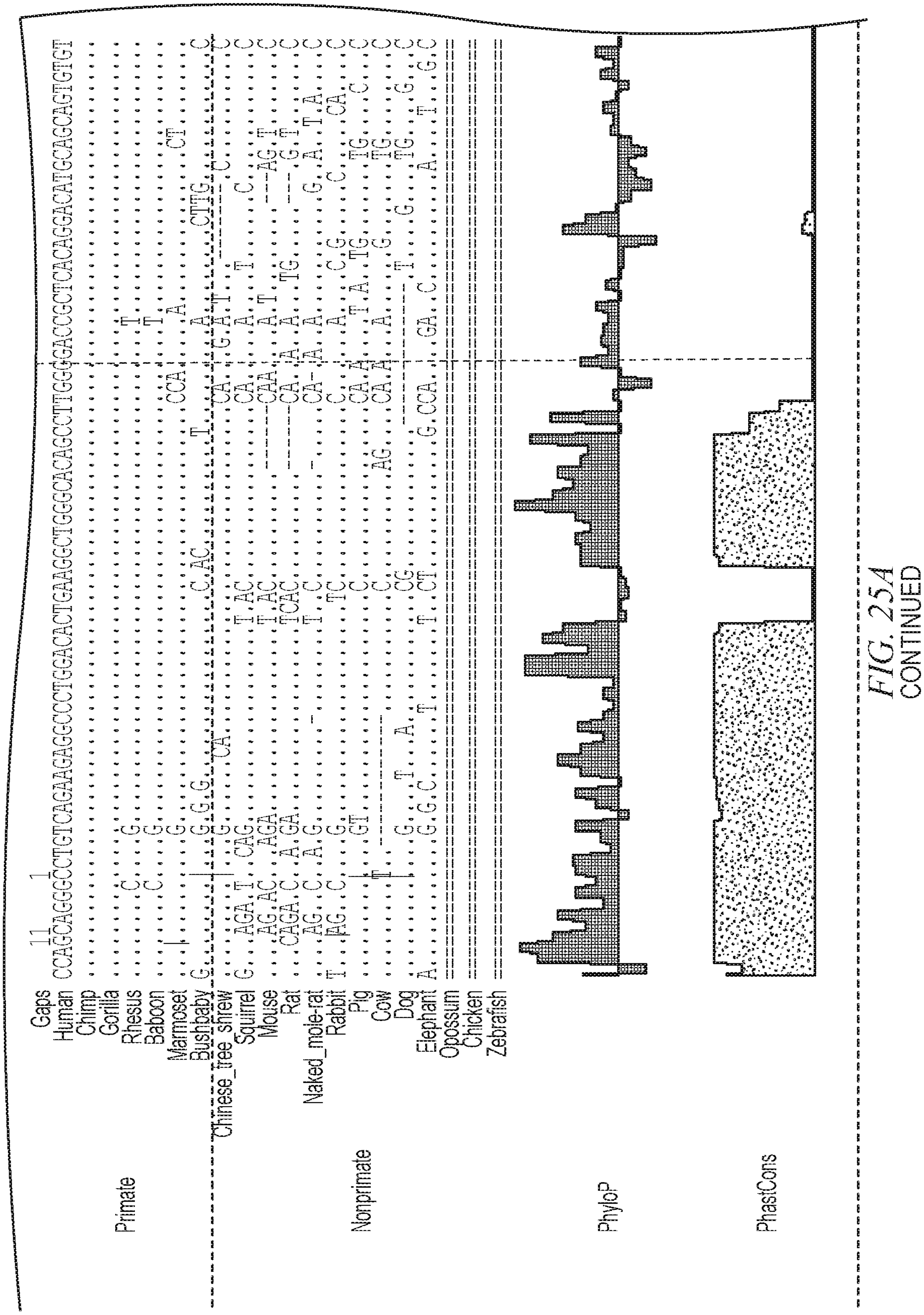
Figure 25A:
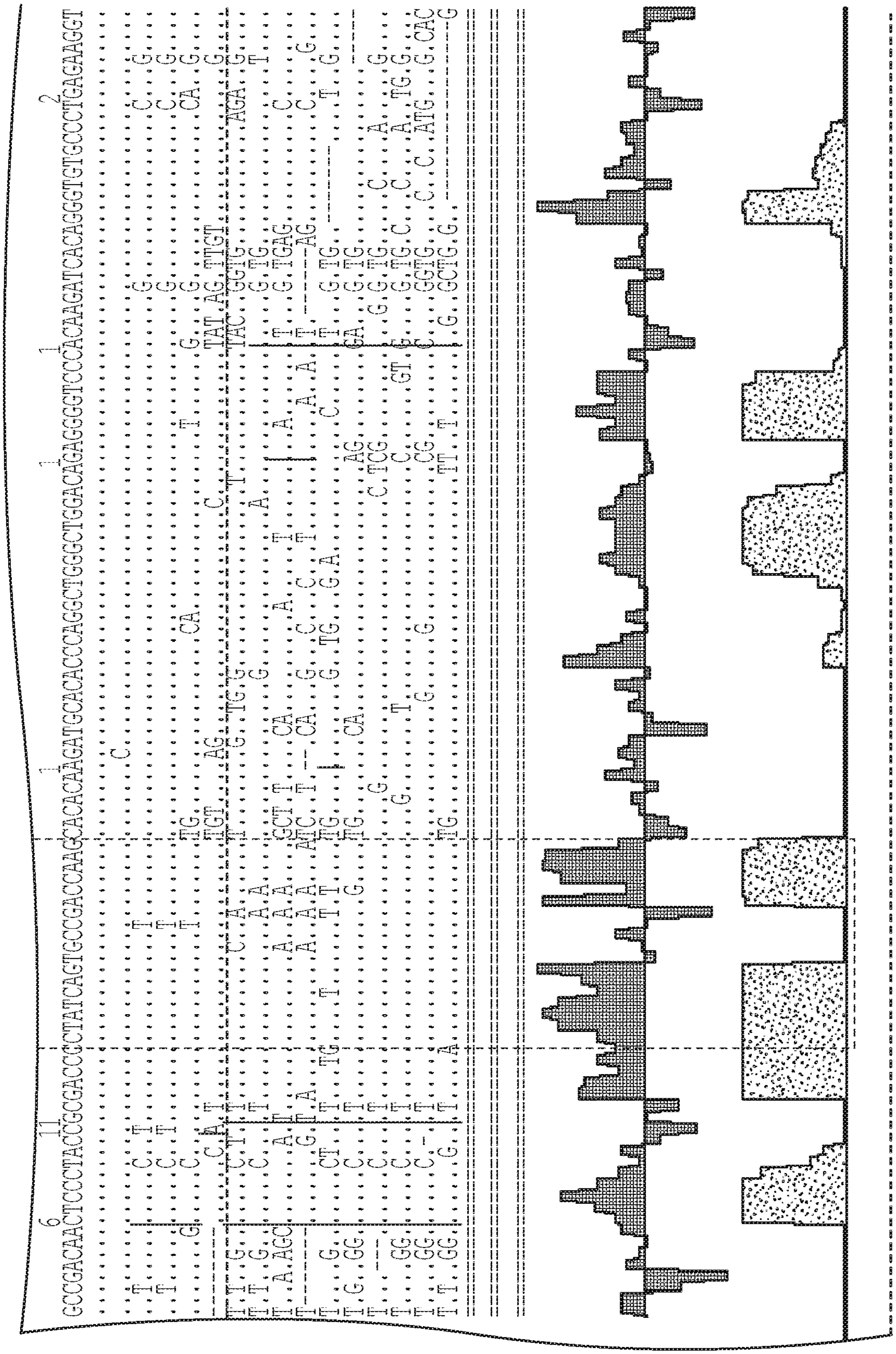
Figure 25B:
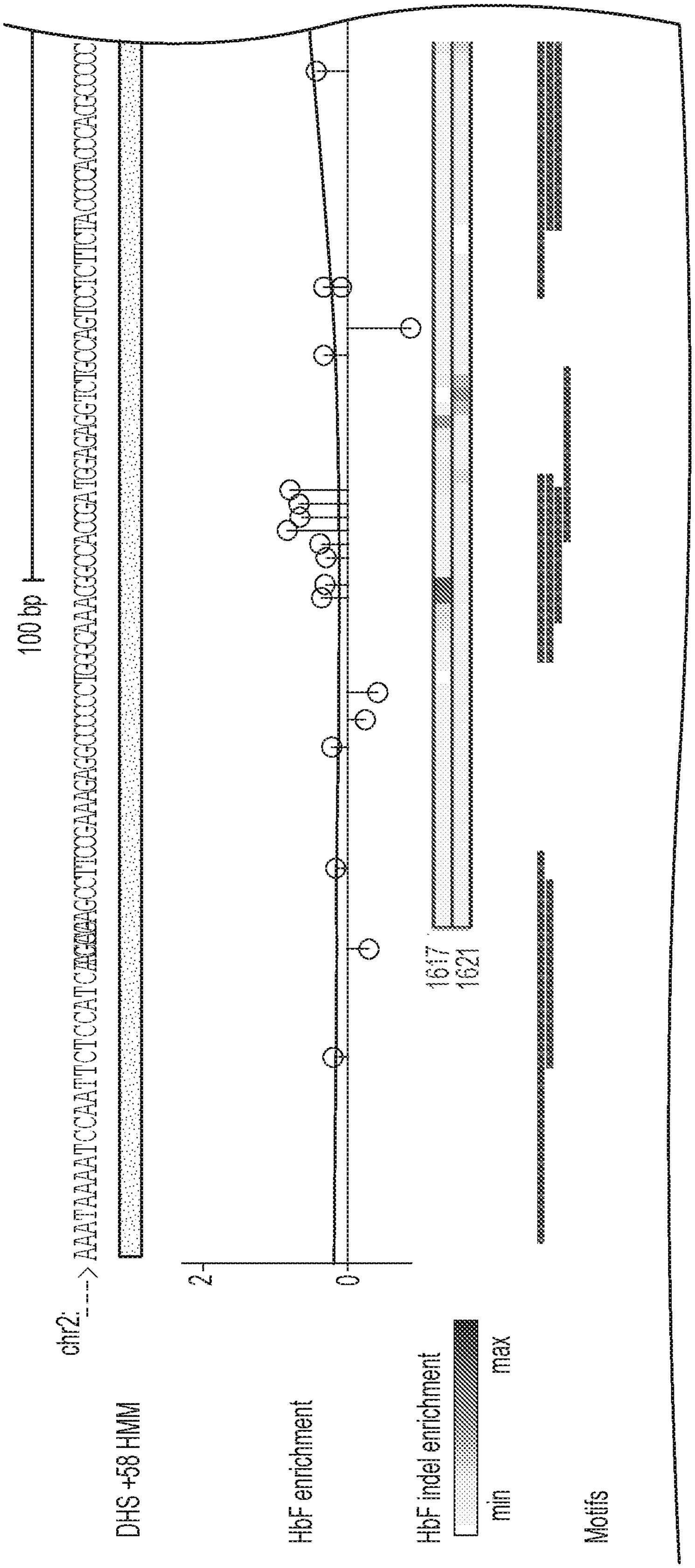
Figure 25B:
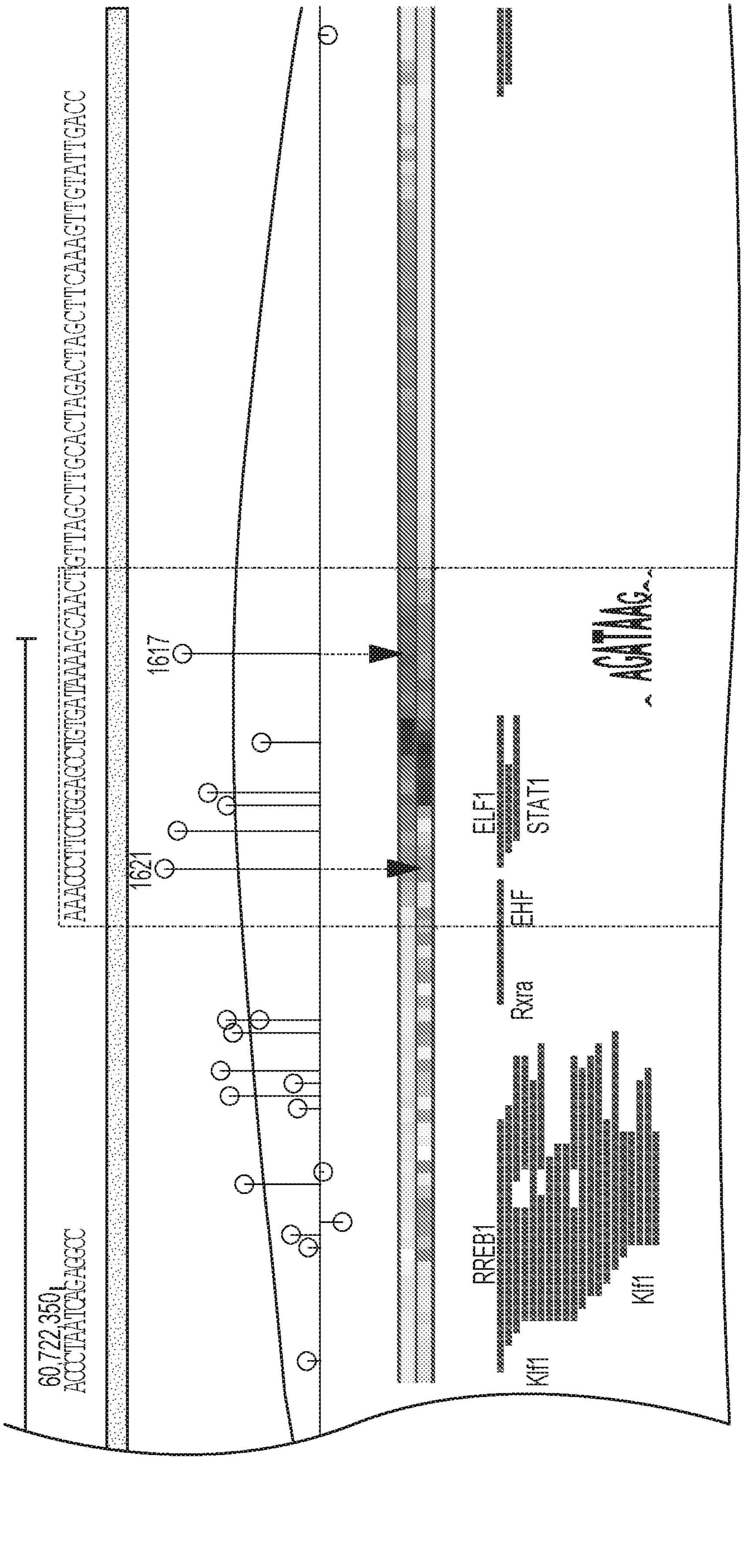
Figure 25B:
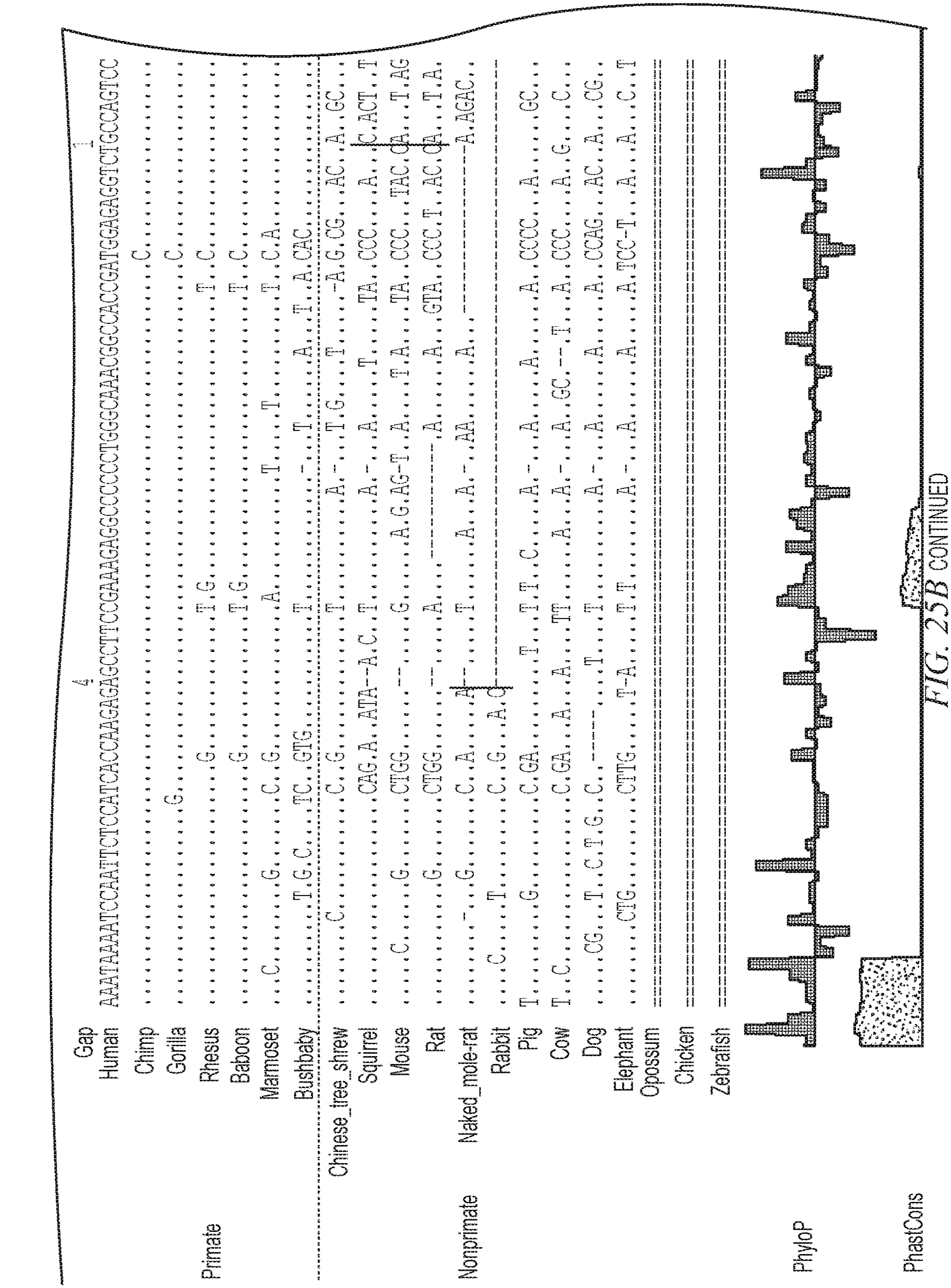
Figure 25B:
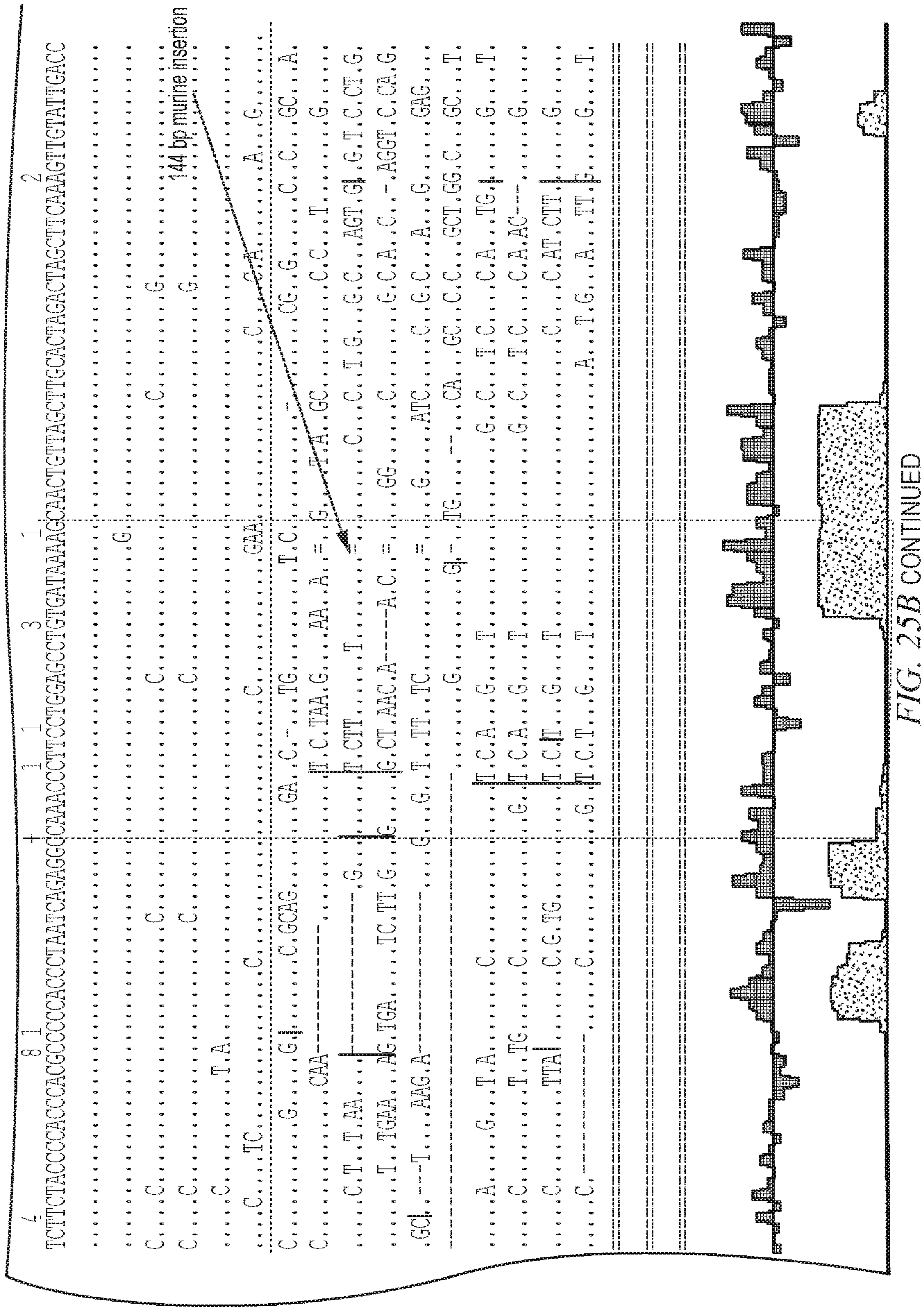
Figure 25C:
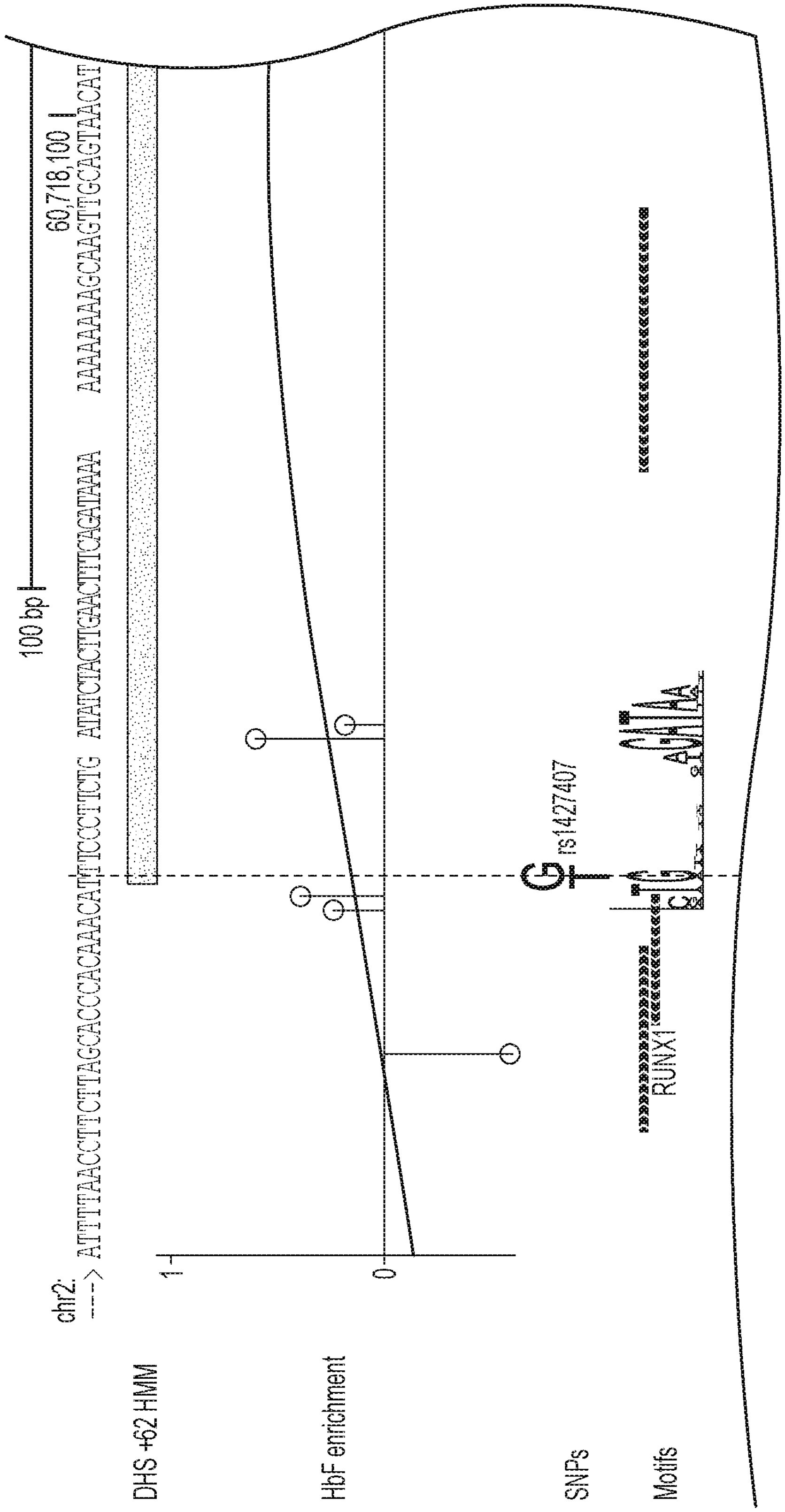
Figure 25C:
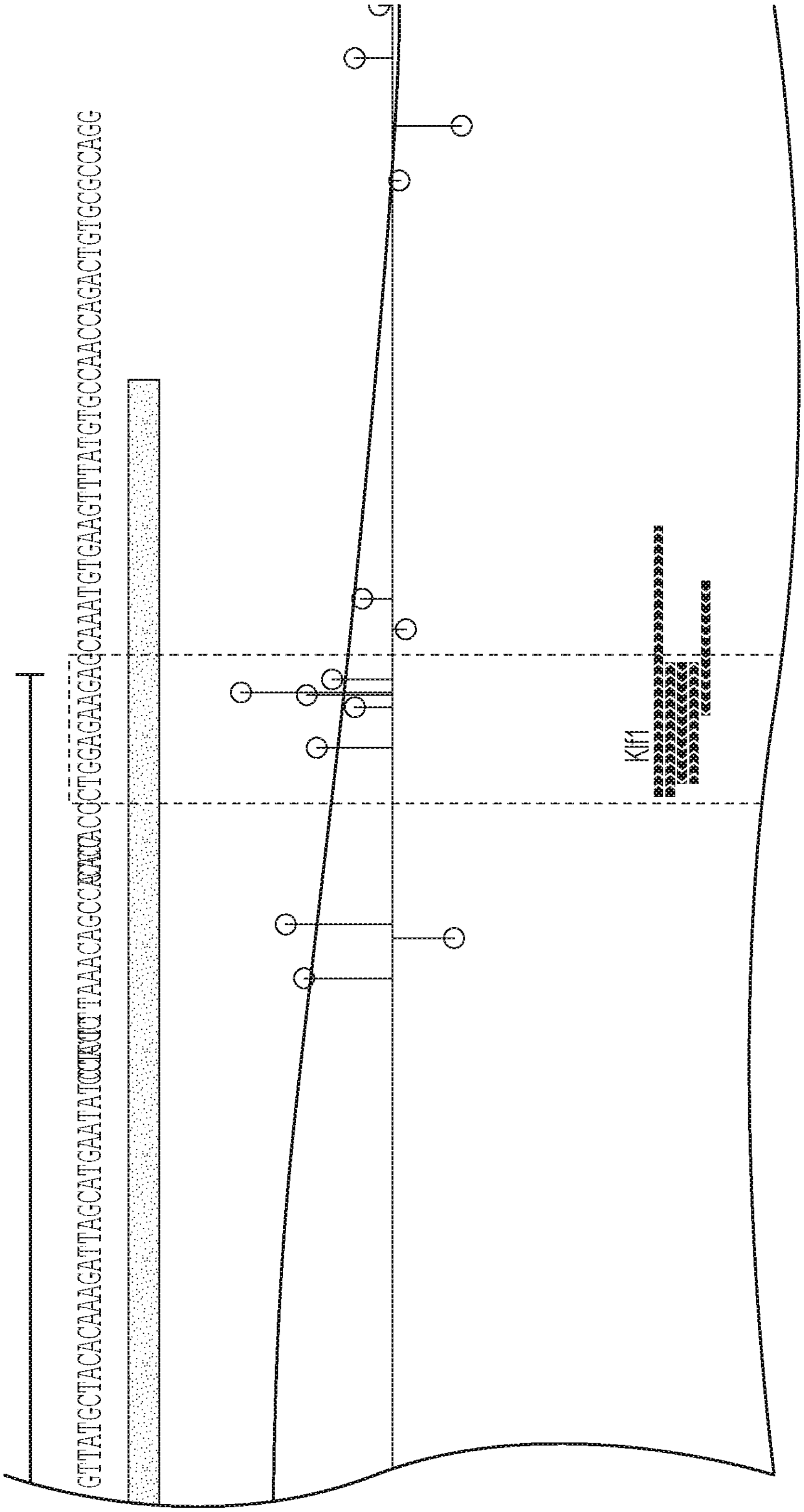
Figure 25C:
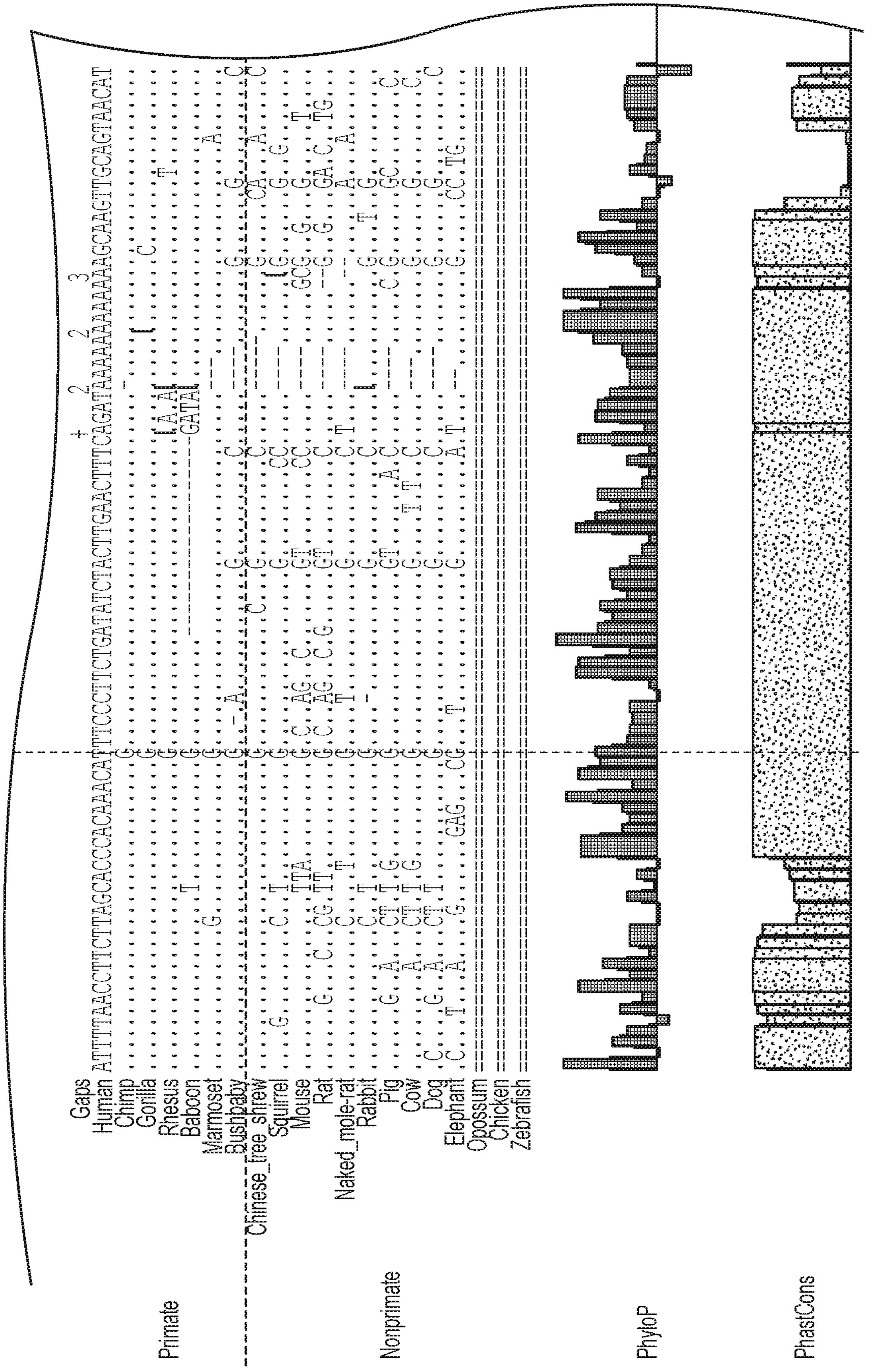
Figure 25C:
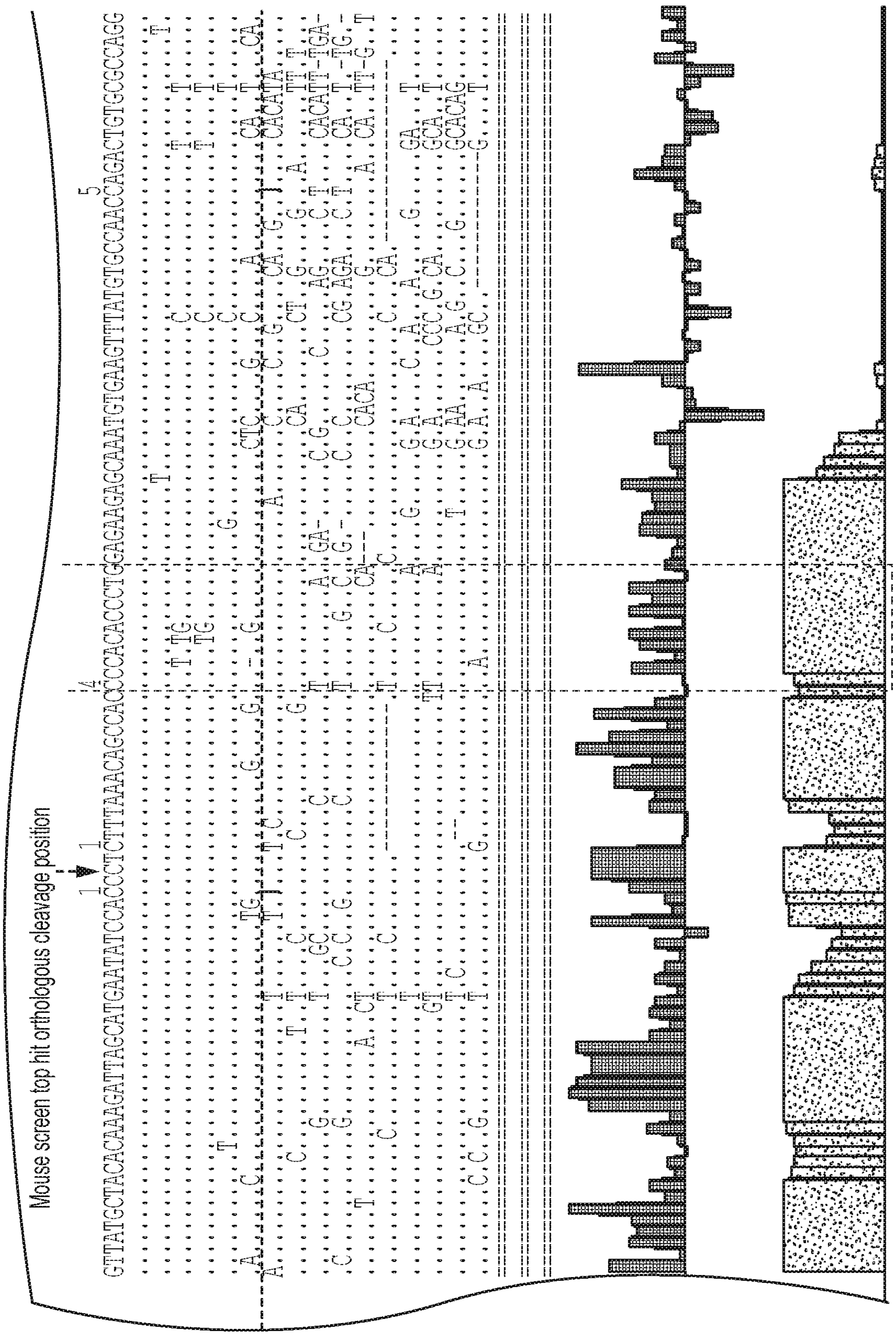
Figure 26A:
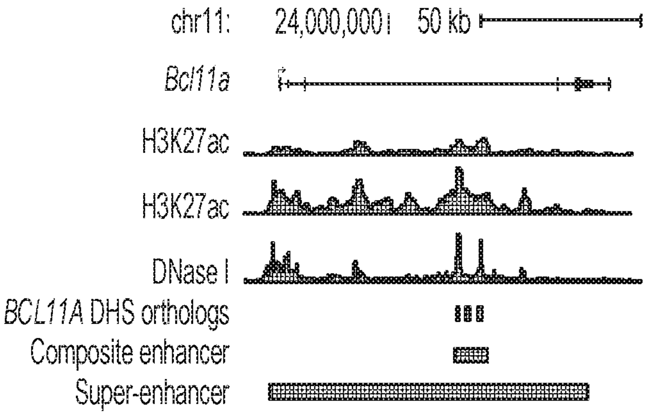
FIG. 26A-26K shows the tiled pooled in situ CRISPR-Cas9 Bcl11a enhancer screen. a, Schematic of the mouse Bcl11a locus (mm9, transcription from left to right) with erythroid chromatin marks (top, dark blue H3K27ac from Kowalczyk et al, middle, light blue H3K27ac from Dogan et al, and bottom, black DNase I from Bauer et al) and regions of primary sequence homology to the human DHSs displayed. Composite enhancer as previously defined. b, Ranked enhancers in mouse erythroid precursors by H3K27ac signal intensity, with super-enhancers shaded. Super-enhancer associated genes indicated by Venn diagram. c, Strategy to knock-in by homology-directed repair the fluorescent protein mCherry into the mouse embryonic globin Hbb-y locus (encoding the εy embryonic globin chain). d, Distribution of NGG and NAG PAM sgRNAs mapped to genomic cleavage position with vertical lines representing cleavage sites for sgRNAs mapped to plus and minus strands. e, Distance to adjacent genomic cleavage position for NGG (left) and NAG (right) PAM sgRNAs. f, Representation of the 1,271 NGG and NAG sgRNAs within the plasmid pool by deep-sequencing. The median was 735 normalized reads and the 10th and 90th percentiles (indicated by the vertical dotted lines) ranged from 393 to 1,240 normalized reads. g, Library composition by target sequence and PAM restriction. h, mCherry expression upon exposure to Cas9 and an individual NGG sgRNA targeting Bcl11a exon 2 in MEL εy:mCherry reporter cells. i, εy:mCherry sort of library transduced cells. j, Control sgRNA enrichment. Boxes demonstrate 25$^{th}$, median, and 75$^{th}$ percentiles and whiskers minimum and maximum values. ****$P<0.0001$. k, Enrichment scores of NGG sgRNAs between four biological replicates.
Figure 26B:
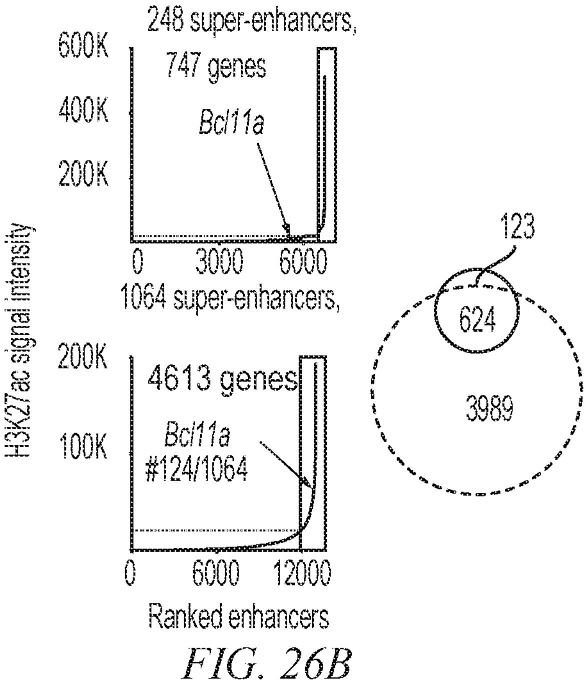
Figure 26C:
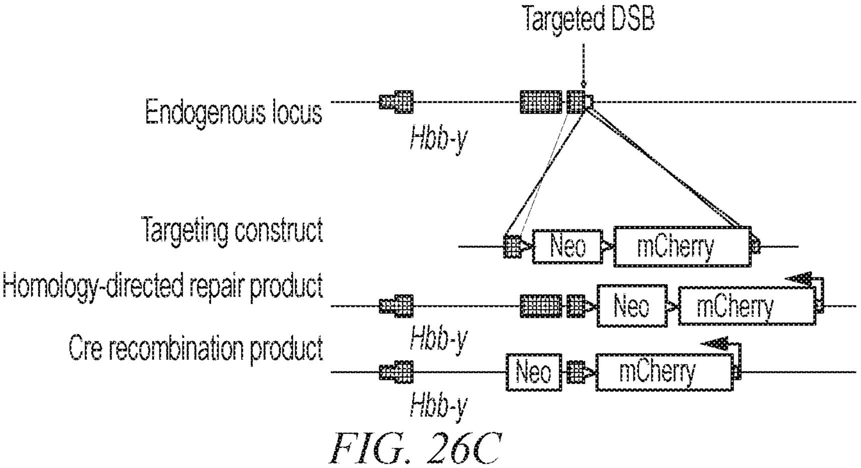
Figure 26D:
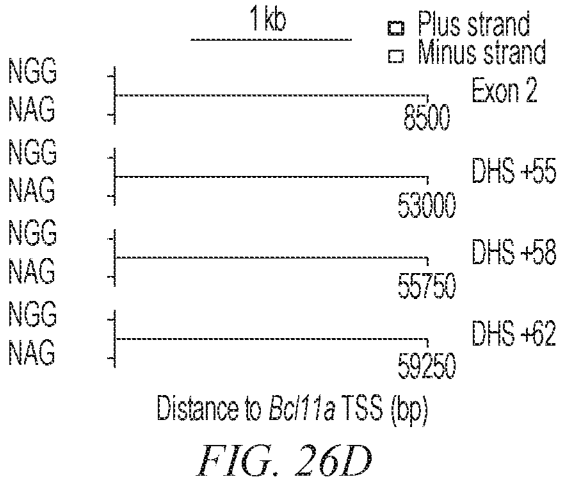
Figure 26E:
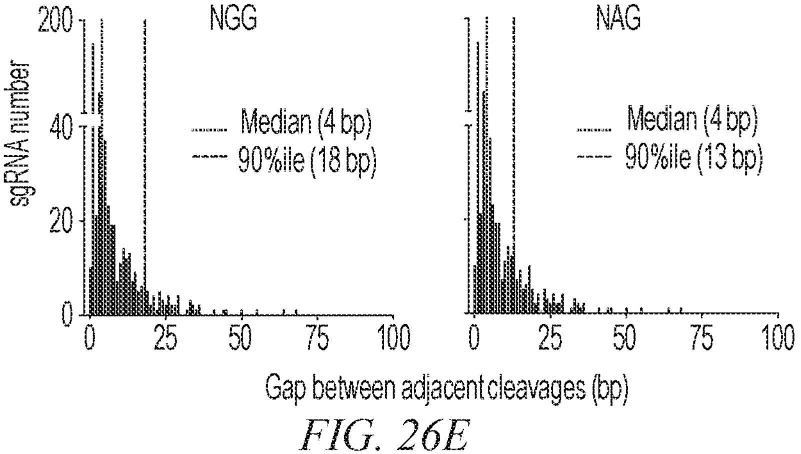
Figure 26F:
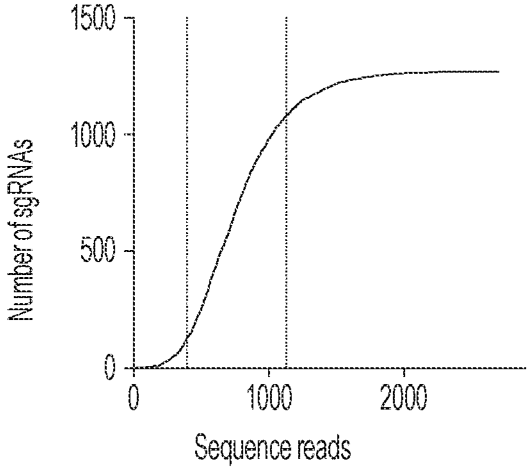
Figure 26G:
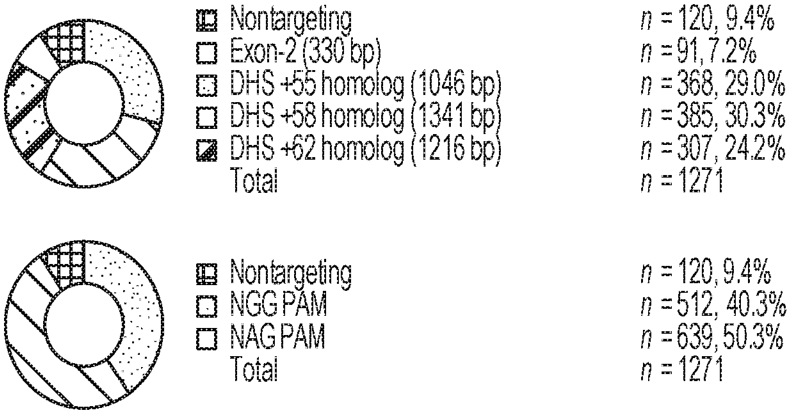
Figure 26H:
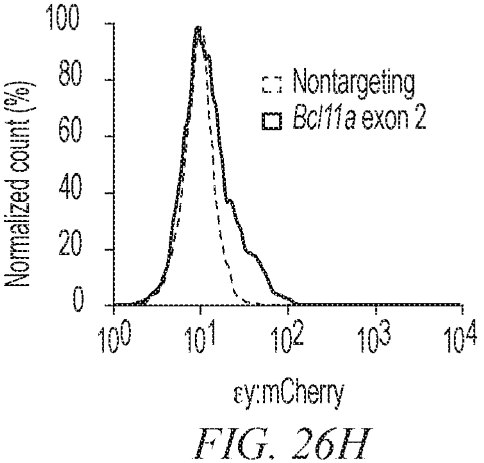
Figure 26I:
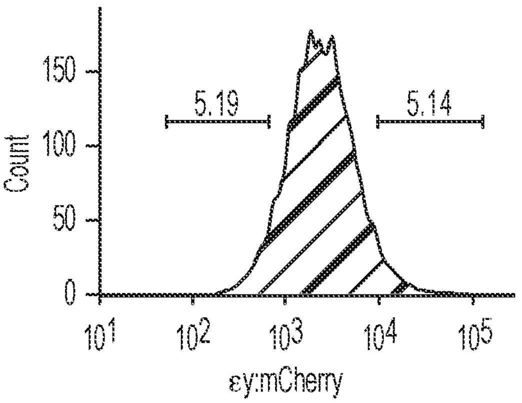
Figure 26J:
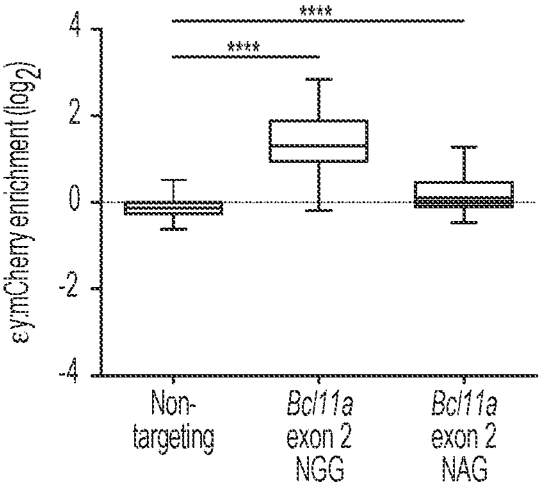
Figure 26K:
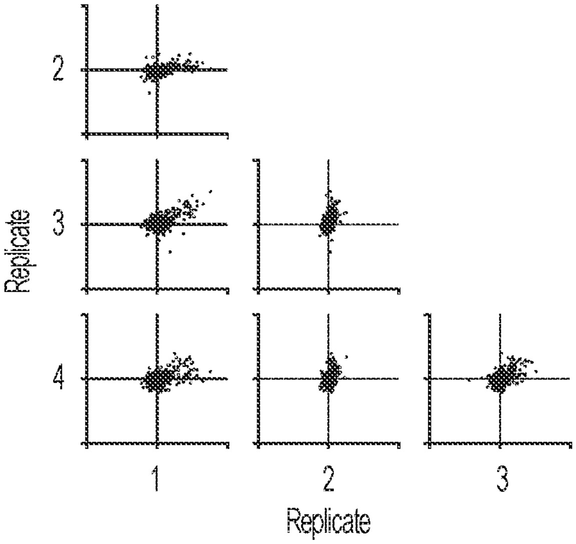
Figure 27A:
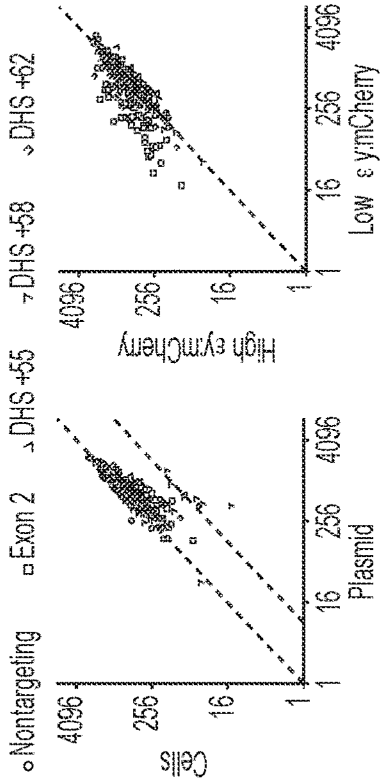
FIG. 27A-27D shows Bcl11a enhancer screen analyses. a, NGG sgRNA representation in plasmid pool and cells at conclusion of experiment (left), and in εy:mCherry-high and εy:mCherry-low pools (right), with dotted lines at x=y and x=8y. b, Quantile-quantile plots of NGG sgRNA εy enrichment scores. c, Cellular dropout scores of NGG sgRNAs relative to genomic cleavage position and repetitive elements. Nontargeting sgRNAs pseudo-mapped with 5 bp spacing. d, Correlation between cellular dropout and εy enrichment scores.
Figure 27B:
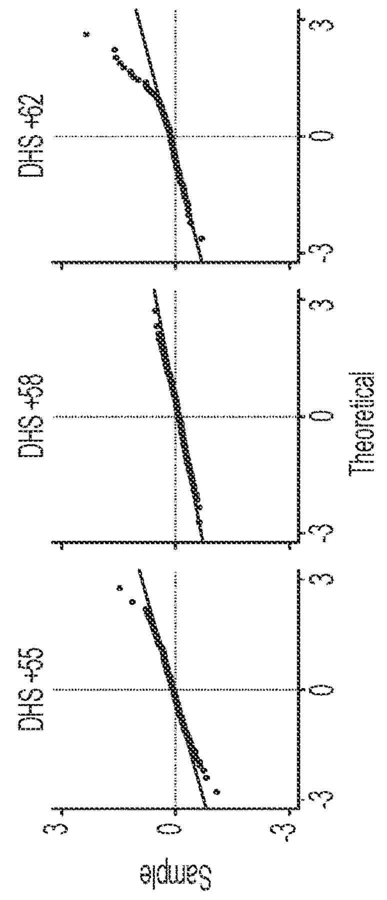
Figure 27C:
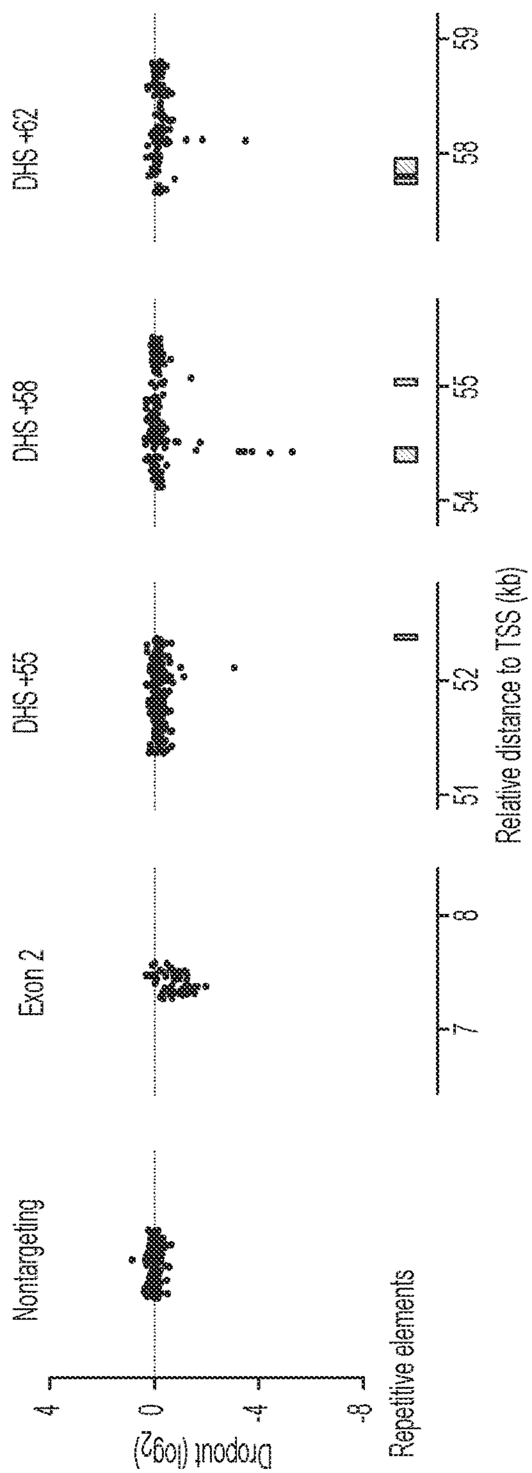
Figure 27D:
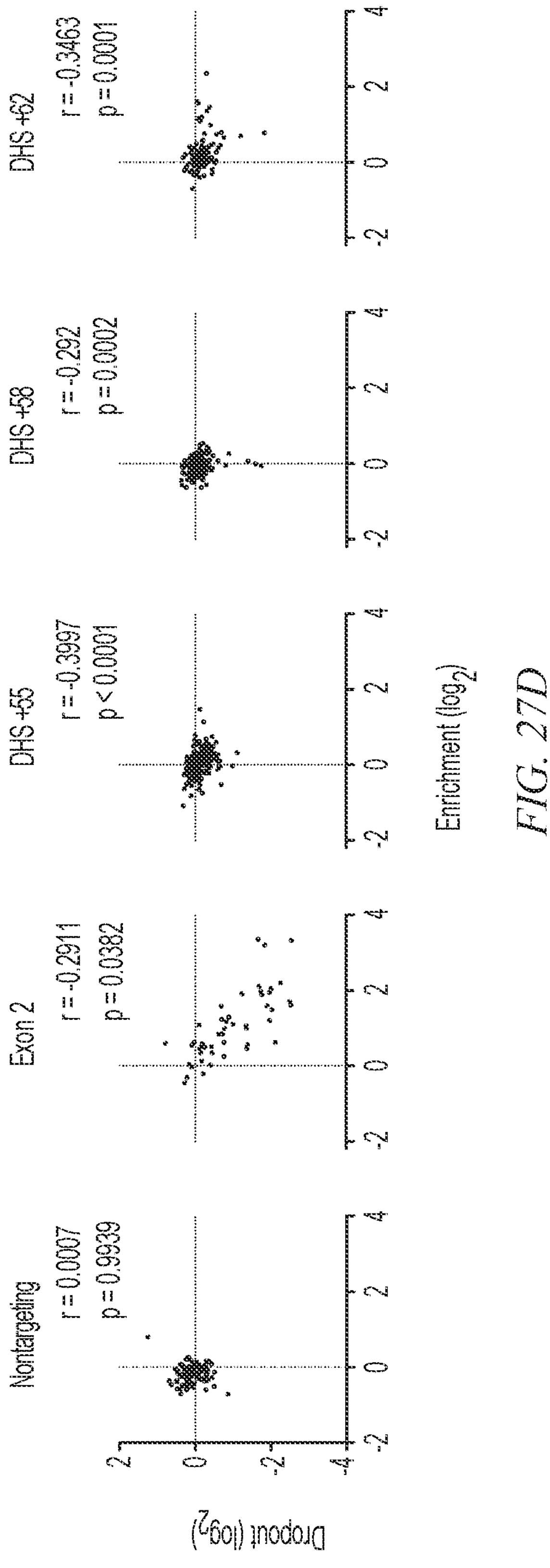
Figure 28A:
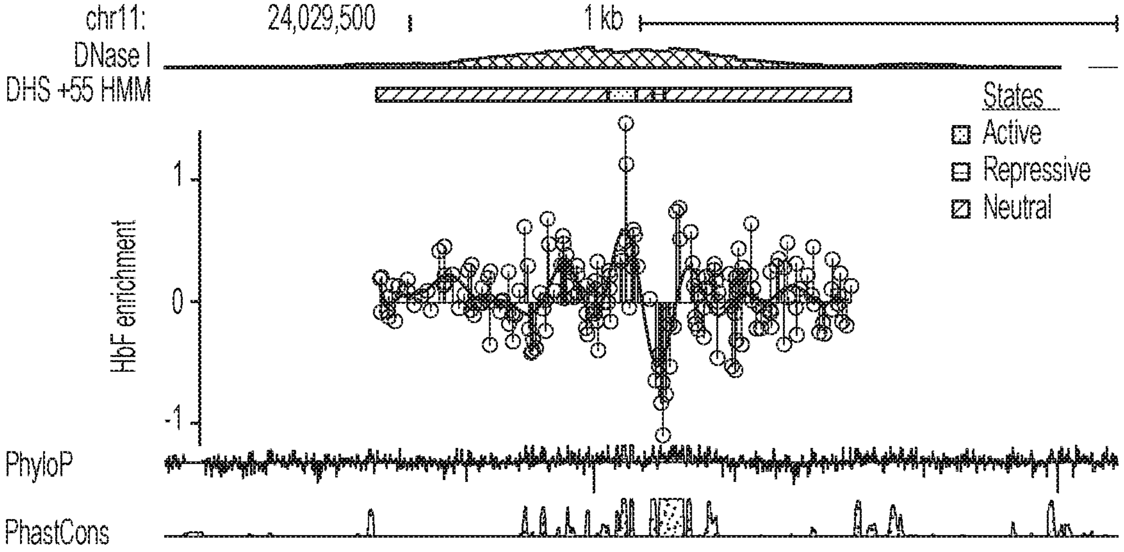
FIG. 28A-28D shows functional sequences at the Bcl11a erythroid enhancer. a-c, HMM segmentation of active functional states at m+55, m+58, and m+62 orthologs. HbF enrichment scores shown as gray lines and circles with blue line representing smoothed enrichment score. DNase I sequencing from mouse fetal liver erythroid precursors (28). PhyloP (scale from −3.3 to 2.1) and PhastCons (from 0 to 1) estimates of evolutionary conservation among 30 vertebrates. d, Top, BCL11A expression determined by RT-qPCR displayed as a heatmap in 108 hemizygous m+62 ortholog deletion clones ordered by genomic position of deletion midpoint. Each bar demonstrates the genomic position of the deletion breakpoints and the associated color demonstrates the level of BCL11A expression. Bottom, BCL11A expression determined by RT-qPCR in 108 hemizygous m+62 ortholog deletion clones. Per nucleotide mean effect size was calculated as the mean fold change in BCL11A expression from all clones in which that nucleotide was deleted. Gray shading represents one s.d. The BCL11A expression data are shown with same x-axis as in FIG. 34*c* immediately above.
Figure 28B:
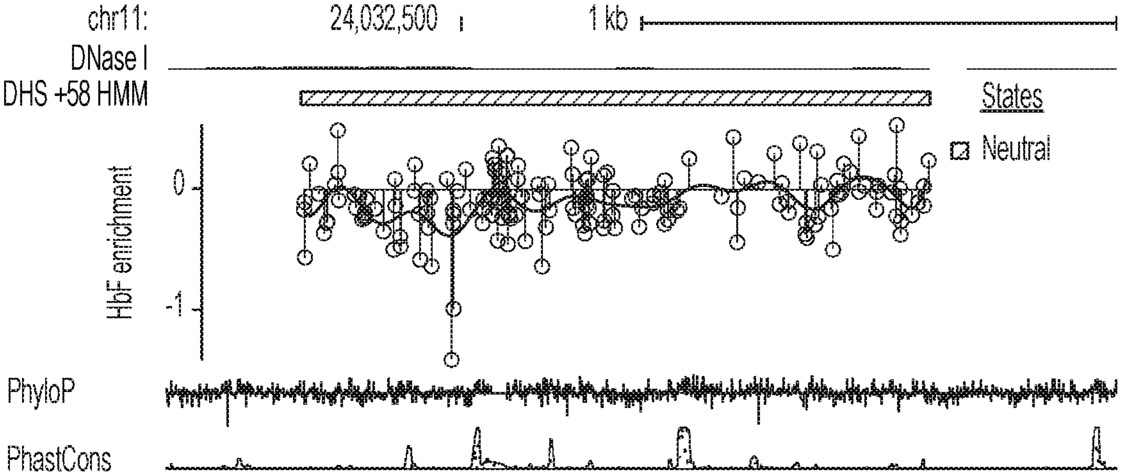
Figure 28C:
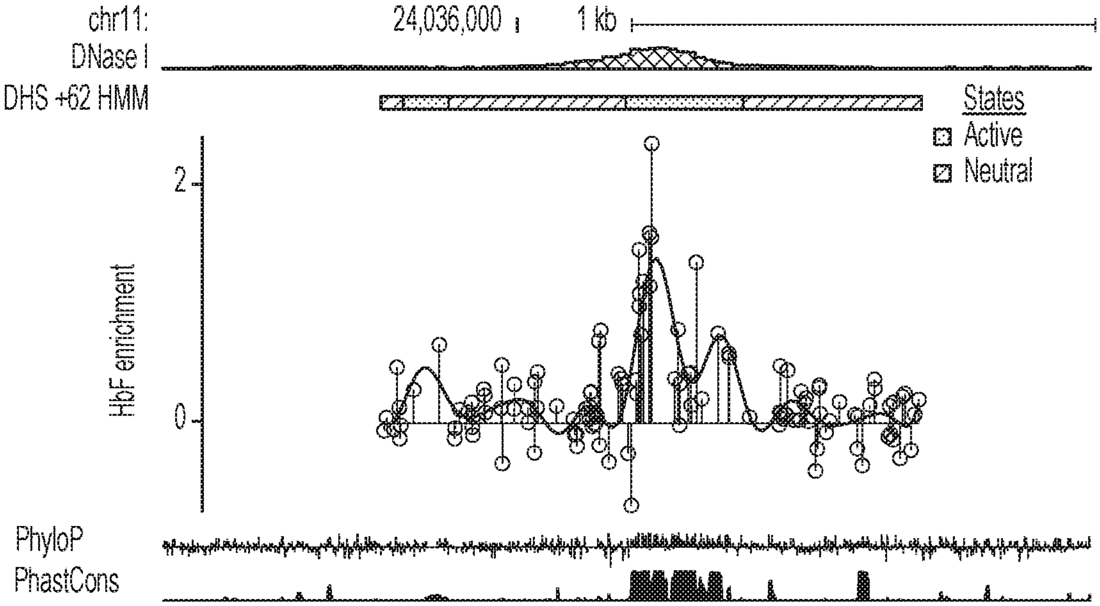
Figure 28D:
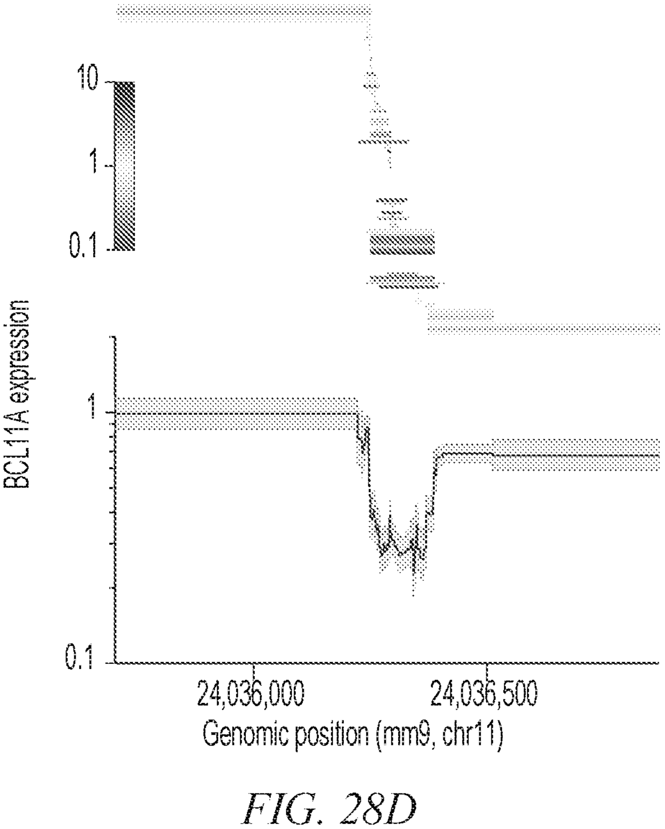
Figure 29:
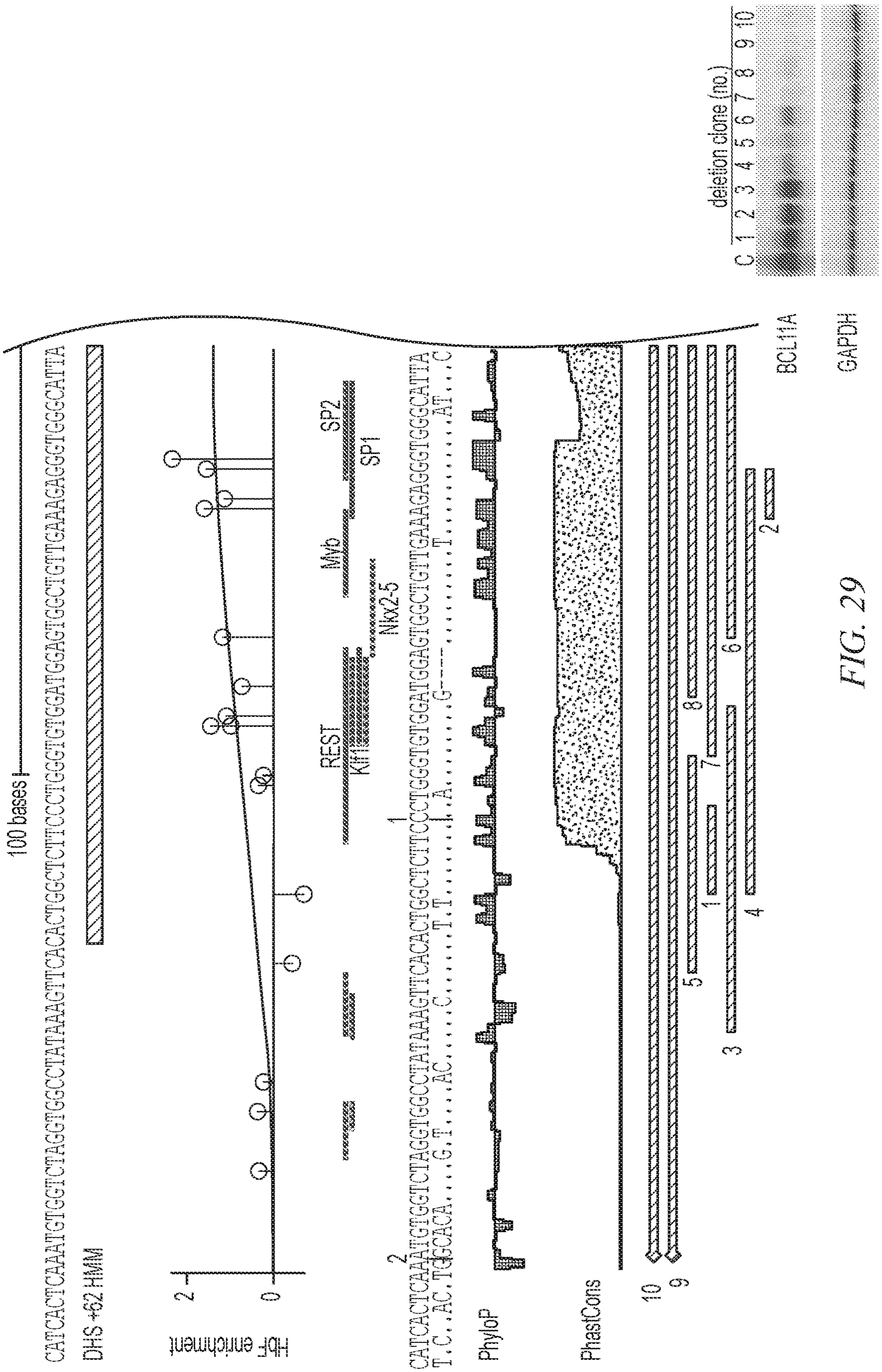
Figure 29:
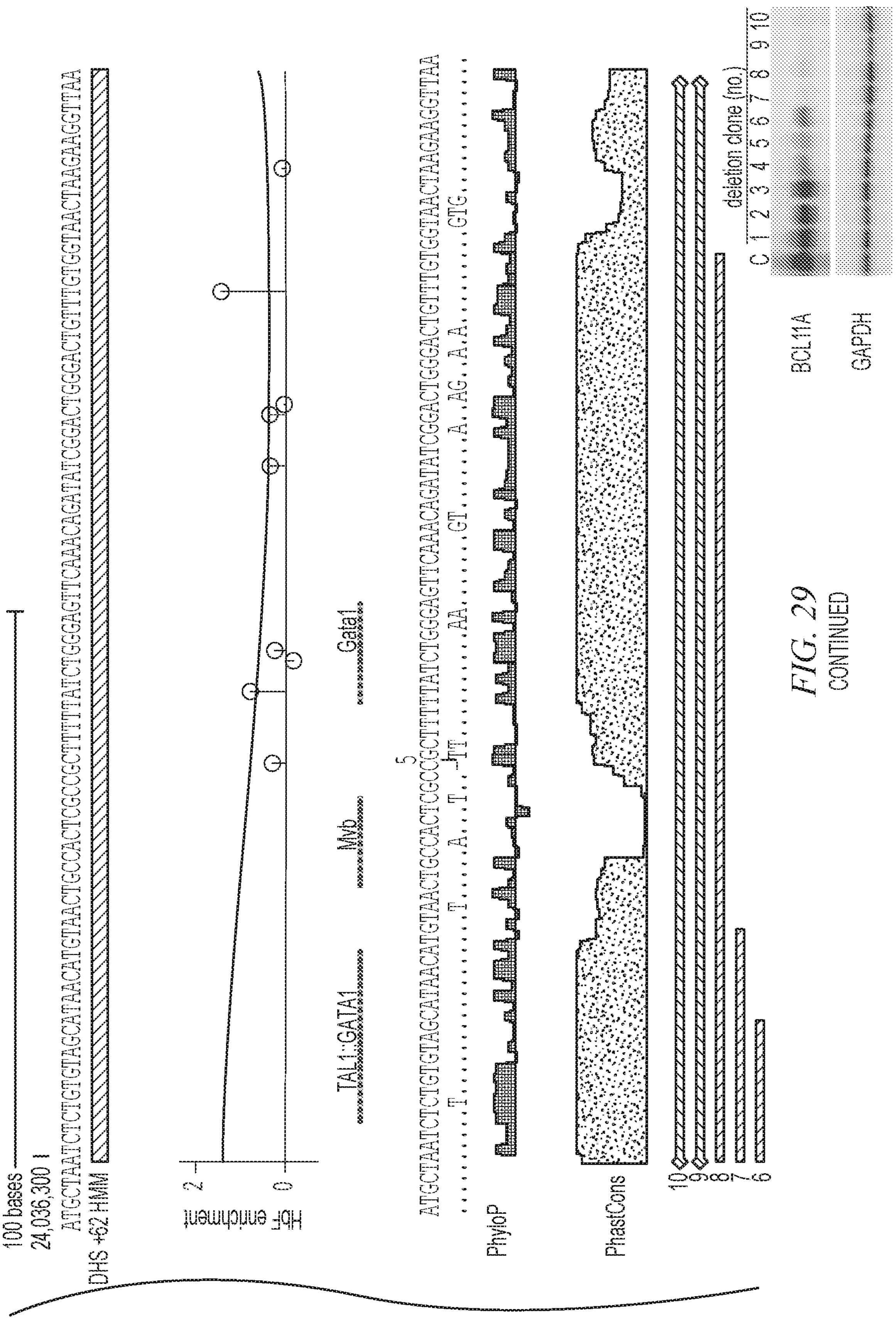

To validate these findings, Applicants generated cells with deletion of each individual DHS, +55, +58, and +62. Deletion of +58 phenocopied deletion of the composite enhancer, while deletion of +55 and +62 had moderate and modest effects respectively, consistent with the magnitude of top-scoring and co localizing sgRNAs from the screen (FIGS. 3*a*, 3*c*-3*e*). Inversion of the +58 or +55 sites had no significant effect on gene expression, demonstrating that the BCL11A enhancer functions in an orientation-independent manner in situ, consistent with the classic enhancer definition! (FIGS. 3*a, c-e*). In arrayed format Applicants tested 24 sgRNAs with enrichment scores ranging from the highest to the lowest in the screen, and representing sgRNAs from all 5 mapping categories. Applicants observed a strong correlation between the HbF enrichment score from the screen and the fraction of HbF+ cells in arrayed format (r=0.816, p<0.0001; FIGS. 8*a* and 23*b*). These results demonstrate that a single enhancer-targeting sgRNA may mediate robust HbF induction.

Figures 3C, 3D, 3E, 3F, 3G, 3H, 3I:
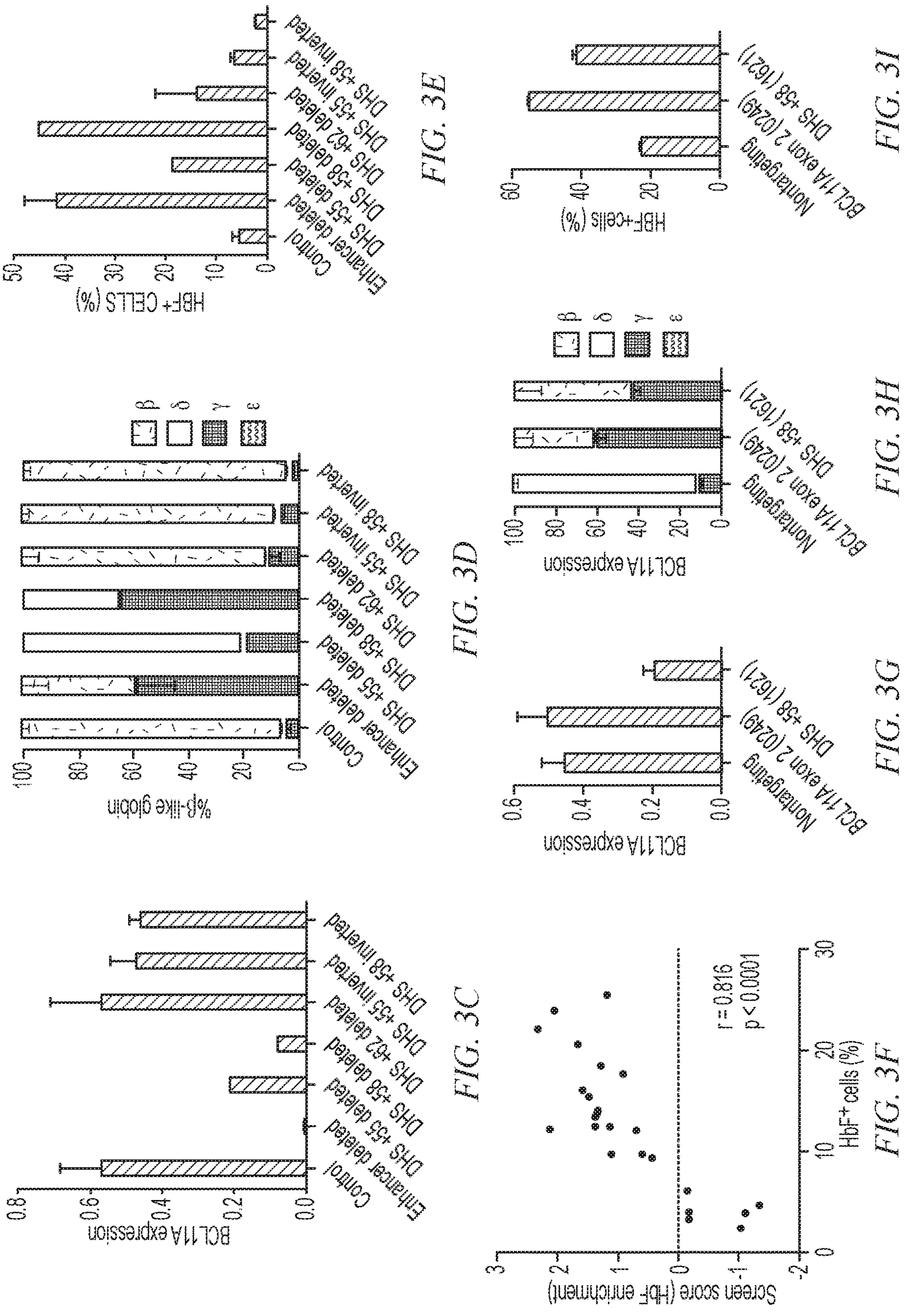
FIG. 3*c*-3*e*, BCL11A expression normalized to GAPDH, P-like globin expression, and HbF+ fraction in HUDEP-2 cells with deletion or inversion of individual DHSs.
FIG. 3*f*, Correlation between HbF enrichment score from pooled sgRNA screen and HbF+ fraction by arrayed validation of individual sgRNAs in HUDEP-2 cells.
FIG. 3*g*-3*i*, BCL11A expression normalized to GAPDH, P-like globin expression, and HbF+ fraction in HUDEP-2 cells from primary human erythroid precursors transduced with Cas9 and individual sgRNAs. Error bars represent SEM. A filtered of the human library targeting sgRNA enrichment score for enrichment of >0.259 and for NGG RC & NGG sgRNA gave the 135 targeting sequences shown in Table 7. These are the sgRNA targeting the +62, +58, and +55 functional regions in the BCL11A enhancer as well as a set of sgRNA that target the exon 2 of BCL11A.
Figure 8B:
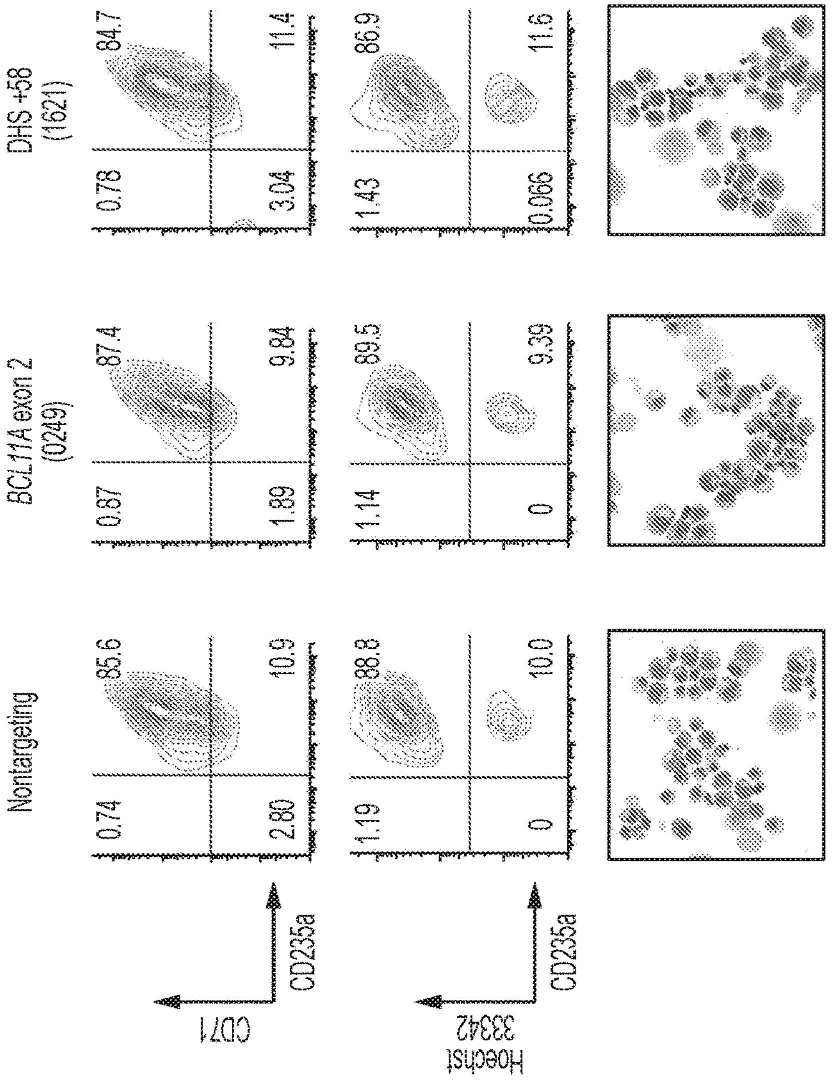

To validate the findings from the HUDEP-2 cells, the top-scoring enhancer targeting sgRNA from the screen (#1621 at +58) was tested in primary human erythroblasts by lentiviral transduction of CD34+ HSPCs exposed to ex vivo erythroid culture conditions. Consistent with the screen results, sgRNA-1621 resulted in downregulation of BCL11A expression and corresponding upregulation of γ-globin expression and increase in HbF+ cells (FIG. 3*g*-3*i*). Notably, sgRNA-1621 did not alter surface marker profile, enucleation frequency, or cellular morphology. Together these results indicate proof-of-principle of an individual sgRNA targeting a noncoding element for therapeutic genome editing of β-hemoglobin disorders. Notably, sgRNA-1621 did not alter surface marker profile, enucleation frequency, or cellular morphology (FIG. 8*b*). Together these results suggest proof-of-principle of an individual sgRNA targeting a noncoding element for therapeutic genome editing of β-hemoglobin disorders.

Primate-Specific Enhancer Sequences

Figure 4A:
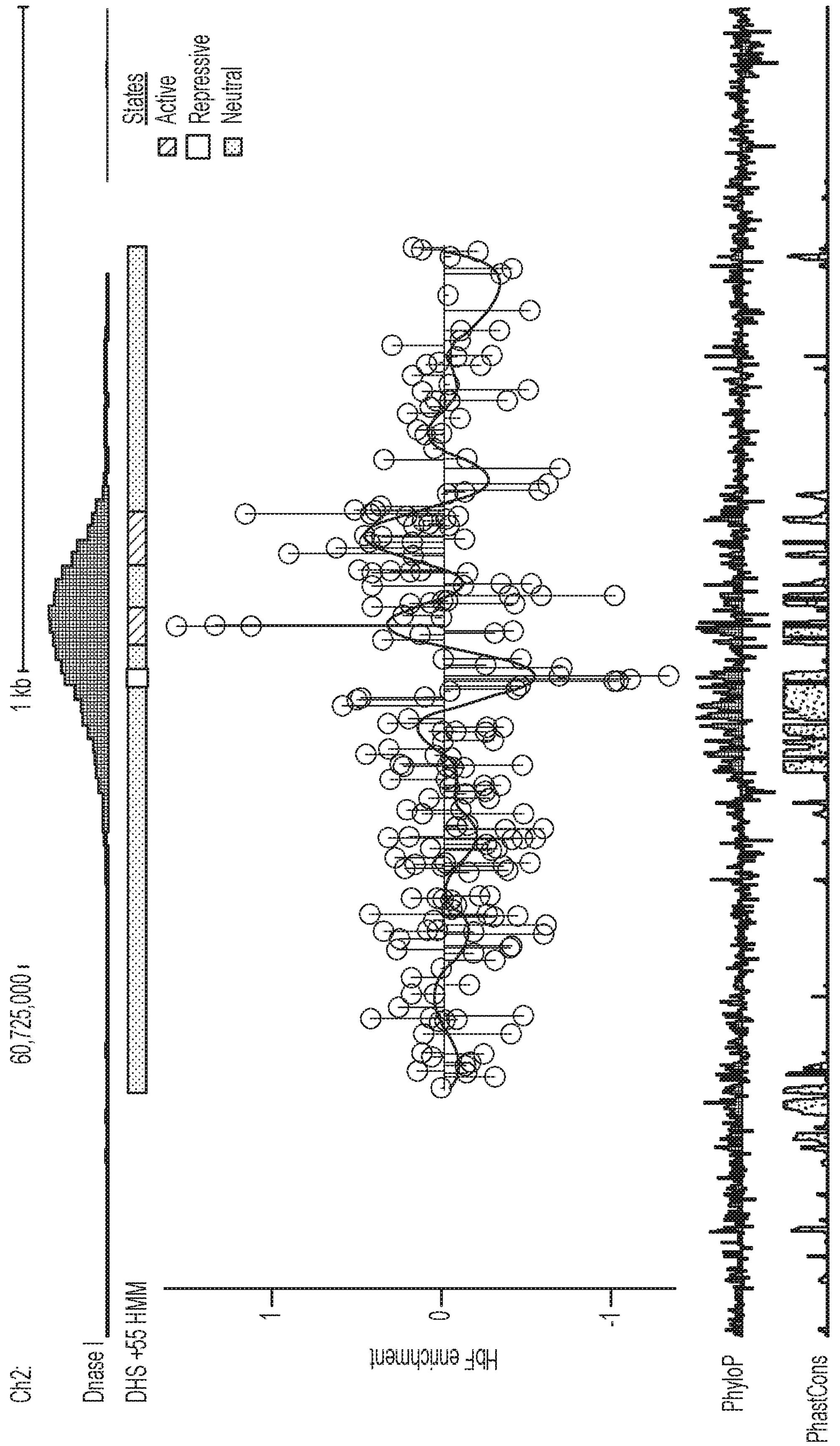
FIGS. 4A-4C show the inferred functional enhancer states relative to genomic features.
Figure 4B:
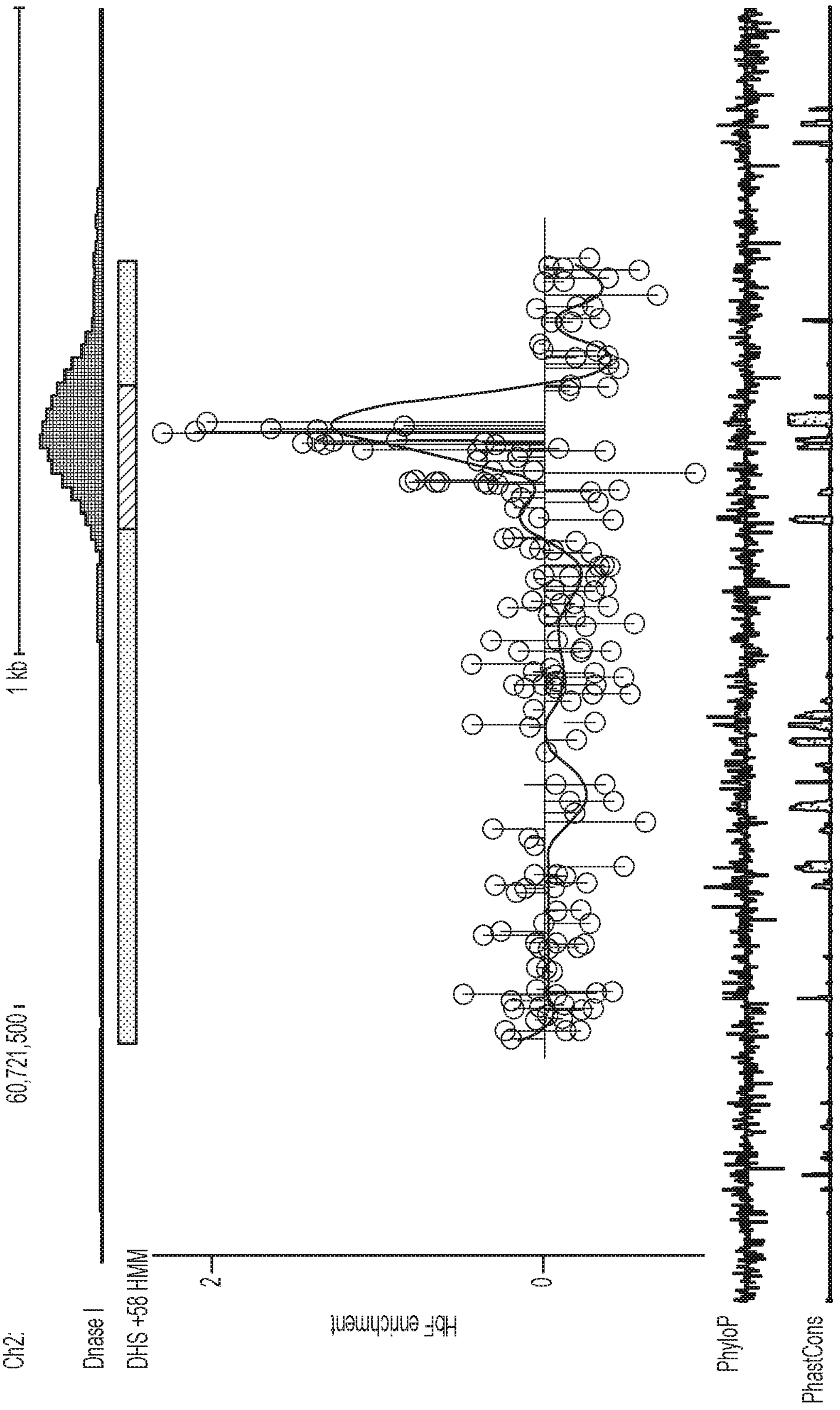
Figure 4C:
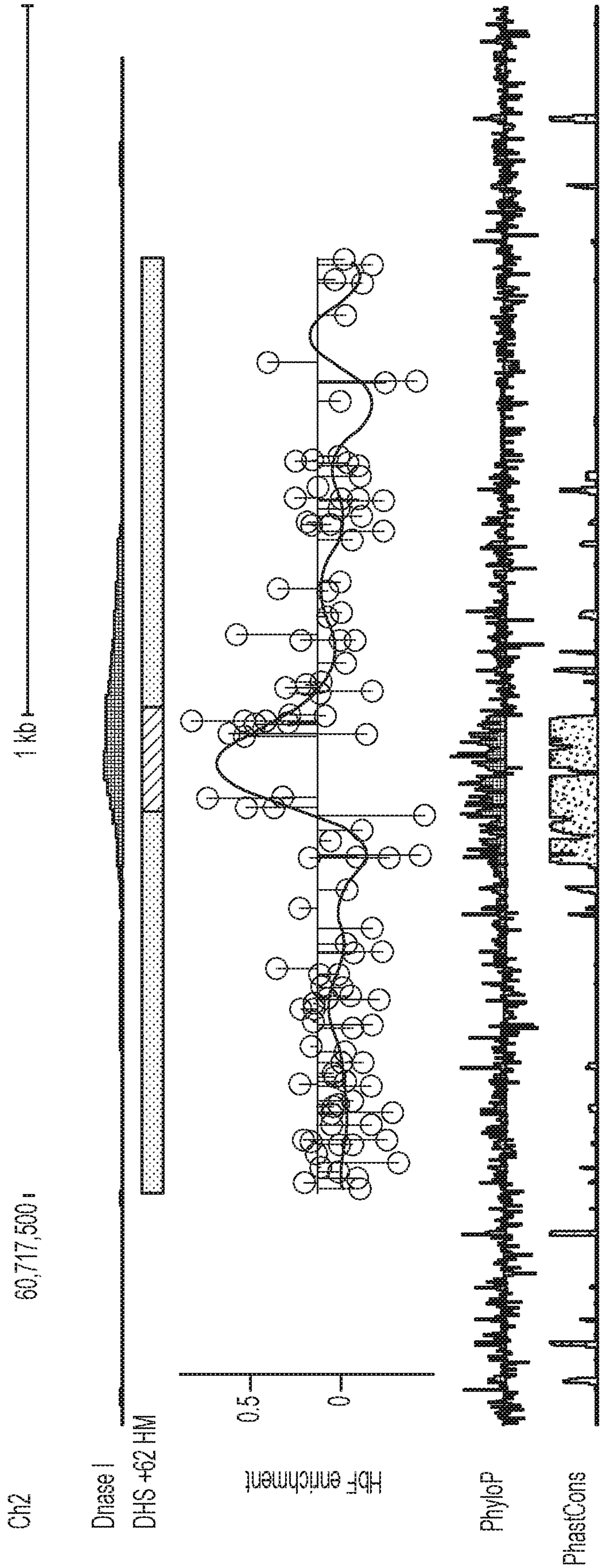

Applicants applied a hidden Markov model (HMM) to the sgRNA enrichment score data to infer functionally important sequences within each DHS. This model defined three functional states, Active, Repressive, and Neutral, based on likelihood to encompass sequences that positively, negatively, and neutrally regulate target gene expression, respectively. The model identified functional states within each DHS (FIG. 4*a*-4*c*). At each of the three DHSs, the Active states were precisely located at regions with the highest degree of DNase I sensitivity.

The +62 Active region contains only one common SNP (MAF>1%), the variant rs1427407, which was previously identified by fine-mapping as the most highly trait-associated SNP42. The high-HbF Tallele is disruptive of an apparent half E-box/GAT A composite motif ($P=9.74\times10^{-4}$ for T-allele, $P=1.69\times10^{-4}$ for G-allele, though neither met our predefined threshold for significance of $P<10^{-4}$ and associated with reduced GATA1 and TAL1 occupancy in primary human erythroid chromatin (42). Multiple sgRNAs with cleavages mapping directly to the motif demonstrated positive enrichment scores (FIG. 4*c*). Of note, there was a gap of 88 nucleotides between sgRNA cleavages at the core of the Active region due to lack of NGG PAM motifs. Despite this uncommon limitation of functional resolution by SpCas9 and NGG PAM restricted sgRNAs (FIG. 2*d*), the HMM model was still able to identify the region. Substantial interspecies conservation as evaluated by both PhyloP and PhastCons (which model individual nucleotide and multi-base element conservation, respectively) was observed at this +62 Active state region as compared to flanking regions (FIG. 4*c*).

DHS +55 encompasses the SNP rs7606173, which along with rs1427407 defines the most highly trait-associated haplotype. Previous fine-mapping was unable to find additional SNPs at BCL11A with predictive power for the trait association beyond the rs1427407-rs7606173 haplotype based on conditional or rare-variant analyses. No common SNPs were found directly within the Active or Repressive state regions of +55, however rs7606173 resides merely 3 bp from the Repressive region and 34 bp from the Active region The next closest common SNP to an Active or Repressive state within +55 is rs62142646, which is 739 bp from an Active state. The major, ancestral G allele at rs7606163 is associated with highHbF. The HUDEP-2 cells used in this screen are homozygous for this G variant. Given a model in which high-HbF trait is due to disruption of TF binding sequences at the BCL11A enhancer, sgRNA-mediated disruption of the high-HbF rs7606173-G allele might not be expected to lead to further functional impact. Applicants did observe six motifs predicted ($P<1\ 0^{-4}$) to be differentially impacted by the rs7606173 genotype. The top-scoring sgRNAs in +55 cluster 56-58 bp from rs7606173, at a site with a predicted TAL1:GATA1 motif ($P<10^{-4}$). This sequence element possesses high vertebrate conservation. The entire region encompassing the Active/Repressive +55 states appears to have elevated sequence conservation as compared to flanking sequences (FIG. 4*a*).

Figure 5:
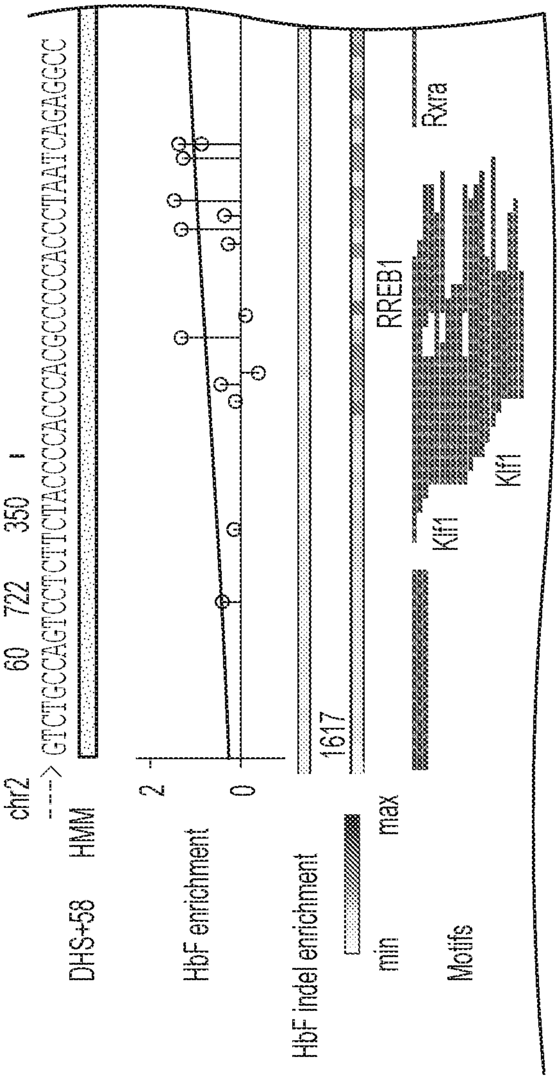
Figure 5:
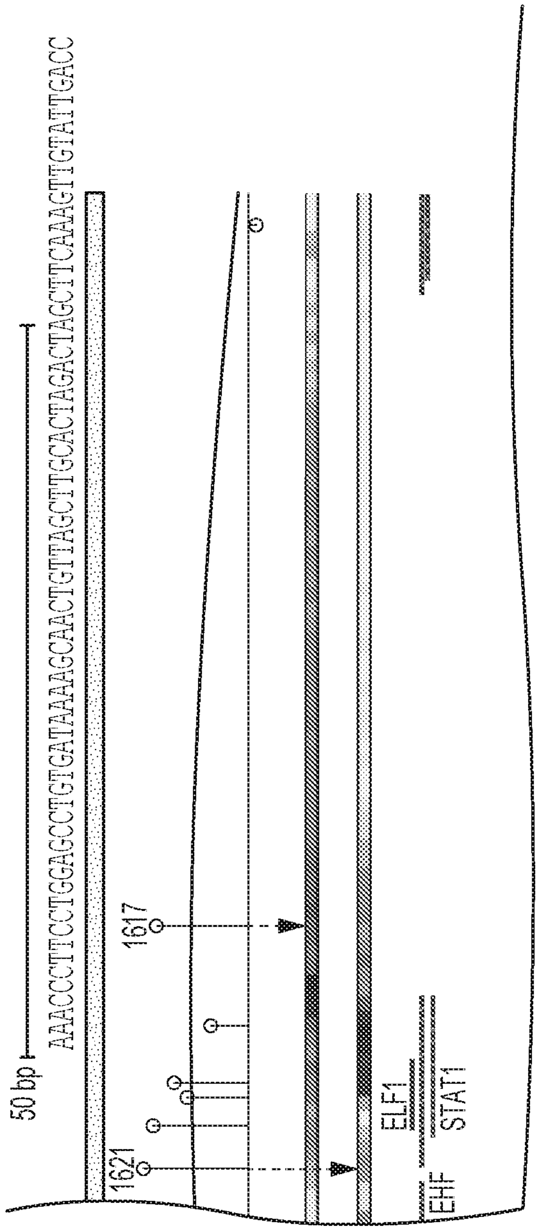
Figure 5:
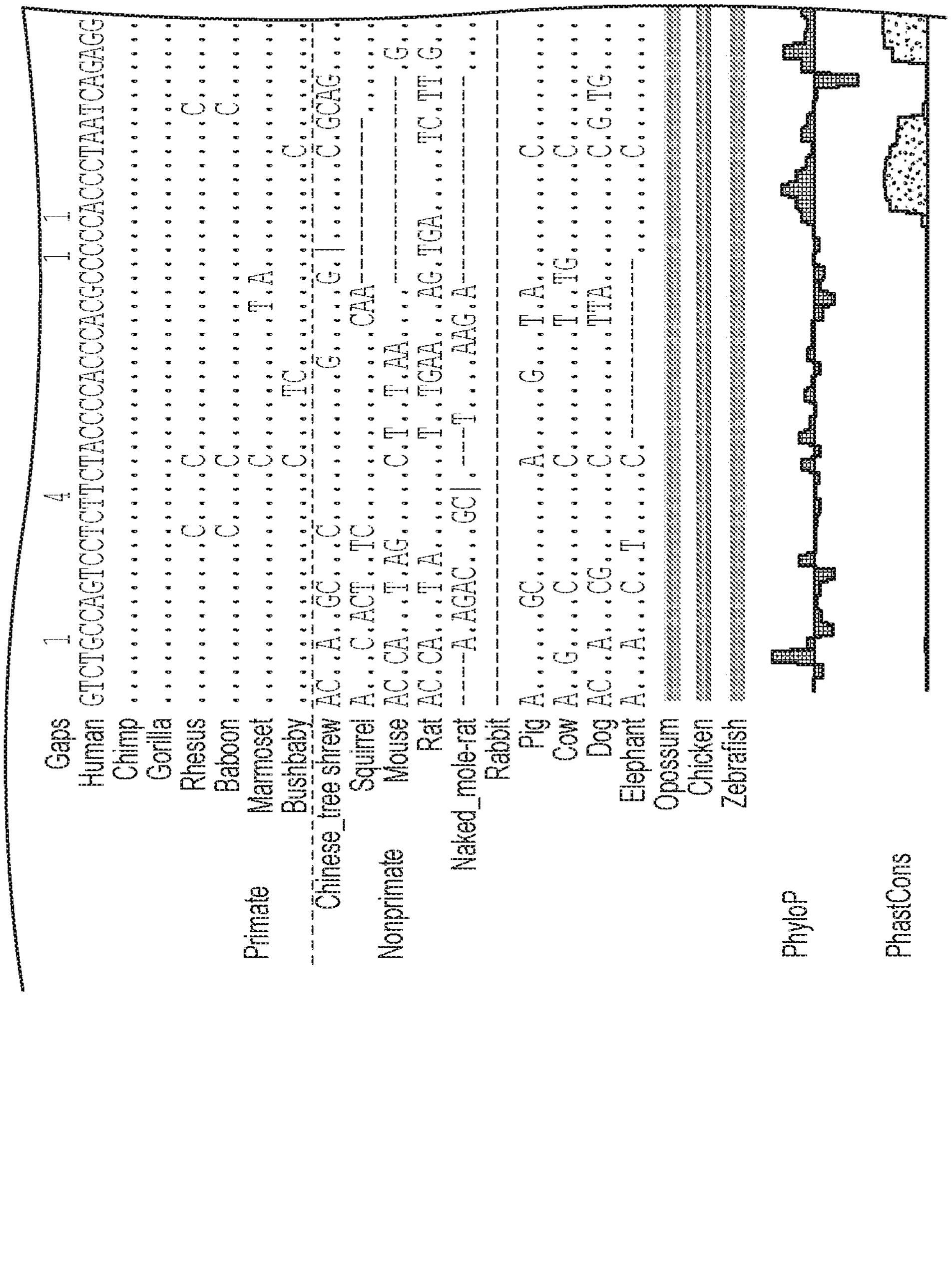
Figure 5:
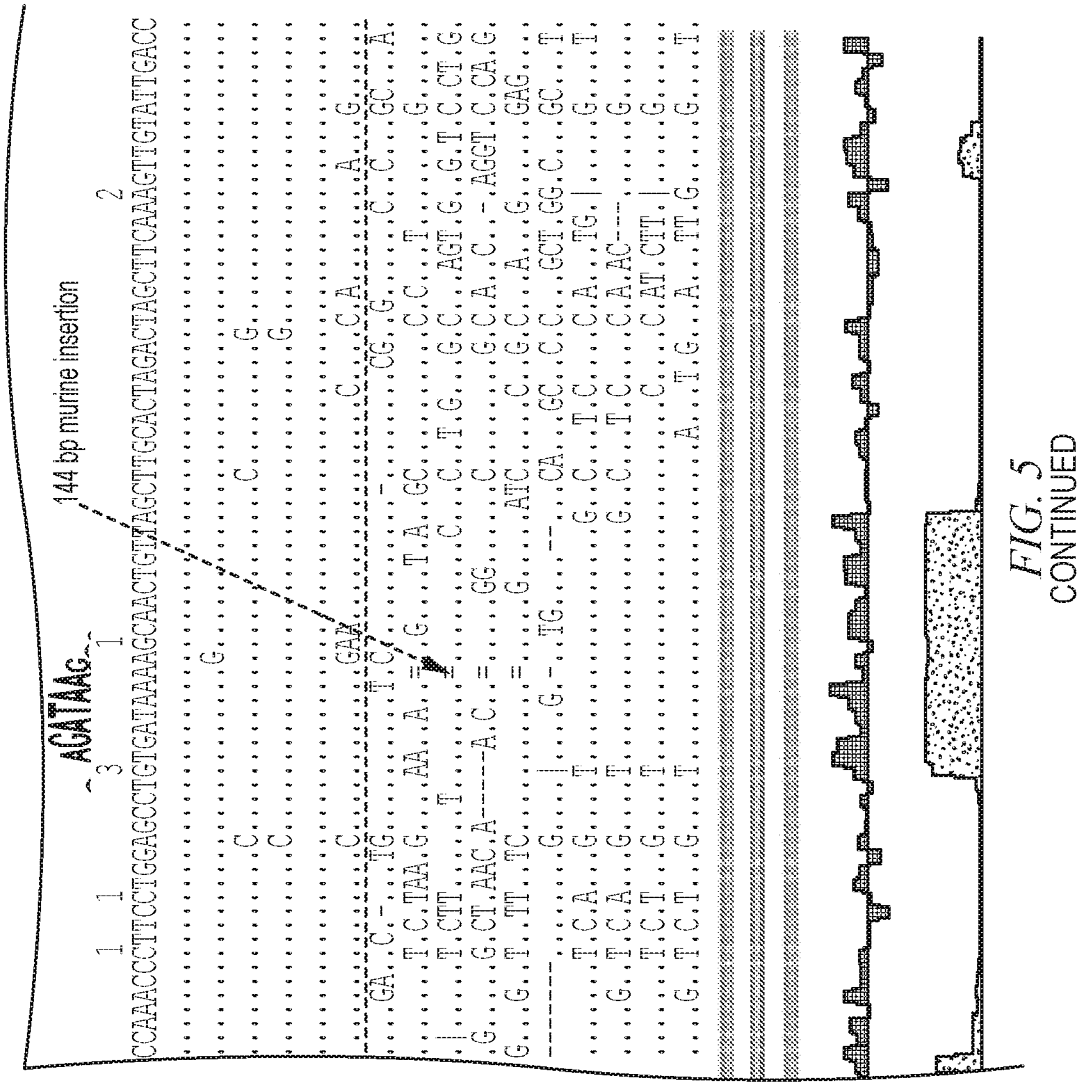
Figure 10B:
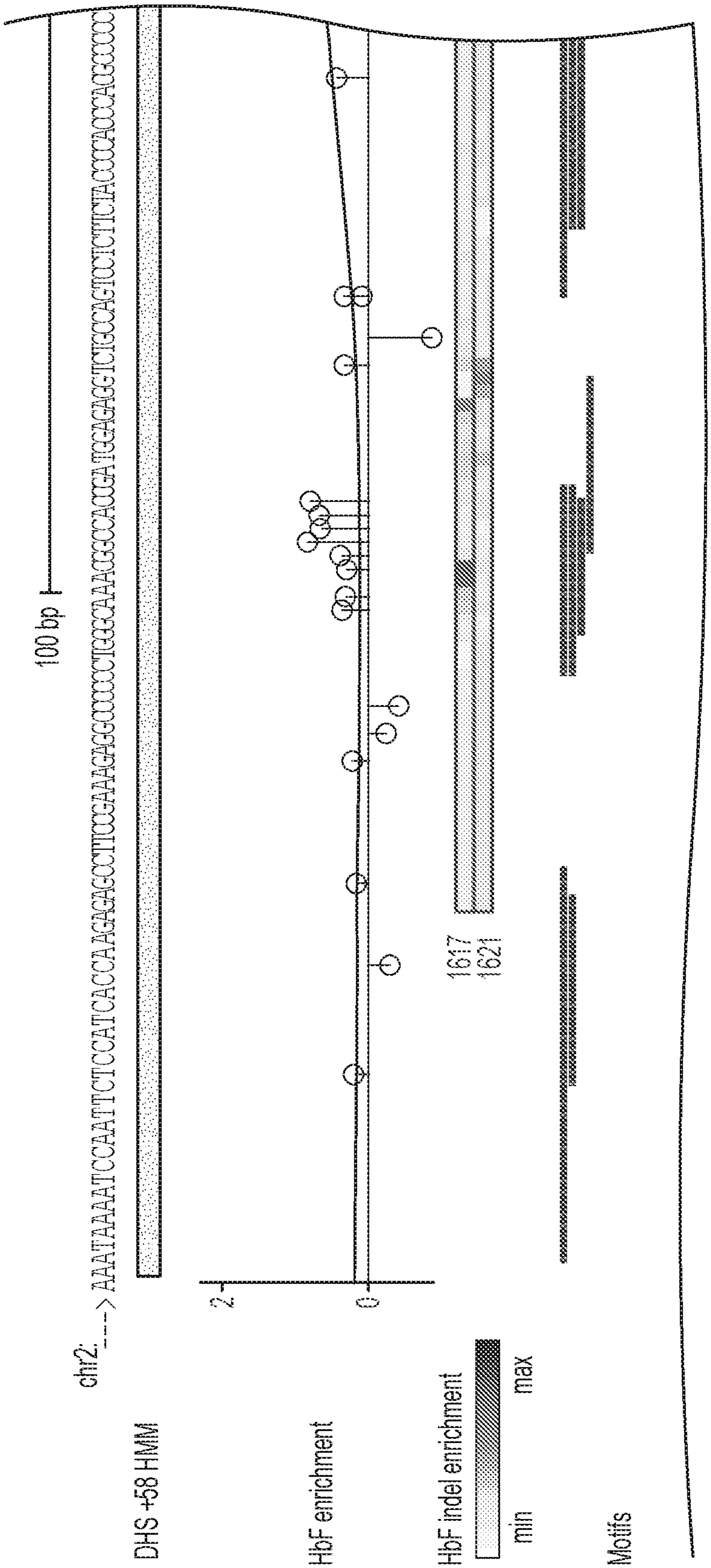
Figure 10B:
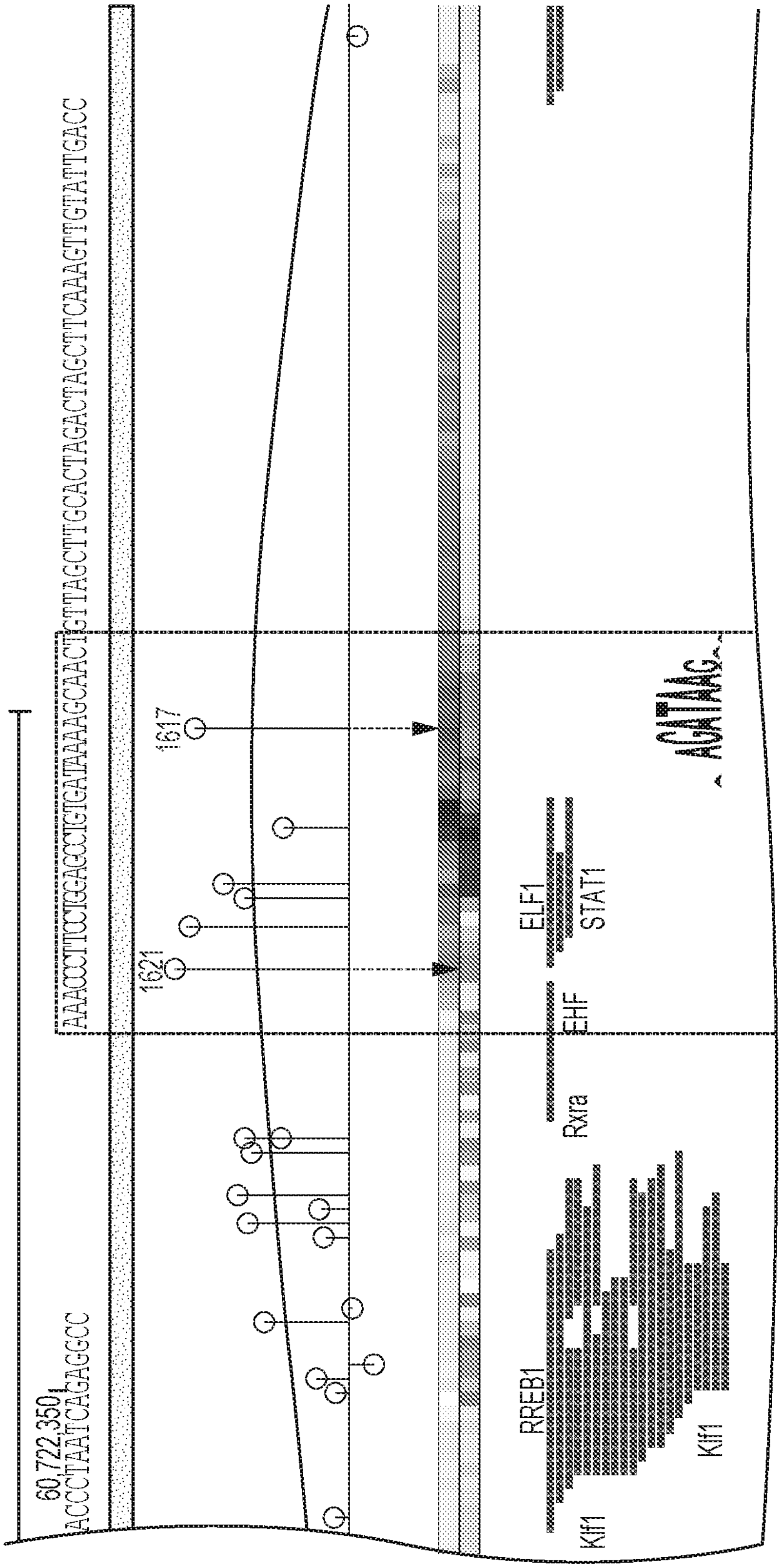
Figure 10B:
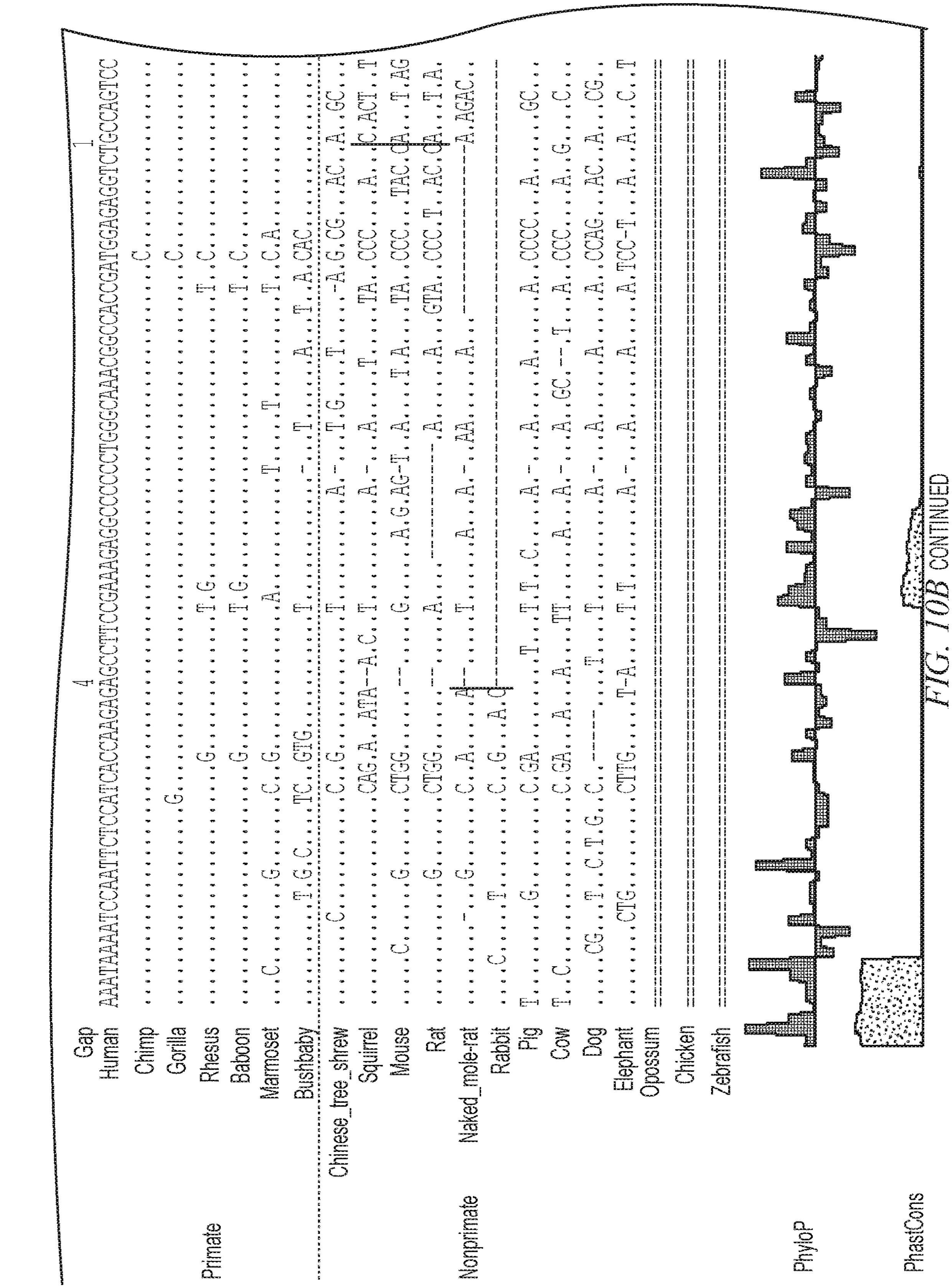
Figure 10B:
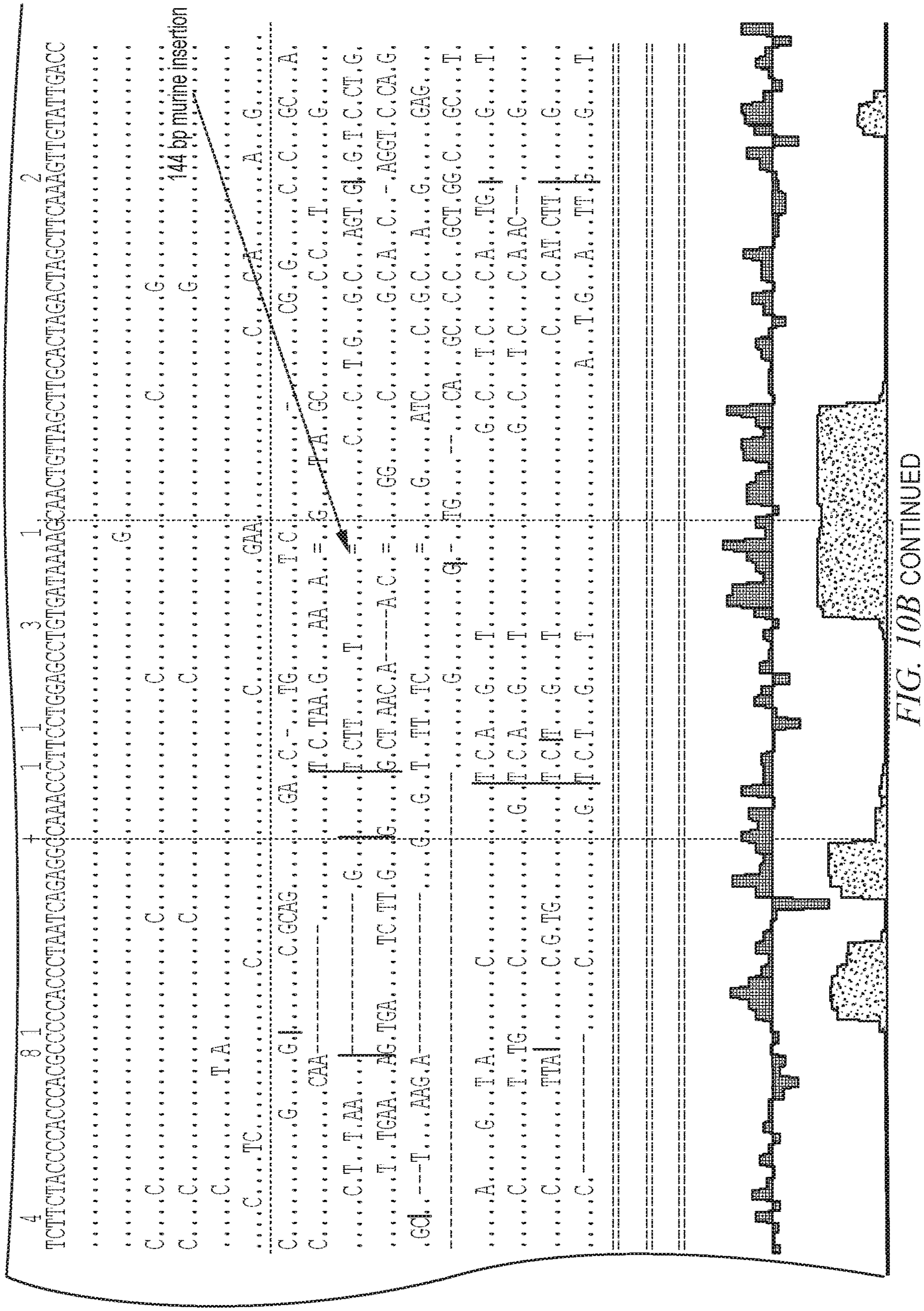
Figure 10C:
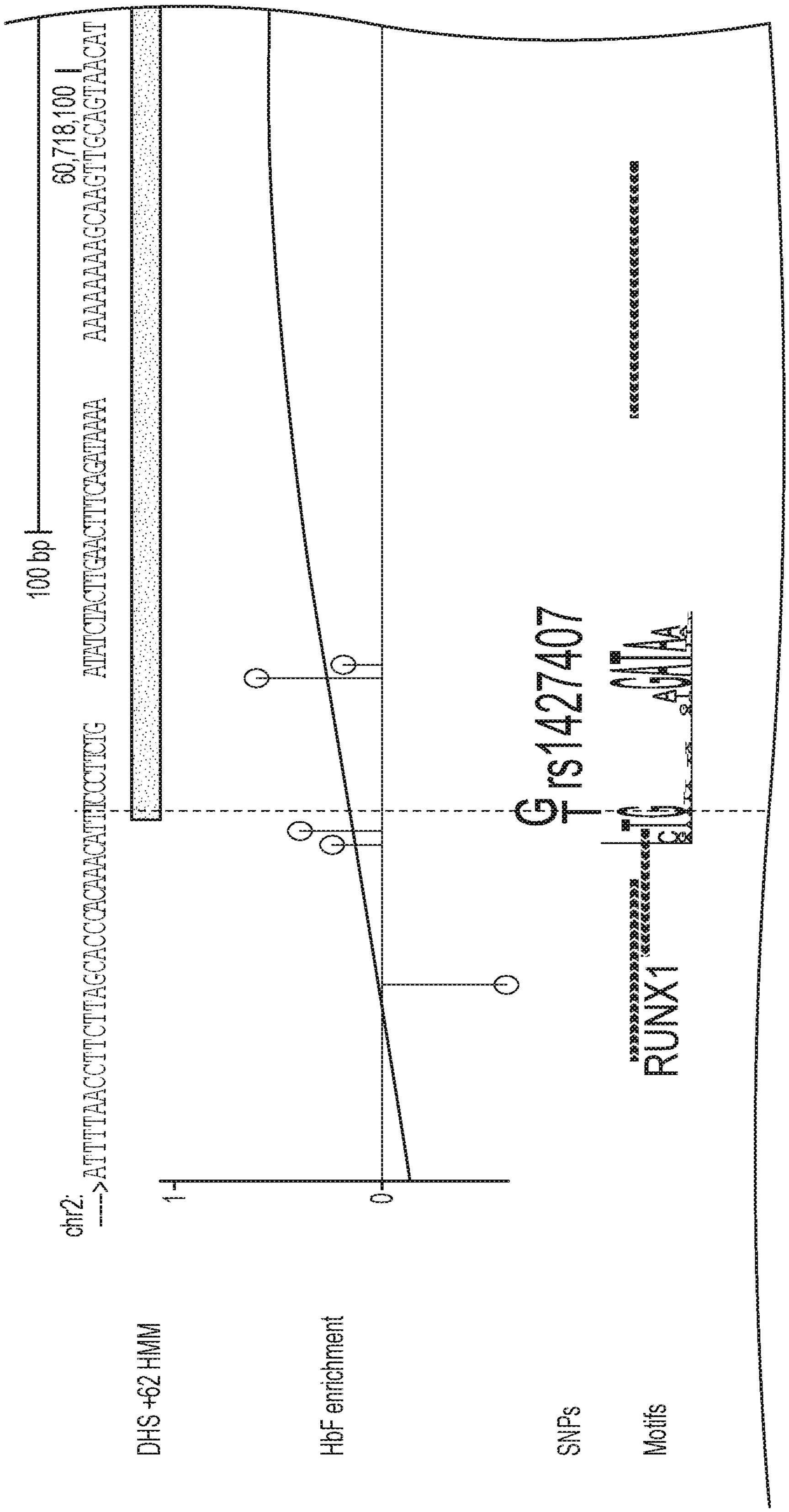
Figure 10C:
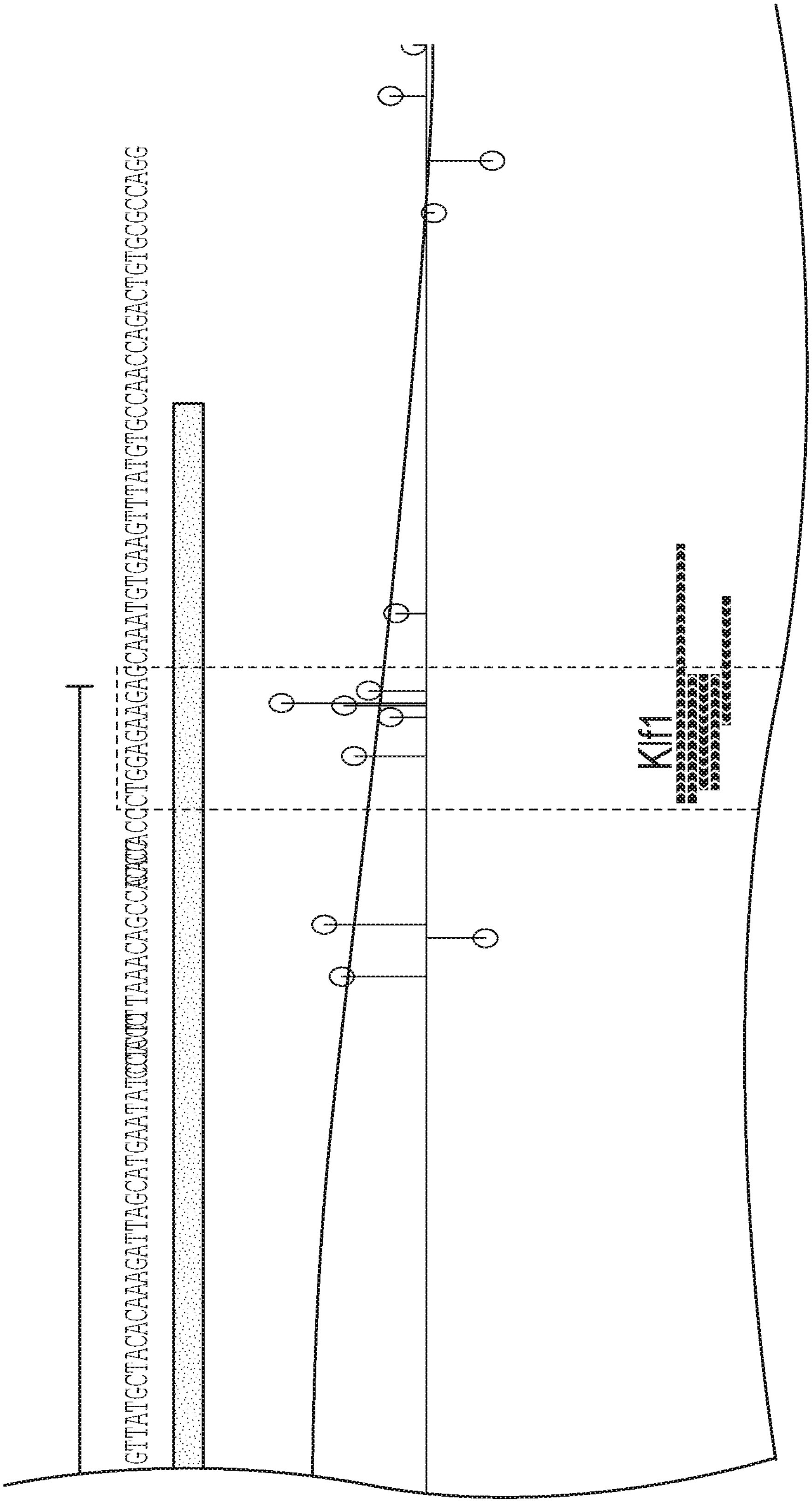
Figure 10C:
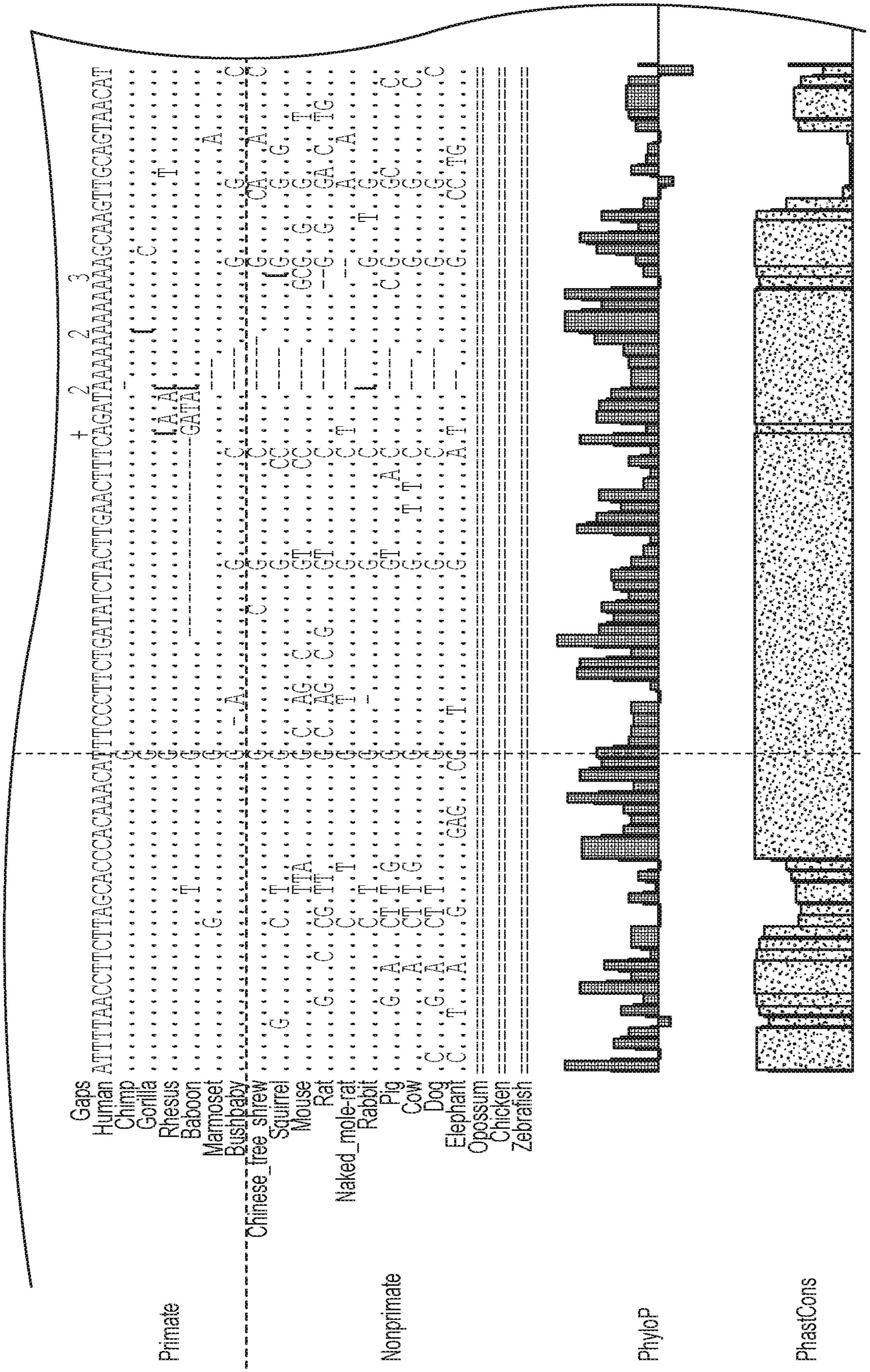
Figure 10C:
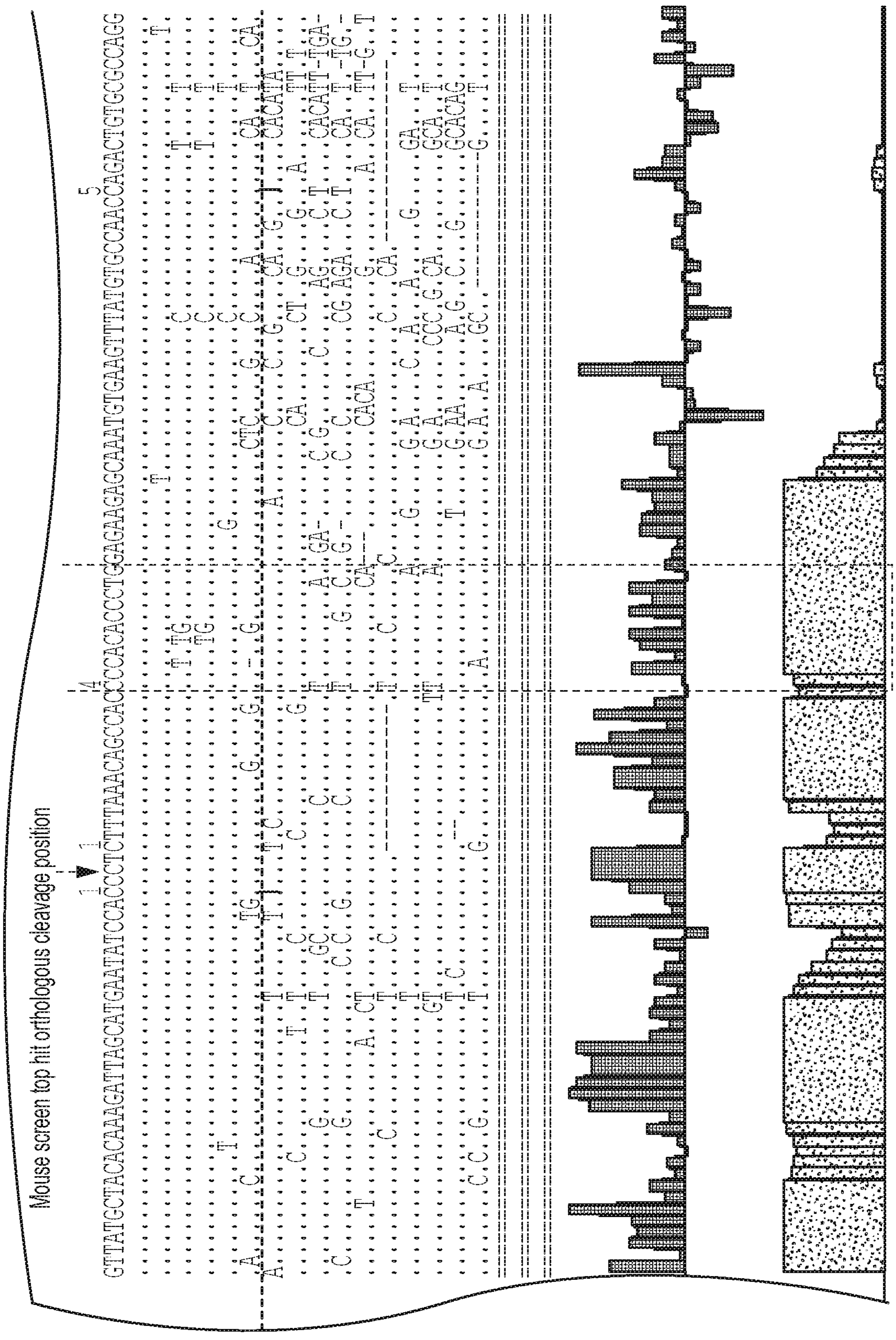

The overall sequence conservation at the +58 Active region appears both less intense and less distinct from flanking sequences as compared to those of +62 and +55 (FIG. 4*a*-*c*). The top-scoring sgRNAs in the screen colocalize to 42 bp within +58 (FIG. 5; FIG. 10*b*). The third-highest scoring enhancer-targeted sgRNA (sgRNA-1617) mapped directly onto an apparent GATA motif (FIG. 5). This motif was below a genome-scale significance threshold ($P=3.74\times10^{-4}$). Of note, there is a 144 bp insertion in the mouse genome relative to the human reference directly adjacent to the orthologous position. The mouse orthologous sequence has a GATA1 motif P-value only modestly higher than the human ($p=4.33\times10^{-4}$). This GATA1 motif appears to have relatively high vertebrate conservation, with exact human identity in rabbits, pigs, dogs, and elephants.

The top-scoring sgRNA (sgRNA-1621) mapped to a position 15 bp from this GATA 1 motif (FIG. 5). An additional four sgRNAs mapping between sgRNA-1621 and 1617, including the second-highest scoring sgRNA in the screen, each had substantially elevated HbF enrichment scores. Underlying these sgRNAs were additional predicted motifs (i.e. Rxra, EHF, ELF1, and STAT1). Although these sequences showed a high level of conservation among primates, they showed high degeneracy among nonprimate vertebrates (FIG. 5).

Figure 9B:
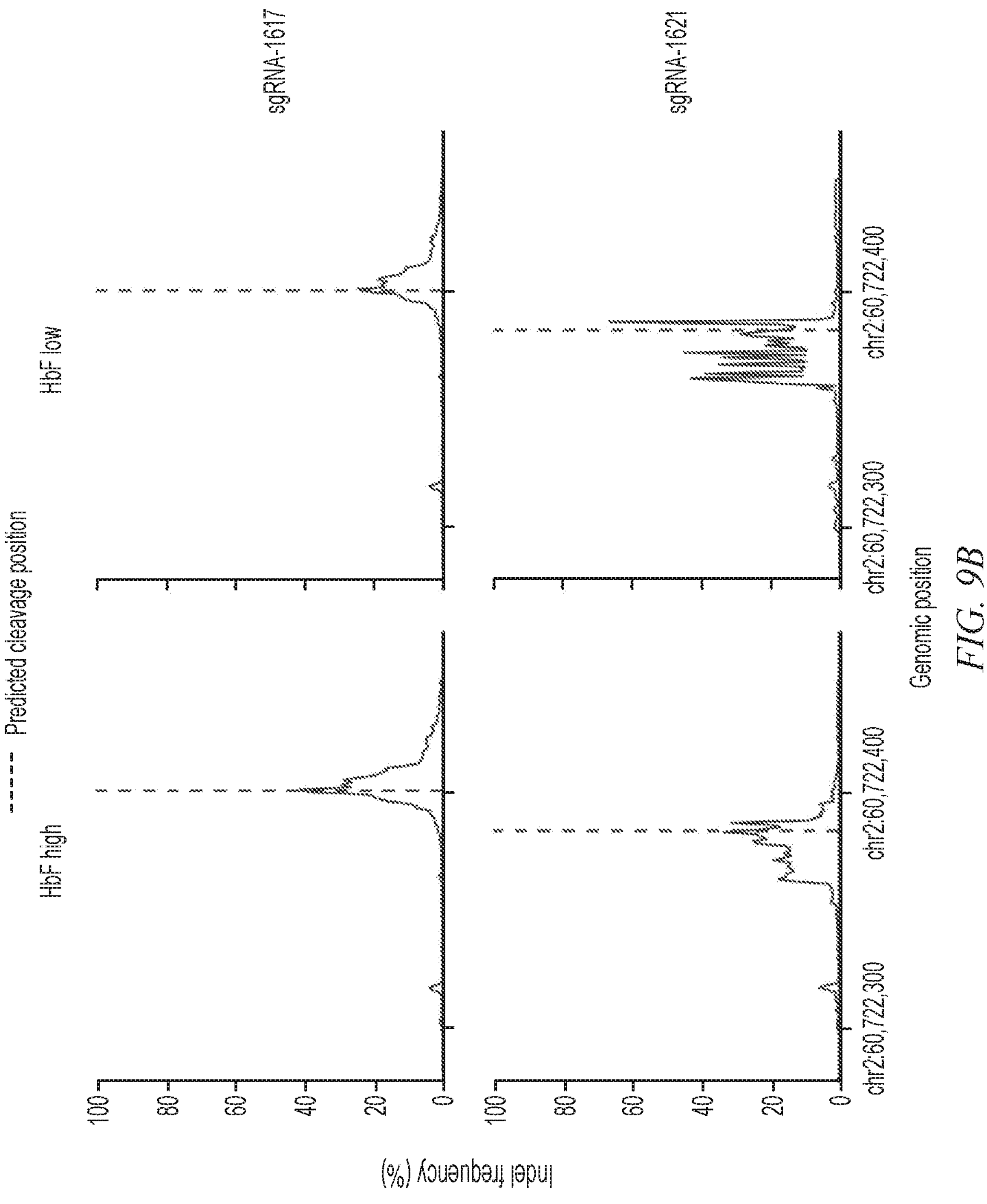

Applicants tested the pattern of mutations observed upon treatment of cells with either sgRNA-1621 or sgRNA-1617 by deep sequencing. Each of these sgRNAs is sufficient to substantially induce HbF in human erythroid cells (FIG. 3*i*; FIGS. 8*a* and 23*b*). Applicants sorted cells exposed to Cas9 and these sgRNAs into HbF-high and HbF-low pools. Applicants determined the indel spectrum in each population by deep sequencing (FIG. 9*b*). As expected Applicants observed indels clustering around the predicted cleavage positions. By comparing the per nucleotide indel ratio between cells from the HbF-high and HbF-low pools, Applicants were able to calculate a relative enrichment across the amplicon used for deep sequencing. Notably both sgRNAs yielded maximal HbF enriching indels not precisely at the expected cleavage position but offset by about 10 bp (FIG. 5). In the case of 1621, the positions of maximal HbF indel enrichment were towards the 1617 cleavage site. In the case of 1617, the positions of maximal HbF indel enrichment were towards the 1621 cleavage site. These results indicate that the sequences intervening these two cleavages are particularly required for BCL11A expression. These sites of maximal HbF mutation enrichment mapped to 7 bp directly overlapping the predicted motifs intervening the sgRNA cleavages (FIG. 5). Taken together, these data indicate that a conserved GATA1 motif scoring below the prediction threshold surrounded by primate-specific sequences form the core of an enhancer essential for human erythroid BCL1 1A expression and HbF repression.

Mouse Enhancer Dissection

To test functional conservation of the BCL11A enhancer, Applicants examined the orthologous mouse BCL11a enhancer in greater detail. Although moderately marked by H3K27ac, mouse Bcl11a does not meet the criteria for a super-enhancer element. Erythroid DNase I sensitivity is only observed at those sequences homologous to +55 and +62 and not at +58 (FIG. 11*l*), consistent with the reduced sequence homology within the +58 Active region (FIG. 4*b*). Applicants previously observed that deletion of the entire composite enhancer (encompassing the homologous sequences to DHS +55, +58, and +62) in mouse erythroleukemia (MEL) cells resulted in dramatic reduction of BCL11A expression. Applicants generated a MEL cell reporter line with the mCherry fluorescent reporter knocked-in to the embryonic globin Hbb-y locus. Introduction of Cas9 and sgRNA targeting Bcl11a exon-2 resulted in the appearance of cells with elevated εy:mCherry expression, indicating derepression of the BCL11A target εγ-globin. Applicants designed a pooled CRISPR enhancer saturation mutagenesis screen in these εy:mCherry reporter cells, similar to the human screen described above (FIGS. 11 and 12).

Applicants determined enrichment score as the log 2-ratio between representation in the high—as compared to low-εy:mCherry pools. Applicants noted almost all exon-2 targeting sgRNAs demonstrated both positive enrichment scores and negative dropout scores with high correlation. The majority of enhancer targeting sgRNAs showed no significant enrichment. Applicants detected sgRNAs with both modest enrichment and depletion from high-εy: mCherry at the +55 ortholog, similar to as seen at human +55. Applicants detected a set of sgRNAs with marked enrichment at the +62 ortholog, exceeding the potency of those enriching at human +62. At the +58 ortholog Applicants did not observe any evidence of enriching or depleting sgRNAs.

Figure 6A:
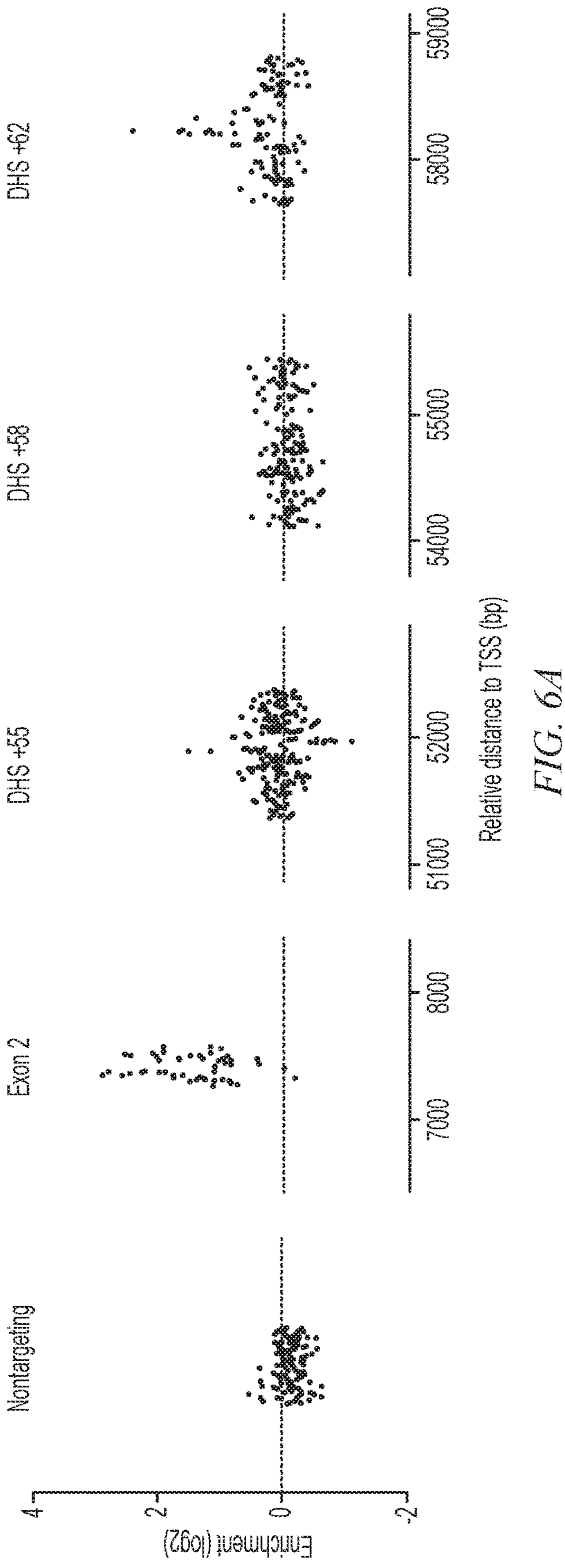
FIGS. 6A-6F shows the functional sequence requirement at the mouse Bcl11a erythroid enhancer for in vivo hemoglobin switching.

Upon mapping the sgRNA cleavage positions to the genome, Applicants again observed colocalization of sets of sgRNAs (FIG. 6*a*). There was a similar complex pattern at the +55 ortholog as at human +55, with adjacent regions with enriching and depleting sgRNAs from the high-εy: mCherry pool at the DHS core. At the +62 ortholog there was a marked peak, with five sgRNA with enrichment scores exceeding 1.30, the median enrichment score of Bcl11a exon-2 targeting sgRNAs (FIG. 6*a*). This potent impact of the +62 ortholog was in contrast to the modest impact of individual sgRNAs or DHS deletion at human +62.

Figure 6B:
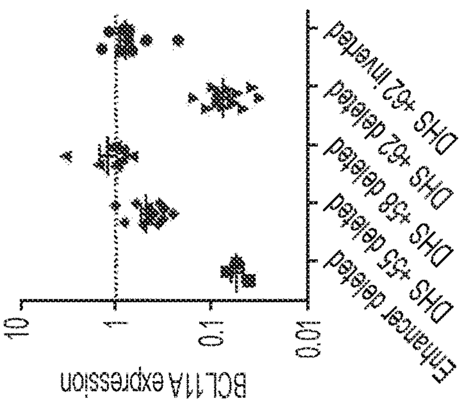

Applicants used pairs of sgRNAs in the presence of Cas9 to produce MEL clones with deletions of various substituent elements at the BCL 1 1 A enhancer. Applicants compared the expression of clones with deletions of the +55, +58, and +62 orthologs (FIG. 6*b*). Deletion of the DNase-insensitive +58 ortholog had no apparent effect on BCL11A expression consistent with the pooled screen result. Deletion of the +55 ortholog led to an approximately two-fold reduction in BCL11A expression (mean residual level 49%, p<0.0001), whereas deletion of the +62 ortholog mimicked deletion of the entire composite enhancer in terms of reduction in BCL11A expression (mean residual levels of 8% (p<0.0001) and 6% (p<0.0001) respectively (FIG. 6*b*, FIG. 13). In addition, clones were isolated in which the +62 ortholog was inverted in which there was no change in BCL11A expression, indicating that the mouse, like the human, enhancer functions independent of orientation in situ (FIGS. 3*c-e;* 6b).

Figure 6C:
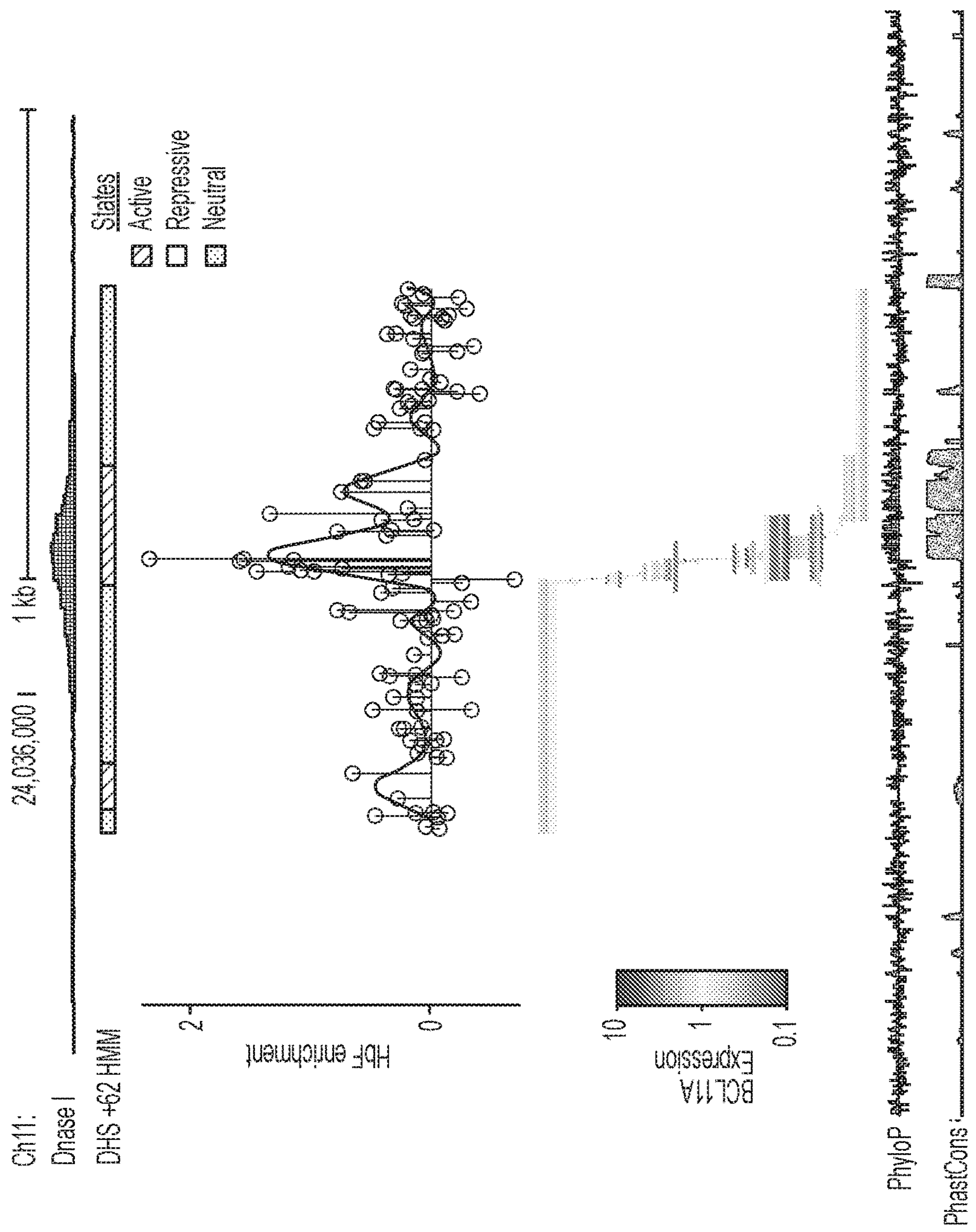

Applicants applied the same HMM model to infer Active, Repressive, and Neutral states at the mouse BCL11A enhancer orthologs (FIG. 6*c*). Applicants identified an Active state at the +62 ortholog and Active and Repressive states at the +55 ortholog. Only the Neutral state was identified at the +58 ortholog. The regions of the +55 and +62 DHSs with peak DNase I sensitivity were inferred as possessing Active states (FIG. 6*c*).

Applicants analyzed 108 clones in which the entire composite enhancer was first monoallelically deleted and subsequent mutations were produced by individual or pairs of sgRNAs targeting the +62 ortholog on the remaining allele. Applicants measured BCL11A expression by RT-qPCR in each of these 108 clones normalized to 25 control clones not exposed to +62 targeting sgRNAs. This clonal analysis identified a core region of the +62 ortholog containing functional sequences required for BCL11A expression and embryonic εγ-globin repression (FIG. 6*c*). The region is rich with TF-binding motifs, particularly those of key factors involved in erythropoiesis and globin gene regulation, including Gata1, Klfl, and Myb. Of note, despite the presence of relatively high vertebrate conservation throughout the mouse and human +62 Active state regions (FIG. 4*c*, 6*c*), the potent impact of the mouse +62 ortholog on BCL11A and globin gene regulation greatly exceeded that of human +62 (FIGS. 3*a*, 3*c-e*, 6*a-c*).

Enhancer Function In Vivo

Figure 6D:
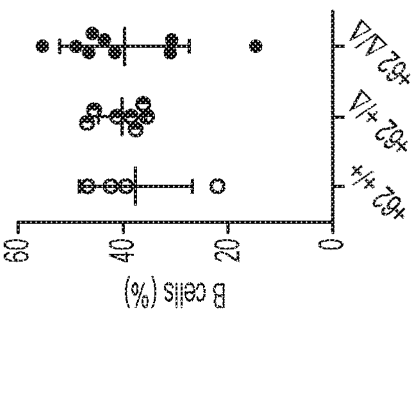

To substantiate the importance of the mouse +62 ortholog in BCL11A expression as well as to validate BCL11A enhancer disruption as a therapeutic strategy, Applicants generated mouse Bcl11a+62 ortholog deficient animals. Applicants generated mouse embryonic stem cells (mESCs) transgenic for the human β-globin cluster (β-YAC mESCs) to model the role of BCL11A in hemoglobin switching (55). The +62 ortholog was deleted from these mESCs with the same Cas9 and paired sgRNA strategy. To determine the role of the +62 ortholog in developmental regulation of globin gene expression in vivo, two unique +62 ortholog biallelic deletion β-YAC mESC clones were injected into E3.5 non-β-YAC blastocysts and implanted into pseudopregnant females. At E 16.5, analysis revealed a 9.4-fold (p<0.0001) and 11.4-fold (p<0.0001) increase in y-globin gene expression of +62 deletion chimeras with contributions from clones 1 and 2, respectively (FIG. 6*d*). These results indicated that murine erythroid cells have a cell-intrinsic functional requirement of the Bcl11a+62 ortholog for appropriate globin gene regulation in vivo.

Figure 6F:
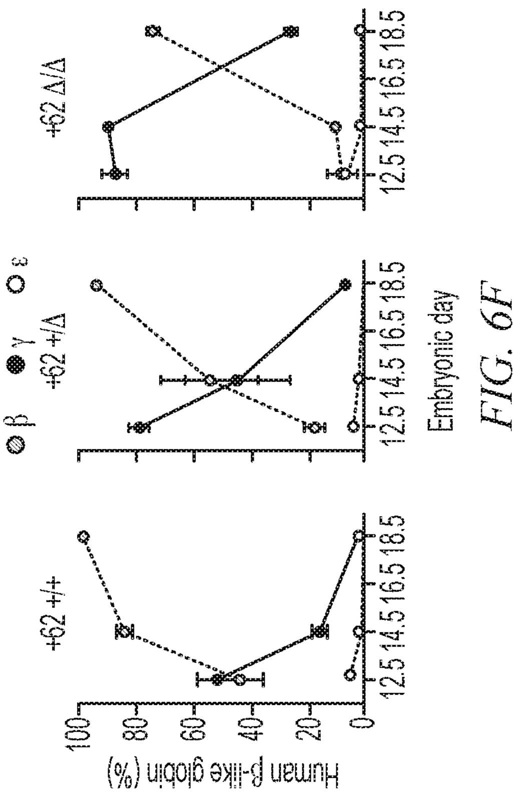
Figure 6E:
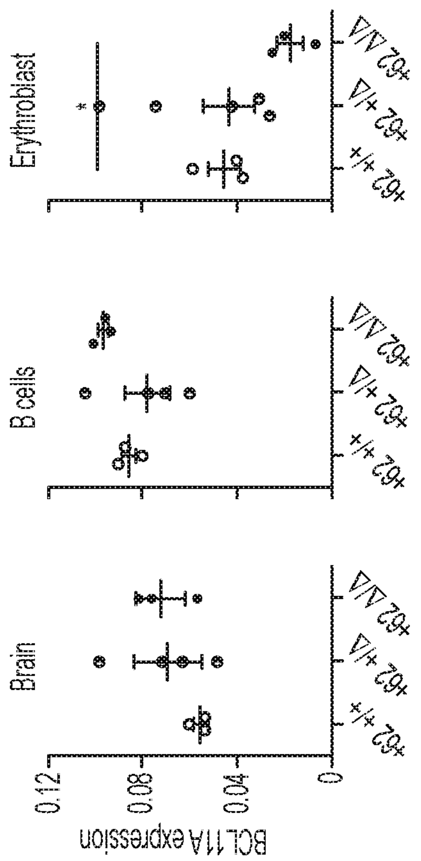

Germline +62 deletion mice were derived from CJ9 mESCs and bred with β-YAC mice. Previous studies have demonstrated an essential role for Bel11a in structural development of the central nervous system as well as in B-lymphocyte ontogeny (56,57). BCL11A expression was unperturbed in the brain or sorted B cell precursors from E 16.5 embryos (FIG. 6*e*). In contrast, there was substantial reduction in BCL11A levels in sorted E16. 5 erythroid precursors (FIG. 6*e*). Strikingly, unlike conventional Bcl11a knockouts that die a few hours after birth, +62 ortholog deletion mice were born healthy at expected Mendelian ratios (FIG. 15*a*). Bcl11a is required for the production of B-lymphocyte progenitors during both embryogenesis and adulthood (56,58). The mice with biallelic deletion of the +62 ortholog appear to have normal numbers of B-cell progenitors in the fetal liver. Furthermore, at four weeks of age these mutant animals demonstrated circulating peripheral blood B-lymphocyte frequencies comparable to wild-type littermates (FIG. 6*f*; FIG. 15*b, c*)). Other hematopoietic lineages also appeared present at similar frequencies as wild-type littermates. Developmental regulation of transgenic human globin genes occurs in the mid-gestation mouse fetal liver. Fetal livers were evaluated every two days between E12.5 and E18.5 to monitor hemoglobin switching. Repression of human γ-globin and activation of human β-globin was markedly delayed in the +62 ortholog deleted mice. These results indicate that disrupting the erythroid enhancer of BCL11A in vivo results in erythroid-specific disruption of BCL11A expression and relaxed repression of γ-globin, unaccompanied by the obvious neurologic or immunologic toxicities seen in the BCL11A conventional knockout context.

Figure 7B:
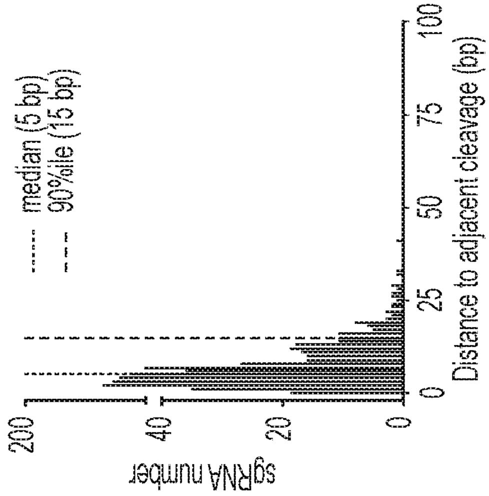
FIGS. 7A-7F shows the tiled pooled in situ CRISPR-Cas9 BCL11A enhancer screen. Distribution of NAG PAM sgRNAs mapped to genomic cleavage position. The vertical lines represent sgRNA cleavage sites for sgRNAs mapped to plus and minus strands. Distance to adjacent genomic cleavage position for NAG PAM sgRNAs. Deep sequencing the lentiviral plasmid library demonstrated that 1,337 of 1,338 sgRNAs (99.9%) were successfully cloned. The representation of sgRNAs within the library showed a relatively narrow distribution, with a median of 718 and the 10% and 90% percentiles ranging from 337 to 1,205 normalized reads as indicated by the vertical dotted lines. HbF distribution in HUDEP-2 cells transduced with Cas9 and individual sgRNAs, either nontargeting or targeting BCL119A exon 2. Enrichment scores of NGG sgRNAs between six biological replicates. Mapping sgRNA dropout scores of NGG sgRNAs relative to genomic cleavage positions and repetitive elements. Nontargeting sgRNAs pseudo-mapped with 5 bp spacing.
Figure 7A:
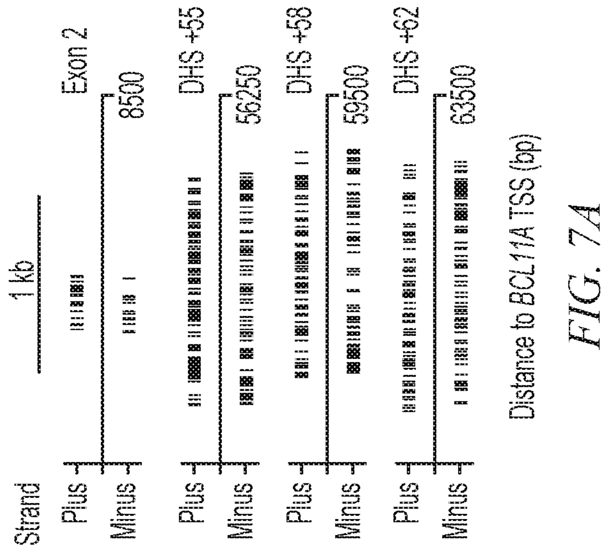
Figure 7C:
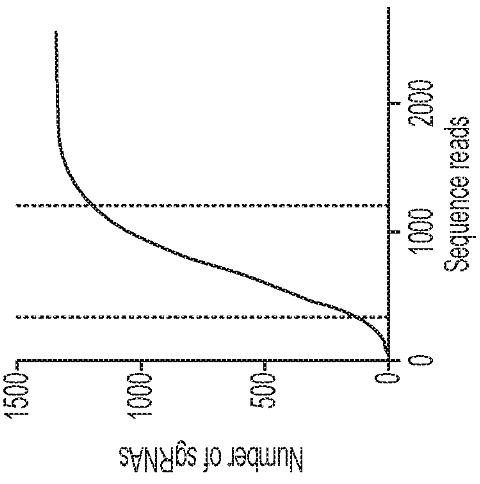
Figure 7D:
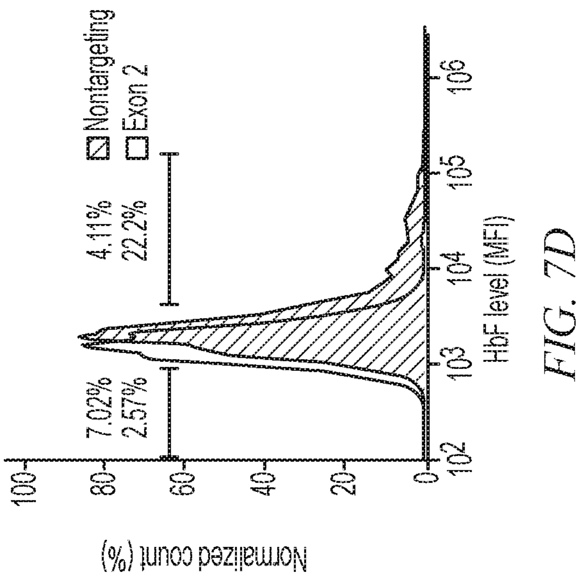
Figure 7E:
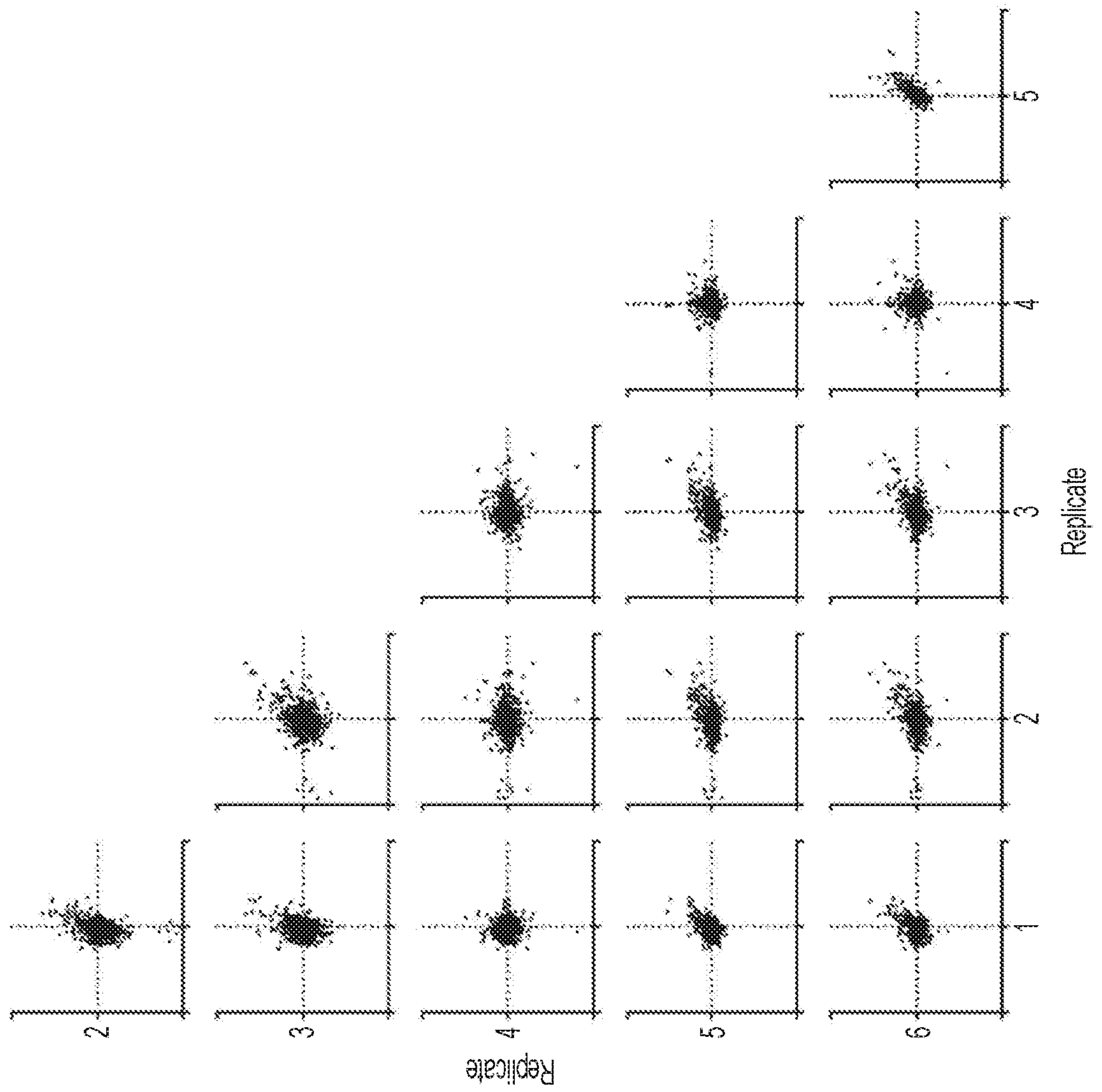
Figure 7F:
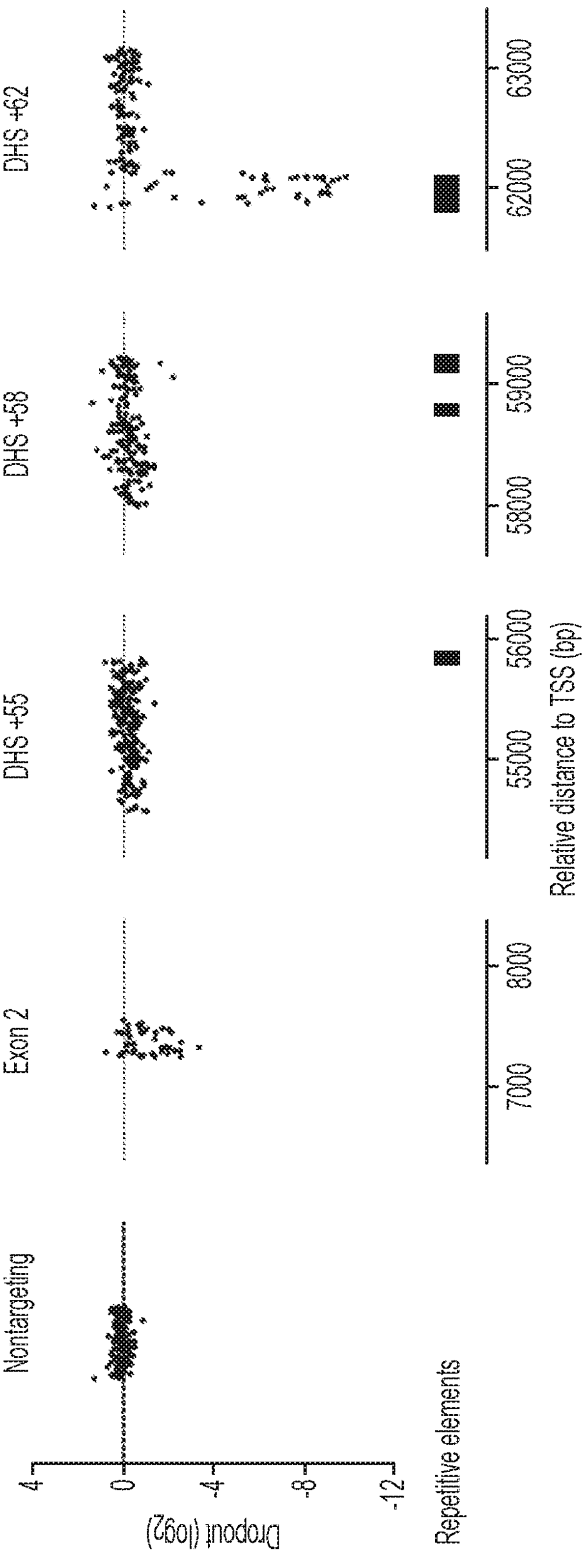
Figure 11A:
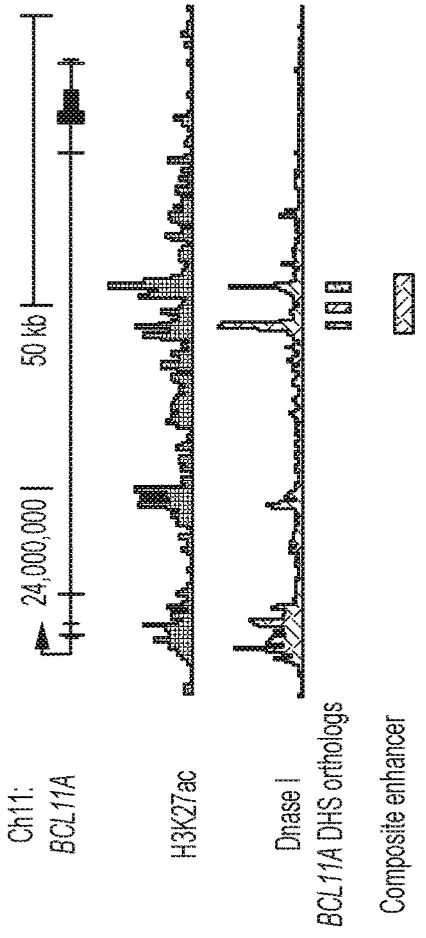
FIGS. 11A-11N shows the tiled pooled in situ CRISPR-Cas9 Bcl11a enhancer screen.
Figure 11B:
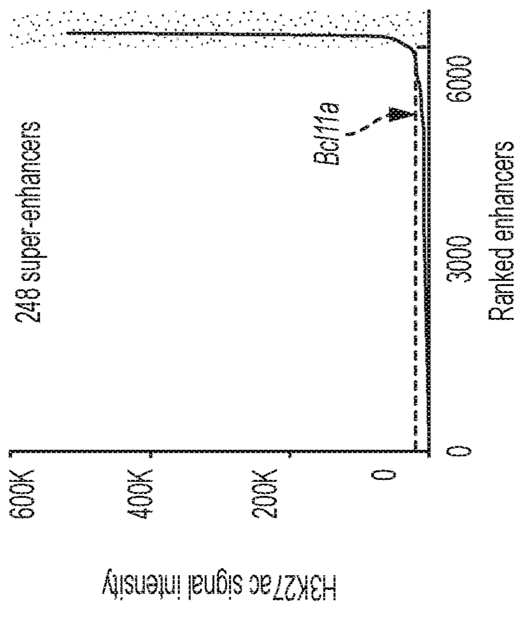
FIG. 11*b*, Ranked enhancers in mouse fetal liver erythroid precursors by H3K27ac signal intensity, with super-enhancers shaded.
Figure 11C:
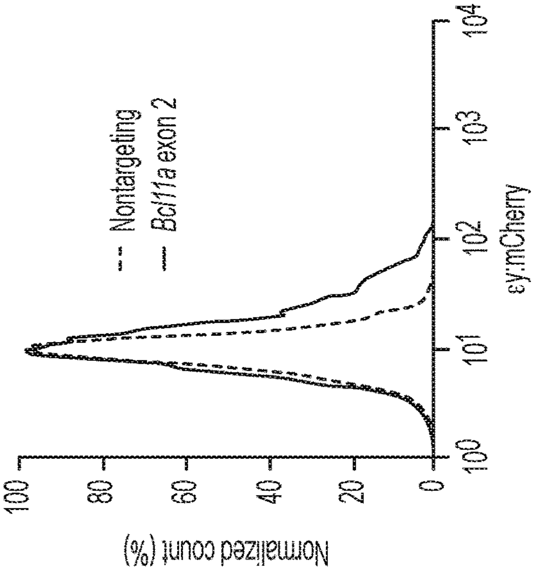
FIG. 11*c*, mCherry expression upon exposure to Cas9 and an individual sgRNA targeting BCL11A exon 2 in MEL εy:mCherry reporter cells.
Figure 11D:
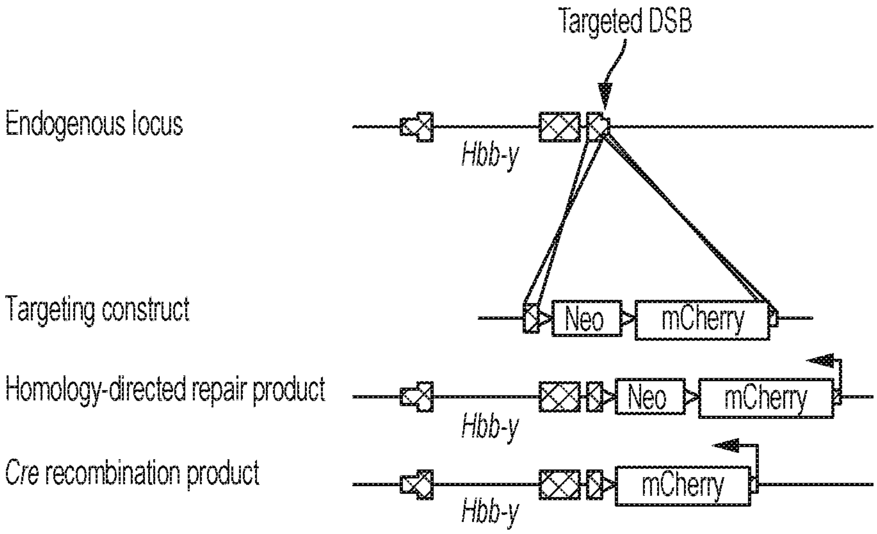
FIG. 11*d*, Strategy to knock-in by homology-directed repair the fluorescent protein mCherry into the mouse embryonic globin Hbb-y locus (encoding the εy embryonic globin chain).
Figure 11E:
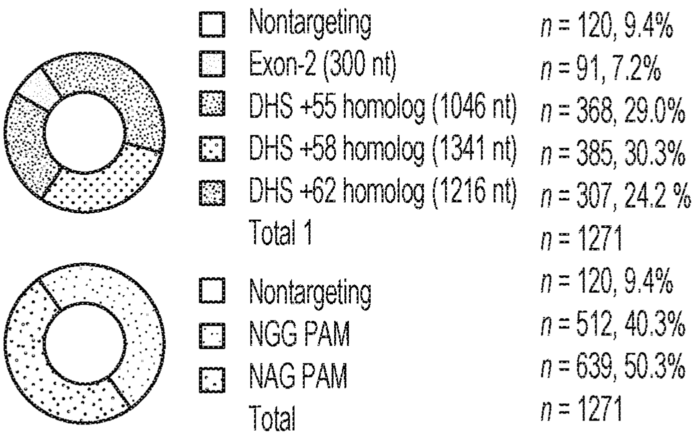
FIG. 11*e*, Library composition by target sequence and PAM restriction.
Figure 11G:
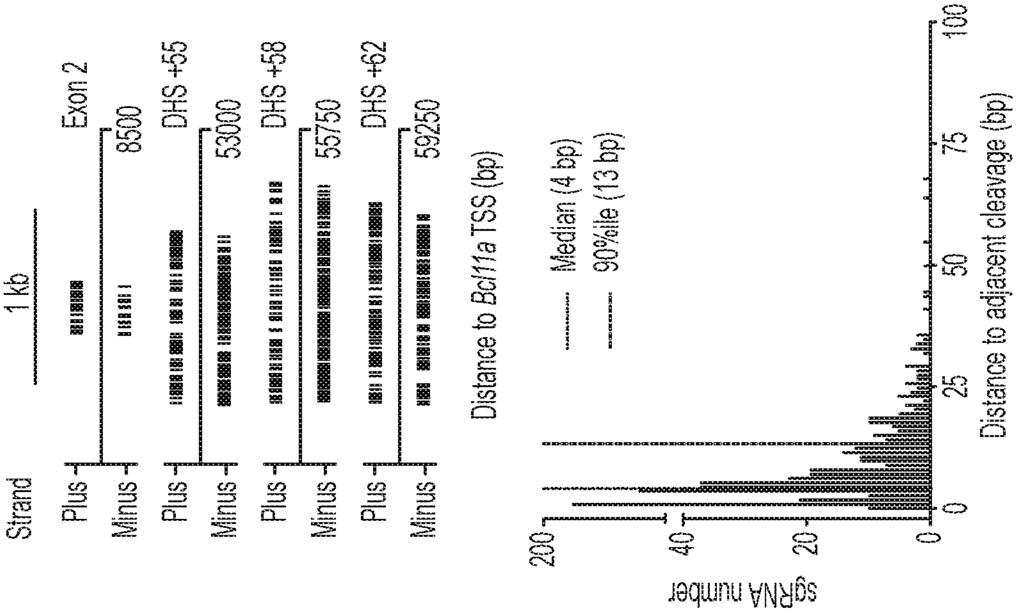
FIG. 11*g*, Deep sequencing the lentiviral plasmid library demonstrated that 1,271 of 1,271 sgRNAs (100%) were successfully cloned. The representation of sgRNAs within the library showed a relatively narrow distribution, with a median of 735 and the 10% and 90% percentiles ranging from 393 to 1,240 normalized reads as indicated by the vertical dotted lines.
Figure 11F:
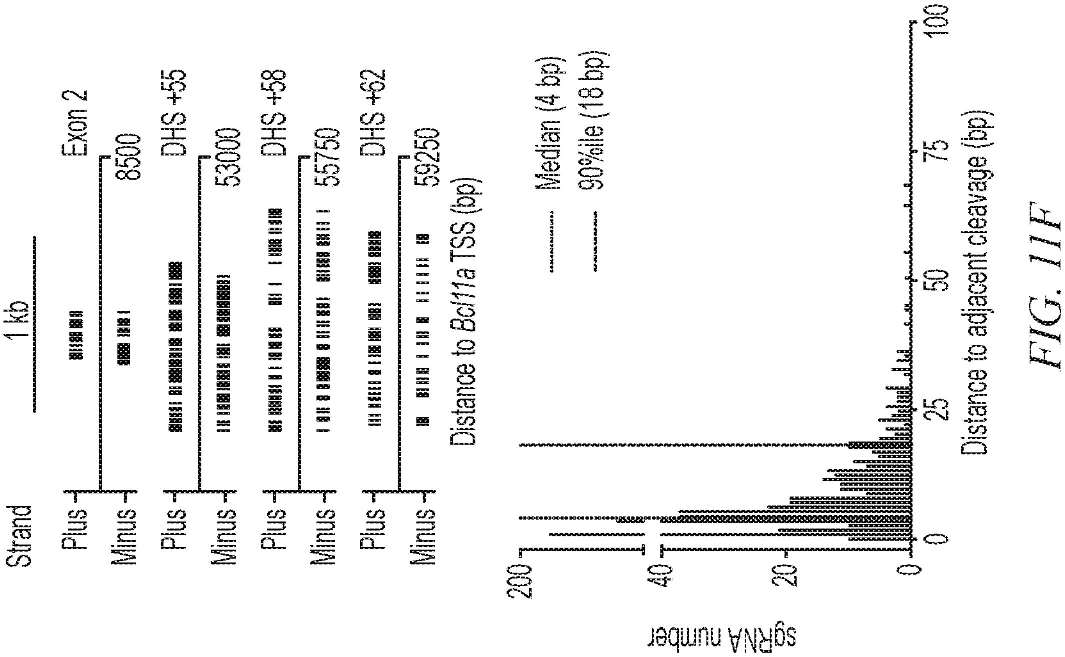
FIG. 11*f*, Distribution of NGG (upper left) and NAG (upper right) PAM sgRNAs mapped to genomic cleavage position. The vertical lines represent sgRNA cleavage sites for sgRNAs mapped to plus and minus strands. Distance to adjacent genomic cleavage position for NGG (lower left) and NAG (lower right) PAM sgRNAs.
Figure 11H:
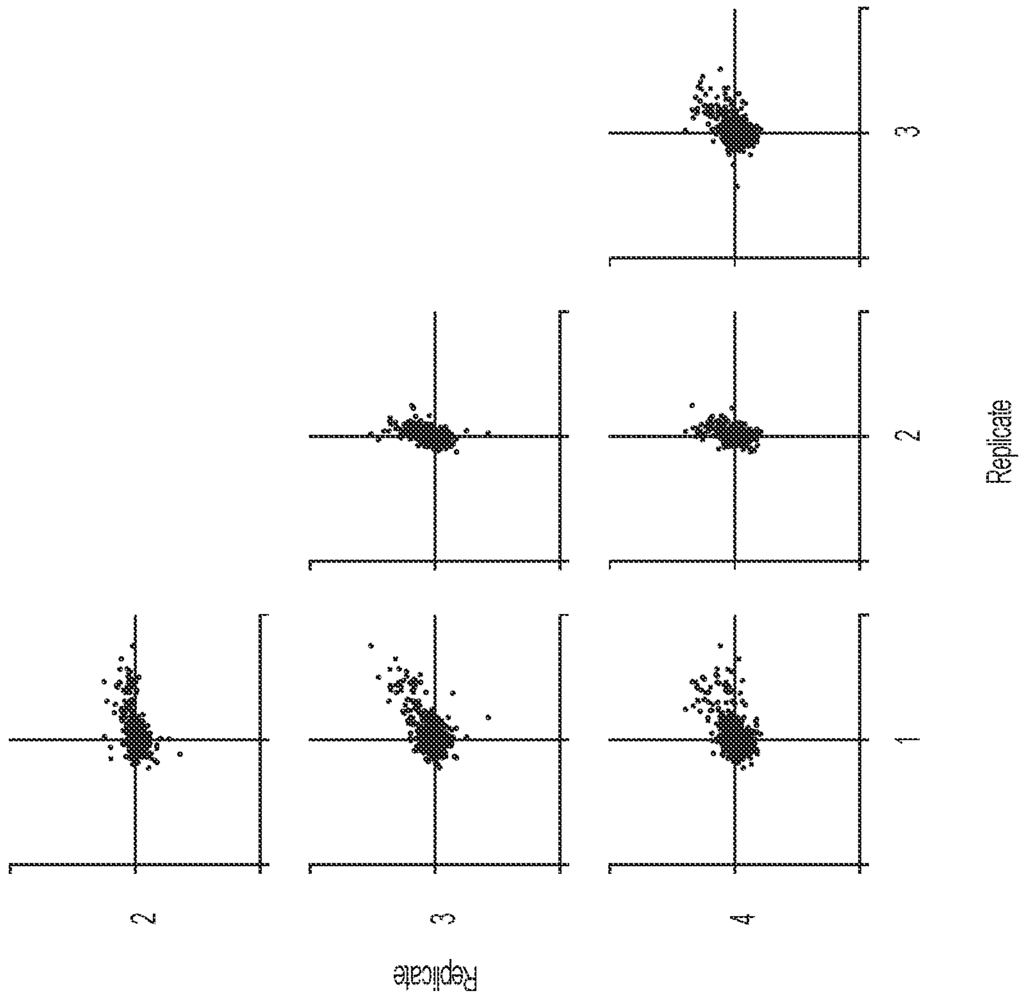
FIG. 11*h*, εy:mCherry sort of library transduced cells.
Figure 11K:
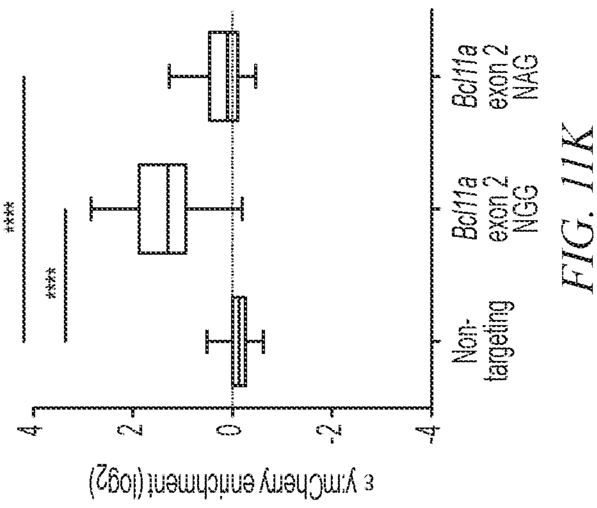
Figure 11J:
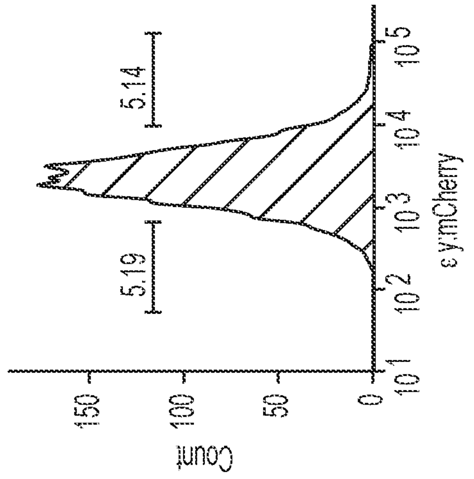
Figure 12A:
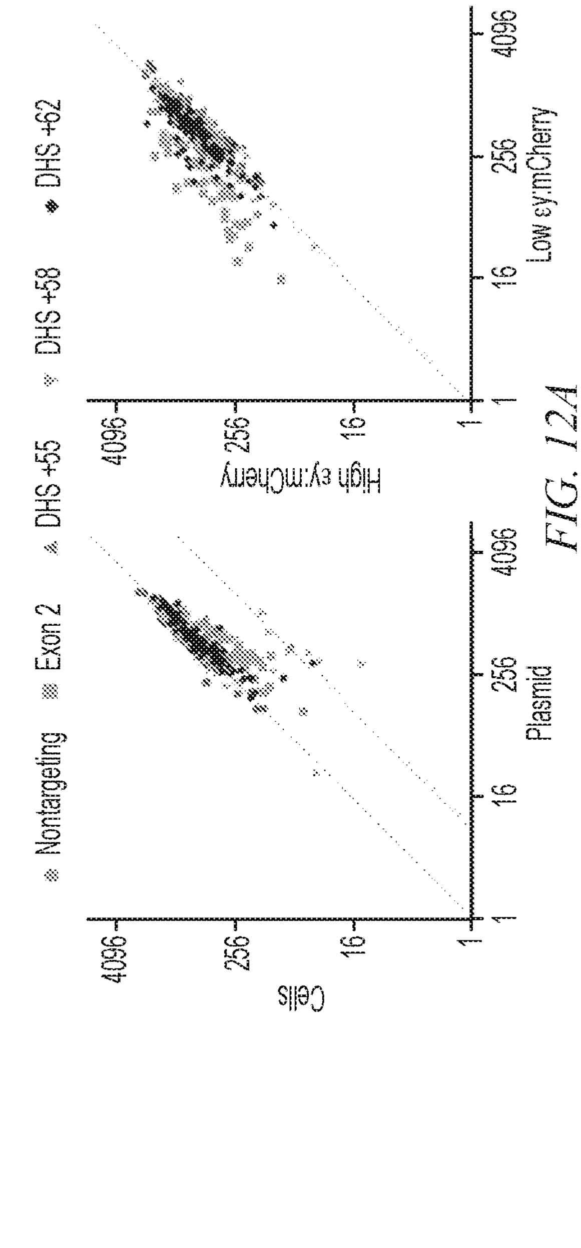
FIGS. 12A-12D shows BCL11A enhancer screen analyses.
Figure 12B:
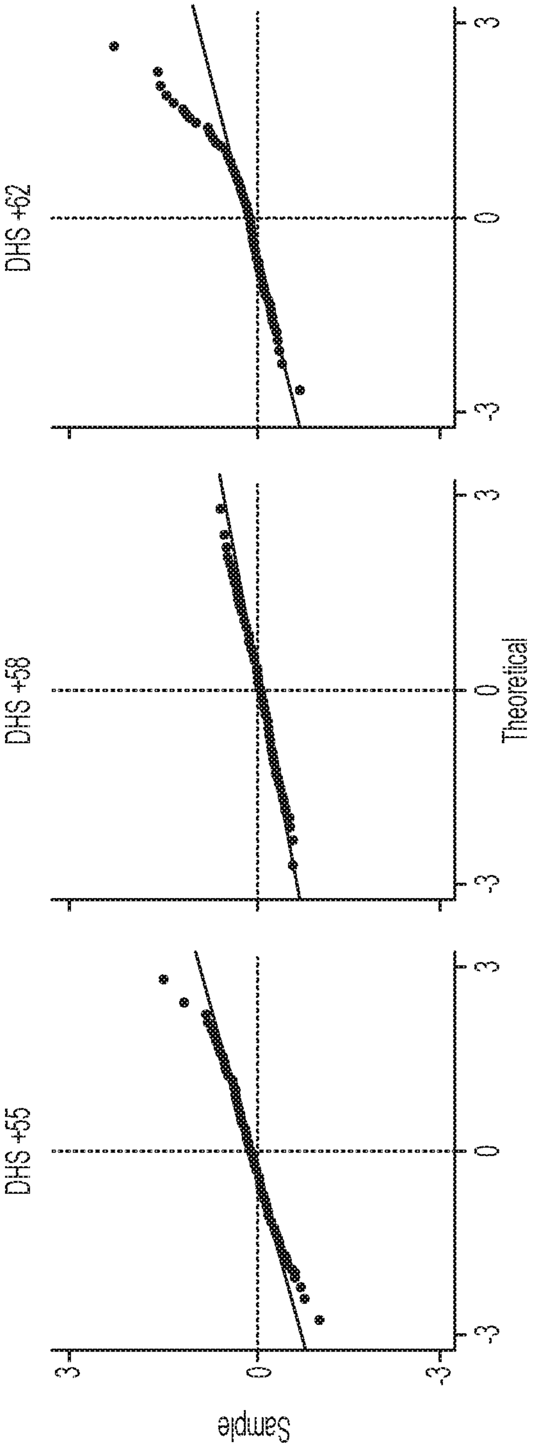
Figures 12C, 12D:
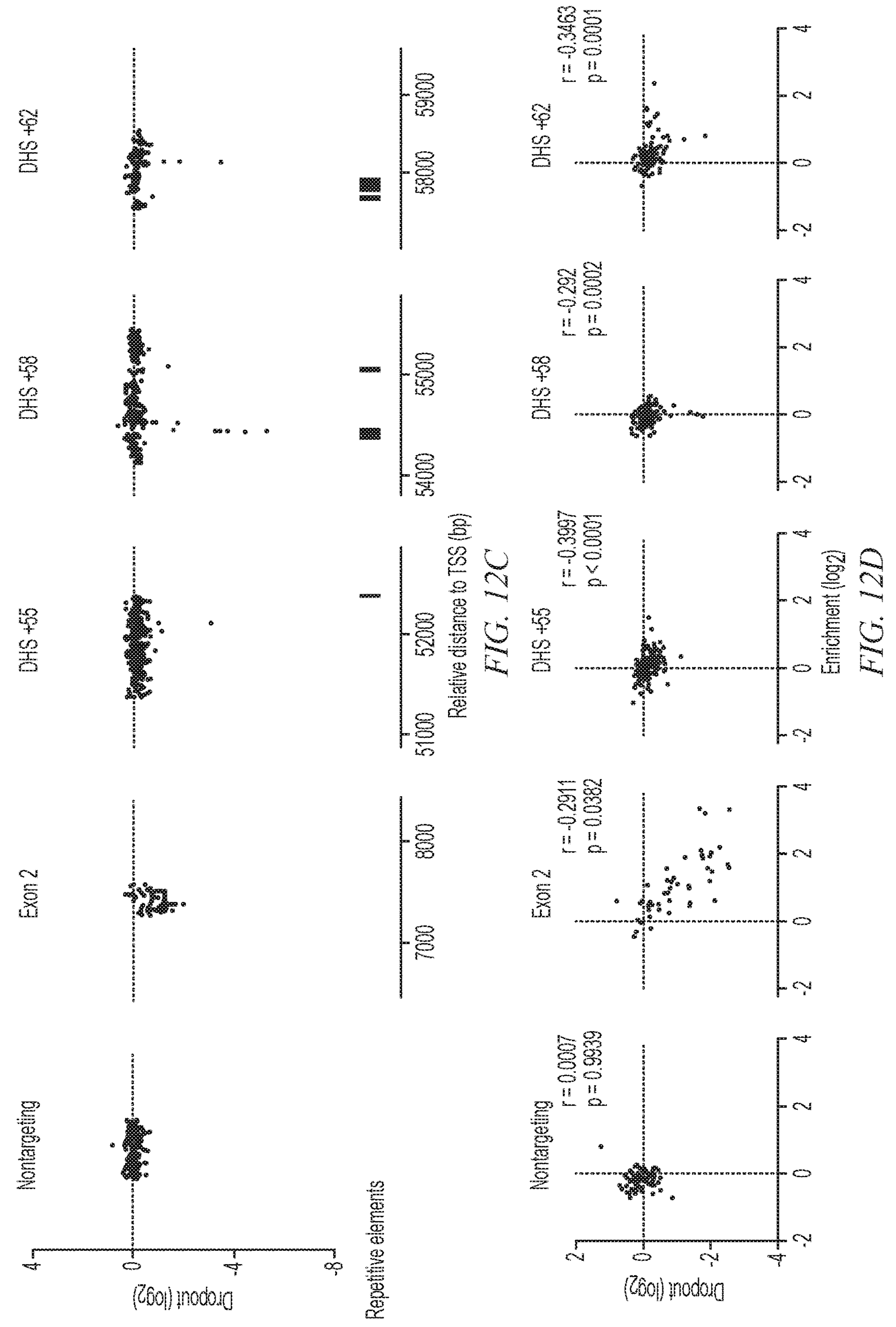
Figure 13A:
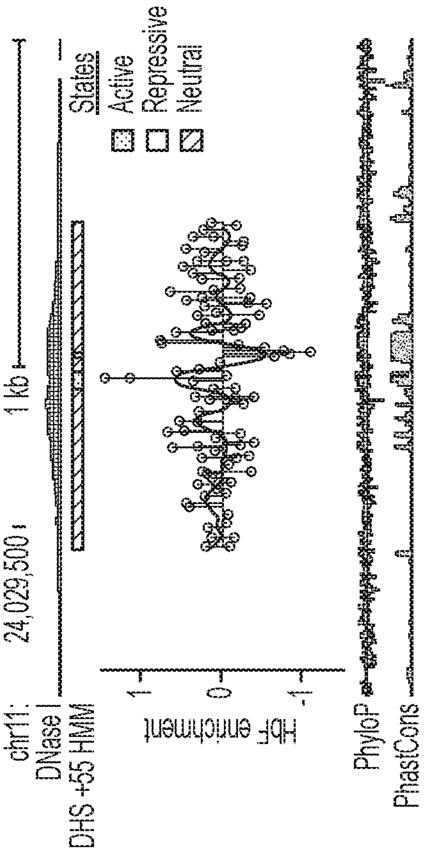
FIGS. 13A-13E shows functional sequences at the BCL11A erythroid enhancer.
Figure 13B:
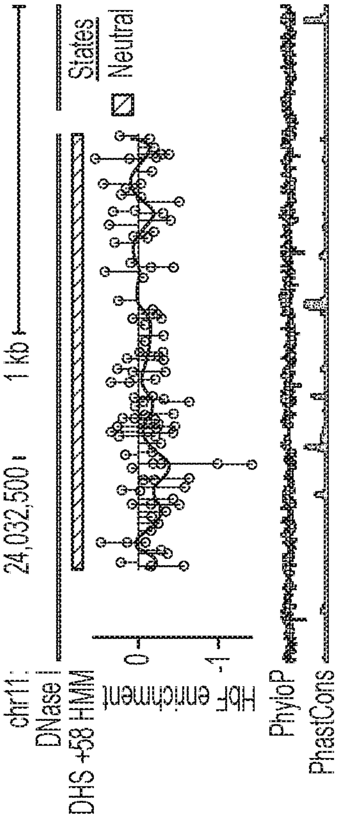
Figure 13C:
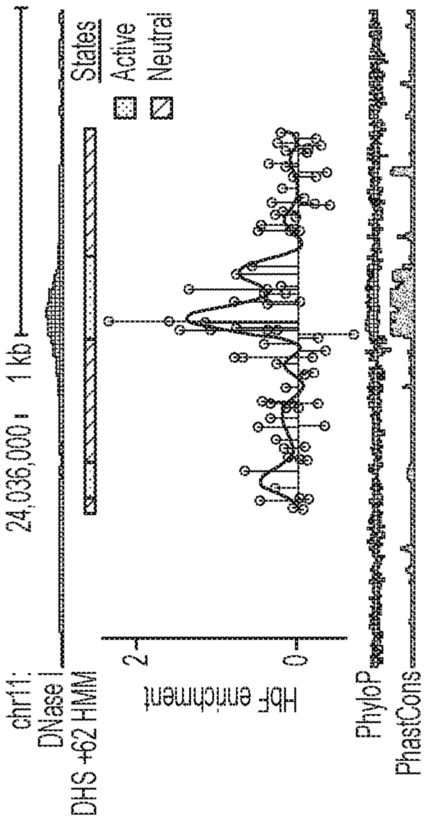
Figure 13D:
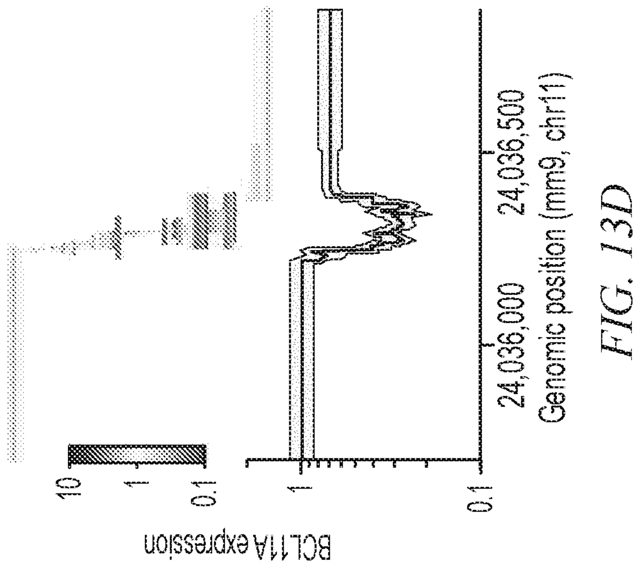
Figure 13E:
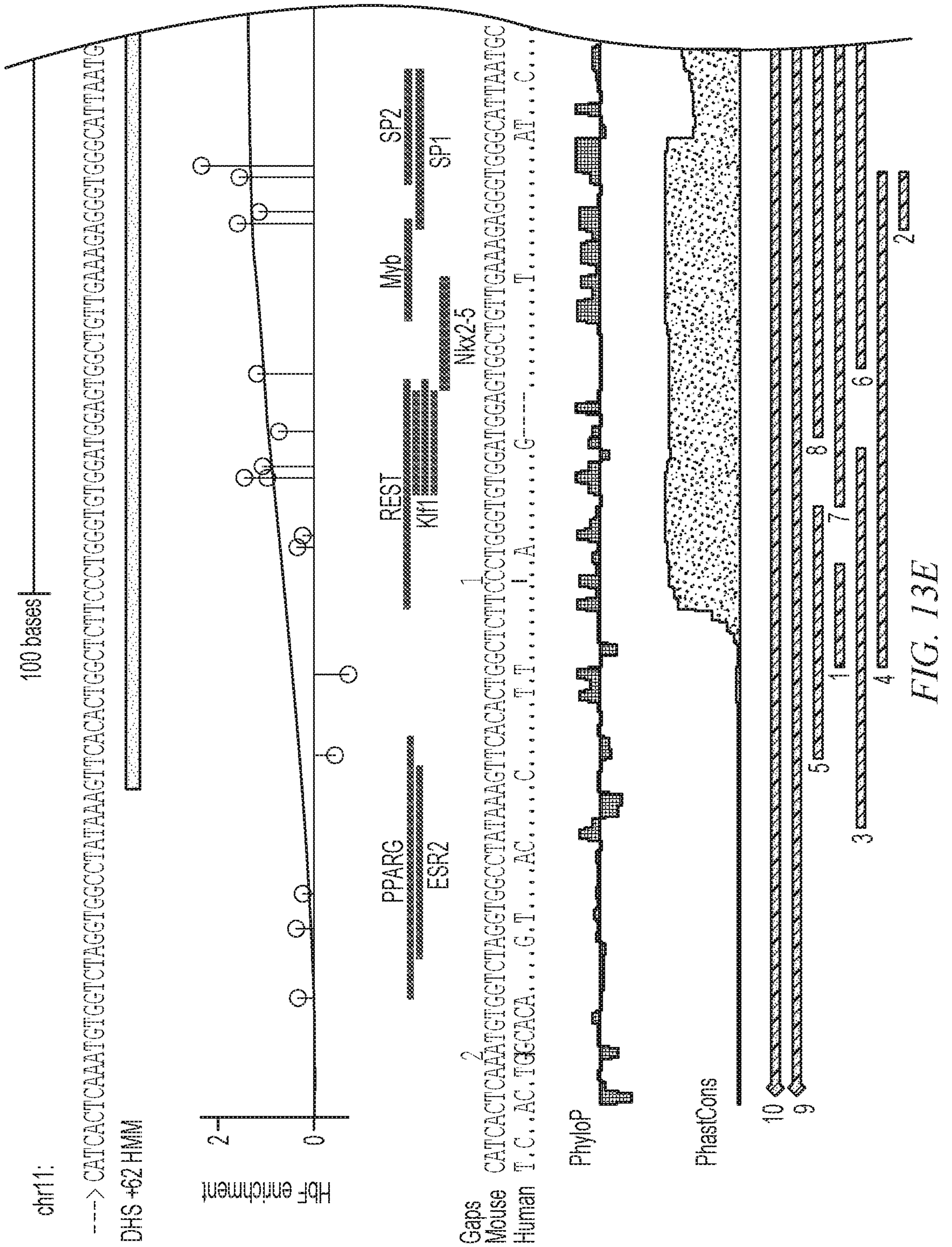
Figure 13E:
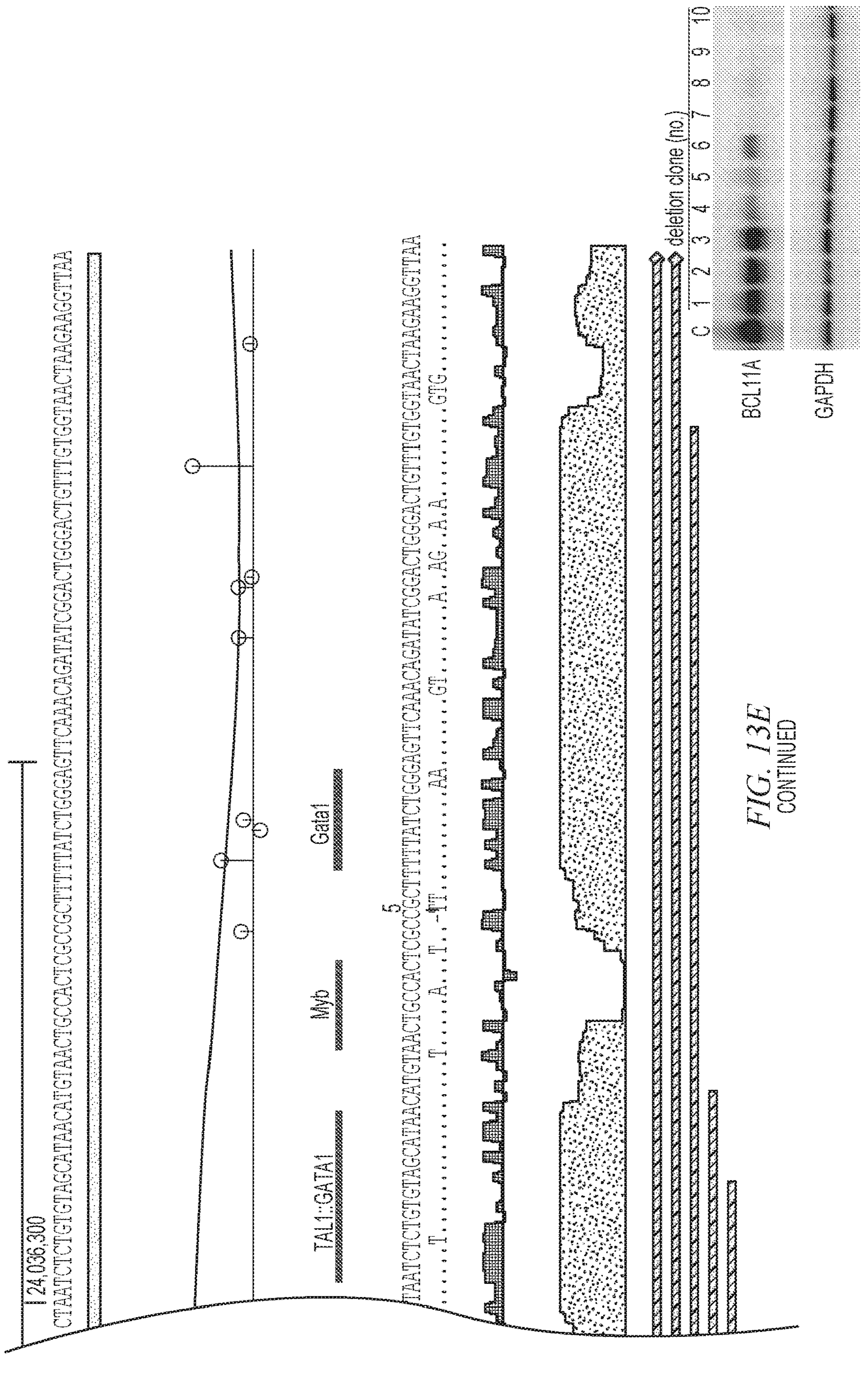

Applicants have employed a novel application of CRISPR-Cas9 genome editing, saturating mutagenesis of noncoding elements in situ, to provide important insight into the organization and function of the BCL11A erythroid enhancer. Traditional tests of enhancer function rely on ectopic heterologous reporter assays and/or correlative biochemical features such as the pattern of chromatin decoration. Genome editing allows facile evaluation of the requirement of enhancer sequences within their endogenous chromatin context for appropriate gene regulation. As shown here, high-resolution high-throughput pooled tiling sgRNA reveals underlying enhancer sequence requirements approaching nucleotide resolution. Although enhancers are composed of transcription factor binding motifs, the presence of motifs alone is inadequate to predict enhancers. Motif predictions can be overly sensitive, in that only a small fraction of predicted motifs tend to be corroborated by ChiP-seq occupancy studies. On the other hand, motif prediction can also be insensitive; for example, a recent report highlights the importance of low-affinity motifs for achieving specificity of enhancer function (59). Previously Applicants showed that GATA1 occupies +58 in primary erythroid precursors (42). Applicants did not observe efficient editing by SpCas9 with NAG restricted sgRNAs (FIGS. 7*e*, 11*j*).

However this region possesses neither DNase sensitivity nor functional requirement in mouse erythroid cells. Despite this divergence, the human core GATA 1 motif has a similar P-value in the nonfunctional mouse ortholog. These results are consistent with a model in which the motif context is critically important in enhancer activity. The sequences immediately adjacent to the GATA 1 motif, where both HbF-associated sgRNAs and mutations enrich, are candidates to fulfill this contextual requirement.

Enhancers paradoxically demonstrate both evolutionary conservation and heightened turnover. Common trait-associated enhancer variation indicates the frequent occurrence of intraspecies polymorphic sequences sufficient to modulate enhancer function and thereby produce novel phenotypes. At BCL11A, Applicants previously described a trait-associated enhancer haplotype defined by two SNPs (42). The pooled CRISPR screening revealed that each of these SNPs reside near functional enhancer states consistent with their roles as causal variants. The most potent enhancer region, within +58, has no common variants near its functional core. This example demonstrates how fine-mapping GWAS associations to individual SNPs can substantially underestimate the biologic importance of the underlying elements to the associated trait. In addition, these data demonstrate that apparent sequence conservation at the BCL11A enhancer masks underlying functional divergence. The mouse and human BCL11A erythroid composite enhancers share primary sequence homology, an erythroid enhancer chromatin signature, and syntenic intronic position relative to coding sequences. Moreover, both are required for erythroid expression of BCL11A and repression of embryonic/fetal globin genes. However, our high-resolution CRISPR mutagenesis analysis reveals divergence in the architecture of these enhancers. The mouse enhancer is composed of two DHSs, of which +62 has functional dominance, as validated in vivo. In contrast, the human enhancer has three DHSs, of which +62 is of the least and +58 of the greatest functional importance. Of note, human BCL11A enforces the γ- to β-globin developmental switch around the time of birth. The timing and nature of these switches and the globin genes themselves are distinct in primates as compared to nonprimate vertebrates that only exhibit a mid-gestation embryonic to adult switch (60-62). Therefore it would seem plausible that critical regulatory mechanisms at BCL11A might differ between species.

Recent appreciation for the wide variation in intensity of biochemical features associated with enhancer elements has led to a renewed interest in clustered enhancer elements and so-called super-enhancers. Here Applicants show that one such super-enhancer is organized as a hierarchy of constituent DHSs, with some critical and others minimally required for gene expression. Moreover even within a critical DHS such as BCL11A +58, there are many dispensable and only a few critical sequences. These experiments show how a super-enhancer may be vulnerable to single DSBs.

The hemoglobin disorders represent the most common Mendelian inherited human conditions. The level of HbF is a key modifier of clinical severity of these diseases and BCL11A is the chief regulator of HbF level (63). Natural occurring genetic variation at the BCL11A enhancer is well-tolerated and associated with HbF level and β-hemoglobin disorder clinical severity. The work presented here offers a framework for therapeutic genome editing of the BCL11A enhancer for β-hemoglobin disorders. Enhancer disruption by individual sgRNAs in primary erythroid precursors results in substantial HbF induction. This approach may mitigate erythroid-specific growth disadvantages of complete BCL11A loss. Furthermore it may spare BCL11A expression in nonerythroid contexts, such as B-lymphopoiesis (FIG. 15*b-d*). For example Applicants observed normal B-lymphopoiesis in mice deficient for the +62 ortholog. A challenge for the field is that it is not yet possible to accurately model HbF repression experimentally. However, individuals haploinsufficient for BCL11A due to microdeletions exhibit marked neurologic deficits, and elevated HbF, well beyond that seen in homozygotes for high-HbF common enhancer haplotypes (Basak et al, JCI, in press). Taken together, these data indicate that perturbation of the critical sequences within the BCL11A enhancer defined here may result in HbF levels exceeding a clinical threshold required to ameliorate the 0-hemoglobin disorders.

Common SNP in human DHS +58. The only common SNP within the Active region is rs6738440 at the edge of state region (chr2: 60722241), 118 to 160 bp from the cluster of top-scoring sgRNAs (chr2:60722359-60722401); the next closest common SNP was rs62142615 (chr2: 60722120), 119 bp away. Neither sgRNAs with significant adjacent enrichment nor overlying genome-scale significant motifs with either the major A- or minor G-allele were observed at rs6738440. Previous conditional analysis of the rs 1427407-rs7606173 haplotype was unable to demonstrate residual significant trait association for this variant (42).

Human and mouse DHS sequence homology. Sequence homology is detectable at an approximately similar intronic position with respect to the TSS for each of the mouse sequences homologous to the three human DHSs: human +55 (length 1283 bp) has 402 positions of nucleotide identity (31.3%) to the mouse +55 ortholog (length 1046 bp), human +58 (1264 bp) has 367 positions of nucleotide identity (28.6%) to the mouse +58 ortholog (length 1341 bp), and human +62 (length 1369 bp) has 281 positions of nucleotide identity (20.5%) to the mouse +62 ortholog (length 1216 bp). By comparison, of the 2508 bp in human BCL11A coding sequence, 2424 nucleotides demonstrate identity (96.7%) to mouse Bcl11a coding sequence.

Pooled CRISPR enhancer saturation mutagenesis screen in these MEL εy:mCherry reporter cells. The mouse sgRNA library was comprised of both NGG and NAG PAM restricted sgRNAs. Similar to the human enhancer screen, the sgRNAs were distributed throughout the target sites, with a median distance to adjacent cleavage site of 4 bp and 90% of adjacent cleavage sites falling within 18 bp for NGG PAM restricted sgRNAs. Applicants successfully cloned into lentiviral plasmids all 1271 members of the library with a relatively narrow distribution of representation (median 735, 10% ile 393, 90% ile 1240 normalized reads.

Figure 11I:
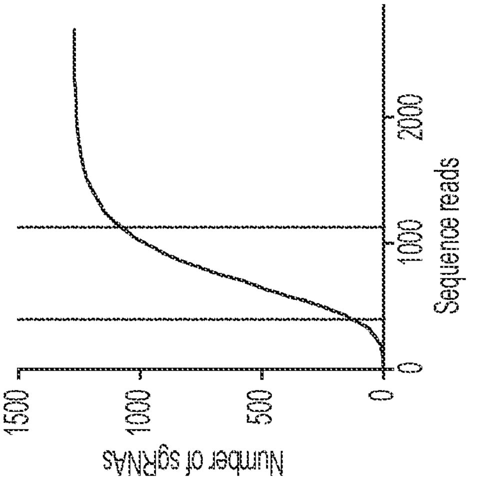
FIG. 11*i*, Control sgRNA enrichment. Boxes demonstrate 25th, median, and 75th percentiles and whiskers minimum and maximum values. **P<0.0001.
Figure 11M:
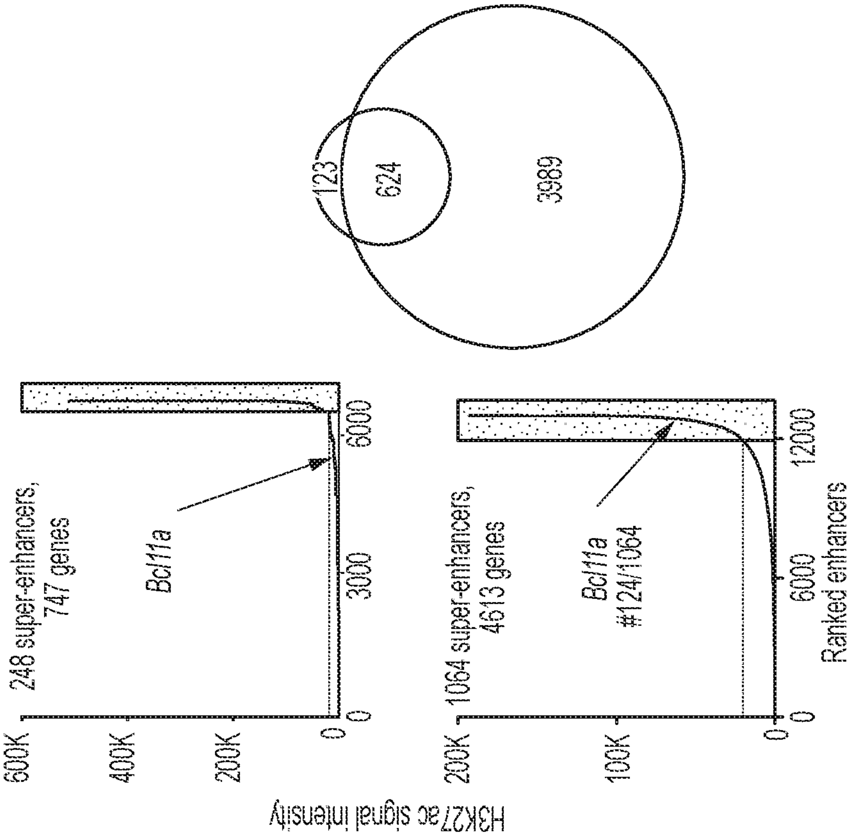
FIG. 11*m*, Ranked enhancers in mouse erythroid precursors by H3K27ac signal intensity, with super-enhancers shaded. Super-enhancer associated genes indicated by Venn diagram.
Figure 11L:
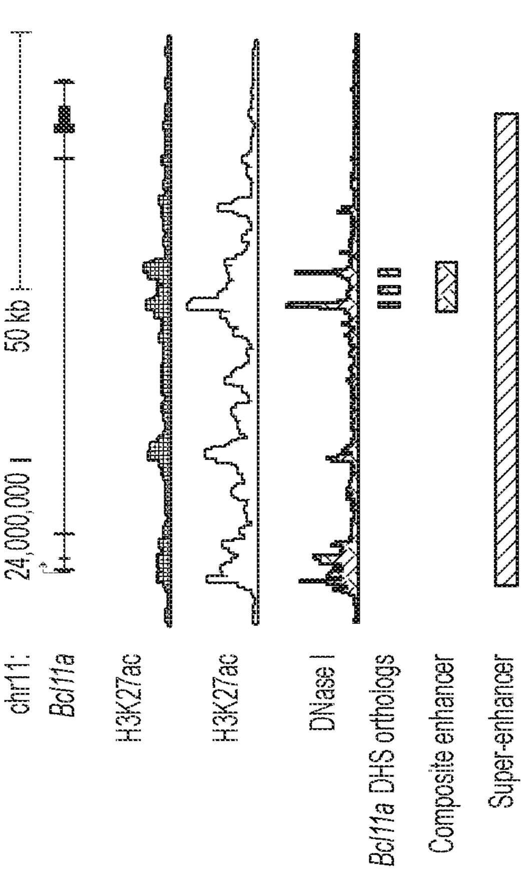
FIG. 11*l*, Schematic of the mouse Bcl11a locus (mm9, transcription from left to right) with erythroid chromatin marks (top, dark blue H3K27ac from Kowalczyk et al, middle, light blue H3K27ac from Dogan et al, and bottom, black DNase I from Bauer et al) and regions of primary sequence homology to the human DHSs displayed. Y-axes for H3K27ac tracks are both scaled to maximum 3.5 reads per million. Composite enhancer as previously defined.
Figure 11N:
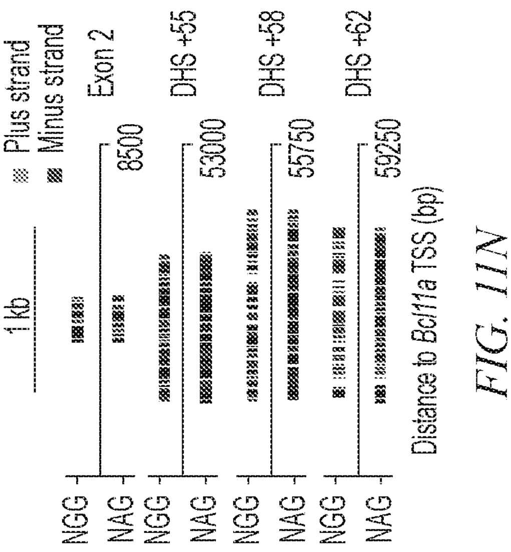

Although there was slight enrichment that reached statistical significance, the NAG PAM restricted sgRNAs showed substantially reduced overrepresentation relative to the potent NGG restricted sgRNAs, so further analysis was restricted to the NGG PAM restricted sgRNAs (FIG. 11*i*).

The library included sgRNA sets tiling the mouse DHS +55, +58, and +62 orthologs, as well as 120 nontargeting negative controls and 91 Bcl11exon-2 targeting positive controls.

Following transduction at low multiplicity by the lentiviral library, and in vitro culture for two weeks, cells were sorted into high- and low-εy:mCherry pools. Deep sequencing was performed of the genomic DNA to evaluate the representation of sgRNA libraries in the pools. The nontargeting negative control sgRNAs were evenly represented in the high—as compared to low-εy:mCherry pools whereas the positive control Bcl11a exon-2 targeting sgRNAs with NGG PAM were significantly overrepresented in the εy:mCherry-high pool. Applicants observed a strong correlation of enrichment scores for individual sgRNAs between the four biological replicates of the screen.

Applicants analyzed the representation of the library in cells that had completed two weeks of in vitro culture (sum of the high- and low-εy:mCherry pools) as compared to the initial lentiviral plasmid pool. The large majority of sgRNAs showed equivalent representation in the initial plasmid pool and as integrants in cells at the completion of the experiment. A small number of sgRNAs (n=8) showed substantial dropout $>2^{-3}$ and were removed from subsequent enrichment analysis. Similar to the human screen, these mapped to repetitive elements.

Example 2

Vemurafenib is a potent inhibitor of mutant BRAF, which is found in 50-70% of melanomas (83,84). Resistance to vemurafenib arises within months in almost all patients (85) and surviving tumor cells display increased malignancy that rapidly leads to lethality (86). Previously, Applicants used a genome-scale CRISPR library to identify genes in which loss-of-function mutations result in resistance to vemurafenib in a melanoma cell line with a V600E BRAF mutation (37).

Materials and Methods

Noncoding Library Design and Cloning

To design the noncoding libraries for NF1, NF2, and CUL3, Applicants selected regions of 100 kb flanking the coding sequence for both of the most highly expressed RefSeq isoforms as determined by RNA-seq quantification in BRAF-mutant A375 melanoma cells (NF1 primary: NM_001042492, NF1 alternate: NM_000267; NF2 primary: NM_000268, NF2 alternate: NM_016418; CUL3 primary: NM_003590, CUL3 alternate: NM_001257197). Applicants also included the 5' and 3' untranslated regions (UTRs). For these regions, Applicants identified all Cas9-targetable sites on both strands, i.e. those containing the protospacer-adjacent motif (PAM) NGG. Applicants eliminated sgRNAs with potential off-targets elsewhere in the genome as described previously (Sanjana et al. 2014; Hsu et al. 2013), which yielded 18,315 sgRNAs with the following median distances between neighboring sgRNAs for each library: NF1 17 bp, NF2 12 bp, CUL3 19 bp. Genomic sequences were retrieved using the UCSC Genome Browser (hg19) and Galaxy. Custom Python and C scripts were used for sgRNA guide design and off-target optimization.

The sgRNA sequences were synthesized as single-stranded oligonucleotides on a CustomArray synthesizer, PCR amplified using Phusion Flash (ThermoFisher Scientific F548L) polymerase (15 cycles), and Gibson cloned into a guide-only lentiviral vector (lentiGuide-Puro, Addgene 52963).

Vemurafenib Pooled Lentiviral Production and Screening

The vemurafenib resistance screen was conducted similarly to a previously described genome-wide CRISPR screen (Shalem et al. 2014). Lentivirus was produced via transfection of library plasmid with appropriate packaging plasmids (psPAX2: Addgene 12260; pMD2.G: Addgene 12259) using Lipofectamine 2000 and Plus reagent (ThermoFisher Scientific, 11668019 and 11514015) in HEK293FT (ThermoFisher Scientific, R70007). At 3 days post-transfection, virus was collected and passed through a 0.45 um filter and stored at 80° C. until use (supernatant, unpurified virus).

For the screen, A375 human melanoma cells (ATCC CRL-1619) were cultured in RPMI-1640 media (ThermoFisher Scientific 61870127) with 10% fetal bovine serum (Seradigm 1500-500) and no antibiotics ("R10 media"). To first introduce Cas9, A375 was transduced with a Cas9-expressing lentivirus (lentiCas9-Blast, Addgene 52962) and selected for 7 days with 10 ug/mL blasticidin. Resistant cells were expanded and transduced with the CUL3 library (lentiGuide-Puro) pooled lentivirus in 2 separate infection replicates with $3.45\times10^{7}$ cells per infection replicate using a standard spinfection protocol. After 24 hours, cells were selected with 1 ug/mL puromycin for 7 days, resulting in ~30% cell survival. The overall representation was ~1000 cells per construct (830 in replicate 1 and 1130 in replicate 2) with ~83% of surviving cells receiving a single sgRNA construct (see Chen et al. for details of Poisson infection model and single-infection percentage calculation).

After 7 days, Applicants removed puromycin and split cells into separate flasks with either 2 uM vemurafenib (PLX4032, Selleckchem S1267 in DMSO) or an equal volume of DMSO. At this point, a representative sample of $3\times10^7$ cells from each infection replicate was frozen at 20° C. as an early time point ("Day 0") for screen readout. All flasks were either passaged or had fresh media added every 2 days. At day 14 after addition of vemurafenib/DMSO, the screen was terminated and 1-$3\times10^7$ cells were frozen at −20° C. for each condition/replicate ("Day 14").

Screen Readout and Data Analysis

For each timepoint/sample, genomic DNA was extracted following a modified salting-out precipitation method described previously in detail (Chen et al. 2015). The sgRNA readout was performed using two rounds of PCR (Shalem et al. 2014). For the first PCR step, a region containing the sgRNA cassette in the lentiviral genomic integrant was amplified from extracted genomic DNA using the following primers:

```
ReadoutPCR1_F
                                          (SEQ ID NO: 148)
AATGGACTATCATATGCTTACCGTAACTTGAAAGTATTTCG

ReadoutPCR1_R
                                          (SEQ ID NO: 149)
CTTTAGTTTGTATGTCTGTTGCTATTATGTCTACTATTCTTTCC
```

For each sample, Applicants performed 12 duplicate PCR reactions with 3 ug of gDNA in each reaction (total gDNA=36 ug per sample for representation of ~$5\times10^6$ cells). Applicants pooled the unpurified PCR products and used the mixture for a single second PCR reaction per biological sample. This second PCR adds on Illumina sequencing adaptors, barcodes and stagger sequences to prevent monotemplate sequencing issues. Complete sequences of the 12 forward and 12 reverse Illumina readout primers used are:

| ReadoutPCR2_F Primers 1 to 12: | | |
|---|---|---|
| F01 | SEQ ID NO: 150 | AATGATACGGCGACCACCGAGATCTACACTCTTTCCCTACACGACGCTCTTCCGATCTtAAGTAGAGtcttgtggaaaggacgaaacaccg |
| F02 | SEQ ID NO: 151 | AATGATACGGCGACCACCGAGATCTACACTCTTTCCCTACACGACGCTCTTCCGATCTatACACGATCtcttgtggaaaggacgaaacaccg |
| F03 | SEQ ID NO: 152 | AATGATACGGCGACCACCGAGATCTACACTCTTTCCCTACACGACGCTCTTCCGATCTgatCGCGCGGTtcttgtggaaaggacgaaacaccg |
| F04 | SEQ ID NO: 153 | AATGATACGGCGACCACCGAGATCTACACTCTTTCCCTACACGACGCTCTTCCGATCTcgatCATGATCGtcttgtggaaaggacgaaacaccg |
| F05 | SEQ ID NO: 154 | AATGATACGGCGACCACCGAGATCTACACTCTTTCCCTACACGACGCTCTTCCGATCTtcgatCGTTACCAtcttgtggaaaggacgaaacaccg |
| F06 | SEQ ID NO: 155 | AATGATACGGCGACCACCGAGATCTACACTCTTTCCCTACACGACGCTCTTCCGATCTatcgatTCCTTGGTtcttgtggaaaggacgaaacaccg |
| F07 | SEQ ID NO: 156 | AATGATACGGCGACCACCGAGATCTACACTCTTTCCCTACACGACGCTCTTCCGATCTgatcgatAACGCATTtcttgtggaaaggacgaaacaccg |

-continued

| | | |
|---|---|---|
| F08 | SEQ ID NO: 157 | AATGATACGGCGACCACCGAGATCTACACTCTTTCCCTACACGACGCTCTTCCGATCTcgatcgatACAGGTATtcttgtggaaaggacgaaacaccg |
| F09 | SEQ ID NO: 158 | AATGATACGGCGACCACCGAGATCTACACTCTTTCCCTACACGACGCTCTTCCGATCTacgatcgatAGGTAAGGtcttgtggaaaggacgaaacaccg |
| F10 | SEQ ID NO: 159 | AATGATACGGCGACCACCGAGATCTACACTCTTTCCCTACACGACGCTCTTCCGATCTtAACAATGGtcttgtggaaaggacgaaacaccg |
| F11 | SEQ ID NO: 160 | AATGATACGGCGACCACCGAGATCTACACTCTTTCCCTACACGACGCTCTTCCGATCTatACTGTATCtcttgtggaaaggacgaacaccg |
| F12 | SEQ ID NO: 161 | AATGATACGGCGACCACCGAGATCTACACTCTTTCCCTACACGACGCTCTTCCGATCTgatAGGTCGCAtcttgtggaaaggacgaaacaccg |

| ReadoutPCR2_R Primers 1 to 12: | | |
|---|---|---|
| R01 | SEQ ID NO: 162 | CAAGCAGAAGACGGCATACGAGATAAGTAGAGGTGACTGGAGTTCAGACGTGTGCTCTTCCGATCTtTCTACTATTCTTTCCCCTGCACTGT |
| R02 | SEQ ID NO: 163 | CAAGCAGAAGACGGCATACGAGATACACGATCGTGACTGGAGTTCAGACGTGTGCTCTTCCGATCTatTCTACTATTCTTTCCCCTGCACTGT |
| R03 | SEQ ID NO: 164 | CAAGCAGAAGACGGCATACGAGATCGCGCGGTGTGACTGGAGTTCAGACGTGTGCTCTTCCGATCTgatTCTACTATTCTTTCCCCTGCACTGT |
| R04 | SEQ ID NO: 165 | CAAGCAGAAGACGGCATACGAGATCATGATCGGTGACTGGAGTTCAGACGTGTGCTCTTCCGATCTcgatTCTACTATTCTTTCCCCTGCACTGT |
| R05 | SEQ ID NO: 166 | CAAGCAGAAGACGGCATACGAGATCGTTACCAGTGACTGGAGTTCAGACGTGTGCTCTTCCGATCTtcgatTCTACTATTCTTTCCCCTGCACTGT |
| R06 | SEQ ID NO: 167 | CAAGCAGAAGACGGCATACGAGATTCCTTGGTGTGACTGGAGTTCAGACGTGTGCTCTTCCGATCTatcgatTCTACTATTCTTTCCCCTGCACTGT |
| R07 | SEQ ID NO: 168 | CAAGCAGAAGACGGCATACGAGATAACGCATTGTGACTGGAGTTCAGACGTGTGCTCTTCCGATCTgatcgatTCTACTATTGTTTCCCCTGCACTGT |
| R08 | SEQ ID NO: 169 | CAAGCAGAAGACGGCATACGAGATACAGGTATGTGACTGGAGTTCAGACGTGTGCTCTTCCGATCTcgatcgatTCTACTATTCTTTCCCTGCACTGT |
| R09 | SEQ ID NO: 170 | CAAGCAGAAGACGGCATACGAGATAGGTAAGGGTGACTGGAGTTCAGACGTGTGCTCTTCCGATCTacgatcgatTCTACTATTCTTTCCCCTGCACTGT |
| R10 | SEQ ID NO: 171 | CAAGCAGAAGACGGCATACGAGATAACAATGGGTGACTGGAGTTCAGACGTGTGCTCTTCCGATCTtTCTACTATTCTTTCCCCTGCACTGT |
| R11 | SEQ ID NO: 172 | CAAGCAGAAGACGGCATACGAGATACTGTATCGTGACTGGAGTTCAGACGTGTGCTCTTCCGATCTatTCTACTATTCTTTCCCCTGCACTGT |
| R12 | SEQ ID NO: 173 | CAAGCAGAAGACGGCATACGAGATAGGTCGCAGTGACTGGAGTTCAGACGTGTGCTCTTCCGATCTgatTCTACTATTCTTTCCCCTGCACTGT |

All PCR reactions were performed using Phusion Flash (ThermoFisher Scientific F548L) polymerase following the manufacturer's protocol with an annealing temperature of 62° C. and 20 cycles.

Amplicons from the second PCR were pooled in equimolar ratios (by gel quantification) and then purified using a QiaQuick PCR Purification kit (Qiagen 28104). Purified products were loaded onto a 2% E-gel EX and gel extracted using a QiaQuick Gel Extraction kit (Qiagen 28704). The concentration of the gel-extracted PCR product was gel quantified using the Low-Range Quantitative Ladder (ThermoFisher Scientific 12373031) and then diluted and sequenced on an Illumina MiSeq using a v3 kit (Illumina MS-102-3001).

Reads were demultiplexed using FASTX-Toolkit and aligned to the designed sgRNAs using bowtie (with parameters-v 1-m 1—norc) (Langmead et al. 2009). Read counts were imported into R/RStudio and normalized within each sample. All plots and analyses are from the average of the two infection replicates, unless indicated otherwise.

RNA-Sequencing (RNA-Seq) from Human A375 (V600E BRAF) Melanoma Cells

RNA from A375 cells was harvested using the RNeasy Plus Mini Kit (Qiagen 74134) and prepared with TruSeq Stranded Total RNA Kit with Ribo-Zero Gold (Illumina RS-122-2303). Samples were deep-sequenced on the Illumina NextSeq platform (>20 million reads per condition). A Bowtie index was created based on the human hg19 UCSC reference genome and RefSeq known transcriptome, and RSEM v1.27 was run with default parameters to align paired-end reads to this index to estimate expression levels.

Chromatin Conformation Capture (3C) with Droplet Digital PCR (ddPCR) Quantification To map physical interactions between distal sites and the CUL3 promoter in A375 cells, Applicants made three independent 3C libraries using different 6-cutter restriction enzymes (EcoRI, BglII, and HindIII). For each library, $1\times10^8$ log-phase A375 cells were cross-linked, digested and ligated using a standard protocol from Job Dekker and colleagues (Wright et al. 2010; Miele et al. 2006). For quantitative PCR of the purified genomic DNA from the 3C libraries, Applicants designed unidirectional primers flanking each cut site in the region using Rebase (New England Biolabs) (see table 51 for primer sequences and enzyme cut sites).

As 3C results are influenced heavily by differences in primer amplification efficiency, Applicants used droplet digital PCR (ddPCR) with EvaGreen to quantify interaction frequencies. For each droplet (~20,000 per PCR reaction), a digital readout of amplification/no-amplification is used after saturation PCR (40 cycles). For each library, Applicants optimized over a range of input template concentrations to find the ideal template concentration for droplet quantification (i.e. sufficient positive and negative droplets for Poisson estimation). ddPCR reactions were performed in triplicate and Applicants found good agreement between the three independent libraries. Overall enrichment was plotted by smoothing the combined data from the three independent 3C libraries with a Gaussian kernel with a standard deviation equal to half of the average distance between restriction enzyme cut sites ($\sigma$=2.15 kb, kernel window size=5 kb). For the 12 strongest interactions, Applicants separately PCR amplified and Sanger sequenced the products to validate that they contained the predicted junction.

To correlate enrichment with 3C interaction frequency, Applicants created windows across the library region because the resolution of 3C is much coarser than the resolution of the sgRNA library. Applicants set the length of each window equal to the average distance between 3C restriction enzyme cut sites (4.3 kb) with a ~75% overlap between windows (i.e. one window every kilobase). For each window, Applicants calculated the average enrichment (loge Vem/DMSO) of the sgRNAs in the window and used this quantity as the enrichment score of the window. Typically, each 4.3 kb window contained ~100 sgRNAs. For each 3C interaction, Applicants identified the closest sgRNA window (defined as the window center) and assigned its enrichment score to the 3C interaction.

Assay for Transposable and Accessible Chromatin Sequencing (ATAC-Seq)

For ATAC-seq, human melanoma A375 (ATCC CIS,-1619), mammary gland adenocarcinoma MCF-7 (ATCC HTB-22), and glioblastoma U87-MG (ATCC HTB-14) cells were cultured in R10 media (RPMI-1640+10% FBS, as described above). For each line, $5\times10^4$ cells in log-phase growth were harvested using an existing ATAC library preparation protocol with minor modifications (Buenrostro et al. 2013). Library quality was validated using an Agilent TapeStation before pooling barcoded samples and sequencing using an Illumina NextSeq with 36 bp paired-end reads. Each sample was sequenced to a depth of ~75M reads.

Samples were aligned using bowtie (with parameters—chunkmbs 256-p 24-S-m 1-X 2000) to the human genome reference sequence (hg19/GRCh37). The resulting BAM files were subset using samtools to the region our sgRNA library targets (hg19 coordinates: chr2: 225,234,905-225,550,015). For quality control, Applicants measured the duplicate read rate using Picard-Tools MarkDuplicates ($10^{-}$ 30%) and also the mitochondrial read rate (<5%) (Van der Auwera et al. 2013). Applicants also verified that our alignment region did not contain any sites on the ENCODE blacklist (ENCODE Project Consortium 2012). Aligned BAM files were converted to BEDgraph format using bedtools (Quinlan & Hall 2010) and imported for analysis into R/RStudio.

DNAse I Hypersensitivity and Chromatin Immunoprecipitation Sequencing (ChIP-Seq) Datasets For comparison with screen enrichment, Applicants used DNAse I hypersensitivity and ChIP-seq data from the ENCODE project. DNAse I hypersensitivity data for Colo829 melanoma, MCF7 mammary gland, and Gliobla D54 glioblastoma data is from the OpenChrom/Duke University collection. All ChIP-seq data is from K562 cells: YY1 and ZNF263 are from the Stanford/Yale/USC/Harvard dataset; CTCF is from the Open Chrom/UT Austin dataset; and c-Fos and JunD are from the U. Chicago dataset. All files were downloaded as variable-step wig format using the UCSC Table Browser.

Fold Enrichment of Screen sgRNAs Near Chromatin Accessibility and Sequence Conservation Peaks To calculate the fold enrichment of the sgRNAs in proximity to other molecular hallmarks (DNAse-seq, ATAC-seq, conservation), Applicants examined the average sgRNA enrichment of sgRNAs near the peaks of these molecular hallmarks. Applicants then followed a Monte Carlo procedure: Applicants randomized the peak locations over the screen region and recomputed the average sgRNA enrichment. Applicants performed 10,000 random reshufflings of the peak locations over the screen region to get a distribution of average sgRNA enrichments. Fold enrichment is the ratio of the average sgRNA enrichment using the actual peak locations divided by the mean of the Monte Carlo distribution (average sgRNA enrichment with reshuffled peak locations). PhastCons data for primates, placental mammals, and vertebrates were downloaded from UCSC for hg19.

Array Validation of Primary Screen Hits

For individual (array) validation of noncoding sgRNAs, Applicants first identified sgRNAs enriched in the top 5% of the library as given by the normalized log 2(Vemu/DMSO) read ratio. In order to have high confidence in these sgRNAs, Applicants used the minimum of the two infection replicates for the normalized $\log_2$ (Vemu/DMSO) read ratio. From this group, Applicants eliminated any sgRNAs that did not have another similarly enriched sgRNA within 500 bp. This ensures that putative noncoding functional elements were supported by the presence of at least 2 enriched sgRNAs. From this group, Applicants picked 25 sgRNAs distributed across different genomic regions for individual validation (see table S2 for a list of sgRNA sequences). Applicants also included 3 exon-targeting and 3 non-targeting sgRNAs to serve as positive and negative controls, respectively.

For each sgRNA, standard desalted short oligonucleotides (Integrated DNA Technologies) were annealed, phosphorylated and cloned into a lentiviral vector (lentiCRISPRv2, Addgene 52961) that contained Cas9 and an sgRNA cassette. For each sgRNA, A375 cells were transduced with lentiviral supernatants. After 24 hours, media was replaced with R10 with 1 ug/mL of puromycin. Viral volumes were titered such that 20-40% of cells survived after puromycin selection. After selection and expansion for 7 days in puromycin, cell were plated for DNA/RNA extraction, vemurafenib resistance, or ChIP assays.

RNA Extraction and ddPCR Quantification of CUL3 Expression

After 7 days of puromycin selection, A375 cells transduced with individual lentiCRISPRv2 sgRNAs were plated in 3 replicate wells ($2\times10^3$ cells/well) in 96-well plates. After 4 days (70-90% confluent), RNA was extracted using a homemade version of a rapid lysis kit for quantitative PCR (similar to commercial "Cells-to-Ct"-style kits). This procedure (detailed below) enables rapid RNA extraction and qPCR/ddPCR readout from 96-well plates with minimal hands-on time.

Cells were first washed in 100 ul of chilled phosphate-buffered saline (PBS). Then, cells were incubated at room temperature for 8 minutes in 50 ul of Complete Lysis Buffer. The Complete Lysis Buffer consists of the Base Lysis Buffer with freshly added 100 ug/ml Proteinase K (Sigma P2308) and 300 U/mL DNase I (Sigma D2821). When adding DNase I, it is important to not vortex but mix only by gentle pipetting. The Base Lysis Buffer is made in RNAse-free water (ThermoFisher Scientific 10977015) with 10 mM Tris pH8 (Ambion AM9856), 0.5 mM $MgCl_2$ (Sigma M1028), 0.44 mM $CaCl_2$ (Sigma 21115), 10 uM DTT (Sigma 43816), 0.1% Triton X-114 (Calbiochem 648468), and 1.73 mN HCl (Sigma 318965) and should have a final pH of 7.8. The Base Lysis Buffer is stable at 4° C. for up to 6 months.

After the 8-minute incubation in Complete Lysis Buffer, 30 ul of the cell lysis was added to new PCR plates containing 3 ul of STOP buffer in each well to stop the lysis reaction. The STOP buffer is made in RNAse-free water with 1 mM Proteinase K inhibitor AAPF N-(Methoxysuccinyl)-Ala-Ala-Pro-Phe-chloromethyl ketone (SEQ ID NO: 174) (Millipore 539470), 90 mM EDTA (ThermoFisher Scientific 15575020), and 113 uM DTT (Sigma 43816). The final pH of the STOP buffer should be 8, adjusted appropriately with HCl and KOH. The STOP buffer is stable for up to 6 months at 20° C. The lysis reaction was mixed with the STOP buffer by pipetting up and down 5 times. Applicants then incubated the lysis and STOP buffer for at least 2 minutes but not more than 20 minutes. (Extra stopped lysis can be stored at −80° C. for up to 5 months.)

Applicants transferred 5 ul of the stopped lysis to new PCR plates with 20 ul of RT master mix. The RT master mix is from the RevertAid Reverse Transcriptase kit (ThermoFisher Scientific K1691) and is as described in the manufacturer's protocol but with an added oligo-dT primer. Each 20 ul RT master mix reaction consists of 10.41 ul RNAse-free water, 5 ul of 5× RT Buffer, 1.09 ul of 100 uM random hexmers, 0.88 ul of 100 uM oligo-dT (ThermoFisher Scientific SO132), 1.25 ul of 10 mM dNTP, 0.13 ul of 20 U/ul RiboLock RNase Inhibitor, and 1.25 ul of RevertAid Reverse Transcriptase. To create cDNA, Applicants then thermocycled the plates as follows: 25° C. for 10 min, 37° C. for 60 min, 95° C. for 5 min.

To measure CUL3 expression, Applicants used a ddPCR-based TaqMan assay (dual-label probe hydrolysis by Taq polymerase exonuclease activity). Applicants first tested two different CUL3 TaqMan probe designs to determine which one provided better separation between amplification/no-amplification droplets. Of the two probes tested (Hs00180183_m1 and Hs00950986_m1), Applicants found that Hs00950986_m1 achieved the best separation in the droplet analysis and used it for all CUL3 expression assays as the FAM channel probe (ThermoFisher Scientific). For normalization, Applicants used a TaqMan probe for TBP (TATA-box binding protein) in the VIC channel (ThermoFisher Scientific 4326322E). In each 24 ul reaction, Applicants used 9.6 ul of the cDNA produced by our homemade RNA extraction/reverse transcription protocol and 1.2 ul of each probe (CUL3 and TBP). Droplets were formed using the 96-well droplet generator (BioRad AutoDG), thermocycled following BioRad's standard TaqMan protocol, and then analyzed using a two-channel ddPCR reader (BioRad QX200). CUL3 expression was first normalized by TBP expression in each well and then normalized across samples using the expression level from the average of 3 different non-targeting sgRNAs.

Vemurafenib Resistance Assay

After 7 days of puromycin selection, A375 cells transduced with individual lentiCRISPRv2 sgRNAs were plated in 8 replicate wells ($2\times10^3$ cells/well) in 96-well black-bottom plates. After 24 hours, the media was replaced with R10 with 2 uM vemurafenib (4 wells) or R10 with an equal volume of DMSO (4 wells). Drug/vehicle media was replaced every other day. After 3 days, cell viability was measured using CellTiter Glo (Promega). After cells were equilibrated to room temperature (30 minutes), media was aspirated and replaced with CellTiterGlo reagent diluted 1:4 in phosphate-buffered saline. Cells were placed on an orbital shaker for 2 minutes and then incubated for an additional 10 minutes before luminescence measurement (1 s integration time) on a plate reader (Biotek Synergy H1).

Deep Sequencing after CRISPR Mutagenesis

After 7 days of puromycin selection, A375 cells transduced with individual lentiCRISPRv2 sgRNAs were plated in 2 replicate wells (2×10 3 cells/well) in 96-well plates. Cells were plated in either R10+DMSO or R10+vemurafenib (2 uM). After 4 days (70-90% confluent), Applicants extracted gDNA from all wells (Illumina/Epicentre QuickExtract QE09050) and performed amplification and deep sequencing as previously described (Shalem et al. 2014). Briefly, for each sgRNA target site, Applicants designed PCR primers to amplify genomic regions surrounding the site (100-200 bp amplicons) and to add universal handles for the second stage of amplification (see table S3 for all deep sequencing primers). Applicants then used a second PCR step to add sequences needed for Illumina sequencing and sample barcoding. Applicants pooled all samples together and sequenced them on a MiSeq using a 250 bp single-end read (Illumina MS-102-2002).

Custom Python scripts were used for barcode demultiplexing and insertion-deletion (indel) length measurement. To measure indel length and eliminate any potential off-target or primer-dimer reads, Applicants first identified our genomic (first PCR step) primers in each read. Applicants then checked that each read contained at least 5 bases beyond each of the genomic primers. Typically, 80-90% of demultiplexed reads matched this criterion. Reads matching this criterion were used to measure indel length by comparing distances between the identified primer-adjacent sequences with those in the reference sequence. Further multiple alignment analysis for specific sgRNAs was done using Geneious's iterative k-mer multiple alignment tool (Geneious 6.1.7).

Chromatin Immunoprecipitation (ChIP) for Histone Modifications and Transcription Factors After 7 days of puromycin selection, A375 cells transduced with individual lentiCRISPRv2 sgRNAs were plated in T-225 flasks and grown to 70-90% confluence (6 days). At this point, chromatin fixation was initiated by adding formaldehyde directly to the growth media (final concentration 1%) and incubating at 37° C. for 10 minutes. The entire two-day ChIP procedure was performed using the *Magna* ChIP HiSens Chromatin Immunoprecipitation Kit (Millipore 1710460), as specified in the manufacturer's protocol. Sonication conditions were 2 rounds of 10 minutes of pulse sonication (30 s on-off cycles, high frequency) in a rotating water bath sonicator (Diagenode Bioruptor) with 5 minutes on ice between each round. The following antibodies (and individually optimized concentrations) were used for the ChIP assays:

| Antibody | Manufacturer | Product number | Antibody/ $10^6$ cells (uL) |
|---|---|---|---|
| p300 (EP300) | Millipore | 05-257 | 1.2 uL |
| CTCF | Millipore | 17-10044 | 2 uL |
| ZNF263 | Abcam | ab56831 | 1 uL |
| FOS | Cell Signaling Technologies | 2250S | 1 uL |
| JUN | Cell Signaling Technologies | 9165S | 1 uL |
| YY1 | Cell Signaling Technologies | 2185S | 2 uL |
| H3K4me2 | Millipore | 17-677 | 0.5 uL |
| H3K4me3 | Millipore | 04-745 | 0.5 uL |
| H3K27Ac | Millipore | 17-683 | 0.5 uL |
| IgG | Millipore | 12-370 | 1 uL |

Using BatchPrimer3, Applicants designed primers centered on the sgRNA target site with a target amplicon size of 80-120 bp (see table S4 for ChIP-ddPCR primers). Droplet digital PCR (ddPCR) reactions using EvaGreen (BioRad 1864034) were used to quantify changes between input, histone/TF ChIP, and IgG ChIP samples for A375 cells transduced with specific sgRNAs and untransduced A375 cells. Applicants first used the IgG ChIP (negative control) to make sure that there was minimal background. For all histones/TFs, Applicants also designed primers using the same method (BatchPrimer3) for positive control regions (unrelated to the CUL3 locus) and verified that they were unchanged after editing by validation sgRNAs. Applicants calculated the percent change in ChIP signal after genome editing by normalizing each ChIP sample to its corresponding input sample and then comparing the normalized ChIP between A375s transduced with specific sgRNAs and untransduced (control) A375 cells.

Transcription Factor Motif Prediction

At validation set sgRNA sites, transcription factor binding site prediction was carried out by using 100 bp of genomic sequence centered on each cut site. This sequence was entered into the JASPAR database (jaspar.genereg.net), a non-redundant set of transcription factor binding profiles derived from published datasets of transcription factors binding sites (Mathelier et al. 2016). For programmatic access to the JASPAR database and relative score calculations, Applicants used the R/Bioconductor package TFBSTools (Tan & Lenhard 2016). Candidate transcription factor binding sites were identified by overlap of sgRNA cut sites with predicted motifs using a relative profile score threshold of 80% (i.e. the default JASPAR setting). The relative profile score is the sum of the loge normalized position-weight matrix probabilities for each base relative to the sum of the loge normalized maximum likelihood (i.e. max scoring) sequence for the position-weight matrix (Wasserman & Sandelin 2004).

Results

Figure 31A:
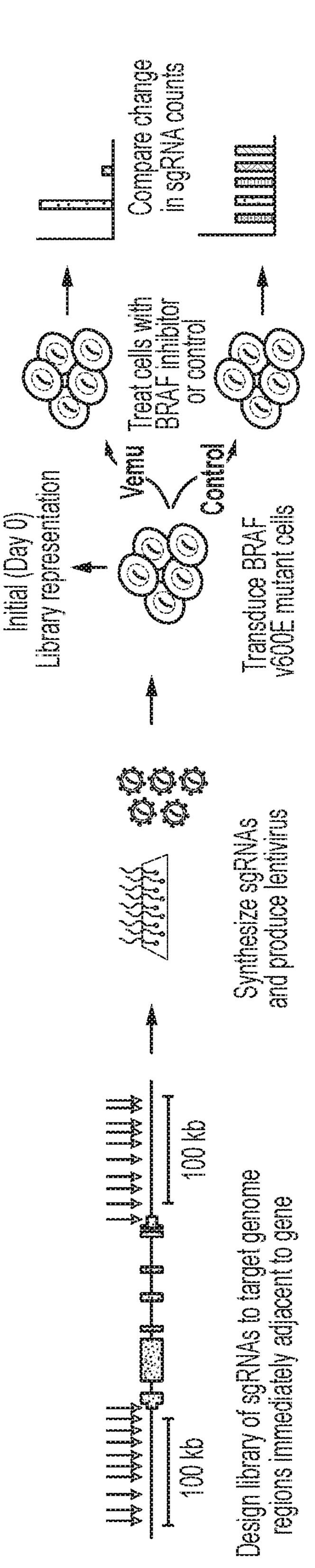
FIG. 31A-31H shows CRISPR mutagenesis of ~200 kb noncoding regions flanking three genes involved in BRAF inhibitor resistance. a, Design of sgRNA libraries targeting 100 kb 5' and 100 kb 3' of a gene locus. After library design, sgRNAs are synthesized on an array and cloned into a lentiviral vector. BRAF mutant cells are transduced with the pooled lentivirus and treated with control (DMSO) or the BRAF inhibitor vemurafenib (vemu) for 14 days. Using a deep sequencing readout, sgRNAs that are enriched after treatment with vemurafenib are identified by comparison with an early time point (Day 0) and cells treated with control. b-d, (left) Scatterplot of normalized read counts for each sgRNA at Day 0 (x axis) and at Day 14 (y axis) for 3 mutagenesis screens (B: NF1, C: NF2, D: CUL3). Gray dots indicate read counts from control cells and red dots indicate read counts from vemurafenib-treated cells. Dotted line denotes 4 standard deviations from the mean of the control cell distribution. The percentage of enriched sgRNAs in vemurafenib (>4 s.d.) is shown. (right) Enrichment ratio for 3 separate mutagenesis screens targeting ~200 kb near gene loci (B: NF1, c, NF2, d, CUL3) in A375 BRAF mutant cells. sgRNAs are plotted by genome coordinates (hg19) of their target site. The enrichment ratio is the loge ratio of the normalized read count for each sgRNA in vemurafenib to its normalized read count in control (minimum from 2 replicate screens). Enriched sgRNAs are plotted in red with their enrichment ratio. For depleted sgRNAs (blue), only position is shown. Relative expression from RNA-seq in A375 of the top two RefSeq isoforms for each gene is indicated next to the corresponding transcript. All gene-specific libraries were designed to target the proximal 100 kb from the start/end of each RefSeq isoform's coding sequence. e, Distribution of loge ratio of the normalized read count for each sgRNA in vemurafenib to its normalized read count in control (minimum over 2 replicate screens). f, Percent of sgRNAs that are enriched (>4 s.d. from control cells) with target sites in coding regions (left) or noncoding regions (right) for the NF1, NF2, and CUL3 pooled screens. g, Total expression quantitative trait loci (eQTLs) found in the Genotype-Tissue Expression (GTEx) v6 analysis release (7,051 tissue samples from 449 donors) for NF1, NF2, and CUL3. Shaded regions indicate eQTLs that are contained within the region targeted by each sgRNA library. h, Percent of enriched sgRNAs by genomic category (coding sequence [CDS], 5' UTR, promoter/first intron, UTR, and intergenic) in day 14 vemurafenib-treated cells.
Figure 31B:
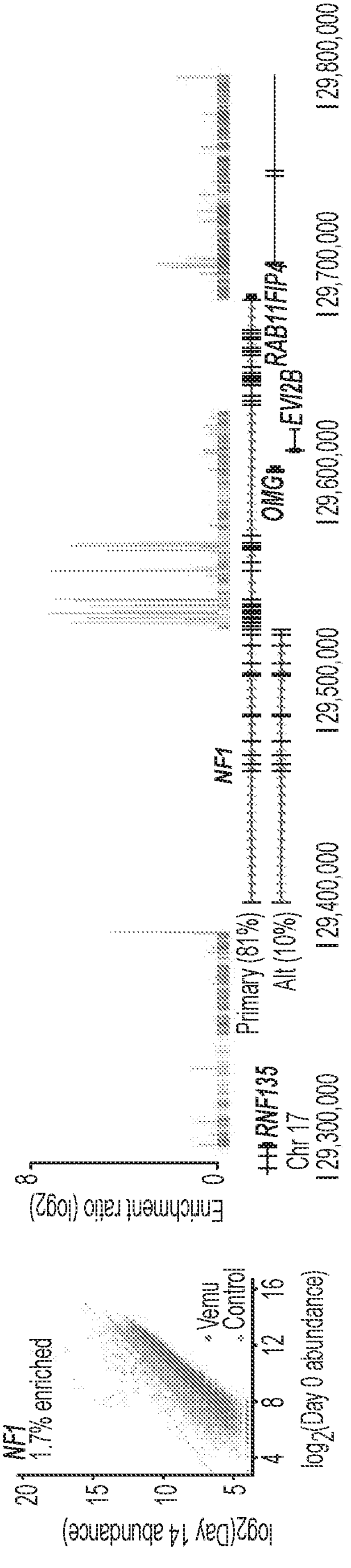
Figure 31C:
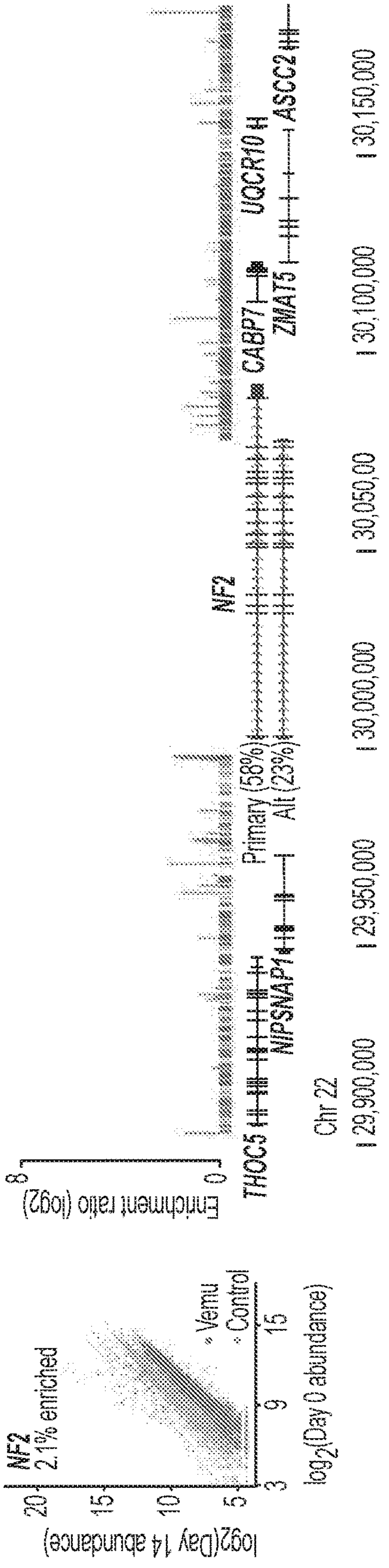
Figure 31D:
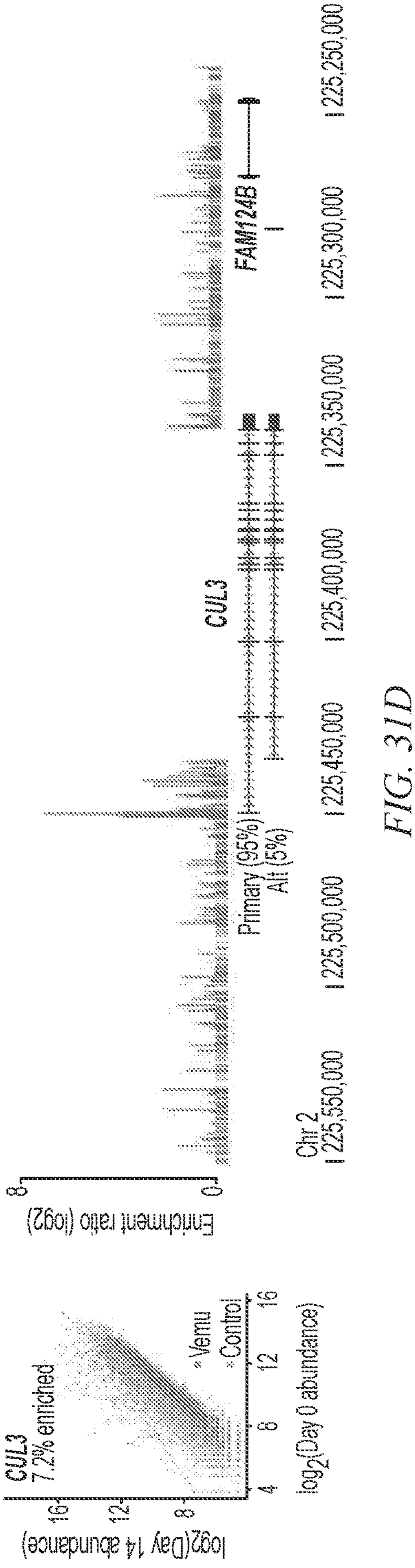
Figure 35A:
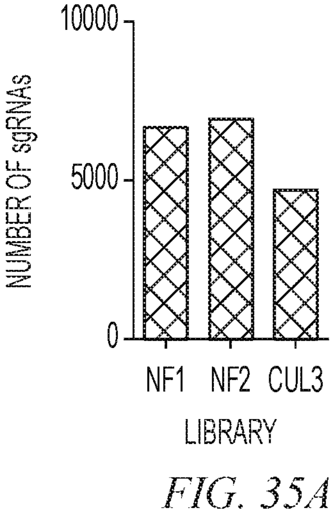
FIG. 35A-35C shows statistics of library design, sgRNA cut sites, and the locations of enriched sgRNA target sites after vemurafenib treatment in libraries targeting genomic regions near NF1, NF2, and CUL3. a, Total number of single guide RNAs (sgRNAs) in each of the 3 gene-specific libraries. b, Median distance between consecutive sgRNAs (in bp) in each of the 3 libraries. c, Each library targets ~100 kb on both 5' and 3' sides of the gene. In all 3 libraries, after vemurafenib treatment, there are more enriched sgRNAs (>4 standard deviations from the mean of the control/DMSO distribution) that target regions on the 5' side than on the 3' side of the gene.
Figure 35B:
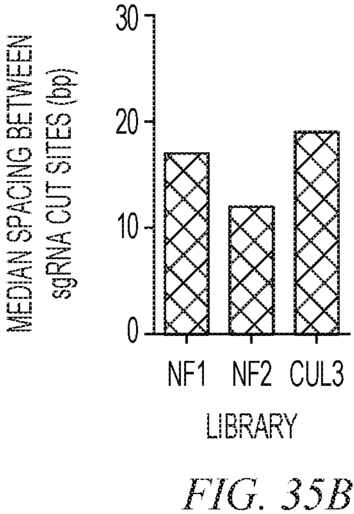

To explore if mutations in the noncoding regions around three of the previously validated resistance genes (NF1, NF2, and CUL3) could similarly impact drug resistance, Applicants designed three single-guide RNA (sgRNA) libraries tiling across 100 kb regions 5' and 3' of each gene (FIG. 31A). For each library, Applicants synthesized the sgRNAs as a pool (6,682 for NF1, 6,934 for NF2, and 4,699 for CUL3; 18,315 sgRNAs total) and cloned them into a lentiviral vector (FIG. 35A, B). Using the A375 BRAF V600E human melanoma cell line expressing Cas9, Applicants transduced cells with these pooled sgRNA libraries at a low multiplicity of infection (~0.2 virions/cell) and selected for cells that received a sgRNA (64). After 7 days of selection (and Cas9-mediated genome modification), A375 cells were cultured in 2 uM vemurafenib or control (DMSO) for 14 days. Using deep sequencing, Applicants counted the representation of sgRNAs in the library in each condition and compared it with an early time point taken immediately before the drug/control treatment (FIG. 31B-D, left). Compared to this early time point, control cells had minimal changes in library representation, whereas cells treated with vemurafenib showed greater variability in sgRNA representation. Applicants fit a linear model to the control distribution to detect enriched sgRNAs in vemurafenib-treated cells (enriched >4 standard deviations from the control distribution), which Applicants displayed as a function of genomic coordinates in a genome browser-style view (FIG. 31B-D, right). An enriched sgRNA suggests that the sgRNA target site may contain a functional noncoding sequence that increases vemurafenib resistance and improves the survival of A375 cells.

Figure 31E:
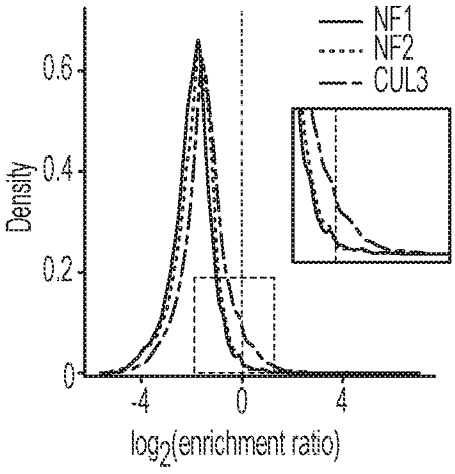
Figure 31F:
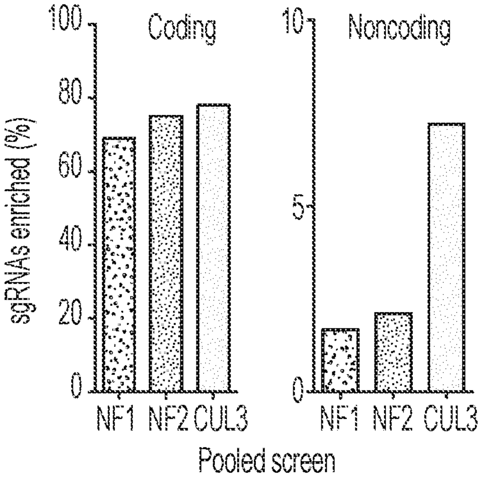
Figure 31G:
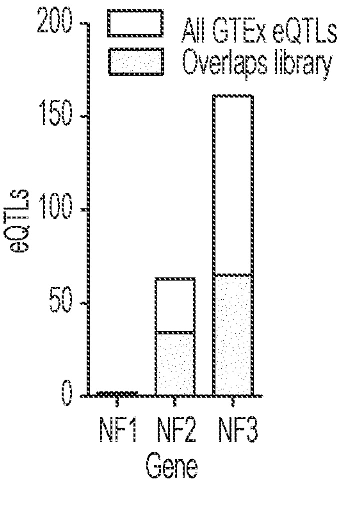
Figure 31H:
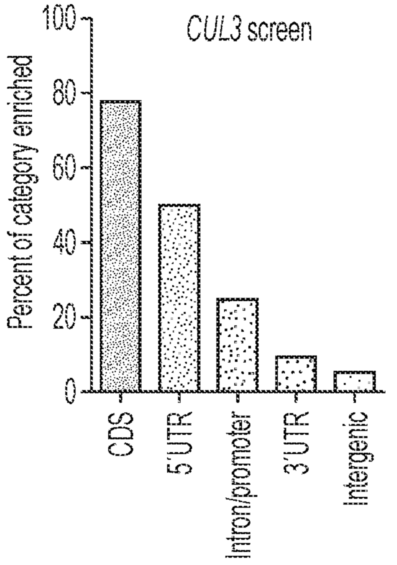
Figure 35C:
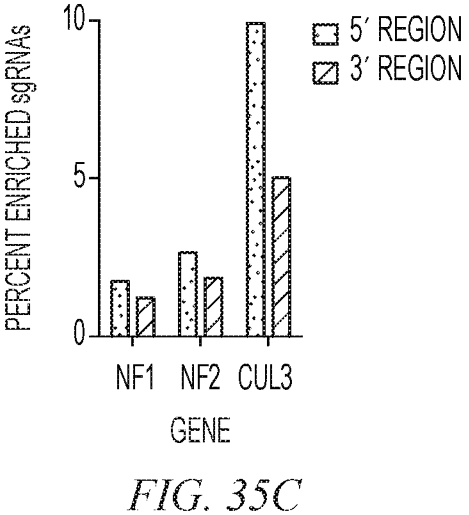

Overall, most sgRNAs were depleted after treatment with vemurafenib, which is expected since vemurafenib targets the oncogene addiction that drives A375 growth (FIG. 31E). However, in all three libraries, Applicants found a small group of sgRNAs that were enriched after vemurafenib treatment (loge ratio of Vemu/Control>0), with the CUL3 library having the largest percentage of enriched sgRNAs. In our library design, Applicants also included a small number of sgRNAs targeting the coding region of each gene and, as expected, most sgRNAs targeting coding regions (70-80%) were enriched for each gene. However, amongst the sgRNAs targeting noncoding regions, approximately 4-fold more sgRNAs were enriched in the CUL3 library than in the NF1 or NF2 libraries (7.2% of noncoding sgRNAs in the CUL3 library, 1.7% in the NF1 library, and 2.1% in the NF2 library), suggesting the presence of more gene regulatory elements in the noncoding regions flanking the gene (FIG. 31F). To determine if this increase in putative gene regulatory elements in the 200 kb region surrounding CUL3 is also reflected in human gene expression and genotyping data, Applicants queried expression array and RNA sequencing data from the Genotype-Tissue Expression (GTEx) database v6 (7,051 tissue samples from 449 donors). Indeed, Applicants found that CUL3 had the largest number of cis-expression quantitative trait loci (eQTL) (n=161 eQTLs, mean effect size=−0.21), and the region targeted by the sgRNA library overlaps with a large number of these eQTLs (FIG. 31G) (87). Given the relatively greater number of putative regulatory elements from our CRISPR screen and from the GTEx data, Applicants chose to focus our downstream analysis and validation efforts on CUL3. Among noncoding regions targeted in the CUL3 library, Applicants found that a higher percentage of sgRNAs targeting gene-proximal elements were enriched compared to other noncoding regions (FIG. 31H) and, in general, Applicants observed greater enrichment for sgRNAs targeting noncoding elements on the 5' side of the gene (e.g. promoter, 5' untranslated region [UTR]) than for those on the 3' side (FIG. 35C).

Figure 32A:
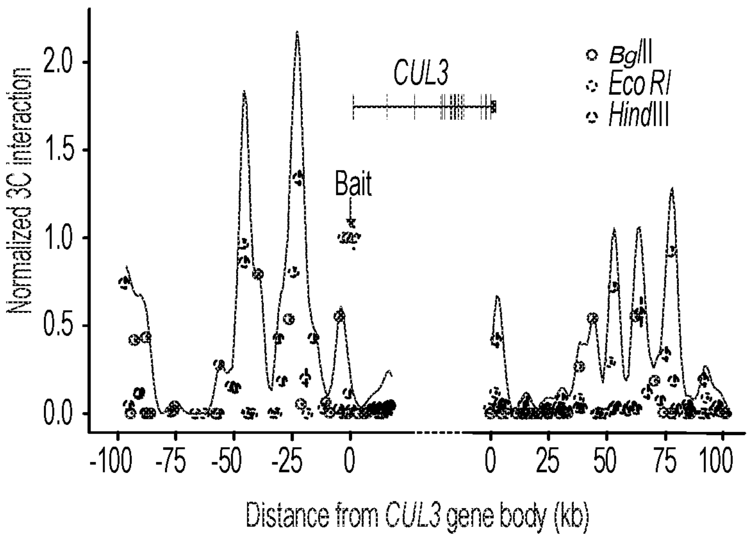
FIG. 32A-32G shows functional noncoding elements at the CUL3 locus correlate with physical chromatin interactions, chromatin accessibility and recent evolutionary conservation. a, Plot of interaction frequencies with the CUL3 promoter based on chromatin conformation capture (3C) in A375 cells. Data points represent three independent 3C libraries generated with three separate restriction enzymes (BglII, EcoRI, and HindIII). The grey curve shows a smoothed estimate of interaction frequency by convolution of the 3C data points with a Gaussian kernel. For the Gaussian kernel, the standard deviation is half the average distance between restriction sites in each library (4.3 kb). b, The average enrichment of sgRNAs (loge ratio of vemurafenib/DMSO reads) near all 3C sites with an interaction frequency with the CUL3 promoter equal to or greater than the indicated value. Nearby sgRNAs were grouped into overlapping windows of the same size as the average distance between restriction sites in each library (4.3 kb) and the closest window was selected for each 3C site. c, An example of enriched sgRNAs (red) that overlap with a melanoma-specific region of open chromatin. Assay for Transposable and Accessible Chromatin Sequencing (ATAC-seq) in A375 melanoma (orange), MCF-7 breast cancer (purple) and U-87 glioblastoma (blue) and Melanoma DNAse I hypersensitivity sequencing (DNAse I HS-seq) (green, ENCODE/OpenChromatin/Duke Colo-829). Approximate location of region (3' of CUL3) is shown at top (yellow highlighted region). Scale bar: 500 bp. d, Fold enrichment of enriched sgRNAs near ATAC-seq open chromatin peaks in melanoma, breast cancer and glioblastoma cell lines. Fold-enrichment is computed by first finding the average sgRNA enrichment near ATAC peaks over the entire region targeted by the sgRNA library. This quantity is then divided by the mean of a distribution of the same quantity calculated from 10,000 random reshufflings of open chromatin peaks. e, Fold enrichment of enriched sgRNAs near DNAse I HS-seq (below) open chromatin peaks in melanoma, breast cancer and glioblastoma cell lines. Fold-enrichment is computed by first finding the average sgRNA enrichment near DNAse peaks over the entire region targeted by the sgRNA library. This quantity is then divided by the mean of a distribution of the same quantity calculated from 10,000 random reshufflings of open chromatin peaks. DNAse I HS data is from ENCODE/OpenChromatin/Duke. f, An example of enriched sgRNAs (red) that coincide with regions that show primate-specific conservation. Primate, placental mammal and vertebrate conservation represented as phastCons probabilities (two-state phylogenetic hidden Markov model). Approximate location of region (5' of CUL3) is shown at top (yellow highlighted region). Scale bar: 200 bp. g, Fold enrichment of enriched sgRNAs near phastCons (conserved sequence) peaks in primates, placental mammals and vertebrates. Fold-enrichment is computed by first finding the average sgRNA enrichment near phastCons peaks over the entire region targeted by the sgRNA library. This quantity is then divided by the mean of a distribution of the same quantity calculated from 10,000 random reshufflings of phastCons peaks.
Figure 32B:
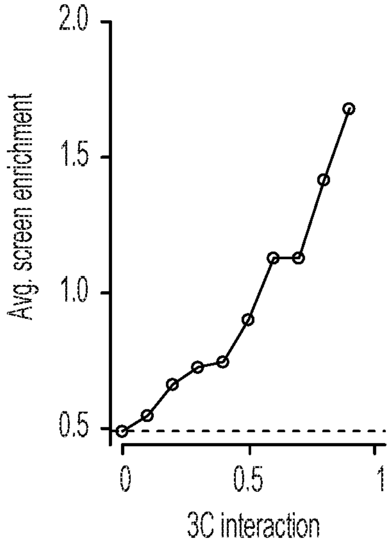

To understand the distribution of enriched sgRNAs from the CUL3 locus, Applicants designed multiple analyses to identify the properties of the enriched sgRNA target sites. One method by which distal elements can regulate gene expression is through interactions with the promoter region. This can occur due to chromatin looping and close proximity between regions in three dimensions despite large (linear) distances (28). To test if regions targeted by enriched sgRNAs from the screen physically interact with the CUL3 promoter, Applicants created three independent chromosome conformation capture (3C) libraries to test for interactions over the screened region with the CUL3 promoter (FIG. 32A) (88,89). Applicants designed droplet digital PCR (ddPCR) probe combinations to quantify the interaction frequency for each potential interacting site across the ~200 kb region. In total, the interaction frequencies of 156 possible interactions with the CUL3 promoter region were measured (table 51). Applicants found that regions on the 5' side of CUL3 tend to interact more strongly with the promoter (in agreement with greater sgRNA enrichment on the 5' side) and that regions with higher 3C interaction contain, on average, more vemurafenib-enriched sgRNAs (FIG. 32B).

Figure 32C:
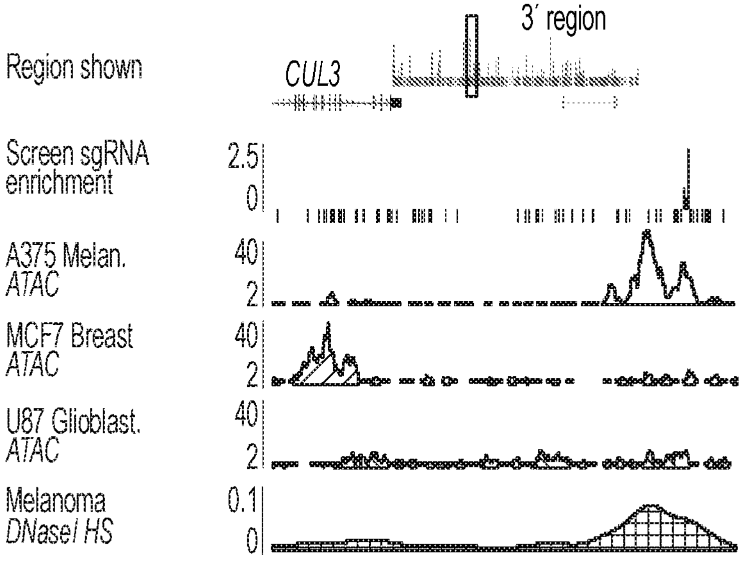
Figure 32D:
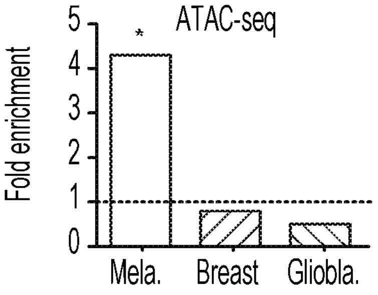
Figure 32E:
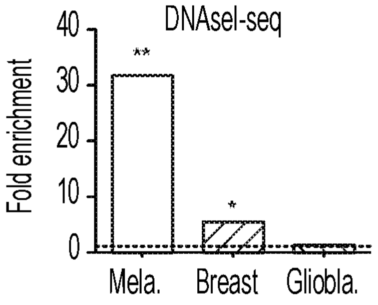
Figure 36:
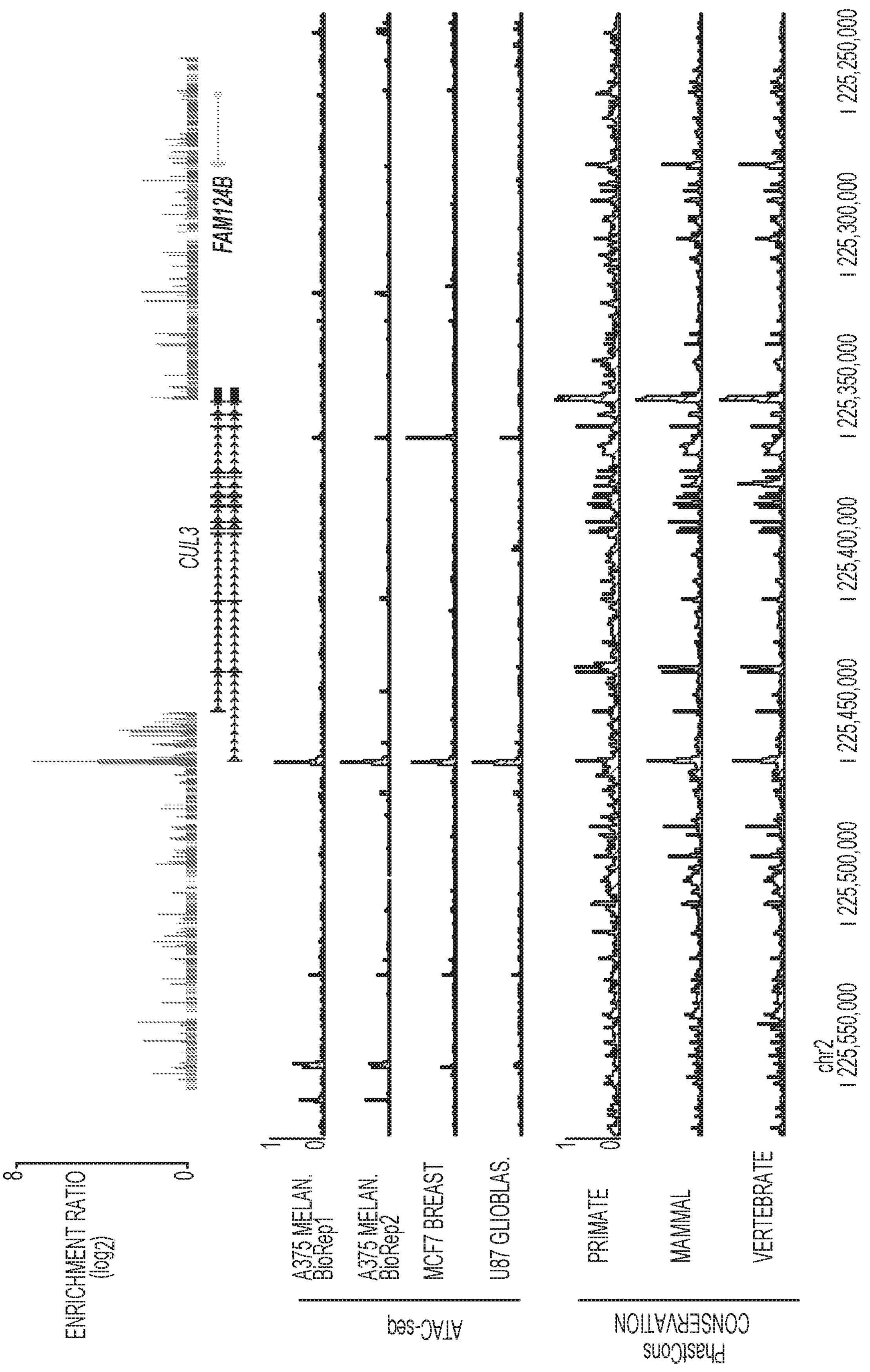
FIG. 36 shows an assay for Transposable and Accessible Chromatin sequencing (ATAC-seq) from 3 human cancer cell lines and phastCons conservation probabilities over the entire region targeted by the CUL3 CRISPR library. ATAC-seq analysis (normalized read counts) of chromatin accessibility in 3 human cancer cell lines: A375 V600E melanoma, MCF7 breast cancer, and U87 glioblastoma. Peaks indicate regions with more open chromatin. phastCons conservation scores from a phylogenetic Hidden Markov Model (HMM) trained on data from primate, mammalian, and vertebrate genomes. Higher phastCons probabilities indicate regions that are more conserved within the indicated group of organisms. The topmost track (enrichment ratio) shows the loge (Vemu/Control) ratio for each sgRNA. Values are the minimum from 2 independent infections replicates. For clarity, only enrichment values for enriched (>0) sgRNAs are plotted (red); depleted sgRNAs are indicated by a short bar (blue).

In addition to physical interactions, chromatin accessibility is often used to identify regulatory elements (90,91). To quantify chromatin accessibility, Applicants performed Assay of Transposase-Accessible Chromatin with high-throughput sequencing (ATAC-seq) using A375 melanoma cells and two human cancer cell lines that originate from different tissues: MCF7 breast cancer (lung metastasis to breast) and U87 glioblastoma. Applicants also examined available DNase I hypersensitivity with high-throughput sequencing (DNase-seq) data from ENCODE for similar cell lines. Applicants identified regions with enriched sgRNAs that overlapped with A375-specific ATAC-seq peaks and melanoma-specific DNase-seq peaks (FIG. 32C) and, overall, Applicants found higher sgRNA enrichment near A375-specific ATAC and melanoma-specific DNAse peaks than with chromatin accessibility from other cell types (FIG. 32D, E and FIG. 36). This indicates that regions with enriched sgRNAs correlate with melanoma-specific open chromatin and may contain cell type-specific enhancers, consistent with previous results showing that enhancer histone marks are specific to particular cell or tissue types (9,13,92,93).

Figure 32F:
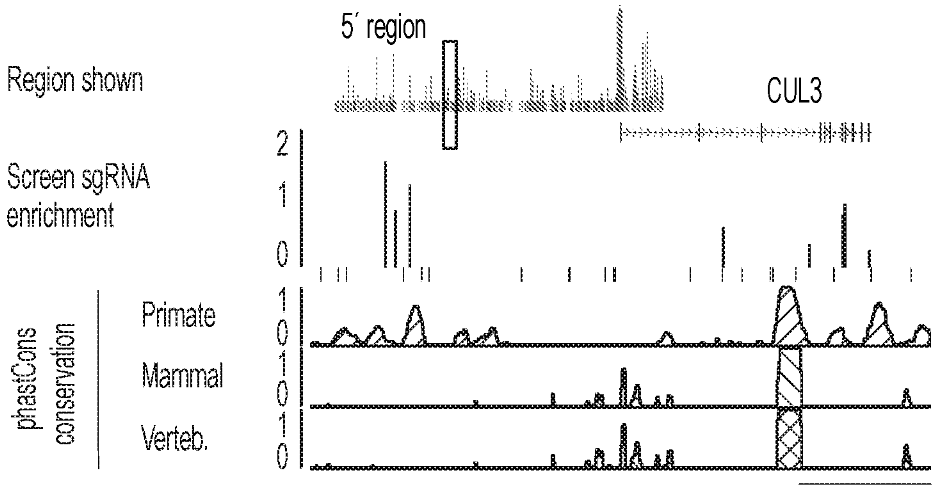
Figure 32G:
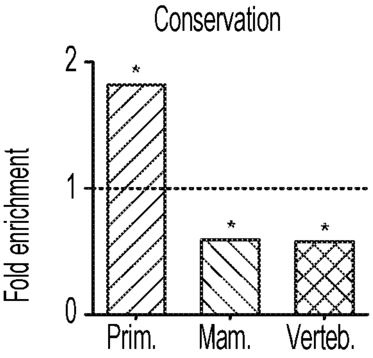

A major hallmark of functional genome elements is evolutionary conservation of DNA sequence. As conservation varies widely across the noncoding genome, Applicants tested whether more conserved regions harbor more enriched sgRNAs than less conserved regions. Applicants examined phastCons conservation scores among primates (n=10 animals), placental mammals (n=33), and vertebrates (n=46) in the CUL3 locus (FIG. 32F) (94). Overall, enriched sgRNAs are ~1.8-fold more likely to be found near peaks of primate conservation and are ~1.7-fold less likely to be found near conservation peaks among mammals and vertebrates (FIG. 32G and FIG. 36). In contrast, the genomic sites of sgRNAs targeting coding regions of CUL3 do not demonstrate differential conservation (phastCons probability ~0.95 in primates, mammals and vertebrates). Although the magnitudes of the effects are smaller than those with chromatin accessibility, enriched noncoding sgRNAs preferentially target genomic regions that are more recently conserved (e.g. in primates) versus those conserved over longer evolutionary timescales.

Figure 33A:
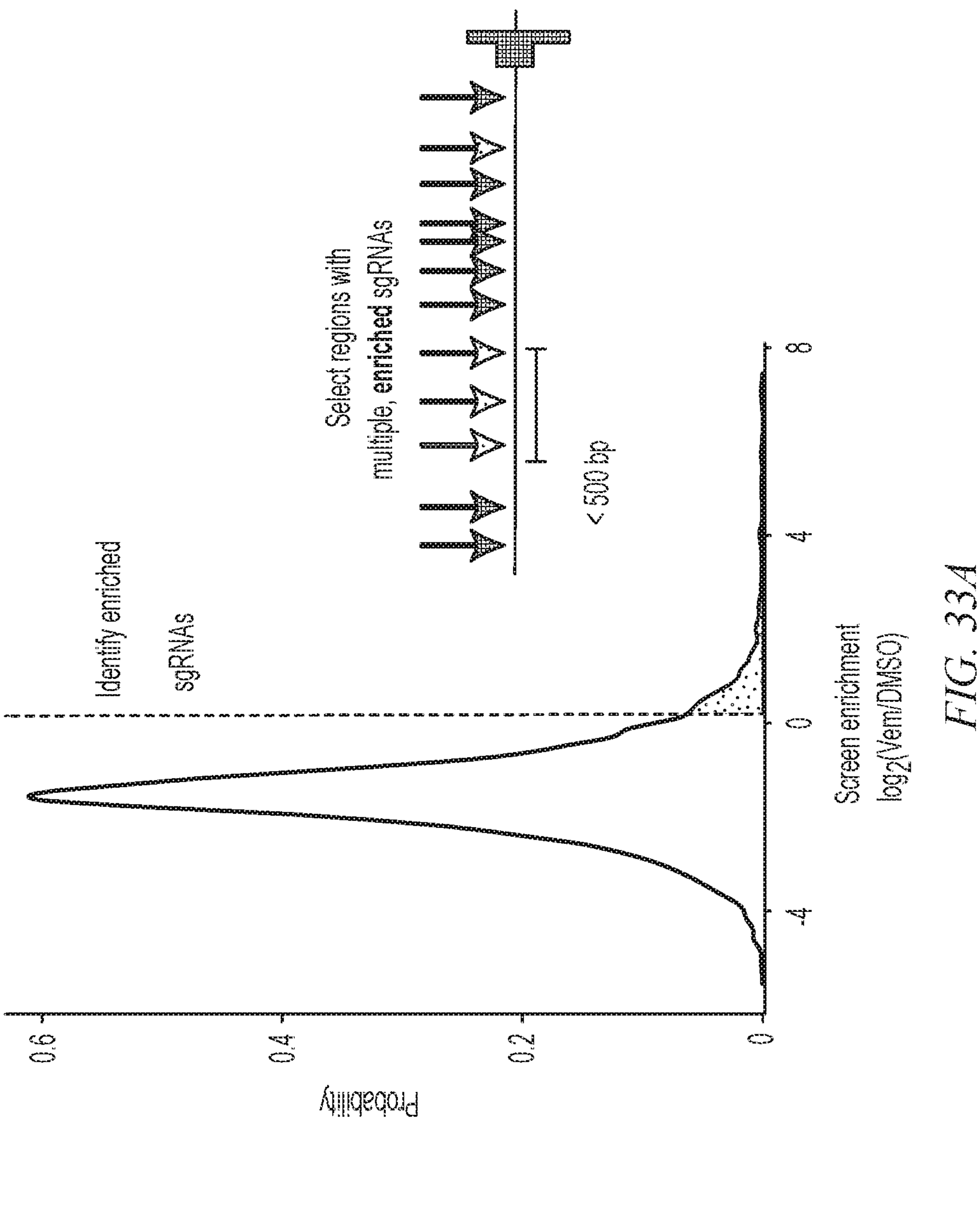
FIG. 33A-33J shows that noncoding mutations impact CUL3 expression via long-range and local changes to the epigenetic landscape. a, Criteria for selection of a subset of library sgRNAs targeting noncoding regions for individual cloning and validation. The sgRNAs chosen for follow-up validation are enriched (loge ratio of normalized vemurafenib/DMSO read counts>0) and have at least one other similarly enriched sgRNA within 500 bp. From this group, a subset of 25 sgRNAs across the diversity of genomic categories (CDS, 5' UTR, promoter/first intron, UTR, neighboring gene exon, and intergenic) was chosen for follow up studies. b, (left) CUL3 RNA expression in A375 cells after transduction with lentivirus carrying non-targeting (triangles), selected noncoding region-targeting (colored circles) and exon-targeting (squares) sgRNAs. Changes in CUL3 mRNA were quantified using droplet digital PCR (ddPCR) and all values are normalized to the median of cells transduced with non-targeting sgRNAs. (right) Relationship between CUL3 expression and cell survival in A375 cells after 3 days of treatment with 2 uM vemurafenib. Cells were transduced with lentivirus carrying non-targeting (triangles), selected noncoding region-targeting (colored circles) and exon-targeting (squares) sgRNAs. Linear fit and correlation is only to noncoding sgRNAs ($r=-0.54$, $p=0.005$) and does not include exon-targeting or non-targeting sgRNAs. c, Schematic of histone modifications typically found at promoter proximal and distal regulatory elements. H3K4me3 is often found at the transcription start site of active or poised genes, whereas H3K27ac and H3K4me2 are found both at promoters and distal regulatory elements. d, Percent change in average H3K4me3 chromatin immunoprecipitation (ChIP) at 7 days post-transduction for all validation sgRNAs within 1 kb of the transcription start site of CUL3. Percent change in average H3K27ac and average H3K4me2 chromatin immunoprecipitation (ChIP) at 7 days post-transduction for all validation sgRNAs outside of the promoter proximal region of CUL3. e, Screen enrichment near a promoter proximal and a distal sgRNA site that coincide with p300 ChIP-seq peaks (ENCODE/SYDH/p300). Dashed arrow indicates a strong interaction frequency measured between the distal site and the CUL3 promoter by 3C. Scale bars: 10 kb (screen enrichment), 250 bp (p300 ChIP-seq). f, Smoothed 3C signal measuring CUL3 promoter interaction around distal sgRNA site in (e). g, Model of chromatin looping interaction to bring p300 enhancer element into proximity with the CUL3 promoter. h, p300 ChIP around cut sites at 7 days post-transduction with distal element-targeting or promoter-targeting sgRNA (normalized to cells transduced with non-targeting sgRNA). H3K27ac ChIP at promoter-proximal and distal sites at 7 days post-transduction with distal element-targeting sgRNA (normalized to cells transduced with a non-targeting sgRNA). j, CUL3 expression at 7 days post-transduction with distal element- and promoter-targeting sgRNA (normalized to cells transduced with non-targeting sgRNAs).
Figure 33B:
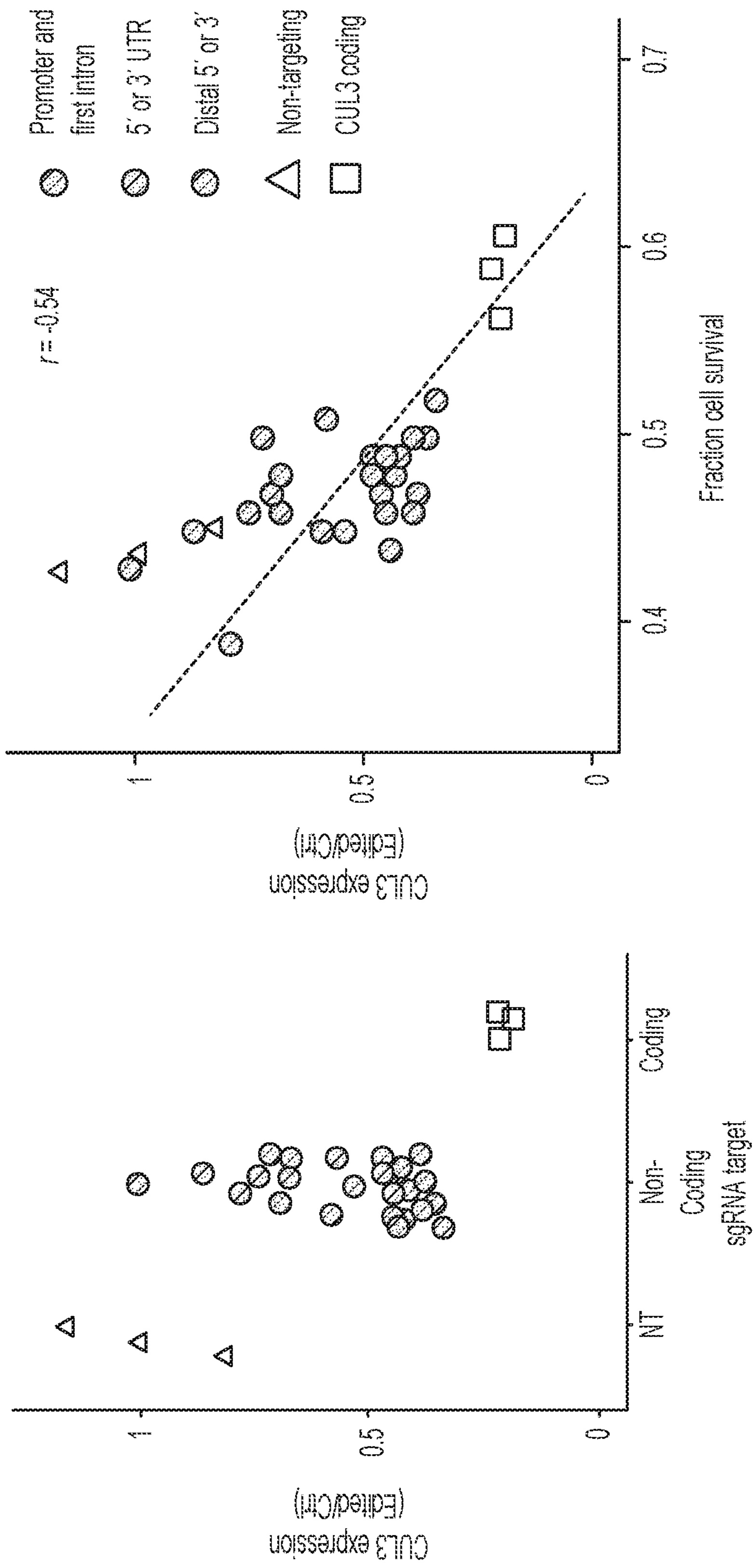
Figure 37A:
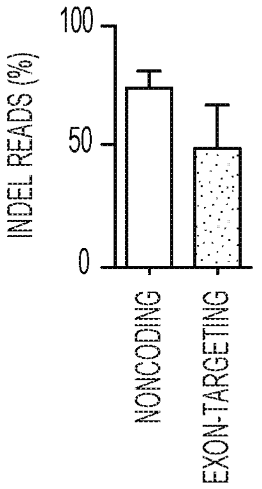
FIG. 37A-37C shows deep-sequencing analysis of insertion-deletion (indel) mutations after genome modification using validation set sgRNAs. a, Mean and standard error of the percent of reads containing an indel mutation for sgRNAs targeting noncoding regions near CUL3 and coding exons of CUL3 (n=24 noncoding sgRNAs, 4 exon-targeting sgRNAs). Cells were selected for lentiviral CRISPR constructs using puromycin for 7 days and then plated in R10+DMSO for a further 4 days. b, Average size of insertions (left) and deletions (right) in sgRNAs targeting noncoding regions near CUL3 and CUL3 exons. c, Histograms of indel mutation sizes for 2 sgRNAs that target noncoding regions near CUL3. Deletions are shown in red and insertions are shown in blue. The larger deletion size (shown in aggregate in b,) can also be seen for these 2 sgRNAs.
Figure 37B:
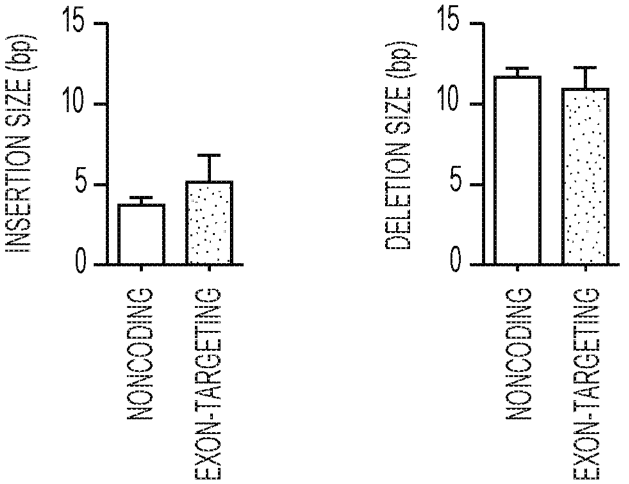
Figure 37C:
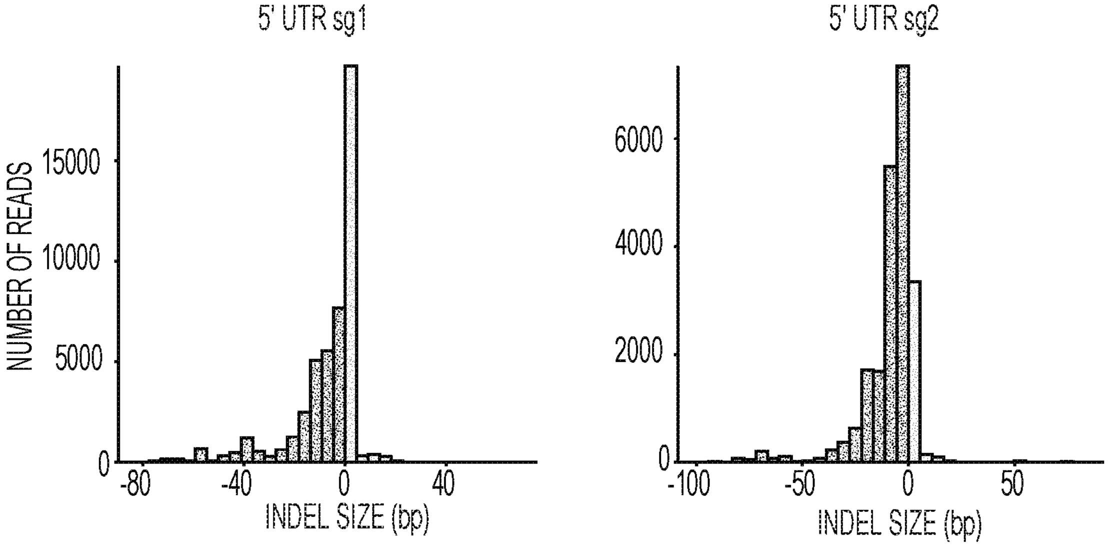

Although these properties of enriched sgRNA target sites suggest functionality, Applicants wanted to confirm that mutations in these specific noncoding regions lead to altered drug resistance and to test if these changes were mediated by CUL3. To assay specific sites for noncoding function, Applicants individually cloned 25 sgRNAs that had a positive enrichment ratio into lentiviral vectors and produced virus (FIG. 33A and table S2). For this validation set, Applicants selected sgRNAs that have at least one other similarly enriched sgRNA within 500 bp. Applicants also attempted to choose these groups of sgRNAs for our validation set from several different genomic regions (e.g. 5' and 3' UTRs, promoter, intron, distal 5' and 3' regions) in order to understand the relative regulatory ability of noncoding elements across different locations. Applicants transduced each lentivirus individually into A375 cells. After selection for 7 days, Applicants amplified genomic DNA regions surrounding each sgRNA target and found an average of 85% of amplicons contained insertion-deletion (indel) mutations with near complete genome editing at most target sites (mean deletion size=11 bp, mean insertion size=4 bp, n>5000 reads per site) (FIG. 37) (table S3). After verifying genome modification at the targeted sites, Applicants measured CUL3 expression using a sensitive ddPCR hydrolysis probe assay. Applicants found that 24 out of the 25 validation sgRNAs resulted in decreased CUL3 expression relative to non-targeting sgRNAs (FIG. 33B, left). As expected, sgRNAs that target coding exons of CUL3 resulted in an even greater loss of CUL3 expression. Applicants also treated cells transduced with sgRNAs from out validation set with 2 uM vemurafenib and measured cell survival (vemurafenib resistance) individually: As expected, there is a negative correlation between CUL3 gene expression and vemurafenib resistance (r=−0.54, p=0.005, correlation does not include non-targeting sgRNAs or sgRNAs that target CUL3 coding exons) (FIG. 33B, right). As a group, the validation sgRNAs targeting noncoding regions around CUL3 produce moderate decreases in CUL3 expression, which result in moderate increases in vemurafenib resistance.

Figure 33C:
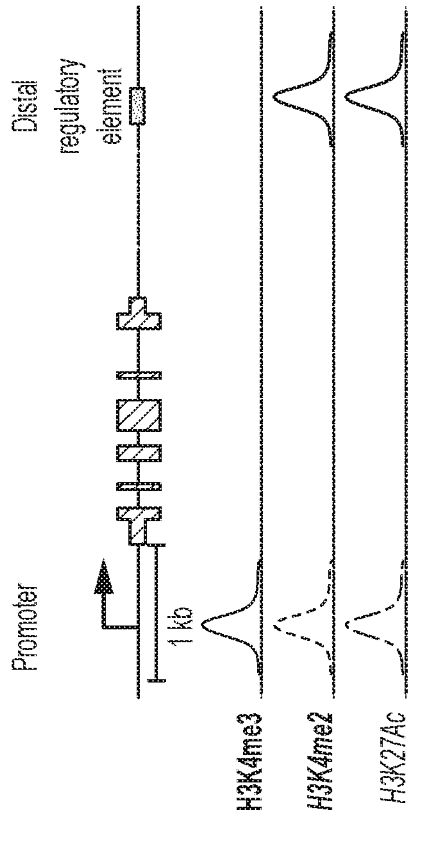
Figure 33D:
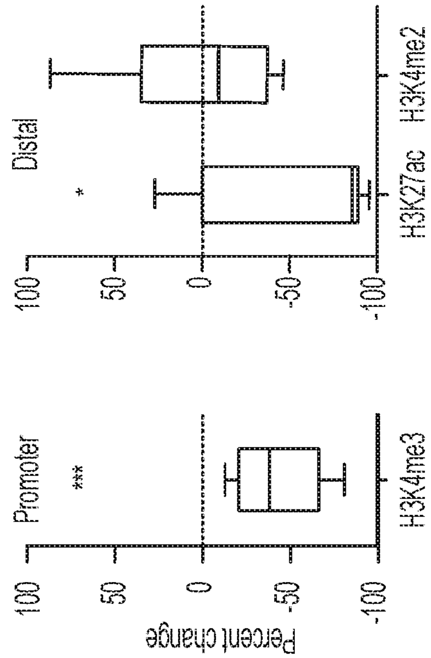
Figure 38A:
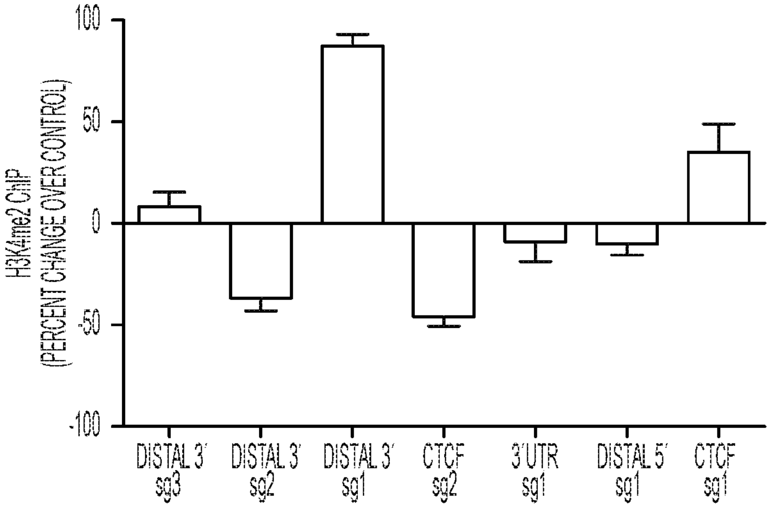
FIG. 38A-38B shows chromatin immunoprecipitation (ChIP) for individual sgRNAs for H3K4me2 and for positive control regions for all ChIP antibodies used. a, Percent change in ChIP signal (as measured by ddPCR quantification) for the H3K4me2 histone modification after genome editing by the indicated validation sgRNA. A subset of sites shows a decrease in H3K4me2 after genome editing at the site but, across all sites, there is not a significant, consistent change (p=0.82, two-sided t-test). b, Percent input for transcription factors and histone post-translational modifications in wild-type A375 cells and after transduction with different validation sgRNAs. In positive control regions (distant from the CUL3 locus), the percent input is comparable between wild-type A375 and A375 transduced with validation sgRNAs. Pulldown with antibody to IgG does not result in similar levels of enrichment at any of the positive control regions. Sample labeling on the x-axis is written as [Genome modification/Control]-[Antibody]. The variability in percent input between different ChIP targets are due to genomic abundance (e.g. transcription factors are less abundant that histones) and differences in pulldown efficiency between antibodies.

To understand the mechanism by which mutations in the noncoding region reduce CUL3 expression, Applicants surveyed changes in post-translational histone modifications at these sites. Applicants divided our validation set of noncoding sgRNAs into two categories: sgRNAs that target within 1 kb of the CUL3 coding region ("promoter") and those outside this region ("distal regulatory") (9,92). At most promoters, lysine 4 of histone H3 is tri-methylated (H3K4me3) and marks transcription start sites of genes that are active or poised (95). At active enhancer elements, there is increased acetylation of lysine 27 of histone H3 (H3K27Ac) (10) and di-methylation of H3K4 (H3K4me2) without enrichment of H3K4me3 (92) (FIG. 33C). For sgRNAs within 1 kb of the transcription start site of the primary CUL3 isoform, Applicants performed chromatin immunoprecipitation followed by ddPCR (ChIP-ddPCR) and quantified the enrichment of H3K4me3 (table S4). Applicants found a 56% decrease, on average, of H3K4me3 levels after editing ($p=7\times10^{-4}$, n=9 edited sites) (FIG. 33D), consistent with the reduced gene expression. At distal regulatory sgRNAs target sites, Applicants quantified changes in H3K27ac and H3K4me2 using ChIP-ddPCR, finding a 41% decrease, on average, in H3K27ac (p=0.02, n=7 edited sites) after editing and no significant change in H3K4me2 (p=0.82, n=7 edited sites) (FIG. 33D), although a subset of these sites did show a decrease in H3K4me2 levels after editing (FIG. 38A).

Figure 33F:
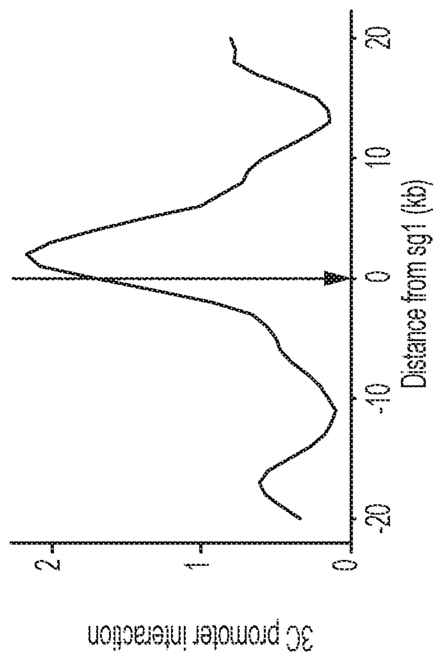
Figure 33E:
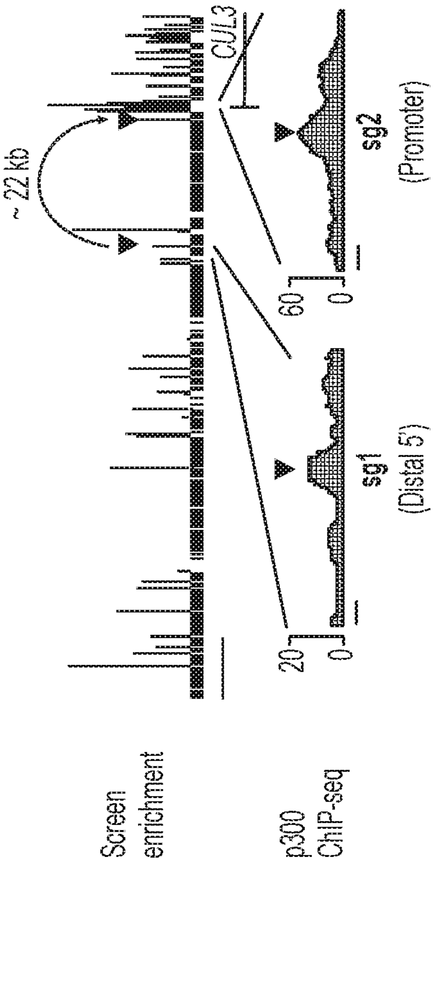
Figure 33G:
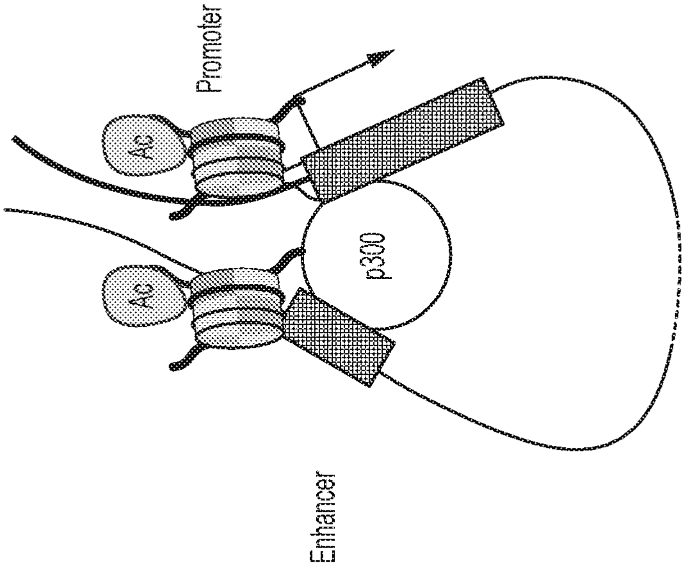
Figure 33H:
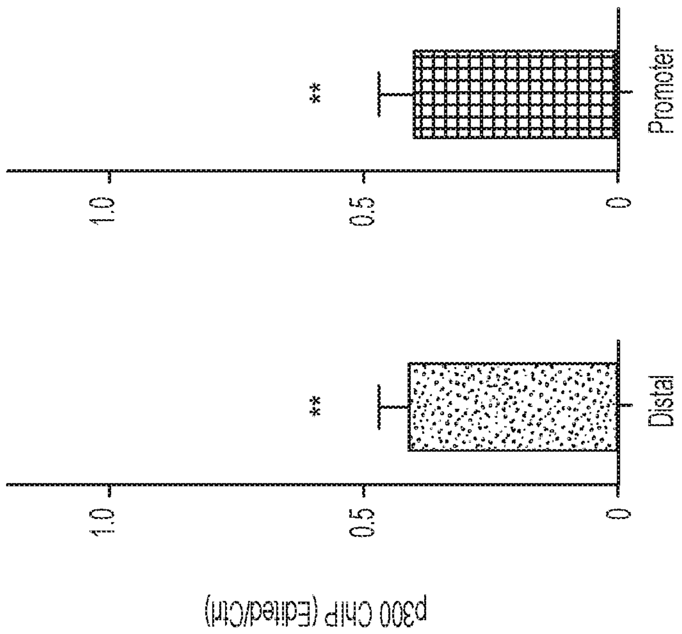
Figure 33J:
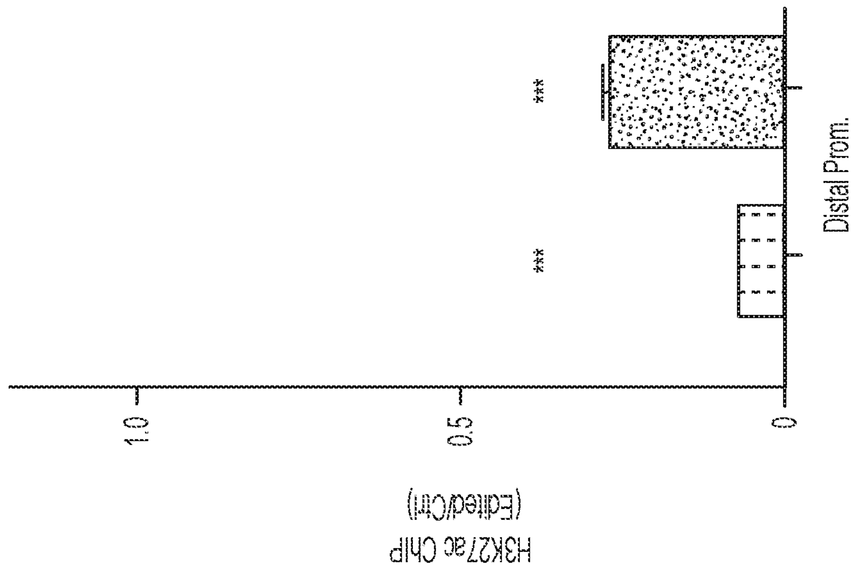
Figure 33I:
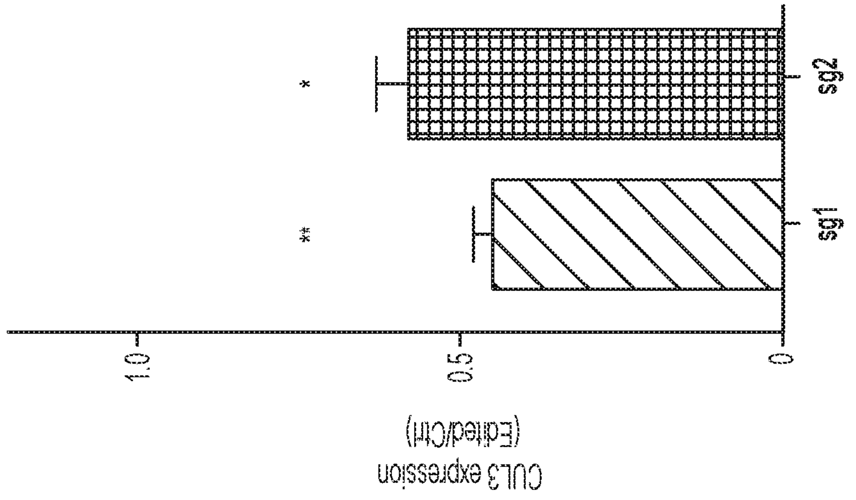
Figure 38B:
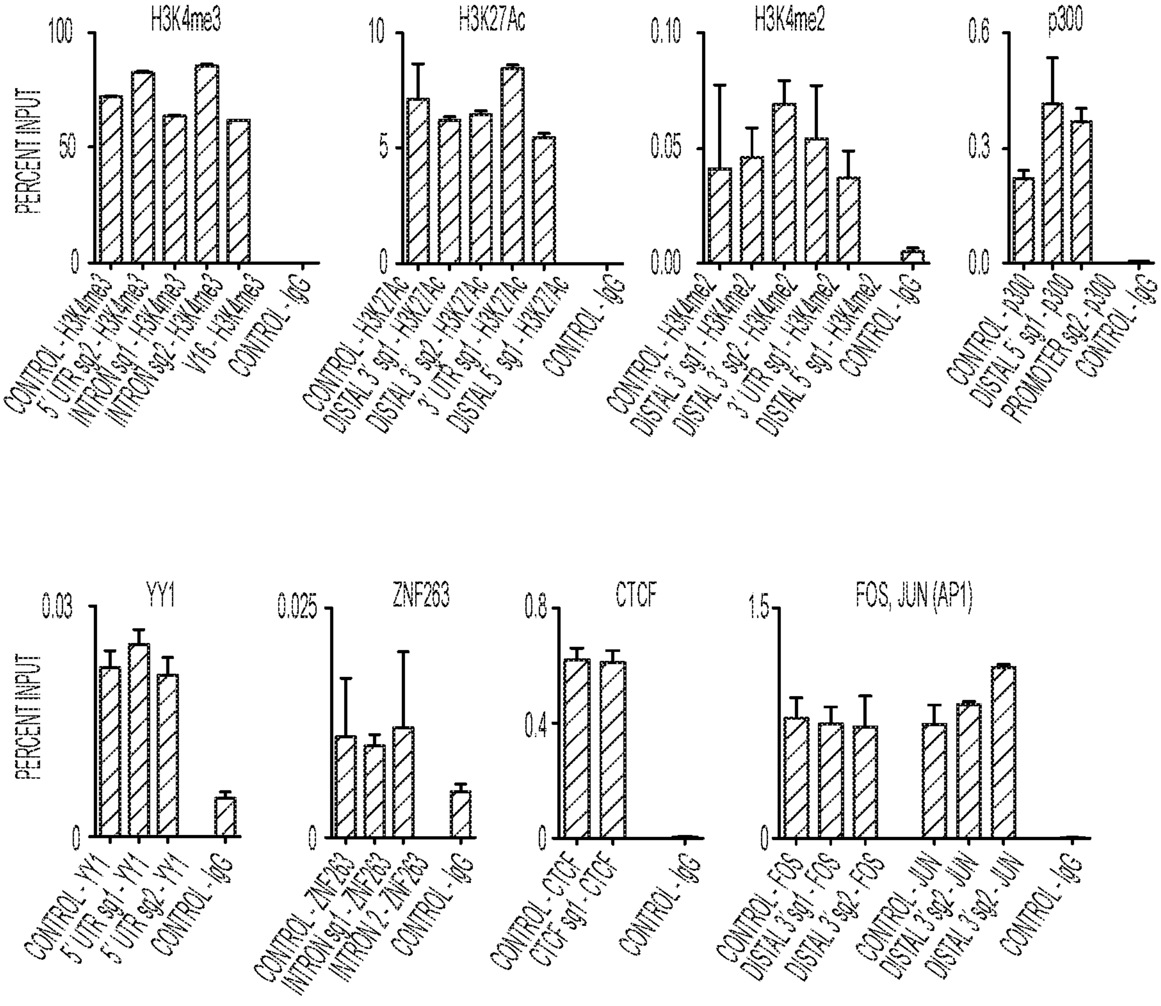

Given the observed changes in CUL3 expression and the surrounding epigenetic environment, Applicants explored the impact of noncoding mutagenesis on histone-modifying protein occupancy and activity. Two sites targeted by validation sgRNAs occupy local peaks of enrichment for a histone acetyl-transferase and transcriptional co-activator, p300 (FIG. 33E). p300 expression and localization is prognostic in BRAF mutant melanoma (96), and histone deacetylase inhibitors have been shown to work synergistically with vemurafenib to treat cancer (97). Although the two p300 sites are separated by ~22 kb, our 3C data indicates a strong interaction (FIG. 33F) that could bring the distal p300 site close to the proximal p300 site, which overlaps with the promoter region of CUL3 (FIG. 33G). To explore if sgRNAs targeting these p300 sites alter occupancy and acetylation, Applicants performed ChIP-ddPCR at both sites using antibodies for p300 and H3K27ac. After genome modification with the respective sgRNAs, Applicants found a ~50% loss of p300 occupancy at each site (FIG. 33H) and a similar decrease in CUL3 expression (FIG. 33I). In addition, after editing at the distal site, Applicants detect a 93% loss of H3K27ac at that site (FIG. 33J) while levels of H3K27ac at a positive control region distant from the CUL3 locus were unchanged (FIG. 38B). Furthermore, Applicants find a 75% decline in H3K27ac at the promoter site after editing at the distal site (FIG. 33J). These findings suggest that a distal p300 binding site contributes to maintenance of promoter-proximal histone acetylation, which promotes gene expression.

Figure 34A:
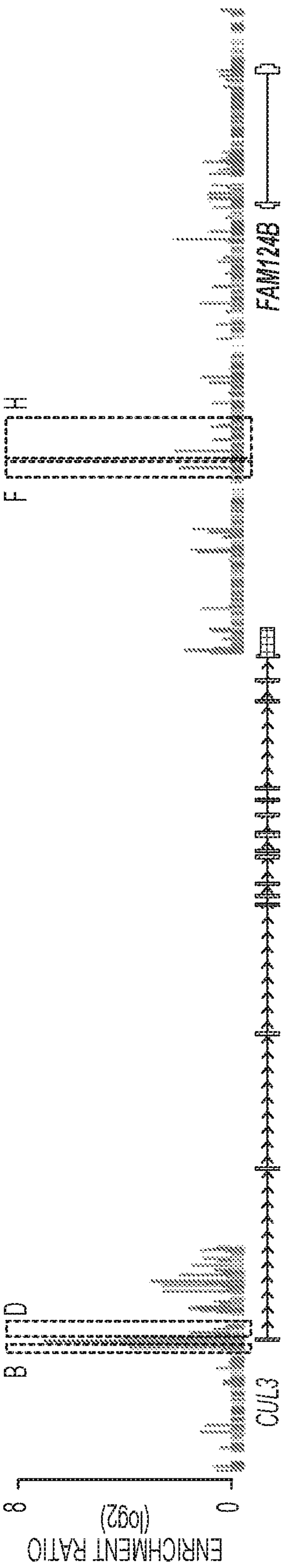
FIG. 34A-34I shows Cas9 mutagenesis disrupts binding of predicted transcription factors and DNA binding proteins at target sites of vemurafenib enriched sgRNAs. a, Location and noncoding screen enrichment of selected sgRNA target sites in the 5'-UTR (b), first intron (d) and 3' distal sites (f, g) for transcription factor binding analysis. b-i, (top) Target locations for sgRNAs in relation to bioinformatically-predicted binding sites. Motifs are from the Jaspar vertebrate database and motif scores are Jaspar relative scores (defined as 1 for the maximum-likelihood sequence). ChIP-seq for each region/protein is from K562 cells from ENCODE datasets (SYDH, UChicago OpenChrom/UTAustin). (bottom) Change in transcription factor/DNA binding protein occupancy by ChIP around cut site at 7 days post-transduction and change in CUL3 expression by ddPCR at 7 days post-transduction. Both measurements are normalized to cells transduced with non-targeting sgRNAs.
Figure 34B:
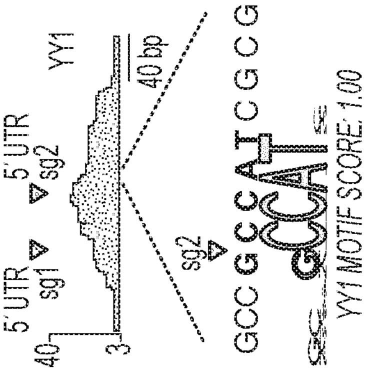
Figure 34C:
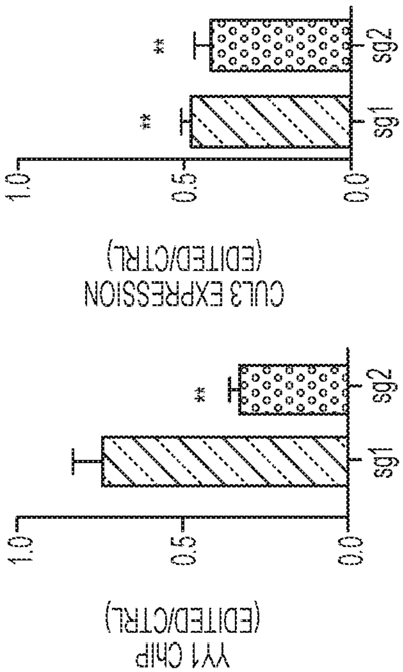
Figure 34D:
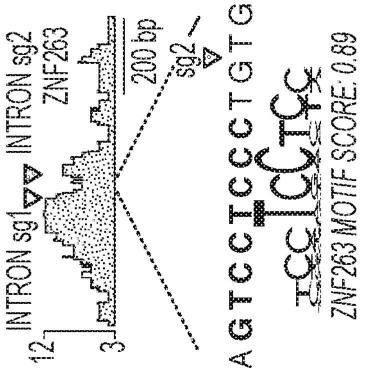
Figure 34E:
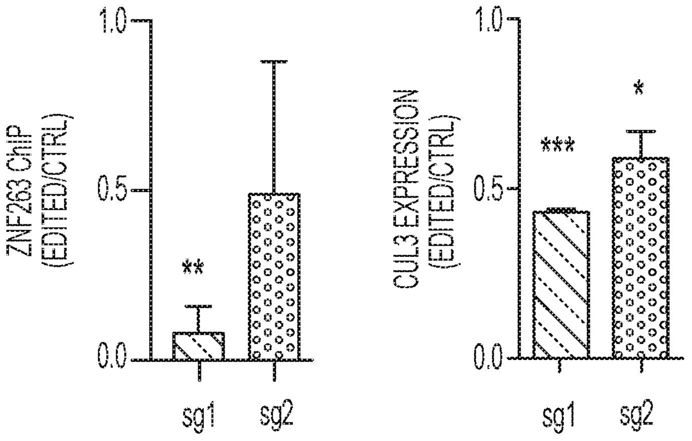
Figure 39A:
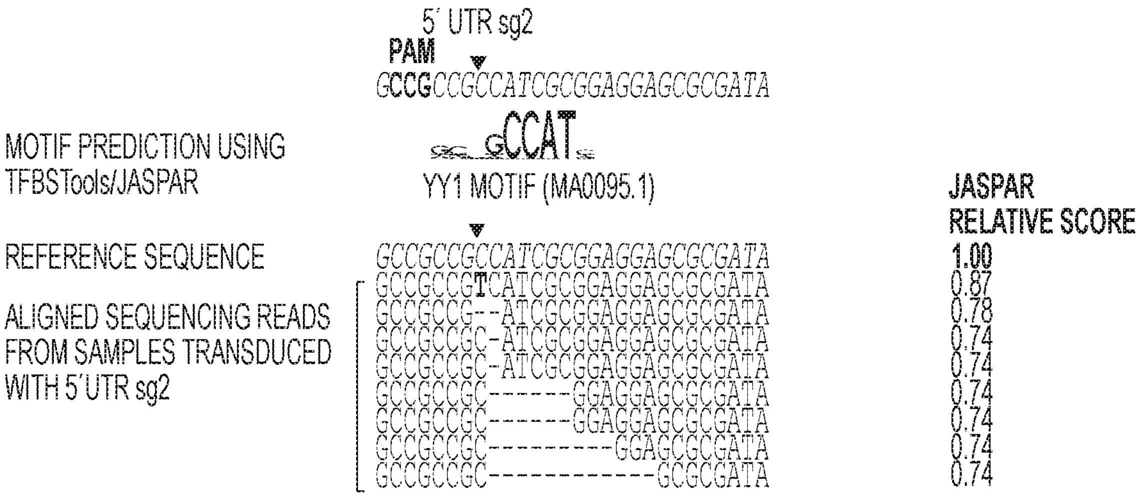
FIG. 39A-39B shows deep sequencing of indel mutations after genome modification to bioinformatically predict disrupted transcription factor (TF) binding sites. a, An example of a predicted TF binding motif for one validation sgRNA. In this case, JASPAR relative scores for the TF binding (using the indicated position-weight matrix from the JASPAR database) were computed both for the genome reference sequence (hg19) and sequences from cells transduced with a validation sgRNA (5' UTR sg2) after 7 days of puromycin selection (followed by 4 additional days of cell culture with R10+DMSO). A JASPAR relative score of 1 (as scored by the reference sequence) is defined as the maximum likelihood sequence for the motif. That is, the most probable motif base at each position is found in the tested sequence. Sequences with various indel mutations near the sgRNA cut site (blue arrow) have different (and, in this case, lower) JASPAR relative scores, implying that the TF binding site may have altered affinity for the TF after genome modification. b, Comparison of JASPAR relative scores for the indicated TF before (red bars) and after (purple bars) genome modification. Relative scores before genome modification were computed using the reference sequence (as in a,). Relative scores after genome modification were computed by random sampling of 1,000 sequencing reads containing indels after genome modification by the corresponding validation sgRNA and computing the average JASPAR relative score (error bars are standard error). Validation sgRNAs and JASPAR motifs used were: 5' UTR sg2 (YY1, MA0095.1), intron sg2 (ZNF263, MA0528.1 modified to match DeepBind motif (Alipanahi et al. 2015)), CTCF sg1 (CTCF, MA0139.1), Distal 3' sg1 (Jun/Fos, MA0099.2). Applicants also generated random DNA sequences the same length as the indel reads to estimate a background binding rate (assuming a randomly distribution of nucleotides) for each TF motif. This is useful because some motifs are quite short and thus high-scoring binding sites can occur by chance frequently. Applicants then computed JASPAR relative scores for these 1,000 length-matched random DNA sequences. In all cases, the reference sequence provided the best match (highest JASPAR relative score) for the TF shown and, in all cases, the average relative score was lower after genome modification. In many of the cases, there was no significant difference between the JASPAR relative score after genome modification and relative scores computed from length-matched random DNA sequences, suggesting a complete loss of the motif.
Figure 39B:
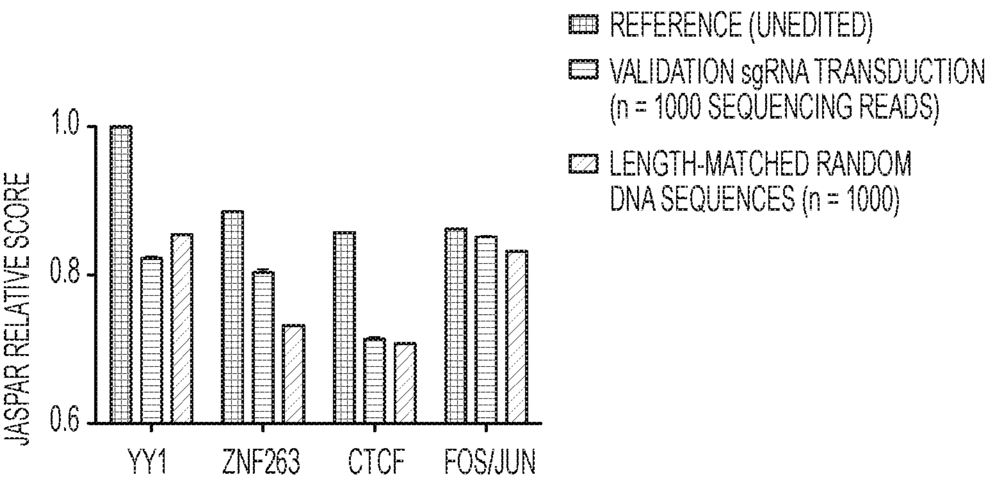
Figure 40:
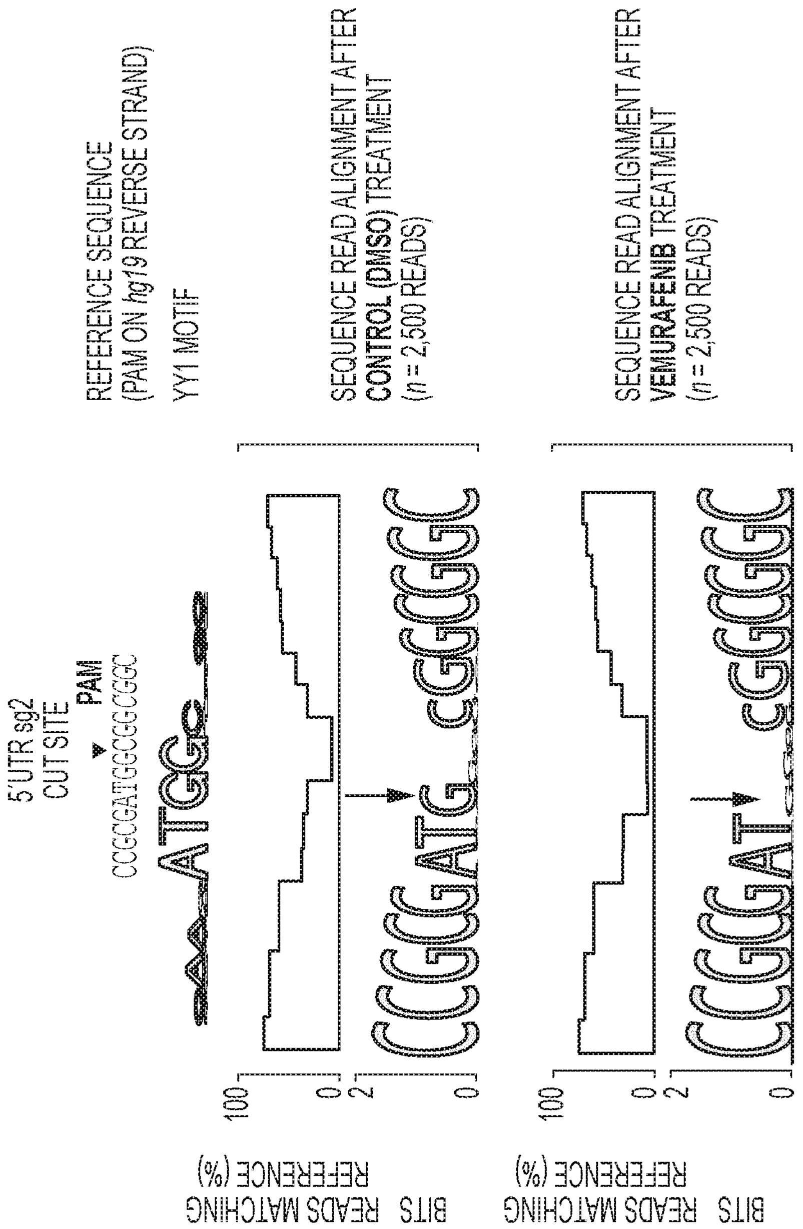
FIG. 40 shows vemurafenib treatment selects for YY1 motif-damaging indel mutations. Multiple sequence alignment (iterative k-mer aligner from Geneious R6) of 2,500 sequencing reads from A375 cells transduced with an sgRNA from the validation set (5' UTR sg2) and selected with puromycin for 7 days. After selection, cells were replaced in either R10+vemurafenib or R10+DMSO (control) and grown for 4 days before extracting genomic DNA and preparing libraries for sequencing. Compared to the control treatment, A375 cells treated with vemurafenib have more indel mutations that damage a YY1 binding motif. After vemurafenib, there is a decrease in the number of reads matching the reference sequence at the indicated base (black arrow) and an increase in entropy (as measured by information content in bits) at the indicated base.

Identification of other noncoding elements, such as transcription factor binding sites, that regulate CUL3 may provide new mechanistic insights into resistance or identify therapeutically tractable targets. To identify candidate transcription factors whose binding sites might be disrupted, Applicants further analyzed via next generation sequencing specific sgRNA target sites after editing and queried these target sites for disruption of known transcription factor motifs using the JASPAR database of transcription factors. At four sgRNA target sites, the canonical transcription factor motifs for Yin Yang 1 (YY1), Zinc Finger Protein 263 (ZNF263), CCCTC-binding factor (CTCF) and activation protein 1 (AP-1) complex were severely disrupted after editing (FIG. 34A) (FIG. 39). Based on these observations Applicants hypothesized that mutations within these binding sites abrogate transcription factor recruitment leading to loss of CUL3 expression and increased vemurafenib resistance. To test these hypotheses, Applicants compared ChIP-ddPCR enrichment of each transcription factor in cells transduced with a sgRNA from our validation set and in control cells (transduced with a non-targeting sgRNA). In the 5' UTR, two sgRNAs (5'-UTR sg1, sg2) spaced <50 bp apart overlap a YY1 ChIP-seq peak (FIG. 34B). YY1 is a multifunctional transcription factor capable of both gene activation and repression and its overexpression has been observed in various human malignancies (98,99). Analysis of the region using the JASPAR motif and scoring algorithm identifies a canonical YY1 motif with 100% relative score (i.e. the unedited reference sequence perfectly matches the maximum likelihood YY1 motif) (FIG. 39A) (100,101). After editing with 5'-UTR sg1, the average relative score for the YY1 motif falls to 82% (n=1000 sequencing reads), which is nearly the same as the average score for this motif in random DNA sequences (n=1000 length-matched random sequences) (FIG. 39B). Furthermore, Applicants found an increased disruption of the YY1 motif in vemurafenib-treated cells versus vehicle treatment (FIG. 40), suggesting that vemurafenib treatment enriches for binding site-damaging mutations. ChIP-ddPCR shows that both sg1 and sg2 decrease YY1 binding, and sg2 (which cuts closer to YY1) more efficiently disrupts YY1 binding than sg1 (67% vs. 26%) (FIG. 34C). In addition, both sg1 and sg2 significantly decrease CUL3 expression (FIG. 34C). Similarly, 2 sgRNAs in the first intron of CUL3 (Intron-sg1, sg2) spaced 30 bp apart overlap a ZNF263 ChIP-seq peak (JASPAR relative score: 89%) (FIG. 34D). Both sg1 and sg2 result in a significant decrease in ZNF263 occupancy via ChIP-ddPCR and a decrease in CUL3 expression (FIG. 34E).

Figure 34F:
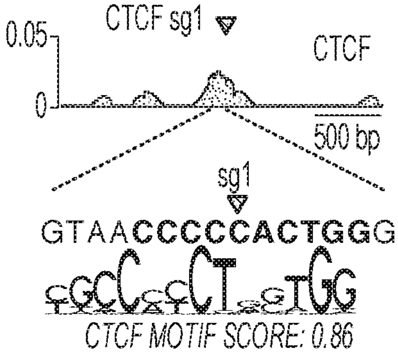
Figure 34G:
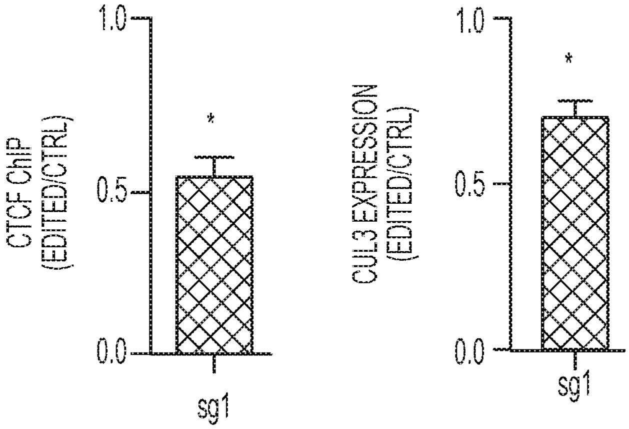
Figure 34H:
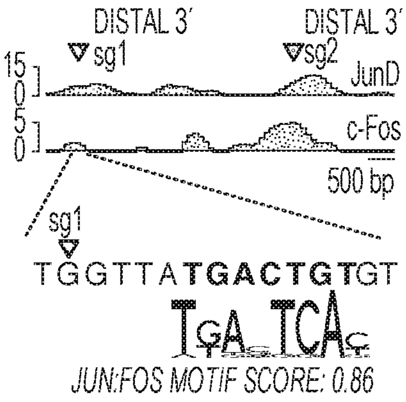
Figure 34I:
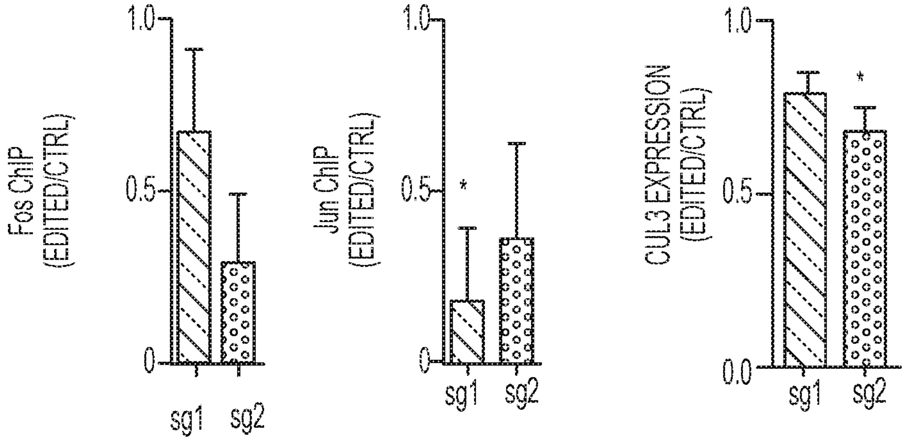
Figure 41:
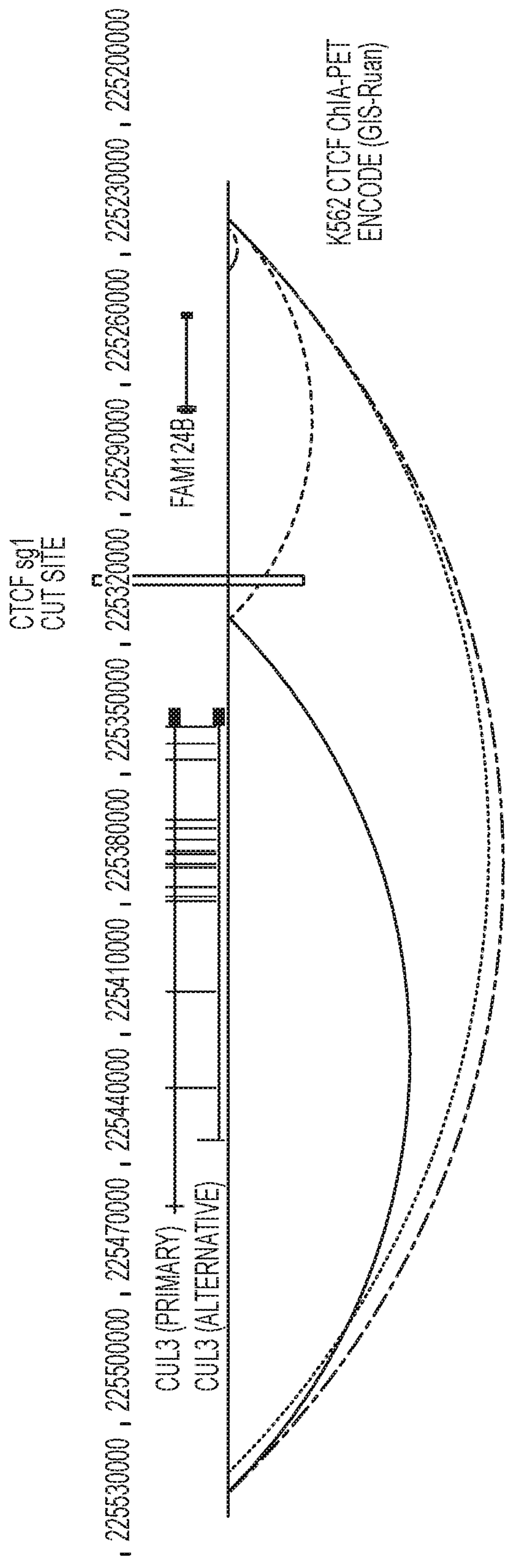
FIG. 41 shows CTCF sg1 targets a CTCF site without a strong direct interaction with the CUL3 promoter. Using a publicly available CTCF chromatin interaction analysis by paired-end tag sequencing (ChIA-PET) dataset from K562 cells (ENCODE/GIS-Ruan), Applicants did not find any evidence of a strong interaction between the region targeted by CTCF sg 1 (yellow highlight) and the CUL3 promoter. There is some evidence for interaction at a nearby site (<10 kb away) with the promoter.

Although Applicants observe a bias in the presence of regulatory elements 5' of the transcription start site, Applicants did find several highly enriched sgRNAs downstream of CUL3, including two sgRNAs that overlap with AP-1 complex binding sites (distal 3' sg1, sg2) and another sgRNA that targets a CTCF binding site (CTCF sg1) (FIG. 34F-I). The CTCF sg1 site lies ~30 kb from the 3' end of CUL3 and overlaps with non-tissue specific CTCF ChIP-seq peaks of enrichment (FIG. 34F). CTCF sites are frequently mutated in cancer, and CTCF has been shown to act as an activator, repressor, insulator and mediator of chromatin organization and chromatin loop formation (102,103). Although Applicants did not find evidence for a strong interaction between this CTCF site and the CUL3 promoter in our 3C data (— 0.15 normalized promoter interaction) or in publicly available CTCF chromatin interaction analysis by paired-end tag sequencing (ChIA-PET) (FIG. 41), the sgRNA cut site is located in the middle of the predicted CTCF binding motif (JASPAR relative score: 86%). Deep sequencing of the site found mutations in 96% of alleles with a mean indel size (−9.5 bp±13.7 bp) that is comparable in size to the canonical CTCF motif. Using ChIP-ddPCR, Applicants found that CTCF occupancy at this site is decreased by 45% after editing and there is a 30% decrease in CUL3 expression (FIG. 34G). Applicants also explored two putative AP-1 sgRNA target sites that confer drug resistance (FIG. 34H). AP-1 is a heterodimeric basic leucine zipper transcription factor, composed of FOS and JUN subunits, and its over-activation promotes metastasis in carcinomas, breast cancer, and melanoma (104). After editing at distal 3' sg1 and sg2, Applicants found decreased FOS and JUN binding compared with control cells. Editing at either site resulted in an ~25% decrease in CUL3 expression (FIG. 34I). In keeping with observations in the global screen data, mutation of these 3' noncoding sites does not have as strong of an effect on gene regulation and function as mutations in the 5' noncoding region.

Together, the results demonstrate that Cas9-mediated systematic dissection of noncoding loci can identify functional elements involved in gene regulation and altered cancer drug resistance. In combination with other genome-wide assays and datasets, Applicants demonstrate high-throughput identification of regions where changes in chromatin context and transcription factor binding are causally linked to loss of gene expression and a specific, disease-relevant phenotype. This is a generalizable approach, and the extension of pooled CRISPR screens into the noncoding genome will open new inroads into the detection of phenotypically relevant elements and further advance methods for unbiased interrogation of the "Dark Matter" of the genome and its importance in gene regulation.

REFERENCES

1. Banerji, J., Rusconi, S. & Schaffner, W. Expression of a beta-globin gene is enhanced by remote SV40 DNA sequences. Cell 27, 299-308 (1981).
2. Visel, A. et al. ChiP-seq accurately predicts tissue-specific activity of enhancers. Nature 457, 854-858 (2009).
3. Thurman, R. E. et al. The accessible chromatin landscape of the human genome. Nature 489, 75-82 (2012).
4. Dunham, I. et al. An integrated encyclopedia of DNA elements in the human genome. Nature 489, 57-74 (2012).
5. Johnson, D. S., Mortazavi, A. & Myers, R. M. Genome-Wide Mapping ofin Vivo Protein-DNA Interactions. Science 83:316, 1497-1503 (2007).
6. Barski, A. et al. High-Resolution Profiling of Histone Methylations in the Human Genome. Cell, 129, 823-837 (2007).
7. Andersson, R. et al. An atlas of active enhancers across human cell types and tissues. Nature 507, 455-61 (2014).
8. Consortium, R. E. e t al. Integrative analysis of 111 reference human epigenomes. Nature 518, 7539 (2015).
9. Heintzman, N. D. et al. Histone modifications at human enhancers reflect global cell type-specific gene expression. Nature 459, 108-112 (2009).
10. Creyghton, M. P. et al. Histone H3K27ac separates active from poised enhancers and predicts developmental state. Proc. Natl. Acad. Sci. U.S.A. 107, 21931-21936 (2010).
11. Rada-Iglesias, A. et al. A unique chromatin signature uncovers early developmental enhancers in humans. Nature 470, 279-283 (2011).
12. Xu, J. e t al. Combinatorial assembly of developmental stage-specific enhancers controls gene expression programs during human erythropoiesis. Dev. Cell 23, 796-811 (2012).
13. Ernst, J. et al. Mapping and analysis o f chromatin state dynamics in nine human cell types. Nature 473, 43-49 (2011).
14. Parker, S. C. J. et al. Chromatin stretch enhancer states drive cell-specific gene regulation and harbor human disease risk variants. Proc. N atl. Acad. Sci. U.S.A 110, 17921-6 (2013).
15. Whyte, W. A. et al. Master transcription factors and mediator establish super-enhancers at key cell identity genes. Cell 153, 307-319 (2013).
16. Paul, D. S. et al. Maps of open chromatin guide the functional follow-up of genome-wide association signals: Application to hematological traits. PLoS Genet. 7, (2011).
17. Maurano, M. T. et al. Systematic localization of common disease-associated variation in regulatory DNA. Science (80), 337, 1190-1195 (2012).
18. Hnisz, D. et al. Super-enhancers in the control of cell identity and disease. Cell 155, 934-47 (2013).
19. Farh, K. K.-H. et al. Genetic and epigenetic fine mapping of causal autoimmune disease variants. Nature (2014). doi: 10. 1038/nature13835
20. Hardison, R. C. Variable evolutionary signatures at the heart of enhancers. Nat. Genet. 42, 734-735 (2010).
21. Blow, M. J. et al. ChiP-Seq identification of weakly conserved heart enhancers. Nat. Genet. 42, 806-810 (2010).
22. May, D. et al. Large-scale discovery of enhancers from human heart tissue. Nat. Genet. 44, 89-93 (2011).
23. Vierstra, J. et al. Mouse regulatory DNA landscapes reveal global principles of cis-regulatory evolution. Science 346, 1007-1012 (2014).
24. Villar, D. et al. Enhancer Evolution across 20 Mammalian Species. Cell 160, 554-566 (2015).
25. Pennacchio, L. a et al. In vivo enhancer analysis of human conserved non-coding sequences. Nature 444, 499-502 (2006).
26. Melnikov, A. et al. Systematic dissection and optimization of inducible enhancers in human cells using a massively parallel reporter assay. Nat. Biotechnol. 30, 271-277 (2012).
27. Patwardhan, R. P. et al. Massively parallel functional dissection of mammalian enhancers in vivo. Nat. Biotechnol. 3 0, 265-270 (20 1 2).
28. Lieberman-Aiden, E. et al. Comprehensive Mapping of Long-Range Interactions Reveals Folding Principles of the Human Genome. Science 326, 289-294 (2009).
29. Dixon, J. R. et al. Topological domains in mammalian genomes identified by analysis of chromatin interactions. Nature 485, 3 76-3 80 (20 1 2).
30. Nord, A. S. et al. Rapid and pervasive changes in genome-wide enhancer usage during mammalian development. Cell 1 55, 1 52 1-1 53 1 (20 1 3).
31. Sexton, T. & Cavalli, G. Review The Role of Chromosome Domains in Shaping the Functional Genome. Cell 1 60, 1 049-1 059 (20 1 5).
32. Bender, M., Bulger, M., Close, J. & Groudine, M. Beta-globin gene switching and DNase I sensitivity of the endogenous beta-globin locus in mice do not require the locus control region. Mol. Cell S, 3 8 7-393 (2000).
33. Johnson, K. D. et al. Cis-element mutated in GATA2-dependent immunodeficiency governs hematopoiesis and vascular integrity. J. Clin. Invest. 1 22, 3 692-3 704 (20 12).
34. Cong, L. et al. Multiplex genome engineering using CRISPR/Cas systems. Science 339, 819-23 (2013).
35. Mali, P. et al. RNA-guided human genome engineering via Cas9. Science. 339, 823-6 (2013).
36. Wang, T., Wei, J. J., Sabatini, D. M. & Lander, E. S. Genetic screens in human cells using the CRISPR-Cas9 system. Science. 343, 80-4 (2014).
37. Shalem, O. et al. Genome-scale CRISPR-Cas9 knockout screening in human cells. Science. 343, 84-7 (2014).
38. Koike-Yusa, H., Li, Y., Tan, E.-P., Del Castillo Velasco-Herrera, M. & Yusa, K. Genome-wide recessive genetic screening in mammalian cells with a lentiviral CRISPR-guide RNA library. Nat. Biotechnol. 1-10 (1AD). at <//dx.doi.org/10.1038/nbt.2800>
39. Mathelier, A. et al. JASPAR 2014: An extensively expanded and updated open-access database of transcription factor binding profiles. Nucleic Acids Res. 42, 142-147 (2014).
40. Zhou, Y. et al. High-throughput screening of a CRISPR/Cas9 library for functional genomics in human cells. Nature (2014).
41. Chen, S. et al. Genome-wide CRISPR Screen in a Mouse Model of Tumor Growth and Metastasis Resource Genome-wide CRISPR Screen in a Mouse Model of Tumor Growth and Metastasis. Cell 160, 1-15 (2015).

42. Bauer, D. E. et al. An Erythroid Enhancer of BCL11A Subject to Genetic Variation Determines Fetal Hemoglobin Level. Science. 342, 253-257 (2013).

43. Groschel, S. et al. A single oncogenic enhancer rearrangement causes concomitant EVI 1 and GATA2 deregulation in Leukemia. Cell 157, 369-381 (2014).

44. Mansour, M. R. et al. An oncogenic super-enhancer formed through somatic mutation of a noncoding intergenic element. Science. 10-15 (2014).

45. Sankaran, V. G. et al. Human fetal hemoglobin expression is regulated by the developmental stage-specific repressor BCL 11 A. Science. 322, 1839-1842 (2008).

46. Sankaran, V. G. et al. Developmental and species-divergent globin switching are driven by BCL11A. Nature 460, 1093-1097 (2009).

47. Xu, J. et al. Correction of sickle cell disease in adult mice by interference with fetal hemoglobin silencing. Science. 334, 993-996 (2011).

48. Hardison, R. C. & Blobel, G. A. GWA S to therapy by genome edits? Science. 342, 206-7 (2013).

49. Kurita, R. et al. Establishment of Immortalized Human Erythroid Progenitor Cell Lines Able to Produce Enucleated Red Blood Cells. PLoS One 8, e59890 (2013).

50. Canver, M. C. et al. Characterization of Genomic Deletion Efficiency Mediated by Clusted Regularly Interspaced Palindromic Repeats (CRISPR)/Cas9 Nuclease System in Mammalian Cells. J. Biol. Chem. 289, 21312-21324 (2014).

51. Mandal, P. K. et al. Efficient Ablation of Genes in Human Hematopoietic Stem and Effector Cells using CRISPR/Cas9. Cell Stem Cell 15, 643-652 (2014).

52. Ran, F. A. et al. Double nicking by RNA-guided CRISPR Cas9 for enhanced genome editing specificity. Cell 154, 1380-9 (2013).

53. Hsu, P. D. et al. DNA targeting specificity of RNA-guided Cas9 nucleases. Nat. Biotechnol. 31, 827-32 (2013).

54. Cui, F., Sirotin, M. V & Zhurkin, V. B. Impact of Alu repeats on the evolution of human p53 binding sites. Biol. Direct 6, 2 (2011).

55. Porcu, B. S. et al. The human B globin locus introduced by YAC transfer exhibits a specific and reproducible pattern of developmental regulation in transgenic mice. Blood 90, 4602-4609 (1997).

56. Liu, P. et al. Bcl11a is essential for normal lymphoid development. Nat. Immunol. 4, 525-532 (2003).

57. John, A. et al. Bcl 1 1 a is required for neuronal morphogenesis and sensory circuit formation in dorsal spinal cord development. Development 139, 1831-41 (2012).

58. Yu, Y. et al. Bcl 1 1 a is essential for lymphoid development and negatively regulates p53. J. Exp. Med. 209, 2467-83 (2012).

59. Crocker, J. et al. Low Affinity Binding Site Clusters Confer Hox Specificity and Regulatory Robustness. Cell 191-203 (2015). doi: 10.1016/j.cell2014.11.041

60. Bauer, D. E. & Orkin, S. H. Update on fetal hemoglobin gene regulation in hemoglobinopathies. Curr. Opin. Pediatr. 23, 1-8 (2011).

61. Bauer, D. E., Kamran, S. C. & Orkin, S. H. Reawakening fetal hemoglobin: Prospects for new therapies for the beta-globin disorders. Blood 120, 2945-2953 (2012).

62. Sankaran, V. G. & Orkin, S. H. The switch from fetal to adult hemoglobin. Cold Spring Harb. Perspect. Med. 3, 1-14 (2013).

63. Bauer, D. E. E., Kamran, S. C. C. & Orkin, S. H. H. Reawakening fetal hemoglobin: prospects for new therapies for the p-globin disorders. Blood 120, 2945-2953 (2012).

64. Sanjana, N. E., Shalem, 0. & Zhang, F. Improved vectors and genome-wide libraries for CRISPR screening. Nat. Methods 11, 783-784 (2014).

65. Giarratana, M. et al. Proof of principle for transfusion of in vitro generated red blood cells. Blood 118, 5071-5079 (2011).

66. Brinkman, E. K., Chen, T., Amendola, M. & van Steensel, B. Easy quantitative assessment ofngenome editing by sequence trace decomposition. Nucleic Acids Res. 1-8 (2014). doi: 10.1093/nar/gku936

67. Bauer, D. E., Canver, M. C. & Orkin, S. H. Generation of Genomic Deletions in Mammalian Cell Lines via CRISPR/Cas9. J. Vis. Exp. 1-10 (2014). doi:103791/52118

68. Canver, M. C. et al. Characterization of Genomic Deletion Efficiency Mediated by CRISPR/Cas9 in Mammalian Cells. J. Biol. Chem. 289, 21312-21324 (2014).

69. Kowalczyk, M. S. et al. Intragenic Enhancers Act as Alternative Promoters. Mol. Cell 45, 447-458 (2012).

70. Grant, C. E., Bailey, T. L. & Noble, W. S. FIMO: Scanning for occurrences of a given motif. Bioinformatics 27, 1017-1018 (2011).

71. Weber, K., Bartsch, U., Stocking, C. & Fehse, B. A multicolor panel of novel lentiviral 'gene ontology' (LeGO) vectors for functional gene analysis. Mol. Ther. 16,698-706 (2008).

72. Doench, J. G. et al. Rational design of highly active sgRNAs for CRISPR-Cas9-mediated gene inactivation. Nat Biotechnol 32, (2014).

73. B. B. Maher, ENCODE: The human encyclopedia. *Nature.* 489 (2012), pp. 46-48.

74. L. A. Hindorff et al., *Proc Natl Acad Sci USA.* 106, 9362-9367 (2009).

75. M. A. Schaub, A. P. Boyle, A. Kundaje, S. Batzoglou, M. Snyder, *Genome Res.* 22, 1748-1759 (2012).

76. Roadmap Epigenomics Consortium et al., *Nature.* 518, 317-330 (2015).

77. J. C. Kwasnieski, C. Fiore, H. G. Chaudhari, B. A. Cohen, *Genome Res.* 24, 1595-1602 (2014).

78. R. Mundade, H. G. Ozer, H. Wei, L. Prabhu, T. Lu, *Cell Cycle.* 13, 2847-2852 (2014).

79. S. Chen et al., *Cell.* 160, 1246-1260 (2015).

80. M. C. Canver et al., *Nature.* 527, 192-197 (2015).

81. Y. Diao et al., *Genome Res.* 26, 397-405 (2016).

82. G. Korkmaz et al., *Nat Biotechnol.* 34, 192-198 (2016).

83. E. Hodis et al., *Cell.* 150, 251-263 (2012).

84. Cancer Genome Atlas Network, *Cell.* 161, 1681-1696 (2015).

85. J. A. Sosman et al., *N. Engl. J. Med.* 366, 707-714 (2012).

86. I. Zubrilov et al., *Cancer Lett.* 361, 86-96 (2015).

87. GTEx Consortium, *Science.* 348, 648-660 (2015).

88. J. Dekker, K. Rippe, M. Dekker, N. Kleckner, *Science.* 295, 1306-1311 (2002).

89. A. Miele, N. Gheldof, T. M. Tabuchi, J. Dostie, J. Dekker, *Curr Protoc Mol Biol.* Chapter 21, (2006).

90. G. E. Crawford et al., *Proc Natl Acad Sci USA.* 101, 992-997 (2004).

91. J. D. Buenrostro et al., *Nat. Methods.* 10, 1213-1218 (2013).
92. N. D. Heintzman et al., *Nat. Genet.* 39, 311-318 (2007).
93. N. C. Sheffield et al., *Genome Res.* 23, 777-788 (2013).
94. J. Felsenstein, G. A. Churchill, *Mol. Biol. Evol.* 13, 93-104 (1996).
95. H. Santos-Rosa et al., *Nature.* 419, 407-411 (2002).
96. M. Bhandaru et al., *BMC Cancer.* 14, 398 (2014).
97. F. Lai et al., *Cell Death Dis.* 4, e655 (2013).
98. S. Bushmeyer, K. Park, M. L. Atchison, *J. Biol. Chem.* 270, 30213-30220 (1995).
99. Q. Zhang, D. B. Stovall, K. Inoue, G. Sui, *Crit Rev Oncog.* 16, 163-197 (2011).
100. W. W. Wasserman, A. Sandelin, *Nat. Rev. Genet.* 5, 276-287 (2004).
101. A. Mathelier et al., *Nucleic Acids Res.* 44, D110-5 (2016).
102. R. Katainen et al., *Nat. Genet.* 47, 818-821 (2015).
103. A. L. Sanborn et al., *Proc Natl Acad Sci USA.* 112, E6456-65 (2015).
104. X. Ding et al., *Sci Signal.* 6, ra28.1-13-S0-15 (2013).
105. Alipanahi, B. et al., 2015. Predicting the sequence specificities of DNA- and RNA-binding proteins by deep learning. *Nature Biotechnology,* 33(8), pp. 831-838.
106. ENCODE Project Consortium, 2012. An integrated encyclopedia of DNA elements in the human genome. *Nature,* 489(7414), pp. 57-74.
107. Langmead, B. et al., 2009. Ultrafast and memory-efficient alignment of short DNA sequences to the human genome. *Genome biology,* 10(3), p. R25.
108. Quinlan, A. R. & Hall, I. M., 2010. BEDTools: a flexible suite of utilities for comparing genomic features. *Bioinformatics* (Oxford, England), 26(6), pp. 841-842.
109. Tan, G. & Lenhard, B., 2016. TFBSTools: an R/Bioconductor package for transcription factor binding site analysis. *Bioinformatics* (Oxford, England).
110. Van der Auwera, G. A. et al., 2013. From FastQ data to high confidence variant calls: the Genome Analysis Toolkit best practices pipeline. *Current protocols in bioinformatics/editorial board*, Andreas D. Baxevanis . . . [et al.], 11(1110), pp. 11.10.1-11.10.33.
111. Wright, J. B., Brown, S. J. & Cole, M. D., 2010. Upregulation of c-MYC in cis through a large chromatin loop linked to a cancer risk-associated single-nucleotide polymorphism in colorectal cancer cells. *Molecular and cellular biology,* 30(6), pp. 1411-1420.

TABLE 1 sgRNA Sequences

| sgRNA Target Gene or Region | Species | Sequence | SEQ ID NO: |
|---|---|---|---|
| Composite Enhancer 5' Target 1 | Human | TGGAAAGGAGAACGGCCCGG | 175 |
| Composite Enhancer 5' Target 2 | Human | TGAACACCCTCGTTAAAGGC | 176 |
| Composite Enhancer 5' Target 3 | Human | AACACTAGCCCACATGCCAA | 177 |
| Composite Enhancer 3' Target 1 | Human | GCCCACAGAGGCACGGTTAA | 178 |
| Composite Enhancer 3' Target 2 | Human | AGGCACGGTTAATGGTGGCG | 179 |
| Composite Enhancer 3' Target 3 | Human | CACAGGAAGCCATGGTCCTT | 180 |
| +55 5' Target 1 | Human | GCACTGACGTAGGTAGTGAC | 181 |
| +55 5' Target 2 | Human | ATAGGATATGGCACTGACGT | 182 |
| +55 3' Target 1 | Human | CATTATCTTCTCTGGTCTCG | 183 |
| +55 3' Target 2 | Human | ATACTGGGGAACACATTGTA | 184 |
| +58 5' Target 1 | Human | TGAGCACATTCTTACGCCTA | 185 |
| +58 5' Target 2 | Human | CTAGGCGTAAGAATGTGCTC | 186 |
| +58 3' Target 1 | Human | GAACCCCCTATAAACTAGTC | 187 |
| +58 3' Target 2 | Human | GGCAAACCAGACTAGTTTAT | 188 |
| +62 5' Target 1 | Human | CAGGGGAGAACTCGGCATGA | 189 |
| +62 5' Target 2 | Human | GATGGAGTTGGTTGACCGTA | 190 |
| +62 3' Target 1 | Human | GGTAGGACCCAACACTACGC | 191 |
| +62 3' Target 2 | Human | ATGCCTAGGGTGTTTTGACG | 192 |
| BCL11A Exon 2 Target 2 | Human | TGAACCAGACCACGGCCCGT | 193 |
| BCL11A Exon 2 Target 3 | Human | GCATCCAATCCCGTGGAGGT | 194 |
| +55 5' Target | Mouse | CACTGGCTTCCTGTTCTTGT | 195 |
| +55 3' Target | Mouse | AAGGTTTTCAAGGCAAATAA | 196 |
| +58 5' Target | Mouse | GTAATGGAGCCCGCATGCTG | 197 |
| +58 3' Target | Mouse | GCCAGTGTACAGGCAAGTAC | 198 |
| +62 5' Target | Mouse | TCGCTGCCTTCAGTTCTGCT | 199 |
| +62 3' Target | Mouse | TTATGGAACTCAGGAACTGC | 200 |
| Bcl11a Exon 2 Target | Mouse | GATGCCTTTTTCATCTCGAT | 201 |
| +62 Target 1 | Mouse | ATTCCTTGAGTGTCATATAT | 202 |
| +62 Target 2 | Mouse | TCTGGAATCACTATGTATAT | 203 |

TABLE 2

Oligonucleotides for Deletion Clone Screening

| Gene or Region | Species | Non-Deletion (ND) or Deletion (D) | CRISPR Pair | Orientation | Sequence | SEQ ID NO: |
|---|---|---|---|---|---|---|
| Composite Enhancer | Human | ND | 5' Target 3 | Forward | TGCTCCGAGCTTGTGAACTA | 204 |
| | | | 3' Target 1 | Reverse | TATCACAGGCTCCAGGAAGG | 205 |
| Composite Enhancer | Human | D | 5' Target 3 | Forward | TAGTTTGCTTCCCCCAATGA | 206 |
| | | | 3' Target 1 | Reverse | GCCAGGAAATTGGTGGTAGA | 207 |
| Composite Enhancer | Human | ND | 5' Target 2 | Forward | TGCTCCGAGCTTGTGAACTA | 208 |
| | | | 3' Target 2 | Reverse | TATCACAGGCTCCAGGAAGG | 209 |
| Composite Enhancer | Human | D | 5' Target 2 | Forward | GTGGGCAGTTACGTTTTCGT | 210 |
| | | | 3' Target 2 | Reverse | GCCAGGAAATTGGTGGTAGA | 211 |
| +55 | Human | ND | 5' Target 1 or 2 | Forward | GGTCAGGGTGTTGCAGAGAT | 212 |
| | | | 3' Target 1 or 2 | Reverse | CACACCCTGTGATCTTGTGG | 213 |
| +55 | Human | D | 5' Target 1 or 2 | Forward | GACTTAAACTGCCGCTCCTG | 214 |
| | | | 3' Target 1 or 2 | Reverse | GGGCCTCAGGCTCTTTATCT | 215 |
| +58 | Human | ND | 5' Target 1 or 2 | Forward | CCCAGAGCTCAGTGAGATGA | 216 |
| | | | 3' Target 1 or 2 | Reverse | GGGAAAGGGCCTGATAACTT | 217 |
| +58 | Human | D | 5' Target 1 or 2 | Forward | GAACAGAGACCACTACTGGCAAT | 218 |
| | | | 3' Target 1 or 2 | Reverse | CTCAGAAPAATGACAGCACCA | 219 |
| +62 | Human | ND | 5' Target 1 or 2 | Forward | TTTGAAAGTACCAGCACAGCA | 720 |
| | | | 3' Target 1 or 2 | Reverse | CCCTCTGGCATCAAAATGAG | 221 |
| +62 | Human | D | 5' Target 1 or 2 | Forward | AACAGACCCATGTGCTAGGC | 222 |
| | | | 3' Target 1 or 2 | Reverse | TGCTGAATTCCTGTAAAGTGAGG | 223 |
| +55 | Mouse | ND | 5' Target | Forward | GAGGTGACCAGGGTGTGAGT | 224 |
| | | | 3' Target | Reverse | AAGAAGAGGCCCTGGACATT | 225 |
| +55 | Mouse | D | 5' Target | Forward | CATCTTAAGGCAAGAATCACT | 226 |
| | | | 3' Target | Reverse | CCAGTCAATCCAAACCCTGT | 227 |
| +58 | Mouse | ND | 5' Target | Forward | TATTAATGCCCAGCCAGCTC | 228 |
| | | | 3' Target | Reverse | GTGGTCCAGACCTAGCCAAG | 229 |
| +58 | Mouse | D | 5' Target | Forward | TTTGAGCAGGAGGGAATTTG | 230 |
| | | | 3' Target | Reverse | ATAGGTGGTTGGGCTTCTCC | 231 |
| +62 | Mouse | ND | 5' Target | Forward | GGAGTGGCTGTTGAAAGAGG | 232 |
| | | | 3' Target | Reverse | CACTCAAGGAATGCAAGCAA | 233 |
| +62 | Mouse | D | 5' Target | Forward | TACTTGGTGGCTTTCCCAAC | 234 |
| | | | 3' Target | Reverse | AGATGGTCCTCTGCATCCAC | 235 |

TABLE 3

Oligonucleotides for Inversion Clone Screening

| Inverted Region | Species | CRISPR Pair | Orientation | Sequence | SEQ ID NO: |
|---|---|---|---|---|---|
| +55 | Human | 5' Target 1 or 2 | Forward | GACTTAAACTGCCGCTCCTG | 236 |
| | | 3' Target 1 or 2 | Forward | AGGCATCCAAAGGGAAGAAT | 237 |
| +55 | Human | 5' Target 1 or 2 | Reverse | ACTTCAGCCTCCAGCACTGT | 238 |
| | | 3' Target 1 or 2 | Reverse | CCACTGGAGTGGAACCAAGT | 239 |
| +58 | Human | 5' Target 1 or 2 | Forward | GGGATCAGAGGTGAACAGGA | 240 |
| | | 3' Target 1 or 2 | Forward | TGGACTTTGCACTGGAATCA | 241 |
| +58 | Human | 5' Target 1 or 2 | Reverse | TTGTTTACAGAGGGGCAACC | 242 |
| | | 3' Target 1 or 2 | Reverse | GGGGAAGGGGTATTGAATTG | 243 |

TABLE 3 -continued

Oligonucleotides for Inversion Clone Screening

| Inverted Region | Species | CRISPR Pair | Orientation | Sequence | SEQ ID NO: |
|---|---|---|---|---|---|
| +62 | Mouse | 5' Target 1 or 2 | Forward | AACAGACCCATGTGCTAGGC | 244 |
| | | 3' Target 1 or 2 | Forward | GAACCTGGGAGGCAGAAGAT | 245 |
| +62 | Mouse | 5' Target 1 or 2 | Reverse | TGTGTGGACTGCCTTTTCTG | 246 |
| | | 3' Target 1 or 2 | Reverse | TGTGGAGCTCTGGAATGATG | 247 |

TABLE 4

Oligonucleotides for Mouse +62 Deletion Analysis

| Region | Species | CRISPR Pair | Orientation | Sequence | SEQ ID NO: |
|---|---|---|---|---|---|
| +62 | Mouse | Screen 0484 | Forward | GGTAGTGTGGGGGTGGAGT | 248 |
| | | Screen 0475 | Reverse | TCAGCCTGTTCCCTCAGTG | 249 |
| +62 | Mouse | Screen 0484 | Forward | GGTAGTGTGGGGGTGGAGT | 250 |
| | | Screen 2456 | Reverse | TCAGCCTGTTCCCTCAGTG | 251 |
| +62 | Mouse | Screen 0475 | Forward | GGTAGTGTGGGGGTGGAGT | 252 |
| | | Screen 0490 | Reverse | TCAGCCTGTTCCCTCAGTG | 253 |
| +62 | Mouse | Screen 0490 | Forward | GGTAGTGTGGGGGTGGAGT | 254 |
| | | +62 3' Target | Reverse | AGATGGTCCTCTGCATCCAC | 255 |
| +62 | Mouse | Screen 0490 | Forward | GGTAGTGTGGGGGTGGAGT | 256 |
| | | Target 1 | Reverse | TCAGCCTGTTCCCTCAGTG | 257 |
| +62 | Mouse | +62 5' Target | Fotward | TACTTGGTGGCTTTCCCAAC | 258 |
| | | Screen 0475 | Reverse | TCAGCCTGTTCCCTCAGTG | 259 |
| +62 | Mouse | +62 Target 2 | Forward | ATGCTTGGTTGTCGCCTTAT | 260 |
| | | Screen 0475 | Reverse | CACTCAAGGAATGCAAGCAA | 261 |

TABLE 5

RT qPCR Oligonucleotides

| Gene | Species | Orientation | Sequence | SEQ ID NO: |
|---|---|---|---|---|
| GAPDH | Human | Forward | ACCCAGAAGACTGTGGATGG | 262 |
| | | Reverse | TTCAGCTCAGGGATGACCTT | 263 |
| HBB | Human | Forward | CTGAGGAGAAGTCTGCCGTTA | 264 |
| | | Reverse | AGCATCAGGAGTGGACAGAT | 265 |
| HBG | Human | Forward | TGGATGATCTCAAGGGCAC | 266 |
| | | Reverse | TCAGTGGTATCTGGAGGACA | 267 |
| HBE | Human | Forward | GCAAGAAGGTGCTGACTTCC | 268 |
| | | Reverse | ACCATCACGTTACCCAGGAG | 269 |
| HBD | Human | Forward | GAGGAGAAGACTGCTGTCAATG | 270 |
| | | Reverse | AGGGTAGACCACCAGTAATCTG | 271 |
| BCL11A | Human | Forward | AACCCCAGCACTTAAGCAAA | 272 |
| | | Reverse | GGAGGTCATGATCCCCTTCT | 273 |
| Gapdh | Mouse | Forward | TGGTGAAGGTCGGTGTGAAC | 274 |
| | | Reverse | CCATGTAGTTGAGGTCAATGAAGG | 275 |
| β-Major | Mouse | Forward | TTTAACGATGGCCTGAATCACTT | 276 |
| | | Reverse | CAGCACAATCACGATCATATTGC | 277 |

TABLE 5 -continued

RT qPCR Oligonucleotides

| Gene | Species | Orientation | Sequence | SEQ ID NO: |
|---|---|---|---|---|
| Hbb-εy | Mouse | Forward | TGGCCTGTGGAGTAAGGTCAA | 278 |
| | | Reverse | GAAGCAGAGGACAAGTTCCCA | 279 |
| Hbb-βh1 | Mouse | Forward | TGGACAACCTCAAGGAGACC | 280 |
| | | Reverse | ACCTCTGGGGTGAATTCCTT | 281 |
| Bcl11a | Mouse | Forward | AACCCCAGCACTTAAGCAAA | 282 |
| | | Reverse | ACAGGTGAGAAGGTCGTGGT | 283 |

TABLE 6

Location of BCL11A enhancer region for targeting to achieve BCL11A knockdown

| chromosome | coordinate start (hg19) | coordinate end (hg19) | name |
|---|---|---|---|
| chr2 | 60725424 | 60725688 | +55 functional region |
| chr2 | 60722238 | 60722466 | +58 functional region |
| chr2 | 60718042 | 60718186 | +62 functional region |

TABLE 7 sgRNA targeting sequences that produced HbF enrichment over 0.259

| SEQ ID NO: | Identifer | sgRNA Sequence | PAM | Targeted Site | Coordi-nate Relative to TSS | Chr2 Genomic Coordinate (hg19) | Enrichment Score | Dropout Score |
|---|---|---|---|---|---|---|---|---|
| 1 | BCL_00108_H_D55 | TCTGAGGAGCTAGAGACTTGNGG | | DHS_55 | 54701 | 60725932 | 0.3065268 | -0.64986 |
| 2 | BCL_00096_H_D55 | AGCAAATAGGCTTAGTGTGCNGG | | DHS_55 | 54874 | 60725759 | 0.35208854 | -0.23956 |
| 3 | BCL_01427_H_D55 | GGCTAAATAATGAATGTCCCNGG | RC | DHS_55 | 54944 | 60725689 | 0.36697304 | -0.27163 |
| 4 | BCL_00093_H_D55 | TCCCTTCCTAGAATTGGCCTNGG | | DHS_55 | 54950 | 60725683 | 0.52834198 | -0.56164 |
| 5 | BCL_00092_H_D55 | TTCCCTTCCTAGAATTGGCCNGG | | DHS_55 | 54951 | 60725682 | 0.40353821 | -0.43691 |
| 6 | BCL_01428_H_D55 | GAATGTCCCAGGCCAATTCTNGG | RC | DHS_55 | 54955 | 60725678 | 0.4298807 | -0.54353 |
| 7 | BCL_00091_H_D55 | CCCACTTCCCTTCCTAGAATNGG | | DHS_55 | 54956 | 60725677 | 1.16779598 | -0.50425 |
| 8 | BCL_00090_H_D55 | CCTGGTACCAGGAAGGCAATNGG | | DHS_55 | 54989 | 60725644 | 0.46505933 | -0.52917 |
| 9 | BCL_00089_H_D55 | TCCTGGTACCAGGAAGGCAANGG | | DHS_55 | 54990 | 60725643 | 0.35594471 | -0.78622 |
| 10 | BCL_00088_H_D55 | GCATCATCCTGGTACCAGGANGG | | DHS_55 | 54996 | 60725637 | 0.43864112 | -0.37134 |
| 11 | BCL_00087_H_D55 | CATTGCATCATCCTGGTACCNGG | | DHS_55 | 55000 | 60725633 | 0.43801718 | -0.22534 |
| 12 | BCL_00086_H_D55 | CTCCAAGCATTGCATCATCCNGG | | DHS_55 | 55007 | 60725626 | 0.63433419 | -0.27033 |
| 13 | BCL_01438_H_D55 | TACCAGGATGATGCAATGCTNGG | RC | DHS_55 | 55016 | 60725617 | 0.91292075 | -0.4122 |
| 14 | BCL_00085_H_D55 | GGGTGTGCCCTGAGAAGGTGNGG | | DHS_55 | 55040 | 60725593 | 0.50114706 | -0.6263 |
| 15 | BCL_00084_H_D55 | AGGGTGTGCCCTGAGAAGGTNGG | | DHS_55 | 55041 | 60725592 | 0.31100243 | -0.36912 |
| 16 | BCL_00082_H_D55 | TCACAGGGTGTGCCCTGAGANGG | | DHS_55 | 55045 | 60725588 | 0.41742767 | -1.08709 |
| 17 | BCL_01443_H_D55 | GGCACACCCTGTGATCTTGTNGG | RC | DHS_55 | 55065 | 60725568 | 0.41807361 | 0.257924 |
| 18 | BCL_00073_H_D55 | AGCACACAAGATGCACACCCNGG | | DHS_55 | 55096 | 60725537 | 0.41986965 | -0.83722 |
| 19 | BCL_01448_H_D55 | TGTGCTTGGTCGGCACTGATNGG | RC | DHS_55 | 55124 | 60725509 | 1.34772811 | -0.49527 |
| 20 | BCL_01449_H_D55 | GTGCTTGGTCGGCACTGATANGG | RC | DHS_55 | 55125 | 60725508 | 1.13392025 | -0.61013 |
| 21 | BCL_01450_H_D55 | TGCTTGGTCGGCACTGATAGNGG | RC | DHS_55 | 55126 | 60725507 | 1.5783257 | -0.31949 |
| 22 | BCL_01454_H_D55 | GGGTCGCGGTAGGGAGTTGTNGG | RC | DHS_55 | 55146 | 60725487 | 0.35789318 | -0.55774 |
| 23 | BCL_00065_H_D55 | GCCAACAGTGATAACCAGCANGG | | DHS_55 | 55235 | 60725398 | 0.48864454 | -0.54147 |
| 24 | BCL_00064_H_D55 | TGCCAACAGTGATAACCAGCNGG | | DHS_55 | 55236 | 60725397 | 0.51080164 | -0.35814 |
| 25 | BCL_01461_H_D55 | GCCCTGCTGGTTATCACTGTNGG | RC | DHS_55 | 55245 | 60725388 | 0.5924098 | -0.51154 |
| 26 | BCL_00062_H_D55 | AGCAGCCCTGGGCACAGAAGNGG | | DHS_55 | 55272 | 60725361 | 0.32514466 | -0.64013 |
| 27 | BCL_00058_H_D55 | CCTCTATGTAGACGGGTGTGNGG | | DHS_55 | 55311 | 60725322 | 0.32368336 | -0.4848 |
| 28 | BCL_00057_H_D55 | GGAAGGGCCTCTATGTAGACNGG | | DHS_55 | 55318 | 60725315 | 0.45996809 | -0.44507 |
| 29 | BCL_00051_H_D55 | GGAGGTGTGGAGGGGATAACNGG | | DHS_55 | 55356 | 60725277 | 0.31408916 | -0.16554 |
| 30 | BCL_00031_H_D55 | CTGGCAGACCCTCAAGAGCANGG | | DHS_55 | 55444 | 60725189 | 0.32158621 | -1.35414 |
| 31 | BCL_00027_H_D55 | CCCATGGAGGTGGGGAGATGNGG | | DHS_55 | 55474 | 60725159 | 0.28225491 | -0.45625 |
| 32 | BCL_01483_H_D55 | GTCATCCTCGGCCAATGAAGNGG | RC | DHS_55 | 55559 | 60725074 | 0.43184473 | -0.40557 |
| 33 | BCL_00012_H_D55 | AAGTGAGCCAGGTGATAGAANGG | | DHS_55 | 55585 | 60725048 | 0.35107033 | -0.01983 |
| 34 | BCL_00008_H_D55 | TGAAACCAAGCTTCCTCTGCNGG | | DHS_55 | 55612 | 60725021 | 0.27412127 | -0.23029 |
| 35 | BCL_01495_H_D55 | AGGGAGAAATGAGACAAAAGNGG | RC | DHS_55 | 55700 | 60724933 | 0.26434414 | -0.49318 |
| 36 | BCL_01497_H_D55 | AAGAGGCCACTGAGTCCTTTNGG | RC | DHS_55 | 55717 | 60724916 | 0.43002762 | 0.456237 |
| 37 | BCL_01617_H_D58 | CTAACAGTTGCTTTTATCACNGG | RC | DHS_58 | 58232 | 60722401 | 2.4948208 | -0.71934 |

TABLE 7 -continued sgRNA targeting sequences that produced HbF enrichment over 0.259

| SEQ ID NO: | Identifer | sgRNA Sequence | PAM | Targeted Site | Coordi-nate Relative to TSS | Chr2 Genomic Coordinate (hg19) | Enrichment Score | Dropout Score |
|---|---|---|---|---|---|---|---|---|
| 38 | BCL_01618_H_D58 | TTGCTTTTATCACAGGCTCCNGG | RC | DHS_58 | 58239 | 60722394 | 0.85613918 | -0.81273 |
| 39 | BCL_01619_H_D58 | TTTTATCACAGGCTCCAGGANGG | RC | DHS_58 | 58243 | 60722390 | 1.66244771 | -0.31469 |
| 40 | BCL_01620_H_D58 | TTTATCACAGGCTCCAGGAANGG | RC | DHS_58 | 58244 | 60722389 | 1.38026011 | -0.94808 |
| 41 | BCL_00187_H_D58 | ATCAGAGGCCAAACCCTTCCNGG | | DHS_58 | 58246 | 60722387 | 2.12232899 | -0.74438 |
| 42 | BCL_01621_H_D58 | CACAGGCTCCAGGAAGGGTTNGG | RC | DHS_58 | 58249 | 60722384 | 2.31905068 | -0.60048 |
| 43 | BCL_00186_H_D58 | CACGCCCCCACCCTAATCAGNGG | | DHS_58 | 58261 | 60722372 | 0.89714161 | -0.79647 |
| 44 | BCL_01622_H_D58 | GAAGGGTTTGGCCTCTGATTNGG | RC | DHS_58 | 58261 | 60722372 | 1.37845184 | -0.66954 |
| 45 | BCL_01623_H_D58 | AAGGGTTTGGCCTCTGATTANGG | RC | DHS_58 | 58262 | 60722371 | 1.28521056 | -0.26686 |
| 46 | BCL_01624_H_D58 | GGTTTGGCCTCTGATTAGGGNGG | RC | DHS_58 | 58265 | 60722368 | 1.47218462 | -0.77128 |
| 47 | BCL_01625_H_D58 | GTTTGGCCTCTGATTAGGGTNGG | RC | DHS_58 | 58266 | 60722367 | 0.37182118 | -0.94511 |
| 48 | BCL_01626_H_D55 | TTTGGCCTCTGATTAGGGTGNGG | RC | DHS_58 | 58267 | 60722366 | 1.33557005 | -0.27239 |
| 49 | BCL_01627_H_D58 | TTGGCCTCTGATTAGGGTGGNGG | RC | DHS_58 | 58268 | 60722365 | 0.30537167 | -0.2564 |
| 50 | BCL_01629_H_D58 | TCTGATTAGGGTGGGGGCGTNGG | RC | DHS_58 | 58274 | 60722359 | 1.10417515 | 0.18067 |
| 51 | BCL_01631_H_D58 | ATTAGGGTGGGGGCGTGGGTNGG | RC | DHS_58 | 58278 | 60722355 | 0.40981324 | -0.16153 |
| 52 | BCL_01634_H_D58 | TGGGTGGGGTAGAAGAGGACNGG | RC | DHS_58 | 58293 | 60722340 | 0.41467523 | -1.07834 |
| 53 | BCL_00185_H_D58 | GCAAACGGCCACCGATGGAGNGG | | DHS_58 | 58309 | 60722324 | 0.3196407 | -0.51601 |
| 54 | BCL_00184_H_D58 | CCTGGGCAAACGGCCACCGANGG | | DHS_58 | 58314 | 60722319 | 0.31547607 | -0.54143 |
| 55 | BCL_00183_H_D58 | AAGAGGCCCCCCTGGGCAAANGG | | DHS_58 | 58324 | 60722309 | 0.78527241 | -0.59129 |
| 56 | BCL_01637_H_D58 | CCATCGGTGGCCGTTTGCCCNGG | RC | DHS_58 | 58325 | 60722308 | 0.66904064 | -0.50156 |
| 57 | BCL_01638_H_D58 | CATCGGTGGCCGTTTGCCCANGG | RC | DHS_58 | 58326 | 60722307 | 0.63502753 | -0.59285 |
| 58 | BCL_01639_H_D58 | ATCGGTGGCCGTTGCCCAGGNGG | RC | DHS_58 | 58327 | 60722306 | 0.82185918 | -0.89805 |
| 59 | BCL_01640_H_D58 | TCGGTGGCCGTTTGCCCAGGNGG | RC | DHS_58 | 58328 | 60722305 | 0.36580154 | -1.01297 |
| 60 | BCL_01641_H_D55 | CGGTGGCCGTTTGCCCAGGGNGG | RC | DHS_58 | 58329 | 60722304 | 0.28196886 | -0.46328 |
| 61 | BCL_00182_H_D58 | CTTCCGAAAGAGGCCCCCCTNGG | | DHS_58 | 58331 | 60722302 | 0.29420004 | 0.023956 |
| 62 | BCL_00181_H_D58 | CCTTCCGAAAGAGGCCCCCCNGG | | DHS_58 | 58332 | 60722304 | 0.33994629 | 0.262073 |
| 63 | BCL_00160_H_D58 | TCAGGGGGAGGCAAGTCAGTNGG | | DHS_58 | 58575 | 60722058 | 0.32935479 | -0.31801 |
| 64 | BCL_00154_H_D58 | AGGGAAAAGGGAGAGGAAAANGG | | DHS_58 | 58612 | 60722021 | 0.4446489 | -0.39917 |
| 65 | BCL_01665_H_D58 | TGTAACTAATAAATACCAGGNGG | RC | DHS_58 | 58706 | 60721927 | 0.44183247 | -0.65165 |
| 66 | BCL_01669_H_D58 | CCAGCTGAAGAAAGAACATTNGG | RC | DHS_58 | 58870 | 60721763 | 0.31959971 | -0.00075 |
| 67 | BCL_00135_H_D58 | CCATCTCCCTAATCTCCAATNGG | | DHS_58 | 58958 | 60721675 | 0.29845544 | -0.04502 |
| 68 | BCL_00131_H_D58 | TGGGGAGAGAAGAGTGGAAANGG | | DHS_58 | 59030 | 60721603 | 0.26979883 | -0.3654 |
| 69 | BCL_00130_H_D58 | GGAGTATGGGGAGAGAAGAGNGG | | DHS_62 | 59036 | 60721597 | 0.37521645 | -2.21246 |
| 70 | BCL_01684_H_D58 | ACAACCTCCTTGTTTACAGANGG | RC | DHS_62 | 59129 | 60721504 | 0.49451625 | 0.36739 |
| 71 | BCL_01788_H_D62 | GAGATTTACTCTTGTTGCCCNGG | | DHS_62 | 61848 | 60718785 | 1.29003182 | -5.46287 |
| 72 | BCL_01790_H_D62 | TTGCCCGGGCTGGAATGCAANGG | RC | DHS_62 | 61862 | 60718771 | 0.46730546 | -8.12292 |
| 73 | BCL_00245_H_D62 | GGAGATCGCTTGAACCTGGGNGG | | DHS_62 | 61901 | 60718732 | 0.47622708 | -5.06663 |

TABLE 7 -continued sgRNA targeting sequences that produced HbF enrichment over 0.259

| SEQ ID NO: | Identifer | sgRNA Sequence | PAM | Targeted Site | Coordi-nate Relative to TSS | Chr2 Genomic Coordinate (hg19) | Enrichment Score | Dropout Score |
|---|---|---|---|---|---|---|---|---|
| 74 | BCL_00241_H_D62 | CTCAGCTACTCGGGAGGCTGNGG | | DHS_62 | 61926 | 60718707 | 0.6113192 | -9.05154 |
| 75 | BCL_00240_H_D62 | TGTAATCTCAGCTACTCGGGNGG | | DHS_62 | 61932 | 60718701 | 0.79003182 | -8.69099 |
| 76 | BCL_00239_H_D62 | GCCTGTAATCTCAGCTACTCNGG | | DHS_62 | 61935 | 60718698 | 1.91594174 | -6.03102 |
| 77 | BCL_00238_H_D62 | TGCCTGTAATCTCAGCTACTNGG | | DHS_62 | 61936 | 60718697 | 0.6113192 | -8.92274 |
| 78 | BCL_01794_H_D62 | CAGGCATGTATTACCATGCCNGG | RC | DHS_62 | 61964 | 60718669 | 0.28012743 | -1.01079 |
| 79 | BCL_00233_H_D62 | CAGGAGGATCACCTGAGGTCNGG | | DHS_62 | 62037 | 60718596 | 0.6113192 | -9.20231 |
| 80 | BCL_01799_H_D62 | CTCAGGTGATCCTCCTGCCCNGG | RC | DHS_62 | 62054 | 60718579 | 0.91082485 | -9.47845 |
| 81 | BCL_00229_H_D62 | CCCAGCACTTTGGGAGGCCGNGG | | DHS_62 | 62060 | 60718573 | 0.6113192 | -8.71688 |
| 82 | BCL_00228_H_D62 | TCCCAGCACTTTGGGAGGCCNGG | | DHS_62 | 62061 | 60718572 | 0.76104471 | -5.65759 |
| 83 | BCL_00227_H_D62 | ATCCCAGCACTTTGGGAGGCNGG | | DHS_62 | 62062 | 60718571 | 0.79003182 | -8.09896 |
| 84 | BCL_00225_H_D62 | ACCTGTAATCCCAGCACTTTNGG | | DHS_62 | 62069 | 60718564 | 0.33277348 | -8.82052 |
| 85 | BCL_01800_H_D62 | GCCCCGGCCTCCCAAAGTGCNGG | RC | DHS_62 | 62070 | 60718563 | 0.6113192 | -7.64956 |
| 86 | BCL_01801_H_D62 | CCCCGGCCTCCCAAAGTGCTNGG | RC | DHS_62 | 62071 | 60718562 | 0.6113192 | -8.0566 |
| 87 | BCL_01825_H_D62 | ATTTGCTCTTCTCCAGGGTGNGG | RC | DHS_62 | 62469 | 60718164 | 0.28180883 | -0.39453 |
| 88 | BCL_00210_H_D62 | TAAACAGCCACCCCACACCCNGG | | DHS_62 | 62470 | 60718163 | 0.70263344 | -0.87051 |
| 89 | BCL_01826_H_D62 | TTTGCTCTTCTCCAGGGTGTNGG | | DHS_62 | 62470 | 60718163 | 0.40028858 | -0.33863 |
| 90 | BCL_01828_H_D62 | CTCTTCTCCAGGGTGTGGGGNGG | RC | DHS_62 | 62474 | 60718159 | 0.34846068 | -0.39104 |
| 91 | BCL_01829_H_D62 | TGTGGGGTGGCTGTTTAAAGNGG | | DHS_62 | 62487 | 60718146 | 0.49598477 | -0.14693 |
| 92 | BCL_01831_H_D62 | GGGTGGCTGTTTAAAGAGGGNGG | RC | DHS_62 | 62491 | 60718142 | 0.41044562 | -0.14856 |
| 93 | BCL_01833_H_D62 | AGTTCAAGTAGATATCAGAANGG | RC | DHS_62 | 62580 | 60718053 | 0.61158376 | 0.228869 |
| 94 | BCL_01834_H_D62 | TATCAGAAGGGAACTGTTTGNGG | RC | DHS_62 | 62592 | 60718041 | 0.40286685 | 0.023271 |
| 95 | BCL_02015_H_exon2 | AAGAATGGCTTCAAGAGGCTNGG | RC | exon2 | 7218 | 60773415 | 1.06436679 | -1.34908 |
| 96 | BCL_02014_H_exon2 | TCTGTAAGAATGGCTTCAAGNGG | RC | exon2 | 7223 | 60773410 | 0.99011778 | -0.7711 |
| 97 | BCL_00248_H_exon2 | ACAGATGATGAACCAGACCANGG | | exon2 | 7224 | 60773409 | 1.60874074 | -2.53181 |
| 98 | BCL_00249_H_exon2 | TGAACCAGACCACGGCCCGTNGG | | exon2 | 7232 | 60773401 | 1.1752178 | -0.82211 |
| 99 | BCL_00250_H_exon2 | GAACCAGACCACGGCCCGTTNGG | | exon2 | 7233 | 60773400 | 1.58125311 | -0.68474 |
| 100 | BCL_00251_H_exon2 | GGCCCGTTGGGAGCTCCAGANGG | | exon2 | 7245 | 60773388 | 1.91082485 | -1.23576 |
| 101 | BCL_00252_H_exon2 | GCCCGTTGGGAGCTCCAGAANGG | | exon2 | 7246 | 60773387 | 0.54529072 | 0.092119 |
| 102 | BCL_00253_H_exon2 | CCCGTTGGGAGCTCCAGAAGNGG | | exon2 | 7247 | 60773386 | 1.20485173 | -1.96839 |
| 103 | BCL_02011_H_exon2 | CTGGAGCTCCCAACGGGCCGNGG | RC | exon2 | 7258 | 60773375 | 0.6044195 | 0.791184 |
| 104 | BCL_02010_H_exon2 | CCCCTTCTGGAGCTCCCAACNGG | RC | exon2 | 7264 | 60773369 | 0.50032578 | -0.14628 |
| 105 | BCL_02009_H_exon2 | TCCCCTTCTGGAGCTCCCAANGG | RC | exon2 | 7265 | 60773368 | 2.10774428 | -1.69298 |
| 106 | BCL_00254_H_exon2 | GATCATGACCTCCTCACCTGNGG | | exon2 | 7269 | 60773364 | 2.19780485 | -2.25564 |
| 107 | BCL_00255_H_exon2 | ATCATGACCTCCTCACCTGTNGG | | exon2 | 7270 | 60773363 | 1.70330708 | -2.49715 |
| 108 | BCL_02008_H_exon2 | AGGAGGTCATGATCCCCTTCNGG | RC | exon2 | 7277 | 60773356 | 0.34947658 | -0.44825 |
| 109 | BCL_02007_H_exon2 | GGCACTGCCCACAGGTGAGGNGG | RC | exon2 | 7294 | 60773339 | 3.35094127 | -1.66199 |
| 110 | BCL_00256_H_exon2 | GTGCCAGATGAACTTCCCATNG6 | | exon2 | 7295 | 60773338 | 1.89017832 | -1.76407 |

TABLE 7 -continued

| sgRNA targeting sequences that produced HbF enrichment over 0.259 | | | | | | | | |
|---|---|---|---|---|---|---|---|---|
| SEQ ID NO: | Identifer | sgRNA Sequence | PAM | Targeted Site | Coordi-nate Relative to TSS | Chr2 Genomic Coordinate (hg19) | Enrichment Score | Dropout Score |
| 111 | BCL_00257_H_exon2 | TGCCAGATGAACTTCCCATTNGG | | exon2 | 7296 | 60773337 | 1.94508027 | -1.9609 |
| 112 | BCL_00258_H_exon2 | GCCAGATGAACTTCCCATTGNGG | | exon2 | 7297 | 60773336 | 1.59275545 | -1.89857 |
| 113 | BCL_02006_H_exon2 | TCTGGCACTGCCCACAGGTGNGG | RC | exon2 | 7297 | 60773336 | 1.48917633 | -2.02947 |
| 114 | BCL_00259_H_exon2 | CCAGATGAACTTCCCATTGGNGG | | exon2 | 7298 | 60773335 | 3.26617426 | -3.32127 |
| 115 | BCL_02005_H_exon2 | GTTCATCTGGCACTGCCCACNGG | RC | exon2 | 7302 | 60773331 | 3.20226887 | -1.83694 |
| 116 | BCL_02004_H_exon2 | CCCCCAATGGGAAGTTCATCNGG | RC | exon2 | 7315 | 60773318 | 0.46854155 | -0.11887 |
| 117 | BCL_02003_H_exon2 | AAATAAGAATGTCCCCCAATNGG | RC | exon2 | 7327 | 60773306 | 1.08475851 | -0.09695 |
| 118 | BCL_02002_H_exon2 | AAAATAAGAATGTCCCCCAANGG | RC | exon2 | 7328 | 60773305 | 0.50500271 | -0.4259 |
| 119 | BCL_00261_H_exon2 | CACAAACGGAAACAATGCAANGG | | exon2 | 7341 | 60773292 | 3.32908014 | -2.54324 |
| 120 | BCL_00262_H_exon2 | CCTCTGCTTAGAAAAAGCTGNGG | | exon2 | 7367 | 60773266 | 1.00055405 | -1.35239 |
| 121 | BCL_02001_H_exon2 | CCACAGCTTTTTCTAAGCAGNGG | RC | exon2 | 7384 | 60773249 | 0.49127532 | -0.24954 |
| 122 | BCL_02000_H_exon2 | TCGATTGGTGAAGGGGAAGGNGG | RC | exon2 | 7412 | 60773221 | 0.46242001 | -1.36477 |
| 123 | BCL_01999_H_exon2 | ATCTCGATTGGTGAAGGGGANGG | RC | exon2 | 7415 | 60773218 | 0.62036667 | -0.76015 |
| 124 | BCL_01998_H_exon2 | TTTCATCTCGATTGGTGAAGNGG | RC | exon2 | 7419 | 60773214 | 0.34887409 | -0.14262 |
| 125 | BCL_00263_H_exon2 | GAAAAAAGCATCCAATCCCGNGG | | exon2 | 7421 | 60773212 | 0.6213377 | -2.11505 |
| 126 | BCL_00264_H_exon2 | AAAAGCATCCAATCCCGTGGNGG | | exon2 | 7424 | 60773209 | 0.55781702 | -1.37569 |
| 127 | BCL_00265_H_exon2 | GCATCCAATCCCGTGGAGGTNGG | | exon2 | 7428 | 60773205 | 1.290845 | -0.88953 |
| 128 | BCL_00266_H_exon2 | TCCCGTGGAGGTTGGCATCCNGG | | exon2 | 7436 | 60773197 | 0.58892468 | -0.18023 |
| 129 | BCL_00267_H_exon2 | TGGCATCCAGGTCACGCCAGNGG | | exon2 | 7448 | 60773185 | 2.04934363 | -2.00635 |
| 130 | BCL_01994_H_exon2 | GATGCCAACCTCCACGGGATNGG | RC | exon2 | 7449 | 60773184 | 1.10977009 | -0.99042 |
| 131 | BCL_01993_H_exon2 | ACCTGGATGCCAACCTCCACNGG | RC | exon2 | 7454 | 60773179 | 1.97417272 | -1.73599 |
| 132 | BCL_01992_H_exon2 | GACCTGGATGCCAACCTCCANGG | RC | exon2 | 7455 | 60773178 | 1.23389832 | -0.6955 |
| 133 | BCL_01991_H_exon2 | CGTCATCCTCTGGCGTGACCNGG | RC | exon2 | 7471 | 60773162 | 0.85232011 | -0.71662 |
| 134 | BCL_01990_H_exon2 | GATAAACAATCGTCATCCTCNGG | RC | exon2 | 7481 | 60773152 | 0.84221705 | -0.61283 |
| 135 | BCL_01989_H_exon2 | CTGCTATGTGTTCCTGTTTGNGG | RC | exon2 | 7525 | 60773108 | 0.62008756 | 0.033203 |

TABLE 8

| Sequences of the BCL11A enhancer +62, +58, and +55 functional regions | | | | | |
|---|---|---|---|---|---|
| SEQ ID NO: | chromo-some | coordi-nate start (hg19) | coordi-nate end (hg19) | name | sequence |
| 136 | chr2 | 60725424 | 60725688 | +55 functional region | GACACTGAAGGCTGGGCACAGCCTTGG GGACCGCTCACAGGACATGCAGCAGTG TGTGCCGACAACTCCCTACCGCGACCC CTATCAGTGCCGACCAAGCACACAAGA TGCACACCCAGGCTGGGCTGGACAGAG GGGTCCCACAAGATCACAGGGTGTGCC CTGAGAAGGTGGGGAGCTCACAGCCTC |

TABLE 8 -continued

Sequences of the BCL11A enhancer +62, +58, and +55 functional regions

| SEQ ID NO: | chromosome | coordinate start (hg19) | coordinate end (hg19) | name | sequence |
|---|---|---|---|---|---|
| | | | | | CAAGCATTGCATCATCCTGGTACCAGG AAGGCAATGGGCTGCCCCATACCCACT TCCCTTCCTAGAATTGGCCTGG |
| 137 | chr2 | 60722238 | 60722466 | +58 functional region | TTCATTCCCATTGAGAAATAAAATCCA ATTCTCCATCACCAAGAGAGCCTTCCC AAAGAGGCCCCCCTGGGCAAACGGCCA CCGATGGAGAGGTCTGCCAGTCCTCTT CTACCCCACCCACGCCCCCACCCTAAT CAGAGGCCAAACCCTTCCTGGAGCCTG TGATAAAAGCAACTGTTAGCTTGCACT AGACTAGCTTCAAAGTTGTATTGACCC TGGTGTGTTATGT |
| 138 | chr2 | 60718042 | 60718186 | +62 functional region | ATTTCCCTTCTGATATCTACTTGAACT TTCAGATAAAAAAAAAAAAGCAAGTTG CAGTAACATGTTATGCTACACAAAGAT TAGCATGAATATCCACCCTCTTTAAAC AGCCACCCCACACCCTGGAGAAGAGCA AATGTGAAGT |

TABLE S1

Chromosome conformation capture (3C) enzyme cut sites and primers

| Enzyme | Side | Primer sequence | SEQ ID NO: | Primer coordinates | Enzyme coordinates |
|---|---|---|---|---|---|
| BglII | bait | **CCTGAGCGAGACGAGAT** | 284 | 225450119 | 225450242 |
| BglII | left | TGGTGGGAGGTGATTGA | 285 | 225235052 | 225235111 |
| BglII | left | ATAGTTTGGCTGTATCCCTATG | 286 | 225234985 | 225235111 |
| BglII | left | TTTCTAAGTGACGTGGGTTTAG | 287 | 225237511 | 225237570 |
| BglII | left | GCATCTAGGCCTTCAGTTAG | 288 | 225250239 | 225250285 |
| BglII | left | CCTGGGAGCTCTGAGAATA | 289 | 225258453 | 225258548 |
| BglII | left | CTGCCACAATTCCCATGT | 290 | 225261858 | 225261950 |
| BglII | left | GACCCTAAGGGACGCTAATA | 291 | 225265655 | 225265733 |
| BglII | left | CCTGTGTCTGCAGTTTCTC | 292 | 225274018 | 225274128 |
| BglII | left | GCATATTCTGGTCTCCTAAGTC | 293 | 225274085 | 225274128 |
| BglII | left | GTCTGCCCCTGCAGAATAAAG | 294 | 225298258 | 225298356 |
| BglII | left | TTTCTGGAGAATCCTGACTAATG | 295 | 225303341 | 225303422 |
| BglII | left | TTTGAGGAGGAGTTTCGCT | 296 | 225312056 | 225312090 |
| BglII | left | CGTGACACATGCCTGTAAT | 297 | 225312885 | 225312888 |
| BglII | left | TGTGCCACTCAAGACAATC | 298 | 225315736 | 225315839 |
| BglII | left | TGAAGAAACCATCTAAGTCATC | 299 | 225317872 | 225317938 |
| BglII | left | AATTAGCTGGGCATGGTG | 300 | 225320413 | 225320501 |
| BglII | left | CCTCACAATCATGGCAGAAG | 301 | 225322279 | 225322374 |
| BglII | left | AGAAACACTGCATCATCTAGG | 302 | 225332147 | 225332241 |
| BglII | left | CCAGCAATCTCCAACCATTC | 303 | 225336843 | 225336935 |

TABLE S1 -continued

Chromosome conformation capture (3C) enzyme cut sites and primers

| Enzyme | Side | Primer sequence | SEQ ID NO: | Primer coordinates | Enzyme coordinates |
|---|---|---|---|---|---|
| BglII | right | CGAAGGCTTCTTCCAACTC | 304 | 225438282 | 225438352 |
| BglII | right | TCCTCTAGCATTAGGGAGTG | 305 | 225444385 | 225444475 |
| BglII | right | CATTGTGGAGATCAAATGTGC | 306 | 225445725 | 225445789 |
| BglII | right | TCTTTCCTCACTGCAACTG | 307 | 225448537 | 225448639 |
| BglII | right | TTTCTGTGCCCAGTCATATTC | 308 | 225453043 | 225453146 |
| BglII | right | CCTCTTCTTGACCATCAGTTTC | 309 | 225453380 | 225453424 |
| BglII | right | TCCCATTGTGTGAACCTAAC | 310 | 225456453 | 225456557 |
| BglII | right | GTACTATGGGTAGGAAACTGTTC | 311 | 225460687 | 225460810 |
| BglII | right | CGCTTGACCCTGTCTTTAC | 312 | 225462338 | 225462439 |
| BglII | right | AGAGACGGAGACACACATAG | 313 | 225473151 | 225473257 |
| BglII | right | GTTGAAAGAAGGCAACIAGAATAAG | 314 | 225478405 | 225478486 |
| BglII | right | CAGTGATACACACACAGACAC | 315 | 225491758 | 225491920 |
| BglII | right | GGGATCTAAATGAGAGGATCAC | 316 | 225509977 | 225510067 |
| BglII | right | TTCTTCTGCCAGATACCTAAATC | 317 | 225527904 | 225527934 |
| BglII | right | TGGGAGGCCTCAGAATC | 318 | 225528355 | 225528448 |
| BglII | right | ATCGTGCCACTGCACTC | 319 | 225538300 | 225538470 |
| BglII | right | TAGCATAGTGTGTTCAAGGTTC | 320 | 225538680 | 225538812 |
| BglII | right | GTGAGCAGATCAAACGATTATG | 321 | 225540095 | 225540204 |
| BglII | right | CTTACCATCATGGCAGAAGG | 322 | 225540360 | 225540466 |
| BglII | right | GGCTCAGCCTTGGTATTC | 323 | 225543376 | 225543454 |
| BglII | right | GGGACACATGCAATTATTGAG | 324 | 225545398 | 225545433 |
| BglII | right | TCTGGTTTACCATGGCTTATAG | 325 | 225546972 | 225547061 |
| BglII | ctrl | **CTTCCTTCAGTTCCCTGTTC** | 326 | 225450347 | 225450242 |
| HindIII | bait | **ACAGCTGTCAGGACTGGAAGGTG** | 327 | 225450817 | 225450856 |
| HindIII | left | CCTGCTCCACCCTCAAATCTCACATC | 328 | 225238223 | 225238265 |
| HindIII | left | GCCTATACAGGCATACCTTGTTTTATTG | 329 | 225238415 | 225238479 |
| HindIII | left | CATTGGAAGAAGATGCCATCTAGGAC | 330 | 225239728 | 225239765 |
| HindIII | left | GCCAAAATAAGTCTGCCTGGGTTCAG | 331 | 225244542 | 225244590 |
| HindIII | left | GCATCTAGGCCTTCAGTTAGCGTC | 332 | 225250243 | 225250298 |
| HindIII | left | CTTCTGTGTGGGATGTGCATCCTCTAG | 333 | 225251015 | 225251056 |
| HindIII | left | GTATGTCCAGTGCCTAGCACAGTG | 334 | 225251461 | 225251518 |
| HindIII | left | CAATTCTATGTGCTATATTCTTTAAAACTGTAATGG | 335 | 225256337 | 225256408 |
| HindIII | left | GGCAACAGACCAAGACTCTGTCTC | 336 | 225257470 | 225257549 |
| HindIII | left | CACCTGTTTGAGACACCCTTGCTC | 337 | 225261045 | 225261118 |
| HindIII | left | GCCTTTACACACTTTCCTCAGGCAC | 338 | 225263223 | 225263289 |
| HindIII | left | GTTTCCTAGTTATTGTGAGCAGCTCAG | 339 | 225268958 | 225269034 |
| HindIII | left | GGCTCCTTCTAGGGCAGAGGTG | 340 | 225272032 | 225272096 |

TABLE S1 -continued

Chromosome conformation capture (3C) enzyme cut sites and primers

| Enzyme | Side | Primer sequence | SEQ ID NO: | Primer coordinates | Enzyme coordinates |
|---|---|---|---|---|---|
| HindIII | left | GAGGCTCAAAGAAGGGTATGAGAC | 341 | 225273516 | 225273571 |
| HindIII | left | CATGGCACCTGTAGCAAATGCTAGAC | 342 | 225275607 | 225275666 |
| HindIII | left | CTGAGACTGTGGTTTCTATGGCTG | 343 | 225277244 | 225277303 |
| HindIII | left | GAGCTGGGAGGGAATTGCATACC | 344 | 225279524 | 225279548 |
| HindIII | left | GCTCTTAAGAGGTCTAAGAAGAAACTTCC | 345 | 225282405 | 225282465 |
| HindIII | left | CTTCCATAGATGCTTACCCAGTGG | 346 | 225283454 | 225283502 |
| HindIII | left | GCACTGATGCAAAGGAATGCTCTGG | 347 | 225283670 | 225283718 |
| HindIII | left | GGTTTCTCTTCTGGTGAACTTCAAACAC | 348 | 225297233 | 225297289 |
| HindIII | left | GATTCCCAGTGCCTGACACATACTAG | 349 | 225298673 | 225298686 |
| HindIII | left | CATGGCCACAGAAGACATTCTGCC | 350 | 225303645 | 225303721 |
| HindIII | left | GGGTGAGCATTACATAAGCAACCTG | 351 | 225305863 | 225305928 |
| HindIII | left | GGTTCTATTCTGGCCCAGGTAGTCAG | 352 | 225305986 | 225306128 |
| HindIII | left | GACCTGGTCCATCCOGTTCTGATG | 353 | 225307447 | 225307472 |
| HindIII | left | CTTTGTTACAGCAGCIGGAACAGACCAAG | 354 | 225313300 | 225313362 |
| HindIII | left | GTTTCTGACATTTAAGTGGCATTTTGCAG | 355 | 225321344 | 225321366 |
| HindIII | left | GATCAGGGAAGGTGCAATGAAACC | 336 | 225322604 | 225322644 |
| HindIII | left | GAGAACTCACTAAGTGACAGATACCC | 357 | 225331162 | 225331220 |
| HindIII | left | GCTGCCCACAAGAATCACCTCAG | 358 | 225332810 | 225332867 |
| HindIII | left | GCTCAAGGGAAGACTGGAGAATATGG | 359 | 225333349 | 225333445 |
| HindIII | left | GCCTATTGCTAGAGTTGCACTGGAAC | 360 | 225333625 | 225333678 |
| HindIII | left | GATGACAGCCTAGGCAACACAGCAAG | 361 | 225334357 | 225334413 |
| HindIII | right | CAAGGGAAAATACTTGATCTTAATTTCAAGCTC | 362 | 225434665 | 225434697 |
| HindIII | right | CTACTTATGACATCTGCAATAATACCATTTATCC | 363 | 225434971 | 225435027 |
| HindIII | right | GAGTAGGCTATCCAAAACTCAATTTGAG | 364 | 225435575 | 225435622 |
| HindIII | right | CAACTCTTTCGACTATATCTCTGTGAATGAC | 365 | 225435712 | 225435817 |
| HindIII | right | GGAGCTAGAATAAGCCTAAGGTAACC | 366 | 225436619 | 225436671 |
| HindIII | right | GTACCATGTCAACTCAAATAATCAGAGTG | 367 | 225436762 | 225436880 |
| HindIII | right | CAAATGTTACTGAACAATACACATTTCCCAAG | 368 | 225438193 | 225438248 |
| HindIII | right | GCTTATTATGTGCCAAGCACTATTC | 369 | 225440350 | 225440359 |
| HindIII | right | CTCATGTAATCAATCATTCACTAACCACTC | 370 | 225441310 | 225441358 |
| HindIII | right | GGCCTAATCGIGGCTAAATATTGG | 371 | 225441846 | 225441888 |
| HindIII | right | GCTGTCCATGCTACACAAGTGGAGTTC | 372 | 225444367 | 225444429 |
| HindIII | right | GTGGTCCTTGTTCCTCTGCATAC | 373 | 225444868 | 225444933 |
| HindIII | right | GTTGACTGTAAGGTTGAATTTGCCC | 374 | 225451431 | 225451460 |
| HindIII | right | GCTGCGTCTAAAAGCATCACTGTGAACTG | 375 | 225452687 | 225452703 |
| HindIII | right | CCTGCAAGGGCCATTATCACCTGGAG | 376 | 225456766 | 225456815 |
| HindIII | right | GCGGTGAGTGTTACAGCTCATAAAAGCAG | 377 | 225467755 | 225467814 |

TABLE S1 -continued

Chromosome conformation capture (3C) enzyme cut sites and primers

| Enzyme | Side | Primer sequence | SEQ ID NO: | Primer coordinates | Enzyme coordinates |
|---|---|---|---|---|---|
| HindIII | right | CATCTTAAATTCGAACTCTATTAAATGGTG | 378 | 225471353 | 225471400 |
| HindIII | right | GATATATTTGTATACTCATGTTCATAGAAGC | 379 | 225474373 | 225474400 |
| HindIII | right | GTGTATCACCTAAAGGCCTTCAGATTC | 380 | 225481444 | 225481505 |
| HindIII | right | CCAGGTATGATGCCATGGATCTTTGG | 381 | 225482978 | 225483026 |
| HindIII | right | CCAGCCTGGGCAACAAGAATGAAAC | 382 | 225485107 | 225485167 |
| HindIII | right | GAGATTCATCCTGGGGGATTCATGGC | 383 | 225497789 | 225497844 |
| HindIII | right | GTGGTGAATGGATACGCCAGTTCCAG | 384 | 225501679 | 225501727 |
| HindIII | right | CCGTCCTAGAATAAACATAGCCATCAG | 385 | 225503620 | 225503676 |
| HindIII | right | CTTTGGGGGACTCTGTGGGAAG | 386 | 225508744 | 225508766 |
| HindIII | right | CCTCATCTGAAAGGCAGAGTAGTAATAATTATG | 387 | 225508863 | 225508926 |
| HindIII | right | GAGATCAACCATGCCTACTTGTCTCC | 388 | 225519049 | 225519083 |
| HindIII | right | GCAGTACTGTTTCTGTGGTTCCCAG | 389 | 225529590 | 225529636 |
| HindIII | right | GACACAGCTAAACCATATTAACTAGCTAC | 390 | 225540629 | 225540671 |
| HindIII | right | CAGAAACCACAGGGGTAAGCTCTTAAAAG | 391 | 225543135 | 225543215 |
| HindIII | right | CTTTTAATAGTTTGAATTCTGTTTGGCTTCTG | 392 | 225547828 | 225547853 |
| HindIII | right | GTGCCAAGGTTCTTTCAAGTGGTTG | 393 | 225549840 | 225549868 |
| EcoRI | ctrl | **CATGAATAAGCCCTGGGTCCACCAG** | 394 | 225450909 | 225450856 |
| EcoRI | bait | **TTCTTCTAAATTCCATCGTACC** | 395 | 225448349 | 225448415 |
| EcoRI | left | CCCAGAACTTGGGATACAAAC | 396 | 225234594 | 225234653 |
| EcoRI | left | TGCTCAAGGTCACATCAATAG | 397 | 225241814 | 225241896 |
| EcoRI | left | CATATGGGCAACGAGAATTTG | 398 | 225243160 | 225243294 |
| EcoRI | left | CCCTCAGATGAACAACTAACAG | 399 | 225244211 | 225244302 |
| EcoRI | left | ACCTCACTGGATGTTGTAAATG | 400 | 225245271 | 225245361 |
| EcoRI | left | ATGTTTGGCATTGGAATGAAG | 401 | 225251793 | 225251893 |
| EcoRI | left | ATGTCAGTACAGGGAGGTAAC | 402 | 225256743 | 225256852 |
| EcoRI | left | CAGGAGAAGTGGGTAAAGAAG | 403 | 225258393 | 225258498 |
| EcoRI | left | ATCACGCCATTGCACTC | 404 | 225283346 | 225283493 |
| EcoRI | left | CAGGAGGATCGCTTGAG | 405 | 225284395 | 225285041 |
| EcoRI | left | TCTCCTCAGAGAGACTATAAACC | 406 | 225286854 | 225286944 |
| EcoRI | left | CATCACTAATCATCAGGGAAATG | 407 | 225288766 | 225288871 |
| EcoRI | left | TAAATGCAGGCTGTGGTG | 408 | 225290229 | 225290366 |
| EcoRI | left | AACTGAATACACAGTGAGAAGG | 409 | 225290839 | 225290932 |
| EcoRI | left | TGACTAGTTATTGGGTCCTATTATG | 410 | 225291051 | 225291152 |
| EcoRI | left | GCATACCTCCCAAAGAGAAC | 411 | 225298351 | 225298478 |
| EcoRI | left | GAACCAATCTCCCACAGATAC | 412 | 225304880 | 225304962 |
| EcoRI | left | TGTTTGTGTAGGATGCAAAGTG | 413 | 225306745 | 225306813 |
| EcoRI | left | CTCAGCCTCCCAAGAAG | 414 | 225310296 | 225310390 |

TABLE S1 -continued

Chromosome conformation capture (3C) enzyme cut sites and primers

| Enzyme | Side | Primer sequence | SEQ ID NO: | Primer coordinates | Enzyme coordinates |
|---|---|---|---|---|---|
| EcoRI | left | GTGCATGACCAAGAGAAGAC | 415 | 225310572 | 225310651 |
| EcoRI | left | CTTGACCTCAAGTGATCCTC | 416 | 225311732 | 225314802 |
| EcoRI | left | AGTATTCTCGTCTTACATATGCTG | 417 | 225311856 | 225311996 |
| EcoRI | left | CCATGATCCACTCTTAATTTC | 418 | 225314744 | 225314855 |
| EcoRI | left | AACTGTTTCTTTGCCTTTCTTC | 419 | 225318893 | 225318948 |
| EcoRI | left | ACCACACTCAGCCTGTTAG | 420 | 225320916 | 225321043 |
| EcoRI | left | CCAAGTTAAGCTTAGAGAGTACAT | 421 | 225322656 | 225322751 |
| EcoRI | left | CCCATTGTTTGTCTGGTATAGA | 422 | 225323019 | 225323101 |
| EcoRI | left | GGCATGGGCCAATAAATAGA | 423 | 225325226 | 225325322 |
| EcoRI | left | CCATGGTTGGACTTCCATTA | 424 | 225329455 | 225329534 |
| EcoRI | left | GTGCCTACATCCACTACATAC | 425 | 225334816 | 225334867 |
| EcoRI | left | TCTACAGTACAGATGGAGACA | 426 | 225337404 | 225337502 |
| EcoRI | right | CACATCTTGAAGGTTCTGTGA | 427 | 225434424 | 225434480 |
| EcoRI | right | GCTTGTCACTGTCCTACTATT | 428 | 225435835 | 225435927 |
| EcoRI | right | AACCCTTGTGAATGGGATTAG | 429 | 225437427 | 225437520 |
| EcoRI | right | GACAGGGCAAACAGAAGAG | 430 | 225438742 | 225438810 |
| EcoRI | right | GAGGGAAGGAGTCGAGAAT | 431 | 225439791 | 225439925 |
| EcoRI | right | AGCCTGGACACCAAGAG | 432 | 225455161 | 225455243 |
| EcoRI | right | GCACTTCGTAAATATCTGCTTG | 433 | 225463459 | 225463590 |
| EcoRI | right | TTGTATCATTTATGTCAGACTCCTG | 434 | 225470402 | 225470431 |
| EcoRI | right | AGAAATCAAGAGGAGTATATGACC | 435 | 225476429 | 225476444 |
| EcoRI | right | AGACCGAAGTTGCAATGAG | 436 | 225483683 | 225483799 |
| EcoRI | right | TGAACTCTGACTTACCCTGAG | 437 | 225494198 | 225494335 |
| EcoRI | right | CAGATCATGTAGAGCCTGATG | 438 | 225495947 | 225496039 |
| EcoRI | right | CTCTCAAAGTGCTGGGATTAC | 439 | 225496576 | 225496666 |
| EcoRI | right | GAAGCAATCGTTTCATCATAGTC | 440 | 225498192 | 225498260 |
| EcoRI | right | CTGAACGTAACTGCCTAGC | 441 | 225515099 | 225515192 |
| EcoRI | ctrl | AGTTGCAGTGAGGAAAGAC | 442 | 225448536 | 225448450 |

TABLE S2

List of validation sgRNAs and target sites

| sgRNA | sgRNA guide sequence (5' to 3') | SEQ ID NO: | Target location | Name in FIGS. |
|---|---|---|---|---|
| V01 | GGCACTTGGAATCCACATGA | 443 | 3' of CUL3 | |
| V02 | GCAGCGTCCGGAGTTGGCAC | 444 | 3' of CUL3 | FIG. 4E: Distal 3' sg2 |
| V03 | AGOACACAGTCATAACCACA | 445 | 3' of CUL3 | FIG. 4E: Distal 3' sg1 |

TABLE S2 -continued

| List of validation sgRNAs and target sites | | | | |
|---|---|---|---|---|
| sgRNA | sgRNA guide sequence (5' to 3') | SEQ ID NO: | Target location | Name in FIGS. |
| V04 | GCCACAGCCATGCCCAGTOG | 446 | 3' of CUL3 | FIG. 4D: CTCF sg1 |
| V05 | ACTGGCTGGAATCTGCCAAG | 447 | 3' of CUL3 | |
| V06 | CTGATCTTGAGTTGGTCCTT | 448 | 3' of CUL3 | |
| V07 | TTAGGGGCAGGGAGGACCTA | 449 | 3' UTR | |
| V08 | GGAAATCTCAAATTACAACA | 450 | 3' UTR | |
| V09 | AAATGTACTGTTAACGAACT | 451 | Intron and promoter | |
| V10 | AGTATATAGGATATAACTTT | 452 | Intron and promoter | |
| v11 | CAAGAGTTTGTAAAGTGCTT | 453 | Intron and promoter | |
| V12 | TCCGCGGCTGCTAGCAGCGC | 454 | Intron and promoter | FIG. 4C: Intron sg1 |
| V13 | CGCGGAGTCCTCCCTGTGTG | 455 | Intron and promoter | FIG. 4C: Intron sg2 |
| V14 | GCGCTCCTCCGCGATGGCGG | 456 | 5' UTR | FIG. 4B: 5' UTR sg2 |
| V15 | AGGAGGAGGAGGACGACGTT | 457 | 5' uTR | FIG. 4B: 5' UTR sg1 |
| V16 | AGGGGGGAAGTTCGGAGAGC | 458 | 4 Intron and promoter | |
| V17 | ATAGTCTTGAGGAGGAGCGT | 459 | 4 Intron and promoter | FIG. 3: Promoter sg2 |
| V18 | AAAAACACAGGAACCAGTTC | 460 | Intron and promoter | |
| V19 | ATCTTTGTCTGACTACCTGC | 461 | 5' of CUL3 | FIG. 3: Distal 5' sg1 |
| V20 | AATTTGGCTCGTCCAAACTG | 462 | 5' of CUL3 | |
| V21 | ACAGCTTCTACTCTTAGGTC | 463 | 5' of CUL3 | |
| V22 | GATATAGTGAAGTCCAACAA | 464 | 5' of CUL3 | |
| V23 | TGTAGGAGAATGTGCAAGGA | 465 | 5' of CUL3 | |
| V24 | CACACACTCAGATGGCTACA | 466 | 5' of CUL3 | |
| V25 | GTTAGAGCACCAGGAACCAC | 467 | 5' of CUL3 | |
| Exon01 | GACCTAAAATCATTAACATC | 468 | Exon 5 of CUL3 | |
| Exon02 | GCACTGCCTTGACAAATCAA | 469 | Exon 6 of CUL3 | |
| Exon03 | CTTACCTGGATATAGTCAAC | 470 | Exon 7 of CUL3 | |
| Non-targeting 1 | AACCACGGCATTGAGAGGTG | 471 | n/a | |

TABLE S2 -continued

| List of validation sgRNAs and target sites | | | | |
|---|---|---|---|---|
| sgRNA | sgRNA guide sequence (5' to 3') | SEQ ID NO: | Target location | Name in FIGS. |
| Non-targeting 2 | TACATGGTATAGTGTTTATT | 472 | n/a | |
| Non-targeting 3 | GGGCAGAAGTTGCTGTCCTG | 473 | n/a | |

TABLE S3

| Genomic and barcode primers for targeted indel sequencing | | | | |
|---|---|---|---|---|
| sgRNA | Indel PCR1 forward primer (5' to 3') | SEQ ID NO: | Indel PCR1 reverse primer (5' to 3') | SEQ ID NO: |
| V01 | ccatctcatccctgcgtgtctccTGAAGTCCAGACATTTTGTTGC | 474 | cctctctatgggcagtcggtgatgCTGTCTTGGCCCTATCCTCA | 502 |
| V02 | ccatctcatccctgcgtgtctccAGGAAGAGAGACCAGAGTTAGCA | 475 | cctctctatgggcagtcggtgatgTGGGAGATCCAAGGTTGAAG | 503 |
| V03 | ccatctcatccctgcgtgtctccGCTGGCACATTTTAGTGCA | 476 | cctctctatgggcagtcggtgatgGACCCATCTCCTTTGGATGA | 504 |
| V04 | ccatctcatccctgcgtgtctccTGCTTGTTTTATAGGCCAAGTCT | 477 | cctctctatgggcagtcggtgatgGGCTGGATGGTCCTGTCTT | 505 |
| V05 | ccatctcatccctgcgtgtctccCATGAGTTCACCCCTTCCAG | 478 | cctctctatgggcagtcggtgatgTATCAGCAGCGTGAAAATGG | 506 |
| V06 | ccatctcatccctgcgtgtctccCCCCCAATTCAATTATCTCC | 479 | cctctctatgggcagtcggtgatgTGGAGTGGAGCTGAGTCTTG | 507 |
| V07 | ccatctcatccctgcgtgtctccTAGTGCACCACACTTCACC | 480 | cctctctatgggcagtcggtgatgCAAAGTTGGCAGCTGGTTATATT | 508 |
| V08 | ccatctcatccctgcgtgtctccGAAATAACTCAGAACAAAACCTAATCA | 481 | cctctctatgggcagtcggtgatgGCCTTATGACCAGGAACCTTT | 509 |
| V09 | ccatctcatccctgcgtgtctccTCTGTCCGATTGCTAGTTCG | 482 | cctctctatgggcagtcggtgatgTGGGTGTCAAATCTGGTTCA | 510 |
| V10 | ccatctcatccctgcgtgtctccGCAAGTATGCCCAGTTCGTT | 483 | cctctctatgggcagtcggtgatgTTTGGCATTACGTTGAGTCG | 511 |
| V11 | ccatctcatccctgcgtgtctccCGGTTTGCTCTCTGTTGCTT | 484 | cctctctatgggcagtcggtgatgGGAATGCTCCGTGGTCATAA | 512 |
| V12 | ccatctcatccctgcgtgtctccAGCCCCTTCATCACCCTAAA | 485 | cctctctatgggcagtcggtgatgGGGTTGTAGGCCCAGTCTC | 513 |
| V13 | ccatctcatccctgcgtgtctccCCCTAAAAGCTAGGCTGGGTA | 486 | cctctctatgggcagtcggtgatgGGGTTGTAGGCCCAGTCTC | 514 |
| V14 | ccatctcatccctgcgtgtctccACTCTGGCGACTCCGATG | 487 | cctctctatgggcagtcggtgatgCTGCGCAGTGAGATGTTTGT | 515 |
| V15 | ccatctcatccctgcgtgtctccCGACGGACAAACATCTCACT | 488 | cctctctatgggcagtcggtgatgTCTCTCACTCTCCGGCTCTC | 516 |
| V16 | ccatctcatccctgcgtgtctccAGGGTCCTGGTCACATGGT | 489 | cctctctatgggcagtcggtgatgCACGCTCCTCCTCAAGACTA | 517 |
| V17 | ccatctcatccctgcgtgtctccCTGGGACAGCAGGAGGATAG | 490 | cctatatatgggcagtcggtgatgAACTCTTCAAGTTGCAGGCTTC | 518 |
| V18 | ccatctcatccctgcgtgtctccCTGGGACAGCAGGAGGATAG | 491 | cctctctatgggcagtcggtgatgAACTCTTCAAGTTGCAGGCTTC | 519 |

TABLE S3-continued

| | | | | |
|---|---|---|---|---|
| V19 | ccatctcatccctgcgtgtctccCAGGAAGAGA CGGAGACACA | 492 | cctctctatgggcagtcggtgatgCTGGAAA GATCTCTGAAATCAAAA | 520 |
| V20 | ccatctcatccctgcgtgtctccCACTAAATTC TGGTGTGCGTTT | 493 | cctctctatgggcagtcggtgatgAACTGTT CTGTGTCTGCACTGTC | 521 |
| V21 | ccatctcatccctgcgtgtctccGCGCTAGCAG GAGCTGTTT | 494 | cctctctatgggcagtcggtgatgCCGGCTC ATATCTGCTTCTT | 522 |
| V22 | ccatctcatccctgcgtgtctccTGAGCAGGAA TGGACACATC | 495 | cctctctatgggcagtcggtgatgGCATCTT TGACAACAAAGTGACTC | 523 |
| V23 | ccatctcatccctgcgtgtctccGCCCTGGGGA CAAGTTCT | 496 | cctctctatgggcagtcggtgatgATTTTTC CTCCCACTGCTCTG | 524 |
| V24 | ccatctcatccctgcgtgtctccCACACAAATC TAATCTCTGGGATCT | 497 | cctctctatgggcagtcggtgatgTTCTGAT TGTGGACCCTTCA | 525 |
| V25 | ccatctcatccctgcgtgtctccTTTGTGAGAC CAGCCAGAAA | 498 | cctctctatgggcagtcggtgatgTGCTCCC AAGTCCAGTCTTT | 526 |
| Exon01 | ccatctcatccctgcgtgtctccTGGCCTTTT AGCACTTGTCA | 499 | cctctctatgggcagtcggtgatgTCCTATT TGAGGGAGCAAGG | 527 |
| Exon02 | ccatctcatccctgcgtgtctccTTTACATTTT CACGGATTACCTG | 500 | cctctctatgggcagtcggtgatgAGAGGCG CAATAAGAAATGC | 528 |
| Exon03 | ccatctcatccctgcgtgtctccTGGTTCTTCC GTTGATTTGTC | 501 | cctctctatgggcagtcggtgatgGCAGATG GAAAGCCAGAAAT | 529 |

| Name | SEQ ID NO: | Indel PCR2 prime (5' to 3') |
|---|---|---|
| Indel_BC_F01 | 530 | AATGATACGGCGACCACCGAGATCTACACTCTTTCCCTACACGACGCTCTTCCGATCTtcagAAGTAGAG CCATCTCATCCCTGCGTGTCTCC |
| Indel_BC_F02 | 531 | AATGATACGGCGACCACCGAGATCTACACTCTTTCCCTACACGACGCTCTTCCGATCTttcagCATGCTT ACCATCTCATCCCTGCGTGTCTCC |
| Indel_BC_F03 | 532 | AATGATACGGCGACCACCGAGATCTACACTCTTTCCCTACACGACGCTCTTCCGATCTattcagGCACAT CTCCATCTCATCCCTGCGTGTCTCC |
| Indel_BC_F04 | 533 | AATGATACGGCGACCACCGAGATCTACACTCTTTCCCTACACGACGCTCTTCCGATCTGATTCAGTGCTC GACCCATCTCATCCCTGCGTGTCTCC |
| Indel_BC_F05 | 534 | AATGATACGGCGACCACCGAGATCTACACTCTTTCCCTACACGACGCTCTTCCGATCTcgattcagAGCA ATTCCCATCTCATCCCTGCGTGTCTCC |
| Indel_BC_F06 | 535 | AATGATACGGCGACCACCGAGATCTACACTCTTTCCCTACACGACGCTCTTCCGATCTtcgattcagAGT TGCTTCCATCTCATCCCTGCGTGTCTCC |
| Indel_BC_F07 | 536 | AATGATACGGCGACCACCGAGATCTACACTCTTTCCCTACACGACGCTCTTCCGATCTatcgattcagCC AGTTAGCCATCTCATCCCTGCGTGTCTCC |
| Indel_BC_F08 | 537 | AATGATACGGCGACCACCGAGATCTACACTCTTTCCCTACACGACGCTCTTCCGATCTgatcgattcagT TGAGCCTCCATCTCATCCCTGCGTGTCTCC |
| Indel_BC_F09 | 538 | AATGATACGGCGACCACCGAGATCTACACTCTTTCCCTAGACGACGCTCTTCCGATCTtcagACACGATC CCATCTCATCCCTGCGTGTCTCC |
| Indel_BC_F10 | 539 | AATGATACGGCGACCACCGAGATCTACACTCTTTCCCTACACGACGCTCTTCCGATCTttcagGGTCCAG ACCATCTCATCCCTGCGTGTCTCC |
| Indel_BC_F11 | 540 | AATGATACGGCGACCACCGAGATCTACACTCTTTCCCTACACGACGCTCTTCCGATCTattcagGTATAA CACCATCTCATCCCTGCGTGTCTCC |
| Indel_BC_F12 | 541 | AATGATACGGCGACCACCGAGATCTACACTCTTTCCCTACACGACGCTCTTCCGATCTgattcagTTCGC TGACCATCTCATCCCTGCGTGTCTCC |
| Indel_BC_F13 | 542 | AATGATACGGCGACCACCGAGATCTACACTCTTTCCCTACACGACGCTCTTCCGATCTcgattcagAACT TGACCCATCTCATCCCTGCGTGTCTCC |
| Indel_BC_F14 | 543 | AATGATACGGCGACCACCGAGATCTACACTCTTTCCCTACACGACGCTCTTCCGATCTtcgattcagCAC ATCCTCCATCTCATCCCTGCGTGTCTCC |
| Indel_BC_F15 | 544 | AATGATACGGCGACCACCGAGATCTACACTCTTTCCCTACACGACGCTCTTCCGATCTatcgattcagTC GGAATGCCATCTCATCCCTGCGTGTCTCC |
| Indel_BC_F16 | 545 | AATGATACGGCGACCACCGAGATCTACACTCTTTCCCTACACGACGCTCTTCCGATCTgatcgattcagA ACGCATTCCATCTCATCCCTGCGTGTCTCC |

TABLE S3-continued

| | | |
|---|---|---|
| Indel_BC_F17 | 546 | AATGATACGGCGACCACCGAGATCTACACTCTTTCCCTACACGACGCTCTTCCGATCTtcagCGCGCGGTCCATCTCATCCCTGCGTGTCTCC |
| Indel_BC_F18 | 547 | AATGATACGGCGACCACCGAGATCTACACTCTTTCCCTACACGACGCTCTTCCGATCTttcagTCTGGCGACCATCTCATCCCTGCGTGTCTCC |
| Indel_BC_F19 | 548 | AATGATACGGCGACCACCGAGATCTACACTCTTTCCCTACACGACGCTCTTCCGATCTattcagCATAGCGACCATCTCATCCCTGCGTGTCTCC |
| Indel_BC_F20 | 549 | AATGATACGGCGACCACCGAGATCTACACTCTTTCCCTACACGACGCTCTTCCGATCTgattcagCAGGAGCCCCATCTCATCCCTGCGTGTCTCC |
| Indel_BC_F21 | 550 | AATGATACGGCGACCACCGAGATCTACACTCTTTCCCTACACGACGCTCTTCCGATCTcgattcagTGTCGGATCCATCTCATCCCTGCGTGTCTCC |
| Indel_BC_F22 | 551 | AATGATACGGCGACCACCGAGATCTACACTCTTTCCCTACACGACGCTCTTCCGATCTtcgattcagATTATGTTCCATCTCATCCCTGCGTGTCTCC |
| Indel_BC_F23 | 552 | AATGATACGGCGACCACCGAGATCTACACTCTTTCCCTACACGACGCTCTTCCGATCTatcgattcagCCTACCATCCATCTCATCCCTGCGTGTCTCC |
| Indel_BC_F24 | 553 | AATGATACGGCGACCACCGAGATCTACACTCTTTCCCTACACGACGCTCTTCCGATCTgatcgattcagTACTTAGCCCATCTCATCCCTGCGTGTCTCC |
| Indel_BC_R01 | 554 | CAAGCAGAAGACGGCATACGAGATCATGATCGGTGACTGGAGTTCAGACGTGTGCTCTTCCGATCTCCTCTCTATGGGCAGTCGGTGATg |
| Indel_BC_R02 | 555 | CAAGCAGAAGACGGCATACGAGATAGGATCTAGTGACTGGAGTTCAGACGTGTGCTCTTCCGATCTtCCTCTCTATGGGCAGTCGGTGATg |
| Indel_BC_R03 | 556 | CAAGCAGAAGACGGCATACGAGATGACAGTAAGTGACTGGAGTTCAGACGTGTGCTCTTCCGATCTatCCTCTCTATGGGCAGTCGGTGATg |
| Indel_BC_R04 | 557 | CAAGCAGAAGACGGCATACGAGATCCTATGCCGTGACTGGAGTTCAGACGTGTGCTCTTCCGATCTgatCCTCTCTATGGGCAGTCGGTGATg |
| Indel_BC_R05 | 558 | CAAGCAGAAGACGGCATACGAGATTCGCCTTGGTGACTGGAGTTCAGACGTGTGCTCTTCCGATCTcgatCCTCTCTATGGGCAGTCGGTGATg |
| Indel_BC_R06 | 559 | CAAGCAGAAGACGGCATACGAGATATAGCGTCGTGACTGGAGTTCAGACGTGTGCTCTTCCGATCTtcgatCCTCTCTATGGGCAGTCGGTGATg |
| Indel_BC_R07 | 560 | CAAGCAGAAGACGGCATACGAGATGAAGAAGTGTGACTGGAGTTCAGACGTGTGCTCTTCCGATCTatcgatCCTCTCTATGGGCAGTCGGTGATg |
| Indel_BC_R08 | 561 | CAAGCAGAAGACGGCATACGAGATATTCTAGGGTGACTGGAGTTCAGACGTGTGCTCTTCCGATCTgatcgatCCTCTCTATGGGCAGTCGGTGATg |
| Indel_BC_R09 | 562 | CAAGCAGAAGACGGCATACGAGATCGTTACCAGTGACTGGAGTTCAGACGTGTGCTCTTCCGATCTcgatcgatCCTCTCTATGGGCAGTCGGTGATg |
| Indel_BC_R10 | 563 | CAAGCAGAAGACGGCATACGAGATGTCTGATGGTGACTGGAGTTCAGACGTGTGCTCTTCCGATCTtcgatcgatCCTCTCTATGGGCAGTCGGTGATg |
| Indel_BC_R11 | 564 | CAAGCAGAAGACGGCATACGAGATTTACGCACGTGACTGGAGTTCAGACGTGTGCTCTTCCGATCTatcgatcgatCCTCTCTATGGGCAGTCGGTGATg |
| Indel_BC_R12 | 565 | CAAGCAGAAGACGGCATACGAGATTTGAATAGGTGACTGGAGTTCAGACGTGTGCTCTTCCGATCTCCTCTCTATGGGCAGTCGGTGATg |
| Indel_BC_R13 | 566 | CAAGCAGAAGACGGCATACGAGATTCCTTGGTGTGACTGGAGTTCAGACGTGTGCTCTTCCGATCTtCCTCTCTATGGGCAGTCGGTGATg |
| Indel_BC_R14 | 567 | CAAGCAGAAGACGGCATACGAGATACAGGTATGTGACTGGAGTTCAGACGTGTGCTCTTCCGATCTatCCTCTCTATGGGCAGTCGGTGATg |
| Indel_BC_R15 | 568 | CAAGCAGAAGACGGCATACGAGATAGGTAAGGGTGACTGGAGTTCAGACGTGTGCTCTTCCGATCTgatCCTCTCTATGGGCAGTCGGTGATg |
| Indel_BC_R16 | 569 | CAAGCAGAAGACGGCATACGAGATAACAATGGGTGACTGGAGTTCAGACGTGTGCTCTTCCGATCTcgatCCTCTCTATGGGCAGTCGGTGATg |
| Indel_BC_R17 | 570 | CAAGCAGAAGACGGCATACGAGATACTGTATCGTGACTGGAGTTCAGACGTGTGCTCTTCCGATCTtcgatCCTCTCTATGGGCAGTCGGTGATg |
| Indel_BC_R18 | 571 | CAAGCAGAAGACGGCATACGAGATAGGTCGCAGTGACTGGAGTTCAGACGTGTGCTCTTCCGATCTatcgatCCTCTCTATGGGCAGTCGGTGATg |

TABLE S3-continued

| | | |
|---|---|---|
| Indel_BC_R19 | 572 | CAAGCAGAAGACGGCATACGAGATAGGTTATCGTGACTGGAGTTCAGACGTGTGCTCTTCCGATCTgatcgatCCTCTCTATGGGCAGTCGGTGATg |
| Indel_BC_R20 | 573 | CAAGCAGAAGACGGCATACGAGATCAACTCTCGTGACTGGAGTTCAGACGTGTGCTCTTCCGATCTcgatcgatCCTCTCTATGGGCAGTCGGTGATg |
| Indel_BC_F21 | 574 | CAAGCAGAAGACGGCATACGAGATCCAACATTGTGACTGGAGTTCAGACGTGTGCTCTTCCGATCTtcgatcgatCCTCTCTATGGGCAGTCGGTGATg |
| Indel_BC_R22 | 575 | CAAGCAGAAGACGGCATACGAGATCTAACTCGGTGACTGGAGTTCAGACGTGTGCTCTTCCGATCTatcgatcgatCCTCTCTATGGGCAGTCGGTGATg |
| Indel_BC_R23 | 576 | CAAGCAGAAGACGGCATACGAGATATTCCTCTGTGACTGGAGTTCAGACGTGTGCTCTTCCGATCTCCTCTCTATGGGCAGTCGGTGATg |
| Indel_BC_R24 | 577 | CAAGCAGAAGACGGCATACGAGATCTACCAGGGTGACTGGAGTTCAGACGTGTGCTCTTCCGATCTtCCTCTCTATGGGCAGTCGGTGATg |

TABLE S4

Chromatin immunoprecipitation-droplet digital PCR (ChIP-ddPCR) primers

| sgRNA | ChIP-ddPCR forward primer (5' to 3') | SEQ ID NO: | ChIP-ddPCR reverse primer (5' to 3') | SEQ ID NO: |
|---|---|---|---|---|
| v01 | GCACTTCGAATCCACATGAA | 578 | TCACTGTCTTGGCCCTATCC | 599 |
| V02 | ATAGCAAACTCAGCCCCATT | 579 | GCATCTGGTCAGAGCCTTCT | 600 |
| V03 | GCTGGCACATTTTAGTGCAA | 580 | TGGCAATCCACTCTTCTTCA | 601 |
| V04 | GTGCACCGAATTGAAGACAG | 581 | TGGCTGTGGCTTTTATATGCT | 602 |
| V07 | TAGTGCACCACAGCTTCACC | 582 | GCCCCTCTGAAAAGCACATA | 603 |
| V14 | GGCTCGGCTCCCTTTATC | 583 | GAGAAGGAGGAGGAGGAGGA | 604 |
| V15 | TCCTCCTCCTCCTCCTTCTC | 584 | TCTCTCACTCTCCGGCTCTC | 605 |
| V19 | TGAGAGAGGGAGGAAAAAGGA | 585 | ATCTGCGCCACTCACAGAAC | 606 |
| V24 | TCCTTGCTGATTTTGTGTTCC | 586 | CCCCTCTAGCCATCTCAGTG | 607 |
| V25 | TGGTTAGAGCACCAGGAACC | 587 | CTTCTTGCTCCCAAGTCCAG | 608 |
| V10 | GCAAGTATGCCCAGTTCGTT | 588 | GTCGTACCCTTGCGATGTTT | 609 |
| V13 | GAGGCAATCCTGCACAAGAG | 589 | GGAATGCTCCGTGGTCATAA | 610 |
| V12 | AGCCCCTTCATCACCCTAAA | 590 | CGGAGTCCTCCCTGTGTG | 611 |
| V13 | GAAACCCCACGTGAAAAGTT | 591 | GGGTTGTAGGCCCAGTCTC | 612 |
| V16 | AGGGTCCTGGTCACATGGT | 592 | CGCTCCTCCTCAAGACTATCC | 613 |
| V17 | CTGGGACAGCACGGAGGATAG | 593 | CCACATGCCCTAGAAAAACA | 614 |
| V18 | CCGAACTGGTTCCTGTOTTT | 594 | CTGCAGCTAACTCCTGCACA | 615 |
| NegRegion1 | ATGTGCCCAGAAACTCCTC | 595 | ATTTGACTGGGCCACAAGG | 616 |
| NegRegion2 | AATGGAATGTGGGCAGAAGT | 396 | CAATGGGGGAGAAAATCTGA | 617 |
| PosRegioa1 | ACTAAACAGCATGCCCTTCC | 597 | CCTCTCCCCCTTCAGGATAC | 618 |
| PosRegion2 | GCATGAGCTTCAGCTCTCTCA | 598 | TCGCAATTGAACTCCATCTC | 619 |

The invention is further described by the following numbered paragraphs:

1. A deep scanning mutagenesis library to interrogate phenotypic changes in a population of cells comprising a plurality of CRISPR-Cas system guide RNAs comprising guide sequences that are capable of targeting a plurality of genomic sequences within at least one continuous genomic region, wherein the guide RNAs target at least 100 genomic sequences comprising non-overlapping cleavage sites upstream of a PAM sequence for every 1000 base pairs within the continuous genomic region.

2. The library of numbered paragraph 1, wherein the library comprises guide RNAs targeting genomic sequences upstream of every PAM sequence within the continuous genomic region.
3. The library of numbered paragraph 1, wherein the frequency of off target sites for a guide RNA is less than 500.
4. The library according to any of numbered paragraphs 1 to 3, wherein the PAM sequence is specific to at least one Cas protein.
5. The library according to any of the preceding numbered paragraphs, wherein the CRISPR-Cas system guide RNAs are selected based upon more than one PAM sequence specific to at least one Cas protein.
6. The library according to any of the preceding numbered paragraphs, wherein expression of a gene of interest is altered by said targeting by at least one guide RNA within the plurality of CRISPR-Cas system guide RNAs.
7. The library according to any of the preceding numbered paragraphs, wherein the at least one continuous genomic region comprises up to the entire genome.
8. The library according to any of the preceding numbered paragraphs, wherein the at least one continuous genomic region comprises a functional element of the genome.
9. The library according to any of the preceding numbered paragraphs, wherein the at least one continuous genomic region comprises at least 50 kb of genomic DNA.
10. The library according to any of the preceding numbered paragraphs, wherein the at least one continuous genomic region comprises a transcription factor binding site.
11. The library according to any of the preceding numbered paragraphs, wherein the at least one continuous genomic region comprises a region of DNase I hypersensitivity.
12. The library according to any of the preceding numbered paragraphs, wherein the at least one continuous genomic region comprises a transcription enhancer or repressor element.
13. The library according to any of the preceding numbered paragraphs, wherein the at least one continuous genomic region comprises a site enriched for an epigenetic signature.
14. The library according to any of the preceding numbered paragraphs, wherein the at least one continuous genomic DNA region comprises an epigenetic insulator.
15. The library according to any of the preceding numbered paragraphs, wherein the at least one continuous genomic region comprises two or more continuous genomic regions that physically interact.
16. The library according to numbered paragraph 13, wherein the epigenetic signature comprises histone acetylation, histone methylation, histone ubiquitination, histone phosphorylation, DNA methylation, or a lack thereof.
17. The library according to any of the preceding numbered paragraphs, wherein the at least one continuous genomic region is human chromosome 2, wherein the human chromosome 2 is that according to UCSC Genome Browser hg 19 human genome assembly.
18. The library according to numbered paragraph 17, wherein the at least one continuous genomic region comprises the BCL11A enhancer functional regions.
19. The library according to numbered paragraph 18, wherein the at least one continuous genomic region comprises the human chromosome 2 at location 60725424 to 60725688 (+55 functional region), the human chromosome 2 at location 60722238 to 60722466 (+58 functional region), or the human chromosome 2 at location 60718042 to 60718186 (+62 functional region).
20. The library according to any of the preceding numbered paragraphs, wherein the population of cells is a population of eukaryotic cells or prokaryotic cells.
21. The library according to numbered paragraph 20, wherein the population of eukaryotic cells is a population of embryonic stem (ES) cells, neuronal cells, epithelial cells, immune cells, endocrine cells, muscle cells, erythrocytes, lymphocytes, plant cells, or yeast cells.
22. The library according to any of numbered paragraphs 1 to 21, wherein said targeting results in NHEJ of the continuous genomic region.
23. The library according to any of numbered paragraphs 1 to 21, wherein said targeting results in editing of the continuous genomic region.
24. The library according to any of the preceding numbered paragraphs, wherein the targeting is of about 100 or more sequences.
25. The library according to any of the preceding numbered paragraphs, wherein the targeting is of about 1,000 or more sequences.
26. The library according to any of the preceding numbered paragraphs, wherein the targeting is of about 100,000 or more sequences.
27. The library according to any of the preceding numbered paragraphs, wherein targeting comprises introducing into each cell in the population of cells a vector system of one or more vectors comprising an engineered, non-naturally occurring CRISPR-Cas system comprising:

I. at least one Cas protein, and

II. one or more guide RNAs of the library, wherein components I and II may be on the same or on different vectors of the system, wherein components I and II are integrated into each cell, wherein the guide sequence targets a sequence within the continuous genomic region in each cell in the population of cells, wherein the at least one Cas protein is operably linked to a regulatory element, and wherein when transcribed, the guide RNA comprising the guide sequence directs sequence-specific binding of a CRISPR-Cas system to a target sequence in the continuous genomic region, inducing cleavage of the continuous genomic region by the Cas protein.

28. The library of numbered paragraph 27, wherein the one or more vectors are plasmid vectors.
29. The library of numbered paragraph 27 or 28, wherein the regulatory element is an inducible promoter.
30. The library of numbered paragraph 29, wherein the inducible promoter is a doxycycline inducible promoter.
31. A method of screening for genomic sites associated with a change in a phenotype comprising:

(a) introducing the library of any of the preceding numbered paragraphs into a population of cells that are adapted to contain a Cas protein, wherein each cell of the population contains no more than one guide RNA;

(b) sorting the cells into at least two groups based on the phenotype; and (c) determining relative representation of the guide RNAs present in each group, whereby genomic sites associated with the change in phenotype are determined by the representation of guide RNAs present in each group.

32. The method of numbered paragraph 31, wherein the change in phenotype is expression of a gene of interest.

33. The method of numbered paragraph 32, wherein the cells are sorted into a high expression group and a low expression group.

34. A method of screening for genomic sites associated with resistance to a chemical compound comprising:

(a) introducing the library of any of the preceding numbered paragraphs into a population of cells that are adapted to contain a Cas protein, wherein each cell of the population contains no more than one guide RNA;

(b) treating the population of cells with the chemical compound; and (c) determining the representation of guide RNAs after treatment with the chemical compound at a later time point as compared to an early time point, whereby genomic sites associated with resistance to the chemical compound are determined by enrichment of guide RNAs.

35. The method according to any of numbered paragraphs 31 to 34, further comprising validation of alteration of the genomic sites targeted by a guide RNA.

36. The method of numbered paragraph 35, wherein the validation of alteration of the genomic sites is by whole genome sequencing.

37. The method according to any of numbered paragraphs 31 to 34, further comprising determining indels associated with a change in phenotype or resistance to a chemical compound.

38. The method of numbered paragraph 37, wherein determining indels is by DNA sequencing.

39. A method for generating a deep scanning mutagenesis library to interrogate a genomic region of interest, the method comprising generating a plurality of CRISPR-Cas system guide RNAs comprising guide sequences that are capable of targeting a plurality of genomic sequences within said genomic region, wherein the guide RNAs target at least 100 genomic sequences comprising non-overlapping cleavage sites within said genomic region of interest upstream of a PAM sequence.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated modified eukaryotic cell obtained by a method comprising introducing a deep scanning mutagenesis guide library into a population of cells for screening non-coding genomic sites associated with a change in a phenotype, the population of cells comprising a plurality of Type II CRISPR-Cas system guide molecules, wherein each cell of the population contains a Cas polypeptide and no more than one guide molecule, wherein each guide molecule targets a non-coding genomic sequence to generate an indel mutation within a continuous genomic region, wherein the indel mutation has a mean deletion size of 11 bp and a mean insertion size of 4 bp that is offset by about 10 bp from an expected cleavage point, wherein the plurality of guide molecules target at least 100 genomic non-coding sequences comprising non-overlapping cleavage sites upstream of a PAM sequence for every 1000 base pairs within the at least one continuous genomic region;

wherein the plurality of guide molecules are capable of targeting two or more continuous genomic regions that physically interact, the at least one continuous genomic region comprising noncoding sequences, wherein the guide molecules have a median adjacent genomic cleavage distance between 4 bp and 20 bp, and sorting the cells into at least two groups based on the change in phenotype; and determining relative representation of the guide molecules present in each group, whereby genomic sites associated with the change in phenotype are determined by the representation of guide molecules present in each group;

preparing a Type II CRISPR-Cas composition comprising the one or more guide molecules identified in the library that target the non-coding genomic sites determined to be associated with the change in phenotype;

administering the Type II CRISPR-Cas composition to an unmodified eukaryotic cell to obtain the modified eukaryotic cell comprising one or more single-site indel mutations at the non-coding genomic site determined to be associated with the change in phenotype, wherein the genomic sites associated with the change in phenotype comprise one or more transcription enhancer or repressor elements.

2. The isolated modified eukaryotic cell of claim 1, wherein the change in phenotype is expression of a gene product.

3. The isolated modified eukaryotic cell of claim 2, wherein the gene product is a transcription factor.

4. The isolated modified eukaryotic cell of claim 3, wherein the transcription factor is BCL11A.

5. The isolated modified eukaryotic cell of claim 1, wherein the modified eukaryotic cell is a hematopoietic stem cell.

6. The isolated modified eukaryotic cell of claim 1, wherein the CRISPR-Cas composition comprises a *S. pneumoniae, S. pyogenes*, or *S. thermophilus* Cas9.

* * * * *

SEQUENCE LISTING

```
Sequence total quantity: 719
SEQ ID NO: 1           moltype = DNA  length = 23
FEATURE                Location/Qualifiers
variation              21
                       note = a, c, t, or g
source                 1..23
                       mol_type = other DNA
                       organism = synthetic construct
SEQUENCE: 1
tctgaggagc tagagacttg ngg                                              23

SEQ ID NO: 2           moltype = DNA  length = 23
FEATURE                Location/Qualifiers
variation              21
                       note = a, c, t, or g
source                 1..23
                       mol_type = other DNA
                       organism = synthetic construct
SEQUENCE: 2
agcaaatagg cttagtgtgc ngg                                              23

SEQ ID NO: 3           moltype = DNA  length = 25
FEATURE                Location/Qualifiers
variation              21
                       note = a, c, t, or g
source                 1..25
                       mol_type = other DNA
                       organism = synthetic construct
SEQUENCE: 3
ggctaaataa tgaatgtccc nggrc                                            25

SEQ ID NO: 4           moltype = DNA  length = 23
FEATURE                Location/Qualifiers
variation              21
                       note = a, c, t, or g
source                 1..23
                       mol_type = other DNA
                       organism = synthetic construct
SEQUENCE: 4
tcccttccta gaattggcct ngg                                              23
```

```
SEQ ID NO: 5           moltype = DNA  length = 23
FEATURE                Location/Qualifiers
variation              21
                       note = a, c, t, or g
source                 1..23
                       mol_type = other DNA
                       organism = synthetic construct
SEQUENCE: 5
ttcccttcct agaattggcc ngg                                          23

SEQ ID NO: 6           moltype = DNA  length = 25
FEATURE                Location/Qualifiers
variation              21
                       note = a, c, t, or g
source                 1..25
                       mol_type = other DNA
                       organism = synthetic construct
SEQUENCE: 6
gaatgtccca ggccaattct nggrc                                        25

SEQ ID NO: 7           moltype = DNA  length = 23
FEATURE                Location/Qualifiers
variation              21
                       note = a, c, t, or g
source                 1..23
                       mol_type = other DNA
                       organism = synthetic construct
SEQUENCE: 7
cccacttccc ttcctagaat ngg                                          23

SEQ ID NO: 8           moltype = DNA  length = 23
FEATURE                Location/Qualifiers
variation              21
                       note = a, c, t, or g
source                 1..23
                       mol_type = other DNA
                       organism = synthetic construct
SEQUENCE: 8
cctggtacca ggaaggcaat ngg                                          23

SEQ ID NO: 9           moltype = DNA  length = 23
FEATURE                Location/Qualifiers
variation              21
                       note = a, c, t, or g
source                 1..23
                       mol_type = other DNA
                       organism = synthetic construct
SEQUENCE: 9
tcctggtacc aggaaggcaa ngg                                          23

SEQ ID NO: 10          moltype = DNA  length = 23
FEATURE                Location/Qualifiers
variation              21
                       note = a, c, t, or g
source                 1..23
                       mol_type = other DNA
                       organism = synthetic construct
SEQUENCE: 10
gcatcatcct ggtaccagga ngg                                          23

SEQ ID NO: 11          moltype = DNA  length = 23
FEATURE                Location/Qualifiers
variation              21
                       note = a, c, t, or g
source                 1..23
                       mol_type = other DNA
                       organism = synthetic construct
SEQUENCE: 11
cattgcatca tcctggtacc ngg                                          23

SEQ ID NO: 12          moltype = DNA  length = 23
FEATURE                Location/Qualifiers
variation              21
                       note = a, c, t, or g
source                 1..23
                       mol_type = other DNA
                       organism = synthetic construct
SEQUENCE: 12
```

```
ctccaagcat tgcatcatcc ngg                                          23

SEQ ID NO: 13          moltype = DNA  length = 25
FEATURE                Location/Qualifiers
variation              21
                       note = a, c, t, or g
source                 1..25
                       mol_type = other DNA
                       organism = synthetic construct
SEQUENCE: 13
taccaggatg atgcaatgct nggrc                                        25

SEQ ID NO: 14          moltype = DNA  length = 23
FEATURE                Location/Qualifiers
variation              21
                       note = a, c, t, or g
source                 1..23
                       mol_type = other DNA
                       organism = synthetic construct
SEQUENCE: 14
gggtgtgccc tgagaaggtg ngg                                          23

SEQ ID NO: 15          moltype = DNA  length = 23
FEATURE                Location/Qualifiers
variation              21
                       note = a, c, t, or g
source                 1..23
                       mol_type = other DNA
                       organism = synthetic construct
SEQUENCE: 15
agggtgtgcc ctgagaaggt ngg                                          23

SEQ ID NO: 16          moltype = DNA  length = 23
FEATURE                Location/Qualifiers
variation              21
                       note = a, c, t, or g
source                 1..23
                       mol_type = other DNA
                       organism = synthetic construct
SEQUENCE: 16
tcacagggtg tgccctgaga ngg                                          23

SEQ ID NO: 17          moltype = DNA  length = 25
FEATURE                Location/Qualifiers
variation              21
                       note = a, c, t, or g
source                 1..25
                       mol_type = other DNA
                       organism = synthetic construct
SEQUENCE: 17
ggcacaccct gtgatcttgt nggrc                                        25

SEQ ID NO: 18          moltype = DNA  length = 23
FEATURE                Location/Qualifiers
variation              21
                       note = a, c, t, or g
source                 1..23
                       mol_type = other DNA
                       organism = synthetic construct
SEQUENCE: 18
agcacacaag atgcacaccc ngg                                          23

SEQ ID NO: 19          moltype = DNA  length = 25
FEATURE                Location/Qualifiers
variation              21
                       note = a, c, t, or g
source                 1..25
                       mol_type = other DNA
                       organism = synthetic construct
SEQUENCE: 19
tgtgcttggt cggcactgat nggrc                                        25

SEQ ID NO: 20          moltype = DNA  length = 25
FEATURE                Location/Qualifiers
variation              21
                       note = a, c, t, or g
source                 1..25
                       mol_type = other DNA
                       organism = synthetic construct
```

```
SEQUENCE: 20
gtgcttggtc ggcactgata nggrc                                        25

SEQ ID NO: 21          moltype = DNA  length = 25
FEATURE                Location/Qualifiers
variation              21
                       note = a, c, t, or g
source                 1..25
                       mol_type = other DNA
                       organism = synthetic construct
SEQUENCE: 21
tgcttggtcg gcactgatag nggrc                                        25

SEQ ID NO: 22          moltype = DNA  length = 25
FEATURE                Location/Qualifiers
variation              21
                       note = a, c, t, or g
source                 1..25
                       mol_type = other DNA
                       organism = synthetic construct
SEQUENCE: 22
gggtcgcggt agggagttgt nggrc                                        25

SEQ ID NO: 23          moltype = DNA  length = 23
FEATURE                Location/Qualifiers
variation              21
                       note = a, c, t, or g
source                 1..23
                       mol_type = other DNA
                       organism = synthetic construct
SEQUENCE: 23
gccaacagtg ataaccagca ngg                                          23

SEQ ID NO: 24          moltype = DNA  length = 23
FEATURE                Location/Qualifiers
variation              21
                       note = a, c, t, or g
source                 1..23
                       mol_type = other DNA
                       organism = synthetic construct
SEQUENCE: 24
tgccaacagt gataaccagc ngg                                          23

SEQ ID NO: 25          moltype = DNA  length = 25
FEATURE                Location/Qualifiers
variation              21
                       note = a, c, t, or g
source                 1..25
                       mol_type = other DNA
                       organism = synthetic construct
SEQUENCE: 25
gccctgctgg ttatcactgt nggrc                                        25

SEQ ID NO: 26          moltype = DNA  length = 23
FEATURE                Location/Qualifiers
variation              21
                       note = a, c, t, or g
source                 1..23
                       mol_type = other DNA
                       organism = synthetic construct
SEQUENCE: 26
agcagccctg ggcacagaag ngg                                          23

SEQ ID NO: 27          moltype = DNA  length = 23
FEATURE                Location/Qualifiers
variation              21
                       note = a, c, t, or g
source                 1..23
                       mol_type = other DNA
                       organism = synthetic construct
SEQUENCE: 27
cctctatgta gacgggtgtg ngg                                          23

SEQ ID NO: 28          moltype = DNA  length = 23
FEATURE                Location/Qualifiers
variation              21
                       note = a, c, t, or g
source                 1..23
                       mol_type = other DNA
```

```
                        organism = synthetic construct
SEQUENCE: 28
ggaagggcct ctatgtagac ngg                                              23

SEQ ID NO: 29           moltype = DNA  length = 23
FEATURE                 Location/Qualifiers
variation               21
                        note = a, c, t, or g
source                  1..23
                        mol_type = other DNA
                        organism = synthetic construct
SEQUENCE: 29
ggaggtgtgg aggggataac ngg                                              23

SEQ ID NO: 30           moltype = DNA  length = 23
FEATURE                 Location/Qualifiers
variation               21
                        note = a, c, t, or g
source                  1..23
                        mol_type = other DNA
                        organism = synthetic construct
SEQUENCE: 30
ctggcagacc ctcaagagca ngg                                              23

SEQ ID NO: 31           moltype = DNA  length = 23
FEATURE                 Location/Qualifiers
variation               21
                        note = a, c, t, or g
source                  1..23
                        mol_type = other DNA
                        organism = synthetic construct
SEQUENCE: 31
cccatggagg tggggagatg ngg                                              23

SEQ ID NO: 32           moltype = DNA  length = 25
FEATURE                 Location/Qualifiers
variation               21
                        note = a, c, t, or g
source                  1..25
                        mol_type = other DNA
                        organism = synthetic construct
SEQUENCE: 32
gtcatcctcg gccaatgaag nggrc                                            25

SEQ ID NO: 33           moltype = DNA  length = 23
FEATURE                 Location/Qualifiers
variation               21
                        note = a, c, t, or g
source                  1..23
                        mol_type = other DNA
                        organism = synthetic construct
SEQUENCE: 33
aagtgagcca ggtgatagaa ngg                                              23

SEQ ID NO: 34           moltype = DNA  length = 23
FEATURE                 Location/Qualifiers
variation               21
                        note = a, c, t, or g
source                  1..23
                        mol_type = other DNA
                        organism = synthetic construct
SEQUENCE: 34
tgaaaccaag cttcctctgc ngg                                              23

SEQ ID NO: 35           moltype = DNA  length = 25
FEATURE                 Location/Qualifiers
variation               21
                        note = a, c, t, or g
source                  1..25
                        mol_type = other DNA
                        organism = synthetic construct
SEQUENCE: 35
agggagaaat gagacaaaag nggrc                                            25

SEQ ID NO: 36           moltype = DNA  length = 25
FEATURE                 Location/Qualifiers
variation               21
                        note = a, c, t, or g
source                  1..25
```

```
                        mol_type = other DNA
                        organism = synthetic construct
SEQUENCE: 36
aagaggccac tgagtccttt nggrc                                         25

SEQ ID NO: 37           moltype = DNA  length = 25
FEATURE                 Location/Qualifiers
variation               21
                        note = a, c, t, or g
source                  1..25
                        mol_type = other DNA
                        organism = synthetic construct
SEQUENCE: 37
ctaacagttg cttttatcac nggrc                                         25

SEQ ID NO: 38           moltype = DNA  length = 25
FEATURE                 Location/Qualifiers
variation               21
                        note = a, c, t, or g
source                  1..25
                        mol_type = other DNA
                        organism = synthetic construct
SEQUENCE: 38
ttgcttttat cacaggctcc nggrc                                         25

SEQ ID NO: 39           moltype = DNA  length = 25
FEATURE                 Location/Qualifiers
variation               21
                        note = a, c, t, or g
source                  1..25
                        mol_type = other DNA
                        organism = synthetic construct
SEQUENCE: 39
ttttatcaca ggctccagga nggrc                                         25

SEQ ID NO: 40           moltype = DNA  length = 25
FEATURE                 Location/Qualifiers
variation               21
                        note = a, c, t, or g
source                  1..25
                        mol_type = other DNA
                        organism = synthetic construct
SEQUENCE: 40
tttatcacag gctccaggaa nggrc                                         25

SEQ ID NO: 41           moltype = DNA  length = 23
FEATURE                 Location/Qualifiers
variation               21
                        note = a, c, t, or g
source                  1..23
                        mol_type = other DNA
                        organism = synthetic construct
SEQUENCE: 41
atcagaggcc aaacccttcc ngg                                           23

SEQ ID NO: 42           moltype = DNA  length = 25
FEATURE                 Location/Qualifiers
variation               21
                        note = a, c, t, or g
source                  1..25
                        mol_type = other DNA
                        organism = synthetic construct
SEQUENCE: 42
cacaggctcc aggaagggtt nggrc                                         25

SEQ ID NO: 43           moltype = DNA  length = 23
FEATURE                 Location/Qualifiers
variation               21
                        note = a, c, t, or g
source                  1..23
                        mol_type = other DNA
                        organism = synthetic construct
SEQUENCE: 43
cacgccccca ccctaatcag ngg                                           23

SEQ ID NO: 44           moltype = DNA  length = 25
FEATURE                 Location/Qualifiers
variation               21
                        note = a, c, t, or g
```

```
source                1..25
                      mol_type = other DNA
                      organism = synthetic construct
SEQUENCE: 44
gaagggtttg gcctctgatt nggrc                                         25

SEQ ID NO: 45         moltype = DNA  length = 25
FEATURE               Location/Qualifiers
variation             21
                      note = a, c, t, or g
source                1..25
                      mol_type = other DNA
                      organism = synthetic construct
SEQUENCE: 45
aagggtttgg cctctgatta nggrc                                         25

SEQ ID NO: 46         moltype = DNA  length = 25
FEATURE               Location/Qualifiers
variation             21
                      note = a, c, t, or g
source                1..25
                      mol_type = other DNA
                      organism = synthetic construct
SEQUENCE: 46
ggtttggcct ctgattaggg nggrc                                         25

SEQ ID NO: 47         moltype = DNA  length = 25
FEATURE               Location/Qualifiers
variation             21
                      note = a, c, t, or g
source                1..25
                      mol_type = other DNA
                      organism = synthetic construct
SEQUENCE: 47
gtttggcctc tgattagggt nggrc                                         25

SEQ ID NO: 48         moltype = DNA  length = 25
FEATURE               Location/Qualifiers
variation             21
                      note = a, c, t, or g
source                1..25
                      mol_type = other DNA
                      organism = synthetic construct
SEQUENCE: 48
tttggcctct gattagggtg nggrc                                         25

SEQ ID NO: 49         moltype = DNA  length = 25
FEATURE               Location/Qualifiers
variation             21
                      note = a, c, t, or g
source                1..25
                      mol_type = other DNA
                      organism = synthetic construct
SEQUENCE: 49
ttggcctctg attagggtgg nggrc                                         25

SEQ ID NO: 50         moltype = DNA  length = 25
FEATURE               Location/Qualifiers
variation             21
                      note = a, c, t, or g
source                1..25
                      mol_type = other DNA
                      organism = synthetic construct
SEQUENCE: 50
tctgattagg gtgggggcgt nggrc                                         25

SEQ ID NO: 51         moltype = DNA  length = 25
FEATURE               Location/Qualifiers
variation             21
                      note = a, c, t, or g
source                1..25
                      mol_type = other DNA
                      organism = synthetic construct
SEQUENCE: 51
attagggtgg gggcgtgggt nggrc                                         25

SEQ ID NO: 52         moltype = DNA  length = 25
FEATURE               Location/Qualifiers
variation             21
```

```
                        note = a, c, t, or g
source                  1..25
                        mol_type = other DNA
                        organism = synthetic construct
SEQUENCE: 52
tgggtggggt agaagaggac nggrc                                              25

SEQ ID NO: 53           moltype = DNA  length = 23
FEATURE                 Location/Qualifiers
variation               21
                        note = a, c, t, or g
source                  1..23
                        mol_type = other DNA
                        organism = synthetic construct
SEQUENCE: 53
gcaaacggcc accgatggag ngg                                                23

SEQ ID NO: 54           moltype = DNA  length = 23
FEATURE                 Location/Qualifiers
variation               21
                        note = a, c, t, or g
source                  1..23
                        mol_type = other DNA
                        organism = synthetic construct
SEQUENCE: 54
cctgggcaaa cggccaccga ngg                                                23

SEQ ID NO: 55           moltype = DNA  length = 23
FEATURE                 Location/Qualifiers
variation               21
                        note = a, c, t, or g
source                  1..23
                        mol_type = other DNA
                        organism = synthetic construct
SEQUENCE: 55
aagaggcccc cctgggcaaa ngg                                                23

SEQ ID NO: 56           moltype = DNA  length = 25
FEATURE                 Location/Qualifiers
variation               21
                        note = a, c, t, or g
source                  1..25
                        mol_type = other DNA
                        organism = synthetic construct
SEQUENCE: 56
ccatcggtgg ccgtttgccc nggrc                                              25

SEQ ID NO: 57           moltype = DNA  length = 25
FEATURE                 Location/Qualifiers
variation               21
                        note = a, c, t, or g
source                  1..25
                        mol_type = other DNA
                        organism = synthetic construct
SEQUENCE: 57
catcggtggc cgtttgccca nggrc                                              25

SEQ ID NO: 58           moltype = DNA  length = 25
FEATURE                 Location/Qualifiers
variation               21
                        note = a, c, t, or g
source                  1..25
                        mol_type = other DNA
                        organism = synthetic construct
SEQUENCE: 58
atcggtggcc gtttgcccag nggrc                                              25

SEQ ID NO: 59           moltype = DNA  length = 25
FEATURE                 Location/Qualifiers
variation               21
                        note = a, c, t, or g
source                  1..25
                        mol_type = other DNA
                        organism = synthetic construct
SEQUENCE: 59
tcggtggccg tttgcccagg nggrc                                              25

SEQ ID NO: 60           moltype = DNA  length = 25
FEATURE                 Location/Qualifiers
```

```
variation             21
                      note = a, c, t, or g
source                1..25
                      mol_type = other DNA
                      organism = synthetic construct
SEQUENCE: 60
cggtggccgt ttgcccaggg nggrc                                   25

SEQ ID NO: 61         moltype = DNA  length = 23
FEATURE               Location/Qualifiers
variation             21
                      note = a, c, t, or g
source                1..23
                      mol_type = other DNA
                      organism = synthetic construct
SEQUENCE: 61
cttccgaaag aggccccct ngg                                      23

SEQ ID NO: 62         moltype = DNA  length = 23
FEATURE               Location/Qualifiers
variation             21
                      note = a, c, t, or g
source                1..23
                      mol_type = other DNA
                      organism = synthetic construct
SEQUENCE: 62
ccttccgaaa gaggcccccc ngg                                     23

SEQ ID NO: 63         moltype = DNA  length = 23
FEATURE               Location/Qualifiers
variation             21
                      note = a, c, t, or g
source                1..23
                      mol_type = other DNA
                      organism = synthetic construct
SEQUENCE: 63
tcagggggag gcaagtcagt ngg                                     23

SEQ ID NO: 64         moltype = DNA  length = 23
FEATURE               Location/Qualifiers
variation             21
                      note = a, c, t,or g
source                1..23
                      mol_type = other DNA
                      organism = synthetic construct
SEQUENCE: 64
agggaaaagg gagaggaaaa ngg                                     23

SEQ ID NO: 65         moltype = DNA  length = 25
FEATURE               Location/Qualifiers
variation             21
                      note = a, c, t, or g
source                1..25
                      mol_type = other DNA
                      organism = synthetic construct
SEQUENCE: 65
tgtaactaat aaataccagg nggrc                                   25

SEQ ID NO: 66         moltype = DNA  length = 25
FEATURE               Location/Qualifiers
variation             21
                      note = a, c, t, or g
source                1..25
                      mol_type = other DNA
                      organism = synthetic construct
SEQUENCE: 66
ccagctgaag aaagaacatt nggrc                                   25

SEQ ID NO: 67         moltype = DNA  length = 23
FEATURE               Location/Qualifiers
variation             21
                      note = a, c, t, or g
source                1..23
                      mol_type = other DNA
                      organism = synthetic construct
SEQUENCE: 67
ccatctccct aatctccaat ngg                                     23

SEQ ID NO: 68         moltype = DNA  length = 23
```

```
FEATURE                Location/Qualifiers
variation              21
                       note = a, c, t, or g
source                 1..23
                       mol_type = other DNA
                       organism = synthetic construct
SEQUENCE: 68
tggggagaga agagtggaaa ngg                                           23

SEQ ID NO: 69          moltype = DNA  length = 23
FEATURE                Location/Qualifiers
variation              21
                       note = a, c, t, or g
source                 1..23
                       mol_type = other DNA
                       organism = synthetic construct
SEQUENCE: 69
ggagtatggg gagagaagag ngg                                           23

SEQ ID NO: 70          moltype = DNA  length = 25
FEATURE                Location/Qualifiers
variation              21
                       note = a, c, t, or g
source                 1..25
                       mol_type = other DNA
                       organism = synthetic construct
SEQUENCE: 70
acaacctcct tgtttacaga nggrc                                         25

SEQ ID NO: 71          moltype = DNA  length = 25
FEATURE                Location/Qualifiers
variation              21
                       note = a, c, t, or g
source                 1..25
                       mol_type = other DNA
                       organism = synthetic construct
SEQUENCE: 71
gagatttact cttgttgccc nggrc                                         25

SEQ ID NO: 72          moltype = DNA  length = 25
FEATURE                Location/Qualifiers
variation              21
                       note = a, c, t, or g
source                 1..25
                       mol_type = other DNA
                       organism = synthetic construct
SEQUENCE: 72
ttgcccgggc tggaatgcaa nggrc                                         25

SEQ ID NO: 73          moltype = DNA  length = 23
FEATURE                Location/Qualifiers
variation              21
                       note = a, c, t, or g
source                 1..23
                       mol_type = other DNA
                       organism = synthetic construct
SEQUENCE: 73
ggagatcgct tgaacctggg ngg                                           23

SEQ ID NO: 74          moltype = DNA  length = 23
FEATURE                Location/Qualifiers
variation              21
                       note = a, c, t, or g
source                 1..23
                       mol_type = other DNA
                       organism = synthetic construct
SEQUENCE: 74
ctcagctact cgggaggctg ngg                                           23

SEQ ID NO: 75          moltype = DNA  length = 23
FEATURE                Location/Qualifiers
variation              21
                       note = a, c, t, or g
source                 1..23
                       mol_type = other DNA
                       organism = synthetic construct
SEQUENCE: 75
tgtaatctca gctactcggg ngg                                           23
```

```
SEQ ID NO: 76          moltype = DNA  length = 23
FEATURE                Location/Qualifiers
variation              21
                       note = a, c, t, or g
source                 1..23
                       mol_type = other DNA
                       organism = synthetic construct
SEQUENCE: 76
gcctgtaatc tcagctactc ngg                                         23

SEQ ID NO: 77          moltype = DNA  length = 23
FEATURE                Location/Qualifiers
variation              21
                       note = a, c, t, or g
source                 1..23
                       mol_type = other DNA
                       organism = synthetic construct
SEQUENCE: 77
tgcctgtaat ctcagctact ngg                                         23

SEQ ID NO: 78          moltype = DNA  length = 25
FEATURE                Location/Qualifiers
variation              21
                       note = a, c, t, or g
source                 1..25
                       mol_type = other DNA
                       organism = synthetic construct
SEQUENCE: 78
caggcatgta ttaccatgcc nggrc                                       25

SEQ ID NO: 79          moltype = DNA  length = 23
FEATURE                Location/Qualifiers
variation              21
                       note = a, c, t, or g
source                 1..23
                       mol_type = other DNA
                       organism = synthetic construct
SEQUENCE: 79
caggaggatc acctgaggtc ngg                                         23

SEQ ID NO: 80          moltype = DNA  length = 25
FEATURE                Location/Qualifiers
variation              21
                       note = a, c, t, or g
source                 1..25
                       mol_type = other DNA
                       organism = synthetic construct
SEQUENCE: 80
ctcaggtgat cctcctgccc nggrc                                       25

SEQ ID NO: 81          moltype = DNA  length = 23
FEATURE                Location/Qualifiers
variation              21
                       note = a, c, t, or g
source                 1..23
                       mol_type = other DNA
                       organism = synthetic construct
SEQUENCE: 81
cccagcactt tgggaggccg ngg                                         23

SEQ ID NO: 82          moltype = DNA  length = 23
FEATURE                Location/Qualifiers
variation              21
                       note = a, c, t, or g
source                 1..23
                       mol_type = other DNA
                       organism = synthetic construct
SEQUENCE: 82
tcccagcact ttgggaggcc ngg                                         23

SEQ ID NO: 83          moltype = DNA  length = 23
FEATURE                Location/Qualifiers
variation              21
                       note = a, c, t, or g
source                 1..23
                       mol_type = other DNA
                       organism = synthetic construct
SEQUENCE: 83
atcccagcac tttgggaggc ngg                                         23
```

```
SEQ ID NO: 84          moltype = DNA  length = 23
FEATURE                Location/Qualifiers
variation              21
                       note = a, c, t, or g
source                 1..23
                       mol_type = other DNA
                       organism = synthetic construct
SEQUENCE: 84
acctgtaatc ccagcacttt ngg                                          23

SEQ ID NO: 85          moltype = DNA  length = 25
FEATURE                Location/Qualifiers
variation              21
                       note = a, c, t, or g
source                 1..25
                       mol_type = other DNA
                       organism = synthetic construct
SEQUENCE: 85
gccccggcct cccaaagtgc nggrc                                        25

SEQ ID NO: 86          moltype = DNA  length = 25
FEATURE                Location/Qualifiers
variation              21
                       note = a, c, t, or g
source                 1..25
                       mol_type = other DNA
                       organism = synthetic construct
SEQUENCE: 86
ccccggcctc ccaaagtgct nggrc                                        25

SEQ ID NO: 87          moltype = DNA  length = 25
FEATURE                Location/Qualifiers
variation              21
                       note = a, c, t, or g
source                 1..25
                       mol_type = other DNA
                       organism = synthetic construct
SEQUENCE: 87
atttgctctt ctccagggtg nggrc                                        25

SEQ ID NO: 88          moltype = DNA  length = 23
FEATURE                Location/Qualifiers
variation              21
                       note = a, c, t, or g
source                 1..23
                       mol_type = other DNA
                       organism = synthetic construct
SEQUENCE: 88
taaacagcca ccccacaccc ngg                                          23

SEQ ID NO: 89          moltype = DNA  length = 25
FEATURE                Location/Qualifiers
variation              21
                       note = a, c, t, or g
source                 1..25
                       mol_type = other DNA
                       organism = synthetic construct
SEQUENCE: 89
tttgctcttc tccagggtgt nggrc                                        25

SEQ ID NO: 90          moltype = DNA  length = 25
FEATURE                Location/Qualifiers
variation              21
                       note = a, c, t, or g
source                 1..25
                       mol_type = other DNA
                       organism = synthetic construct
SEQUENCE: 90
ctcttctcca gggtgtgggg nggrc                                        25

SEQ ID NO: 91          moltype = DNA  length = 25
FEATURE                Location/Qualifiers
variation              21
                       note = a, c, t, or g
source                 1..25
                       mol_type = other DNA
                       organism = synthetic construct
SEQUENCE: 91
```

```
tgtggggtgg ctgtttaaag nggrc                                           25

SEQ ID NO: 92          moltype = DNA  length = 25
FEATURE                Location/Qualifiers
variation              21
                       note = a, c, t, or g
source                 1..25
                       mol_type = other DNA
                       organism = synthetic construct
SEQUENCE: 92
gggtggctgt ttaaagaggg nggrc                                           25

SEQ ID NO: 93          moltype = DNA  length = 25
FEATURE                Location/Qualifiers
variation              21
                       note = a, c, t, or g
source                 1..25
                       mol_type = other DNA
                       organism = synthetic construct
SEQUENCE: 93
agttcaagta gatatcagaa nggrc                                           25

SEQ ID NO: 94          moltype = DNA  length = 25
FEATURE                Location/Qualifiers
variation              21
                       note = a, c, t, or g
source                 1..25
                       mol_type = other DNA
                       organism = synthetic construct
SEQUENCE: 94
tatcagaagg gaactgtttg nggrc                                           25

SEQ ID NO: 95          moltype = DNA  length = 25
FEATURE                Location/Qualifiers
variation              21
                       note = a, c, t, or g
source                 1..25
                       mol_type = other DNA
                       organism = synthetic construct
SEQUENCE: 95
aagaatggct tcaagaggct nggrc                                           25

SEQ ID NO: 96          moltype = DNA  length = 25
FEATURE                Location/Qualifiers
variation              21
                       note = a, c, t, or g
source                 1..25
                       mol_type = other DNA
                       organism = synthetic construct
SEQUENCE: 96
tctgtaagaa tggcttcaag nggrc                                           25

SEQ ID NO: 97          moltype = DNA  length = 23
FEATURE                Location/Qualifiers
variation              21
                       note = a, c, t, or g
source                 1..23
                       mol_type = other DNA
                       organism = synthetic construct
SEQUENCE: 97
acagatgatg aaccagacca ngg                                             23

SEQ ID NO: 98          moltype = DNA  length = 23
FEATURE                Location/Qualifiers
variation              21
                       note = a, c, t, or g
source                 1..23
                       mol_type = other DNA
                       organism = synthetic construct
SEQUENCE: 98
tgaaccagac cacggcccgt ngg                                             23

SEQ ID NO: 99          moltype = DNA  length = 23
FEATURE                Location/Qualifiers
variation              21
                       note = a, c, t, or g
source                 1..23
                       mol_type = other DNA
                       organism = synthetic construct
```

```
SEQUENCE: 99
gaaccagacc acggcccgtt ngg                                          23

SEQ ID NO: 100         moltype = DNA  length = 23
FEATURE                Location/Qualifiers
variation              21
                       note = a, c, t, or g
source                 1..23
                       mol_type = other DNA
                       organism = synthetic construct
SEQUENCE: 100
ggcccgttgg gagctccaga ngg                                          23

SEQ ID NO: 101         moltype = DNA  length = 23
FEATURE                Location/Qualifiers
variation              21
                       note = a, c, t, or g
source                 1..23
                       mol_type = other DNA
                       organism = synthetic construct
SEQUENCE: 101
gcccgttggg agctccagaa ngg                                          23

SEQ ID NO: 102         moltype = DNA  length = 23
FEATURE                Location/Qualifiers
variation              21
                       note = a, c, t, or g
source                 1..23
                       mol_type = other DNA
                       organism = synthetic construct
SEQUENCE: 102
cccgttggga gctccagaag ngg                                          23

SEQ ID NO: 103         moltype = DNA  length = 25
FEATURE                Location/Qualifiers
variation              21
                       note = a, c, t, or g
source                 1..25
                       mol_type = other DNA
                       organism = synthetic construct
SEQUENCE: 103
ctggagctcc caacgggccg nggrc                                        25

SEQ ID NO: 104         moltype = DNA  length = 25
FEATURE                Location/Qualifiers
variation              21
                       note = a, c, t, or g
source                 1..25
                       mol_type = other DNA
                       organism = synthetic construct
SEQUENCE: 104
ccccttctgg agctcccaac nggrc                                        25

SEQ ID NO: 105         moltype = DNA  length = 25
FEATURE                Location/Qualifiers
variation              21
                       note = a, c, t, or g
source                 1..25
                       mol_type = other DNA
                       organism = synthetic construct
SEQUENCE: 105
tccccttctg gagctcccaa nggrc                                        25

SEQ ID NO: 106         moltype = DNA  length = 23
FEATURE                Location/Qualifiers
variation              21
                       note = a, c, t, or g
source                 1..23
                       mol_type = other DNA
                       organism = synthetic construct
SEQUENCE: 106
gatcatgacc tcctcacctg ngg                                          23

SEQ ID NO: 107         moltype = DNA  length = 23
FEATURE                Location/Qualifiers
variation              21
                       note = a, c, t, or g
source                 1..23
                       mol_type = other DNA
```

```
                       organism = synthetic construct
SEQUENCE: 107
atcatgacct cctcacctgt ngg                                    23

SEQ ID NO: 108         moltype = DNA  length = 25
FEATURE                Location/Qualifiers
variation              21
                       note = a, c, t, or g
source                 1..25
                       mol_type = other DNA
                       organism = synthetic construct
SEQUENCE: 108
aggaggtcat gatccccttc nggrc                                  25

SEQ ID NO: 109         moltype = DNA  length = 25
FEATURE                Location/Qualifiers
variation              21
                       note = a, c, t, or g
source                 1..25
                       mol_type = other DNA
                       organism = synthetic construct
SEQUENCE: 109
ggcactgccc acaggtgagg nggrc                                  25

SEQ ID NO: 110         moltype = DNA  length = 23
FEATURE                Location/Qualifiers
variation              21
                       note = a, c, t, or g
source                 1..23
                       mol_type = other DNA
                       organism = synthetic construct
SEQUENCE: 110
gtgccagatg aacttcccat ngg                                    23

SEQ ID NO: 111         moltype = DNA  length = 23
FEATURE                Location/Qualifiers
variation              21
                       note = a, c, t, or g
source                 1..23
                       mol_type = other DNA
                       organism = synthetic construct
SEQUENCE: 111
tgccagatga acttcccatt ngg                                    23

SEQ ID NO: 112         moltype = DNA  length = 23
FEATURE                Location/Qualifiers
variation              21
                       note = a, c, t, or g
source                 1..23
                       mol_type = other DNA
                       organism = synthetic construct
SEQUENCE: 112
gccagatgaa cttcccattg ngg                                    23

SEQ ID NO: 113         moltype = DNA  length = 25
FEATURE                Location/Qualifiers
variation              21
                       note = a, c, t, or g
source                 1..25
                       mol_type = other DNA
                       organism = synthetic construct
SEQUENCE: 113
tctggcactg cccacaggtg nggrc                                  25

SEQ ID NO: 114         moltype = DNA  length = 23
FEATURE                Location/Qualifiers
variation              21
                       note = a, c, t, or g
source                 1..23
                       mol_type = other DNA
                       organism = synthetic construct
SEQUENCE: 114
ccagatgaac ttcccattgg ngg                                    23

SEQ ID NO: 115         moltype = DNA  length = 25
FEATURE                Location/Qualifiers
variation              21
                       note = a, c, t, or g
source                 1..25
```

```
                         mol_type = other DNA
                         organism = synthetic construct
SEQUENCE: 115
gttcatctgg cactgcccac nggrc                                      25

SEQ ID NO: 116           moltype = DNA  length = 25
FEATURE                  Location/Qualifiers
variation                21
                         note = a, c, t, or g
source                   1..25
                         mol_type = other DNA
                         organism = synthetic construct
SEQUENCE: 116
cccccaatgg gaagttcatc nggrc                                      25

SEQ ID NO: 117           moltype = DNA  length = 25
FEATURE                  Location/Qualifiers
variation                21
                         note = a, c, t, or g
source                   1..25
                         mol_type = other DNA
                         organism = synthetic construct
SEQUENCE: 117
aaataagaat gtcccccaat nggrc                                      25

SEQ ID NO: 118           moltype = DNA  length = 25
FEATURE                  Location/Qualifiers
variation                21
                         note = a, c, t,or g
source                   1..25
                         mol_type = other DNA
                         organism = synthetic construct
SEQUENCE: 118
aaaataagaa tgtcccccaa nggrc                                      25

SEQ ID NO: 119           moltype = DNA  length = 23
FEATURE                  Location/Qualifiers
variation                21
                         note = a, c, t, or g
source                   1..23
                         mol_type = other DNA
                         organism = synthetic construct
SEQUENCE: 119
cacaaacgga aacaatgcaa ngg                                        23

SEQ ID NO: 120           moltype = DNA  length = 23
FEATURE                  Location/Qualifiers
variation                21
                         note = a, c, t, or g
source                   1..23
                         mol_type = other DNA
                         organism = synthetic construct
SEQUENCE: 120
cctctgctta gaaaaagctg ngg                                        23

SEQ ID NO: 121           moltype = DNA  length = 25
FEATURE                  Location/Qualifiers
variation                21
                         note = a, c, t, or g
source                   1..25
                         mol_type = other DNA
                         organism = synthetic construct
SEQUENCE: 121
ccacagcttt ttctaagcag nggrc                                      25

SEQ ID NO: 122           moltype = DNA  length = 25
FEATURE                  Location/Qualifiers
variation                21
                         note = a, c, t, or g
source                   1..25
                         mol_type = other DNA
                         organism = synthetic construct
SEQUENCE: 122
tcgattggtg aaggggaagg nggrc                                      25

SEQ ID NO: 123           moltype = DNA  length = 25
FEATURE                  Location/Qualifiers
variation                21
                         note = a, c, t, or g
```

```
source                  1..25
                        mol_type = other DNA
                        organism = synthetic construct
SEQUENCE: 123
atctcgattg gtgaagggga nggrc                                             25

SEQ ID NO: 124          moltype = DNA  length = 25
FEATURE                 Location/Qualifiers
variation               21
                        note = a, c, t, or g
source                  1..25
                        mol_type = other DNA
                        organism = synthetic construct
SEQUENCE: 124
tttcatctcg attggtgaag nggrc                                             25

SEQ ID NO: 125          moltype = DNA  length = 23
FEATURE                 Location/Qualifiers
variation               21
                        note = a, c, t, or g
source                  1..23
                        mol_type = other DNA
                        organism = synthetic construct
SEQUENCE: 125
gaaaaaagca tccaatcccg ngg                                               23

SEQ ID NO: 126          moltype = DNA  length = 23
FEATURE                 Location/Qualifiers
variation               21
                        note = a, c, t, or g
source                  1..23
                        mol_type = other DNA
                        organism = synthetic construct
SEQUENCE: 126
aaaagcatcc aatcccgtgg ngg                                               23

SEQ ID NO: 127          moltype = DNA  length = 23
FEATURE                 Location/Qualifiers
variation               21
                        note = a, c, t, or g
source                  1..23
                        mol_type = other DNA
                        organism = synthetic construct
SEQUENCE: 127
gcatccaatc ccgtggaggt ngg                                               23

SEQ ID NO: 128          moltype = DNA  length = 23
FEATURE                 Location/Qualifiers
variation               21
                        note = a, c, t, or g
source                  1..23
                        mol_type = other DNA
                        organism = synthetic construct
SEQUENCE: 128
tcccgtggag gttggcatcc ngg                                               23

SEQ ID NO: 129          moltype = DNA  length = 23
FEATURE                 Location/Qualifiers
variation               21
                        note = a, c, t, or g
source                  1..23
                        mol_type = other DNA
                        organism = synthetic construct
SEQUENCE: 129
tggcatccag gtcacgccag ngg                                               23

SEQ ID NO: 130          moltype = DNA  length = 25
FEATURE                 Location/Qualifiers
variation               21
                        note = a, c, t, or g
source                  1..25
                        mol_type = other DNA
                        organism = synthetic construct
SEQUENCE: 130
gatgccaacc tccacgggat nggrc                                             25

SEQ ID NO: 131          moltype = DNA  length = 25
FEATURE                 Location/Qualifiers
variation               21
```

```
                        note = a, c, t, or g
source                  1..25
                        mol_type = other DNA
                        organism = synthetic construct
SEQUENCE: 131
acctggatgc caacctccac nggrc                                   25

SEQ ID NO: 132          moltype = DNA  length = 25
FEATURE                 Location/Qualifiers
variation               21
                        note = a, c, t, or g
source                  1..25
                        mol_type = other DNA
                        organism = synthetic construct
SEQUENCE: 132
gacctggatg ccaacctcca nggrc                                   25

SEQ ID NO: 133          moltype = DNA  length = 25
FEATURE                 Location/Qualifiers
variation               21
                        note = a, c, t, or g
source                  1..25
                        mol_type = other DNA
                        organism = synthetic construct
SEQUENCE: 133
cgtcatcctc tggcgtgacc nggrc                                   25

SEQ ID NO: 134          moltype = DNA  length = 25
FEATURE                 Location/Qualifiers
variation               21
                        note = a, c, t, or g
source                  1..25
                        mol_type = other DNA
                        organism = synthetic construct
SEQUENCE: 134
gataaacaat cgtcatcctc nggrc                                   25

SEQ ID NO: 135          moltype = DNA  length = 25
FEATURE                 Location/Qualifiers
variation               21
                        note = a, c, t, or g
source                  1..25
                        mol_type = other DNA
                        organism = synthetic construct
SEQUENCE: 135
ctgctatgtg ttcctgtttg nggrc                                   25

SEQ ID NO: 136          moltype = DNA  length = 265
FEATURE                 Location/Qualifiers
source                  1..265
                        mol_type = other DNA
                        organism = Homo sapiens
SEQUENCE: 136
gacactgaag gctgggcaca gccttgggga ccgctcacag gacatgcagc agtgtgtgcc  60
gacaactccc taccgcgacc cctatcagtg ccgaccaagc acacaagatg cacacccagg  120
ctgggctgga cagaggggtc ccacaagatc acagggtgtg ccctgagaag gtggggagct  180
cacagcctcc aagcattgca tcatcctggt accaggaagg caatgggctg ccccataccc  240
acttcccttc ctagaattgg cctgg                                   265

SEQ ID NO: 137          moltype = DNA  length = 229
FEATURE                 Location/Qualifiers
source                  1..229
                        mol_type = other DNA
                        organism = Homo sapiens
SEQUENCE: 137
ttcattccca ttgagaaata aaatccaatt ctccatcacc aagagagcct tccgaaagag  60
gcccccctgg gcaaacggcc accgatggag aggtctgcca gtcctcttct accccaccca  120
cgcccccacc ctaatcagag gccaaaccct tcctggagcc tgtgataaaa gcaactgtta  180
gcttgcacta gactagcttc aaagttgtat tgaccctggt gtgttatgt         229

SEQ ID NO: 138          moltype = DNA  length = 145
FEATURE                 Location/Qualifiers
source                  1..145
                        mol_type = other DNA
                        organism = Homo sapiens
SEQUENCE: 138
atttcccttc tgatatctac ttgaactttc agataaaaaa aaaaaagcaa gttgcagtaa  60
catgttatgc tacacaaaga ttagcatgaa tatccaccct ctttaaacag ccaccccaca  120
ccctggagaa gagcaaatgt gaagt                                   145
```

```
SEQ ID NO: 139         moltype = DNA  length = 94
FEATURE                Location/Qualifiers
source                 1..94
                       mol_type = other DNA
                       organism = synthetic construct
SEQUENCE: 139
ggccggccgg atccggcgca acaaacttct ctctgctgaa acaagccgga gatgtcgaag  60
agaatcctgg accgatggtg agcaagggcg agga                              94

SEQ ID NO: 140         moltype = DNA  length = 34
FEATURE                Location/Qualifiers
source                 1..34
                       mol_type = other DNA
                       organism = synthetic construct
SEQUENCE: 140
ggccggccga attcttactt gtacagctcg tcca                              34

SEQ ID NO: 141         moltype = DNA  length = 58
FEATURE                Location/Qualifiers
source                 1..58
                       mol_type = other DNA
                       organism = synthetic construct
SEQUENCE: 141
ggccggcccg tacgcgtacg gccaccatgg atagcactga gaacgtcatc aagccctt    58

SEQ ID NO: 142         moltype = DNA  length = 40
FEATURE                Location/Qualifiers
source                 1..40
                       mol_type = other DNA
                       organism = synthetic construct
SEQUENCE: 142
ggccggccac gcgtctactg gaacaggtgg tggcgggcct                        40

SEQ ID NO: 143         moltype = DNA  length = 30
FEATURE                Location/Qualifiers
source                 1..30
                       mol_type = other DNA
                       organism = synthetic construct
SEQUENCE: 143
cgtaacttga aagtatttcg atttcttggc                                   30

SEQ ID NO: 144         moltype = DNA  length = 30
FEATURE                Location/Qualifiers
source                 1..30
                       mol_type = other DNA
                       organism = synthetic construct
SEQUENCE: 144
ggccggccgc tcgagggagg gcctatttcc                                   30

SEQ ID NO: 145         moltype = DNA  length = 36
FEATURE                Location/Qualifiers
source                 1..36
                       mol_type = other DNA
                       organism = synthetic construct
SEQUENCE: 145
ccggccggcc cgggttgtgg atgaatactg ccattt                            36

SEQ ID NO: 146         moltype = DNA  length = 22
FEATURE                Location/Qualifiers
source                 1..22
                       mol_type = other DNA
                       organism = synthetic construct
SEQUENCE: 146
ggaggcttgg taggtttaag aa                                           22

SEQ ID NO: 147         moltype = DNA  length = 20
FEATURE                Location/Qualifiers
source                 1..20
                       mol_type = other DNA
                       organism = synthetic construct
SEQUENCE: 147
ccaattccca ctcctttcaa                                              20

SEQ ID NO: 148         moltype = DNA  length = 41
FEATURE                Location/Qualifiers
source                 1..41
                       mol_type = other DNA
                       organism = synthetic construct
```

```
SEQUENCE: 148
aatggactat catatgctta ccgtaacttg aaagtatttc g                     41

SEQ ID NO: 149         moltype = DNA  length = 44
FEATURE                Location/Qualifiers
source                 1..44
                       mol_type = other DNA
                       organism = synthetic construct
SEQUENCE: 149
ctttagtttg tatgtctgtt gctattatgt ctactattct ttcc                  44

SEQ ID NO: 150         moltype = DNA  length = 91
FEATURE                Location/Qualifiers
source                 1..91
                       mol_type = other DNA
                       organism = synthetic construct
SEQUENCE: 150
aatgatacgg cgaccaccga gatctacact ctttccctac acgacgctct tccgatctta  60
agtagagtct tgtggaaagg acgaaacacc g                                 91

SEQ ID NO: 151         moltype = DNA  length = 92
FEATURE                Location/Qualifiers
source                 1..92
                       mol_type = other DNA
                       organism = synthetic construct
SEQUENCE: 151
aatgatacgg cgaccaccga gatctacact ctttccctac acgacgctct tccgatctat  60
acacgatctc ttgtggaaag gacgaaacac cg                                92

SEQ ID NO: 152         moltype = DNA  length = 93
FEATURE                Location/Qualifiers
source                 1..93
                       mol_type = other DNA
                       organism = synthetic construct
SEQUENCE: 152
aatgatacgg cgaccaccga gatctacact ctttccctac acgacgctct tccgatctga  60
tcgcgcggtt cttgtggaaa ggacgaaaca ccg                               93

SEQ ID NO: 153         moltype = DNA  length = 94
FEATURE                Location/Qualifiers
source                 1..94
                       mol_type = other DNA
                       organism = synthetic construct
SEQUENCE: 153
aatgatacgg cgaccaccga gatctacact ctttccctac acgacgctct tccgatctcg  60
atcatgatcg tcttgtggaa aggacgaaac accg                              94

SEQ ID NO: 154         moltype = DNA  length = 95
FEATURE                Location/Qualifiers
source                 1..95
                       mol_type = other DNA
                       organism = synthetic construct
SEQUENCE: 154
aatgatacgg cgaccaccga gatctacact ctttccctac acgacgctct tccgatcttc  60
gatcgttacc atcttgtgga aaggacgaaa caccg                             95

SEQ ID NO: 155         moltype = DNA  length = 96
FEATURE                Location/Qualifiers
source                 1..96
                       mol_type = other DNA
                       organism = synthetic construct
SEQUENCE: 155
aatgatacgg cgaccaccga gatctacact ctttccctac acgacgctct tccgatctat  60
cgattccttg gttcttgtgg aaaggacgaa acaccg                            96

SEQ ID NO: 156         moltype = DNA  length = 97
FEATURE                Location/Qualifiers
source                 1..97
                       mol_type = other DNA
                       organism = synthetic construct
SEQUENCE: 156
aatgatacgg cgaccaccga gatctacact ctttccctac acgacgctct tccgatctga  60
tcgataacgc atttcttgtg gaaaggacga aacaccg                           97

SEQ ID NO: 157         moltype = DNA  length = 98
FEATURE                Location/Qualifiers
source                 1..98
                       mol_type = other DNA
                       organism = synthetic construct
```

```
SEQUENCE: 157
aatgatacgg cgaccaccga gatctacact ctttccctac acgacgctct tccgatctcg  60
atcgatacag gtattcttgt ggaaaggacg aaacaccg                          98

SEQ ID NO: 158         moltype = DNA  length = 99
FEATURE                Location/Qualifiers
source                 1..99
                       mol_type = other DNA
                       organism = synthetic construct
SEQUENCE: 158
aatgatacgg cgaccaccga gatctacact ctttccctac acgacgctct tccgatctac  60
gatcgatagg taaggtcttg tggaaaggac gaaacaccg                         99

SEQ ID NO: 159         moltype = DNA  length = 91
FEATURE                Location/Qualifiers
source                 1..91
                       mol_type = other DNA
                       organism = synthetic construct
SEQUENCE: 159
aatgatacgg cgaccaccga gatctacact ctttccctac acgacgctct tccgatctta  60
acaatggtct tgtggaaagg acgaaacacc g                                 91

SEQ ID NO: 160         moltype = DNA  length = 92
FEATURE                Location/Qualifiers
source                 1..92
                       mol_type = other DNA
                       organism = synthetic construct
SEQUENCE: 160
aatgatacgg cgaccaccga gatctacact ctttccctac acgacgctct tccgatctat  60
actgtatctc ttgtggaaag gacgaaacac cg                                92

SEQ ID NO: 161         moltype = DNA  length = 93
FEATURE                Location/Qualifiers
source                 1..93
                       mol_type = other DNA
                       organism = synthetic construct
SEQUENCE: 161
aatgatacgg cgaccaccga gatctacact ctttccctac acgacgctct tccgatctga  60
taggtcgcat cttgtggaaa ggacgaaaca ccg                               93

SEQ ID NO: 162         moltype = DNA  length = 92
FEATURE                Location/Qualifiers
source                 1..92
                       mol_type = other DNA
                       organism = synthetic construct
SEQUENCE: 162
caagcagaag acggcatacg agataagtag aggtgactgg agttcagacg tgtgctcttc  60
cgatctttct actattcttt cccctgcact gt                                92

SEQ ID NO: 163         moltype = DNA  length = 93
FEATURE                Location/Qualifiers
source                 1..93
                       mol_type = other DNA
                       organism = synthetic construct
SEQUENCE: 163
caagcagaag acggcatacg agatacacga tcgtgactgg agttcagacg tgtgctcttc  60
cgatctattc tactattctt tcccctgcac tgt                               93

SEQ ID NO: 164         moltype = DNA  length = 94
FEATURE                Location/Qualifiers
source                 1..94
                       mol_type = other DNA
                       organism = synthetic construct
SEQUENCE: 164
caagcagaag acggcatacg agatcgcgcg gtgtgactgg agttcagacg tgtgctcttc  60
cgatctgatt ctactattct ttcccctgca ctgt                              94

SEQ ID NO: 165         moltype = DNA  length = 95
FEATURE                Location/Qualifiers
source                 1..95
                       mol_type = other DNA
                       organism = synthetic construct
SEQUENCE: 165
caagcagaag acggcatacg agatcatgat cggtgactgg agttcagacg tgtgctcttc  60
cgatctcgat tctactattc tttcccctgc actgt                             95

SEQ ID NO: 166         moltype = DNA  length = 96
FEATURE                Location/Qualifiers
source                 1..96
```

```
                        mol_type = other DNA
                        organism = synthetic construct
SEQUENCE: 166
caagcagaag acggcatacg agatcgttac cagtgactgg agttcagacg tgtgctcttc  60
cgatcttcga ttctactatt ctttccccctg cactgt                           96

SEQ ID NO: 167          moltype = DNA  length = 97
FEATURE                 Location/Qualifiers
source                  1..97
                        mol_type = other DNA
                        organism = synthetic construct
SEQUENCE: 167
caagcagaag acggcatacg agattccttg gtgtgactgg agttcagacg tgtgctcttc  60
cgatctatcg attctactat tctttcccct gcactgt                           97

SEQ ID NO: 168          moltype = DNA  length = 98
FEATURE                 Location/Qualifiers
source                  1..98
                        mol_type = other DNA
                        organism = synthetic construct
SEQUENCE: 168
caagcagaag acggcatacg agataacgca ttgtgactgg agttcagacg tgtgctcttc  60
cgatctgatc gattctacta ttctttcccc tgcactgt                          98

SEQ ID NO: 169          moltype = DNA  length = 99
FEATURE                 Location/Qualifiers
source                  1..99
                        mol_type = other DNA
                        organism = synthetic construct
SEQUENCE: 169
caagcagaag acggcatacg agatacaggt atgtgactgg agttcagacg tgtgctcttc  60
cgatctcgat cgattctact attctttccc ctgcactgt                         99

SEQ ID NO: 170          moltype = DNA  length = 100
FEATURE                 Location/Qualifiers
source                  1..100
                        mol_type = other DNA
                        organism = synthetic construct
SEQUENCE: 170
caagcagaag acggcataa agataggtaa gggtgactgg agttcagacg tgtgctcttc   60
cgatctacga tcgattctac tattctttcc cctgcactgt                        100

SEQ ID NO: 171          moltype = DNA  length = 92
FEATURE                 Location/Qualifiers
source                  1..92
                        mol_type = other DNA
                        organism = synthetic construct
SEQUENCE: 171
caagcagaag acggcatacg agataacaat gggtgactgg agttcagacg tgtgctcttc  60
cgatctttct actattcttt cccctgcact gt                                92

SEQ ID NO: 172          moltype = DNA  length = 93
FEATURE                 Location/Qualifiers
source                  1..93
                        mol_type = other DNA
                        organism = synthetic construct
SEQUENCE: 172
caagcagaag acggcatacg agatactgta tcgtgactgg agttcagacg tgtgctcttc  60
cgatctattc tactattctt tcccctgcac tgt                               93

SEQ ID NO: 173          moltype = DNA  length = 94
FEATURE                 Location/Qualifiers
source                  1..94
                        mol_type = other DNA
                        organism = synthetic construct
SEQUENCE: 173
caagcagaag acggcatacg agataggtcg cagtgactgg agttcagacg tgtgctcttc  60
cgatctgatt ctactattct ttcccctgca ctgt                              94

SEQ ID NO: 174          moltype = AA  length = 4
FEATURE                 Location/Qualifiers
REGION                  1..4
                        note = source = /note="Description of Unknown: Proteinase K
                         inhibitor peptide"
source                  1..4
                        mol_type = protein
                        organism = unidentified
SEQUENCE: 174
AAPF                                                               4
```

```
SEQ ID NO: 175          moltype = DNA  length = 20
FEATURE                 Location/Qualifiers
source                  1..20
                        mol_type = other DNA
                        organism = synthetic construct
SEQUENCE: 175
tggaaaggag aacggcccgg                                              20

SEQ ID NO: 176          moltype = DNA  length = 20
FEATURE                 Location/Qualifiers
source                  1..20
                        mol_type = other DNA
                        organism = synthetic construct
SEQUENCE: 176
tgaacaccct cgttaaaggc                                              20

SEQ ID NO: 177          moltype = DNA  length = 20
FEATURE                 Location/Qualifiers
source                  1..20
                        mol_type = other DNA
                        organism = synthetic construct
SEQUENCE: 177
aacactagcc cacatgccaa                                              20

SEQ ID NO: 178          moltype = DNA  length = 20
FEATURE                 Location/Qualifiers
source                  1..20
                        mol_type = other DNA
                        organism = synthetic construct
SEQUENCE: 178
gcccacagag gcacggttaa                                              20

SEQ ID NO: 179          moltype = DNA  length = 20
FEATURE                 Location/Qualifiers
source                  1..20
                        mol_type = other DNA
                        organism = synthetic construct
SEQUENCE: 179
aggcacggtt aatggtggcg                                              20

SEQ ID NO: 180          moltype = DNA  length = 20
FEATURE                 Location/Qualifiers
source                  1..20
                        mol_type = other DNA
                        organism = synthetic construct
SEQUENCE: 180
cacaggaagc catggtcctt                                              20

SEQ ID NO: 181          moltype = DNA  length = 20
FEATURE                 Location/Qualifiers
source                  1..20
                        mol_type = other DNA
                        organism = synthetic construct
SEQUENCE: 181
gcactgacgt aggtagtgac                                              20

SEQ ID NO: 182          moltype = DNA  length = 20
FEATURE                 Location/Qualifiers
source                  1..20
                        mol_type = other DNA
                        organism = synthetic construct
SEQUENCE: 182
ataggatatg gcactgacgt                                              20

SEQ ID NO: 183          moltype = DNA  length = 20
FEATURE                 Location/Qualifiers
source                  1..20
                        mol_type = other DNA
                        organism = synthetic construct
SEQUENCE: 183
cattatcttc tctggtctcg                                              20

SEQ ID NO: 184          moltype = DNA  length = 20
FEATURE                 Location/Qualifiers
source                  1..20
                        mol_type = other DNA
                        organism = synthetic construct
SEQUENCE: 184
```

```
atactgggga acacattgta                                              20

SEQ ID NO: 185          moltype = DNA  length = 20
FEATURE                 Location/Qualifiers
source                  1..20
                        mol_type = other DNA
                        organism = synthetic construct
SEQUENCE: 185
tgagcacatt cttacgccta                                              20

SEQ ID NO: 186          moltype = DNA  length = 20
FEATURE                 Location/Qualifiers
source                  1..20
                        mol_type = other DNA
                        organism = synthetic construct
SEQUENCE: 186
ctaggcgtaa gaatgtgctc                                              20

SEQ ID NO: 187          moltype = DNA  length = 20
FEATURE                 Location/Qualifiers
source                  1..20
                        mol_type = other DNA
                        organism = synthetic construct
SEQUENCE: 187
gaacccccta taaactagtc                                              20

SEQ ID NO: 188          moltype = DNA  length = 20
FEATURE                 Location/Qualifiers
source                  1..20
                        mol_type = other DNA
                        organism = synthetic construct
SEQUENCE: 188
ggcaaaccag actagtttat                                              20

SEQ ID NO: 189          moltype = DNA  length = 20
FEATURE                 Location/Qualifiers
source                  1..20
                        mol_type = other DNA
                        organism = synthetic construct
SEQUENCE: 189
caggggagaa ctcggcatga                                              20

SEQ ID NO: 190          moltype = DNA  length = 20
FEATURE                 Location/Qualifiers
source                  1..20
                        mol_type = other DNA
                        organism = synthetic construct
SEQUENCE: 190
gatggagttg gttgaccgta                                              20

SEQ ID NO: 191          moltype = DNA  length = 20
FEATURE                 Location/Qualifiers
source                  1..20
                        mol_type = other DNA
                        organism = synthetic construct
SEQUENCE: 191
ggtaggaccc aacactacgc                                              20

SEQ ID NO: 192          moltype = DNA  length = 20
FEATURE                 Location/Qualifiers
source                  1..20
                        mol_type = other DNA
                        organism = synthetic construct
SEQUENCE: 192
atgcctaggg tgttttgacg                                              20

SEQ ID NO: 193          moltype = DNA  length = 20
FEATURE                 Location/Qualifiers
source                  1..20
                        mol_type = other DNA
                        organism = synthetic construct
SEQUENCE: 193
tgaaccagac cacggcccgt                                              20

SEQ ID NO: 194          moltype = DNA  length = 20
FEATURE                 Location/Qualifiers
source                  1..20
                        mol_type = other DNA
                        organism = synthetic construct
```

```
SEQUENCE: 194
gcatccaatc ccgtggaggt                                              20

SEQ ID NO: 195          moltype = DNA  length = 20
FEATURE                 Location/Qualifiers
source                  1..20
                        mol_type = other DNA
                        organism = synthetic construct
SEQUENCE: 195
cactggcttc ctgttcttgt                                              20

SEQ ID NO: 196          moltype = DNA  length = 20
FEATURE                 Location/Qualifiers
source                  1..20
                        mol_type = other DNA
                        organism = synthetic construct
SEQUENCE: 196
aaggttttca aggcaaataa                                              20

SEQ ID NO: 197          moltype = DNA  length = 20
FEATURE                 Location/Qualifiers
source                  1..20
                        mol_type = other DNA
                        organism = synthetic construct
SEQUENCE: 197
gtaatggagc ccgcatgctg                                              20

SEQ ID NO: 198          moltype = DNA  length = 20
FEATURE                 Location/Qualifiers
source                  1..20
                        mol_type = other DNA
                        organism = synthetic construct
SEQUENCE: 198
gccagtgtac aggcaagtac                                              20

SEQ ID NO: 199          moltype = DNA  length = 20
FEATURE                 Location/Qualifiers
source                  1..20
                        mol_type = other DNA
                        organism = synthetic construct
SEQUENCE: 199
tcgctgcctt cagttctgct                                              20

SEQ ID NO: 200          moltype = DNA  length = 20
FEATURE                 Location/Qualifiers
source                  1..20
                        mol_type = other DNA
                        organism = synthetic construct
SEQUENCE: 200
ttatggaact caggaactgc                                              20

SEQ ID NO: 201          moltype = DNA  length = 20
FEATURE                 Location/Qualifiers
source                  1..20
                        mol_type = other DNA
                        organism = synthetic construct
SEQUENCE: 201
gatgcctttt tcatctcgat                                              20

SEQ ID NO: 202          moltype = DNA  length = 20
FEATURE                 Location/Qualifiers
source                  1..20
                        mol_type = other DNA
                        organism = synthetic construct
SEQUENCE: 202
attccttgag tgtcatatat                                              20

SEQ ID NO: 203          moltype = DNA  length = 20
FEATURE                 Location/Qualifiers
source                  1..20
                        mol_type = other DNA
                        organism = synthetic construct
SEQUENCE: 203
tctggaatca ctatgtatat                                              20

SEQ ID NO: 204          moltype = DNA  length = 20
FEATURE                 Location/Qualifiers
source                  1..20
                        mol_type = other DNA
```

```
                        organism = synthetic construct
SEQUENCE: 204
tgctccgagc ttgtgaacta                                              20

SEQ ID NO: 205          moltype = DNA  length = 20
FEATURE                 Location/Qualifiers
source                  1..20
                        mol_type = other DNA
                        organism = synthetic construct
SEQUENCE: 205
tatcacaggc tccaggaagg                                              20

SEQ ID NO: 206          moltype = DNA  length = 20
FEATURE                 Location/Qualifiers
source                  1..20
                        mol_type = other DNA
                        organism = synthetic construct
SEQUENCE: 206
tagtttgctt cccccaatga                                              20

SEQ ID NO: 207          moltype = DNA  length = 20
FEATURE                 Location/Qualifiers
source                  1..20
                        mol_type = other DNA
                        organism = synthetic construct
SEQUENCE: 207
gccaggaaat tggtggtaga                                              20

SEQ ID NO: 208          moltype = DNA  length = 20
FEATURE                 Location/Qualifiers
source                  1..20
                        mol_type = other DNA
                        organism = synthetic construct
SEQUENCE: 208
tgctccgagc ttgtgaacta                                              20

SEQ ID NO: 209          moltype = DNA  length = 20
FEATURE                 Location/Qualifiers
source                  1..20
                        mol_type = other DNA
                        organism = synthetic construct
SEQUENCE: 209
tatcacaggc tccaggaagg                                              20

SEQ ID NO: 210          moltype = DNA  length = 20
FEATURE                 Location/Qualifiers
source                  1..20
                        mol_type = other DNA
                        organism = synthetic construct
SEQUENCE: 210
gtgggcagtt acgttttcgt                                              20

SEQ ID NO: 211          moltype = DNA  length = 20
FEATURE                 Location/Qualifiers
source                  1..20
                        mol_type = other DNA
                        organism = synthetic construct
SEQUENCE: 211
gccaggaaat tggtggtaga                                              20

SEQ ID NO: 212          moltype = DNA  length = 20
FEATURE                 Location/Qualifiers
source                  1..20
                        mol_type = other DNA
                        organism = synthetic construct
SEQUENCE: 212
ggtcagggtg ttgcagagat                                              20

SEQ ID NO: 213          moltype = DNA  length = 20
FEATURE                 Location/Qualifiers
source                  1..20
                        mol_type = other DNA
                        organism = synthetic construct
SEQUENCE: 213
cacaccctgt gatcttgtgg                                              20

SEQ ID NO: 214          moltype = DNA  length = 20
FEATURE                 Location/Qualifiers
source                  1..20
```

```
                        mol_type = other DNA
                        organism = synthetic construct
SEQUENCE: 214
gacttaaact gccgctcctg                                              20

SEQ ID NO: 215          moltype = DNA  length = 20
FEATURE                 Location/Qualifiers
source                  1..20
                        mol_type = other DNA
                        organism = synthetic construct
SEQUENCE: 215
gggcctcagg ctctttatct                                              20

SEQ ID NO: 216          moltype = DNA  length = 20
FEATURE                 Location/Qualifiers
source                  1..20
                        mol_type = other DNA
                        organism = synthetic construct
SEQUENCE: 216
cccagagctc agtgagatga                                              20

SEQ ID NO: 217          moltype = DNA  length = 20
FEATURE                 Location/Qualifiers
source                  1..20
                        mol_type = other DNA
                        organism = synthetic construct
SEQUENCE: 217
gggaaagggc ctgataactt                                              20

SEQ ID NO: 218          moltype = DNA  length = 23
FEATURE                 Location/Qualifiers
source                  1..23
                        mol_type = other DNA
                        organism = synthetic construct
SEQUENCE: 218
gaacagagac cactactggc aat                                          23

SEQ ID NO: 219          moltype = DNA  length = 21
FEATURE                 Location/Qualifiers
source                  1..21
                        mol_type = other DNA
                        organism = synthetic construct
SEQUENCE: 219
ctcagaaaaa tgacagcacc a                                            21

SEQ ID NO: 220          moltype = DNA  length = 21
FEATURE                 Location/Qualifiers
source                  1..21
                        mol_type = other DNA
                        organism = synthetic construct
SEQUENCE: 220
tttgaaagta ccagcacagc a                                            21

SEQ ID NO: 221          moltype = DNA  length = 20
FEATURE                 Location/Qualifiers
source                  1..20
                        mol_type = other DNA
                        organism = synthetic construct
SEQUENCE: 221
ccctctggca tcaaaatgag                                              20

SEQ ID NO: 222          moltype = DNA  length = 20
FEATURE                 Location/Qualifiers
source                  1..20
                        mol_type = other DNA
                        organism = synthetic construct
SEQUENCE: 222
aacagaccca tgtgctaggc                                              20

SEQ ID NO: 223          moltype = DNA  length = 23
FEATURE                 Location/Qualifiers
source                  1..23
                        mol_type = other DNA
                        organism = synthetic construct
SEQUENCE: 223
tgctgaattc ctgtaaagtg agg                                          23

SEQ ID NO: 224          moltype = DNA  length = 20
FEATURE                 Location/Qualifiers
```

```
source                  1..20
                        mol_type = other DNA
                        organism = synthetic construct
SEQUENCE: 224
gaggtgacca gggtgtgagt                                                20

SEQ ID NO: 225          moltype = DNA  length = 20
FEATURE                 Location/Qualifiers
source                  1..20
                        mol_type = other DNA
                        organism = synthetic construct
SEQUENCE: 225
aagaagaggc cctggacatt                                                20

SEQ ID NO: 226          moltype = DNA  length = 21
FEATURE                 Location/Qualifiers
source                  1..21
                        mol_type = other DNA
                        organism = synthetic construct
SEQUENCE: 226
catcttaagg caagaatcac t                                              21

SEQ ID NO: 227          moltype = DNA  length = 20
FEATURE                 Location/Qualifiers
source                  1..20
                        mol_type = other DNA
                        organism = synthetic construct
SEQUENCE: 227
ccagtcaatc caaaccctgt                                                20

SEQ ID NO: 228          moltype = DNA  length = 20
FEATURE                 Location/Qualifiers
source                  1..20
                        mol_type = other DNA
                        organism = synthetic construct
SEQUENCE: 228
tattaatgcc cagccagctc                                                20

SEQ ID NO: 229          moltype = DNA  length = 20
FEATURE                 Location/Qualifiers
source                  1..20
                        mol_type = other DNA
                        organism = synthetic construct
SEQUENCE: 229
gtggtccaga cctagccaag                                                20

SEQ ID NO: 230          moltype = DNA  length = 20
FEATURE                 Location/Qualifiers
source                  1..20
                        mol_type = other DNA
                        organism = synthetic construct
SEQUENCE: 230
tttgagcagg agggaatttg                                                20

SEQ ID NO: 231          moltype = DNA  length = 20
FEATURE                 Location/Qualifiers
source                  1..20
                        mol_type = other DNA
                        organism = synthetic construct
SEQUENCE: 231
ataggtggtt gggcttctcc                                                20

SEQ ID NO: 232          moltype = DNA  length = 20
FEATURE                 Location/Qualifiers
source                  1..20
                        mol_type = other DNA
                        organism = synthetic construct
SEQUENCE: 232
ggagtggctg ttgaaagagg                                                20

SEQ ID NO: 233          moltype = DNA  length = 20
FEATURE                 Location/Qualifiers
source                  1..20
                        mol_type = other DNA
                        organism = synthetic construct
SEQUENCE: 233
cactcaagga atgcaagcaa                                                20

SEQ ID NO: 234          moltype = DNA  length = 20
```

```
FEATURE                Location/Qualifiers
source                 1..20
                       mol_type = other DNA
                       organism = synthetic construct
SEQUENCE: 234
tacttggtgg ctttcccaac                                              20

SEQ ID NO: 235         moltype = DNA  length = 20
FEATURE                Location/Qualifiers
source                 1..20
                       mol_type = other DNA
                       organism = synthetic construct
SEQUENCE: 235
agatggtcct ctgcatccac                                              20

SEQ ID NO: 236         moltype = DNA  length = 20
FEATURE                Location/Qualifiers
source                 1..20
                       mol_type = other DNA
                       organism = synthetic construct
SEQUENCE: 236
gacttaaact gccgctcctg                                              20

SEQ ID NO: 237         moltype = DNA  length = 20
FEATURE                Location/Qualifiers
source                 1..20
                       mol_type = other DNA
                       organism = synthetic construct
SEQUENCE: 237
aggcatccaa agggaagaat                                              20

SEQ ID NO: 238         moltype = DNA  length = 20
FEATURE                Location/Qualifiers
source                 1..20
                       mol_type = other DNA
                       organism = synthetic construct
SEQUENCE: 238
acttcagcct ccagcactgt                                              20

SEQ ID NO: 239         moltype = DNA  length = 20
FEATURE                Location/Qualifiers
source                 1..20
                       mol_type = other DNA
                       organism = synthetic construct
SEQUENCE: 239
ccactggagt ggaaccaagt                                              20

SEQ ID NO: 240         moltype = DNA  length = 20
FEATURE                Location/Qualifiers
source                 1..20
                       mol_type = other DNA
                       organism = synthetic construct
SEQUENCE: 240
gggatcagag gtgaacagga                                              20

SEQ ID NO: 241         moltype = DNA  length = 20
FEATURE                Location/Qualifiers
source                 1..20
                       mol_type = other DNA
                       organism = synthetic construct
SEQUENCE: 241
tggactttgc actggaatca                                              20

SEQ ID NO: 242         moltype = DNA  length = 20
FEATURE                Location/Qualifiers
source                 1..20
                       mol_type = other DNA
                       organism = synthetic construct
SEQUENCE: 242
ttgtttacag aggggcaacc                                              20

SEQ ID NO: 243         moltype = DNA  length = 20
FEATURE                Location/Qualifiers
source                 1..20
                       mol_type = other DNA
                       organism = synthetic construct
SEQUENCE: 243
ggggaagggg tattgaattg                                              20
```

```
SEQ ID NO: 244          moltype = DNA  length = 20
FEATURE                 Location/Qualifiers
source                  1..20
                        mol_type = other DNA
                        organism = synthetic construct
SEQUENCE: 244
aacagaccca tgtgctaggc                                              20

SEQ ID NO: 245          moltype = DNA  length = 20
FEATURE                 Location/Qualifiers
source                  1..20
                        mol_type = other DNA
                        organism = synthetic construct
SEQUENCE: 245
gaacctggga ggcagaagat                                              20

SEQ ID NO: 246          moltype = DNA  length = 20
FEATURE                 Location/Qualifiers
source                  1..20
                        mol_type = other DNA
                        organism = synthetic construct
SEQUENCE: 246
tgtgtggact gccttttctg                                              20

SEQ ID NO: 247          moltype = DNA  length = 20
FEATURE                 Location/Qualifiers
source                  1..20
                        mol_type = other DNA
                        organism = synthetic construct
SEQUENCE: 247
tgtggagctc tggaatgatg                                              20

SEQ ID NO: 248          moltype = DNA  length = 19
FEATURE                 Location/Qualifiers
source                  1..19
                        mol_type = other DNA
                        organism = synthetic construct
SEQUENCE: 248
ggtagtgtgg gggtggagt                                               19

SEQ ID NO: 249          moltype = DNA  length = 19
FEATURE                 Location/Qualifiers
source                  1..19
                        mol_type = other DNA
                        organism = synthetic construct
SEQUENCE: 249
tcagcctgtt ccctcagtg                                               19

SEQ ID NO: 250          moltype = DNA  length = 19
FEATURE                 Location/Qualifiers
source                  1..19
                        mol_type = other DNA
                        organism = synthetic construct
SEQUENCE: 250
ggtagtgtgg gggtggagt                                               19

SEQ ID NO: 251          moltype = DNA  length = 19
FEATURE                 Location/Qualifiers
source                  1..19
                        mol_type = other DNA
                        organism = synthetic construct
SEQUENCE: 251
tcagcctgtt ccctcagtg                                               19

SEQ ID NO: 252          moltype = DNA  length = 19
FEATURE                 Location/Qualifiers
source                  1..19
                        mol_type = other DNA
                        organism = synthetic construct
SEQUENCE: 252
ggtagtgtgg gggtggagt                                               19

SEQ ID NO: 253          moltype = DNA  length = 19
FEATURE                 Location/Qualifiers
source                  1..19
                        mol_type = other DNA
                        organism = synthetic construct
SEQUENCE: 253
tcagcctgtt ccctcagtg                                               19
```

```
SEQ ID NO: 254          moltype = DNA  length = 19
FEATURE                 Location/Qualifiers
source                  1..19
                        mol_type = other DNA
                        organism = synthetic construct
SEQUENCE: 254
ggtagtgtgg gggtggagt                                              19

SEQ ID NO: 255          moltype = DNA  length = 20
FEATURE                 Location/Qualifiers
source                  1..20
                        mol_type = other DNA
                        organism = synthetic construct
SEQUENCE: 255
agatggtcct ctgcatccac                                             20

SEQ ID NO: 256          moltype = DNA  length = 19
FEATURE                 Location/Qualifiers
source                  1..19
                        mol_type = other DNA
                        organism = synthetic construct
SEQUENCE: 256
ggtagtgtgg gggtggagt                                              19

SEQ ID NO: 257          moltype = DNA  length = 19
FEATURE                 Location/Qualifiers
source                  1..19
                        mol_type = other DNA
                        organism = synthetic construct
SEQUENCE: 257
tcagcctgtt ccctcagtg                                              19

SEQ ID NO: 258          moltype = DNA  length = 20
FEATURE                 Location/Qualifiers
source                  1..20
                        mol_type = other DNA
                        organism = synthetic construct
SEQUENCE: 258
tacttggtgg ctttcccaac                                             20

SEQ ID NO: 259          moltype = DNA  length = 19
FEATURE                 Location/Qualifiers
source                  1..19
                        mol_type = other DNA
                        organism = synthetic construct
SEQUENCE: 259
tcagcctgtt ccctcagtg                                              19

SEQ ID NO: 260          moltype = DNA  length = 20
FEATURE                 Location/Qualifiers
source                  1..20
                        mol_type = other DNA
                        organism = synthetic construct
SEQUENCE: 260
atgcttggtt gtcgccttat                                             20

SEQ ID NO: 261          moltype = DNA  length = 20
FEATURE                 Location/Qualifiers
source                  1..20
                        mol_type = other DNA
                        organism = synthetic construct
SEQUENCE: 261
cactcaagga atgcaagcaa                                             20

SEQ ID NO: 262          moltype = DNA  length = 20
FEATURE                 Location/Qualifiers
source                  1..20
                        mol_type = other DNA
                        organism = synthetic construct
SEQUENCE: 262
acccagaaga ctgtggatgg                                             20

SEQ ID NO: 263          moltype = DNA  length = 20
FEATURE                 Location/Qualifiers
source                  1..20
                        mol_type = other DNA
                        organism = synthetic construct
SEQUENCE: 263
```

```
ttcagctcag ggatgacctt                                              20

SEQ ID NO: 264          moltype = DNA  length = 21
FEATURE                 Location/Qualifiers
source                  1..21
                        mol_type = other DNA
                        organism = synthetic construct
SEQUENCE: 264
ctgaggagaa gtctgccgtt a                                            21

SEQ ID NO: 265          moltype = DNA  length = 20
FEATURE                 Location/Qualifiers
source                  1..20
                        mol_type = other DNA
                        organism = synthetic construct
SEQUENCE: 265
agcatcagga gtggacagat                                              20

SEQ ID NO: 266          moltype = DNA  length = 19
FEATURE                 Location/Qualifiers
source                  1..19
                        mol_type = other DNA
                        organism = synthetic construct
SEQUENCE: 266
tggatgatct caagggcac                                               19

SEQ ID NO: 267          moltype = DNA  length = 20
FEATURE                 Location/Qualifiers
source                  1..20
                        mol_type = other DNA
                        organism = synthetic construct
SEQUENCE: 267
tcagtggtat ctggaggaca                                              20

SEQ ID NO: 268          moltype = DNA  length = 20
FEATURE                 Location/Qualifiers
source                  1..20
                        mol_type = other DNA
                        organism = synthetic construct
SEQUENCE: 268
gcaagaaggt gctgacttcc                                              20

SEQ ID NO: 269          moltype = DNA  length = 20
FEATURE                 Location/Qualifiers
source                  1..20
                        mol_type = other DNA
                        organism = synthetic construct
SEQUENCE: 269
accatcacgt tacccaggag                                              20

SEQ ID NO: 270          moltype = DNA  length = 22
FEATURE                 Location/Qualifiers
source                  1..22
                        mol_type = other DNA
                        organism = synthetic construct
SEQUENCE: 270
gaggagaaga ctgctgtcaa tg                                           22

SEQ ID NO: 271          moltype = DNA  length = 22
FEATURE                 Location/Qualifiers
source                  1..22
                        mol_type = other DNA
                        organism = synthetic construct
SEQUENCE: 271
agggtagacc accagtaatc tg                                           22

SEQ ID NO: 272          moltype = DNA  length = 20
FEATURE                 Location/Qualifiers
source                  1..20
                        mol_type = other DNA
                        organism = synthetic construct
SEQUENCE: 272
aaccccagca cttaagcaaa                                              20

SEQ ID NO: 273          moltype = DNA  length = 20
FEATURE                 Location/Qualifiers
source                  1..20
                        mol_type = other DNA
                        organism = synthetic construct
```

```
SEQUENCE: 273
ggaggtcatg atccccttct                                              20

SEQ ID NO: 274         moltype = DNA  length = 20
FEATURE                Location/Qualifiers
source                 1..20
                       mol_type = other DNA
                       organism = synthetic construct
SEQUENCE: 274
tggtgaaggt cggtgtgaac                                              20

SEQ ID NO: 275         moltype = DNA  length = 24
FEATURE                Location/Qualifiers
source                 1..24
                       mol_type = other DNA
                       organism = synthetic construct
SEQUENCE: 275
ccatgtagtt gaggtcaatg aagg                                         24

SEQ ID NO: 276         moltype = DNA  length = 23
FEATURE                Location/Qualifiers
source                 1..23
                       mol_type = other DNA
                       organism = synthetic construct
SEQUENCE: 276
tttaacgatg gcctgaatca ctt                                          23

SEQ ID NO: 277         moltype = DNA  length = 23
FEATURE                Location/Qualifiers
source                 1..23
                       mol_type = other DNA
                       organism = synthetic construct
SEQUENCE: 277
cagcacaatc acgatcatat tgc                                          23

SEQ ID NO: 278         moltype = DNA  length = 21
FEATURE                Location/Qualifiers
source                 1..21
                       mol_type = other DNA
                       organism = synthetic construct
SEQUENCE: 278
tggcctgtgg agtaaggtca a                                            21

SEQ ID NO: 279         moltype = DNA  length = 21
FEATURE                Location/Qualifiers
source                 1..21
                       mol_type = other DNA
                       organism = synthetic construct
SEQUENCE: 279
gaagcagagg acaagttccc a                                            21

SEQ ID NO: 280         moltype = DNA  length = 20
FEATURE                Location/Qualifiers
source                 1..20
                       mol_type = other DNA
                       organism = synthetic construct
SEQUENCE: 280
tggacaacct caaggagacc                                              20

SEQ ID NO: 281         moltype = DNA  length = 20
FEATURE                Location/Qualifiers
source                 1..20
                       mol_type = other DNA
                       organism = synthetic construct
SEQUENCE: 281
acctctgggg tgaattcctt                                              20

SEQ ID NO: 282         moltype = DNA  length = 20
FEATURE                Location/Qualifiers
source                 1..20
                       mol_type = other DNA
                       organism = synthetic construct
SEQUENCE: 282
aaccccagca cttaagcaaa                                              20

SEQ ID NO: 283         moltype = DNA  length = 20
FEATURE                Location/Qualifiers
source                 1..20
                       mol_type = other DNA
```

```
                         organism = synthetic construct
SEQUENCE: 283
acaggtgaga aggtcgtggt                                               20

SEQ ID NO: 284           moltype = DNA  length = 17
FEATURE                  Location/Qualifiers
source                   1..17
                         mol_type = other DNA
                         organism = synthetic construct
SEQUENCE: 284
cctgagcgag acgagat                                                  17

SEQ ID NO: 285           moltype = DNA  length = 17
FEATURE                  Location/Qualifiers
source                   1..17
                         mol_type = other DNA
                         organism = synthetic construct
SEQUENCE: 285
tggtgggagg tgattga                                                  17

SEQ ID NO: 286           moltype = DNA  length = 22
FEATURE                  Location/Qualifiers
source                   1..22
                         mol_type = other DNA
                         organism = synthetic construct
SEQUENCE: 286
atagtttggc tgtatcccta tg                                            22

SEQ ID NO: 287           moltype = DNA  length = 22
FEATURE                  Location/Qualifiers
source                   1..22
                         mol_type = other DNA
                         organism = synthetic construct
SEQUENCE: 287
tttctaagtg acgtgggttt ag                                            22

SEQ ID NO: 288           moltype = DNA  length = 20
FEATURE                  Location/Qualifiers
source                   1..20
                         mol_type = other DNA
                         organism = synthetic construct
SEQUENCE: 288
gcatctaggc cttcagttag                                               20

SEQ ID NO: 289           moltype = DNA  length = 19
FEATURE                  Location/Qualifiers
source                   1..19
                         mol_type = other DNA
                         organism = synthetic construct
SEQUENCE: 289
cctgggagct ctgagaata                                                19

SEQ ID NO: 290           moltype = DNA  length = 18
FEATURE                  Location/Qualifiers
source                   1..18
                         mol_type = other DNA
                         organism = synthetic construct
SEQUENCE: 290
ctgccacaat tcccatgt                                                 18

SEQ ID NO: 291           moltype = DNA  length = 20
FEATURE                  Location/Qualifiers
source                   1..20
                         mol_type = other DNA
                         organism = synthetic construct
SEQUENCE: 291
gaccctaagg gacgctaata                                               20

SEQ ID NO: 292           moltype = DNA  length = 19
FEATURE                  Location/Qualifiers
source                   1..19
                         mol_type = other DNA
                         organism = synthetic construct
SEQUENCE: 292
cctgtgtctg cagtttctc                                                19

SEQ ID NO: 293           moltype = DNA  length = 22
FEATURE                  Location/Qualifiers
source                   1..22
```

```
                        mol_type = other DNA
                        organism = synthetic construct
SEQUENCE: 293
gcatattctg gtctcctaag tc                                              22

SEQ ID NO: 294          moltype = DNA  length = 20
FEATURE                 Location/Qualifiers
source                  1..20
                        mol_type = other DNA
                        organism = synthetic construct
SEQUENCE: 294
gtctgccctg cagaataaag                                                 20

SEQ ID NO: 295          moltype = DNA  length = 23
FEATURE                 Location/Qualifiers
source                  1..23
                        mol_type = other DNA
                        organism = synthetic construct
SEQUENCE: 295
tttctggaga atcctgacta atg                                             23

SEQ ID NO: 296          moltype = DNA  length = 19
FEATURE                 Location/Qualifiers
source                  1..19
                        mol_type = other DNA
                        organism = synthetic construct
SEQUENCE: 296
tttgaggagg agtttcgct                                                  19

SEQ ID NO: 297          moltype = DNA  length = 19
FEATURE                 Location/Qualifiers
source                  1..19
                        mol_type = other DNA
                        organism = synthetic construct
SEQUENCE: 297
ggtgacacat gcctgtaat                                                  19

SEQ ID NO: 298          moltype = DNA  length = 19
FEATURE                 Location/Qualifiers
source                  1..19
                        mol_type = other DNA
                        organism = synthetic construct
SEQUENCE: 298
tgtgccactc aagacaatc                                                  19

SEQ ID NO: 299          moltype = DNA  length = 22
FEATURE                 Location/Qualifiers
source                  1..22
                        mol_type = other DNA
                        organism = synthetic construct
SEQUENCE: 299
tgaagaaacc atctaagtca tc                                              22

SEQ ID NO: 300          moltype = DNA  length = 18
FEATURE                 Location/Qualifiers
source                  1..18
                        mol_type = other DNA
                        organism = synthetic construct
SEQUENCE: 300
aattagctgg gcatggtg                                                   18

SEQ ID NO: 301          moltype = DNA  length = 20
FEATURE                 Location/Qualifiers
source                  1..20
                        mol_type = other DNA
                        organism = synthetic construct
SEQUENCE: 301
cctcacaatc atggcagaag                                                 20

SEQ ID NO: 302          moltype = DNA  length = 21
FEATURE                 Location/Qualifiers
source                  1..21
                        mol_type = other DNA
                        organism = synthetic construct
SEQUENCE: 302
agaaacactg catcatctag g                                               21

SEQ ID NO: 303          moltype = DNA  length = 20
FEATURE                 Location/Qualifiers
```

```
source                  1..20
                        mol_type = other DNA
                        organism = synthetic construct
SEQUENCE: 303
ccagcaatct ccaaccattc                                                    20

SEQ ID NO: 304          moltype = DNA  length = 19
FEATURE                 Location/Qualifiers
source                  1..19
                        mol_type = other DNA
                        organism = synthetic construct
SEQUENCE: 304
cgaaggcttc ttccaactc                                                     19

SEQ ID NO: 305          moltype = DNA  length = 20
FEATURE                 Location/Qualifiers
source                  1..20
                        mol_type = other DNA
                        organism = synthetic construct
SEQUENCE: 305
tcctctagca ttagggagtg                                                    20

SEQ ID NO: 306          moltype = DNA  length = 21
FEATURE                 Location/Qualifiers
source                  1..21
                        mol_type = other DNA
                        organism = synthetic construct
SEQUENCE: 306
cattgtggag atcaaatgtg c                                                  21

SEQ ID NO: 307          moltype = DNA  length = 19
FEATURE                 Location/Qualifiers
source                  1..19
                        mol_type = other DNA
                        organism = synthetic construct
SEQUENCE: 307
tctttcctca ctgcaactg                                                     19

SEQ ID NO: 308          moltype = DNA  length = 21
FEATURE                 Location/Qualifiers
source                  1..21
                        mol_type = other DNA
                        organism = synthetic construct
SEQUENCE: 308
tttctgtgcc cagtcatatt c                                                  21

SEQ ID NO: 309          moltype = DNA  length = 22
FEATURE                 Location/Qualifiers
source                  1..22
                        mol_type = other DNA
                        organism = synthetic construct
SEQUENCE: 309
cctcttcttg accatcagtt tc                                                 22

SEQ ID NO: 310          moltype = DNA  length = 20
FEATURE                 Location/Qualifiers
source                  1..20
                        mol_type = other DNA
                        organism = synthetic construct
SEQUENCE: 310
tcccattgtg tgaacctaac                                                    20

SEQ ID NO: 311          moltype = DNA  length = 23
FEATURE                 Location/Qualifiers
source                  1..23
                        mol_type = other DNA
                        organism = synthetic construct
SEQUENCE: 311
gtactatggg taggaaactg ttc                                                23

SEQ ID NO: 312          moltype = DNA  length = 19
FEATURE                 Location/Qualifiers
source                  1..19
                        mol_type = other DNA
                        organism = synthetic construct
SEQUENCE: 312
cgcttgaccc tgtctttac                                                     19

SEQ ID NO: 313          moltype = DNA  length = 20
```

```
FEATURE                Location/Qualifiers
source                 1..20
                       mol_type = other DNA
                       organism = synthetic construct
SEQUENCE: 313
agagacggag acacacatag                                              20

SEQ ID NO: 314         moltype = DNA  length = 25
FEATURE                Location/Qualifiers
source                 1..25
                       mol_type = other DNA
                       organism = synthetic construct
SEQUENCE: 314
gttgaaagaa ggcaactaga ataag                                        25

SEQ ID NO: 315         moltype = DNA  length = 21
FEATURE                Location/Qualifiers
source                 1..21
                       mol_type = other DNA
                       organism = synthetic construct
SEQUENCE: 315
cagtgataca cacacagaca c                                            21

SEQ ID NO: 316         moltype = DNA  length = 22
FEATURE                Location/Qualifiers
source                 1..22
                       mol_type = other DNA
                       organism = synthetic construct
SEQUENCE: 316
gggatctaaa tgagaggatc ac                                           22

SEQ ID NO: 317         moltype = DNA  length = 23
FEATURE                Location/Qualifiers
source                 1..23
                       mol_type = other DNA
                       organism = synthetic construct
SEQUENCE: 317
ttcttctgcc agatacctaa atc                                          23

SEQ ID NO: 318         moltype = DNA  length = 17
FEATURE                Location/Qualifiers
source                 1..17
                       mol_type = other DNA
                       organism = synthetic construct
SEQUENCE: 318
tgggaggcct cagaatc                                                 17

SEQ ID NO: 319         moltype = DNA  length = 17
FEATURE                Location/Qualifiers
source                 1..17
                       mol_type = other DNA
                       organism = synthetic construct
SEQUENCE: 319
atcgtgccac tgcactc                                                 17

SEQ ID NO: 320         moltype = DNA  length = 22
FEATURE                Location/Qualifiers
source                 1..22
                       mol_type = other DNA
                       organism = synthetic construct
SEQUENCE: 320
tagcatagtg tgttcaaggt tc                                           22

SEQ ID NO: 321         moltype = DNA  length = 22
FEATURE                Location/Qualifiers
source                 1..22
                       mol_type = other DNA
                       organism = synthetic construct
SEQUENCE: 321
gtgagcagat caaacgatta tg                                           22

SEQ ID NO: 322         moltype = DNA  length = 20
FEATURE                Location/Qualifiers
source                 1..20
                       mol_type = other DNA
                       organism = synthetic construct
SEQUENCE: 322
cttacgatca tggcagaagg                                              20
```

```
SEQ ID NO: 323         moltype = DNA  length = 19
FEATURE                Location/Qualifiers
source                 1..19
                       mol_type = other DNA
                       organism = synthetic construct
SEQUENCE: 323
ggctacagcc ttggtattg                                              19

SEQ ID NO: 324         moltype = DNA  length = 21
FEATURE                Location/Qualifiers
source                 1..21
                       mol_type = other DNA
                       organism = synthetic construct
SEQUENCE: 324
gggacacatg caattattga g                                           21

SEQ ID NO: 325         moltype = DNA  length = 22
FEATURE                Location/Qualifiers
source                 1..22
                       mol_type = other DNA
                       organism = synthetic construct
SEQUENCE: 325
tctggtttag catggcttat ag                                          22

SEQ ID NO: 326         moltype = DNA  length = 20
FEATURE                Location/Qualifiers
source                 1..20
                       mol_type = other DNA
                       organism = synthetic construct
SEQUENCE: 326
cttccttcag ttccctgttc                                             20

SEQ ID NO: 327         moltype = DNA  length = 23
FEATURE                Location/Qualifiers
source                 1..23
                       mol_type = other DNA
                       organism = synthetic construct
SEQUENCE: 327
acagctctca ggactggaag gtg                                         23

SEQ ID NO: 328         moltype = DNA  length = 26
FEATURE                Location/Qualifiers
source                 1..26
                       mol_type = other DNA
                       organism = synthetic construct
SEQUENCE: 328
cctgctccac cctcaaatct cacatc                                      26

SEQ ID NO: 329         moltype = DNA  length = 28
FEATURE                Location/Qualifiers
source                 1..28
                       mol_type = other DNA
                       organism = synthetic construct
SEQUENCE: 329
gcctatacag gcataccttg ttttattg                                    28

SEQ ID NO: 330         moltype = DNA  length = 26
FEATURE                Location/Qualifiers
source                 1..26
                       mol_type = other DNA
                       organism = synthetic construct
SEQUENCE: 330
cattggaaga agatgccatc taggac                                      26

SEQ ID NO: 331         moltype = DNA  length = 26
FEATURE                Location/Qualifiers
source                 1..26
                       mol_type = other DNA
                       organism = synthetic construct
SEQUENCE: 331
gccaaaataa gtctgcctgg gttcag                                      26

SEQ ID NO: 332         moltype = DNA  length = 24
FEATURE                Location/Qualifiers
source                 1..24
                       mol_type = other DNA
                       organism = synthetic construct
SEQUENCE: 332
gcatctaggc cttcagttag cgtc                                        24
```

```
SEQ ID NO: 333         moltype = DNA  length = 27
FEATURE                Location/Qualifiers
source                 1..27
                       mol_type = other DNA
                       organism = synthetic construct
SEQUENCE: 333
cttctgtgtg ggatgtgcat cctctag                                      27

SEQ ID NO: 334         moltype = DNA  length = 24
FEATURE                Location/Qualifiers
source                 1..24
                       mol_type = other DNA
                       organism = synthetic construct
SEQUENCE: 334
gtatgtccag tgcctagcac agtg                                         24

SEQ ID NO: 335         moltype = DNA  length = 36
FEATURE                Location/Qualifiers
source                 1..36
                       mol_type = other DNA
                       organism = synthetic construct
SEQUENCE: 335
caattctatg tgctatattc tttaaaactg taatgg                            36

SEQ ID NO: 336         moltype = DNA  length = 24
FEATURE                Location/Qualifiers
source                 1..24
                       mol_type = other DNA
                       organism = synthetic construct
SEQUENCE: 336
ggcaacagac caagactctg tctc                                         24

SEQ ID NO: 337         moltype = DNA  length = 24
FEATURE                Location/Qualifiers
source                 1..24
                       mol_type = other DNA
                       organism = synthetic construct
SEQUENCE: 337
cacctgtttg agacaccctt gctc                                         24

SEQ ID NO: 338         moltype = DNA  length = 25
FEATURE                Location/Qualifiers
source                 1..25
                       mol_type = other DNA
                       organism = synthetic construct
SEQUENCE: 338
gcctttacac actttcctca ggcac                                        25

SEQ ID NO: 339         moltype = DNA  length = 27
FEATURE                Location/Qualifiers
source                 1..27
                       mol_type = other DNA
                       organism = synthetic construct
SEQUENCE: 339
gtttcctagt tattgtgagc agctcag                                      27

SEQ ID NO: 340         moltype = DNA  length = 22
FEATURE                Location/Qualifiers
source                 1..22
                       mol_type = other DNA
                       organism = synthetic construct
SEQUENCE: 340
ggctccttct agggcagagg tg                                           22

SEQ ID NO: 341         moltype = DNA  length = 24
FEATURE                Location/Qualifiers
source                 1..24
                       mol_type = other DNA
                       organism = synthetic construct
SEQUENCE: 341
gaggctcaaa gaagggtatg agac                                         24

SEQ ID NO: 342         moltype = DNA  length = 26
FEATURE                Location/Qualifiers
source                 1..26
                       mol_type = other DNA
                       organism = synthetic construct
SEQUENCE: 342
```

```
catggcacct gtagcaaatg ctagac                                    26

SEQ ID NO: 343          moltype = DNA  length = 24
FEATURE                 Location/Qualifiers
source                  1..24
                        mol_type = other DNA
                        organism = synthetic construct
SEQUENCE: 343
ctgagactgt ggtttctatg gctg                                      24

SEQ ID NO: 344          moltype = DNA  length = 23
FEATURE                 Location/Qualifiers
source                  1..23
                        mol_type = other DNA
                        organism = synthetic construct
SEQUENCE: 344
gagctgggag ggaattgcat acc                                       23

SEQ ID NO: 345          moltype = DNA  length = 29
FEATURE                 Location/Qualifiers
source                  1..29
                        mol_type = other DNA
                        organism = synthetic construct
SEQUENCE: 345
gctcttaaga ggtctaagaa gaaacttcc                                 29

SEQ ID NO: 346          moltype = DNA  length = 24
FEATURE                 Location/Qualifiers
source                  1..24
                        mol_type = other DNA
                        organism = synthetic construct
SEQUENCE: 346
cttccataga tgcttaccca gtgg                                      24

SEQ ID NO: 347          moltype = DNA  length = 25
FEATURE                 Location/Qualifiers
source                  1..25
                        mol_type = other DNA
                        organism = synthetic construct
SEQUENCE: 347
gcactgatgc aaaggaatgc tctgg                                     25

SEQ ID NO: 348          moltype = DNA  length = 28
FEATURE                 Location/Qualifiers
source                  1..28
                        mol_type = other DNA
                        organism = synthetic construct
SEQUENCE: 348
ggtttctctt ctggtgaact tcaaacac                                  28

SEQ ID NO: 349          moltype = DNA  length = 26
FEATURE                 Location/Qualifiers
source                  1..26
                        mol_type = other DNA
                        organism = synthetic construct
SEQUENCE: 349
gattcccagt gcctgacaca tactag                                    26

SEQ ID NO: 350          moltype = DNA  length = 24
FEATURE                 Location/Qualifiers
source                  1..24
                        mol_type = other DNA
                        organism = synthetic construct
SEQUENCE: 350
catggccaca gaagacattc tgcc                                      24

SEQ ID NO: 351          moltype = DNA  length = 25
FEATURE                 Location/Qualifiers
source                  1..25
                        mol_type = other DNA
                        organism = synthetic construct
SEQUENCE: 351
gggtgagcat tacataagca acctg                                     25

SEQ ID NO: 352          moltype = DNA  length = 26
FEATURE                 Location/Qualifiers
source                  1..26
                        mol_type = other DNA
                        organism = synthetic construct
```

```
SEQUENCE: 352
ggttctattc tggcccaggt agtcag                                26

SEQ ID NO: 353          moltype = DNA  length = 24
FEATURE                 Location/Qualifiers
source                  1..24
                        mol_type = other DNA
                        organism = synthetic construct
SEQUENCE: 353
gacctggtcc atccggttct gatg                                  24

SEQ ID NO: 354          moltype = DNA  length = 29
FEATURE                 Location/Qualifiers
source                  1..29
                        mol_type = other DNA
                        organism = synthetic construct
SEQUENCE: 354
ctttgttaca gcagctggaa cagaccaag                             29

SEQ ID NO: 355          moltype = DNA  length = 29
FEATURE                 Location/Qualifiers
source                  1..29
                        mol_type = other DNA
                        organism = synthetic construct
SEQUENCE: 355
gtttctgaca tttaagtggc attttgcag                             29

SEQ ID NO: 356          moltype = DNA  length = 24
FEATURE                 Location/Qualifiers
source                  1..24
                        mol_type = other DNA
                        organism = synthetic construct
SEQUENCE: 356
gatcagggaa ggtgcaatga aacc                                  24

SEQ ID NO: 357          moltype = DNA  length = 26
FEATURE                 Location/Qualifiers
source                  1..26
                        mol_type = other DNA
                        organism = synthetic construct
SEQUENCE: 357
gagaactcac taagtgacag ataccc                                26

SEQ ID NO: 358          moltype = DNA  length = 23
FEATURE                 Location/Qualifiers
source                  1..23
                        mol_type = other DNA
                        organism = synthetic construct
SEQUENCE: 358
gctgcccaca agaatcacct cag                                   23

SEQ ID NO: 359          moltype = DNA  length = 26
FEATURE                 Location/Qualifiers
source                  1..26
                        mol_type = other DNA
                        organism = synthetic construct
SEQUENCE: 359
gctcaaggga agactggaga atatgg                                26

SEQ ID NO: 360          moltype = DNA  length = 26
FEATURE                 Location/Qualifiers
source                  1..26
                        mol_type = other DNA
                        organism = synthetic construct
SEQUENCE: 360
gcctattgct agagttgcac tggaac                                26

SEQ ID NO: 361          moltype = DNA  length = 26
FEATURE                 Location/Qualifiers
source                  1..26
                        mol_type = other DNA
                        organism = synthetic construct
SEQUENCE: 361
gatgacagcc taggcaacac agcaag                                26

SEQ ID NO: 362          moltype = DNA  length = 33
FEATURE                 Location/Qualifiers
source                  1..33
                        mol_type = other DNA
```

```
                        organism = synthetic construct
SEQUENCE: 362
caagggaaaa tacttgatct taatttcaag ctc                                     33

SEQ ID NO: 363          moltype = DNA  length = 34
FEATURE                 Location/Qualifiers
source                  1..34
                        mol_type = other DNA
                        organism = synthetic construct
SEQUENCE: 363
ctacttatga catctgcaat aataccattt atcc                                    34

SEQ ID NO: 364          moltype = DNA  length = 28
FEATURE                 Location/Qualifiers
source                  1..28
                        mol_type = other DNA
                        organism = synthetic construct
SEQUENCE: 364
gagtaggcta tccaaaactc aatttgag                                           28

SEQ ID NO: 365          moltype = DNA  length = 31
FEATURE                 Location/Qualifiers
source                  1..31
                        mol_type = other DNA
                        organism = synthetic construct
SEQUENCE: 365
caactctttc gactatatct ctgtgaatga c                                       31

SEQ ID NO: 366          moltype = DNA  length = 26
FEATURE                 Location/Qualifiers
source                  1..26
                        mol_type = other DNA
                        organism = synthetic construct
SEQUENCE: 366
ggagctagaa taagcctaag gtaacc                                             26

SEQ ID NO: 367          moltype = DNA  length = 29
FEATURE                 Location/Qualifiers
source                  1..29
                        mol_type = other DNA
                        organism = synthetic construct
SEQUENCE: 367
gtaccatgtc aactcaaata atcagagtg                                          29

SEQ ID NO: 368          moltype = DNA  length = 32
FEATURE                 Location/Qualifiers
source                  1..32
                        mol_type = other DNA
                        organism = synthetic construct
SEQUENCE: 368
caaatgttac tgaacaatac acatttccca ag                                      32

SEQ ID NO: 369          moltype = DNA  length = 25
FEATURE                 Location/Qualifiers
source                  1..25
                        mol_type = other DNA
                        organism = synthetic construct
SEQUENCE: 369
gcttattatg tgccaagcac tattc                                              25

SEQ ID NO: 370          moltype = DNA  length = 30
FEATURE                 Location/Qualifiers
source                  1..30
                        mol_type = other DNA
                        organism = synthetic construct
SEQUENCE: 370
ctcatgtaat caatcattca ctaaccactc                                         30

SEQ ID NO: 371          moltype = DNA  length = 24
FEATURE                 Location/Qualifiers
source                  1..24
                        mol_type = other DNA
                        organism = synthetic construct
SEQUENCE: 371
ggcctaatcg tggctaaata ttgg                                               24

SEQ ID NO: 372          moltype = DNA  length = 27
FEATURE                 Location/Qualifiers
source                  1..27
```

```
                        mol_type = other DNA
                        organism = synthetic construct
SEQUENCE: 372
gctgtccatg ctacacaagt ggagttc                                       27

SEQ ID NO: 373          moltype = DNA  length = 23
FEATURE                 Location/Qualifiers
source                  1..23
                        mol_type = other DNA
                        organism = synthetic construct
SEQUENCE: 373
gtggtccttg ttcctctgca tac                                           23

SEQ ID NO: 374          moltype = DNA  length = 25
FEATURE                 Location/Qualifiers
source                  1..25
                        mol_type = other DNA
                        organism = synthetic construct
SEQUENCE: 374
gttgactgta aggttgaatt tgccc                                         25

SEQ ID NO: 375          moltype = DNA  length = 29
FEATURE                 Location/Qualifiers
source                  1..29
                        mol_type = other DNA
                        organism = synthetic construct
SEQUENCE: 375
gctgcgtcta aaagcatcac tgtgaactg                                     29

SEQ ID NO: 376          moltype = DNA  length = 26
FEATURE                 Location/Qualifiers
source                  1..26
                        mol_type = other DNA
                        organism = synthetic construct
SEQUENCE: 376
cctgcaaggg ccattatcac ctggag                                        26

SEQ ID NO: 377          moltype = DNA  length = 29
FEATURE                 Location/Qualifiers
source                  1..29
                        mol_type = other DNA
                        organism = synthetic construct
SEQUENCE: 377
gcggtgagtg ttacagctca taaaagcag                                     29

SEQ ID NO: 378          moltype = DNA  length = 30
FEATURE                 Location/Qualifiers
source                  1..30
                        mol_type = other DNA
                        organism = synthetic construct
SEQUENCE: 378
catcttaaat tcgaactcta ttaaatggtg                                    30

SEQ ID NO: 379          moltype = DNA  length = 31
FEATURE                 Location/Qualifiers
source                  1..31
                        mol_type = other DNA
                        organism = synthetic construct
SEQUENCE: 379
gatatatttg tatactcatg ttcatagaag c                                  31

SEQ ID NO: 380          moltype = DNA  length = 27
FEATURE                 Location/Qualifiers
source                  1..27
                        mol_type = other DNA
                        organism = synthetic construct
SEQUENCE: 380
gtgtatcacc taaaggcctt cagattc                                       27

SEQ ID NO: 381          moltype = DNA  length = 26
FEATURE                 Location/Qualifiers
source                  1..26
                        mol_type = other DNA
                        organism = synthetic construct
SEQUENCE: 381
ccaggtatga tgccatggat ctttgg                                        26

SEQ ID NO: 382          moltype = DNA  length = 25
FEATURE                 Location/Qualifiers
```

```
source                 1..25
                       mol_type = other DNA
                       organism = synthetic construct
SEQUENCE: 382
ccagcctggg caacaagaat gaaac                                    25

SEQ ID NO: 383         moltype = DNA  length = 26
FEATURE                Location/Qualifiers
source                 1..26
                       mol_type = other DNA
                       organism = synthetic construct
SEQUENCE: 383
gagattcatc ctgggggatt catggc                                   26

SEQ ID NO: 384         moltype = DNA  length = 26
FEATURE                Location/Qualifiers
source                 1..26
                       mol_type = other DNA
                       organism = synthetic construct
SEQUENCE: 384
gtggtgaatg gatacgccag ttccag                                   26

SEQ ID NO: 385         moltype = DNA  length = 27
FEATURE                Location/Qualifiers
source                 1..27
                       mol_type = other DNA
                       organism = synthetic construct
SEQUENCE: 385
ccgtcctaga ataaacatag ccatcag                                  27

SEQ ID NO: 386         moltype = DNA  length = 23
FEATURE                Location/Qualifiers
source                 1..23
                       mol_type = other DNA
                       organism = synthetic construct
SEQUENCE: 386
ctttgggctg actctgtggg aag                                      23

SEQ ID NO: 387         moltype = DNA  length = 33
FEATURE                Location/Qualifiers
source                 1..33
                       mol_type = other DNA
                       organism = synthetic construct
SEQUENCE: 387
cctcatctga aaggcagagt agtaataatt atg                           33

SEQ ID NO: 388         moltype = DNA  length = 26
FEATURE                Location/Qualifiers
source                 1..26
                       mol_type = other DNA
                       organism = synthetic construct
SEQUENCE: 388
gagatcaacc atgcctactt gtctcc                                   26

SEQ ID NO: 389         moltype = DNA  length = 25
FEATURE                Location/Qualifiers
source                 1..25
                       mol_type = other DNA
                       organism = synthetic construct
SEQUENCE: 389
gcagtactgt ttctgtggtt cccag                                    25

SEQ ID NO: 390         moltype = DNA  length = 29
FEATURE                Location/Qualifiers
source                 1..29
                       mol_type = other DNA
                       organism = synthetic construct
SEQUENCE: 390
gacacagcta aaccatatta actagctac                                29

SEQ ID NO: 391         moltype = DNA  length = 29
FEATURE                Location/Qualifiers
source                 1..29
                       mol_type = other DNA
                       organism = synthetic construct
SEQUENCE: 391
cagaaaccac aggggtaagc tcttaaaag                                29

SEQ ID NO: 392         moltype = DNA  length = 32
```

```
FEATURE                Location/Qualifiers
source                 1..32
                       mol_type = other DNA
                       organism = synthetic construct
SEQUENCE: 392
cttttaatag tttgaattct gtttggcttc tg                                  32

SEQ ID NO: 393         moltype = DNA  length = 25
FEATURE                Location/Qualifiers
source                 1..25
                       mol_type = other DNA
                       organism = synthetic construct
SEQUENCE: 393
gtgccaaggt tctttcaagt ggttg                                          25

SEQ ID NO: 394         moltype = DNA  length = 25
FEATURE                Location/Qualifiers
source                 1..25
                       mol_type = other DNA
                       organism = synthetic construct
SEQUENCE: 394
catgaataag ccctgggtcc accag                                          25

SEQ ID NO: 395         moltype = DNA  length = 22
FEATURE                Location/Qualifiers
source                 1..22
                       mol_type = other DNA
                       organism = synthetic construct
SEQUENCE: 395
ttctcctaaa ttccatcgta cc                                             22

SEQ ID NO: 396         moltype = DNA  length = 21
FEATURE                Location/Qualifiers
source                 1..21
                       mol_type = other DNA
                       organism = synthetic construct
SEQUENCE: 396
cccagaactt gggatacaaa c                                              21

SEQ ID NO: 397         moltype = DNA  length = 21
FEATURE                Location/Qualifiers
source                 1..21
                       mol_type = other DNA
                       organism = synthetic construct
SEQUENCE: 397
tgctcaaggt cacatcaata g                                              21

SEQ ID NO: 398         moltype = DNA  length = 21
FEATURE                Location/Qualifiers
source                 1..21
                       mol_type = other DNA
                       organism = synthetic construct
SEQUENCE: 398
catatgggca acgagaattt g                                              21

SEQ ID NO: 399         moltype = DNA  length = 22
FEATURE                Location/Qualifiers
source                 1..22
                       mol_type = other DNA
                       organism = synthetic construct
SEQUENCE: 399
ccctcagatg aacaactaac ag                                             22

SEQ ID NO: 400         moltype = DNA  length = 22
FEATURE                Location/Qualifiers
source                 1..22
                       mol_type = other DNA
                       organism = synthetic construct
SEQUENCE: 400
acctcactgg atgttgtaaa tg                                             22

SEQ ID NO: 401         moltype = DNA  length = 21
FEATURE                Location/Qualifiers
source                 1..21
                       mol_type = other DNA
                       organism = synthetic construct
SEQUENCE: 401
atgtttggca ttggaatgaa g                                              21
```

```
SEQ ID NO: 402          moltype = DNA  length = 20
FEATURE                 Location/Qualifiers
source                  1..20
                        mol_type = other DNA
                        organism = synthetic construct
SEQUENCE: 402
tctcagtaca gggaggtaac                                              20

SEQ ID NO: 403          moltype = DNA  length = 21
FEATURE                 Location/Qualifiers
source                  1..21
                        mol_type = other DNA
                        organism = synthetic construct
SEQUENCE: 403
caggagaagt gggtaaagaa g                                            21

SEQ ID NO: 404          moltype = DNA  length = 17
FEATURE                 Location/Qualifiers
source                  1..17
                        mol_type = other DNA
                        organism = synthetic construct
SEQUENCE: 404
atcacgccat tgcactc                                                 17

SEQ ID NO: 405          moltype = DNA  length = 17
FEATURE                 Location/Qualifiers
source                  1..17
                        mol_type = other DNA
                        organism = synthetic construct
SEQUENCE: 405
caggaggatc gcttgag                                                 17

SEQ ID NO: 406          moltype = DNA  length = 23
FEATURE                 Location/Qualifiers
source                  1..23
                        mol_type = other DNA
                        organism = synthetic construct
SEQUENCE: 406
tctcctcaga gagactataa acc                                          23

SEQ ID NO: 407          moltype = DNA  length = 23
FEATURE                 Location/Qualifiers
source                  1..23
                        mol_type = other DNA
                        organism = synthetic construct
SEQUENCE: 407
catcactaat catcagggaa atg                                          23

SEQ ID NO: 408          moltype = DNA  length = 18
FEATURE                 Location/Qualifiers
source                  1..18
                        mol_type = other DNA
                        organism = synthetic construct
SEQUENCE: 408
taaatgcagg ctgtggtg                                                18

SEQ ID NO: 409          moltype = DNA  length = 22
FEATURE                 Location/Qualifiers
source                  1..22
                        mol_type = other DNA
                        organism = synthetic construct
SEQUENCE: 409
aactgaatac acagtgagaa gg                                           22

SEQ ID NO: 410          moltype = DNA  length = 25
FEATURE                 Location/Qualifiers
source                  1..25
                        mol_type = other DNA
                        organism = synthetic construct
SEQUENCE: 410
tgactagtta ttgggtccta ttatg                                        25

SEQ ID NO: 411          moltype = DNA  length = 20
FEATURE                 Location/Qualifiers
source                  1..20
                        mol_type = other DNA
                        organism = synthetic construct
SEQUENCE: 411
gcatacctcc caaagagaac                                              20
```

```
SEQ ID NO: 412          moltype = DNA  length = 21
FEATURE                 Location/Qualifiers
source                  1..21
                        mol_type = other DNA
                        organism = synthetic construct
SEQUENCE: 412
gaaccaatct cccacagata c                                              21

SEQ ID NO: 413          moltype = DNA  length = 22
FEATURE                 Location/Qualifiers
source                  1..22
                        mol_type = other DNA
                        organism = synthetic construct
SEQUENCE: 413
tgtttgtgta ggatgcaaag tg                                             22

SEQ ID NO: 414          moltype = DNA  length = 17
FEATURE                 Location/Qualifiers
source                  1..17
                        mol_type = other DNA
                        organism = synthetic construct
SEQUENCE: 414
ctcagcctcc caagaag                                                   17

SEQ ID NO: 415          moltype = DNA  length = 20
FEATURE                 Location/Qualifiers
source                  1..20
                        mol_type = other DNA
                        organism = synthetic construct
SEQUENCE: 415
gtgcatgacc aagagaagac                                                20

SEQ ID NO: 416          moltype = DNA  length = 20
FEATURE                 Location/Qualifiers
source                  1..20
                        mol_type = other DNA
                        organism = synthetic construct
SEQUENCE: 416
cttgacctca agtgatcctc                                                20

SEQ ID NO: 417          moltype = DNA  length = 24
FEATURE                 Location/Qualifiers
source                  1..24
                        mol_type = other DNA
                        organism = synthetic construct
SEQUENCE: 417
agtattctcg tcttacatat gctg                                           24

SEQ ID NO: 418          moltype = DNA  length = 21
FEATURE                 Location/Qualifiers
source                  1..21
                        mol_type = other DNA
                        organism = synthetic construct
SEQUENCE: 418
ccatgatcca ctcttaattt c                                              21

SEQ ID NO: 419          moltype = DNA  length = 22
FEATURE                 Location/Qualifiers
source                  1..22
                        mol_type = other DNA
                        organism = synthetic construct
SEQUENCE: 419
aactgtttct ttgcctttct tc                                             22

SEQ ID NO: 420          moltype = DNA  length = 19
FEATURE                 Location/Qualifiers
source                  1..19
                        mol_type = other DNA
                        organism = synthetic construct
SEQUENCE: 420
accacactca gcctgttag                                                 19

SEQ ID NO: 421          moltype = DNA  length = 24
FEATURE                 Location/Qualifiers
source                  1..24
                        mol_type = other DNA
                        organism = synthetic construct
SEQUENCE: 421
```

```
ccaagttaag cttagagagt acat                                         24

SEQ ID NO: 422         moltype = DNA  length = 22
FEATURE                Location/Qualifiers
source                 1..22
                       mol_type = other DNA
                       organism = synthetic construct
SEQUENCE: 422
cccattgttt gtctggtata ga                                           22

SEQ ID NO: 423         moltype = DNA  length = 20
FEATURE                Location/Qualifiers
source                 1..20
                       mol_type = other DNA
                       organism = synthetic construct
SEQUENCE: 423
ggcatgggcc aataaataga                                              20

SEQ ID NO: 424         moltype = DNA  length = 20
FEATURE                Location/Qualifiers
source                 1..20
                       mol_type = other DNA
                       organism = synthetic construct
SEQUENCE: 424
ccatggttgg acttccatta                                              20

SEQ ID NO: 425         moltype = DNA  length = 21
FEATURE                Location/Qualifiers
source                 1..21
                       mol_type = other DNA
                       organism = synthetic construct
SEQUENCE: 425
gtgcctacat ccactacata c                                            21

SEQ ID NO: 426         moltype = DNA  length = 21
FEATURE                Location/Qualifiers
source                 1..21
                       mol_type = other DNA
                       organism = synthetic construct
SEQUENCE: 426
tctacagtac agatggagac a                                            21

SEQ ID NO: 427         moltype = DNA  length = 21
FEATURE                Location/Qualifiers
source                 1..21
                       mol_type = other DNA
                       organism = synthetic construct
SEQUENCE: 427
cacatcttga aggttctgtg a                                            21

SEQ ID NO: 428         moltype = DNA  length = 21
FEATURE                Location/Qualifiers
source                 1..21
                       mol_type = other DNA
                       organism = synthetic construct
SEQUENCE: 428
gcttgtcact gtcctactat t                                            21

SEQ ID NO: 429         moltype = DNA  length = 21
FEATURE                Location/Qualifiers
source                 1..21
                       mol_type = other DNA
                       organism = synthetic construct
SEQUENCE: 429
aacccttgtg aatgggatta g                                            21

SEQ ID NO: 430         moltype = DNA  length = 19
FEATURE                Location/Qualifiers
source                 1..19
                       mol_type = other DNA
                       organism = synthetic construct
SEQUENCE: 430
gacagggcaa acagaagag                                               19

SEQ ID NO: 431         moltype = DNA  length = 19
FEATURE                Location/Qualifiers
source                 1..19
                       mol_type = other DNA
                       organism = synthetic construct
```

```
SEQUENCE: 431
gagggaagga gtcgagaat                                           19

SEQ ID NO: 432          moltype = DNA  length = 17
FEATURE                 Location/Qualifiers
source                  1..17
                        mol_type = other DNA
                        organism = synthetic construct
SEQUENCE: 432
agcctggaca ccaagag                                             17

SEQ ID NO: 433          moltype = DNA  length = 22
FEATURE                 Location/Qualifiers
source                  1..22
                        mol_type = other DNA
                        organism = synthetic construct
SEQUENCE: 433
gcacttcgta aatatctgct tg                                       22

SEQ ID NO: 434          moltype = DNA  length = 24
FEATURE                 Location/Qualifiers
source                  1..24
                        mol_type = other DNA
                        organism = synthetic construct
SEQUENCE: 434
tgtatcattt atgtcagact cctg                                     24

SEQ ID NO: 435          moltype = DNA  length = 24
FEATURE                 Location/Qualifiers
source                  1..24
                        mol_type = other DNA
                        organism = synthetic construct
SEQUENCE: 435
agaaatcaag aggagtatat gacc                                     24

SEQ ID NO: 436          moltype = DNA  length = 19
FEATURE                 Location/Qualifiers
source                  1..19
                        mol_type = other DNA
                        organism = synthetic construct
SEQUENCE: 436
agacggaagt tgcaatgag                                           19

SEQ ID NO: 437          moltype = DNA  length = 21
FEATURE                 Location/Qualifiers
source                  1..21
                        mol_type = other DNA
                        organism = synthetic construct
SEQUENCE: 437
tgaactctga cttaccctga g                                        21

SEQ ID NO: 438          moltype = DNA  length = 21
FEATURE                 Location/Qualifiers
source                  1..21
                        mol_type = other DNA
                        organism = synthetic construct
SEQUENCE: 438
cagatcatgt agagcctgat g                                        21

SEQ ID NO: 439          moltype = DNA  length = 21
FEATURE                 Location/Qualifiers
source                  1..21
                        mol_type = other DNA
                        organism = synthetic construct
SEQUENCE: 439
ctctcaaagt gctgggatta c                                        21

SEQ ID NO: 440          moltype = DNA  length = 23
FEATURE                 Location/Qualifiers
source                  1..23
                        mol_type = other DNA
                        organism = synthetic construct
SEQUENCE: 440
gaagcaatcg tttcatcata gtc                                      23

SEQ ID NO: 441          moltype = DNA  length = 19
FEATURE                 Location/Qualifiers
source                  1..19
                        mol_type = other DNA
```

```
                        organism = synthetic construct
SEQUENCE: 441
ctgaacgtaa ctgcctagc                                             19

SEQ ID NO: 442          moltype = DNA  length = 19
FEATURE                 Location/Qualifiers
source                  1..19
                        mol_type = other DNA
                        organism = synthetic construct
SEQUENCE: 442
agttgcagtg aggaaagac                                             19

SEQ ID NO: 443          moltype = DNA  length = 20
FEATURE                 Location/Qualifiers
source                  1..20
                        mol_type = other DNA
                        organism = synthetic construct
SEQUENCE: 443
ggcacttgga atccacatga                                            20

SEQ ID NO: 444          moltype = DNA  length = 20
FEATURE                 Location/Qualifiers
source                  1..20
                        mol_type = other DNA
                        organism = synthetic construct
SEQUENCE: 444
gcagcgtccg gagttggcac                                            20

SEQ ID NO: 445          moltype = DNA  length = 20
FEATURE                 Location/Qualifiers
source                  1..20
                        mol_type = other DNA
                        organism = synthetic construct
SEQUENCE: 445
agcacacagt cataaccaca                                            20

SEQ ID NO: 446          moltype = DNA  length = 20
FEATURE                 Location/Qualifiers
source                  1..20
                        mol_type = other DNA
                        organism = synthetic construct
SEQUENCE: 446
gccacagcca tgcccagtgg                                            20

SEQ ID NO: 447          moltype = DNA  length = 20
FEATURE                 Location/Qualifiers
source                  1..20
                        mol_type = other DNA
                        organism = synthetic construct
SEQUENCE: 447
actggctgga atctgccaag                                            20

SEQ ID NO: 448          moltype = DNA  length = 20
FEATURE                 Location/Qualifiers
source                  1..20
                        mol_type = other DNA
                        organism = synthetic construct
SEQUENCE: 448
ctgatcttga gttggtcctt                                            20

SEQ ID NO: 449          moltype = DNA  length = 20
FEATURE                 Location/Qualifiers
source                  1..20
                        mol_type = other DNA
                        organism = synthetic construct
SEQUENCE: 449
ttaggggcag ggaggaccta                                            20

SEQ ID NO: 450          moltype = DNA  length = 20
FEATURE                 Location/Qualifiers
source                  1..20
                        mol_type = other DNA
                        organism = synthetic construct
SEQUENCE: 450
ggaaatctca aattacaaca                                            20

SEQ ID NO: 451          moltype = DNA  length = 20
FEATURE                 Location/Qualifiers
source                  1..20
```

```
                        mol_type = other DNA
                        organism = synthetic construct
SEQUENCE: 451
aaatgtactg ttaacgaact                                              20

SEQ ID NO: 452          moltype = DNA  length = 20
FEATURE                 Location/Qualifiers
source                  1..20
                        mol_type = other DNA
                        organism = synthetic construct
SEQUENCE: 452
agtatatagg atataacttt                                              20

SEQ ID NO: 453          moltype = DNA  length = 20
FEATURE                 Location/Qualifiers
source                  1..20
                        mol_type = other DNA
                        organism = synthetic construct
SEQUENCE: 453
caagagtttg taaagtgctt                                              20

SEQ ID NO: 454          moltype = DNA  length = 20
FEATURE                 Location/Qualifiers
source                  1..20
                        mol_type = other DNA
                        organism = synthetic construct
SEQUENCE: 454
tccgcggctg ctagcagcgc                                              20

SEQ ID NO: 455          moltype = DNA  length = 20
FEATURE                 Location/Qualifiers
source                  1..20
                        mol_type = other DNA
                        organism = synthetic construct
SEQUENCE: 455
cgcggagtcc tccctgtgtg                                              20

SEQ ID NO: 456          moltype = DNA  length = 20
FEATURE                 Location/Qualifiers
source                  1..20
                        mol_type = other DNA
                        organism = synthetic construct
SEQUENCE: 456
gcgctcctcc gcgatggcgg                                              20

SEQ ID NO: 457          moltype = DNA  length = 20
FEATURE                 Location/Qualifiers
source                  1..20
                        mol_type = other DNA
                        organism = synthetic construct
SEQUENCE: 457
aggaggagga ggacgacgtt                                              20

SEQ ID NO: 458          moltype = DNA  length = 20
FEATURE                 Location/Qualifiers
source                  1..20
                        mol_type = other DNA
                        organism = synthetic construct
SEQUENCE: 458
aggggggaag ttcggagagc                                              20

SEQ ID NO: 459          moltype = DNA  length = 20
FEATURE                 Location/Qualifiers
source                  1..20
                        mol_type = other DNA
                        organism = synthetic construct
SEQUENCE: 459
atagtcttga ggaggagcgt                                              20

SEQ ID NO: 460          moltype = DNA  length = 20
FEATURE                 Location/Qualifiers
source                  1..20
                        mol_type = other DNA
                        organism = synthetic construct
SEQUENCE: 460
aaaaacacag gaaccagttc                                              20

SEQ ID NO: 461          moltype = DNA  length = 20
FEATURE                 Location/Qualifiers
```

```
source                  1..20
                        mol_type = other DNA
                        organism = synthetic construct
SEQUENCE: 461
atctttgtct gactacctgc                                             20

SEQ ID NO: 462          moltype = DNA  length = 20
FEATURE                 Location/Qualifiers
source                  1..20
                        mol_type = other DNA
                        organism = synthetic construct
SEQUENCE: 462
aatttggctc gtccaaactg                                             20

SEQ ID NO: 463          moltype = DNA  length = 20
FEATURE                 Location/Qualifiers
source                  1..20
                        mol_type = other DNA
                        organism = synthetic construct
SEQUENCE: 463
acagcttcta ctcttaggtc                                             20

SEQ ID NO: 464          moltype = DNA  length = 20
FEATURE                 Location/Qualifiers
source                  1..20
                        mol_type = other DNA
                        organism = synthetic construct
SEQUENCE: 464
gatatagtga agtccaacaa                                             20

SEQ ID NO: 465          moltype = DNA  length = 20
FEATURE                 Location/Qualifiers
source                  1..20
                        mol_type = other DNA
                        organism = synthetic construct
SEQUENCE: 465
tgtaggagaa tgtgcaagga                                             20

SEQ ID NO: 466          moltype = DNA  length = 20
FEATURE                 Location/Qualifiers
source                  1..20
                        mol_type = other DNA
                        organism = synthetic construct
SEQUENCE: 466
cacacactca gatggctaca                                             20

SEQ ID NO: 467          moltype = DNA  length = 20
FEATURE                 Location/Qualifiers
source                  1..20
                        mol_type = other DNA
                        organism = synthetic construct
SEQUENCE: 467
gttagagcac caggaaccac                                             20

SEQ ID NO: 468          moltype = DNA  length = 20
FEATURE                 Location/Qualifiers
source                  1..20
                        mol_type = other DNA
                        organism = synthetic construct
SEQUENCE: 468
gacctaaaat cattaacatc                                             20

SEQ ID NO: 469          moltype = DNA  length = 20
FEATURE                 Location/Qualifiers
source                  1..20
                        mol_type = other DNA
                        organism = synthetic construct
SEQUENCE: 469
gcactgcctt gacaaatcaa                                             20

SEQ ID NO: 470          moltype = DNA  length = 20
FEATURE                 Location/Qualifiers
source                  1..20
                        mol_type = other DNA
                        organism = synthetic construct
SEQUENCE: 470
cttacctgga tatagtcaac                                             20

SEQ ID NO: 471          moltype = DNA  length = 20
```

```
FEATURE                 Location/Qualifiers
source                  1..20
                        mol_type = other DNA
                        organism = synthetic construct
SEQUENCE: 471
aaccacggca ttgagaggtg                                              20

SEQ ID NO: 472          moltype = DNA  length = 20
FEATURE                 Location/Qualifiers
source                  1..20
                        mol_type = other DNA
                        organism = synthetic construct
SEQUENCE: 472
tacatggtat agtgtttatt                                              20

SEQ ID NO: 473          moltype = DNA  length = 20
FEATURE                 Location/Qualifiers
source                  1..20
                        mol_type = other DNA
                        organism = synthetic construct
SEQUENCE: 473
gggcagaagt tgctgtcctg                                              20

SEQ ID NO: 474          moltype = DNA  length = 45
FEATURE                 Location/Qualifiers
source                  1..45
                        mol_type = other DNA
                        organism = synthetic construct
SEQUENCE: 474
ccatctcatc cctgcgtgtc tcctgaagtc cagacatttt gttgc                  45

SEQ ID NO: 475          moltype = DNA  length = 46
FEATURE                 Location/Qualifiers
source                  1..46
                        mol_type = other DNA
                        organism = synthetic construct
SEQUENCE: 475
ccatctcatc cctgcgtgtc tccaggaaga gagaccagag ttagca                 46

SEQ ID NO: 476          moltype = DNA  length = 43
FEATURE                 Location/Qualifiers
source                  1..43
                        mol_type = other DNA
                        organism = synthetic construct
SEQUENCE: 476
ccatctcatc cctgcgtgtc tccgctggca cattttagtg caa                    43

SEQ ID NO: 477          moltype = DNA  length = 46
FEATURE                 Location/Qualifiers
source                  1..46
                        mol_type = other DNA
                        organism = synthetic construct
SEQUENCE: 477
ccatctcatc cctgcgtgtc tcctgcttgt tttataggcc aagtct                 46

SEQ ID NO: 478          moltype = DNA  length = 43
FEATURE                 Location/Qualifiers
source                  1..43
                        mol_type = other DNA
                        organism = synthetic construct
SEQUENCE: 478
ccatctcatc cctgcgtgtc tcccatgagt tcaccccttc cag                    43

SEQ ID NO: 479          moltype = DNA  length = 43
FEATURE                 Location/Qualifiers
source                  1..43
                        mol_type = other DNA
                        organism = synthetic construct
SEQUENCE: 479
ccatctcatc cctgcgtgtc tcccccccaa ttcaattatc tcc                    43

SEQ ID NO: 480          moltype = DNA  length = 43
FEATURE                 Location/Qualifiers
source                  1..43
                        mol_type = other DNA
                        organism = synthetic construct
SEQUENCE: 480
ccatctcatc cctgcgtgtc tcctagtgca ccacagcttc acc                    43
```

```
SEQ ID NO: 481         moltype = DNA  length = 50
FEATURE                Location/Qualifiers
source                 1..50
                       mol_type = other DNA
                       organism = synthetic construct
SEQUENCE: 481
ccatctcatc cctgcgtgtc tccgaaataa ctcagaacaa aacctaatca            50

SEQ ID NO: 482         moltype = DNA  length = 43
FEATURE                Location/Qualifiers
source                 1..43
                       mol_type = other DNA
                       organism = synthetic construct
SEQUENCE: 482
ccatctcatc cctgcgtgtc tcctctgtcc gattgctagt tcg                   43

SEQ ID NO: 483         moltype = DNA  length = 43
FEATURE                Location/Qualifiers
source                 1..43
                       mol_type = other DNA
                       organism = synthetic construct
SEQUENCE: 483
ccatctcatc cctgcgtgtc tccgcaagta tgcccagttc gtt                   43

SEQ ID NO: 484         moltype = DNA  length = 43
FEATURE                Location/Qualifiers
source                 1..43
                       mol_type = other DNA
                       organism = synthetic construct
SEQUENCE: 484
ccatctcatc cctgcgtgtc tcccggtttg ctctctgttg ctt                   43

SEQ ID NO: 485         moltype = DNA  length = 43
FEATURE                Location/Qualifiers
source                 1..43
                       mol_type = other DNA
                       organism = synthetic construct
SEQUENCE: 485
ccatctcatc cctgcgtgtc tccagcccct tcatcaccct aaa                   43

SEQ ID NO: 486         moltype = DNA  length = 44
FEATURE                Location/Qualifiers
source                 1..44
                       mol_type = other DNA
                       organism = synthetic construct
SEQUENCE: 486
ccatctcatc cctgcgtgtc tccccctaaa agctaggctg ggta                  44

SEQ ID NO: 487         moltype = DNA  length = 41
FEATURE                Location/Qualifiers
source                 1..41
                       mol_type = other DNA
                       organism = synthetic construct
SEQUENCE: 487
ccatctcatc cctgcgtgtc tccactctgg cgactccgat g                     41

SEQ ID NO: 488         moltype = DNA  length = 43
FEATURE                Location/Qualifiers
source                 1..43
                       mol_type = other DNA
                       organism = synthetic construct
SEQUENCE: 488
ccatctcatc cctgcgtgtc tcccgacgga caaacatctc act                   43

SEQ ID NO: 489         moltype = DNA  length = 42
FEATURE                Location/Qualifiers
source                 1..42
                       mol_type = other DNA
                       organism = synthetic construct
SEQUENCE: 489
ccatctcatc cctgcgtgtc tccagggtcc tggtcacatg gt                    42

SEQ ID NO: 490         moltype = DNA  length = 43
FEATURE                Location/Qualifiers
source                 1..43
                       mol_type = other DNA
                       organism = synthetic construct
SEQUENCE: 490
ccatctcatc cctgcgtgtc tccctgggac agcaggagga tag                   43
```

```
SEQ ID NO: 491          moltype = DNA  length = 43
FEATURE                 Location/Qualifiers
source                  1..43
                        mol_type = other DNA
                        organism = synthetic construct
SEQUENCE: 491
ccatctcatc cctgcgtgtc tccctgggac agcaggagga tag                   43

SEQ ID NO: 492          moltype = DNA  length = 43
FEATURE                 Location/Qualifiers
source                  1..43
                        mol_type = other DNA
                        organism = synthetic construct
SEQUENCE: 492
ccatctcatc cctgcgtgtc tcccaggaag agacggagac aca                   43

SEQ ID NO: 493          moltype = DNA  length = 45
FEATURE                 Location/Qualifiers
source                  1..45
                        mol_type = other DNA
                        organism = synthetic construct
SEQUENCE: 493
ccatctcatc cctgcgtgtc tcccactaaa ttctggtgtg cgttt                 45

SEQ ID NO: 494          moltype = DNA  length = 42
FEATURE                 Location/Qualifiers
source                  1..42
                        mol_type = other DNA
                        organism = synthetic construct
SEQUENCE: 494
ccatctcatc cctgcgtgtc tccgcgctag caggagctgt tt                    42

SEQ ID NO: 495          moltype = DNA  length = 43
FEATURE                 Location/Qualifiers
source                  1..43
                        mol_type = other DNA
                        organism = synthetic construct
SEQUENCE: 495
ccatctcatc cctgcgtgtc tcctgagcag gaatggacac atc                   43

SEQ ID NO: 496          moltype = DNA  length = 41
FEATURE                 Location/Qualifiers
source                  1..41
                        mol_type = other DNA
                        organism = synthetic construct
SEQUENCE: 496
ccatctcatc cctgcgtgtc tccgccctgg ggacaagttc t                     41

SEQ ID NO: 497          moltype = DNA  length = 48
FEATURE                 Location/Qualifiers
source                  1..48
                        mol_type = other DNA
                        organism = synthetic construct
SEQUENCE: 497
ccatctcatc cctgcgtgtc tcccacacaa atctaatctc tgggatct              48

SEQ ID NO: 498          moltype = DNA  length = 43
FEATURE                 Location/Qualifiers
source                  1..43
                        mol_type = other DNA
                        organism = synthetic construct
SEQUENCE: 498
ccatctcatc cctgcgtgtc tcctttgtga gaccagccag aaa                   43

SEQ ID NO: 499          moltype = DNA  length = 44
FEATURE                 Location/Qualifiers
source                  1..44
                        mol_type = other DNA
                        organism = synthetic construct
SEQUENCE: 499
ccatctcatc cctgcgtgtc tcctggcctt tttagcactt gtca                  44

SEQ ID NO: 500          moltype = DNA  length = 46
FEATURE                 Location/Qualifiers
source                  1..46
                        mol_type = other DNA
                        organism = synthetic construct
SEQUENCE: 500
```

```
ccatctcatc cctgcgtgtc tcctttacat tttcacggat tacctg                46

SEQ ID NO: 501          moltype = DNA  length = 44
FEATURE                 Location/Qualifiers
source                  1..44
                        mol_type = other DNA
                        organism = synthetic construct
SEQUENCE: 501
ccatctcatc cctgcgtgtc tcctggttct tccgttgatt tgtc                  44

SEQ ID NO: 502          moltype = DNA  length = 44
FEATURE                 Location/Qualifiers
source                  1..44
                        mol_type = other DNA
                        organism = synthetic construct
SEQUENCE: 502
cctctctatg ggcagtcggt gatgctgtct tggccctatc ctca                  44

SEQ ID NO: 503          moltype = DNA  length = 44
FEATURE                 Location/Qualifiers
source                  1..44
                        mol_type = other DNA
                        organism = synthetic construct
SEQUENCE: 503
cctctctatg ggcagtcggt gatgtgggag atccaaggtt gaag                  44

SEQ ID NO: 504          moltype = DNA  length = 44
FEATURE                 Location/Qualifiers
source                  1..44
                        mol_type = other DNA
                        organism = synthetic construct
SEQUENCE: 504
cctctctatg ggcagtcggt gatggaccca tctcctttgg atga                  44

SEQ ID NO: 505          moltype = DNA  length = 43
FEATURE                 Location/Qualifiers
source                  1..43
                        mol_type = other DNA
                        organism = synthetic construct
SEQUENCE: 505
cctctctatg ggcagtcggt gatgggctgg atggtcctgt ctt                   43

SEQ ID NO: 506          moltype = DNA  length = 44
FEATURE                 Location/Qualifiers
source                  1..44
                        mol_type = other DNA
                        organism = synthetic construct
SEQUENCE: 506
cctctctatg ggcagtcggt gatgtatcag cagcgtgaaa atgg                  44

SEQ ID NO: 507          moltype = DNA  length = 44
FEATURE                 Location/Qualifiers
source                  1..44
                        mol_type = other DNA
                        organism = synthetic construct
SEQUENCE: 507
cctctctatg ggcagtcggt gatgtggagt ggagctgagt cttg                  44

SEQ ID NO: 508          moltype = DNA  length = 47
FEATURE                 Location/Qualifiers
source                  1..47
                        mol_type = other DNA
                        organism = synthetic construct
SEQUENCE: 508
cctctctatg ggcagtcggt gatgcaaagt tggcagctgg ttatatt               47

SEQ ID NO: 509          moltype = DNA  length = 45
FEATURE                 Location/Qualifiers
source                  1..45
                        mol_type = other DNA
                        organism = synthetic construct
SEQUENCE: 509
cctctctatg ggcagtcggt gatggcctta tgaccaggaa ccttt                 45

SEQ ID NO: 510          moltype = DNA  length = 44
FEATURE                 Location/Qualifiers
source                  1..44
                        mol_type = other DNA
                        organism = synthetic construct
```

```
SEQUENCE: 510
cctctctatg ggcagtcggt gatgtgggtg tcaaatctgg ttca                      44

SEQ ID NO: 511          moltype = DNA  length = 44
FEATURE                 Location/Qualifiers
source                  1..44
                        mol_type = other DNA
                        organism = synthetic construct
SEQUENCE: 511
cctctctatg ggcagtcggt gatgtttggc attacgttga gtcg                      44

SEQ ID NO: 512          moltype = DNA  length = 44
FEATURE                 Location/Qualifiers
source                  1..44
                        mol_type = other DNA
                        organism = synthetic construct
SEQUENCE: 512
cctctctatg ggcagtcggt gatgggaatg ctccgtggtc ataa                      44

SEQ ID NO: 513          moltype = DNA  length = 43
FEATURE                 Location/Qualifiers
source                  1..43
                        mol_type = other DNA
                        organism = synthetic construct
SEQUENCE: 513
cctctctatg ggcagtcggt gatggggttg taggcccagt ctc                       43

SEQ ID NO: 514          moltype = DNA  length = 43
FEATURE                 Location/Qualifiers
source                  1..43
                        mol_type = other DNA
                        organism = synthetic construct
SEQUENCE: 514
cctctctatg ggcagtcggt gatggggttg taggcccagt ctc                       43

SEQ ID NO: 515          moltype = DNA  length = 44
FEATURE                 Location/Qualifiers
source                  1..44
                        mol_type = other DNA
                        organism = synthetic construct
SEQUENCE: 515
cctctctatg ggcagtcggt gatgctgcgc agtgagatgt ttgt                      44

SEQ ID NO: 516          moltype = DNA  length = 44
FEATURE                 Location/Qualifiers
source                  1..44
                        mol_type = other DNA
                        organism = synthetic construct
SEQUENCE: 516
cctctctatg ggcagtcggt gatgtctctc actctccggc tctc                      44

SEQ ID NO: 517          moltype = DNA  length = 44
FEATURE                 Location/Qualifiers
source                  1..44
                        mol_type = other DNA
                        organism = synthetic construct
SEQUENCE: 517
cctctctatg ggcagtcggt gatgcacgct cctcctcaag acta                      44

SEQ ID NO: 518          moltype = DNA  length = 46
FEATURE                 Location/Qualifiers
source                  1..46
                        mol_type = other DNA
                        organism = synthetic construct
SEQUENCE: 518
cctctctatg ggcagtcggt gatgaactct tcaagttgca ggcttc                    46

SEQ ID NO: 519          moltype = DNA  length = 46
FEATURE                 Location/Qualifiers
source                  1..46
                        mol_type = other DNA
                        organism = synthetic construct
SEQUENCE: 519
cctctctatg ggcagtcggt gatgaactct tcaagttgca ggcttc                    46

SEQ ID NO: 520          moltype = DNA  length = 48
FEATURE                 Location/Qualifiers
source                  1..48
                        mol_type = other DNA
```

```
                        organism = synthetic construct
SEQUENCE: 520
cctctctatg ggcagtcggt gatgctggaa agatctctga aatcaaaa              48

SEQ ID NO: 521          moltype = DNA  length = 47
FEATURE                 Location/Qualifiers
source                  1..47
                        mol_type = other DNA
                        organism = synthetic construct
SEQUENCE: 521
cctctctatg ggcagtcggt gatgaactgt tctgtgtctg cactgtc               47

SEQ ID NO: 522          moltype = DNA  length = 44
FEATURE                 Location/Qualifiers
source                  1..44
                        mol_type = other DNA
                        organism = synthetic construct
SEQUENCE: 522
cctctctatg ggcagtcggt gatgccggct catatctgct tctt                  44

SEQ ID NO: 523          moltype = DNA  length = 48
FEATURE                 Location/Qualifiers
source                  1..48
                        mol_type = other DNA
                        organism = synthetic construct
SEQUENCE: 523
cctctctatg ggcagtcggt gatggcatct ttgacaacaa agtgactc              48

SEQ ID NO: 524          moltype = DNA  length = 45
FEATURE                 Location/Qualifiers
source                  1..45
                        mol_type = other DNA
                        organism = synthetic construct
SEQUENCE: 524
cctctctatg ggcagtcggt gatgattttt cctcccactg ctctg                 45

SEQ ID NO: 525          moltype = DNA  length = 44
FEATURE                 Location/Qualifiers
source                  1..44
                        mol_type = other DNA
                        organism = synthetic construct
SEQUENCE: 525
cctctctatg ggcagtcggt gatgttctga ttgtggaccc ttca                  44

SEQ ID NO: 526          moltype = DNA  length = 44
FEATURE                 Location/Qualifiers
source                  1..44
                        mol_type = other DNA
                        organism = synthetic construct
SEQUENCE: 526
cctctctatg ggcagtcggt gatgtgctcc caagtccagt cttt                  44

SEQ ID NO: 527          moltype = DNA  length = 44
FEATURE                 Location/Qualifiers
source                  1..44
                        mol_type = other DNA
                        organism = synthetic construct
SEQUENCE: 527
cctctctatg ggcagtcggt gatgtcctat ttgagggagc aagg                  44

SEQ ID NO: 528          moltype = DNA  length = 44
FEATURE                 Location/Qualifiers
source                  1..44
                        mol_type = other DNA
                        organism = synthetic construct
SEQUENCE: 528
cctctctatg ggcagtcggt gatgagaggc gcaataagaa atgc                  44

SEQ ID NO: 529          moltype = DNA  length = 44
FEATURE                 Location/Qualifiers
source                  1..44
                        mol_type = other DNA
                        organism = synthetic construct
SEQUENCE: 529
cctctctatg ggcagtcggt gatggcagat ggaaagccag aaat                  44

SEQ ID NO: 530          moltype = DNA  length = 93
FEATURE                 Location/Qualifiers
source                  1..93
```

```
                        mol_type = other DNA
                        organism = synthetic construct
SEQUENCE: 530
aatgatacgg cgaccaccga gatctacact ctttccctac acgacgctct tccgatcttc  60
agaagtagag ccatctcatc cctgcgtgtc tcc                               93

SEQ ID NO: 531          moltype = DNA  length = 94
FEATURE                 Location/Qualifiers
source                  1..94
                        mol_type = other DNA
                        organism = synthetic construct
SEQUENCE: 531
aatgatacgg cgaccaccga gatctacact ctttccctac acgacgctct tccgatcttt  60
cagcatgctt accatctcat ccctgcgtgt ctcc                              94

SEQ ID NO: 532          moltype = DNA  length = 95
FEATURE                 Location/Qualifiers
source                  1..95
                        mol_type = other DNA
                        organism = synthetic construct
SEQUENCE: 532
aatgatacgg cgaccaccga gatctacact ctttccctac acgacgctct tccgatctat  60
tcaggcacat ctccatctca tccctgcgtg tctcc                             95

SEQ ID NO: 533          moltype = DNA  length = 96
FEATURE                 Location/Qualifiers
source                  1..96
                        mol_type = other DNA
                        organism = synthetic construct
SEQUENCE: 533
aatgatacgg cgaccaccga gatctacact ctttccctac acgacgctct tccgatctga  60
ttcagtgctc gacccatctc atccctgcgt gtctcc                            96

SEQ ID NO: 534          moltype = DNA  length = 97
FEATURE                 Location/Qualifiers
source                  1..97
                        mol_type = other DNA
                        organism = synthetic construct
SEQUENCE: 534
aatgatacgg cgaccaccga gatctacact ctttccctac acgacgctct tccgatctcg  60
attcagagca attcccatct catccctgcg tgtctcc                           97

SEQ ID NO: 535          moltype = DNA  length = 98
FEATURE                 Location/Qualifiers
source                  1..98
                        mol_type = other DNA
                        organism = synthetic construct
SEQUENCE: 535
aatgatacgg cgaccaccga gatctacact ctttccctac acgacgctct tccgatcttc  60
gattcagagt tgcttccatc tcatccctgc gtgtctcc                          98

SEQ ID NO: 536          moltype = DNA  length = 99
FEATURE                 Location/Qualifiers
source                  1..99
                        mol_type = other DNA
                        organism = synthetic construct
SEQUENCE: 536
aatgatacgg cgaccaccga gatctacact ctttccctac acgacgctct tccgatctat  60
cgattcagcc agttagccat ctcatccctg cgtgtctcc                         99

SEQ ID NO: 537          moltype = DNA  length = 100
FEATURE                 Location/Qualifiers
source                  1..100
                        mol_type = other DNA
                        organism = synthetic construct
SEQUENCE: 537
aatgatacgg cgaccaccga gatctacact ctttccctac acgacgctct tccgatctga  60
tcgattcagt tgagcctcca tctcatccct gcgtgtctcc                        100

SEQ ID NO: 538          moltype = DNA  length = 93
FEATURE                 Location/Qualifiers
source                  1..93
                        mol_type = other DNA
                        organism = synthetic construct
SEQUENCE: 538
aatgatacgg cgaccaccga gatctacact ctttccctac acgacgctct tccgatcttc  60
agacacgatc ccatctcatc cctgcgtgtc tcc                               93

SEQ ID NO: 539          moltype = DNA  length = 94
```

```
FEATURE                Location/Qualifiers
source                 1..94
                       mol_type = other DNA
                       organism = synthetic construct
SEQUENCE: 539
aatgatacgg cgaccaccga gatctacact ctttccctac acgacgctct tccgatcttt  60
cagggtccag accatctcat ccctgcgtgt ctcc                              94

SEQ ID NO: 540         moltype = DNA  length = 95
FEATURE                Location/Qualifiers
source                 1..95
                       mol_type = other DNA
                       organism = synthetic construct
SEQUENCE: 540
aatgatacgg cgaccaccga gatctacact ctttccctac acgacgctct tccgatctat  60
tcaggtataa caccatctca tccctgcgtg tctcc                             95

SEQ ID NO: 541         moltype = DNA  length = 96
FEATURE                Location/Qualifiers
source                 1..96
                       mol_type = other DNA
                       organism = synthetic construct
SEQUENCE: 541
aatgatacgg cgaccaccga gatctacact ctttccctac acgacgctct tccgatctga  60
ttcagttcgc tgaccatctc atccctgcgt gtctcc                            96

SEQ ID NO: 542         moltype = DNA  length = 97
FEATURE                Location/Qualifiers
source                 1..97
                       mol_type = other DNA
                       organism = synthetic construct
SEQUENCE: 542
aatgatacgg cgaccaccga gatctacact ctttccctac acgacgctct tccgatctcg  60
attcagaact tgacccatct catccctgcg tgtctcc                           97

SEQ ID NO: 543         moltype = DNA  length = 98
FEATURE                Location/Qualifiers
source                 1..98
                       mol_type = other DNA
                       organism = synthetic construct
SEQUENCE: 543
aatgatacgg cgaccaccga gatctacact ctttccctac acgacgctct tccgatcttc  60
gattcagcac atcctccatc tcatccctgc gtgtctcc                          98

SEQ ID NO: 544         moltype = DNA  length = 99
FEATURE                Location/Qualifiers
source                 1..99
                       mol_type = other DNA
                       organism = synthetic construct
SEQUENCE: 544
aatgatacgg cgaccaccga gatctacact ctttccctac acgacgctct tccgatctat  60
cgattcagtc ggaatgccat ctcatccctg cgtgtctcc                         99

SEQ ID NO: 545         moltype = DNA  length = 100
FEATURE                Location/Qualifiers
source                 1..100
                       mol_type = other DNA
                       organism = synthetic construct
SEQUENCE: 545
aatgatacgg cgaccaccga gatctacact ctttccctac acgacgctct tccgatctga  60
tcgattcaga acgcattcca tctcatccct gcgtgtctcc                        100

SEQ ID NO: 546         moltype = DNA  length = 93
FEATURE                Location/Qualifiers
source                 1..93
                       mol_type = other DNA
                       organism = synthetic construct
SEQUENCE: 546
aatgatacgg cgaccaccga gatctacact ctttccctac acgacgctct tccgatcttc  60
agcgcgcggt ccatctcatc cctgcgtgtc tcc                               93

SEQ ID NO: 547         moltype = DNA  length = 94
FEATURE                Location/Qualifiers
source                 1..94
                       mol_type = other DNA
                       organism = synthetic construct
SEQUENCE: 547
aatgatacgg cgaccaccga gatctacact ctttccctac acgacgctct tccgatcttt  60
cagtctggcg accatctcat ccctgcgtgt ctcc                              94
```

```
SEQ ID NO: 548          moltype = DNA  length = 95
FEATURE                 Location/Qualifiers
source                  1..95
                        mol_type = other DNA
                        organism = synthetic construct
SEQUENCE: 548
aatgatacgg cgaccaccga gatctacact ctttccctac acgacgctct tccgatctat  60
tcagcatagc gaccatctca tccctgcgtg tctcc                             95

SEQ ID NO: 549          moltype = DNA  length = 96
FEATURE                 Location/Qualifiers
source                  1..96
                        mol_type = other DNA
                        organism = synthetic construct
SEQUENCE: 549
aatgatacgg cgaccaccga gatctacact ctttccctac acgacgctct tccgatctga  60
ttcagcagga gccccatctc atccctgcgt gtctcc                            96

SEQ ID NO: 550          moltype = DNA  length = 97
FEATURE                 Location/Qualifiers
source                  1..97
                        mol_type = other DNA
                        organism = synthetic construct
SEQUENCE: 550
aatgatacgg cgaccaccga gatctacact ctttccctac acgacgctct tccgatctcg  60
attcagtgtc ggatccatct catccctgcg tgtctcc                           97

SEQ ID NO: 551          moltype = DNA  length = 98
FEATURE                 Location/Qualifiers
source                  1..98
                        mol_type = other DNA
                        organism = synthetic construct
SEQUENCE: 551
aatgatacgg cgaccaccga gatctacact ctttccctac acgacgctct tccgatcttc  60
gattcagatt atgttccatc tcatccctgc gtgtctcc                          98

SEQ ID NO: 552          moltype = DNA  length = 99
FEATURE                 Location/Qualifiers
source                  1..99
                        mol_type = other DNA
                        organism = synthetic construct
SEQUENCE: 552
aatgatacgg cgaccaccga gatctacact ctttccctac acgacgctct tccgatctat  60
cgattcagcc taccatccat ctcatccctg cgtgtctcc                         99

SEQ ID NO: 553          moltype = DNA  length = 100
FEATURE                 Location/Qualifiers
source                  1..100
                        mol_type = other DNA
                        organism = synthetic construct
SEQUENCE: 553
aatgatacgg cgaccaccga gatctacact ctttccctac acgacgctct tccgatctga  60
tcgattcagt acttagccca tctcatccct gcgtgtctcc                        100

SEQ ID NO: 554          moltype = DNA  length = 90
FEATURE                 Location/Qualifiers
source                  1..90
                        mol_type = other DNA
                        organism = synthetic construct
SEQUENCE: 554
caagcagaag acggcatacg agatcatgat cggtgactgg agttcagacg tgtgctcttc  60
cgatctcctc tctatgggca gtcggtgatg                                   90

SEQ ID NO: 555          moltype = DNA  length = 91
FEATURE                 Location/Qualifiers
source                  1..91
                        mol_type = other DNA
                        organism = synthetic construct
SEQUENCE: 555
caagcagaag acggcatacg agataggatc tagtgactgg agttcagacg tgtgctcttc  60
cgatcttcct ctctatgggc agtcggtgat g                                 91

SEQ ID NO: 556          moltype = DNA  length = 92
FEATURE                 Location/Qualifiers
source                  1..92
                        mol_type = other DNA
                        organism = synthetic construct
SEQUENCE: 556
```

```
caagcagaag acggcatacg agatgacagt aagtgactgg agttcagacg tgtgctcttc  60
cgatctatcc tctctatggg cagtcggtga tg                                92

SEQ ID NO: 557          moltype = DNA  length = 93
FEATURE                 Location/Qualifiers
source                  1..93
                        mol_type = other DNA
                        organism = synthetic construct
SEQUENCE: 557
caagcagaag acggcatacg agatcctatg ccgtgactgg agttcagacg tgtgctcttc  60
cgatctgatc ctctctatgg gcagtcggtg atg                               93

SEQ ID NO: 558          moltype = DNA  length = 94
FEATURE                 Location/Qualifiers
source                  1..94
                        mol_type = other DNA
                        organism = synthetic construct
SEQUENCE: 558
caagcagaag acggcatacg agattcgcct tggtgactgg agttcagacg tgtgctcttc  60
cgatctcgat cctctctatg ggcagtcggt gatg                              94

SEQ ID NO: 559          moltype = DNA  length = 95
FEATURE                 Location/Qualifiers
source                  1..95
                        mol_type = other DNA
                        organism = synthetic construct
SEQUENCE: 559
caagcagaag acggcatacg agatatagcg tcgtgactgg agttcagacg tgtgctcttc  60
cgatcttcga tcctctctat gggcagtcgg tgatg                             95

SEQ ID NO: 560          moltype = DNA  length = 96
FEATURE                 Location/Qualifiers
source                  1..96
                        mol_type = other DNA
                        organism = synthetic construct
SEQUENCE: 560
caagcagaag acggcatacg agatgaagaa gtgtgactgg agttcagacg tgtgctcttc  60
cgatctatcg atcctctcta tgggcagtcg gtgatg                            96

SEQ ID NO: 561          moltype = DNA  length = 97
FEATURE                 Location/Qualifiers
source                  1..97
                        mol_type = other DNA
                        organism = synthetic construct
SEQUENCE: 561
caagcagaag acggcatacg agatattcta gggtgactgg agttcagacg tgtgctcttc  60
cgatctgatc gatcctctct atgggcagtc ggtgatg                           97

SEQ ID NO: 562          moltype = DNA  length = 98
FEATURE                 Location/Qualifiers
source                  1..98
                        mol_type = other DNA
                        organism = synthetic construct
SEQUENCE: 562
caagcagaag acggcatacg agatcgttac cagtgactgg agttcagacg tgtgctcttc  60
cgatctcgat cgatcctctc tatgggcagt cggtgatg                          98

SEQ ID NO: 563          moltype = DNA  length = 99
FEATURE                 Location/Qualifiers
source                  1..99
                        mol_type = other DNA
                        organism = synthetic construct
SEQUENCE: 563
caagcagaag acggcatacg agatgtctga tggtgactgg agttcagacg tgtgctcttc  60
cgatcttcga tcgatcctct ctatgggcag tcggtgatg                         99

SEQ ID NO: 564          moltype = DNA  length = 100
FEATURE                 Location/Qualifiers
source                  1..100
                        mol_type = other DNA
                        organism = synthetic construct
SEQUENCE: 564
caagcagaag acggcatacg agatttacgc acgtgactgg agttcagacg tgtgctcttc  60
cgatctatcg atcgatcctc tctatgggca gtcggtgatg                        100

SEQ ID NO: 565          moltype = DNA  length = 90
FEATURE                 Location/Qualifiers
source                  1..90
                        mol_type = other DNA
```

```
                         organism = synthetic construct
SEQUENCE: 565
caagcagaag acggcatacg agatttgaat aggtgactgg agttcagacg tgtgctcttc  60
cgatctcctc tctatgggca gtcggtgatg                                    90

SEQ ID NO: 566           moltype = DNA  length = 91
FEATURE                  Location/Qualifiers
source                   1..91
                         mol_type = other DNA
                         organism = synthetic construct
SEQUENCE: 566
caagcagaag acggcatacg agattccttg gtgtgactgg agttcagacg tgtgctcttc  60
cgatcttcct ctctatgggc agtcggtgat g                                  91

SEQ ID NO: 567           moltype = DNA  length = 92
FEATURE                  Location/Qualifiers
source                   1..92
                         mol_type = other DNA
                         organism = synthetic construct
SEQUENCE: 567
caagcagaag acggcatacg agatacaggt atgtgactgg agttcagacg tgtgctcttc  60
cgatctatcc tctctatggg cagtcggtga tg                                 92

SEQ ID NO: 568           moltype = DNA  length = 93
FEATURE                  Location/Qualifiers
source                   1..93
                         mol_type = other DNA
                         organism = synthetic construct
SEQUENCE: 568
caagcagaag acggcatacg agataggtaa gggtgactgg agttcagacg tgtgctcttc  60
cgatctgatc ctctctatgg gcagtcggtg atg                                93

SEQ ID NO: 569           moltype = DNA  length = 94
FEATURE                  Location/Qualifiers
source                   1..94
                         mol_type = other DNA
                         organism = synthetic construct
SEQUENCE: 569
caagcagaag acggcatacg agataacaat gggtgactgg agttcagacg tgtgctcttc  60
cgatctcgat cctctctatg ggcagtcggt gatg                               94

SEQ ID NO: 570           moltype = DNA  length = 95
FEATURE                  Location/Qualifiers
source                   1..95
                         mol_type = other DNA
                         organism = synthetic construct
SEQUENCE: 570
caagcagaag acggcatacg agatactgta tcgtgactgg agttcagacg tgtgctcttc  60
cgatcttcga tcctctctat gggcagtcgg tgatg                              95

SEQ ID NO: 571           moltype = DNA  length = 96
FEATURE                  Location/Qualifiers
source                   1..96
                         mol_type = other DNA
                         organism = synthetic construct
SEQUENCE: 571
caagcagaag acggcatacg agataggtcg cagtgactgg agttcagacg tgtgctcttc  60
cgatctatcg atcctctcta tgggcagtcg gtgatg                             96

SEQ ID NO: 572           moltype = DNA  length = 97
FEATURE                  Location/Qualifiers
source                   1..97
                         mol_type = other DNA
                         organism = synthetic construct
SEQUENCE: 572
caagcagaag acggcatacg agataggtta tcgtgactgg agttcagacg tgtgctcttc  60
cgatctgatc gatcctctct atgggcagtc ggtgatg                            97

SEQ ID NO: 573           moltype = DNA  length = 98
FEATURE                  Location/Qualifiers
source                   1..98
                         mol_type = other DNA
                         organism = synthetic construct
SEQUENCE: 573
caagcagaag acggcatacg agatcaactc tcgtgactgg agttcagacg tgtgctcttc  60
cgatctcgat cgatcctctc tatgggcagt cggtgatg                           98

SEQ ID NO: 574           moltype = DNA  length = 99
FEATURE                  Location/Qualifiers
```

```
source                  1..99
                        mol_type = other DNA
                        organism = synthetic construct
SEQUENCE: 574
caagcagaag acggcatacg agatccaaca ttgtgactgg agttcagacg tgtgctcttc  60
cgatcttcga tcgatcctct ctatgggcag tcggtgatg                         99

SEQ ID NO: 575          moltype = DNA  length = 100
FEATURE                 Location/Qualifiers
source                  1..100
                        mol_type = other DNA
                        organism = synthetic construct
SEQUENCE: 575
caagcagaag acggcatacg agatctaact cggtgactgg agttcagacg tgtgctcttc  60
cgatctatcg atcgatcctc tctatgggca gtcggtgatg                        100

SEQ ID NO: 576          moltype = DNA  length = 90
FEATURE                 Location/Qualifiers
source                  1..90
                        mol_type = other DNA
                        organism = synthetic construct
SEQUENCE: 576
caagcagaag acggcatacg agatattcct ctgtgactgg agttcagacg tgtgctcttc  60
cgatctcctc tctatgggca gtcggtgatg                                   90

SEQ ID NO: 577          moltype = DNA  length = 91
FEATURE                 Location/Qualifiers
source                  1..91
                        mol_type = other DNA
                        organism = synthetic construct
SEQUENCE: 577
caagcagaag acggcatacg agatctacca gggtgactgg agttcagacg tgtgctcttc  60
cgatcttcct ctctatgggc agtcggtgat g                                 91

SEQ ID NO: 578          moltype = DNA  length = 20
FEATURE                 Location/Qualifiers
source                  1..20
                        mol_type = other DNA
                        organism = synthetic construct
SEQUENCE: 578
gcacttggaa tccacatgaa                                              20

SEQ ID NO: 579          moltype = DNA  length = 20
FEATURE                 Location/Qualifiers
source                  1..20
                        mol_type = other DNA
                        organism = synthetic construct
SEQUENCE: 579
atagcaaact cagccccatt                                              20

SEQ ID NO: 580          moltype = DNA  length = 20
FEATURE                 Location/Qualifiers
source                  1..20
                        mol_type = other DNA
                        organism = synthetic construct
SEQUENCE: 580
gctggcacat tttagtgcaa                                              20

SEQ ID NO: 581          moltype = DNA  length = 20
FEATURE                 Location/Qualifiers
source                  1..20
                        mol_type = other DNA
                        organism = synthetic construct
SEQUENCE: 581
gtgcaccgaa ttgaagacag                                              20

SEQ ID NO: 582          moltype = DNA  length = 20
FEATURE                 Location/Qualifiers
source                  1..20
                        mol_type = other DNA
                        organism = synthetic construct
SEQUENCE: 582
tagtgcacca cagcttcacc                                              20

SEQ ID NO: 583          moltype = DNA  length = 18
FEATURE                 Location/Qualifiers
source                  1..18
                        mol_type = other DNA
                        organism = synthetic construct
```

```
SEQUENCE: 583
ggctcggctc cctttatc                                              18

SEQ ID NO: 584         moltype = DNA  length = 20
FEATURE                Location/Qualifiers
source                 1..20
                       mol_type = other DNA
                       organism = synthetic construct
SEQUENCE: 584
tcctcctcct cctccttctc                                            20

SEQ ID NO: 585         moltype = DNA  length = 21
FEATURE                Location/Qualifiers
source                 1..21
                       mol_type = other DNA
                       organism = synthetic construct
SEQUENCE: 585
tgagagaggg aggaaaaagg a                                          21

SEQ ID NO: 586         moltype = DNA  length = 21
FEATURE                Location/Qualifiers
source                 1..21
                       mol_type = other DNA
                       organism = synthetic construct
SEQUENCE: 586
tccttgctga ttttgtgttc c                                          21

SEQ ID NO: 587         moltype = DNA  length = 20
FEATURE                Location/Qualifiers
source                 1..20
                       mol_type = other DNA
                       organism = synthetic construct
SEQUENCE: 587
tggttagagc accaggaacc                                            20

SEQ ID NO: 588         moltype = DNA  length = 20
FEATURE                Location/Qualifiers
source                 1..20
                       mol_type = other DNA
                       organism = synthetic construct
SEQUENCE: 588
gcaagtatgc ccagttcgtt                                            20

SEQ ID NO: 589         moltype = DNA  length = 20
FEATURE                Location/Qualifiers
source                 1..20
                       mol_type = other DNA
                       organism = synthetic construct
SEQUENCE: 589
gaggcaatcc tgcacaagag                                            20

SEQ ID NO: 590         moltype = DNA  length = 20
FEATURE                Location/Qualifiers
source                 1..20
                       mol_type = other DNA
                       organism = synthetic construct
SEQUENCE: 590
agccccttca tcaccctaaa                                            20

SEQ ID NO: 591         moltype = DNA  length = 20
FEATURE                Location/Qualifiers
source                 1..20
                       mol_type = other DNA
                       organism = synthetic construct
SEQUENCE: 591
gaaaccccac gtgaaaagtt                                            20

SEQ ID NO: 592         moltype = DNA  length = 19
FEATURE                Location/Qualifiers
source                 1..19
                       mol_type = other DNA
                       organism = synthetic construct
SEQUENCE: 592
agggtcctgg tcacatggt                                             19

SEQ ID NO: 593         moltype = DNA  length = 20
FEATURE                Location/Qualifiers
source                 1..20
                       mol_type = other DNA
```

```
                        organism = synthetic construct
SEQUENCE: 593
ctgggacagc aggaggatag                                            20

SEQ ID NO: 594          moltype = DNA  length = 20
FEATURE                 Location/Qualifiers
source                  1..20
                        mol_type = other DNA
                        organism = synthetic construct
SEQUENCE: 594
ccgaactggt tcctgtgttt                                            20

SEQ ID NO: 595          moltype = DNA  length = 20
FEATURE                 Location/Qualifiers
source                  1..20
                        mol_type = other DNA
                        organism = synthetic construct
SEQUENCE: 595
atgttgccca gaaactcctc                                            20

SEQ ID NO: 596          moltype = DNA  length = 20
FEATURE                 Location/Qualifiers
source                  1..20
                        mol_type = other DNA
                        organism = synthetic construct
SEQUENCE: 596
aatggaatgt gggcagaagt                                            20

SEQ ID NO: 597          moltype = DNA  length = 20
FEATURE                 Location/Qualifiers
source                  1..20
                        mol_type = other DNA
                        organism = synthetic construct
SEQUENCE: 597
actaaacagc atgcccttcc                                            20

SEQ ID NO: 598          moltype = DNA  length = 21
FEATURE                 Location/Qualifiers
source                  1..21
                        mol_type = other DNA
                        organism = synthetic construct
SEQUENCE: 598
gcatgagctt cagctctctc a                                          21

SEQ ID NO: 599          moltype = DNA  length = 20
FEATURE                 Location/Qualifiers
source                  1..20
                        mol_type = other DNA
                        organism = synthetic construct
SEQUENCE: 599
tcactgtctt ggccctatcc                                            20

SEQ ID NO: 600          moltype = DNA  length = 20
FEATURE                 Location/Qualifiers
source                  1..20
                        mol_type = other DNA
                        organism = synthetic construct
SEQUENCE: 600
gcatctggtg agagccttct                                            20

SEQ ID NO: 601          moltype = DNA  length = 20
FEATURE                 Location/Qualifiers
source                  1..20
                        mol_type = other DNA
                        organism = synthetic construct
SEQUENCE: 601
tggcaatcca ctcttcttca                                            20

SEQ ID NO: 602          moltype = DNA  length = 21
FEATURE                 Location/Qualifiers
source                  1..21
                        mol_type = other DNA
                        organism = synthetic construct
SEQUENCE: 602
tggctgtggc ttttatatgc t                                          21

SEQ ID NO: 603          moltype = DNA  length = 20
FEATURE                 Location/Qualifiers
source                  1..20
```

```
                        mol_type = other DNA
                        organism = synthetic construct
SEQUENCE: 603
gcccctctga aaagcacata                                            20

SEQ ID NO: 604          moltype = DNA  length = 20
FEATURE                 Location/Qualifiers
source                  1..20
                        mol_type = other DNA
                        organism = synthetic construct
SEQUENCE: 604
gagaaggagg aggaggagga                                            20

SEQ ID NO: 605          moltype = DNA  length = 20
FEATURE                 Location/Qualifiers
source                  1..20
                        mol_type = other DNA
                        organism = synthetic construct
SEQUENCE: 605
tctctcactc tccggctctc                                            20

SEQ ID NO: 606          moltype = DNA  length = 20
FEATURE                 Location/Qualifiers
source                  1..20
                        mol_type = other DNA
                        organism = synthetic construct
SEQUENCE: 606
atctgggcca ctcacagaac                                            20

SEQ ID NO: 607          moltype = DNA  length = 20
FEATURE                 Location/Qualifiers
source                  1..20
                        mol_type = other DNA
                        organism = synthetic construct
SEQUENCE: 607
cccctgtagc catctgagtg                                            20

SEQ ID NO: 608          moltype = DNA  length = 20
FEATURE                 Location/Qualifiers
source                  1..20
                        mol_type = other DNA
                        organism = synthetic construct
SEQUENCE: 608
cttcttgctc ccaagtccag                                            20

SEQ ID NO: 609          moltype = DNA  length = 20
FEATURE                 Location/Qualifiers
source                  1..20
                        mol_type = other DNA
                        organism = synthetic construct
SEQUENCE: 609
gtcgtaccct tgcgatgttt                                            20

SEQ ID NO: 610          moltype = DNA  length = 20
FEATURE                 Location/Qualifiers
source                  1..20
                        mol_type = other DNA
                        organism = synthetic construct
SEQUENCE: 610
ggaatgctcc gtggtcataa                                            20

SEQ ID NO: 611          moltype = DNA  length = 18
FEATURE                 Location/Qualifiers
source                  1..18
                        mol_type = other DNA
                        organism = synthetic construct
SEQUENCE: 611
cggagtcctc cctgtgtg                                              18

SEQ ID NO: 612          moltype = DNA  length = 19
FEATURE                 Location/Qualifiers
source                  1..19
                        mol_type = other DNA
                        organism = synthetic construct
SEQUENCE: 612
gggttgtagg cccagtctc                                             19

SEQ ID NO: 613          moltype = DNA  length = 21
FEATURE                 Location/Qualifiers
```

```
source                 1..21
                       mol_type = other DNA
                       organism = synthetic construct
SEQUENCE: 613
cgctcctcct caagactatc c                                                21

SEQ ID NO: 614         moltype = DNA  length = 20
FEATURE                Location/Qualifiers
source                 1..20
                       mol_type = other DNA
                       organism = synthetic construct
SEQUENCE: 614
ccacatgccc tagaaaaaca                                                  20

SEQ ID NO: 615         moltype = DNA  length = 20
FEATURE                Location/Qualifiers
source                 1..20
                       mol_type = other DNA
                       organism = synthetic construct
SEQUENCE: 615
ctgcagctaa ctcctgcaca                                                  20

SEQ ID NO: 616         moltype = DNA  length = 19
FEATURE                Location/Qualifiers
source                 1..19
                       mol_type = other DNA
                       organism = synthetic construct
SEQUENCE: 616
atttgactgg gccacaagg                                                   19

SEQ ID NO: 617         moltype = DNA  length = 20
FEATURE                Location/Qualifiers
source                 1..20
                       mol_type = other DNA
                       organism = synthetic construct
SEQUENCE: 617
caatggggga gaaaatctga                                                  20

SEQ ID NO: 618         moltype = DNA  length = 20
FEATURE                Location/Qualifiers
source                 1..20
                       mol_type = other DNA
                       organism = synthetic construct
SEQUENCE: 618
cctctccccc ttcaggatac                                                  20

SEQ ID NO: 619         moltype = DNA  length = 20
FEATURE                Location/Qualifiers
source                 1..20
                       mol_type = other DNA
                       organism = synthetic construct
SEQUENCE: 619
tcgcaattga actccatctc                                                  20

SEQ ID NO: 620         moltype = DNA  length = 51
FEATURE                Location/Qualifiers
source                 1..51
                       mol_type = other DNA
                       organism = Homo sapiens
SEQUENCE: 620
gtctgccagt cctcttctac cccacccacg cccccaccct aatcagaggc c               51

SEQ ID NO: 621         moltype = DNA  length = 72
FEATURE                Location/Qualifiers
source                 1..72
                       mol_type = other DNA
                       organism = Homo sapiens
SEQUENCE: 621
aaacccttcc tggagcctgt gataaaagca actgttagct tgcactagac tagcttcaaa  60
gttgtattga cc                                                          72

SEQ ID NO: 622         moltype = DNA  length = 123
FEATURE                Location/Qualifiers
source                 1..123
                       mol_type = other DNA
                       organism = Homo sapiens
SEQUENCE: 622
gtctgccagt cctcttctac cccacccacg cccccaccct aatcagaggc caaacccttc  60
ctggagcctg tgataaaagc aactgttagc ttgcactaga ctagcttcaa agttgtattg  120
```

```
acc                                                              123

SEQ ID NO: 623          moltype = DNA  length = 123
FEATURE                 Location/Qualifiers
source                  1..123
                        mol_type = other DNA
                        organism = Pan sp.
SEQUENCE: 623
gtctgccagt cctcttctac cccacccacg cccccaccct aatcagaggc caaacccttc  60
ctggagcctg tgataaaagc aactgttagc ttgcactaga ctagcttcaa agttgtattg  120
acc                                                              123

SEQ ID NO: 624          moltype = DNA  length = 123
FEATURE                 Location/Qualifiers
source                  1..123
                        mol_type = other DNA
                        organism = Gorilla sp.
SEQUENCE: 624
gtctgccagt cctcttctac cccacccacg cccccaccct aatcagaggc caaacccttc  60
ctggagcctg tgataaaggc aactgttagc ttgcactaga ctagcttcaa agttgtattg  120
acc                                                              123

SEQ ID NO: 625          moltype = DNA  length = 123
FEATURE                 Location/Qualifiers
source                  1..123
                        mol_type = other DNA
                        organism = Macaca mulatta
SEQUENCE: 625
gtctgccagt cccccttccac cccacccacg cccccaccct aaccagaggc caaacccttc  60
ctggcgcctg tgataaaagc aactgttagc ctgcactaga gtagcttcaa agttgtattg  120
acc                                                              123

SEQ ID NO: 626          moltype = DNA  length = 123
FEATURE                 Location/Qualifiers
source                  1..123
                        mol_type = other DNA
                        organism = Papio sp.
SEQUENCE: 626
gtctgccagt ccccttccac cccacccacg cccccaccct aaccagaggc caaacccttc  60
ctggcgcctg tgataaaagc aactgttagc ttgcactaga gtagcttcaa agttgtattg  120
acc                                                              123

SEQ ID NO: 627          moltype = DNA  length = 123
FEATURE                 Location/Qualifiers
misc_feature            1..123
                        note = source = /note="Description of Unknown: Marmoset
                         polynucleotide"
source                  1..123
                        mol_type = other DNA
                        organism = unidentified
SEQUENCE: 627
gtctgccagt cctcttccac cccacccatg accccaccct aatcagaggc caaacccttc  60
ctggagcctg tgataaaagc aactgttagc ttgcactaga ctagcttcaa agttgtattg  120
acc                                                              123

SEQ ID NO: 628          moltype = DNA  length = 123
FEATURE                 Location/Qualifiers
misc_feature            1..123
                        note = source = /note="Description of Unknown: Bushbaby
                         polynucleotide"
source                  1..123
                        mol_type = other DNA
                        organism = unidentified
SEQUENCE: 628
gtctgccagt cctcttccac cctccccacg cccccacccc aatcagaggc caaacccttc  60
ctggcgcctg tgataaagaa aactgttagc ttgcaccaga ccaacttcaa agatgtgttg  120
acc                                                              123

SEQ ID NO: 629          moltype = DNA  length = 122
FEATURE                 Location/Qualifiers
variation               33
                        note = a, c, t or g
source                  1..122
                        mol_type = other DNA
                        organism = Tupaia chinensis
SEQUENCE: 629
acctaccgct ccccttctac cccagccacg gcncccaccc cagcaggagg ccaagaccct  60
ctgtggcctg tgatatacgc aactgttagt tgcactacgc tggcttcaca gctgtgctga  120
ac                                                               122
```

```
SEQ ID NO: 630          moltype = DNA  length = 252
FEATURE                 Location/Qualifiers
variation               5
                        note = a, c, t or g
variation               46
                        note = a, c, t or g
variation               67..206
                        note = a, c, t or g
misc_feature            1..252
                        note = source = /note="Description of Unknown: Squirrel
                         polynucleotide"
source                  1..252
                        mol_type = other DNA
                        organism = unidentified
SEQUENCE: 630
atctnccact tctccttcta ccccacccca atcagaggcc aaaccnttcc taagggccta  60
agaaaannnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnagga actttaaggc tgcactagac cacctttaaa  240
gttgtgttga cc                                                       252

SEQ ID NO: 631          moltype = DNA  length = 47
FEATURE                 Location/Qualifiers
variation               5
                        note = a, c, t or g
variation               32..42
                        note = a, c, t or g
source                  1..47
                        mol_type = other DNA
                        organism = Mus sp.
SEQUENCE: 631
acccnaccat tagtcttcca tcctaaacac gnnnnnnnnn nnggggc                 47

SEQ ID NO: 632          moltype = DNA  length = 215
FEATURE                 Location/Qualifiers
variation               7
                        note = a, c, t or g
variation               28..167
                        note = a, c, t or g
variation               201..202
                        note = a, c, t or g
source                  1..215
                        mol_type = other DNA
                        organism = Mus sp.
SEQUENCE: 632
caaaccnttc tttggagctt gtgataannn nnnnnnnnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnagc aactgtcagc  180
ctgtagtagg ccagcagtag nnaggtttct ctagc                              215

SEQ ID NO: 633          moltype = DNA  length = 258
FEATURE                 Location/Qualifiers
variation               5
                        note = a, c, t or g
variation               58
                        note = a, c, t or g
variation               74..213
                        note = a, c, t or g
source                  1..258
                        mol_type = other DNA
                        organism = Rattus sp.
SEQUENCE: 633
acccnaccat tactcttcta tcctgaacac agctgaaccc ttctttgggg cgaaaccngt  60
ctcaacaaaa caannnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnagcaagg gttagcctgc actaggccaa  240
ctccaaaggt tctcaagc                                                 258

SEQ ID NO: 634          moltype = DNA  length = 245
FEATURE                 Location/Qualifiers
variation               12..15
                        note = a, c, t or g
variation               39
                        note = a, c, t or g
variation               60..199
                        note = a, c, t or g
source                  1..245
                        mol_type = other DNA
```

```
                        organism = Heterocephalus glaber
SEQUENCE: 634
acagaccctg cnnnntctcc acaagcagag ggcaagccnt tttttgtcgc ctgtgataan  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnna gcaagtgtta atctgcacca ggccagcatc agagttgtga  240
ggacc                                                               245

SEQ ID NO: 635          moltype = DNA  length = 67
FEATURE                 Location/Qualifiers
variation               14..16
                        note = a, c, t or g
source                  1..67
                        mol_type = other DNA
                        organism = Oryctolagus cuniculus
SEQUENCE: 635
cttcctgggg cctnnngtga tgaagtgact gagccagcag cagcccagcg ctagggctgt  60
gctgatc                                                             67

SEQ ID NO: 636          moltype = DNA  length = 126
FEATURE                 Location/Qualifiers
variation               57
                        note = a, c, t or g
variation               112..113
                        note = a, c, t or g
source                  1..126
                        mol_type = other DNA
                        organism = Sus scrofa
SEQUENCE: 636
atctgccgct cctcttcaac cccgccctca cccccacccc aatcagaggc caaaccnttc  60
catggggcct ttgataaaag caactgttgg cctgctccag accaactttg annagttgtg  120
ttgatc                                                              126

SEQ ID NO: 637          moltype = DNA  length = 121
FEATURE                 Location/Qualifiers
variation               57
                        note = a, c, t or g
source                  1..121
                        mol_type = other DNA
                        organism = Bos taurus
SEQUENCE: 637
atcggccact cctcttccac cccaccctcg tgcccacccc aatcagaggc caagccnttc  60
catggggcct ttgataaaag caactgttgg cctgctccag accaacacag ttgtgttgac  120
c                                                                   121

SEQ ID NO: 638          moltype = DNA  length = 137
FEATURE                 Location/Qualifiers
variation               31..41
                        note = a, c, t or g
variation               68
                        note = a, c, t or g
variation               123..124
                        note = a, c, t or g
source                  1..137
                        mol_type = other DNA
                        organism = Canis lupus
SEQUENCE: 638
acctaccacg cctcttccac cccaccctta nnnnnnnnnn ncccccaccc cagttggagg  60
ccaaaccntt ccttggggcc tttgataaaa gcaactgtta gcttgcacca gaccaattct  120
tannagttgt gttgacc                                                  137

SEQ ID NO: 639          moltype = DNA  length = 111
FEATURE                 Location/Qualifiers
variation               44
                        note = a, c, t or g
misc_feature            1..111
                        note = source = /note="Description of Unknown: Elephant
                         polynucleotide"
source                  1..111
                        mol_type = other DNA
                        organism = unidentified
SEQUENCE: 639
atctaccact cttcttccac ccaccccaat cagaggccaa gccnttcctt ggggcctttg  60
ataaaagcaa ctgttagctt gaacttggct aacttttagg ttgtgttgat c            111

SEQ ID NO: 640          moltype = DNA  length = 79
FEATURE                 Location/Qualifiers
source                  1..79
                        mol_type = other DNA
```

```
                         organism = Homo sapiens
SEQUENCE: 640
ccagcagggc ctgtcagaag aggccctgga cactgaaggc tgggcacagc cttggggacc  60
gctcacagga catgcagca                                               79

SEQ ID NO: 641           moltype = DNA  length = 90
FEATURE                  Location/Qualifiers
source                   1..90
                         mol_type = other DNA
                         organism = Homo sapiens
SEQUENCE: 641
gtgtgtgccg acaactccct accgcgaccc ctatcagtgc cgaccaagca cacaagatgc  60
acacccaggc tgggctggac agaggggtcc                                   90

SEQ ID NO: 642           moltype = DNA  length = 31
FEATURE                  Location/Qualifiers
source                   1..31
                         mol_type = other DNA
                         organism = Homo sapiens
SEQUENCE: 642
cacaagatca cagggtgtgc cctgagaagg t                                 31

SEQ ID NO: 643           moltype = DNA  length = 200
FEATURE                  Location/Qualifiers
source                   1..200
                         mol_type = other DNA
                         organism = Homo sapiens
SEQUENCE: 643
ccagcagggc ctgtcagaag aggccctgga cactgaaggc tgggcacagc cttggggacc  60
gctcacagga catgcagcag tgtgtgccga caactcccta ccgcgacccc tatcagtgcc  120
gaccaagcac acaagatgca cacccaggct gggctggaca gaggggtccc acaagatcac  180
agggtgtgcc ctgagaaggt                                              200

SEQ ID NO: 644           moltype = DNA  length = 200
FEATURE                  Location/Qualifiers
source                   1..200
                         mol_type = other DNA
                         organism = Pan sp.
SEQUENCE: 644
ccagcagggc ctgtcagaag aggccctgga cactgaaggc tgggcacagc cttggggacc  60
gctcacagga catgcagcag tgtgtgccga caactcccta ccgcgacccc tatcagtgcc  120
gaccaagcac acaagatgca cacccaggct gggctggaca gaggggtccc acaagatcac  180
agggtgtgcc ctgagaaggt                                              200

SEQ ID NO: 645           moltype = DNA  length = 200
FEATURE                  Location/Qualifiers
source                   1..200
                         mol_type = other DNA
                         organism = Gorilla sp.
SEQUENCE: 645
ccagcagggc ctgtcagaag aggccctgga cactgaaggc tgggcacagc cttggggacc  60
gctcacagga catgcagcag tgtgtgccga caactcccta ccgcgacccc tatcagtgcc  120
gaccaagcac acaacatgca cacccaggct gggctggaca gaggggtccc acaagatcac  180
agggtgtgcc ctgagaaggt                                              200

SEQ ID NO: 646           moltype = DNA  length = 206
FEATURE                  Location/Qualifiers
variation                94..99
                         note = a, c, t or g
source                   1..206
                         mol_type = other DNA
                         organism = Macaca mulatta
SEQUENCE: 646
ccagcaggcc ctggcagaag aggccctgga cactgaaggc tgggcacagc cttggggact  60
gctcacagga catgcagcag tgtgtgctga caannnnnnc tccccactgc gacccctatc  120
agtgctgacc aagcacacaa gatgcacacc caggctgggc tggacagagg ggtcccacaa  180
ggtcacaggg tgtgccccga ggaggt                                       206

SEQ ID NO: 647           moltype = DNA  length = 206
FEATURE                  Location/Qualifiers
variation                94..99
                         note = a, c, t or g
source                   1..206
                         mol_type = other DNA
                         organism = Papio sp.
SEQUENCE: 647
ccagcaggcc ctggcagaag aggccctgga cactgaaggc tgggcacagc cttggggact  60
gctcacagga catgcagcag tgtgtgctga caannnnnnc tccccactgc gacccctatc  120
agtgctgacc aagcacacaa gatgcacacc caggctgggc tggacagagg ggtcccacaa  180
```

```
ggtcacaggg tgtgccccga ggaggt                                  206

SEQ ID NO: 648         moltype = DNA  length = 207
FEATURE                Location/Qualifiers
variation              4
                       note = a, c, t or g
variation              95..100
                       note = a, c, t or g
misc_feature           1..207
                       note = source = /note="Description of Unknown: Marmoset
                        polynucleotide"
source                 1..207
                       mol_type = other DNA
                       organism = unidentified
SEQUENCE: 648
ccangcaggg cctggcagaa gaggccctgg acactgaagg ctgggcacag cctccaggac  60
cactcacagg acatgcctca gtgtgtgccg acagnnnnnn ctccccaccg cgacccctat  120
cagtgctgac caagtgcaca agatgcacac cccagctggg ctggacagag tggtcccgca  180
aggtcacagg gtgtgcccca aggaggt                                 207

SEQ ID NO: 649         moltype = DNA  length = 194
FEATURE                Location/Qualifiers
variation              10
                       note = a, c, t or g
variation              95
                       note = a, c, t or g
misc_feature           1..194
                       note = source = /note="Description of Unknown: Bushbaby
                        polynucleotide"
source                 1..194
                       mol_type = other DNA
                       organism = unidentified
SEQUENCE: 649
gcagcagggn cctggcggga gaggccctgg acactgcaac ctgggcacag tcttggggac  60
agctcacagc ttgtgcagca gtgtgcctcc ctccnagtga cccctatcag tgccgaccaa  120
gtgtacaaag tgcacaccca ggctgggctg cacagagggg tccctataag tttgtgggtg  180
tgccctgagg aggt                                               194

SEQ ID NO: 650         moltype = DNA  length = 201
FEATURE                Location/Qualifiers
variation              10
                       note = a, c, t or g
variation              88..93
                       note = a, c, t or g
variation              103
                       note = a, c, t or g
source                 1..201
                       mol_type = other DNA
                       organism = Tupaia chinensis
SEQUENCE: 650
ccagcagggn cctggcagaa gcagccctgg acactgaagg ctgggcacag cctcaggggc  60
agttcatcca gcagtgtgct ctgagaannn nnnctcccca tcngtgaccc ctatcagtcc  120
caaccaagta cacaaggtgt gcgcccaggc tgggctggat agaggggtcc ctacagggtg  180
cagggtgtgc cagaaggagg t                                       201

SEQ ID NO: 651         moltype = DNA  length = 208
FEATURE                Location/Qualifiers
variation              94..99
                       note = a, c, t or g
variation              109
                       note = a, c, t or g
variation              178
                       note = a, c, t or g
misc_feature           1..208
                       note = source = /note="Description of Unknown: Squirrel
                        polynucleotide"
source                 1..208
                       mol_type = other DNA
                       organism = unidentified
SEQUENCE: 651
gcagagagtc ccagcagaag aggccctgga cattacaggc tgggcacagc ctcagggaca  60
gctctcagga cctgcagcag tgtgctctga gaannnnnnc tccccaccng tgacccctat  120
cagtgccaaa caagcacaca agatgcacgc ccaggctggg ctgaacagag gggtcccnac  180
aaggttgcag ggtgtgccct gagtaggt                                208

SEQ ID NO: 652         moltype = DNA  length = 200
FEATURE                Location/Qualifiers
variation              85..90
                       note = a, c, t or g
```

```
variation             100
                      note = a, c, t or g
variation             159
                      note = a, c, t or g
variation             170
                      note = a, c, t or g
source                1..200
                      mol_type = other DNA
                      organism = Mus sp.
SEQUENCE: 652
ccagaggacc ctagaagaag aggccctgga cattacaggc tgggcacaag gacagttcac  60
aggaagatca gtgtgctcca aagcnnnnnn ctccctaacn tcgaccccta tcagtaccaa  120
acaaggctat aagacacaca cccagactgg gttggacang agaggtcccn ataaggttga  180
ggggtgtgcc ccgagaaggt                                              200

SEQ ID NO: 653        moltype = DNA  length = 185
FEATURE               Location/Qualifiers
variation             78..83
                      note = a, c, t or g
variation             93
                      note = a, c, t or g
variation             150
                      note = a, c, t or g
variation             161
                      note = a, c, t or g
source                1..185
                      mol_type = other DNA
                      organism = Rattus sp.
SEQUENCE: 653
ccacagagcc caggaagaag aggccctgga catcacaggc tgggcacagg aacagcttgc  60
aggaggatca gtgtgctnnn nnnctcccta gcntcaaccc ctatcagtac caaacaaatc  120
cataacacac gccccggccg ggttggacan gagggatcac nataaggggt gtgccccgag  180
agggt                                                              185

SEQ ID NO: 654        moltype = DNA  length = 201
FEATURE               Location/Qualifiers
variation             91..96
                      note = a, c, t or g
variation             106
                      note = a, c, t or g
variation             138
                      note = a, c, t or g
variation             176
                      note = a, c, t or g
variation             192..193
                      note = a, c, t or g
source                1..201
                      mol_type = other DNA
                      organism = Heterocephalus glaber
SEQUENCE: 654
ccagagggcc caggcagaag aggcctggac attgcaggct gggcaagcct cagaacagct  60
cacaggacgt gaagtaatgt gctccgagaa nnnnnnctcc cctccngtga ctgctattag  120
tgcctatcaa gtgcacanag atgcacgcct gggcggagct ggacagaggc gtcccnataa  180
ggttgcaccc tnntaggagg t                                            201

SEQ ID NO: 655        moltype = DNA  length = 204
FEATURE               Location/Qualifiers
variation             5
                      note = a, c, t or g
variation             94..99
                      note = a, c, t or g
variation             109
                      note = a, c, t or g
variation             168
                      note = a, c, t or g
variation             179
                      note = a, c, t or g
source                1..204
                      mol_type = other DNA
                      organism = Oryctolagus cuniculus
SEQUENCE: 655
tcagnagggc cctggcagaa gaggccctgg acacttcagg ctgggcacag cctcggggac  60
agctcccgga cacgcagcca tgtgctcgga ggannnnnnc tccccaccng tgacccctat  120
cagtgccgag caagtgcaca agacacacac ccaggctggg ctggacanag gggtcccng   180
aaaggttgca gggtgtgccc tgag                                         204

SEQ ID NO: 656        moltype = DNA  length = 206
FEATURE               Location/Qualifiers
variation             10
```

```
                        note = a, c, t or g
variation               92..97
                        note = a, c, t or g
variation               107
                        note = a, c, t or g
variation               176
                        note = a, c, t or g
source                  1..206
                        mol_type = other DNA
                        organism = Sus scrofa
SEQUENCE: 656
ccagcagggn cctggtagaa gaggccctgg acactgcagg ctgggcacag cctcagagac  60
ctcacatggg acatgtggca gcgtgctccg annnnnnctc cccaccngtg acccctatca  120
gtgccgacca agcacagaag atgcacaccc aggctgggct ggcctcgggg gtcccnacag  180
ggttgcaggg cgtgcactga ggaggt                                       206

SEQ ID NO: 657          moltype = DNA  length = 197
FEATURE                 Location/Qualifiers
variation               10
                        note = a, c, t or g
variation               83..88
                        note = a, c, t or g
variation               98
                        note = a, c, t or g
variation               167
                        note = a, c, t or g
source                  1..197
                        mol_type = other DNA
                        organism = Bos taurus
SEQUENCE: 657
ccagcagggn tctcctggac actgcaggct gggcaaggcc tcagagacag ctcacgggac  60
atgtggcagt gtgctccgag gannnnnnct ccccaccngt gacccctatc agtgccgacc  120
aagcacgcaa gatgtacacc caggctgggc tggacacagg ggtgtcngca aggttgccgg  180
gcgtgcactt gggaggt                                                 197

SEQ ID NO: 658          moltype = DNA  length = 195
FEATURE                 Location/Qualifiers
variation               10
                        note = a, c, t or g
variation               82..87
                        note = a, c, t or g
variation               96
                        note = a, c, t or g
variation               165
                        note = a, c, t or g
source                  1..195
                        mol_type = other DNA
                        organism = Canis lupus
SEQUENCE: 658
ccagcagggn cctggcagat gagaccctgg acactgcggg ctgggcacag cctcagggca  60
tgtggcaggg tgctccgagg annnnnnctc cccacngtga cccctatcag tgccgaccaa  120
gcacacaaga tgcgcacccg ggctgggctg gacacggggg tcccnccaag ggtgcaggct  180
gcgcatggag gacac                                                   195

SEQ ID NO: 659          moltype = DNA  length = 192
FEATURE                 Location/Qualifiers
variation               94..99
                        note = a, c, t or g
variation               109
                        note = a, c, t or g
variation               178
                        note = a, c, t or g
misc_feature            1..192
                        note = source = /note="Description of Unknown: Elephant
                         polynucleotide"
source                  1..192
                        mol_type = other DNA
                        organism = unidentified
SEQUENCE: 659
acagcagggc ctggcggcag aggctctgga cattgctggc tgggcacagg cccagggaga  60
gcccacagga catacagctg tgggctctga ggannnnnnc tccctgccng tgaccactat  120
cagtgccgac caagtgcaca agatgcacac ccaggctggg ctggacttag tggtcccnac  180
gaggctgcgg gg                                                      192

SEQ ID NO: 660          moltype = DNA  length = 128
FEATURE                 Location/Qualifiers
source                  1..128
                        mol_type = other DNA
                        organism = Homo sapiens
```

```
SEQUENCE: 660
aaataaaatc caattctcca tcaccaagag agccttccga aagaggcccc cctgggcaaa  60
cggccaccga tggagaggtc tgccagtcct cttctacccc acccacgccc ccaccctaat  120
cagaggcc                                                           128

SEQ ID NO: 661         moltype = DNA  length = 72
FEATURE                Location/Qualifiers
source                 1..72
                       mol_type = other DNA
                       organism = Homo sapiens
SEQUENCE: 661
aaacccttcc tggagcctgt gataaaagca actgttagct tgcactagac tagcttcaaa  60
gttgtattga cc                                                      72

SEQ ID NO: 662         moltype = DNA  length = 200
FEATURE                Location/Qualifiers
source                 1..200
                       mol_type = other DNA
                       organism = Homo sapiens
SEQUENCE: 662
aaataaaatc caattctcca tcaccaagag agccttccga aagaggcccc cctgggcaaa  60
cggccaccga tggagaggtc tgccagtcct cttctacccc acccacgccc ccaccctaat  120
cagaggccaa acccttcctg gagcctgtga taaaagcaac tgttagcttg cactagacta  180
gcttcaaagt tgtattgacc                                              200

SEQ ID NO: 663         moltype = DNA  length = 200
FEATURE                Location/Qualifiers
source                 1..200
                       mol_type = other DNA
                       organism = Pan sp.
SEQUENCE: 663
aaataaaatc caattctcca tcaccaagag agccttccga aagaggcccc cctgggcaaa  60
cggccaccga cggagaggtc tgccagtcct cttctacccc acccacgccc ccaccctaat  120
cagaggccaa acccttcctg gagcctgtga taaaagcaac tgttagcttg cactagacta  180
gcttcaaagt tgtattgacc                                              200

SEQ ID NO: 664         moltype = DNA  length = 200
FEATURE                Location/Qualifiers
source                 1..200
                       mol_type = other DNA
                       organism = Gorilla sp.
SEQUENCE: 664
aaataaaatc caattctccg tcaccaagag agccttccga aagaggcccc cctgggcaaa  60
cggccaccga cggagaggtc tgccagtcct cttctacccc acccacgccc ccaccctaat  120
cagaggccaa acccttcctg gagcctgtga taaaggcaac tgttagcttg cactagacta  180
gcttcaaagt tgtattgacc                                              200

SEQ ID NO: 665         moltype = DNA  length = 200
FEATURE                Location/Qualifiers
source                 1..200
                       mol_type = other DNA
                       organism = Macaca mulatta
SEQUENCE: 665
aaataaaatc caattctcca tcagcaagag agccttctgg aagaggcccc cctgggcaaa  60
cggccactga cggagaggtc tgccagtccc cttccacccc acccacgccc ccaccctaac  120
cagaggccaa acccttcctg gcgcctgtga taaaagcaac tgttagcctg cactagagta  180
gcttcaaagt tgtattgacc                                              200

SEQ ID NO: 666         moltype = DNA  length = 200
FEATURE                Location/Qualifiers
source                 1..200
                       mol_type = other DNA
                       organism = Papio sp.
SEQUENCE: 666
aaataaaatc caattctcca tcagcaagag agccttctgg aagaggcccc cctgggcaaa  60
cggccactga cggagaggtc tgccagtccc cttccacccc acccacgccc ccaccctaac  120
cagaggccaa acccttcctg gcgcctgtga taaaagcaac tgttagcttg cactagagta  180
gcttcaaagt tgtattgacc                                              200

SEQ ID NO: 667         moltype = DNA  length = 200
FEATURE                Location/Qualifiers
misc_feature           1..200
                       note = source = /note="Description of Unknown: Marmoset
                        polynucleotide"
source                 1..200
                       mol_type = other DNA
                       organism = unidentified
SEQUENCE: 667
aaacaaaatc cagttctcca ccagcaagag agccttccaa aagaggcccc tctgggtaaa  60
```

```
cggccactga cgaagaggtc tgccagtcct cttccacccc acccatgacc ccaccctaat  120
cagaggccaa acccttcctg gagcctgtga taaaagcaac tgttagcttg cactagacta  180
gcttcaaagt tgtattgacc                                              200

SEQ ID NO: 668         moltype = DNA  length = 200
FEATURE                Location/Qualifiers
variation              155
                       note = a, c, t or g
misc_feature           1..200
                       note = source = /note="Description of Unknown: Bushbaby
                        polynucleotide"
source                 1..200
                       mol_type = other DNA
                       organism = unidentified
SEQUENCE: 668
aaataaaatc tagtcctcct ccagtgagag agccttctga aagaggcccc ctgtgcaaac  60
agcctccaac acagaggtct gccagtcctc ttccaccctc cccacgcccc caccccaatc  120
agaggccaaa cccttcctgg cgcctgtgat aaagnaaaac tgttagcttg caccagacca  180
acttcaaaga tgtgttgacc                                              200

SEQ ID NO: 669         moltype = DNA  length = 197
FEATURE                Location/Qualifiers
variation              108
                       note = a, c, t or g
source                 1..197
                       mol_type = other DNA
                       organism = Tupaia chinensis
SEQUENCE: 669
aaataaaacc caattctcca ccagcaagag agccttctga aagaggccac ctgtggaaac  60
tgccacaagg cggagaccta ccgctcccct tctaccccag ccacggcncc caccccagca  120
ggaggccaag accctctgtg gcctgtgata tacgcaactg ttagttgcac tacgctggct  180
tcacagctgt gctgaac                                                 197

SEQ ID NO: 670         moltype = DNA  length = 326
FEATURE                Location/Qualifiers
variation              79
                       note = a, c, t or g
variation              120
                       note = a, c, t or g
variation              141..280
                       note = a, c, t or g
misc_feature           1..326
                       note = source = /note="Description of Unknown: Squirrel
                        polynucleotide"
source                 1..326
                       mol_type = other DNA
                       organism = unidentified
SEQUENCE: 670
aaataaaatc caattctcca cagcaaaata acctctgaaa gaggccacct gagcaaatgg  60
ccatagaccc agagatctnc cacttctcct tctaccccac cccaatcaga ggccaaaccn  120
ttcctaaggg cctaagaaaa nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn aggaacttta aggctgcact  300
agaccacctt taaagttgtg ttgacc                                       326

SEQ ID NO: 671         moltype = DNA  length = 118
FEATURE                Location/Qualifiers
variation              79
                       note = a, c, t or g
variation              106..113
                       note = a, c, t or g
source                 1..118
                       mol_type = other DNA
                       organism = Mus sp.
SEQUENCE: 671
aaatacaatc cagttctcca ctggcaagag ccttcggaaa gaaggcagtt gagcaatcag  60
ccatagaccc agatacccna gcattagtct tccatcctaa acacgnnnnn nnnggggc    118

SEQ ID NO: 672         moltype = DNA  length = 215
FEATURE                Location/Qualifiers
variation              7
                       note = a, c, t or g
variation              28..167
                       note = a, c, t or g
variation              201..202
                       note = a, c, t or g
source                 1..215
                       mol_type = other DNA
                       organism = Mus sp.
```

```
SEQUENCE: 672
caaaccnttc tttggagctt gtgataannn nnnnnnnnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnagc aactgtcagc  180
ctgtagtagg ccagcagtag nnaggtttct ctagc                              215

SEQ ID NO: 673         moltype = DNA  length = 123
FEATURE                Location/Qualifiers
variation              69
                       note = a, c, t or g
variation              96..103
                       note = a, c, t or g
source                 1..123
                       mol_type = other DNA
                       organism = Rattus sp.
SEQUENCE: 673
aaataaaatc cagttctcca ctggcaagag ccttcagaaa gagcaaacag ccgtagaccc  60
atagacccna ccattactct tctatcctga acacannnnn nnngctgaac ccttctttgg  120
ggc                                                                 123

SEQ ID NO: 674         moltype = DNA  length = 207
FEATURE                Location/Qualifiers
variation              7
                       note = a, c, t or g
variation              23..162
                       note = a, c, t or g
source                 1..207
                       mol_type = other DNA
                       organism = Rattus sp.
SEQUENCE: 674
gaaaccngtc tcaacaaaac aannnnnnnn nnnnnnnnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnagcaaggg ttagcctgca  180
ctaggccaac tccaaaggtt ctcaagc                                       207

SEQ ID NO: 675         moltype = DNA  length = 310
FEATURE                Location/Qualifiers
variation              30..33
                       note = a, c, t or g
variation              77..80
                       note = a, c, t or g
variation              104
                       note = a, c, t or g
variation              125..264
                       note = a, c, t or g
source                 1..310
                       mol_type = other DNA
                       organism = Heterocephalus glaber
SEQUENCE: 675
aaataaaacc agttctccac caacaagaan nnnccttctg aaagaagcca cctaagcaaa  60
cagccacaga ccctgcnnnn tctccacaag cagagggcaa gccntttttt gtcgcctgtg  120
ataannnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnagcaag tgttaatctg caccaggcca gcatcagagt  300
tgtgaggacc                                                          310

SEQ ID NO: 676         moltype = DNA  length = 101
FEATURE                Location/Qualifiers
variation              31..34
                       note = a, c, t or g
variation              48..50
                       note = a, c, t or g
source                 1..101
                       mol_type = other DNA
                       organism = Oryctolagus cuniculus
SEQUENCE: 676
aaatcaaatc taattctcca ccagcaaaac nnnncttcct ggggcctnnn gtgatgaagt  60
gactgagcca gcagcagccc agcgctaggg ctgtgctgat c                       101

SEQ ID NO: 677         moltype = DNA  length = 201
FEATURE                Location/Qualifiers
variation              132
                       note = a, c, t or g
variation              187..188
                       note = a, c, t or g
source                 1..201
                       mol_type = other DNA
                       organism = Sus scrofa
SEQUENCE: 677
```

```
taataaaatc gaattctcca ccgacaagag agctttctgt aacaggccac ctgagcaaaa  60
gccacagacc ccgagatctg ccgctcctct tcaaccccgc cctcaccccc accccaatca  120
gaggccaaac cnttccatgg ggcctttgat aaaagcaact gttggcctgc tccagaccaa  180
ctttgannag ttgtgttgat c                                            201

SEQ ID NO: 678         moltype = DNA  length = 196
FEATURE                Location/Qualifiers
variation              132
                       note = a, c, t or g
source                 1..196
                       mol_type = other DNA
                       organism = Bos taurus
SEQUENCE: 678
taacaaaatc caattctcca ccgacaaaag aacctttga aagaagccac ctgagcgcac  60
gtcacagacc cagagatcgg ccactcctct tccaccccac cctcgtgccc accccaatca  120
gaggccaagc cnttccatgg ggcctttgat aaaagcaact gttggcctgc tccagaccaa  180
cacagttgtg ttgacc                                                  196

SEQ ID NO: 679         moltype = DNA  length = 206
FEATURE                Location/Qualifiers
variation              102..109
                       note = a, c, t or g
variation              136
                       note = a, c, t or g
variation              141
                       note = a, c, t or g
variation              192..193
                       note = a, c, t or g
source                 1..206
                       mol_type = other DNA
                       organism = Canis lupus
SEQUENCE: 679
aaatacgatc taactttgca ccaagagtct tctgaaagag gccacctgag caaacagcca  60
cagaccagga gacctaccac gcctcttcca ccccaccctt annnnnnnnc ccccacccca  120
gttggaggcc aaaccnttcc nttggggcct ttgataaaag caactgttag cttgcaccag  180
accaattctt annagttgtg ttgacc                                       206

SEQ ID NO: 680         moltype = DNA  length = 187
FEATURE                Location/Qualifiers
variation              118
                       note = a, c, t or g
variation              173..174
                       note = a, c, t or g
misc_feature           1..187
                       note = source = /note="Description of Unknown: Elephant
                        polynucleotide"
source                 1..187
                       mol_type = other DNA
                       organism = unidentified
SEQUENCE: 680
aaataaaact gaattctcca cttgcaagat accttctgta agaggccacc tgagcaaaca  60
gccacagtcc tgagatctac cactcttctt ccacccaccc caatcagagg ccaagccntt  120
ccttggggcc tttgataaaa gcaactgtta gcttgaactt ggctaacttt tanngggttgt  180
gttgatc                                                            187

SEQ ID NO: 681         moltype = DNA  length = 20
FEATURE                Location/Qualifiers
source                 1..20
                       mol_type = other DNA
                       organism = Homo sapiens
SEQUENCE: 681
attttaacct tcttagcacc                                              20

SEQ ID NO: 682         moltype = DNA  length = 19
FEATURE                Location/Qualifiers
source                 1..19
                       mol_type = other DNA
                       organism = Homo sapiens
SEQUENCE: 682
cacaaacatt tcccttctg                                               19

SEQ ID NO: 683         moltype = DNA  length = 26
FEATURE                Location/Qualifiers
source                 1..26
                       mol_type = other DNA
                       organism = Homo sapiens
SEQUENCE: 683
atatctactt gaactttcag ataaaa                                       26
```

```
SEQ ID NO: 684          moltype = DNA  length = 33
FEATURE                 Location/Qualifiers
source                  1..33
                        mol_type = other DNA
                        organism = Homo sapiens
SEQUENCE: 684
aaaaaaaagc aagttgcagt aacatgttat gct                              33

SEQ ID NO: 685          moltype = DNA  length = 102
FEATURE                 Location/Qualifiers
source                  1..102
                        mol_type = other DNA
                        organism = Homo sapiens
SEQUENCE: 685
acacaaagat tagcatgaat atccaccctc tttaaacagc caccccacac cctggagaag  60
agcaaatgtg aagtttatgt gccaaccaga ctgtgcgcca gg                     102

SEQ ID NO: 686          moltype = DNA  length = 200
FEATURE                 Location/Qualifiers
source                  1..200
                        mol_type = other DNA
                        organism = Homo sapiens
SEQUENCE: 686
attttaacct tcttagcacc cacaaacatt tcccttctga tatctacttg aactttcaga  60
taaaaaaaaa aaagcaagtt gcagtaacat gttatgctac acaaagatta gcatgaatat  120
ccaccctctt taaacagcca ccccacaccc tggagaagag caaatgtgaa gtttatgtgc  180
caaccagact gtgcgccagg                                              200

SEQ ID NO: 687          moltype = DNA  length = 199
FEATURE                 Location/Qualifiers
source                  1..199
                        mol_type = other DNA
                        organism = Pan sp.
SEQUENCE: 687
attttaacct tcttagcacc cacaaacagt tcccttctga tatctacttg aactttcaga  60
taaaaaaaaa aagcaagttg cagtaacatg ttatgctaca caaagattag catgaatatc  120
caccctcttt aaacagccac cccacaccct ggagaagagc aaatgtgaag tttatgtgcc  180
aaccagactg tgcgccagg                                               199

SEQ ID NO: 688          moltype = DNA  length = 202
FEATURE                 Location/Qualifiers
variation               67..68
                        note = a, c, t or g
source                  1..202
                        mol_type = other DNA
                        organism = Gorilla sp.
SEQUENCE: 688
attttaacct tcttagcacc cacaaacagt tcccttctga tatctacttg aactttcaga  60
taaaaannaa aaaaaccaag ttgcagtaac atgttatgct acacaaagat tagcatgaat  120
atccaccctc tttaaacagc caccccacac cctggagaag atcaaatgtg aagtttatgt  180
gccaaccaga ctgtgcgcca tg                                           202

SEQ ID NO: 689          moltype = DNA  length = 57
FEATURE                 Location/Qualifiers
source                  1..57
                        mol_type = other DNA
                        organism = Macaca mulatta
SEQUENCE: 689
attttaacct tcttagcacc cacaaacagt tcccttctga tatctacttg aactttc     57

SEQ ID NO: 690          moltype = DNA  length = 145
FEATURE                 Location/Qualifiers
variation               5..6
                        note = a, c, t or g
source                  1..145
                        mol_type = other DNA
                        organism = Macaca mulatta
SEQUENCE: 690
aaaannaaaa aaaaaaaagc aagtttcagt aacatgttat gctacacaaa gattagcatg  60
aatatccacc ctctttaaac agccacccta tgccctggag aagagcaaat gtgaagttca  120
tgtgccaacc agattgtgtg ccagg                                        145

SEQ ID NO: 691          moltype = DNA  length = 184
FEATURE                 Location/Qualifiers
variation               44..45
                        note = a, c, t or g
source                  1..184
                        mol_type = other DNA
                        organism = Papio sp.
```

```
SEQUENCE: 691
atttaacct tcttagtacc cacaaacagt tcccttctgg atannaaaaa aaaaaaagca  60
agttgcagta acatgttatg ctacacaaag attagcatga atatccaccc tctttaaaca  120
gccaccccat gccctggaga agagcaaatg tgaagttcat gtgccaacca gattgtgtgc  180
cagg                                                               184

SEQ ID NO: 692         moltype = DNA  length = 197
FEATURE                Location/Qualifiers
misc_feature           1..197
                       note = source = /note="Description of Unknown: Marmoset
                        polynucleotide"
source                 1..197
                       mol_type = other DNA
                       organism = unidentified
SEQUENCE: 692
atttaacct tctgagcacc cacaaacagt tcccttctga tatctacttg aactttcaga  60
taaaaaaaaa gcaagttgca ataacatgtt atgctacata aagattagca tgaatatcca  120
ccctctttaa acagccaccc cacaccctgg aggagagcaa atgtgaagtt catgtgccaa  180
ccagactgtg tgccagg                                                 197

SEQ ID NO: 693         moltype = DNA  length = 194
FEATURE                Location/Qualifiers
misc_feature           1..194
                       note = source = /note="Description of Unknown: Bushbaby
                        polynucleotide"
source                 1..194
                       mol_type = other DNA
                       organism = unidentified
SEQUENCE: 693
atttaacct tcttagcacc cacaaacagt tcattctgat atctgcttga acttccagat  60
aaaaaaaggc aagtggcagt aacacgatat gctccacaaa gattagcatg aatatctgcc  120
ctctttaaag agccgcccac gccctggaga agagcactcg tgaggttcat gtaccaacca  180
gaccatgtgc ccag                                                    194

SEQ ID NO: 694         moltype = DNA  length = 201
FEATURE                Location/Qualifiers
variation              119
                       note = a, c, t or g
variation              181..185
                       note = a, c, t or g
source                 1..201
                       mol_type = other DNA
                       organism = Tupaia chinensis
SEQUENCE: 694
atttaacct tcttagcacc cacaaacagt tcccttctga tctctgcttg aacttccaga  60
taaaaaaggc aagcagcaat aacacattat gctacacaaa gattagcatt aatatctanc  120
cctttctaaa cagccacccc acaccctgga gaaaagcaaa cgtgacgtgt atgcaccgac  180
nnnnncagac cacataccag g                                            201

SEQ ID NO: 695         moltype = DNA  length = 199
FEATURE                Location/Qualifiers
variation              68..70
                       note = a, c, t or g
misc_feature           1..199
                       note = source = /note="Description of Unknown: Squirrel
                        polynucleotide"
source                 1..199
                       mol_type = other DNA
                       organism = unidentified
SEQUENCE: 695
atttgaacct tctcagtacc cacaaacagt tcccttctga tatctgcttg aactcccaga  60
taaaaaannn aggcaagtgg cggtaacatg ttatgctacc caaagattag tattaatacc  120
caccctcctt aaacagccgc cccacaccct ggagaagagc aaacatgaag ttcttgggcc  180
agccaaactg tgttctagg                                               199

SEQ ID NO: 696         moltype = DNA  length = 197
FEATURE                Location/Qualifiers
variation              138..141
                       note = a, c, t or g
source                 1..197
                       mol_type = other DNA
                       organism = Mus sp.
SEQUENCE: 696
atttaacct tcttagttac cacaaacagt cccagtccga tatctgtttg aactcccaga  60
taaaaagcgg cgagtggcag ttacatgtta tgctacacag agattagcat taatgcccac  120
cctctttcaa cagccacnnn ntccacaccc agggaagagc cagtgtgaac tttataggcc  180
acctagacca catttga                                                 197

SEQ ID NO: 697         moltype = DNA  length = 191
```

```
FEATURE              Location/Qualifiers
source               1..191
                     mol_type = other DNA
                     organism = Rattus sp.
SEQUENCE: 697
attttagcct cctcggttcc cacaaacagt cccagtccgg tatctgtttg aacttccaga  60
taaaaaggcg agtgaccgtt gcatgctatg ctacacagag attagcatga acacccgccc  120
tctttcaaca gccactccac agcccgggga gagccaacgt gaagttcgta gaccacctag  180
accatgtgtg g                                                       191

SEQ ID NO: 698       moltype = DNA  length = 190
FEATURE              Location/Qualifiers
source               1..190
                     mol_type = other DNA
                     organism = Heterocephalus glaber
SEQUENCE: 698
attttaacct tctcagcatc cacaaacagt tcctttctga tatctgcttg aacttcctga  60
taaaaaagca agtagcaata acatgttatg ttacacaaag attaacacta atatccaccc  120
tctttaaaca gccaccccac accccaaaga gcaaacacaa agtttatggg ccaaccaaac  180
catgttgagt                                                         190

SEQ ID NO: 699       moltype = DNA  length = 172
FEATURE              Location/Qualifiers
variation            61..62
                     note = a, c, t or g
source               1..172
                     mol_type = other DNA
                     organism = Oryctolagus cuniculus
SEQUENCE: 699
attttaacct tctcagtacc cacaaacagt tccttctgat atctgcttga acttccagat  60
nnaaaaaaaa aaaggcatgt ggcagtaaca tgttatgcta caccaagatt agcattaata  120
cccaccctct ccaccccctg cagaagagca aatgtgaagt tcatgcacca gg          172

SEQ ID NO: 700       moltype = DNA  length = 196
FEATURE              Location/Qualifiers
source               1..196
                     mol_type = other DNA
                     organism = Sus scrofa
SEQUENCE: 700
attttagcca tctctgtagc cacaaacagt tcccttctga tatctgtttg aacatccaga  60
taaaaacagg caagtgccag taacctgtta tgctacacaa agattagcat taatatccac  120
cctctttaaa cagccacccc acaccctaga gaggagcaga agtgacgtat atatgccagc  180
cagagagtgt gccagg                                                  196

SEQ ID NO: 701       moltype = DNA  length = 197
FEATURE              Location/Qualifiers
source               1..197
                     mol_type = other DNA
                     organism = Bos taurus
SEQUENCE: 701
attttaacca tctctgtagc cacaaacagt tcccttctga tatctgcttg tatttccaga  60
taaaaaaaag gcaagtggca gtaacctgtt atgctacaca aagattagca gtaatatcca  120
ccctctttaa acagccattc cacaccctag agaagagcag aagtgaagcc caggcaccaa  180
ccagagcatg tgccagg                                                 197

SEQ ID NO: 702       moltype = DNA  length = 194
FEATURE              Location/Qualifiers
source               1..194
                     mol_type = other DNA
                     organism = Canis lupus
SEQUENCE: 702
actttagcca tctctgtacc cacaaacagt tcccttctga tatctgcttg aacttccaga  60
taaaaaaagg caagtggcag taacacgtta tgctacacaa agattagcat tactatccac  120
cctctaaaca gccaccccac accctggaga tgagcagaaa tgaagtatgt gcgccgacca  180
gagcacaggc cagg                                                    194

SEQ ID NO: 703       moltype = DNA  length = 187
FEATURE              Location/Qualifiers
variation            126
                     note = a, c, t or g
misc_feature         1..187
                     note = source = /note="Description of Unknown: Elephant
                      polynucleotide"
source               1..187
                     mol_type = other DNA
                     organism = unidentified
SEQUENCE: 703
acttttacca tcttggcacc cgagaaccgt tctcttctga tatctgcttg aacttactga  60
taaaaaaaaa ggcaagccgt ggtaacatgt tatgctcccc agagattagc attaatatcc  120
```

```
accctngttt aaacagccac ccaacaccct ggagaagagc agaagtaaag tgcatgtgtg  180
tgccagg                                                             187

SEQ ID NO: 704         moltype = DNA  length = 200
FEATURE                Location/Qualifiers
source                 1..200
                       mol_type = other DNA
                       organism = Mus sp.
SEQUENCE: 704
catcactcaa atgtggtcta ggtggcctat aaagttcaca ctggctcttc cctgggtgtg  60
gatggagtgg ctgttgaaag agggtgggca ttaatgctaa tctctgtgta gcataacatg  120
taactgccac tcgccgcttt ttatctggga gttcaaacag atatcggact gggactgttt  180
gtggtaacta agaaggttaa                                               200

SEQ ID NO: 705         moltype = DNA  length = 203
FEATURE                Location/Qualifiers
variation              11..12
                       note = a, c, t or g
variation              53
                       note = a, c, t or g
variation              134..138
                       note = a, c, t or g
source                 1..203
                       mol_type = other DNA
                       organism = Homo sapiens
SEQUENCE: 705
taccaacctg nngcacagtc tggttggcac ataaacttca catttgctct tcnccagggt  60
gtggggtggc tgtttaaaga gggtggatat tcatgctaat ctttgtgtag cataacatgt  120
tactgcaact tgcnnnnntt tttttatctg aaagttcaag tagatatcag aagggaaatg  180
tttgtgggtg ctaagaaggt taa                                           203

SEQ ID NO: 706         moltype = DNA  length = 12
FEATURE                Location/Qualifiers
source                 1..12
                       mol_type = other DNA
                       organism = synthetic construct
SEQUENCE: 706
gccgccatcg cg                                                       12

SEQ ID NO: 707         moltype = DNA  length = 13
FEATURE                Location/Qualifiers
source                 1..13
                       mol_type = other DNA
                       organism = synthetic construct
SEQUENCE: 707
agtcctccct gtg                                                      13

SEQ ID NO: 708         moltype = DNA  length = 15
FEATURE                Location/Qualifiers
source                 1..15
                       mol_type = other DNA
                       organism = synthetic construct
SEQUENCE: 708
gtaaccccca ctggg                                                    15

SEQ ID NO: 709         moltype = DNA  length = 15
FEATURE                Location/Qualifiers
source                 1..15
                       mol_type = other DNA
                       organism = synthetic construct
SEQUENCE: 709
tggttatgac tgtgt                                                    15

SEQ ID NO: 710         moltype = DNA  length = 28
FEATURE                Location/Qualifiers
source                 1..28
                       mol_type = other DNA
                       organism = synthetic construct
SEQUENCE: 710
gccgccgcca tcgcggagga gcgcgata                                      28

SEQ ID NO: 711         moltype = DNA  length = 28
FEATURE                Location/Qualifiers
source                 1..28
                       mol_type = other DNA
                       organism = synthetic construct
SEQUENCE: 711
gccgccgtca tcgcggagga gcgcgata                                      28
```

-continued

```
SEQ ID NO: 712          moltype = DNA  length = 26
FEATURE                 Location/Qualifiers
source                  1..26
                        mol_type = other DNA
                        organism = synthetic construct
SEQUENCE: 712
gccgccgatc gcggaggagc gcgata                                        26

SEQ ID NO: 713          moltype = DNA  length = 27
FEATURE                 Location/Qualifiers
source                  1..27
                        mol_type = other DNA
                        organism = synthetic construct
SEQUENCE: 713
gccgccgcat cgcggaggag cgcgata                                       27

SEQ ID NO: 714          moltype = DNA  length = 27
FEATURE                 Location/Qualifiers
source                  1..27
                        mol_type = other DNA
                        organism = synthetic construct
SEQUENCE: 714
gccgccgcat cgcggaggag cgcgata                                       27

SEQ ID NO: 715          moltype = DNA  length = 22
FEATURE                 Location/Qualifiers
source                  1..22
                        mol_type = other DNA
                        organism = synthetic construct
SEQUENCE: 715
gccgccgcgg aggagcgcga ta                                            22

SEQ ID NO: 716          moltype = DNA  length = 22
FEATURE                 Location/Qualifiers
source                  1..22
                        mol_type = other DNA
                        organism = synthetic construct
SEQUENCE: 716
gccgccgcgg aggagcgcga ta                                            22

SEQ ID NO: 717          moltype = DNA  length = 19
FEATURE                 Location/Qualifiers
source                  1..19
                        mol_type = other DNA
                        organism = synthetic construct
SEQUENCE: 717
gccgccgcgg agcgcgata                                                19

SEQ ID NO: 718          moltype = DNA  length = 16
FEATURE                 Location/Qualifiers
source                  1..16
                        mol_type = other DNA
                        organism = synthetic construct
SEQUENCE: 718
gccgccgcgc gcgata                                                   16

SEQ ID NO: 719          moltype = DNA  length = 16
FEATURE                 Location/Qualifiers
source                  1..16
                        mol_type = other DNA
                        organism = synthetic construct
SEQUENCE: 719
ccgcgatggc ggcggc                                                   16
```